(12) United States Patent
Cheng et al.

(10) Patent No.: US 8,883,782 B2
(45) Date of Patent: *Nov. 11, 2014

(54) SPIRO-TETRACYCLIC RING COMPOUNDS AS BETA-SECRETASE MODULATORS AND METHODS OF USE

(75) Inventors: Yuan Cheng, Newbury Park, CA (US); Ryan White, Somerville, MA (US); Albert Amegadzie, Moorpark, CA (US); James Brown, Moorpark, CA (US); Alan C. Cheng, San Francisco, CA (US); Erin F. Dimauro, Cambridge, MA (US); Thomas Dineen, Somerville, MA (US); Oleg Epstein, Belmont, MA (US); Vijay Keshav Gore, Thousand Oaks, CA (US); Jason Brooks Human, Boston, MA (US); Ted Judd, Simi Valley, CA (US); Charles Kreiman, Watertown, MA (US); Qingyian Liu, Camarillo, CA (US); Patricia Lopez, West Hills, CA (US); Vu Van Ma, Simi Valley, CA (US); Isaac Marx, Somerville, MA (US); Ana Minatti, Woodland Hills, CA (US); Hanh Nho Nguyen, Arlington, MA (US); Nick A. Paras, Glendale, CA (US); Vinod F. Patel, Acton, MA (US); Wenyuan Qian, Camarillo, CA (US); Matthew Weiss, Boston, MA (US); Qiufen Xue, Newbury Park, CA (US); Xiao Mei Zheng, Natick, MA (US); Wenge Zhong, Thousand Oaks, CA (US)

(73) Assignee: Amgen Inc., Thousands Oaks, CA (US)

(*) Notice: Subject to any disclaimer, the term of this patent is extended or adjusted under 35 U.S.C. 154(b) by 770 days.

This patent is subject to a terminal disclaimer.

(21) Appl. No.: 13/047,734

(22) Filed: Mar. 14, 2011

(65) Prior Publication Data
US 2011/0251190 A1 Oct. 13, 2011

Related U.S. Application Data

(60) Provisional application No. 61/314,129, filed on Mar. 15, 2010.

(51) Int. Cl.
*A61K 31/42* (2006.01)
*A61K 31/422* (2006.01)
(Continued)

(52) U.S. Cl.
CPC ............ *C07D 491/10* (2013.01); *C07D 498/10* (2013.01); *C07D 221/20* (2013.01); *C07D 235/02* (2013.01); *C07D 263/08* (2013.01); *C07D 295/135* (2013.01); *A61K 31/42* (2013.01); *A61K 31/422* (2013.01); *A61K 31/506* (2013.01); *A61K 31/4439* (2013.01); *A61K 31/5377* (2013.01)

USPC ........ 514/232.8; 514/278; 514/377; 544/230; 546/15; 548/216

(58) Field of Classification Search
CPC ... A61K 31/42; A61K 31/422; A61K 31/506; A61K 31/4439; A61K 31/5377; C07D 221/20; C07D 235/02; C07D 263/08; C07D 295/135; C07D 491/10; C07D 498/10
USPC .......... 514/232.8, 278, 377; 544/230; 546/15; 548/216
See application file for complete search history.

(56) References Cited

U.S. PATENT DOCUMENTS

| 2,683,718 A | 7/1954 | Clinton et al. |
| 3,185,696 A | 5/1965 | Tien et al. |

(Continued)

FOREIGN PATENT DOCUMENTS

| EP | 01942105 A1 | 9/2008 |
| EP | 02305672 A1 | 6/2011 |

(Continued)

OTHER PUBLICATIONS

West, Anthony R., Solid State Chemistry and Its Applications, Wiley, New York, 1988, 358.*

(Continued)

*Primary Examiner* — Erich A Lesser
(74) *Attorney, Agent, or Firm* — G. Prabhakar Reddy

(57) ABSTRACT

The present invention comprises a new class of compounds useful for the modulation of Beta-secretase enzyme activity and for the treatment of Beta-secretase mediated diseases, including Alzheimer's disease (AD) and other related conditions. In one embodiment, the compounds have a general Formula I

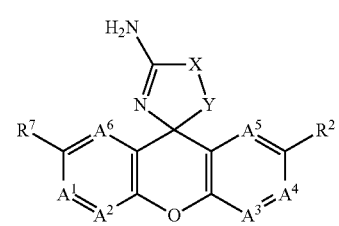

wherein $A^1$, $A^2$, $A^3$, $A^4$, $A^5$, $A^6$, $R^2$, $R^7$, X and Y of Formula I are defined herein. The invention also includes use of these compounds in pharmaceutical compositions for treatment, prophylactic or therapeutic, of disorders and conditions related to the activity of beta-secretase protein. Such disorders include, for example, Alzheimer's Disease, cognitive deficits, cognitive impairment, schizophrenia and other central nervous system conditions related to and/or caused by the formation and/or deposition of plaque on the brain. The invention also comprises further embodiments of Formula I, intermediates and processes useful for the preparation of compounds of Formula I.

18 Claims, No Drawings

(51) Int. Cl.
*A61K 31/506* (2006.01)
*A61K 31/4439* (2006.01)
*A61K 31/5377* (2006.01)
*C07D 221/20* (2006.01)
*C07D 235/02* (2006.01)
*C07D 263/08* (2006.01)
*C07D 295/135* (2006.01)
*C07D 491/10* (2006.01)
*C07D 498/10* (2006.01)

(56) References Cited

U.S. PATENT DOCUMENTS

| | | | |
|---|---|---|---|
| 5,441,870 | A | 8/1995 | Seubert et al. |
| 5,712,130 | A | 1/1998 | Hajko et al. |
| 5,942,400 | A | 8/1999 | Anderson et al. |
| 6,835,565 | B1 | 12/2004 | Gurney et al. |
| 6,864,290 | B2 | 3/2005 | Schostarez et al. |
| 6,962,934 | B2 | 11/2005 | Warpehoski et al. |
| 6,982,264 | B2 | 1/2006 | John et al. |
| 6,992,103 | B2 | 1/2006 | Faller et al. |
| 7,034,182 | B2 | 4/2006 | Fang et al. |
| 7,067,542 | B2 | 6/2006 | Schostarez et al. |
| 7,074,799 | B2 | 7/2006 | Bakthavatchalam et al. |
| 7,109,217 | B2 | 9/2006 | Coburn et al. |
| 7,115,652 | B2 | 10/2006 | Yang |
| 7,132,568 | B2 | 11/2006 | Yang et al. |
| 7,176,242 | B2 | 2/2007 | John et al. |
| 7,223,774 | B2 | 5/2007 | Aquino et al. |
| 7,244,725 | B2 | 7/2007 | John et al. |
| 7,244,755 | B2 | 7/2007 | Fisher et al. |
| 7,253,198 | B2 | 8/2007 | Demont et al. |
| 7,291,620 | B2 | 11/2007 | Coburn et al. |
| 7,312,360 | B2 | 12/2007 | TenBrink et al. |
| 7,348,448 | B2 | 3/2008 | Nantermet et al. |
| 7,371,853 | B2 | 5/2008 | Coburn et al. |
| 7,592,348 | B2 | 9/2009 | Zhu et al. |
| 2003/0109559 | A1 | 6/2003 | Gailunas et al. |
| 2005/0038019 | A1 | 2/2005 | Beck |
| 2005/0054690 | A1 | 3/2005 | Aquino et al. |
| 2005/0282825 | A1 | 12/2005 | Malamas et al. |
| 2006/0111370 | A1 | 5/2006 | Zhu et al. |
| 2006/0211740 | A1 | 9/2006 | Demont et al. |
| 2006/0241133 | A1 | 10/2006 | Shearman et al. |
| 2006/0287297 | A1 | 12/2006 | DeCorte et al. |
| 2007/0004786 | A1 | 1/2007 | Malamas et al. |
| 2007/0027199 | A1 | 2/2007 | Malamas et al. |
| 2007/0072925 | A1 | 3/2007 | Malamas et al. |
| 2007/0203116 | A1 | 8/2007 | Quagliato et al. |
| 2007/0287692 | A1 | 12/2007 | Wu et al. |
| 2008/0200445 | A1 | 8/2008 | Zhu et al. |
| 2009/0082560 | A1 | 3/2009 | Kobayashi et al. |
| 2009/0209529 | A1 | 8/2009 | Andreini et al. |
| 2009/0209755 | A1 | 8/2009 | Suzuki et al. |
| 2009/0306047 | A1 | 12/2009 | Zhu et al. |
| 2010/0075957 | A1 | 3/2010 | Tamura et al. |
| 2010/0087429 | A1* | 4/2010 | White et al. ............... 514/232.8 |
| 2010/0160290 | A1 | 6/2010 | Kobayashi et al. |

FOREIGN PATENT DOCUMENTS

| | | | |
|---|---|---|---|
| WO | 01/70671 | A2 | 9/2001 |
| WO | 03/002518 | A1 | 1/2003 |
| WO | 03/030886 | A2 | 4/2003 |
| WO | 04/000821 | A1 | 12/2003 |
| WO | 2004/099376 | A2 | 11/2004 |
| WO | 2005058311 | A1 | 6/2005 |
| WO | 2005097767 | A1 | 10/2005 |
| WO | 2006041404 | A1 | 4/2006 |
| WO | 2006076284 | A2 | 7/2006 |
| WO | 2006138230 | A2 | 12/2006 |
| WO | 2006138265 | A2 | 12/2006 |
| WO | 2007011810 | A1 | 1/2007 |
| WO | 2007011833 | A1 | 1/2007 |
| WO | 2007038271 | A1 | 4/2007 |
| WO | 2007114771 | A1 | 10/2007 |
| WO | 2007120096 | A1 | 10/2007 |
| WO | 2007145571 | A1 | 12/2007 |
| WO | 2007149033 | A1 | 12/2007 |
| WO | 2008054698 | A1 | 5/2008 |
| WO | 2008076045 | A1 | 6/2008 |
| WO | 2008076046 | A1 | 6/2008 |
| WO | 2008092785 | A1 | 8/2008 |
| WO | 2008103351 | A2 | 8/2008 |
| WO | 2008118379 | A2 | 10/2008 |
| WO | 2008150217 | A1 | 12/2008 |
| WO | 2009131974 | A1 | 10/2009 |
| WO | 2009131975 | A1 | 10/2009 |
| WO | 2009134617 | A1 | 11/2009 |
| WO | 2010010014 | A1 | 1/2010 |
| WO | 2010030954 | A1 | 3/2010 |
| WO | WO 2010/030954 | * | 3/2010 ........... C07D 498/10 |

OTHER PUBLICATIONS

Joachim et al., *Alz. Dis. Assoc. Dis.*, 6:7-34 (1992).
Selkoe, Neuron, 6:487 (1991).
Seubert et al., Nature, 359:325-327 (1992).
Citron, Trends in Pharmacological Sciences, 25(2):92-97 (2004).
Nature Medicine (Jun. 22, 2008).
Nature, 402:537-554 (1999) (p. 510).
Sabbagh, M. et al., Alz. Dis. Rev. 3:1-19 (1997).
Cole, S.L., Vasser, R., Molecular Degeneration 2:22, 2007.
Luo et al., Nature Neuroscience, 4:231-232 (2001).
Bioorganic & Medicinal Chemistry Letters 20 (2010) 2068-2073.
J. Med. Chem. 2009.
Alzheimer's Research & Therapy 2009.
Expert Opin. Emerging Drugs (2008) 13(2):255-271.
J. Med. Chem. 2008, 51, 6259-6262.
Chem. Soc. Rev., 2009, 38, 2698-2715.
Sabbagh_ClinicalDev_2009.
J. Neurosci., Oct. 14, 2009 • 29(41):12787-12794.
Zhou_et_al_ARKIVOC_2010_vi_84-88.
Nowak_Bioorganic_Medicinal_Chemistry_Letters_2009.
Malamas _Bioorganic_Medicinal_Chemistry_Letters_2009.
Zhou_Bioorganic_Medicinal_Chemistry_Letters_2010.
Malamas_JMedChem_2009.

* cited by examiner

SPIRO-TETRACYCLIC RING COMPOUNDS AS BETA-SECRETASE MODULATORS AND METHODS OF USE

RELATED APPLICATIONS

This application claims the benefit of U.S. Provisional Application No. 61/314,129, filed Mar. 15, 2010, which specification is hereby incorporated here in by reference in its entirety.

FIELD OF THE INVENTION

The invention relates generally to pharmaceutically active compounds, pharmaceutical compositions and methods of use thereof, to treat Beta-Secretase mediated diseases and conditions, including, without limitation, Alzheimer's disease, plaque formation on the brain and related disorders.

BACKGROUND OF THE INVENTION

Alzheimer's disease (AD) affects greater than 12 million aging people worldwide. AD accounts for the majority of dementia clinically diagnosed after the age of 60. AD is generally characterized by the progressive decline of memory, reasoning, judgement and orientation. As the disease progresses, motor, sensory, and vocal abilities are affected until there is global impairment of multiple cognitive functions. The loss of cognitive function occurs gradually, typically leading to a diminished cognition of self, family and friends. Patients with severe cognitive impairment and/or diagnosed as end-stage AD are generally bedridden, incontinent, and dependent on custodial care. The AD patient eventually dies in about nine to ten years, on average, after initial diagnosis. Due to the incapacitating, generally humiliating and ultimately fatal effects of AD, there is a need to effectively treat AD upon diagnosis.

AD is characterized by two major physiological changes in the brain. The first change, beta amyloid plaque formation, supports the "amyloid cascade hypothesis" which conveys the thought that AD is caused by the formation of characteristic beta amyloid peptide (A-beta), or A-beta fragments thereof, deposits in the brain (commonly referred to as beta amyloid "plaques" or "plaque deposits") and in cerebral blood vessels (beta amyloid angiopathy). A wealth of evidence suggests that beta-amyloid and accompanying amyloid plaque formation is central to the pathophysiology of AD and is likely to play an early role in this intractable neurodegenerative disorder. The second change in AD is the formation of intraneuronal tangles, consisting of an aggregate form of the protein tau. Besides being found in patients with AD, intraneuronal tangles are also found in other dementia-inducing disorders. Joachim et al., Alz. Dis. Assoc. Dis., 6:7-34 (1992).

Several lines of evidence indicate that progressive cerebral deposition of A-beta plays a seminal role in the pathogenisis of AD and can precede cognitive symptoms by years or even decades. Selkoe, Neuron, 6:487 (1991). Release of A-beta from neuronal cells grown in culture and the presence of A-beta in cerebrospinal fluid (CSF) of both normal individuals and AD patients has been demonstrated. Seubert et al., Nature, 359:325-327 (1992). Autopsies of AD patients have revealed large numbers of lesions comprising these 2 factors in areas of the human brain believed to be important for memory and cognition.

Smaller numbers of these lesions in a more restricted anatomical distribution are found in the brains of most aged humans who do not have clinical AD. Amyloid containing plaques and vascular amyloid angiopathy were also found in the brains of individuals with Down's Syndrome, Hereditary Cerebral Hemorrhage with Amyloidosis of the Dutch-type (HCHWA-D), and other neurodegenerative disorders.

It has been hypothesized that A-beta formation is a causative precursor or factor in the development of AD. More specifically, deposition of A-beta in areas of the brain responsible for cognitive factors is believed to be a major factor in the development of AD. Beta amyloid plaques are primarily composed of amyloid beta peptide (A-beta peptide). A-beta peptide is derived from the proteolytic cleavage of a large transmembrane amyloid precursor protein (APP), and is a peptide ranging in about 39-42 amino acid residues. A-beta 42 (42 amino acids long) is thought to be the major component of these plaque deposits in the brains of Alzheimer's Disease patients. Citron, Trends in Pharmacological Sciences, 25(2):92-97 (2004).

Similar plaques appear in some variants of Lewy body dementia and in inclusion body myositis, a muscle disease. Aβ also forms aggregates coating cerebral blood vessels in cerebral amyloid angiopathy. These plaques are composed of a tangle of regularly ordered fibrillar aggregates called amyloid fibers, a protein fold shared by other peptides such as prions associated with protein misfolding diseases. Research on laboratory rats suggest that the two-molecule, soluble form of the peptide is a causative agent in the development of Alzheimer's and that the two-molecule form is the smallest synaptotoxic species of soluble amyloid beta oligomer. Shankar, G. M., Nature Medicine (Jun. 22, 2008) online doi 10:1038 nm 1782.

Several aspartyl proteases are thought to be involved in the processing or cleavage of APP, resulting in the formation of A-beta peptide. Beta secretase (BACE, also commonly referred to as memapsin) is thought to first cleave APP to generate two fragments: (1) a first N-terminus fragment (beta APP) and (2) a second C-99 fragment, which is subsequently cleaved by gamma secretase to generate the A-beta peptide. APP has also found to be cleaved by alpha-secretase to produce alpha-sAPP, a secreted form of APP that does not result in beta-amyloid plaque formation. This alternate pathway precludes the formation of A-beta peptide. A description of the proteolytic processing fragments of APP is found, for example, in U.S. Pat. Nos. 5,441,870, 5,712,130 and 5,942,400.

BACE is an aspartyl protease enzyme comprising 501 amino acids and responsible for processing APP at the beta-secretase specific cleavage site. BACE is present in two forms, BACE 1 and BACE 2, designated as such depending upon the specific cleavage site of APP. Beta secretase is described in Sinha et al., Nature, 402:537-554 (1999) (p 510) and PCT application WO 2000/17369. It has been proposed that A-beta peptide accumulates as a result of APP processing by BACE. Moreover, in vivo processing of APP at the beta secretase cleavage site is thought to be a rate-limiting step in A-beta production. Sabbagh, M. et al., Alz. Dis. Rev. 3:1-19 (1997). Thus, inhibition of the BACE enzyme activity is desirable for the treatment of AD.

Studies have shown that the inhibition of BACE may be linked to the treatment of AD. The BACE enzyme is essential for the generation of beta-amyloid or A-beta. BACE knockout mice do not produce beta-amyloid and are free from Alzheimer's associated pathologies including neuronal loss and certain memory deficits. Cole, S. L., Vasser, R., Molecular Degeneration 2:22, 2007. When crossed with transgenic mice that over express APP, the progeny of BACE deficient mice show reduced amounts of A-beta in brain extracts as compares with control animals (Luo et al., Nature Neuroscience, 4:231-232 (2001)). The fact that BACE initiates the formation of beta-amyloid, and the observation that BACE levels are elevated in this disease provide direct and compelling reasons to develop therapies directed at BACE inhibition thus reducing beta-amyloid and its associated toxicities. To this end, inhibition of beta secretase activity and a corresponding reduction of A-beta in the brain should provide a therapeutic method for treating AD and other beta amyloid or plaque related disorders.

Several approaches have been taken to potentially treat AD and plaque-related disorders. One approach has been to attempt to reduce the formation of plaque on the brain, by inhibiting or reducing the activity of BACE. For example, each of the following PCT publications: WO 09/091,016, WO 08/108,378, WO 09/134,617, WO 05/097767, WO 08/092,785, WO 06/138265, WO 08/103,351, WO 06/138230, WO 08/200,445, WO 06/111370, WO 07/287,692, WO 05/058311, EP 01942105, WO 08/133,273, WO 08/133,274, WO 07/049,532, US20070027199, WO 07/038,271, US20070072925, US20070203116, WO 08/118,379, WO 06/076284, US20070004786, WO 06/083760, WO 07/011,810, WO 07/011,833 and WO 08/054,698, describe inhibitors of BACE, useful for treating AD and other beta-secretase mediated disorders.

BRIEF DESCRIPTION OF THE INVENTION

The present invention provides a new class of compounds useful for the modulation of beta secretase activity. To that end, the compounds of the invention are useful for the regulation or reduction of the formation of A-beta peptide and, consequently, the regulation and/or reduction of beta amyloid plaque formation on the brain. Accordingly, the compounds are useful for the treatment of Alzheimer's disease and other beta secretase and/or plaque mediated disorders. For example, the compounds are useful for the prophylaxis and/or treatment, acute and/or chronic, of AD and other diseases or conditions involving the deposition or accumulation of beta amyloid peptide, and formation of plaque, on the brain.

The compounds provided by the invention, including stereoisomers, tautomers, solvates, pharmaceutically acceptable salts, derivatives or prodrugs thereof, are generally defined by Formula I

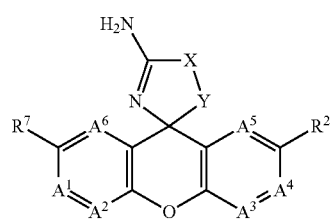

wherein $A^1$, $A^2$, $A^3$, $A^4$, $A^5$, $A^6$, $R^2$, $R^7$, X and Y of Formula I are described below. The invention also provides procedures for making compounds of sub-Formulas thereof, as well as intermediates useful in such procedures.

The invention further provides pharmaceutical compositions, which comprise one or more compounds of the invention, methods for the treatment of beta secretase mediated diseases, such as AD, using the compounds and compositions of the invention. For example, and in one embodiment, the invention provides a pharmaceutical composition comprising an effective dosage amount of a compound of Formula I in association with at least one pharmaceutically acceptable excipient.

The foregoing merely summarizes certain aspects of the invention and is not intended, nor should it be construed, as limiting the invention in any way. All patents and other publications recited herein are hereby incorporated by reference in their entirety.

DETAILED DESCRIPTION OF THE INVENTION

In one embodiment of the invention, the compounds, including stereoisomers, tautomers, solvates, pharmaceutically acceptable salts thereof, are generally defined by the compound of Formula I:

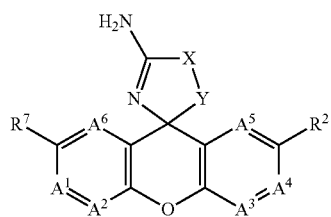

wherein
$A^1$ is CH, CF or N;
$A^2$ is CH, CF or N;
$A^3$ is CH, CF, OH, $OCH_3$, $OCF_3$ or N;
$A^4$ is CH, CF, OH, $OCH_3$, $OCF_3$ or N;
$A^5$ is CH, $CR^1$ or N;
$A^6$ is CH, CF or N, provided that no more than one of $A^1$, $A^2$, $A^3$, $A^4$, $A^5$ and $A^6$ is N;
$R^1$ is F, Br or

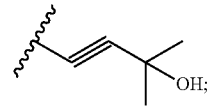 [SMILES: *C#CC(C)(C)O]

$R^2$ is Cl, Br, CN, $C_{1-6}$-alkyl, $C_{2-6}$alkenyl, $C_{2-6}$alkynyl, CN, —$OC_{1-6}$alkyl, —$SC_{1-6}$alkyl, —$NHC_{1-6}$alkyl, —$N(C_{1-6}$alkyl$)_2$, —NH-phenyl, —NH-benzyl, phenyl, pyridyl, pyrimidyl, pyrazinyl, pyridazinyl, pyrazolyl, imidazolyl, oxazolyl, isoxazolyl, thiazolyl, isothiazolyl, diazolyl, thiadiazolyl, thienyl, pyranyl, dihydropyranyl, tetrahydropyranyl, furanyl, dihydrofuranyl, tetrahydrofuranyl, pyrrolidinyl, piperidinyl, piperazinyl, morpholinyl, azetidinyl, 8-oxo-3-aza-bicyclo[3.2.1]oct-3-yl, aza-bicyclo[2.2.1]hept-5-yl, 2-oxo-7-aza-[3,5]-spironon-7-yl, cyclohexyl or —Si(CH$_3$)$_3$, wherein the $C_{1-6}$-alkyl, $C_{2-6}$alkenyl, $C_{2-6}$alkynyl, —$OC_{1-6}$alkyl, —$SC_{1-6}$alkyl, —$NHC_{1-6}$alkyl, —$N(C_{1-6}$alkyl$)_2$, —NH-phenyl, —NH-benzyl, phenyl, pyridyl, pyrimidyl, pyrazinyl, pyridazinyl, pyrazolyl, isoxazolyl, thiazolyl, pyranyl, dihydropyranyl, tetrahydropyranyl, furanyl, dihydrofuranyl, tetrahydrofuranyl, pyrrolidinyl, piperidinyl, piperazinyl, morpholinyl, azetidinyl, 8-oxo-3-aza-bicyclo[3.2.1]oct-3-yl, aza-bicyclo[2.2.1]hept-5-yl, 2-oxo-7-aza-[3,5]-spironon-7-yl and cyclohexyl are optionally substituted, independently, with 1-5 substituents of $R^8$;

$R^7$ is $C_{1-6}$-alkyl, $C_{2-4}$alkenyl, $C_{2-4}$alkynyl, CN, —$OC_{1-6}$alkyl, —$SC_{1-6}$alkyl, —$NHC_{1-6}$alkyl, —$N(C_{1-3}$alkyl$)_2$, —NH-phenyl, —NH-benzyl, —O-phenyl or ring selected from the group consisting of phenyl, pyridyl, pyrimidyl, pyrazinyl, pyridazinyl, pyrazolyl, isoxazolyl, thiazolyl, pyranyl, dihydropyranyl, tetrahydropyranyl, furanyl, dihydrofuranyl, tetrahydrofuranyl, pyrrolidinyl, piperidinyl, piperazinyl, morpholinyl, azetidinyl, 8-oxo-3-aza-bicyclo [3.2.1]oct-3-yl, aza-bicyclo[2.2.1]hept-5-yl, 2-oxo-7-aza-[3,5]-spironon-7-yl and cyclohexyl, wherein the $C_{1-6}$-alkyl, $C_{2-4}$alkenyl, $C_{2-4}$alkynyl, —$OC_{1-6}$alkyl, —$SC_{1-6}$alkyl, —$NHC_{1-6}$alkyl, —$N(C_{1-3}$alkyl$)_2$, —NH-phenyl, —NH-benzyl, —O-phenyl and ring are optionally substituted, independently, with 1-5 substituents of $R^8$;

each $R^8$, independently, is halo, haloalkyl, CN, OH, $NO_2$, $NH_2$, acetyl, —C(O)$NHCH_3$, oxo, $C_{1-6}$alkyl, $C_{2-6}$alkenyl, $C_{2-6}$alkynyl, $C_{3-6}$cycloalkyl, $C_{1-6}$alkylamino-, $C_{1-6}$dialkylamino-, $C_{1-6}$alkoxyl, $C_{1-6}$thioalkoxyl, or a ring selected from the group consisting of pyridyl, pyrimidyl, phenyl, morpholinyl, pyrazolyl, isoxazolyl, dihydropyranyl, pyrrolidinyl, piperazinyl, oxetanyl and dioxolyl, wherein each of the $C_{1-6}$alkyl, $C_{2-6}$alkenyl, $C_{2-6}$alkynyl, $C_{3-6}$cycloalkyl, $C_{1-6}$alkylamino-, $C_{1-6}$dialkylamino-, $C_{1-6}$alkoxyl, $C_{1-6}$thioalkoxyl and ring is optionally substituted independently with 1-5 substituents of F, Cl, Br, CN, $CF_3$, $OCF_3$, $NO_2$, $NH_2$, OH, oxo, methyl, methoxyl, ethyl, ethoxyl, propyl, propoxyl, isopropyl, isopropoxyl, cyclopropyl, cyclopropylmethoxyl, butyl, butoxyl, isobutoxyl, tert-butoxyl, isobutyl, sec-butyl, tert-butyl, $C_{1-3}$alkylamino-, $C_{1-3}$dialkylamino-, $C_{1-3}$thioalkoxyl or oxetanyl;

alternatively, two adjacent $R^8$ substituents together with the same atom to which they are attached form a 3-6 membered spirocyclic ring including 0-3 heteroatoms selected from N, O and S, the spirocyclic ring optionally substituted with 1-3 substituents of 1-5 substituents of F, Cl, CN, $CF_3$, $OCF_3$, $NO_2$, OH, oxo, methyl, methoxyl, ethyl, ethoxyl, propyl, propoxyl, isopropyl, isopropoxyl, cyclopropyl, cyclopropylmethoxyl, butyl, butoxyl, isobutoxyl, tert-butoxyl, isobutyl, sec-butyl, tert-butyl, $C_{1-3}$alkylamino-, $C_{1-3}$dialkylamino-, $C_{1-3}$thioalkoxyl or oxetanyl;

X is O, S or $CF_2$; and

Y is $CR^9R^9$ wherein each $R^9$, independently, is H, F, $C_{1-4}$alkyl or —$CH_2OCH_3$.

In one embodiment of the invention, the compounds, including stereoisomers, tautomers, solvates, pharmaceutically acceptable salts thereof, are generally defined by the compound of Formula I-A:

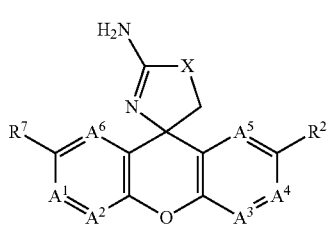

I-A wherein $A^1$ is CH, CF or N;

$A^2$ is CH, CF or N;

$A^3$ is CH, CF, OH, $OCH_3$ or N;

$A^4$ is CH, CF or N;

$A^5$ is CH, $CR^1$ or N;

$A^6$ is CH, CF or N, provided that no more than one of $A^1$, $A^2$, $A^3$, $A^4$, $A^5$ and $A^6$ is N;

$R^1$ is F, Br or

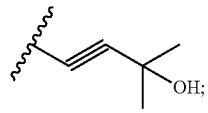 [SMILES: *C#CC(C)(C)O]

$R^2$ is Cl, Br, $C_{1-6}$-alkyl, $C_{2-4}$alkenyl, $C_{2-4}$alkynyl, CN, —$OC_{1-6}$alkyl, —$SC_{1-6}$alkyl, —$NHC_{1-6}$alkyl, —$N(C_{1-3}$alkyl$)_2$, —NH-phenyl, —NH-benzyl, phenyl, pyridyl, pyrimidyl, pyrazinyl, pyridazinyl, pyrazolyl, isoxazolyl, thiazolyl, pyranyl, dihydropyranyl, tetrahydropyranyl, furanyl, dihydrofuranyl, tetrahydrofuranyl, pyrrolidinyl, piperidinyl, piperazinyl, morpholinyl, azetidinyl, 8-oxo-3-aza-bicyclo [3.2.1]oct-3-yl, aza-bicyclo[2.2.1]hept-5-yl, 2-oxo-7-aza-[3,5]-spironon-7-yl, cyclohexyl or —$Si(CH_3)_3$, wherein the $C_{1-6}$-alkyl, $C_{2-4}$alkenyl, $C_{2-4}$alkynyl, —$OC_{1-6}$alkyl, —$SC_{1-6}$alkyl, —$NHC_{1-6}$alkyl, —$N(C_{1-3}$alkyl$)_2$, —NH-phenyl, —NH-benzyl, phenyl, pyridyl, pyrimidyl, pyrazinyl, pyridazinyl, pyrazolyl, isoxazolyl, thiazolyl, pyranyl, dihydropyranyl, tetrahydropyranyl, furanyl, dihydrofuranyl, tetrahydrofuranyl, pyrrolidinyl, piperidinyl, piperazinyl, morpholinyl, azetidinyl, 8-oxo-3-aza-bicyclo[3.2.1]oct-3-yl, aza-bicyclo[2.2.1]hept-5-yl, 2-oxo-7-aza-[3,5]-spironon-7-yl and cyclohexyl are optionally substituted, independently, with 1-3 substituents of $R^8$;

$R^7$ is $C_{1-6}$-alkyl, $C_{2-4}$alkenyl, $C_{2-4}$alkynyl, CN, —$OC_{1-6}$alkyl, —$SC_{1-6}$alkyl, —$NHC_{1-6}$alkyl, —$N(C_{1-3}$alkyl$)_2$, —NH-phenyl, —NH-benzyl, phenyl, pyridyl, pyrimidyl, pyrazinyl, pyridazinyl, pyrazolyl, isoxazolyl, thiazolyl, pyranyl, dihydropyranyl, tetrahydropyranyl, furanyl, dihydrofuranyl, tetrahydrofuranyl, pyrrolidinyl, piperidinyl, piperazinyl, morpholinyl, azetidinyl, 8-oxo-3-aza-bicyclo [3.2.1]oct-3-yl, aza-bicyclo[2.2.1]hept-5-yl, 2-oxo-7-aza-[3,5]-spironon-7-yl or cyclohexyl, wherein the $C_{1-6}$-alkyl, $C_{2-4}$alkenyl, $C_{2-4}$alkynyl, —$OC_{1-6}$alkyl, —$SC_{1-6}$alkyl, —$NHC_{1-6}$alkyl, —$N(C_{1-3}$alkyl$)_2$, —NH-phenyl, —NH-benzyl, phenyl, pyridyl, pyrimidyl, pyrazinyl, pyridazinyl, pyrazolyl, isoxazolyl, thiazolyl, pyranyl, dihydropyranyl, tetrahydropyranyl, furanyl, dihydrofuranyl, tetrahydrofuranyl, pyrrolidinyl, piperidinyl, piperazinyl, morpholinyl, azetidinyl, 8-oxo-3-aza-bicyclo[3.2.1]oct-3-yl, aza-bicyclo[2.2.1] hept-5-yl, 2-oxo-7-aza-[3,5]-spironon-7-yl and cyclohexyl are optionally substituted, independently, with 1-3 substituents of $R^8$;

each $R^8$, independently, is halo, haloalkyl, CN, OH, $NO_2$, $NH_2$, acetyl, —C(O)$NHCH_3$, oxo, $C_{1-6}$alkyl, $C_{2-6}$alkenyl, $C_{2-6}$alkynyl, $C_{3-6}$cycloalkyl, $C_{1-6}$alkylamino-, $C_{1-6}$dialkylamino-, $C_{1-6}$alkoxyl, $C_{1-6}$thioalkoxyl, morpholinyl, pyrazolyl, isoxazolyl, dihydropyranyl, pyrrolidinyl, piperazinyl, oxetanyl or dioxolyl, wherein each of the $C_{1-6}$alkyl, $C_{2-6}$alkenyl, $C_{2-6}$alkynyl, $C_{3-6}$cycloalkyl, $C_{1-6}$alkylamino-, $C_{1-6}$dialkylamino-, $C_{1-6}$alkoxyl, $C_{1-6}$thioalkoxyl, morpholinyl, pyrazolyl, isoxazolyl, dihydropyranyl, pyrrolidinyl, oxetanyl or dioxolyl, is optionally substituted independently with 1-5 substituents of F, Cl, CN, $NO_2$, $NH_2$, OH, oxo, methyl, methoxyl, ethyl, ethoxyl, propyl, propoxyl, isopropyl, isopropoxyl, cyclopropyl, cyclopropylmethoxyl, butyl, butoxyl, isobutoxyl, tert-butoxyl, isobutyl, sec-butyl, tert-butyl, $C_{1-3}$alkylamino-, $C_{1-3}$dialkylamino-, $C_{1-3}$thioalkoxyl, or oxetanyl; and X is O, S or $CF_2$.

In another embodiment of the present invention, the compounds, and solvates, tautomers, stereoisomers and pharmaceutically acceptable salts thereof, are defined by Formula I-B

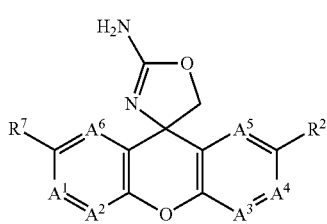

wherein each of $A^1$, $A^2$, $A^3$, $A^4$, $A^5$, $A^6$, $R^2$ and $R^7$ is as defined above.

In another embodiment of the present invention, the compounds, and solvates, tautomers, stereoisomers and pharmaceutically acceptable salts thereof, are defined by Formula I-B

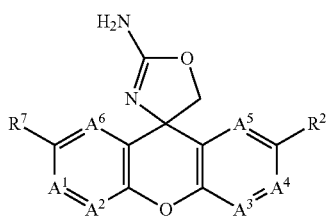

wherein
$A^1$ is CH or CF;
$A^2$ is CH or CF;
$A^3$ is CH, CF or N;
$A^4$ is CH, CF or N;
$A^5$ is CH;
$A^6$ is CH or CF, provided that no more than one of $A^3$ and $A^4$ is N;
$R^2$ is Cl, Br, CN, $C_{1-6}$-alkyl, $C_{2-6}$alkenyl, $C_{2-6}$alkynyl, CN, —$OC_{1-6}$alkyl, —$SC_{1-6}$alkyl, —$NHC_{1-6}$alkyl, —$N(C_{1-6}$alkyl$)_2$, —NH-phenyl, —NH-benzyl, phenyl, pyridyl, pyrimidyl, pyrazinyl, pyridazinyl, pyrazolyl, imidazolyl, oxazolyl, isoxazolyl, thiazolyl, isothiazolyl, diazolyl, thiadiazolyl, thienyl, pyranyl, dihydropyranyl, tetrahydropyranyl, furanyl, dihydrofuranyl, tetrahydrofuranyl, pyrrolidinyl, piperidinyl, piperazinyl, morpholinyl, azetidinyl, 8-oxo-3-aza-bicyclo[3.2.1]oct-3-yl, aza-bicyclo[2.2.1]hept-5-yl, 2-oxo-7-aza-[3,5]-spironon-7-yl, cyclohexyl or —$Si(CH_3)_3$, wherein the $C_{1-6}$-alkyl, $C_{2-6}$alkenyl, $C_{2-6}$alkynyl, —$OC_{1-6}$alkyl, —$SC_{1-6}$alkyl, —$NHC_{1-6}$alkyl, —$N(C_{1-6}$alkyl$)_2$, —NH-phenyl, —NH-benzyl, phenyl, pyridyl, pyrimidyl, pyrazinyl, pyridazinyl, pyrazolyl, isoxazolyl, thiazolyl, pyranyl, dihydropyranyl, tetrahydropyranyl, furanyl, dihydrofuranyl, tetrahydrofuranyl, pyrrolidinyl, piperidinyl, piperazinyl, morpholinyl, azetidinyl, 8-oxo-3-aza-bicyclo[3.2.1]oct-3-yl, aza-bicyclo[2.2.1]hept-5-yl, 2-oxo-7-aza-[3,5]-spironon-7-yl and cyclohexyl are optionally substituted, independently, with 1-5 substituents of $R^8$;
$R^7$ is $C_{1-6}$-alkyl, $C_{2-4}$alkenyl, $C_{2-4}$alkynyl, CN, —$OC_{1-6}$alkyl, —$SC_{1-6}$alkyl, —$NHC_{1-6}$alkyl, —$N(C_{1-3}$alkyl$)_2$, —NH-phenyl, —NH-benzyl, —O-phenyl or ring selected from the group consisting of phenyl, pyridyl, pyrimidyl, pyrazinyl, pyridazinyl, pyrazolyl, isoxazolyl, thiazolyl, pyranyl, dihydropyranyl, tetrahydropyranyl, furanyl, dihydrofuranyl, tetrahydrofuranyl, pyrrolidinyl, piperidinyl, piperazinyl, morpholinyl, azetidinyl, 8-oxo-3-aza-bicyclo[3.2.1]oct-3-yl, aza-bicyclo[2.2.1]hept-5-yl, 2-oxo-7-aza-[3,5]-spironon-7-yl and cyclohexyl, wherein the $C_{1-6}$-alkyl, $C_{2-4}$alkenyl, $C_{2-4}$alkynyl, —$OC_{1-6}$alkyl, —$SC_{1-6}$alkyl, —$NHC_{1-6}$alkyl, —$N(C_{1-3}$alkyl$)_2$, —NH-phenyl, —NH-benzyl, —O-phenyl and ring are optionally substituted, independently, with 1-5 substituents of $R^8$; and each $R^8$, independently, is halo, haloalkyl, CN, OH, $NO_2$, $NH_2$, acetyl, —C(O)$NHCH_3$, oxo, $C_{1-6}$alkyl, $C_{2-6}$alkenyl, $C_{2-6}$alkynyl, $C_{3-6}$cycloalkyl, $C_{1-6}$alkylamino-, $C_{1-6}$dialkylamino-, $C_{1-6}$alkoxyl, $C_{1-6}$thioalkoxyl, or a ring selected from the group consisting of pyridyl, pyrimidyl, phenyl, morpholinyl, pyrazolyl, isoxazolyl, dihydropyranyl, pyrrolidinyl, piperazinyl, oxetanyl and dioxolyl, wherein each of the $C_{1-6}$alkyl, $C_{2-6}$alkenyl, $C_{2-6}$alkynyl, $C_{3-6}$cycloalkyl, $C_{1-6}$alkylamino-, $C_{1-6}$dialkylamino-, $C_{1-6}$alkoxyl, $C_{1-6}$thioalkoxyl and ring is optionally substituted independently with 1-5 substituents of F, Cl, Br, CN, $CF_3$, $OCF_3$, $NO_2$, $NH_2$, OH, oxo, methyl, methoxyl, ethyl, ethoxyl, propyl, propoxyl, isopropyl, isopropoxyl, cyclopropyl, cyclopropylmethoxyl, butyl, butoxyl, isobutoxyl, tert-butoxyl, isobutyl, sec-butyl, tert-butyl, $C_{1-3}$alkylamino-, $C_{1-3}$dialkylamino-, $C_{1-3}$thioalkoxyl or oxetanyl;

alternatively, two adjacent $R^8$ substituents together with the same atom to which they are attached form a 3-6 membered spirocyclic ring including 0-3 heteroatoms selected from N, O and S, the spirocyclic ring optionally substituted with 1-3 substituents of 1-5 substituents of F, Cl, CN, $CF_3$, $OCF_3$, $NO_2$, OH, oxo, methyl, methoxyl, ethyl, ethoxyl, propyl, propoxyl, isopropyl, isopropoxyl, cyclopropyl, cyclopropylmethoxyl, butyl, butoxyl, isobutoxyl, tert-butoxyl, isobutyl, sec-butyl, tert-butyl, $C_{1-3}$alkylamino-, $C_{1-3}$dialkylamino-, $C_{1-3}$thioalkoxyl or oxetanyl.

In another embodiment of the present invention, the compounds, and solvates, tautomers, stereoisomers and pharmaceutically acceptable salts thereof, are defined by Formula I-B, wherein
$A^1$ is CH or CF;
$A^2$ is CH;
$A^3$ is CH, CF or N;
$A^4$ is CH, CF or N;
$A^5$ is CH;
$A^6$ is CH; provided that no more than one of $A^3$ and $A^4$ is N;
$R^2$ is $C_{3-6}$-alkyl, $C_{2-4}$alkynyl, —$OC_{1-6}$alkyl, —$SC_{1-6}$alkyl, phenyl, pyridyl, pyrimidyl, pyrazinyl, pyridazinyl, dihydropyranyl, tetrahydropyranyl, pyrrolidinyl, piperidinyl, morpholinyl or 8-oxo-3-aza-bicyclo[3.2.1]oct-3-yl, wherein the $C_{3-6}$-alkyl, $C_{2-4}$alkynyl, —$OC_{1-6}$alkyl, —$SC_{1-6}$alkyl, phenyl, pyridyl, pyrimidyl, pyrazinyl, pyridazinyl, dihydropyranyl, tetrahydropyranyl, pyrrolidinyl, piperidinyl, morpholinyl and 8-oxo-3-aza-bicyclo[3.2.1]oct-3-yl, are optionally substituted, independently, with 1-3 substituents of $R^8$;
$R^7$ is $C_{2-4}$alkynyl, —$OC_{1-6}$alkyl, phenyl, pyridyl, pyrimidyl, pyrazinyl or pyridazinyl, wherein the $C_{2-4}$alkynyl, —$OC_{1-6}$alkyl, pyridyl, pyrimidyl, pyrazinyl and pyridazinyl are optionally substituted, independently, with 1-3 substituents of $R^8$; and each $R^8$, independently, is F, $CF_3$, CN, $CH_3$, —$OCH_3$, —$SCH_3$, —$NHCH_3$, oxetanyl or $C_{2-3}$alkynyl.

In another embodiment of the invention, the compounds, including stereoisomers, tautomers, solvates, pharmaceutically acceptable salts, are generally defined by Formula I-C

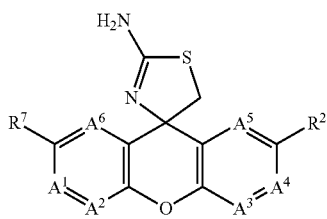

I-C wherein
$A^1$ is CH, CF or N;
$A^2$ is CH, CF or N;
$A^3$ is CH, CF, OH, $OCH_3$ or N;
$A^4$ is CH, CF or N;
$A^5$ is CH, $CR^1$ or N;
$A^6$ is CH, CF or N, provided that no more than one of $A^1$, $A^2$, $A^3$, $A^4$, $A^5$ and $A^6$ is N;
$R^1$ is F, Br or

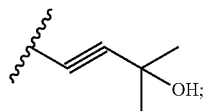 [SMILES: *C#CC(C)(C)O]

$R^2$ is Cl, Br, CN, $C_{1-6}$-alkyl, $C_{2-6}$alkenyl, $C_{2-6}$alkynyl, CN, $-OC_{1-6}$alkyl, $-SC_{1-6}$alkyl, $-NHC_{1-6}$alkyl, $-N(C_{1-6}$alkyl$)_2$, $-NH$-phenyl, $-NH$-benzyl, phenyl, pyridyl, pyrimidyl, pyrazinyl, pyridazinyl, pyrazolyl, imidazolyl, oxazolyl, isoxazolyl, thiazolyl, isothiazolyl, diazolyl, thiadiazolyl, thienyl, pyranyl, dihydropyranyl, tetrahydropyranyl, furanyl, dihydrofuranyl, tetrahydrofuranyl, pyrrolidinyl, piperidinyl, piperazinyl, morpholinyl, azetidinyl, 8-oxo-3-aza-bicyclo[3.2.1]oct-3-yl, aza-bicyclo[2.2.1]hept-5-yl, 2-oxo-7-aza-[3,5]-spironon-7-yl, cyclohexyl or $-Si(CH_3)_3$, wherein the $C_{1-6}$-alkyl, $C_{2-6}$alkenyl, $C_{2-6}$alkynyl, $-OC_{1-6}$alkyl, $-SC_{1-6}$alkyl, $-NHC_{1-6}$alkyl, $-N(C_{1-6}$alkyl$)_2$, $-NH$-phenyl, $-NH$-benzyl, phenyl, pyridyl, pyrimidyl, pyrazinyl, pyridazinyl, pyrazolyl, isoxazolyl, thiazolyl, pyranyl, dihydropyranyl, tetrahydropyranyl, furanyl, dihydrofuranyl, tetrahydrofuranyl, pyrrolidinyl, piperidinyl, piperazinyl, morpholinyl, azetidinyl, 8-oxo-3-aza-bicyclo[3.2.1]oct-3-yl, aza-bicyclo[2.2.1]hept-5-yl, 2-oxo-7-aza-[3,5]-spironon-7-yl and cyclohexyl are optionally substituted, independently, with 1-5 substituents of $R^8$;

$R^7$ is $C_{1-6}$-alkyl, $C_{2-4}$alkenyl, $C_{2-4}$alkynyl, CN, $-OC_{1-6}$alkyl, $-SC_{1-6}$alkyl, $-NHC_{1-6}$alkyl, $-N(C_{1-3}$alkyl$)_2$, $-NH$-phenyl, $-NH$-benzyl, $-O$-phenyl or ring selected from the group consisting of phenyl, pyridyl, pyrimidyl, pyrazinyl, pyridazinyl, pyrazolyl, isoxazolyl, thiazolyl, pyranyl, dihydropyranyl, tetrahydropyranyl, furanyl, dihydrofuranyl, tetrahydrofuranyl, pyrrolidinyl, piperidinyl, piperazinyl, morpholinyl, azetidinyl, 8-oxo-3-aza-bicyclo[3.2.1]oct-3-yl, aza-bicyclo[2.2.1]hept-5-yl, 2-oxo-7-aza-[3,5]-spironon-7-yl and cyclohexyl, wherein the $C_{1-6}$-alkyl, $C_{2-4}$alkenyl, $C_{2-4}$alkynyl, $-OC_{1-6}$alkyl, $-SC_{1-6}$alkyl, $-NHC_{1-6}$alkyl, $-N(C_{1-3}$alkyl$)_2$, $-NH$-phenyl, $-NH$-benzyl, $-O$-phenyl and ring are optionally substituted, independently, with 1-5 substituents of $R^8$;

each $R^8$, independently, is halo, haloalkyl, CN, OH, $NO_2$, $NH_2$, acetyl, $-C(O)NHCH_3$, oxo, $C_{1-6}$alkyl, $C_{2-6}$alkenyl, $C_{2-6}$alkynyl, $C_{3-6}$cycloalkyl, $C_{1-6}$alkylamino-, $C_{1-6}$dialkylamino-, $C_{1-6}$alkoxyl, $C_{1-6}$thioalkoxyl, or a ring selected from the group consisting of pyridyl, pyrimidyl, phenyl, morpholinyl, pyrazolyl, isoxazolyl, dihydropyranyl, pyrrolidinyl, piperazinyl, oxetanyl and dioxolyl, wherein each of the $C_{1-6}$alkyl, $C_{2-6}$alkenyl, $C_{2-6}$alkynyl, $C_{3-6}$cycloalkyl, $C_{1-6}$alkylamino-, $C_{1-6}$dialkylamino-, $C_{1-6}$alkoxyl, $C_{1-6}$thioalkoxyl and ring is optionally substituted independently with 1-5 substituents of F, Cl, Br, CN, $CF_3$, $OCF_3$, $NO_2$, $NH_2$, OH, oxo, methyl, methoxyl, ethyl, ethoxyl, propyl, propoxyl, isopropyl, isopropoxyl, cyclopropyl, cyclopropylmethoxyl, butyl, butoxyl, isobutoxyl, tert-butoxyl, isobutyl, sec-butyl, tert-butyl, $C_{1-3}$alkylamino-, $C_{1-3}$dialkylamino-, $C_{1-3}$thioalkoxyl or oxetanyl;

alternatively, two adjacent $R^8$ substituents together with the same atom to which they are attached form a 3-6 membered spirocyclic ring including 0-3 heteroatoms selected from N, O and S, the spirocyclic ring optionally substituted with 1-3 substituents of 1-5 substituents of F, Cl, CN, $CF_3$, $OCF_3$, $NO_2$, OH, oxo, methyl, methoxyl, ethyl, ethoxyl, propyl, propoxyl, isopropyl, isopropoxyl, cyclopropyl, cyclopropylmethoxyl, butyl, butoxyl, isobutoxyl, tert-butoxyl, isobutyl, sec-butyl, tert-butyl, $C_{1-3}$alkylamino-, $C_{1-3}$dialkylamino-, $C_{1-3}$thioalkoxyl or oxetanyl.

In one embodiment of the invention, the compounds, including stereoisomers, tautomers, solvates, pharmaceutically acceptable salts, are generally defined by Formula I-C, wherein
$A^1$ is CH or CF;
$A^2$ is CH;
$A^3$ is CH, CF or N;
$A^4$ is CH, CF or N;
$A^5$ is CH;
$A^6$ is CH or CF, provided that no more than one of $A^3$ and $A^4$ is N;

$R^2$ is Cl, Br, $C_{1-6}$-alkyl, $C_{2-4}$alkenyl, $C_{2-4}$alkynyl, CN, $-OC_{1-6}$alkyl, $-SC_{1-6}$alkyl, $-NHC_{1-6}$alkyl, $-N(C_{1-3}$alkyl$)_2$, $-NH$-phenyl, $-NH$-benzyl, phenyl, pyridyl, pyrimidyl, pyrazinyl, pyridazinyl, pyrazolyl, isoxazolyl, thiazolyl, pyranyl, dihydropyranyl, tetrahydropyranyl, furanyl, dihydrofuranyl, tetrahydrofuranyl, pyrrolidinyl, piperidinyl, piperazinyl, morpholinyl, azetidinyl, 8-oxo-3-aza-bicyclo[3.2.1]oct-3-yl, aza-bicyclo[2.2.1]hept-5-yl, 2-oxo-7-aza-[3,5]-spironon-7-yl, cyclohexyl or $-Si(CH_3)_3$, wherein the $C_{1-6}$-alkyl, $C_{2-4}$alkenyl, $C_{2-4}$alkynyl, $-OC_{1-6}$alkyl, $-SC_{1-6}$alkyl, $-NHC_{1-6}$alkyl, $-N(C_{1-3}$alkyl$)_2$, $-NH$-phenyl, $-NH$-benzyl, phenyl, pyridyl, pyrimidyl, pyrazinyl, pyridazinyl, pyrazolyl, isoxazolyl, thiazolyl, pyranyl, dihydropyranyl, tetrahydropyranyl, furanyl, dihydrofuranyl, tetrahydrofuranyl, pyrrolidinyl, piperidinyl, piperazinyl, morpholinyl, azetidinyl, 8-oxo-3-aza-bicyclo[3.2.1]oct-3-yl, aza-bicyclo[2.2.1]hept-5-yl, 2-oxo-7-aza-[3,5]-spironon-7-yl and cyclohexyl are optionally substituted, independently, with 1-3 substituents of $R^8$;

$R^7$ is $C_{1-6}$-alkyl, $C_{2-4}$alkenyl, $C_{2-4}$alkynyl, CN, $-OC_{1-6}$alkyl, $-SC_{1-6}$alkyl, $-NHC_{1-6}$alkyl, $-N(C_{1-3}$alkyl$)_2$, $-NH$-phenyl, $-NH$-benzyl, phenyl, pyridyl, pyrimidyl, pyrazinyl, pyridazinyl, pyrazolyl, isoxazolyl, thiazolyl, pyranyl, dihydropyranyl, tetrahydropyranyl, furanyl, dihydrofuranyl, tetrahydrofuranyl, pyrrolidinyl, piperidinyl, piperazinyl, morpholinyl, azetidinyl, 8-oxo-3-aza-bicyclo[3.2.1]oct-3-yl, aza-bicyclo[2.2.1]hept-5-yl, 2-oxo-7-aza-[3,5]-spironon-7-yl or cyclohexyl, wherein the $C_{1-6}$-alkyl, $C_{2-4}$alkenyl, $C_{2-4}$alkynyl, $-OC_{1-6}$alkyl, $-SC_{1-6}$alkyl, $-NHC_{1-6}$alkyl, $-N(C_{1-3}$alkyl$)_2$, $-NH$-phenyl, $-NH$-benzyl, phenyl, pyridyl, pyrimidyl, pyrazinyl, pyridazinyl, pyrazolyl, isoxazolyl, thiazolyl, pyranyl, dihydropyranyl, tetrahydropyranyl, furanyl, dihydrofuranyl, tetrahydrofuranyl, pyrrolidinyl, piperidinyl, piperazinyl, morpholinyl, azetidinyl, 8-oxo-3-aza-bicyclo[3.2.1]oct-3-yl, aza-bicyclo[2.2.1]hept-5-yl, 2-oxo-7-aza-[3,5]-spironon-7-yl and cyclohexyl are optionally substituted, independently, with 1-3 substituents of $R^8$; and each $R^8$, independently, is halo, haloalkyl, CN, OH, $NO_2$, $NH_2$, acetyl, —C(O)$NHCH_3$, oxo, $C_{1-6}$alkyl, $C_{2-6}$alkenyl, $C_{2-6}$alkynyl, $C_{3-6}$cycloalkyl, $C_{1-6}$alkylamino-, $C_{1-6}$dialkylamino-, $C_{1-6}$alkoxyl, $C_{1-6}$thioalkoxyl, or a ring selected from the group consisting of pyridyl, pyrimidyl, phenyl, morpholinyl, pyrazolyl, isoxazolyl, dihydropyranyl, pyrrolidinyl, piperazinyl, oxetanyl and dioxolyl, wherein each of the $C_{1-6}$alkyl, $C_{2-6}$alkenyl, $C_{2-6}$alkynyl, $C_{3-6}$cycloalkyl, $C_{1-6}$alkylamino-, $C_{1-6}$dialkylamino-, $C_{1-6}$alkoxyl, $C_{1-6}$thioalkoxyl and ring is optionally substituted independently with 1-5 substituents of F, Cl, Br, CN, $CF_3$, $OCF_3$, $NO_2$, $NH_2$, OH, oxo, methyl, methoxyl, ethyl, ethoxyl, propyl, propoxyl, isopropyl, isopropoxyl, cyclopropyl, cyclopropylmethoxyl, butyl, butoxyl, isobutoxyl, tert-butoxyl, isobutyl, sec-butyl, tert-butyl, $C_{1-3}$alkylamino-, $C_{1-3}$dialkylamino-, $C_{1-3}$thioalkoxyl or oxetanyl;

alternatively, two adjacent $R^8$ substituents together with the same atom to which they are attached form a 3-6 membered spirocyclic ring including 0-3 heteroatoms selected from N, O and S, the spirocyclic ring optionally substituted with 1-3 substituents of 1-5 substituents of F, Cl, CN, $CF_3$, $OCF_3$, $NO_2$, OH, oxo, methyl, methoxyl, ethyl, ethoxyl, propyl, propoxyl, isopropyl, isopropoxyl, cyclopropyl, cyclopropylmethoxyl, butyl, butoxyl, isobutoxyl, tert-butoxyl, isobutyl, sec-butyl, tert-butyl, $C_{1-3}$alkylamino-, $C_{1-3}$dialkylamino-, $C_{1-3}$thioalkoxyl or oxetanyl.

In another embodiment of the invention, the compounds, including stereoisomers, tautomers, solvates, pharmaceutically acceptable salts, are generally defined by Formula I-C, wherein $A^1$ is CH or CF;
$A^2$ is CH or CF;
$A^3$ is CH, CF or N;
$A^4$ is CH, CF or N;
$A^5$ is CH;
$A^6$ is CH or CF, provided that no more than one of $A^3$ and $A^4$ is N;
$R^2$ is Cl, Br, $C_{1-6}$-alkyl, $C_{2-6}$alkenyl, $C_{2-6}$alkynyl, CN, —$OC_{1-6}$alkyl, tert-butoxymethyl, —$SC_{1-6}$alkyl, —$NR^8C_{1-6}$alkyl, —$NR^8C_{1-6}$alkyl, —$N(C_{1-63}$alkyl)$_2$, —NH-phenyl, —NH-benzyl, 2-fluoro-3-pyridyl, 3-methyl-3-oxetanyl-ethynyl, 3-methyl-3-oxetanyl-methoxyl, 3-pyridinylethynyl, 4-pyridyl, 2-methyl-4-pyridyl, 2-methyl-3-pyridyl, 5,6-dihydro-2H-pyran-3-yl, 5,6-dihydro-2H-pyran-2-yl, 3,6-dihydro-2H-pyran-4-yl, 3,4-dihydro-2H-pyran-6-yl, 3-pyridyl, 2-fluoro-4-pyridyl, tetrahydropyran-4-yl, tetrahydropyran-3-yl, tetrahydrofuran-3-yl, 2-pyrimidinyl, 5-pyrimidinyl, 2-pyrazinyl, 3-pyridazinyl, 2-pyrrolidinyl, 4-morpholinyl, 2(5H)-furanyl, phenyl, cyclopropyl, isoxazol-5-yl, 1-methyl-1H-pyrazol-4-yl, 3-methyl-1H-pyrazol-1-yl, -oxo-5-azabicyclo[2.2.1]hept-5-yl, 3-methyl-3,3-dimethanol-1-propynyl, propyn-1-yl, 3-aza-bicyclo[3.1.0]hex-3-yl, 2-oxa-6-azaspiro[3.3]hept-6-yl, 2-oxo-7-aza-[3,5]-spironon-7-yl, 8-oxo-3-aza-bicyclo[3.2.1]oct-3-yl, azetidinyl or —Si($CH_3$)$_3$, wherein the $C_{1-6}$-alkyl, $C_{2-6}$alkenyl, $C_{2-6}$alkynyl, —$OC_{1-6}$alkyl, —$SC_{1-6}$alkyl, —$NR^8C_{1-6}$alkyl, —$N(C_{1-6}$alkyl)$_2$, —NH-phenyl, —NH-benzyl, 2-fluoro-3-pyridyl, 3-methyl-3-oxetanyl-ethynyl, 3-methyl-3-oxetanyl-methoxyl, 3-pyridinylethynyl, 4-pyridyl, 2-methyl-4-pyridyl, 2-methyl-3-pyridyl, 5,6-dihydro-2H-pyran-3-yl, 5,6-dihydro-2H-pyran-2-yl, 3,6-dihydro-2H-pyran-4-yl, 3,4-dihydro-2H-pyran-6-yl, 3-pyridyl, 2-fluoro-4-pyridyl, tetrahydropyran-4-yl, tetrahydropyran-3-yl, tetrahydrofuran-3-yl, 2-pyrimidinyl, 5-pyrimidinyl, 2-pyrazinyl, 3-pyridazinyl, 2-pyrrolidinyl, 4-morpholinyl, 2(5H)-furanyl, phenyl, cyclopropyl, isoxazol-5-yl, 1-methyl-1H-pyrazol-4-yl, 3-methyl-1H-pyrazol-1-yl, -oxo-5-azabicyclo[2.2.1]hept-5-yl, 3-methyl-3,3-dimethanol-1-propynyl, propyn-1-yl, 3-aza-bicyclo[3.1.0]hex-3-yl, 2-oxa-6-azaspiro[3.3]hept-6-yl, 2-oxo-7-aza-[3,5]-spironon-7-yl, 8-oxo-3-aza-bicyclo[3.2.1]oct-3-yl, azetidinyl or —Si($CH_3$)$_3$ are optionally substituted, independently, with 1-3 substituents of $R^8$;

$R^7$ is $C_{1-6}$-alkyl, $C_{2-4}$alkenyl, $C_{2-4}$alkynyl, CN, —$OC_{1-6}$alkyl, —$SC_{1-6}$alkyl, —$NHC_{1-6}$alkyl, —$N(C_{1-3}$alkyl)$_2$, —NH-phenyl, —NH-benzyl, 3-methyl-3-oxetanylmethoxyl, 3,3-dimethyl-3-cyanoethoxyl, 2,2-dimethylpropoxyl, cyclopropylethynyl, 3-methyl-3-oxetanylethynyl, 3,3-dimethylbutyn-1-yl, phenyl, 3-chlorophenyl, 3-cyanophenyl, 5-methyl-3-pyridyl, 5-methoxy-3-pyridyl, 2,4-difluoropyridyl, 2-fluoro-3-pyridyl, 5-fluoro-3-pyridyl, 6-fluoro-3-pyridyl, 5-chloro-2-fluoro-3-pyridyl, 5-(1-propynyl)-3-pyridyl, 2-fluoro-5-(1-propynyl)-3-pyridyl, 5-(3-methyl-3-oxetanylethynyl)-3-pyridyl, 5-(cyclopropylethynyl)-3-pyridyl, 5-pyrimidyl, pyrazin-2-yl, pyridazinyl or pyrazolyl, wherein the $C_{1-6}$-alkyl, $C_{2-4}$alkenyl, $C_{2-4}$alkynyl, CN, —$OC_{1-6}$alkyl, —$SC_{1-6}$alkyl, —$NHC_{1-6}$alkyl, —$N(C_{1-3}$alkyl)$_2$, —NH-phenyl, —NH-benzyl, 3-methyl-3-oxetanylmethoxyl, 3,3-dimethyl-3-cyanoethoxyl, 2,2-dimethylpropoxyl, cyclopropylethynyl, 3-methyl-3-oxetanylethynyl, 3,3-dimethylbutyn-1-yl, phenyl, 3-chlorophenyl, 3-cyanophenyl, 5-methyl-3-pyridyl, 5-methoxy-3-pyridyl, 2,4-difluoropyridyl, 2-fluoro-3-pyridyl, 5-fluoro-3-pyridyl, 6-fluoro-3-pyridyl, 5-chloro-2-fluoro-3-pyridyl, 5-(1-propynyl)-3-pyridyl, 2-fluoro-5-(1-propynyl)-3-pyridyl, 5-(3-methyl-3-oxetanylethynyl)-3-pyridyl, 5-(cyclopropylethynyl)-3-pyridyl, 5-pyrimidyl, pyrazin-2-yl, pyridazinyl and pyrazolyl are optionally substituted, independently, with 1-3 substituents of $R^8$; and each $R^8$, independently, is halo, haloalkyl, CN, OH, $NO_2$, $NH_2$, acetyl, —C(O)$NHCH_3$, oxo, $C_{1-6}$alkyl, $C_{2-6}$alkenyl, $C_{2-6}$alkynyl, $C_{3-6}$cycloalkyl, $C_{1-6}$alkylamino-, $C_{1-6}$dialkylamino-, $C_{1-6}$alkoxyl, $C_{1-6}$thioalkoxyl, morpholinyl, pyrazolyl, isoxazolyl, dihydropyranyl, pyrrolidinyl, piperazinyl, oxetanyl or dioxolyl, wherein each of the $C_{1-6}$alkyl, $C_{2-6}$alkenyl, $C_{2-6}$alkynyl, $C_{3-6}$cycloalkyl, $C_{1-6}$alkylamino-, $C_{1-6}$dialkylamino-, $C_{1-6}$alkoxyl, $C_{1-6}$thioalkoxyl, morpholinyl, pyrazolyl, isoxazolyl, dihydropyranyl, pyrrolidinyl, oxetanyl or dioxolyl, is optionally substituted independently with 1-5 substituents of F, Cl, CN, $NO_2$, $NH_2$, OH, oxo, methyl, methoxyl, ethyl, ethoxyl, propyl, propoxyl, isopropyl, isopropoxyl, cyclopropyl, cyclopropylmethoxyl, butyl, butoxyl, isobutoxyl, tert-butoxyl, isobutyl, sec-butyl, tert-butyl, $C_{1-3}$alkylamino-, $C_{1-3}$dialkylamino, $C_{1-3}$thioalkoxyl, or oxetanyl.

In another embodiment of the present invention, the compounds, and solvates, tautomers, stereoisomers and pharmaceutically acceptable salts thereof, are defined by Formula I-C, wherein $A^1$ is CH or CF;
$A^2$ is CH;
$A^3$ is CH, CF or N;
$A^4$ is CH, CF or N;
$A^5$ is CH;
$A^6$ is CH; provided that no more than one of $A^3$ and $A^4$ is N;
$R^2$ is $C_{3-6}$-alkyl, $C_{2-4}$alkynyl, —$OC_{1-6}$alkyl, —$SC_{1-6}$alkyl, phenyl, pyridyl, pyrimidyl, pyrazinyl, pyridazinyl, dihydropyranyl, tetrahydropyranyl, pyrrolidinyl, piperidinyl, morpholinyl or 8-oxo-3-aza-bicyclo[3.2.1]oct-3-yl, wherein the $C_{3-6}$-alkyl, $C_{2-4}$alkynyl, —$OC_{1-6}$alkyl, —$SC_{1-6}$alkyl, phenyl, pyridyl, pyrimidyl, pyrazinyl, pyridazinyl, dihydropyranyl, tetrahydropyranyl, pyrrolidinyl, piperidinyl, morpholinyl and 8-oxo-3-aza-bicyclo[3.2.1]oct-3-yl, are optionally substituted, independently, with 1-3 substituents of $R^8$;

$R^7$ is $C_{2-4}$alkynyl, —$OC_{1-6}$alkyl, phenyl, pyridyl, pyrimidyl, pyrazinyl or pyridazinyl, wherein the $C_{2-4}$alkynyl, —$OC_{1-6}$alkyl, pyridyl, pyrimidyl, pyrazinyl and pyridazinyl are optionally substituted, independently, with 1-3 substituents of $R^8$; and each $R^8$, independently, is F, $CF_3$, CN, $CH_3$, —$OCH_3$, —$SCH_3$, —$NHCH_3$, spiro-oxetanyl or $C_{2-4}$alkynyl.

In another embodiment of the invention, the compounds, including stereoisomers, tautomers, solvates, pharmaceutically acceptable salts, are generally defined by Formula I-D

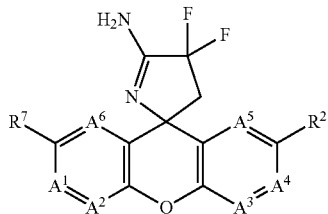

I-D wherein $A^1$ is CH, CF or N;
$A^2$ is CH, CF or N;
$A^3$ is CH, CF or N;
$A^4$ is CH, CF or N;
$A^5$ is CH, $CR^1$ or N;
$A^6$ is CH, CF or N, provided that no more than one of $A^1$, $A^2$, $A^3$, $A^4$, $A^5$ and $A^6$ is N;
$R^1$ is F, Br or

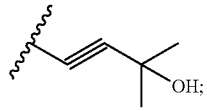 [SMILES: *C#CC(C)(C)O]

$R^2$ is Cl, Br, $C_{1-6}$-alkyl, $C_{2-4}$alkenyl, $C_{2-4}$alkynyl, CN, —$OC_{1-6}$alkyl, —$SC_{1-6}$alkyl, —$NHC_{1-6}$alkyl, —$N(C_{1-3}$alkyl$)_2$, —NH-phenyl, —NH-benzyl, phenyl, pyridyl, pyrimidyl, pyrazinyl, pyridazinyl, pyrazolyl, isoxazolyl, thiazolyl, pyranyl, dihydropyranyl, tetrahydropyranyl, furanyl, dihydrofuranyl, tetrahydrofuranyl, pyrrolidinyl, piperidinyl, piperazinyl, morpholinyl, azetidinyl, 8-oxo-3-aza-bicyclo[3.2.1]oct-3-yl, aza-bicyclo[2.2.1]hept-5-yl, 2-oxo-7-aza-[3,5]-spironon-7-yl, cyclohexyl or —$Si(CH_3)_3$, wherein the $C_{1-6}$-alkyl, $C_{2-4}$alkenyl, $C_{2-4}$alkynyl, —$OC_{1-6}$alkyl, —$SC_{1-6}$alkyl, —$NHC_{1-6}$alkyl, —$N(C_{1-3}$alkyl$)_2$, —NH-phenyl, —NH-benzyl, phenyl, pyridyl, pyrimidyl, pyrazinyl, pyridazinyl, pyrazolyl, isoxazolyl, thiazolyl, pyranyl, dihydropyranyl, tetrahydropyranyl, furanyl, dihydrofuranyl, tetrahydrofuranyl, pyrrolidinyl, piperidinyl, piperazinyl, morpholinyl, azetidinyl, 8-oxo-3-aza-bicyclo[3.2.1]oct-3-yl, aza-bicyclo[2.2.1]hept-5-yl, 2-oxo-7-aza-[3,5]-spironon-7-yl and cyclohexyl are optionally substituted, independently, with 1-3 substituents of $R^8$;

$R^7$ is $C_{1-6}$-alkyl, $C_{2-4}$alkenyl, $C_{2-4}$alkynyl, CN, —$OC_{1-6}$alkyl, —$SC_{1-6}$alkyl, —$NHC_{1-6}$alkyl, —$N(C_{1-3}$alkyl$)_2$, —NH-phenyl, —NH-benzyl, phenyl, pyridyl, pyrimidyl, pyrazinyl, pyridazinyl, pyrazolyl, isoxazolyl, thiazolyl, pyranyl, dihydropyranyl, tetrahydropyranyl, furanyl, dihydrofuranyl, tetrahydrofuranyl, pyrrolidinyl, piperidinyl, piperazinyl, morpholinyl, azetidinyl, 8-oxo-3-aza-bicyclo[3.2.1]oct-3-yl, aza-bicyclo[2.2.1]hept-5-yl, 2-oxo-7-aza-[3,5]-spironon-7-yl or cyclohexyl, wherein the $C_{1-6}$-alkyl, $C_{2-4}$alkenyl, $C_{2-4}$alkynyl, —$OC_{1-6}$alkyl, —$SC_{1-6}$alkyl, —$NHC_{1-6}$alkyl, —$N(C_{1-3}$alkyl$)_2$, —NH-phenyl, —NH-benzyl, phenyl, pyridyl, pyrimidyl, pyrazinyl, pyridazinyl, pyrazolyl, isoxazolyl, thiazolyl, pyranyl, dihydropyranyl, tetrahydropyranyl, furanyl, dihydrofuranyl, tetrahydrofuranyl, pyrrolidinyl, piperidinyl, piperazinyl, morpholinyl, azetidinyl, 8-oxo-3-aza-bicyclo[3.2.1]oct-3-yl, aza-bicyclo[2.2.1]hept-5-yl, 2-oxo-7-aza-[3,5]-spironon-7-yl and cyclohexyl are optionally substituted, independently, with 1-3 substituents of $R^8$;

each $R^8$, independently, is halo, haloalkyl, CN, OH, $NO_2$, $NH_2$, acetyl, —C(O)$NHCH_3$, oxo, $C_{1-6}$alkyl, $C_{2-6}$alkenyl, $C_{2-6}$alkynyl, $C_{3-6}$cycloalkyl, $C_{1-6}$alkylamino-, $C_{1-6}$dialkylamino-, $C_{1-6}$alkoxyl, $C_{1-6}$thioalkoxyl, morpholinyl, pyrazolyl, isoxazolyl, dihydropyranyl, pyrrolidinyl, piperazinyl, oxetanyl or dioxolyl, wherein each of the $C_{1-6}$alkyl, $C_{2-6}$alkenyl, $C_{2-6}$alkynyl, $C_{3-6}$cycloalkyl, $C_{1-6}$alkylamino-, $C_{1-6}$dialkylamino-, $C_{1-6}$alkoxyl, $C_{1-6}$thioalkoxyl, morpholinyl, pyrazolyl, isoxazolyl, dihydropyranyl, pyrrolidinyl, oxetanyl or dioxolyl, is optionally substituted independently with 1-5 substituents of F, Cl, CN, $NO_2$, $NH_2$, OH, oxo, methyl, methoxyl, ethyl, ethoxyl, propyl, propoxyl, isopropyl, isopropoxyl, cyclopropyl, cyclopropylmethoxyl, butyl, butoxyl, isobutoxyl, tert-butoxyl, isobutyl, sec-butyl, tert-butyl, $C_{1-3}$alkylamino-, $C_{1-3}$dialkylamino-, $C_{1-3}$thioalkoxyl, or oxetanyl.

In another embodiment of the present invention, the compounds, and solvates, tautomers, stereoisomers and pharmaceutically acceptable salts thereof, are defined by Formula I-D, wherein $A^1$ is CH or CF;
$A^2$ is CH;
$A^3$ is CH, CF or N;
$A^4$ is CH, CF or N;
$A^5$ is CH;
$A^6$ is CH; provided that no more than one of $A^3$ and $A^4$ is N;
$R^2$ is $C_{3-6}$-alkyl, $C_{2-4}$alkynyl, —$OC_{1-6}$alkyl, —$SC_{1-6}$alkyl, phenyl, pyridyl, pyrimidyl, pyrazinyl, pyridazinyl, dihydropyranyl, tetrahydropyranyl, pyrrolidinyl, piperidinyl, morpholinyl or 8-oxo-3-aza-bicyclo[3.2.1]oct-3-yl, wherein the $C_{3-6}$-alkyl, $C_{2-4}$alkynyl, —$OC_{1-6}$alkyl, —$SC_{1-6}$alkyl, phenyl, pyridyl, pyrimidyl, pyrazinyl, pyridazinyl, dihydropyranyl, tetrahydropyranyl, pyrrolidinyl, piperidinyl, morpholinyl and 8-oxo-3-aza-bicyclo[3.2.1]oct-3-yl, are optionally substituted, independently, with 1-3 substituents of $R^8$;

$R^7$ is $C_{2-4}$alkynyl, —$OC_{1-6}$alkyl, phenyl, pyridyl, pyrimidyl, pyrazinyl or pyridazinyl, wherein the $C_{2-4}$alkynyl, —$OC_{1-6}$alkyl, pyridyl, pyrimidyl, pyrazinyl and pyridazinyl are optionally substituted, independently, with 1-3 substituents of $R^8$; and each $R^8$, independently, is F, $CF_3$, CN, $CH_3$, —$OCH_3$, —$SCH_3$, —$NHCH_3$, spiro-oxetanyl or $C_{2-3}$alkynyl.

In another embodiment of the invention, the compounds, including stereoisomers, tautomers, solvates, pharmaceutically acceptable salts thereof, are generally defined by the compound of Formula II:

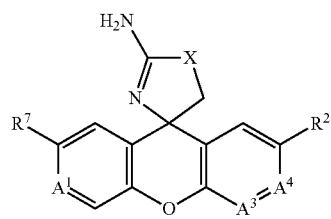

II wherein $A^1$ is CH or CF;
$A^3$ is CH, CF or N;
$A^3$ is CH, CF or N, provided no more than one of $A^3$ and $A^4$ is N;
$R^2$ is Cl, Br, CN, $C_{1-6}$-alkyl, $C_{2-6}$alkenyl, $C_{2-6}$alkynyl, CN, —$OC_{1-6}$alkyl, —$SC_{1-6}$alkyl, —$NHC_{1-6}$alkyl, —$N(C_{1-6}$ alkyl)$_2$, —NH-phenyl, —NH-benzyl, phenyl, pyridyl, pyrimidyl, pyrazinyl, pyridazinyl, pyrazolyl, imidazolyl, oxazolyl, isoxazolyl, thiazolyl, isothiazolyl, diazolyl, thiadiazolyl, thienyl, pyranyl, dihydropyranyl, tetrahydropyranyl, furanyl, dihydrofuranyl, tetrahydrofuranyl, pyrrolidinyl, piperidinyl, piperazinyl, morpholinyl, azetidinyl, 8-oxo-3-aza-bicyclo[3.2.1]oct-3-yl, aza-bicyclo[2.2.1]hept-5-yl, 2-oxo-7-aza-[3,5]-spironon-7-yl, cyclohexyl or —Si(CH$_3$)$_3$, wherein the C$_{1-6}$-alkyl, C$_{2-6}$alkenyl, C$_{2-6}$alkynyl, —OC$_{1-6}$alkyl, —SC$_{1-6}$alkyl, —NHC$_{1-6}$alkyl, —N(C$_{1-6}$alkyl)$_2$, —NH-phenyl, —NH-benzyl, phenyl, pyridyl, pyrimidyl, pyrazinyl, pyridazinyl, pyrazolyl, isoxazolyl, thiazolyl, pyranyl, dihydropyranyl, tetrahydropyranyl, furanyl, dihydrofuranyl, tetrahydrofuranyl, pyrrolidinyl, piperidinyl, piperazinyl, morpholinyl, azetidinyl, 8-oxo-3-aza-bicyclo[3.2.1]oct-3-yl, aza-bicyclo[2.2.1]hept-5-yl, 2-oxo-7-aza-[3,5]-spironon-7-yl and cyclohexyl are optionally substituted, independently, with 1-5 substituents of R$^8$;

R$^7$ is C$_{1-6}$-alkyl, C$_{2-4}$alkenyl, C$_{2-4}$alkynyl, CN, —OC$_{1-6}$alkyl, —SC$_{1-6}$alkyl, —NHC$_{1-6}$alkyl, —N(C$_{1-3}$alkyl)$_2$, —NH-phenyl, —NH-benzyl, —O-phenyl or ring selected from the group consisting of phenyl, pyridyl, pyrimidyl, pyrazinyl, pyridazinyl, pyrazolyl, isoxazolyl, thiazolyl, pyranyl, dihydropyranyl, tetrahydropyranyl, furanyl, dihydrofuranyl, tetrahydrofuranyl, pyrrolidinyl, piperidinyl, piperazinyl, morpholinyl, azetidinyl, 8-oxo-3-aza-bicyclo[3.2.1]oct-3-yl, aza-bicyclo[2.2.1]hept-5-yl, 2-oxo-7-aza-[3,5]-spironon-7-yl and cyclohexyl, wherein the C$_{1-6}$-alkyl, C$_{2-4}$alkenyl, C$_{2-4}$alkynyl, —OC$_{1-6}$alkyl, —SC$_{1-6}$alkyl, —NHC$_{1-6}$alkyl, —N(C$_{1-3}$alkyl)$_2$, —NH-phenyl, —NH-benzyl, —O-phenyl and ring are optionally substituted, independently, with 1-5 substituents of R$^8$;

each R$^8$, independently, is halo, haloalkyl, CN, OH, NO$_2$, NH$_2$, acetyl, —C(O)NHCH$_3$, oxo, C$_{1-6}$alkyl, C$_{2-6}$alkenyl, C$_{2-6}$alkynyl, C$_{3-6}$cycloalkyl, C$_{1-6}$alkylamino-, C$_{1-6}$dialkylamino-, C$_{1-6}$alkoxyl, C$_{1-6}$thioalkoxyl, or a ring selected from the group consisting of pyridyl, pyrimidyl, phenyl, morpholinyl, pyrazolyl, isoxazolyl, dihydropyranyl, pyrrolidinyl, piperazinyl, oxetanyl and dioxolyl, wherein each of the C$_{1-6}$alkyl, C$_{2-6}$alkenyl, C$_{2-6}$alkynyl, C$_{3-6}$cycloalkyl, C$_{1-6}$alkylamino-, C$_{1-6}$dialkylamino-, C$_{1-6}$alkoxyl, C$_{1-6}$thioalkoxyl and ring is optionally substituted independently with 1-5 substituents of F, Cl, Br, CN, CF$_3$, OCF$_3$, NO$_2$, NH$_2$, OH, oxo, methyl, methoxyl, ethyl, ethoxyl, propyl, propoxyl, isopropyl, isopropoxyl, cyclopropyl, cyclopropylmethoxyl, butyl, butoxyl, isobutoxyl, tert-butoxyl, isobutyl, sec-butyl, tert-butyl, C$_{1-3}$alkylamino-, C$_{1-3}$dialkylamino-, C$_{1-3}$thioalkoxyl or oxetanyl;

alternatively, two adjacent R$^8$ substituents together with the same atom to which they are attached form a 3-6 membered spirocyclic ring including 0-3 heteroatoms selected from N, O and S, the spirocyclic ring optionally substituted with 1-3 substituents of 1-5 substituents of F, Cl, CN, CF$_3$, OCF$_3$, NO$_2$, OH, oxo, methyl, methoxyl, ethyl, ethoxyl, propyl, propoxyl, isopropyl, isopropoxyl, cyclopropyl, cyclopropylmethoxyl, butyl, butoxyl, isobutoxyl, tert-butoxyl, isobutyl, sec-butyl, tert-butyl, C$_{1-3}$alkylamino-, C$_{1-3}$dialkylamino-, C$_{1-3}$thioalkoxyl or oxetanyl; and X is O, S or CF$_2$.

In another embodiment of the invention, the compounds, including stereoisomers, tautomers, solvates, pharmaceutically acceptable salts thereof, are generally defined by the compound of Formula II-A:

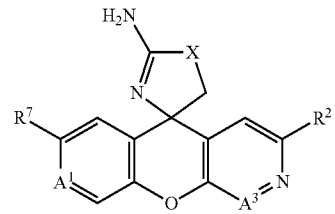

II-A wherein
A$^1$ is CH or CF;
A$^3$ is CH or CF;
R$^2$ is Cl, Br, CN, C$_{1-6}$-alkyl, C$_{2-6}$alkenyl, C$_{2-6}$alkynyl, CN, —OC$_{1-6}$alkyl, —SC$_{1-6}$alkyl, —NHC$_{1-6}$alkyl, —N(C$_{1-6}$alkyl)$_2$, —NH-phenyl, —NH-benzyl, phenyl, pyridyl, pyrimidyl, pyrazinyl, pyridazinyl, pyrazolyl, imidazolyl, oxazolyl, isoxazolyl, thiazolyl, isothiazolyl, diazolyl, thiadiazolyl, thienyl, pyranyl, dihydropyranyl, tetrahydropyranyl, furanyl, dihydrofuranyl, tetrahydrofuranyl, pyrrolidinyl, piperidinyl, piperazinyl, morpholinyl, azetidinyl, 8-oxo-3-aza-bicyclo[3.2.1]oct-3-yl, aza-bicyclo[2.2.1]hept-5-yl, 2-oxo-7-aza-[3,5]-spironon-7-yl, cyclohexyl or —Si(CH$_3$)$_3$, wherein the C$_{1-6}$-alkyl, C$_{2-6}$alkenyl, C$_{2-6}$alkynyl, —OC$_{1-6}$alkyl, —SC$_{1-6}$alkyl, —NHC$_{1-6}$alkyl, —N(C$_{1-6}$alkyl)$_2$, —NH-phenyl, —NH-benzyl, phenyl, pyridyl, pyrimidyl, pyrazinyl, pyridazinyl, pyrazolyl, isoxazolyl, thiazolyl, pyranyl, dihydropyranyl, tetrahydropyranyl, furanyl, dihydrofuranyl, tetrahydrofuranyl, pyrrolidinyl, piperidinyl, piperazinyl, morpholinyl, azetidinyl, 8-oxo-3-aza-bicyclo[3.2.1]oct-3-yl, aza-bicyclo[2.2.1]hept-5-yl, 2-oxo-7-aza-[3,5]-spironon-7-yl and cyclohexyl are optionally substituted, independently, with 1-5 substituents of R$^8$;

R$^7$ is C$_{1-6}$-alkyl, C$_{2-4}$alkenyl, C$_{2-4}$alkynyl, CN, —OC$_{1-6}$alkyl, —SC$_{1-6}$alkyl, —NHC$_{1-6}$alkyl, —N(C$_{1-3}$alkyl)$_2$, —NH-phenyl, —NH-benzyl, —O-phenyl or ring selected from the group consisting of phenyl, pyridyl, pyrimidyl, pyrazinyl, pyridazinyl, pyrazolyl, isoxazolyl, thiazolyl, pyranyl, dihydropyranyl, tetrahydropyranyl, furanyl, dihydrofuranyl, tetrahydrofuranyl, pyrrolidinyl, piperidinyl, piperazinyl, morpholinyl, azetidinyl, 8-oxo-3-aza-bicyclo[3.2.1]oct-3-yl, aza-bicyclo[2.2.1]hept-5-yl, 2-oxo-7-aza-[3,5]-spironon-7-yl and cyclohexyl, wherein the C$_{1-6}$-alkyl, C$_{2-4}$alkenyl, C$_{2-4}$alkynyl, —OC$_{1-6}$alkyl, —SC$_{1-6}$alkyl, —NHC$_{1-6}$alkyl, —N(C$_{1-3}$alkyl)$_2$, —NH-phenyl, —NH-benzyl, —O-phenyl and ring are optionally substituted, independently, with 1-5 substituents of R$^8$;

each R$^8$, independently, is halo, haloalkyl, CN, OH, NO$_2$, NH$_2$, acetyl, —C(O)NHCH$_3$, oxo, C$_{1-6}$alkyl, C$_{2-6}$alkenyl, C$_{2-6}$alkynyl, C$_{3-6}$cycloalkyl, C$_{1-6}$alkylamino-, C$_{1-6}$dialkylamino-, C$_{1-6}$alkoxyl, C$_{1-6}$thioalkoxyl, or a ring selected from the group consisting of pyridyl, pyrimidyl, phenyl, morpholinyl, pyrazolyl, isoxazolyl, dihydropyranyl, pyrrolidinyl, piperazinyl, oxetanyl and dioxolyl, wherein each of the C$_{1-6}$alkyl, C$_{2-6}$alkenyl, C$_{2-6}$alkynyl, C$_{3-6}$cycloalkyl, C$_{1-6}$alkylamino-, C$_{1-6}$dialkylamino-, C$_{1-6}$alkoxyl, C$_{1-6}$thioalkoxyl and ring is optionally substituted independently with 1-5 substituents of F, Cl, Br, CN, CF$_3$, OCF$_3$, NO$_2$, NH$_2$, OH, oxo, methyl, methoxyl, ethyl, ethoxyl, propyl, propoxyl, isopropyl, isopropoxyl, cyclopropyl, cyclopropylmethoxyl, butyl, butoxyl, isobutoxyl, tert-butoxyl, isobutyl, sec-butyl, tert-butyl, C$_{1-3}$alkylamino-, C$_{1-3}$dialkylamino-, C$_{1-3}$thioalkoxyl or oxetanyl;

alternatively, two adjacent R$^8$ substituents together with the same atom to which they are attached form a 3-6 membered spirocyclic ring including 0-3 heteroatoms selected from N, O and S, the spirocyclic ring optionally substituted with 1-3 substituents of 1-5 substituents of F, Cl, CN, $CF_3$, $OCF_3$, $NO_2$, OH, oxo, methyl, methoxyl, ethyl, ethoxyl, propyl, propoxyl, isopropyl, isopropoxyl, cyclopropyl, cyclopropylmethoxyl, butyl, butoxyl, isobutoxyl, tert-butoxyl, isobutyl, sec-butyl, tert-butyl, $C_{1-3}$alkylamino-, $C_{1-3}$dialkylamino-, $C_{1-3}$thioalkoxyl or oxetanyl; and X is O, S or $CF_2$.

In another embodiment of the invention, the compounds, including stereoisomers, tautomers, solvates, pharmaceutically acceptable salts thereof, are generally defined by the compound of Formula III:

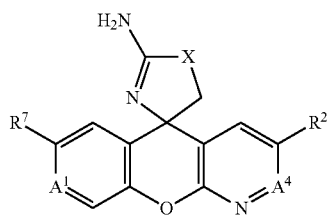

III wherein $A^1$ is CH or CF;

$A^4$ is CH or CF;

$R^2$ is Cl, Br, CN, $C_{1-6}$-alkyl, $C_{2-6}$alkenyl, $C_{2-6}$alkynyl, CN, —$OC_{1-6}$alkyl, —$SC_{1-6}$alkyl, —$NHC_{1-6}$alkyl, —$N(C_{1-6}$alkyl$)_2$, —NH-phenyl, —NH-benzyl, phenyl, pyridyl, pyrimidyl, pyrazinyl, pyridazinyl, pyrazolyl, imidazolyl, oxazolyl, isoxazolyl, thiazolyl, isothiazolyl, diazolyl, thiadiazolyl, thienyl, pyranyl, dihydropyranyl, tetrahydropyranyl, furanyl, dihydrofuranyl, tetrahydrofuranyl, pyrrolidinyl, piperidinyl, piperazinyl, morpholinyl, azetidinyl, 8-oxo-3-aza-bicyclo[3.2.1]oct-3-yl, aza-bicyclo[2.2.1]hept-5-yl, 2-oxo-7-aza-[3,5]-spironon-7-yl, cyclohexyl or —$Si(CH_3)_3$, wherein the $C_{1-6}$-alkyl, $C_{2-6}$alkenyl, $C_{2-6}$alkynyl, —$OC_{1-6}$alkyl, —$SC_{1-6}$alkyl, —$NHC_{1-6}$alkyl, —$N(C_{1-6}$alkyl$)_2$, —NH-phenyl, —NH-benzyl, phenyl, pyridyl, pyrimidyl, pyrazinyl, pyridazinyl, pyrazolyl, isoxazolyl, thiazolyl, pyranyl, dihydropyranyl, tetrahydropyranyl, furanyl, dihydrofuranyl, tetrahydrofuranyl, pyrrolidinyl, piperidinyl, piperazinyl, morpholinyl, azetidinyl, 8-oxo-3-aza-bicyclo[3.2.1]oct-3-yl, aza-bicyclo[2.2.1]hept-5-yl, 2-oxo-7-aza-[3,5]-spironon-7-yl and cyclohexyl are optionally substituted, independently, with 1-5 substituents of $R^8$;

$R^7$ is $C_{1-6}$-alkyl, $C_{2-4}$alkenyl, $C_{2-4}$alkynyl, CN, —$OC_{1-6}$alkyl, —$SC_{1-6}$alkyl, —$NHC_{1-6}$alkyl, —$N(C_{1-3}$alkyl$)_2$, —NH-phenyl, —NH-benzyl, —O-phenyl or ring selected from the group consisting of phenyl, pyridyl, pyrimidyl, pyrazinyl, pyridazinyl, pyrazolyl, isoxazolyl, thiazolyl, pyranyl, dihydropyranyl, tetrahydropyranyl, furanyl, dihydrofuranyl, tetrahydrofuranyl, pyrrolidinyl, piperidinyl, piperazinyl, morpholinyl, azetidinyl, 8-oxo-3-aza-bicyclo[3.2.1]oct-3-yl, aza-bicyclo[2.2.1]hept-5-yl, 2-oxo-7-aza-[3,5]-spironon-7-yl and cyclohexyl, wherein the $C_{1-6}$-alkyl, $C_{2-4}$alkenyl, $C_{2-4}$alkynyl, —$OC_{1-6}$alkyl, —$SC_{1-6}$alkyl, —$NHC_{1-6}$alkyl, —$N(C_{1-3}$alkyl$)_2$, —NH-phenyl, —NH-benzyl, —O-phenyl and ring are optionally substituted, independently, with 1-5 substituents of $R^8$;

each $R^8$, independently, is halo, haloalkyl, CN, OH, $NO_2$, $NH_2$, acetyl, —$C(O)NHCH_3$, oxo, $C_{1-6}$alkyl, $C_{2-6}$alkenyl, $C_{2-6}$alkynyl, $C_{3-6}$cycloalkyl, $C_{1-6}$alkylamino-, $C_{1-6}$dialkylamino-, $C_{1-6}$alkoxyl, $C_{1-6}$thioalkoxyl, or a ring selected from the group consisting of pyridyl, pyrimidyl, phenyl, morpholinyl, pyrazolyl, isoxazolyl, dihydropyranyl, pyrrolidinyl, piperazinyl, oxetanyl and dioxolyl, wherein each of the $C_{1-6}$alkyl, $C_{2-6}$alkenyl, $C_{2-6}$alkynyl, $C_{3-6}$cycloalkyl, $C_{1-6}$alkylamino-, $C_{1-6}$dialkylamino-, $C_{1-6}$alkoxyl, $C_{1-6}$thioalkoxyl and ring is optionally substituted independently with 1-5 substituents of F, Cl, Br, CN, $CF_3$, $OCF_3$, $NO_2$, $NH_2$, OH, oxo, methyl, methoxyl, ethyl, ethoxyl, propyl, propoxyl, isopropyl, isopropoxyl, cyclopropyl, cyclopropylmethoxyl, butyl, butoxyl, isobutoxyl, tert-butoxyl, isobutyl, sec-butyl, tert-butyl, $C_{1-3}$alkylamino-, $C_{1-3}$dialkylamino-, $C_{1-3}$thioalkoxyl or oxetanyl;

alternatively, two adjacent $R^8$ substituents together with the same atom to which they are attached form a 3-6 membered spirocyclic ring including 0-3 heteroatoms selected from N, O and S, the spirocyclic ring optionally substituted with 1-3 substituents of 1-5 substituents of F, Cl, CN, $CF_3$, $OCF_3$, $NO_2$, OH, oxo, methyl, methoxyl, ethyl, ethoxyl, propyl, propoxyl, isopropyl, isopropoxyl, cyclopropyl, cyclopropylmethoxyl, butyl, butoxyl, isobutoxyl, tert-butoxyl, isobutyl, sec-butyl, tert-butyl, $C_{1-3}$alkylamino-, $C_{1-3}$dialkylamino-, $C_{1-3}$thioalkoxyl or oxetanyl; and X is O, S or $CF_2$.

In another embodiment of the invention, the compounds, including stereoisomers, tautomers, solvates, pharmaceutically acceptable salts thereof, are generally defined by the compound of Formula IV:

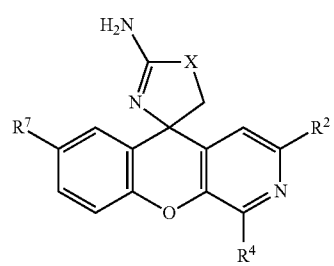

IV wherein $R^2$ is Cl, Br, CN, $C_{1-6}$-alkyl, $C_{2-6}$alkenyl, $C_{2-6}$alkynyl, CN, —$OC_{1-6}$alkyl, —$SC_{1-6}$alkyl, —$NHC_{1-6}$alkyl, —$N(C_{1-6}$alkyl$)_2$, —NH-phenyl, —NH-benzyl, phenyl, pyridyl, pyrimidyl, pyrazinyl, pyridazinyl, pyrazolyl, imidazolyl, oxazolyl, isoxazolyl, thiazolyl, isothiazolyl, diazolyl, thiadiazolyl, thienyl, pyranyl, dihydropyranyl, tetrahydropyranyl, furanyl, dihydrofuranyl, tetrahydrofuranyl, pyrrolidinyl, piperidinyl, piperazinyl, morpholinyl, azetidinyl, 8-oxo-3-aza-bicyclo[3.2.1]oct-3-yl, aza-bicyclo[2.2.1]hept-5-yl, 2-oxo-7-aza-[3,5]-spironon-7-yl, cyclohexyl or —$Si(CH_3)_3$, wherein the $C_{1-6}$-alkyl, $C_{2-6}$alkenyl, $C_{2-6}$alkynyl, —$OC_{1-6}$alkyl, —$SC_{1-6}$alkyl, —$NHC_{1-6}$alkyl, —$N(C_{1-6}$alkyl$)_2$, —NH-phenyl, —NH-benzyl, phenyl, pyridyl, pyrimidyl, pyrazinyl, pyridazinyl, pyrazolyl, isoxazolyl, thiazolyl, pyranyl, dihydropyranyl, tetrahydropyranyl, furanyl, dihydrofuranyl, tetrahydrofuranyl, pyrrolidinyl, piperidinyl, piperazinyl, morpholinyl, azetidinyl, 8-oxo-3-aza-bicyclo[3.2.1]oct-3-yl, aza-bicyclo[2.2.1]hept-5-yl, 2-oxo-7-aza-[3,5]-spironon-7-yl and cyclohexyl are optionally substituted, independently, with 1-5 substituents of $R^8$;

$R^4$ is H or F;

$R^7$ is $C_{1-6}$-alkyl, $C_{2-4}$alkenyl, $C_{2-4}$alkynyl, CN, —$OC_{1-6}$alkyl, —$SC_{1-6}$alkyl, —$NHC_{1-6}$alkyl, —$N(C_{1-3}$alkyl$)_2$, —NH-phenyl, —NH-benzyl, —O-phenyl or ring selected from the group consisting of phenyl, pyridyl, pyrimidyl, pyrazinyl, pyridazinyl, pyrazolyl, isoxazolyl, thiazolyl, pyranyl, dihydropyranyl, tetrahydropyranyl, furanyl, dihydrofuranyl, tetrahydrofuranyl, pyrrolidinyl, piperidinyl, piperazinyl, morpholinyl, azetidinyl, 8-oxo-3-aza-bicyclo[3.2.1]oct-3-yl, aza-bicyclo[2.2.1]hept-5-yl, 2-oxo-7-aza-[3,5]-spironon-7-yl and cyclohexyl, wherein the $C_{1-6}$-alkyl, $C_{2-4}$alkenyl, $C_{2-4}$alkynyl, —$OC_{1-6}$alkyl, —$SC_{1-6}$alkyl, —$NHC_{1-6}$alkyl, —$N(C_{1-3}$alkyl$)_2$, —NH-phenyl, —NH-benzyl, —O-phenyl and ring are optionally substituted, independently, with 1-5 substituents of $R^8$;

each $R^8$, independently, is halo, haloalkyl, CN, OH, $NO_2$, $NH_2$, acetyl, —C(O)$NHCH_3$, oxo, $C_{1-6}$alkyl, $C_{2-6}$alkenyl, $C_{2-6}$alkynyl, $C_{3-6}$cycloalkyl, $C_{1-6}$alkylamino-, $C_{1-6}$dialkylamino-, $C_{1-6}$alkoxyl, $C_{1-6}$thioalkoxyl, or a ring selected from the group consisting of pyridyl, pyrimidyl, phenyl, morpholinyl, pyrazolyl, isoxazolyl, dihydropyranyl, pyrrolidinyl, piperazinyl, oxetanyl and dioxolyl, wherein each of the $C_{1-6}$alkyl, $C_{2-6}$alkenyl, $C_{2-6}$alkynyl, $C_{3-6}$cycloalkyl, $C_{1-6}$alkylamino-, $C_{1-6}$dialkylamino-, $C_{1-6}$alkoxyl, $C_{1-6}$thioalkoxyl and ring is optionally substituted independently with 1-5 substituents of F, Cl, Br, CN, $CF_3$, $OCF_3$, $NO_2$, $NH_2$, OH, oxo, methyl, methoxyl, ethyl, ethoxyl, propyl, propoxyl, isopropyl, isopropoxyl, cyclopropyl, cyclopropylmethoxyl, butyl, butoxyl, isobutoxyl, tert-butoxyl, isobutyl, sec-butyl, tert-butyl, $C_{1-3}$alkylamino-, $C_{1-3}$dialkylamino-, $C_{1-3}$thioalkoxyl or oxetanyl;

alternatively, two adjacent $R^8$ substituents together with the same atom to which they are attached form a 3-6 membered spirocyclic ring including 0-3 heteroatoms selected from N, O and S, the spirocyclic ring optionally substituted with 1-5 substituents of F, Cl, CN, $CF_3$, $OCF_3$, $NO_2$, OH, oxo, methyl, methoxyl, ethyl, ethoxyl, propyl, propoxyl, isopropyl, isopropoxyl, cyclopropyl, cyclopropylmethoxyl, butyl, butoxyl, isobutoxyl, tert-butoxyl, isobutyl, sec-butyl, tert-butyl, $C_{1-3}$alkylamino-, $C_{1-3}$dialkylamino-, $C_{1-3}$thioalkoxyl or oxetanyl; and X is O, S or $CF_2$.

In another embodiment of the invention, the compounds, including stereoisomers and pharmaceutically acceptable salts thereof, are generally defined by the compound of Formula V:

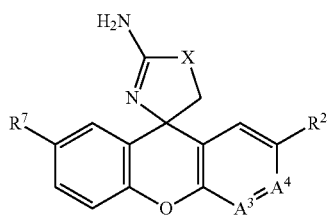

V wherein $A^3$ is CH, CF or N;
$A^4$ is CH, CF or N, provided no more than one of $A^3$ and $A^4$ is N;
$R^2$ is Cl, Br, $C_{1-6}$-alkyl, $C_{2-6}$alkenyl, $C_{2-6}$alkynyl, CN, —$OC_{1-6}$alkyl, tert-butoxymethyl, —$SC_{1-6}$alkyl, —$NR^8C_{1-6}$alkyl, —$NR^8C_{1-6}$alkyl, —$N(C_{1-63}$alkyl$)_2$, —NH-phenyl, —NH-benzyl, 2-fluoro-3-pyridyl, 3-methyl-3-oxetanyl-ethynyl, 3-methyl-3-oxetanyl-methoxyl, 3-pyridinylethynyl, 4-pyridyl, 2-methyl-4-pyridyl, 2-methyl-3-pyridyl, 5,6-dihydro-2H-pyran-3-yl, 5,6-dihydro-2H-pyran-2-yl, 3,6-dihydro-2H-pyran-4-yl, 3,4-dihydro-2H-pyran-6-yl, 3-pyridyl, 2-fluoro-4-pyridyl, tetrahydropyran-4-yl, tetrahydropyran-3-yl, tetrahydrofuran-3-yl, 2-pyrimidinyl, 5-pyrimidinyl, 2-pyrazinyl, 3-pyridazinyl, 2-pyrrolidinyl, 4-morpholinyl, 2(5H)-furanyl, phenyl, cyclopropyl, isoxazol-5-yl, 1-methyl-1H-pyrazol-4-yl, 3-methyl-1H-pyrazol-1-yl, -oxo-5-azabicyclo[2.2.1]hept-5-yl, 3-methyl-3,3-dimethanol-1-propynyl, propyn-1-yl, 3-aza-bicyclo[3.1.0]hex-3-yl, 2-oxa-6-azaspiro[3.3]hept-6-yl, 2-oxo-7-aza-[3,5]-spironon-7-yl, 8-oxo-3-aza-bicyclo[3.2.1]oct-3-yl, azetidinyl or —Si$(CH_3)_3$, wherein the $C_{1-6}$-alkyl, $C_{2-6}$alkenyl, $C_{2-6}$alkynyl, —$OC_{1-6}$alkyl, —$SC_{1-6}$alkyl, —$NR^8C_{1-6}$alkyl, —$N(C_{1-6}$alkyl$)_2$, —NH-phenyl, —NH-benzyl, 2-fluoro-3-pyridyl, 3-methyl-3-oxetanyl-ethynyl, 3-methyl-3-oxetanyl-methoxyl, 3-pyridinylethynyl, 4-pyridyl, 2-methyl-4-pyridyl, 2-methyl-3-pyridyl, 5,6-dihydro-2H-pyran-3-yl, 5,6-dihydro-2H-pyran-2-yl, 3,6-dihydro-2H-pyran-4-yl, 3,4-dihydro-2H-pyran-6-yl, 3-pyridyl, 2-fluoro-4-pyridyl, tetrahydropyran-4-yl, tetrahydropyran-3-yl, tetrahydrofuran-3-yl, 2-pyrimidinyl, 5-pyrimidinyl, 2-pyrazinyl, 3-pyridazinyl, 2-pyrrolidinyl, 4-morpholinyl, 2(5H)-furanyl, phenyl, cyclopropyl, isoxazol-5-yl, 1-methyl-1H-pyrazol-4-yl, 3-methyl-1H-pyrazol-1-yl, -oxo-5-azabicyclo[2.2.1]hept-5-yl, 3-methyl-3,3-dimethanol-1-propynyl, propyn-1-yl, 3-aza-bicyclo[3.1.0]hex-3-yl, 2-oxa-6-azaspiro[3.3]hept-6-yl, 2-oxo-7-aza-[3,5]-spironon-7-yl, 8-oxo-3-aza-bicyclo[3.2.1]oct-3-yl, azetidinyl or —Si$(CH_3)_3$ are optionally substituted, independently, with 1-3 substituents of $R^8$;

$R^7$ is $C_{1-6}$-alkyl, $C_{2-4}$alkenyl, $C_{2-4}$alkynyl, CN, —$OC_{1-6}$ alkyl, —$SC_{1-6}$alkyl, —$NHC_{1-6}$alkyl, —$N(C_{1-3}$alkyl$)_2$, —NH-phenyl, —NH-benzyl, 3-methyl-3-oxetanylmethoxyl, 3,3-dimethyl-3-cyanoethoxyl, 2,2-dimethylpropoxyl, cyclopropylethynyl, 3-methyl-3-oxetanylethynyl, 3,3-dimethylbutyn-1-yl, phenyl, 3-chlorophenyl, 3-cyanophenyl, 5-methyl-3-pyridyl, 5-methoxy-3-pyridyl, 2,4-difluoropyridyl, 2-fluoro-3-pyridyl, 5-fluoro-3-pyridyl, 6-fluoro-3-pyridyl, 5-chloro-2-fluoro-3-pyridyl, 5-(1-propynyl)-3-pyridyl, 2-fluoro-5-(1-propynyl)-3-pyridyl, 5-(3-methyl-3-oxetanylethynyl)-3-pyridyl, 5-(cyclopropylethynyl)-3-pyridyl, 5-pyrimidyl, pyrazin-2-yl, pyridazinyl or pyrazolyl, wherein the $C_{1-6}$-alkyl, $C_{2-4}$alkenyl, $C_{2-4}$alkynyl, CN, —$OC_{1-6}$alkyl, —$SC_{1-6}$alkyl, —$NHC_{1-6}$alkyl, —$N(C_{1-3}$alkyl$)_2$, —NH-phenyl, —NH-benzyl, 3-methyl-3-oxetanylmethoxyl, 3,3-dimethyl-3-cyanoethoxyl, 2,2-dimethylpropoxyl, cyclopropylethynyl, 3-methyl-3-oxetanylethynyl, 3,3-dimethylbutyn-1-yl, phenyl, 3-chlorophenyl, 3-cyanophenyl, 5-methyl-3-pyridyl, 5-methoxy-3-pyridyl, 2,4-difluoropyridyl, 2-fluoro-3-pyridyl, 5-fluoro-3-pyridyl, 6-fluoro-3-pyridyl, 5-chloro-2-fluoro-3-pyridyl, 5-(1-propynyl)-3-pyridyl, 2-fluoro-5-(1-propynyl)-3-pyridyl, 5-(3-methyl-3-oxetanylethynyl)-3-pyridyl, 5-(cyclopropylethynyl)-3-pyridyl, 5-pyrimidyl, pyrazin-2-yl, pyridazinyl and pyrazolyl are optionally substituted, independently, with 1-3 substituents of $R^8$;

each $R^8$, independently, is halo, haloalkyl, CN, OH, $NO_2$, $NH_2$, acetyl, —C(O)$NHCH_3$, oxo, $C_{1-6}$alkyl, $C_{2-6}$alkenyl, $C_{2-6}$alkynyl, $C_{3-6}$cycloalkyl, $C_{1-6}$alkylamino-, $C_{1-6}$dialkylamino-, $C_{1-6}$alkoxyl, $C_{1-6}$thioalkoxyl, morpholinyl, pyrazolyl, isoxazolyl, dihydropyranyl, pyrrolidinyl, piperazinyl, oxetanyl or dioxolyl, wherein each of the $C_{1-6}$alkyl, $C_{2-6}$alkenyl, $C_{2-6}$alkynyl, $C_{3-6}$cycloalkyl, $C_{1-6}$alkylamino-, $C_{1-6}$dialkylamino-, $C_{1-6}$alkoxyl, $C_{1-6}$thioalkoxyl, morpholinyl, pyrazolyl, isoxazolyl, dihydropyranyl, pyrrolidinyl, oxetanyl or dioxolyl, is optionally substituted independently with 1-5 substituents of F, Cl, CN, $NO_2$, $NH_2$, OH, oxo, methyl, methoxyl, ethyl, ethoxyl, propyl, propoxyl, isopropyl, isopropoxyl, cyclopropyl, cyclopropylmethoxyl, butyl, butoxyl, isobutoxyl, tert-butoxyl, isobutyl, sec-butyl, tert-butyl, $C_{1-3}$alkylamino-, $C_{1-3}$dialkylamino, $C_{1-3}$thioalkoxyl, or oxetanyl; and X is O or S.

In another embodiment of the invention, the compounds in the embodiment immediately above, including pharmaceutically acceptable salts thereof, are generally defined by the compound of Formula Va

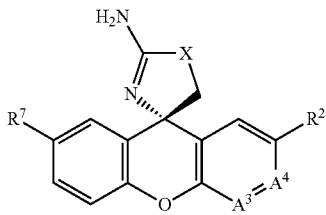

wherein $A^3$, $A^4$, $R^2$, $R^7$ and X are defined immediately above.

In another embodiment of the invention, the compounds, including stereoisomers and pharmaceutically acceptable salts thereof, are generally defined by the compound of Formula V wherein $A^3$ is CH, CF or N;

$A^4$ is CH, CF or N, provided no more than one of $A^3$ and $A^4$ is N;

$R^2$ is 5,6-dihydro-2H-pyran-3-yl, 3,6-dihydro-2H-pyran-4-yl, 3-methyl-3-oxetanyl-ethynyl, 4-morpholinyl, 2-pyrimidinyl, 3-fluoro-pyrrolidin-1-yl, 3,3-difluoro-pyrrolidin-1-yl, 4,4-difluoro-piperidin-1-yl, 6,6-dimethyl-3,6-dihydro-2H-pyran-4-yl, 3-pyridinylethynyl, 1-methyl-1H-pyrazol-4-yl, 2-methyl-2-butyn-2-ol, 4-pyridyl, 2-fluoro-4-pyridyl, tetrahydro-2H-pyran-4-yl, 2-fluoro-2-methylpropoxyl, 2-oxo-5-azabicyclo[2.2.1]hept-5-yl, 6-methyl-3-pyridyl, 3-pyridyl, 2-methyl-5-pyrimidinyl or 2,2-difluoropropoxyl;

$R^7$ is 2,4-difluoro-3pyridyl, 3-pyridyl, 2-fluoro-3-pyridyl, 5-(1-propynyl)-3-pyridyl, 3-cyanophenyl, 2-fluoro-5-methyl-3-pyridyl, 2-fluoro-4-methyl-3-pyridyl, 5-pyrimidyl, 5-fluoro-3-pyridyl, 2-pyrazinyl, 3,3-dimethyl-3-cyanoethoxyl; and X is O or S.

In another embodiment of the invention, the compounds, including stereoisomers and pharmaceutically acceptable salts thereof, are generally defined by the compound of Formula V wherein $A^3$ is CH, CF or N;

$A^4$ is CH, CF or N, provided no more than one of $A^3$ and $A^4$ is N;

$R^2$ is 5,6-dihydro-2H-pyran-3-yl, 3,6-dihydro-2H-pyran-4-yl, 3-methyl-3-oxetanyl-ethynyl, 4-morpholinyl, 2-pyrimidinyl, 3-fluoro-pyrrolidin-1-yl, 3,3-difluoro-pyrrolidin-1-yl, 4,4-difluoro-piperidin-1-yl, 6,6-dimethyl-3,6-dihydro-2H-pyran-4-yl, 3-pyridinylethynyl, 1-methyl-1H-pyrazol-4-yl, 2-methyl-2-butyn-2-ol, 4-pyridyl, 2-fluoro-4-pyridyl, tetrahydro-2H-pyran-4-yl, 2-fluoro-2-methylpropoxyl, 2-oxo-5-azabicyclo[2.2.1]hept-5-yl, 6-methyl-3-pyridyl, 3-pyridyl, 2-methyl-5-pyrimidinyl or 2,2-difluoropropoxyl;

$R^7$ is 2,4-difluoro-3pyridyl, 3-pyridyl, 2-fluoro-3-pyridyl, 5-(1-propynyl)-3-pyridyl, 3-cyanophenyl, 2-fluoro-5-methyl-3-pyridyl, 2-fluoro-4-methyl-3-pyridyl, 5-pyrimidyl, 5-fluoro-3-pyridyl, 2-pyrazinyl, 3,3-dimethyl-3-cyanoethoxyl; and X is O.

In another embodiment of the invention, the compounds, including pharmaceutically acceptable salts thereof, are generally defined by the compound of Formula Va

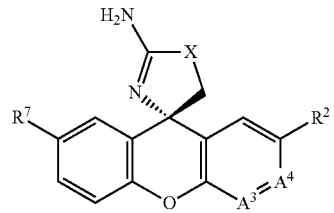

wherein $A^3$ is CH, CF or N;

$A^4$ is CH, CF or N, provided no more than one of $A^3$ and $A^4$ is N;

$R^2$ is 5,6-dihydro-2H-pyran-3-yl, 3,6-dihydro-2H-pyran-4-yl, 3-methyl-3-oxetanyl-ethynyl, 4-morpholinyl, 2-pyrimidinyl, 3-fluoro-pyrrolidin-1-yl, 3,3-difluoro-pyrrolidin-1-yl, 4,4-difluoro-piperidin-1-yl, 6,6-dimethyl-3,6-dihydro-2H-pyran-4-yl, 3-pyridinylethynyl, 1-methyl-1H-pyrazol-4-yl, 2-methyl-2-butyn-2-ol, 4-pyridyl, 2-fluoro-4-pyridyl, tetrahydro-2H-pyran-4-yl, 2-fluoro-2-methylpropoxyl, 2-oxo-5-azabicyclo[2.2.1]hept-5-yl, 6-methyl-3-pyridyl, 3-pyridyl, 2-methyl-5-pyrimidinyl or 2,2-difluoropropoxyl;

$R^7$ is 2,4-difluoro-3pyridyl, 3-pyridyl, 2-fluoro-3-pyridyl, 5-(1-propynyl)-3-pyridyl, 3-cyanophenyl, 2-fluoro-5-methyl-3-pyridyl, 2-fluoro-4-methyl-3-pyridyl, 5-pyrimidyl, 5-fluoro-3-pyridyl, 2-pyrazinyl, 3,3-dimethyl-3-cyanoethoxyl; and X is O or S.

In another embodiment of the invention, the compounds of Formulas I, I-B, I-C and I-D include compounds wherein the stereochemistry at the spirocyclic quaternary center is in the following orientation:

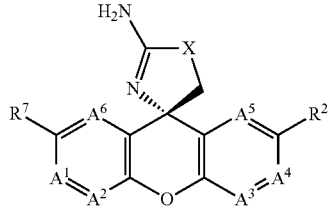

Formula I-A-a

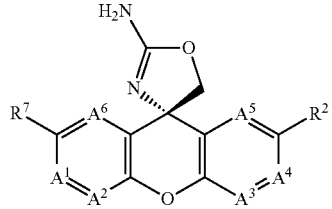

Formula I-B-a

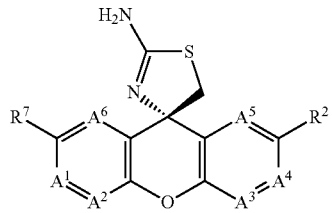

Formula I-C-a

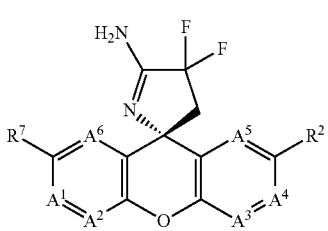

Formula I-D-a in conjunction with any of the above or below embodiments with respect to X (Formula I-A) $A^1, A^2, A^3, A^4, A^5, A^6, R^2$ and $R^7$.

In another embodiment of the invention, the compounds of Formulas II, III and IV include compounds wherein the stereochemistry at the spirocyclic quaternary center is in the following orientation:

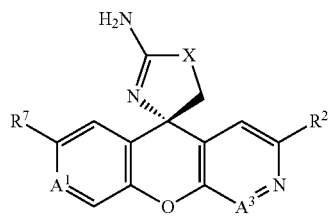

Formula IIa

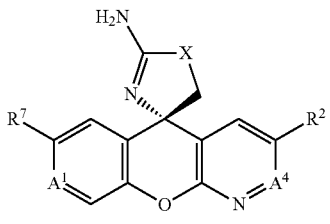

Formula IIIa

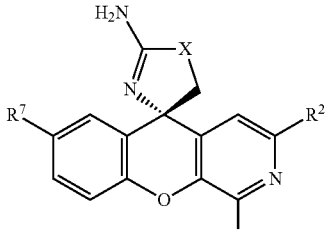

Formula IVa

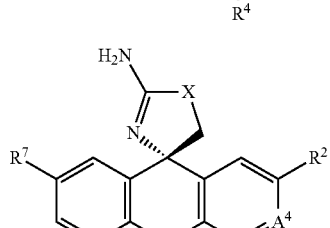

Formula Va in conjunction with any of the above or below embodiments with respect to $A^1, A^3, A^4, R^2, R^4, R^7$ and X In another embodiment of the invention, the compounds of Formulas II, III and IV include compounds wherein X is O, S or $CF_2$.

In another embodiment of the invention, the compounds of Formulas II, III and IV include compounds wherein X is O or S, in conjunction with any of the above or below embodiments.

In another embodiment of the invention, the compounds of Formulas II, III and IV include compounds wherein X is O in conjunction with any of the above or below embodiments.

In another embodiment of the invention, the compounds of Formulas II, III and IV include compounds wherein X is S in conjunction with any of the above or below embodiments.

In another embodiment of the invention, the compounds of Formulas II, III and IV include compounds wherein X is $CF_2$ in conjunction with any of the above or below embodiments.

The present invention contemplates that the various different embodiments below of each individual variable $A^1$, $A^2$, $A^3$, $A^4$, $A^5$, $A^6$, $R^2$, $R^7$ and X, as described below, may be applied "in conjunction with any of the other {above and below} embodiments" to create various embodiments of general Formulas I, II, III and IV and each sub-formula thereof described hereinabove, which are not literally described herein.

In another embodiment, the invention includes compounds wherein $A^1$ is CH, CF or N, in conjunction with any of the above or below embodiments.

In another embodiment, the invention includes compounds wherein $A^1$ is CH, in conjunction with any of the above or below embodiments.

In another embodiment, the invention includes compounds wherein $A^1$ is CF, in conjunction with any of the above or below embodiments.

In another embodiment, the invention includes compounds wherein $A^1$ is N, in conjunction with any of the above or below embodiments.

In another embodiment, the invention includes compounds wherein $A^2$ is CH, CF or N, in conjunction with any of the above or below embodiments.

In another embodiment, the invention includes compounds wherein $A^2$ is CH, in conjunction with any of the above or below embodiments.

In another embodiment, the invention includes compounds wherein $A^2$ is CF, in conjunction with any of the above or below embodiments.

In another embodiment, the invention includes compounds wherein $A^2$ is N, in conjunction with any of the above or below embodiments.

In another embodiment, the invention includes compounds wherein $A^3$ is CH, CF, OH, $OCH_3$ or N, in conjunction with any of the above or below embodiments.

In another embodiment, the invention includes compounds wherein $A^3$ is CH, CF, oxo, $OCH_3$ or N, in conjunction with any of the above or below embodiments.

In another embodiment, the invention includes compounds wherein $A^3$ is CH, CF or N, in conjunction with any of the above or below embodiments.

In another embodiment, the invention includes compounds wherein $A^3$ is CH, in conjunction with any of the above or below embodiments.

In another embodiment, the invention includes compounds wherein $A^3$ is CF, in conjunction with any of the above or below embodiments.

In another embodiment, the invention includes compounds wherein $A^3$ is N, in conjunction with any of the above or below embodiments.

In another embodiment, the invention includes compounds wherein $A^4$ is CH, CF or N, in conjunction with any of the above or below embodiments.

In another embodiment, the invention includes compounds wherein $A^4$ is CH, in conjunction with any of the above or below embodiments.

In another embodiment, the invention includes compounds wherein $A^4$ is CF, in conjunction with any of the above or below embodiments.

In another embodiment, the invention includes compounds wherein $A^4$ is N, in conjunction with any of the above or below embodiments.

In another embodiment, the invention includes compounds wherein $A^5$ is CH, $CR^1$ wherein $R^1$ is F, Br or

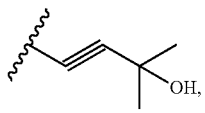 [SMILES: *C#CC(C)(C)O]

or $A^5$ is N, in conjunction with any of the above or below embodiments.

In another embodiment, the invention includes compounds wherein $A^5$ is CH, in conjunction with any of the above or below embodiments.

In another embodiment, the invention includes compounds wherein $A^5$ is $CR^1$ wherein $R^1$ is F, Br or

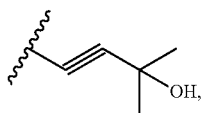 [SMILES: *C#CC(C)(C)O]

in conjunction with any of the above or below embodiments.

In another embodiment, the invention includes compounds wherein $A^5$ is N, in conjunction with any of the above or below embodiments.

In another embodiment, the invention includes compounds wherein $A^6$ is CH, CF or N, in conjunction with any of the above or below embodiments.

In another embodiment, the invention includes compounds wherein $A^6$ is CH, in conjunction with any of the above or below embodiments.

In another embodiment, the invention includes compounds wherein $A^6$ is CF, in conjunction with any of the above or below embodiments.

In another embodiment, the invention includes compounds wherein $A^6$ is N, in conjunction with any of the above or below embodiments.

In another embodiment, the invention includes compounds wherein $R^2$ is Cl, Br, $C_{1-6}$-alkyl, $C_{2-4}$alkenyl, $C_{2-4}$alkynyl, CN, —$OC_{1-6}$alkyl, —$SC_{1-6}$alkyl, —$NHC_{1-6}$alkyl, —$N(C_{1-3}$alkyl$)_2$, —NH-phenyl, —NH-benzyl, phenyl, pyridyl, pyrimidyl, pyrazinyl, pyridazinyl, pyrazolyl, isoxazolyl, thiazolyl, pyranyl, dihydropyranyl, tetrahydropyranyl, furanyl, dihydrofuranyl, tetrahydrofuranyl, pyrrolidinyl, piperidinyl, piperazinyl, morpholinyl, azetidinyl, 8-oxo-3-aza-bicyclo[3.2.1]oct-3-yl, aza-bicyclo[2.2.1]hept-5-yl, 2-oxo-7-aza-[3,5]-spironon-7-yl, cyclohexyl or —$Si(CH_3)_3$, wherein the $C_{1-6}$-alkyl, $C_{2-4}$alkenyl, $C_{2-4}$alkynyl, —$OC_{1-6}$alkyl, —$SC_{1-6}$alkyl, —$NHC_{1-6}$alkyl, —$N(C_{1-3}$alkyl$)_2$, —NH-phenyl, —NH-benzyl, phenyl, pyridyl, pyrimidyl, pyrazinyl, pyridazinyl, pyrazolyl, isoxazolyl, thiazolyl, pyranyl, dihydropyranyl, tetrahydropyranyl, furanyl, dihydrofuranyl, tetrahydrofuranyl, pyrrolidinyl, piperidinyl, piperazinyl, morpholinyl, azetidinyl, 8-oxo-3-aza-bicyclo[3.2.1]oct-3-yl, aza-bicyclo[2.2.1]hept-5-yl, 2-oxo-7-aza-[3,5]-spironon-7-yl and cyclohexyl are optionally substituted, independently, with 1-3 substituents of $R^8$, in conjunction with any of the above or below embodiments.

In another embodiment, the invention includes compounds wherein $R^2$ is $C_{1-6}$-alkyl, $C_{2-4}$alkenyl, $C_{2-4}$alkynyl, —$OC_{1-6}$alkyl, phenyl, pyridyl, pyrimidyl, pyrazinyl, pyridazinyl, pyrazolyl, isoxazolyl, thiazolyl, pyranyl, dihydropyranyl, tetrahydropyranyl, furanyl, dihydrofuranyl, tetrahydrofuranyl, pyrrolidinyl, piperidinyl, piperazinyl, morpholinyl, azetidinyl, 8-oxo-3-aza-bicyclo[3.2.1]oct-3-yl, aza-bicyclo[2.2.1]hept-5-yl, 2-oxo-7-aza-[3,5]-spironon-7-yl, cyclohexyl or —$Si(CH_3)_3$, wherein the $C_{1-6}$-alkyl, $C_{2-4}$alkenyl, $C_{2-4}$alkynyl, —$OC_{1-6}$alkyl, phenyl, pyridyl, pyrimidyl, pyrazinyl, pyridazinyl, pyrazolyl, isoxazolyl, thiazolyl, pyranyl, dihydropyranyl, tetrahydropyranyl, furanyl, dihydrofuranyl, tetrahydrofuranyl, pyrrolidinyl, piperidinyl, piperazinyl, morpholinyl, azetidinyl, 8-oxo-3-aza-bicyclo[3.2.1]oct-3-yl, aza-bicyclo[2.2.1]hept-5-yl, 2-oxo-7-aza-[3,5]-spironon-7-yl and cyclohexyl are optionally substituted, independently, with 1-3 substituents of $R^8$, in conjunction with any of the above or below embodiments.

In another embodiment, the invention includes compounds wherein $R^2$ is Cl, Br, $C_{1-6}$-alkyl, $C_{2-6}$alkenyl, $C_{2-6}$alkynyl, CN, —$OC_{1-6}$alkyl, tert-butoxymethyl, —$SC_{1-6}$alkyl, —$NR^8C_{1-6}$alkyl, —$NR^8C_{1-6}$alkyl, —$N(C_{1-63}$alkyl$)_2$, —NH-phenyl, —NH-benzyl, 2-fluoro-3-pyridyl, 3-methyl-3-oxetanyl-ethynyl, 3-methyl-3-oxetanyl-methoxyl, 3-pyridinylethynyl, 4-pyridyl, 2-methyl-4-pyridyl, 2-methyl-3-pyridyl, 5,6-dihydro-2H-pyran-3-yl, 5,6-dihydro-2H-pyran-2-yl, 3,6-dihydro-2H-pyran-4-yl, 3,4-dihydro-2H-pyran-6-yl, 3-pyridyl, 2-fluoro-4-pyridyl, tetrahydropyran-4-yl, tetrahydropyran-3-yl, tetrahydrofuran-3-yl, 2-pyrimidinyl, 5-pyrimidinyl, 2-pyrazinyl, 3-pyridazinyl, 2-pyrrolidinyl, 4-morpholinyl, 2(5H)-furanyl, phenyl, cyclopropyl, isoxazol-5-yl, 1-methyl-1H-pyrazol-4-yl, 3-methyl-1H-pyrazol-1-yl, -oxo-5-azabicyclo[2.2.1]hept-5-yl, 3-methyl-3,3-dimethanol-1-propynyl, propyn-1-yl, 3-aza-bicyclo[3.1.0]hex-3-yl, 2-oxa-6-azaspiro[3.3]hept-6-yl, 2-oxo-7-aza-[3,5]-spironon-7-yl, 8-oxo-3-aza-bicyclo[3.2.1]oct-3-yl, azetidinyl or —$Si(CH_3)_3$, wherein the $C_{1-6}$-alkyl, $C_{2-6}$alkenyl, $C_{2-6}$alkynyl, —$OC_{1-6}$alkyl, —$SC_{1-6}$alkyl, —$NR^8C_{1-6}$alkyl, —$N(C_{1-6}$alkyl$)_2$, —NH-phenyl, —NH-benzyl, 2-fluoro-3-pyridyl, 3-methyl-3-oxetanyl-ethynyl, 3-methyl-3-oxetanyl-methoxyl, 3-pyridinylethynyl, 4-pyridyl, 2-methyl-4-pyridyl, 2-methyl-3-pyridyl, 5,6-dihydro-2H-pyran-3-yl, 5,6-dihydro-2H-pyran-2-yl, 3,6-dihydro-2H-pyran-4-yl, 3,4-dihydro-2H-pyran-6-yl, 3-pyridyl, 2-fluoro-4-pyridyl, tetrahydropyran-4-yl, tetrahydropyran-3-yl, tetrahydrofuran-3-yl, 2-pyrimidinyl, 5-pyrimidinyl, 2-pyrazinyl, 3-pyridazinyl, 2-pyrrolidinyl, 4-morpholinyl, 2(5H)-furanyl, phenyl, cyclopropyl, isoxazol-5-yl, 1-methyl-1H-pyrazol-4-yl, 3-methyl-1H-pyrazol-1-yl, -oxo-5-azabicyclo[2.2.1]hept-5-yl, 3-methyl-3,3-dimethanol-1-propynyl, propyn-1-yl, 3-aza-bicyclo[3.1.0]hex-3-yl, 2-oxa-6-azaspiro[3.3]hept-6-yl, 2-oxo-7-aza-[3,5]-spironon-7-yl, 8-oxo-3-aza-bicyclo[3.2.1]oct-3-yl, azetidinyl or —$Si(CH_3)_3$ are optionally substituted, independently, with 1-3 substituents of $R^8$, in conjunction with any of the above or below embodiments.

In another embodiment, the invention includes compounds wherein $R^2$ is $C_{3-6}$-alkyl, $C_{2-4}$alkynyl, —$SC_{1-6}$alkyl, phenyl, pyridyl, pyrimidyl, pyrazinyl, pyridazinyl, dihydropyranyl, tetrahydropyranyl, pyrrolidinyl, piperidinyl, morpholinyl or 8-oxo-3-aza-bicyclo[3.2.1]oct-3-yl, wherein the $C_{3-6}$-alkyl, $C_{2-4}$alkynyl, —$SC_{1-6}$alkyl, phenyl, pyridyl, pyrimidyl, pyrazinyl, pyridazinyl, dihydropyranyl, tetrahydropyranyl, pyrrolidinyl, piperidinyl, morpholinyl and 8-oxo-3-aza-bicyclo[3.2.1]oct-3-yl are optionally substituted, independently, with 1-3 substituents of $R^8$, in conjunction with any of the above or below embodiments.

In another embodiment, the invention includes compounds wherein R² is C₂₋₄alkynyl, OC₁₋₆alkyl, pyridyl, pyrimidyl, dihydropyranyl, tetrahydropyranyl, pyrrolidinyl or piperidinyl, wherein the C₂₋₄alkynyl, OC₁₋₆alkyl, pyridyl, pyrimidyl, dihydropyranyl, tetrahydropyranyl, pyrrolidinyl and piperidinyl are optionally substituted, independently, with 1-3 substituents of R⁸, in conjunction with any of the above or below embodiments.

In another embodiment, the invention includes compounds wherein R² is C₂₋₄alkynyl, OC₁₋₆alkyl, pyridyl, dihydropyranyl, pyrrolidinyl or piperidinyl, wherein the C₂₋₄alkynyl, OC₁₋₆alkyl, pyridyl, dihydropyranyl, pyrrolidinyl and piperidinyl are optionally substituted, independently, with 1-3 substituents of R⁸, in conjunction with any of the above or below embodiments.

In another embodiment, the invention includes compounds wherein R² is 5,6-dihydro-2H-pyran-3-yl, 3,6-dihydro-2H-pyran-4-yl, 3-methyl-3-oxetanyl-ethynyl, 4-morpholinyl, 2-pyrimidinyl, 3-fluoro-pyrrolidin-1-yl, 3,3-difluoro-pyrrolidin-1-yl, 4,4-difluoro-piperidin-1-yl, 6,6-dimethyl-3,6-dihydro-2H-pyran-4-yl, 3-pyridinylethynyl, 1-methyl-1H-pyrazol-4-yl, 2-methyl-2-butyn-2-ol, 4-pyridyl, 2-fluoro-4-pyridyl, tetrahydro-2H-pyran-4-yl, 2-fluoro-2-methylpropoxyl, 2-oxo-5-azabicyclo[2.2.1]hept-5-yl, 6-methyl-3-pyridyl, 3-pyridyl, 2-methyl-5-pyrimidinyl or 2,2-difluoropropoxyl, in conjunction with any of the above or below embodiments.

In another embodiment, the invention includes compounds wherein R⁷ is C₁₋₆-alkyl, C₂₋₄alkenyl, C₂₋₄alkynyl, CN, —NHC₁₋₆alkyl, —N(C₁₋₃alkyl)₂, —NH-phenyl, —NH-benzyl, phenyl, pyridyl, pyrimidyl, pyrazinyl, pyridazinyl, pyrazolyl, isoxazolyl, thiazolyl, pyranyl, dihydropyranyl, tetrahydropyranyl, furanyl, dihydrofuranyl, tetrahydrofuranyl, pyrrolidinyl, piperidinyl, piperazinyl, morpholinyl, azetidinyl, 8-oxo-3-aza-bicyclo[3.2.1]oct-3-yl, aza-bicyclo[2.2.1]hept-5-yl, 2-oxo-7-aza-[3,5]-spironon-7-yl or cyclohexyl, wherein the C₁₋₆-alkyl, C₂₋₄alkenyl, C₂₋₄alkynyl, —NHC₁₋₆alkyl, —N(C₁₋₃alkyl)₂, —NH-phenyl, —NH-benzyl, phenyl, pyridyl, pyrimidyl, pyrazinyl, pyridazinyl, pyrazolyl, isoxazolyl, thiazolyl, pyranyl, dihydropyranyl, tetrahydropyranyl, furanyl, dihydrofuranyl, tetrahydrofuranyl, pyrrolidinyl, piperazinyl, morpholinyl, azetidinyl, 8-oxo-3-aza-bicyclo[3.2.1]oct-3-yl, aza-bicyclo[2.2.1]hept-5-yl, 2-oxo-7-aza-[3,5]-spironon-7-yl and cyclohexyl are optionally substituted, independently, with 1-3 substituents of R⁸, in conjunction with any of the above or below embodiments.

In another embodiment, the invention includes compounds wherein R⁷ is C₂₋₄alkynyl, —OC₁₋₆alkyl, phenyl, pyridyl, pyrimidyl, pyrazinyl or pyridazinyl, wherein the C₂₋₄alkynyl, —OC₁₋₆alkyl, pyridyl, pyrimidyl, pyrazinyl and pyridazinyl are optionally substituted, independently, with 1-3 substituents of R⁸, in conjunction with any of the above or below embodiments.

In another embodiment, the invention includes compounds wherein R⁷ is C₂₋₄alkynyl, —OC₁₋₆alkyl, phenyl, 3-pyridyl, 5-pyrimidyl, pyrazinyl or 2-pyridazinyl, wherein the C₂₋₄alkynyl, —OC₁₋₆alkyl, 3-pyridyl, 5-pyrimidyl, pyrazinyl and 2-pyridazinyl are optionally substituted, independently, with 1-3 substituents of R⁸, in conjunction with any of the above or below embodiments.

In another embodiment, the invention includes compounds wherein R⁷ is a ring selected from phenyl, 3-pyridyl, 5-pyrimidyl or 2-pyridazinyl, said ring optionally substituted, independently, with 1-5 substituents of R⁸, in conjunction with any of the above or below embodiments.

In another embodiment, the invention includes compounds wherein R⁷ is phenyl, 3-pyridyl, 5-pyrimidyl or 2-pyridazinyl, each of which is optionally substituted with 1-5 substituents of F, Cl, Br, I, CN, CF₃, C₂F₅, haloalkoxyl, C₁₋₆-alkyl, CN, OH, OC₁₋₆-alkyl, SC₁₋₆-alkyl, oxetanyl or C₂₋₃alkynyl, in conjunction with any of the above or below embodiments.

In another embodiment, the invention includes compounds wherein R⁷ is C₁₋₆-alkyl, C₂₋₄alkenyl, C₂₋₄alkynyl, CN, —OC₁₋₆alkyl, —SC₁₋₆alkyl, —NHC₁₋₆alkyl, —N(C₁₋₃alkyl)₂, —NH-phenyl, —NH-benzyl, 3-methyl-3-oxetanylmethoxyl, 3,3-dimethyl-3-cyanoethoxyl, 2,2-dimethylpropoxyl, cyclopropylethynyl, 3-methyl-3-oxetanylethynyl, 3,3-dimethylbutyn-1-yl, phenyl, 3-chlorophenyl, 3-cyanophenyl, 5-methyl-3-pyridyl, 5-methoxy-3-pyridyl, 2,4-difluoropyridyl, 2-fluoro-3-pyridyl, 5-fluoro-3-pyridyl, 6-fluoro-3-pyridyl, 5-chloro-2-fluoro-3-pyridyl, 5-(1-propynyl)-3-pyridyl, 2-fluoro-5-(1-propynyl)-3-pyridyl, 5-(3-methyl-3-oxetanylethynyl)-3-pyridyl, 5-(cyclopropylethynyl)-3-pyridyl, 5-pyrimidyl, pyrazin-2-yl, pyridazinyl or pyrazolyl, wherein the C₁₋₆-alkyl, C₂₋₄alkenyl, C₂₋₄alkynyl, CN, —OC₁₋₆alkyl, —SC₁₋₆alkyl, —NHC₁₋₆alkyl, —N(C₁₋₃alkyl)₂, —NH-phenyl, —NH-benzyl, 3-methyl-3-oxetanylmethoxyl, 3,3-dimethyl-3-cyanoethoxyl, 2,2-dimethylpropoxyl, cyclopropylethynyl, 3-methyl-3-oxetanylethynyl, 3,3-dimethylbutyn-1-yl, phenyl, 3-chlorophenyl, 3-cyanophenyl, 5-methyl-3-pyridyl, 5-methoxy-3-pyridyl, 2,4-difluoropyridyl, 2-fluoro-3-pyridyl, 5-fluoro-3-pyridyl, 6-fluoro-3-pyridyl, 5-chloro-2-fluoro-3-pyridyl, 5-(1-propynyl)-3-pyridyl, 2-fluoro-5-(1-propynyl)-3-pyridyl, 5-(3-methyl-3-oxetanylethynyl)-3-pyridyl, 5-(cyclopropylethynyl)-3-pyridyl, 5-pyrimidyl, pyrazin-2-yl, pyridazinyl and pyrazolyl are optionally substituted, independently, with 1-3 substituents of R⁸, in conjunction with any of the above or below embodiments.

In another embodiment, the invention includes compounds wherein R⁷ is 2,4-difluoro-3-pyridyl, 3-pyridyl, 2-fluoro-3-pyridyl, 5-(1-propynyl)-3-pyridyl, 3-cyanophenyl, 2-fluoro-5-methyl-3-pyridyl, 2-fluoro-4-methyl-3-pyridyl, 5-pyrimidyl, 5-fluoro-3-pyridyl, 2-pyrazinyl, 3,3-dimethyl-3-cyanoethoxyl, in conjunction with any of the above or below embodiments.

In another embodiment, the invention includes compounds wherein each R⁸, independently, is F, Cl, CF₃, OCF₃, methyl, CN, OH, OCH₃, SCH₃, NHCH₃, oxetanyl, spiro-oxetanyl or C₂₋₃alkynyl, in conjunction with any of the above or below embodiments.

In another embodiment, the invention includes compounds wherein each R⁸, independently, is F, methyl, CN, OH, oxetanyl or C₂₋₃alkynyl, in conjunction with any of the above or below embodiments.

In another embodiment, the invention includes compounds wherein each R⁸, independently, is F, CF₃, CN, CH₃, —OCH₃, —SCH₃, —NHCH₃, spiro-oxetanyl, oxetanyl or C₂₋₃alkynyl, in conjunction with any of the above or below embodiments.

In another embodiment, the invention provides the compound of Formula I, or a pharmaceutically acceptable salt thereof, selected from (5S)-7-(2,4-difluoro-3-pyridinyl)-3-(3,6-dihydro-2H-pyran-4-yl)spiro[chromeno[2,3-c]pyridine-5,4'-[1,3]oxazol]-2'-amine;

3-((5S)-2'-amino-3-((3-methyl-3-oxetanyl)ethynyl)spiro[chromeno[2,3-b]pyridine-5,4'-[1,3]oxazol]-7-yl)benzonitrile;

(4R)-2'-(3,6-dihydro-2H-pyran-4-yl)-7'-(2-fluoro-3-pyridinyl)spiro[1,3-oxazole-4,9'-xanthen]-2-amine;

(4S)-4'-fluoro-7'-(2-fluoro-3-pyridinyl)-2'-(2-pyrimidinyl)spiro[1,3-oxazole-4,9'-xanthen]-2-amine;

(4S)-4'-fluoro-7'-(2-fluoro-5-methyl-3-pyridinyl)-2'-(4-morpholinyl)spiro[1,3-oxazole-4,9'-xanthen]-2-amine;

(4S)-4'-fluoro-7'-(2-fluoro-3-pyridinyl)-2'-(8-oxa-3-azabicyclo[3.2.1]oct-3-yl)spiro[1,3-oxazole-4,9'-xanthen]-2-amine;

(4S)-4'-fluoro-7'-(2-fluoro-3-pyridinyl)-2'-(2-methyl-5-pyrimidinyl)spiro[1,3-oxazole-4,9'-xanthen]-2-amine;

(5S)-3-(3,6-dihydro-2H-pyran-4-yl)-7-(2-fluoro-4-methyl-3-pyridinyl)spiro[chromeno[2,3-c]pyridine-5,4'-[1,3]oxazol]-2'-amine;

(4S)-4'-fluoro-7'-(6-fluoro-3-pyridinyl)-2'-(1-methyl-1H-pyrazol-4-yl)spiro[1,3-oxazole-4,9'-xanthen]-2-amine;

(4S)-4'-fluoro-7'-(2-fluoro-3-pyridinyl)-2'-((3S)-3-fluoro-1-pyrolidinyl)spiro[1,3-oxazole-4,9'-xanthen]-2-amine;

(4S)-4'-fluoro-7'-(2-fluoro-3-pyridinyl)-2'-(4-morpholinyl)spiro[1,3-oxazole-4,9'-xanthen]-2-amine;

(4S)-2'-(5,6-dihydro-2H-pyran-3-yl)-4'-fluoro-7'-(2-fluoro-3-pyridinyl)spiro[1,3-oxazole-4,9'-xanthen]-2-amine;

(5R)-3-(3,3-dimethyl-1-butyn-1-yl)-6-fluoro-7-(5-pyrimidinyl)spiro[chromeno[2,3-b]pyridine-5,4'-[1,3]oxazol]-2'-amine;

(5S)-3-(6,6-dimethyl-3,6-dihydro-2H-pyran-4-yl)-7-(6-fluoro-3-pyridinyl)spiro[chromeno[2,3-c]pyridine-5,4'-[1,3]oxazol]-2'-amine;

(5S)-3-(6,6-dimethyl-3,6-dihydro-2H-pyran-4-yl)-7-(5-fluoro-3-pyridinyl)spiro[chromeno[2,3-c]pyridine-5,4'-[1,3]oxazol]-2'-amine;

(5S)-3-(3,3-difluoro-1-pyrolidinyl)-7-(3-pyridinyl)spiro[chromeno[2,3-c]pyridine-5,4'-[1,3]oxazol]-2'-amine;

(5S)-3-(4,4-difluoro-1-piperidinyl)-7-(3-pyridinyl)spiro[chromeno[2,3-c]pyridine-5,4'-[1,3]oxazol]-2'-amine;

(5S)-3-(3,3-difluoro-1-pyrolidinyl)-7-(2-fluoro-3-pyridinyl)spiro[chromeno[2,3-c]pyridine-5,4'-[1,3]oxazol]-2'-amine;

(5S)-3-(4,4-difluoro-1-piperidinyl)-7-(2-fluoro-3-pyridinyl)spiro[chromeno[2,3-c]pyridine-5,4'-[1,3]oxazol]-2'-amine;

(5S)-3-(4,4-difluoro-1-piperidinyl)-7-(5-fluoro-3-pyridinyl)spiro[chromeno[2,3-c]pyridine-5,4'-[1,3]oxazol]-2'-amine;

(5S)-7-(2-fluoro-3-pyridinyl)-3-((3S)-3-fluoro-1-pyrrolidinyl)spiro[chromeno[2,3-c]pyridine-5,4'-[1,3]oxazol]-2'-amine;

3-((5S)-2'-amino-3-(3,3-difluoro-1-pyrrolidinyl)spiro[chromeno[2,3-c]pyridine-5,4'-[1,3]oxazol]-7-yl)benzonitrile;

3-(((4S)-2-amino-5'-fluoro-7'-(6-methyl-3-pyridinyl)spiro[1,3-oxazole-4,9'-xanthen]-2'-yl)oxy)-2,2-dimethylpropanenitrile;

(4S)-2'-(3,6-dihydro-2H-pyran-4-yl)-4'-fluoro-7'-(2-pyrazinyl)spiro[1,3-oxazole-4,9'-xanthen]-2-amine;

(5S)-7-(3-chloro-2-fluorophenyl)-3-((3-methyl-3-oxetanyl)ethynyl)spiro[chromeno[2,3-b]pyridine-5,4'-[1,3]oxazol]-2'-amine;

(5S)-3-(3,6-dihydro-2H-pyran-4-yl)-1-fluoro-7-(2-fluoro-3-pyridinyl)spiro[chromeno[2,3-c]pyridine-5,4'-[1,3]oxazol]-2'-amine;

(5S)-1-fluoro-7-(2-fluoro-3-pyridinyl)-3-(tetrahydro-2H-pyran-4-yl)spiro[chromeno[2,3-c]pyridine-5,4'-[1,3]oxazol]-2'-amine; and (4R)-7'-(6,6-dimethyl-3,6-dihydro-2H-pyran-4-yl)-3'-fluoro-2'-(5-pyrimidinyl)spiro[1,3-oxazole-4,9'-xanthen]-2-amine In another embodiment, the invention provides the following compounds, or pharmaceutically acceptable salt or stereoisomer thereof, selected from (5S)-7-(2,4-difluoro-3-pyridinyl)-3-(3,6-dihydro-2H-pyran-4-yl)spiro[chromeno[2,3-c]pyridine-5,4'-[1,3]oxazol]-2'-amine;

(5S)-3-(3,6-dihydro-2H-pyran-4-yl)-7-(2-fluoro-3-pyridinyl)spiro[chromeno[2,3-b]pyridine-5,4'-[1,3]thiazol]-2'-amine;

3-((5S)-2'-amino-3-((3-methyl-3-oxetanyl)ethynyl)spiro[chromeno[2,3-b]pyridine-5,4'-[1,3]oxazol]-7-yl)benzonitrile;

(4S)-4'-fluoro-7'-(2-fluoro-3-pyridinyl)-2'-(2-pyrimidinyl)spiro[1,3-oxazole-4,9'-xanthen]-2-amine;

(4S)-2'-(5,6-dihydro-2H-pyran-3-yl)-4'-fluoro-7'-(2-fluoro-3-pyridinyl)spiro[1,3-oxazole-4,9'-xanthen]-2-amine;

(5S)-3-(3,6-dihydro-2H-pyran-4-yl)-1-fluoro-7-(2-fluoro-3-pyridinyl)spiro[chromeno[2,3-c]pyridine-5,4'-[1,3]oxazol]-2'-amine;

(5S)-1-fluoro-7-(2-fluoro-3-pyridinyl)-3-(tetrahydro-2H-pyran-4-yl)spiro[chromeno[2,3-c]pyridine-5,4'-[1,3]oxazol]-2'-amine;

(4S)-4'-fluoro-7'-(2-fluoro-5-methyl-3-pyridinyl)-2'-(4-morpholinyl)spiro[1,3-oxazole-4,9'-xanthen]-2-amine;

(5S)-7-(2-fluoro-3-pyridinyl)-3-((3S)-3-fluoro-1-pyrrolidinyl)spiro[chromeno[2,3-c]pyridine-5,4'-[1,3]oxazol]-2'-amine;

3-((5S)-2'-amino-3-(3,3-difluoro-1-pyrolidinyl)spiro[chromeno[2,3-c]pyridine-5,4'-[1,3]oxazol]-7-yl)benzonitrile;

(5S)-3-(6,6-dimethyl-3,6-dihydro-2H-pyran-4-yl)-7-(5-fluoro-3-pyridinyl)spiro[chromeno[2,3-c]pyridine-5,4'-[1,3]oxazol]-2'-amine;

(4R)-2'-(3,6-dihydro-2H-pyran-4-yl)-7'-(2-fluoro-3-pyridinyl)spiro[1,3-oxazole-4,9'-xanthen]-2-amine;

(5S)-3-(4,4-difluoro-1-piperidinyl)-7-(2-fluoro-3-pyridinyl)spiro[chromeno[2,3-c]pyridine-5,4'-[1,3]oxazol]-2'-amine;

(5S)-3-(3,3-difluoro-1-pyrrolidinyl)-7-(3-pyridinyl)spiro[chromeno[2,3-c]pyridine-5,4'-[1,3]oxazol]-2'-amine;

(4S)-4'-fluoro-7'-(2-fluoro-3-pyridinyl)-2'-(4-morpholinyl)spiro[1,3-oxazole-4,9'-xanthen]-2-amine;

(5S)-3-(3,3-difluoro-1-pyrrolidinyl)-7-(2-fluoro-3-pyridinyl)spiro[chromeno[2,3-c]pyridine-5,4'-[1,3]oxazol]-2'-amine;

(4S)-4'-fluoro-7'-(2-fluoro-3-pyridinyl)-2'-(8-oxa-3-azabicyclo[3.2.1]oct-3-yl)spiro[1,3-oxazole-4,9'-xanthen]-2-amine;

(4S)-4'-fluoro-7'-(2-fluoro-3-pyridinyl)-2'-(2-methyl-5-pyrimidinyl)spiro[1,3-oxazole-4,9'-xanthen]-2-amine;

(5S)-3-(3,6-dihydro-2H-pyran-4-yl)-7-(2-fluoro-4-methyl-3-pyridinyl)spiro[chromeno[2,3-c]pyridine-5,4'-[1,3]oxazol]-2'-amine;

(4S)-4'-fluoro-7'-(6-fluoro-3-pyridinyl)-2'-(1-methyl-1H-pyrazol-4-yl)spiro[1,3-oxazole-4,9'-xanthen]-2-amine;

(4S)-4'-fluoro-7'-(2-fluoro-3-pyridinyl)-2'-((3S)-3-fluoro-1-pyrrolidinyl)spiro[1,3-oxazole-4,9'-xanthen]-2-amine;

(5R)-3-(3,3-dimethyl-1-butyn-1-yl)-8-fluoro-7-(5-pyrimidinyl)spiro[chromeno[2,3-b]pyridine-5,4'-[1,3]oxazol]-2'-amine;

(5S)-3-(6,6-dimethyl-3,6-dihydro-2H-pyran-4-yl)-7-(6-fluoro-3-pyridinyl)spiro[chromeno[2,3-c]pyridine-5,4'-[1,3]oxazol]-2'-amine; and (5S)-3-(5,6-dihydro-2H-pyran-3-yl)-7-(2-fluoro-3-pyridinyl)spiro[chromeno[2,3-c]pyridine-5,4'-[1,3]oxazol]-2'-amine In another embodiment, the invention provides the following compounds, or pharmaceutically acceptable salt or stereoisomer thereof, selected from (5S)-3-(4,4-difluoro-1-piperidinyl)-7-(3-pyridinyl)spiro[chromeno[2,3-c]pyridine-5,4'-[1,3]oxazol]-2'-amine;

(5S)-3-(4,4-difluoro-1-piperidinyl)-7-(5-fluoro-3-pyridinyl)spiro[chromeno[2,3-c]pyridine-5,4'-[1,3]oxazol]-2'-amine;
3-(((4S)-2-amino-5'-fluoro-7'-(6-methyl-3-pyridinyl)spiro[1,3-oxazole-4,9'-xanthen]-2'-yl)oxy)-2,2-dimethylpropanenitrile;
(4S)-2'-(3,6-dihydro-2H-pyran-4-yl)-4'-fluoro-7'-(2-pyrazinyl)spiro[1,3-oxazole-4,9'-xanthen]-2-amine;
(5S)-7-(3-chloro-2-fluorophenyl)-3-(3-methyl-3-oxetanyl)ethynyl)spiro[chromeno[2,3-b]pyridine-5,4'-[1,3]oxazol]-2'-amine;
(5S)-1-fluoro-7-(2-fluoro-3-pyridinyl)-3-(3-pyridinyl)spiro[chromeno[2,3-c]pyridine-5,4'-[1,3]oxazol]-2'-amine;
(4R)-7'-(6,6-dimethyl-3,6-dihydro-2H-pyran-4-yl)-3'-fluoro-2'-(5-pyrimidinyl)spiro[1,3-oxazole-4,9'-xanthen]-2-amine;
(4S)-3',5'-difluoro-7'-(2-fluoro-2-methylpropoxy)-2'-(5-pyrimidinyl)spiro[1,3-oxazole-4,9'-xanthen]-2-amine;
(5S)-3-(5,6-dihydro-2H-pyran-3-yl)-7-(2-fluoro-3-pyridinyl)spiro[chromeno[2,3-b]pyridine-5,4'-[1,3]thiazol]-2'-amine;
(5S)-1-fluoro-7-(2-fluoro-3-pyridinyl)-3-((3R)-3-fluoro-1-pyrrolidinyl)spiro[chromeno[2,3-c]pyridine-5,4'-[1,3]oxazol]-2'-amine;
(5S)-7-(2,4-difluoro-3-pyridinyl)-3-(5,6-dihydro-2H-pyran-3-yl)spiro[chromeno[2,3-c]pyridine-5,4'-[1,3]oxazol]-2'-amine;
(5S)-3-(5,6-dihydro-2H-pyran-3-yl)-1-fluoro-7-(2-fluoro-3-pyridinyl)spiro[chromeno[2,3-c]pyridine-5,4'-[1,3]oxazol]-2'-amine;
(5S)-3-(5,6-dihydro-2H-pyran-3-yl)-1-fluoro-7-(3-pyridinyl)spiro[chromeno[2,3-c]pyridine-5,4'-[1,3]oxazol]-2'-amine;
(5S)-1-fluoro-7-(2-fluoro-3-pyridinyl)-3-(6-methyl-3-pyridinyl)spiro[chromeno[2,3-c]pyridine-5,4'-[1,3]oxazol]-2'-amine;
(5S)-1-fluoro-7-(5-(1-propyn-1-yl)-3-pyridinyl)-3-(3-pyridinyl)spiro[chromeno[2,3-c]pyridine-5,4'-[1,3]oxazol]-2'-amine;
(4S)-2'-(5,6-dihydro-2H-pyran-3-yl)-4'-fluoro-7'-(2-fluoro-3-pyridinyl)spiro[1,3-thiazole-4,9'-xanthen]-2-amine;
(5S)-3-(2-fluoro-4-pyridinyl)-1-methoxy-7-(3-pyridinyl)spiro[chromeno[2,3-c]pyridine-5,4'-[1,3]oxazol]-2'-amine;
3-(((4S)-2-amino-4',6'-difluoro-7'-(3-pyridinyl)spiro[1,3-oxazole-4,9'-xanthen]-2'-yl)oxy)-2,2-dimethylpropanenitrile;
(4S)-7'-(3,6-dihydro-2H-pyran-4-yl)-3',5'-difluoro-2'-(2-fluoro-3-pyridinyl)spiro[1,3-oxazole-4,9'-xanthen]-2-amine;
(4S)-3',5'-difluoro-2'-(2-fluoro-3-pyridinyl)-7'-(4-morpholinyl)spiro[1,3-oxazole-4,9'-xanthen]-2-amine;
(5S)-1-fluoro-7-(2-fluoro-3-pyridinyl)-3-(4-morpholinyl)spiro[chromeno[2,3-c]pyridine-5,4'-[1,3]oxazol]-2'-amine;
(5S)-1-fluoro-7-(5-fluoro-3-pyridinyl)-3-(4-morpholinyl)spiro[chromeno[2,3-c]pyridine-5,4'-[1,3]oxazol]-2'-amine;
3-((5S)-2'-amino-1-fluoro-3-(4-morpholinyl)spiro[chromeno[2,3-c]pyridine-5,4'-[1,3]oxazol]-7-yl)benzonitrile; and
(5S)-2-fluoro-7-(2-fluoro-3-pyridinyl)-3-((3-methyl-3-oxetanyl)ethynyl)spiro[chromeno[2,3-b]pyridine-5,4'-[1,3]oxazol]-2'-amine.

In another embodiment, the invention provides the following compounds, or pharmaceutically acceptable salt or stereoisomer thereof, selected from (5S)-3-(3,3-difluoro-1-pyrolidinyl)-1-fluoro-7-(3-pyridinyl)spiro[chromeno[2,3-c]pyridine-5,4'-[1,3]oxazol]-2'-amine;
(5S)-3-(3,3-difluoro-1-pyrrolidinyl)-1-fluoro-7-(2-fluoro-3-pyridinyl)spiro[chromeno[2,3-c]pyridine-5,4'-[1,3]oxazol]-2'-amine;
(5S)-3-(3,3-difluoro-1-pyrrolidinyl)-1-fluoro-7-(5-fluoro-3-pyridinyl)spiro[chromeno[2,3-c]pyridine-5,4'-[1,3]oxazol]-2'-amine;
(5S)-3-(4,4-difluoro-1-piperidinyl)-1-fluoro-7-(5-fluoro-3-pyridinyl)spiro[chromeno[2,3-c]pyridine-5,4'-[1,3]oxazol]-2'-amine;
(5S)-3-(5,6-dihydro-2H-pyran-3-yl)-7-(2-fluoro-3-pyridinyl)spiro[chromeno[2,3-c]pyridine-5,4'-[1,3]thiazol]-2'-amine;
(5S)-3-(3,6-dihydro-2H-pyran-4-yl)-7-(5-(1-propyn-1-yl)-3-pyridinyl)spiro[chromeno[2,3-b]pyridine-5,4'-[1,3]oxazol]-2'-amine;
(4S)-4'-fluoro-2'-(1-methyl-1H-pyrazol-4-yl)-7'-(5-(1-propyn-1-yl)-3-pyridinyl)spiro[1,3-oxazole-4,9'-xanthen]-2-amine;
4-((4S)-2-amino-4'-fluoro-7'-(5-(1-propyn-1-yl)-3-pyridinyl)spiro[1,3-oxazole-4,9'-xanthen]-2'-yl)-2-methyl-3-butyn-2-ol;
(5S)-1-fluoro-7-(2-fluoro-3-pyridinyl)-3-(2-fluoro-4-pyridinyl)spiro[chromeno[2,3-c]pyridine-5,4'-[1,3]thiazol]-2'-amine;
(5S)-7-(2-fluoro-3-pyridinyl)-3-(4-morpholinyl)spiro[chromeno[2,3-c]pyridine-5,4'-[1,3]thiazol]-2'-amine;
(5S)-7-(2-fluoro-3-pyridinyl)-3-(2-fluoro-4-pyridinyl)spiro[chromeno[2,3-c]pyridine-5,4'-[1,3]thiazol]-2'-amine;
(5S)-3-(3,6-dihydro-2H-pyran-4-yl)-1-fluoro-7-(2-fluoro-3-pyridinyl)spiro[chromeno[2,3-c]pyridine-5,4'-[1,3]thiazol]-2'-amine;
(5S)-1-fluoro-7-(2-fluoro-3-pyridinyl)-3-(tetrahydro-2H-pyran-4-yl)spiro[chromeno[2,3-c]pyridine-5,4'-[1,3]thiazol]-2'-amine;
(5S)-3-(6,6-dimethyl-3,6-dihydro-2H-pyran-4-yl)-1-fluoro-7-(2-fluoro-3-pyridinyl)spiro[chromeno[2,3-c]pyridine-5,4'-[1,3]thiazol]-2'-amine;
(5S)-1-fluoro-7-(2-fluoro-3-pyridinyl)-3-(2-methyl-4-pyridinyl)spiro[chromeno[2,3-c]pyridine-5,4'-[1,3]thiazol]-2'-amine;
(4S)-4'-fluoro-2'-(2-fluoro-2-methylpropoxy)-7'-(2-fluoro-3-pyridinyl)spiro[1,3-thiazole-4,9'-xanthen]-2-amine;
(4S)-2'-(4,4-difluoro-1-piperidinyl)-4'-fluoro-7'-(2-fluoro-3-pyridinyl)spiro[1,3-thiazole-4,9'-xanthen]-2-amine;
(4S)-2'-(3,3-difluoro-1-pyrrolidinyl)-4'-fluoro-7'-(2-fluoro-3-pyridinyl)spiro[1,3-thiazole-4,9'-xanthen]-2-amine;
(4S)-4'-fluoro-7'-(2-fluoro-3-pyridinyl)-2'-(2-pyrimidinyl)spiro[1,3-thiazole-4,9'-xanthen]-2-amine;
(4S)-4'-fluoro-7'-(2-fluoro-3-pyridinyl)-2'-(3-pyridinyl)spiro[1,3-thiazole-4,9'-xanthen]-2-amine; and
(4S)-4'-fluoro-7'-(2-fluoro-3-pyridinyl)-2'-((1S,4S)-2-oxa-5-azabicyclo[2.2.1]hept-5-yl)spiro[1,3-thiazole-4,9'-xanthen]-2-amine.

In another embodiment, the invention provides the following compounds, or pharmaceutically acceptable salt or stereoisomer thereof, selected from (5S)-7-(2,4-difluoro-3-pyridinyl)-3-(3,6-dihydro-2H-pyran-4-yl)spiro[chromeno[2,3-c]pyridine-5,4'-[1,3]oxazol]-2'-amine;
(5S)-3-(5,6-dihydro-2H-pyran-3-yl)-1-fluoro-7-(3-pyridinyl)spiro[chromeno[2,3-c]pyridine-5,4'-[1,3]oxazol]-2'-amine;

(5S)-3-(5,6-dihydro-2H-pyran-3-yl)-1-fluoro-7-(2-fluoro-3-pyridinyl)spiro[chromeno[2,3-c]pyridine-5,4'-[1,3]oxazol]-2'-amine;

(4S)-2'-(5,6-dihydro-2H-pyran-3-yl)-4'-fluoro-7'-(2-fluoro-3-pyridinyl)spiro[1,3-thiazole-4,9'-xanthen]-2-amine;

(5S)-3-(3,6-dihydro-2H-pyran-4-yl)-7-(2-fluoro-4-methyl-3-pyridinyl)spiro[chromeno[2,3-c]pyridine-5,4'-[1,3]oxazol]-2'-amine;

(4S)-7'-(3,6-dihydro-2H-pyran-4-yl)-3',5'-difluoro-2'-(2-fluoro-3-pyridinyl)spiro[1,3-oxazole-4,9'-xanthen]-2-amine;

(4S)-2'-(5,6-dihydro-2H-pyran-3-yl)-4'-fluoro-7'-(2-fluoro-3-pyridinyl)spiro[1,3-oxazole-4,9'-xanthen]-2-amine;

(5S)-3-(5,6-dihydro-2H-pyran-3-yl)-7-(2-fluoro-3-pyridinyl)spiro[chromeno[2,3-c]pyridine-5,4'-[1,3]oxazol]-2'-amine;

(5S)-3-(6,6-dimethyl-3,6-dihydro-2H-pyran-4-yl)-7-(5-fluoro-3-pyridinyl)spiro[chromeno[2,3-c]pyridine-5,4'-[1,3]oxazol]-2'-amine;

(4S)-2'-(3,6-dihydro-2H-pyran-4-yl)-4'-fluoro-7'-(2-pyrazinyl)spiro[1,3-oxazole-4,9'-xanthen]-2-amine;

(5S)-3-(3,6-dihydro-2H-pyran-4-yl)-7-(5-(1-propyn-1-yl)-3-pyridinyl)spiro[chromeno[2,3-b]pyridine-5,4'-[1,3]oxazol]-2'-amine;

(5S)-3-(3,6-dihydro-2H-pyran-4-yl)-7-(2-fluoro-3-pyridinyl)spiro[chromeno[2,3-b]pyridine-5,4'-[1,3]thiazol]-2'-amine;

(5S)-3-(3,6-dihydro-2H-pyran-4-yl)-1-fluoro-7-(2-fluoro-3-pyridinyl)spiro[chromeno[2,3-c]pyridine-5,4'-[1,3]thiazol]-2'-amine;

(5S)-3-(3,6-dihydro-2H-pyran-4-yl)-1-fluoro-7-(2-fluoro-3-pyridinyl)spiro[chromeno[2,3-c]pyridine-5,4'-[1,3]oxazol]-2'-amine; and (5S)-3-(5,6-dihydro-2H-pyran-3-yl)-1-fluoro-7-(2-fluoro-3-pyridinyl)spiro[chromeno[2,3-c]pyridine-5,4'-[1,3]thiazol]-2'-amine.

In another embodiment, the invention provides the following compounds, or pharmaceutically acceptable salt or stereoisomer thereof, selected from (4S)-4'-fluoro-7'-(2-fluoro-3-pyridinyl)-2'-(4-morpholinyl)spiro[1,3-oxazole-4,9'-xanthen]-2-amine;

(5S)-1-fluoro-7-(2-fluoro-3-pyridinyl)-3-(4-morpholinyl)spiro[chromeno[2,3-c]pyridine-5,4'-[1,3]oxazol]-2'-amine;

(5S)-1-fluoro-7-(5-fluoro-3-pyridinyl)-3-(4-morpholinyl)spiro[chromeno[2,3-c]pyridine-5,4'-[1,3]oxazol]-2'-amine;

3-((5S)-2'-amino-1-fluoro-3-(4-morpholinyl)spiro[chromeno[2,3-c]pyridine-5,4'-[1,3]oxazol]-7-yl)benzonitrile; and (4S)-4'-fluoro-7'-(2-fluoro-3-pyridinyl)-2'-((1S,4S)-2-oxa-5-azabicyclo[2.2.1]hept-5-yl)spiro[1,3-thiazole-4,9'-xanthen]-2-amine.

In another embodiment, the invention provides the following compounds, or pharmaceutically acceptable salt or stereoisomer thereof, selected from (5S)-3-(3,3-difluoro-1-pyrrolidinyl)-1-fluoro-7-(3-pyridinyl)spiro[chromeno[2,3-c]pyridine-5,4'-[1,3]oxazol]-2'-amine;

(5S)-3-(4,4-difluoro-1-piperidinyl)-1-fluoro-7-(2-fluoro-3-pyridinyl)spiro[chromeno[2,3-c]pyridine-5,4'-[1,3]oxazol]-2'-amine;

(5S)-3-(3,3-difluoro-1-pyrrolidinyl)-1-fluoro-7-(2-fluoro-3-pyridinyl)spiro[chromeno[2,3-c]pyridine-5,4'-[1,3]oxazol]-2'-amine;

(5S)-3-(3,3-difluoro-1-pyrrolidinyl)-1-fluoro-7-(5-fluoro-3-pyridinyl)spiro[chromeno[2,3-c]pyridine-5,4'-[1,3]oxazol]-2'-amine;

(5S)-3-(4,4-difluoro-1-piperidinyl)-1-fluoro-7-(5-fluoro-3-pyridinyl)spiro[chromeno[2,3-c]pyridine-5,4'-[1,3]oxazol]-2'-amine;

(5S)-3-(3,3-difluoro-1-pyrrolidinyl)-7-(3-pyridinyl)spiro[chromeno[2,3-c]pyridine-5,4'-[1,3]oxazol]-2'-amine;

(5S)-3-(3,3-difluoro-1-pyrrolidinyl)-7-(2-fluoro-3-pyridinyl)spiro[chromeno[2,3-c]pyridine-5,4'-[1,3]oxazol]-2'-amine;

(5S)-3-(4,4-difluoro-1-piperidinyl)-7-(2-fluoro-3-pyridinyl)spiro[chromeno[2,3-c]pyridine-5,4'-[1,3]oxazol]-2'-amine;

(5S)-7-(2-fluoro-3-pyridinyl)-3-((3S)-3-fluoro-1-pyrrolidinyl)spiro[chromeno[2,3-c]pyridine-5,4'-[1,3]oxazol]-2'-amine;

3-((5S)-2'-amino-3-(3,3-difluoro-1-pyrrolidinyl)spiro[chromeno[2,3-c]pyridine-5,4'-[1,3]oxazol]-7-yl)benzonitrile;

(5S)-1-fluoro-7-(2-fluoro-3-pyridinyl)-3-(tetrahydro-2H-pyran-4-yl)spiro[chromeno[2,3-c]pyridine-5,4'-[1,3]oxazol]-2'-amine; and (4S)-2'-(3,3-difluoro-1-pyrrolidinyl)-4'-fluoro-7'-(2-fluoro-3-pyridinyl)spiro[1,3-thiazole-4,9'-xanthen]-2-amine In another embodiment, the invention provides the following compounds, or pharmaceutically acceptable salt or stereoisomer thereof, selected from (4S)-4'-fluoro-7'-(2-fluoro-3-pyridinyl)-2'-(2-pyrimidinyl)spiro[1,3-oxazole-4,9'-xanthen]-2-amine;

(5S)-1-fluoro-7-(2-fluoro-3-pyridinyl)-3-(6-methyl-3-pyridinyl)spiro[chromeno[2,3-c]pyridine-5,4'-[1,3]oxazol]-2'-amine;

(5S)-1-fluoro-7-(5-(1-propyn-1-yl)-3-pyridinyl)-3-(3-pyridinyl)spiro[chromeno[2,3-c]pyridine-5,4'-[1,3]oxazol]-2'-amine;

(4S)-4'-fluoro-2'-(1-methyl-1H-pyrazol-4-yl)-7'-(5-(1-propyn-1-yl)-3-pyridinyl)spiro[1,3-oxazole-4,9'-xanthen]-2-amine;

(5S)-1-fluoro-7-(2-fluoro-3-pyridinyl)-3-(2-fluoro-4-pyridinyl)spiro[chromeno[2,3-c]pyridine-5,4'-[1,3]thiazol]-2'-amine;

(5S)-7-(2-fluoro-3-pyridinyl)-3-(2-fluoro-4-pyridinyl)spiro[chromeno[2,3-c]pyridine-5,4'-[1,3]thiazol]-2'-amine;

(5S)-1-fluoro-7-(2-fluoro-3-pyridinyl)-3-(3-pyridinyl)spiro[chromeno[2,3-c]pyridine-5,4'-[1,3]oxazol]-2'-amine;

(4S)-4'-fluoro-7'-(2-fluoro-3-pyridinyl)-2'-(2-pyrimidinyl)spiro[1,3-thiazole-4,9'-xanthen]-2-amine; and (4S)-4'-fluoro-7'-(2-fluoro-3-pyridinyl)-2'-(3-pyridinyl)spiro[1,3-thiazole-4,9'-xanthen]-2-amine All of the possible embodiments described herein for various of the R groups of the compounds of Formula I may be applied, as appropriate, to compounds of Formulas II, II-A, III, IV and V and any sub-formulas thereof.

In another embodiment, the invention provides each of the Examplary compounds, and stereoisomers, tautomers, solvates, pharmaceutically acceptable salts, derivatives or prodrugs thereof, and related intermediates, described herein.

In another embodiment, the invention provides the exemplified compounds described herein, and pharmaceutically acceptable salt forms of each thereof.

DEFINITIONS

The following definitions should assist in understanding the invention described herein.

The phrase "two adjacent R⁸ substituents together with the same atom to which they are attached form a 3-6 membered spirocyclic ring including 0-3 heteroatoms selected from N, O and S" as used herein referd to a the spirocyclic ring as an R⁸ substituent, which itself may be substituted as specified. For example, the following azetidine R² group has a 6-membered spirocyclic R⁸ substituent including one —O— atom:

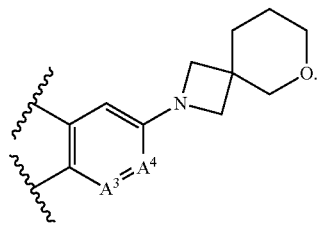

Similarly, the term "spiro-oxetanyl" refers to an oxetan ring attached in a spirocyclic manner, similar to the spirocycic tetrahydropyran shown above.

The term "comprising" is meant to be open ended, i.e., all encompassing and non-limiting. It may be used herein synonymously with "having." Comprising is intended to include each and every indicated or recited component or element(s) while not excluding any other components or elements.

The term "$C_{\alpha-\beta}$alkyl", when used either alone or within other terms such as "haloalkyl" and "alkylamino", embraces linear or branched radicals having $\alpha$ to $\beta$ number of carbon atoms (such as $C_1$-$C_{10}$; $C_1$-$C_6$; or $C_1$-$C_4$). Unless otherwise specified, one or more carbon atoms of the "alkyl" radical may be substituted, such as with a cycloalkyl moiety. Examples of "alkyl" radicals include methyl, cyclopropylmethyl, cyclobutylmethyl, cyclopentylmethyl, ethyl, cyclopropylethyl, cyclobutylethyl, cyclopentylethyl, n-propyl, isopropyl, n-butyl, cyclopropylbutyl, isobutyl, sec-butyl, tert-butyl, pentyl, isoamyl, hexyl and the like.

The term "$C_{\alpha-\beta}$alkenyl", when used alone or in combination, embraces linear or branched radicals having at least one carbon-carbon double bond in a moiety having a number of carbon atoms in the range from $\alpha$ and $\beta$. Included within alkenyl radicals are "lower alkenyl" radicals having two to about six carbon atoms and, for example, those radicals having two to about four carbon atoms. Examples of alkenyl radicals include, without limitation, ethenyl, propenyl, allyl, propenyl, butenyl and 4-methylbutenyl. The terms "alkenyl" and "lower alkenyl", embrace radicals having "cis" and "trans" orientations, or alternatively, "E" and "Z" orientations, as appreciated by those of ordinary skill in the art.

The term "$C_{\alpha-\beta}$alkynyl", when used alone or in combination, denotes linear or branched radicals having at least one carbon-carbon triple bond in a moiety having a number of carbon atoms in the range from $\alpha$ and $\beta$. Examples of alkynyl radicals include "lower alkynyl" radicals having two to about six carbon atoms and, for example, lower alkynyl radicals having two to about four carbon atoms. Examples of such radicals include, without limitation, ethynyl, propynyl (propargyl), butynyl, and the like.

The term "$C_{\alpha-\beta}$-alkyl", "$C_{\alpha-\beta}$-alkenyl" and "$C_{\alpha-\beta}$-alkynyl", when used with other terms such as "wherein 1, 2 or 3 carbon atoms of said $C_{\alpha-\beta}$-alkyl, $C_{\alpha-\beta}$-alkenyl or $C_{2\alpha-\beta}$-alkynyl is optionally replaced with a heteroatom selected from O, S, S(O), S(O)$_2$ and N" embraces linear or branched radicals wherein one or more of the carbon atoms may be replaced with a heteroatom. Examples of such "alkyl" radicals include —O-methyl, —O-ethyl, —CH$_2$—O—CH$_3$, —CH$_2$CH$_2$—O—CH$_3$, —NH—CH$_2$, —CH$_2$CH$_2$—N(CH$_3$)—CH$_3$, —S—(CH$_2$)$_3$CH$_2$, —CH$_2$CH$_2$—S—CH$_3$ and the like. Accordingly, such radicals also include radicals encompassed by —OR⁷ where R⁷ may be defined as a $C_{\alpha-\beta}$-alkyl. Examples of such "alkenyl" radicals include —NH—CH$_2$CH=CH$_2$, —S—CH$_2$CH$_2$CH=CHCH$_3$ and the like. Similar examples exist for such "alkynyl" radicals, as appreciated by those skilled in the art.

The term "$C_{\alpha-\beta}$alkoxyl" when used alone or in combination, embraces linear or branched oxygen-containing alkyl radicals each having $\alpha$ to $\beta$ number of carbon atoms (such as $C_1$-$C_{10}$). The terms "alkoxy" and "alkoxyl", when used alone or in combination, embraces linear or branched oxygen-containing radicals each having alkyl and substituted alkyl portions of one or more carbon atoms. Examples of such radicals include methoxy, ethoxy, propoxy, butoxy and tert-butoxy. Alkoxy radicals may be further substituted with one or more halo atoms, such as fluoro, chloro or bromo, to provide "haloalkoxy" radicals or with other substitution. Examples of such radicals include fluoromethoxy, chloromethoxy, trifluoromethoxy, trifluoroethoxy, fluoroethoxy, fluoropropoxy and cyclopropylmethoxy.

The term "aryl", when used alone or in combination, means a carbocyclic aromatic moiety containing one, two or even three rings wherein such rings may be attached together in a fused manner. Every ring of an "aryl" multi-ring system need not be aromatic, and the ring(s) fused to the aromatic ring may be partially or fully unsaturated and include one or more heteroatoms selected from nitrogen, oxygen and sulfur. Thus, the term "aryl" embraces aromatic radicals such as phenyl, naphthyl, indenyl, tetrahydronaphthyl, dihydrobenzafuranyl, anthracenyl, indanyl, benzodioxazinyl, and the like. The "aryl" group may be substituted, such as with 1 to 5 substituents including lower alkyl, hydroxyl, halo, haloalkyl, nitro, cyano, alkoxy and lower alkylamino, and the like. Phenyl substituted with —O—CH$_2$—O— or —O—CH$_2$—CH$_2$—O— forms an aryl benzodioxolyl substituent.

The term "carbocyclic", also referred to herein as "cycloalkyl", when used alone or in combination, means a partially or fully saturated ring moiety containing one ("monocyclic"), two ("bicyclic") or even three ("tricyclic") rings wherein such rings may be attached together in a fused manner and formed from carbon atoms. Examples of saturated carbocyclic radicals include saturated 3 to 6-membered monocyclic groups such as cyclopropane, cyclobutane, cyclopentane and cyclohexane. Carbocycilc may be substituted as described herein.

The terms "ring" and "ring system" refer to a ring comprising the delineated number of atoms, the atoms being carbon or, where indicated, a heteroatom such as nitrogen, oxygen or sulfur. Where the number of atoms is not delineated, such as a "monocyclic ring system" or a "bicyclic ring system", the numbers of atoms are 3-8 for a monocyclic and 6-12 for a bicyclic ring. The ring itself, as well as any substitutents thereon, may be attached at any atom that allows a stable compound to be formed. The term "nonaromatic" ring or ring system refers to the fact that at least one, but not necessarily all, rings in a bicyclic or tricyclic ring system is nonaromatic.

The term "cycloalkenyl", when used alone or in combination, means a partially or fully saturated cycloalkyl containing one, two or even three rings in a structure having at least one carbon-carbon double bond in the structure. Examples of cycloalkenyl groups include $C_3$-$C_6$ rings, such as compounds including, without limitation, cyclopropene, cyclobutene, cyclopentene and cyclohexene. The term also includes carbocyclic groups having two or more carbon-carbon double bonds such as "cycloalkyldienyl" compounds. Examples of cycloalkyldienyl groups include, without limitation, cyclopentadiene and cycloheptadiene.

The term "halo", when used alone or in combination, means halogens such as fluorine, chlorine, bromine or iodine atoms.

The term "haloalkyl", when used alone or in combination, embraces radicals wherein any one or more of the alkyl carbon atoms is substituted with halo as defined above. For example, this term includes monohaloalkyl, dihaloalkyl and polyhaloalkyl radicals such as a perhaloalkyl. A monohaloalkyl radical, for example, may have either an iodo, bromo, chloro or fluoro atom within the radical. Dihalo and polyhaloalkyl radicals may have two or more of the same halo atoms or a combination of different halo radicals. Examples of haloalkyl radicals include fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl. "Perfluoroalkyl", as used herein, refers to alkyl radicals having all hydrogen atoms replaced with fluoro atoms. Examples include trifluoromethyl and pentafluoroethyl.

The term "heteroaryl", as used herein, either alone or in combination, means a fully unsaturated (aromatic) ring moiety formed from carbon atoms and having one or more heteroatoms selected from nitrogen, oxygen and sulfur. The ring moiety or ring system may contain one ("monocyclic"), two ("bicyclic") or even three ("tricyclic") rings wherein such rings are attached together in a fused manner. Every ring of a "heteroaryl" ring system need not be aromatic, and the ring(s) fused thereto (to the heteroaromatic ring) may be partially or fully saturated and optionally include one or more heteroatoms selected from nitrogen, oxygen and sulfur. The term "heteroaryl" does not include rings having ring members of —O—O—, —O—S— or —S—S—.

Examples of unsaturated heteroaryl radicals, include unsaturated 5- to 6-membered heteromonocyclyl groups containing 1 to 4 nitrogen atoms, including for example, pyrrolyl, imidazolyl, pyrazolyl, 2-pyridyl, 3-pyridyl, 4-pyridyl, pyrimidyl, pyrazinyl, pyridazinyl, triazolyl [e.g., 4H-1,2,4-triazolyl, 1H-1,2,3-triazolyl, 2H-1,2,3-triazolyl] and tetrazole; unsaturated 7- to 10-membered heterobicyclyl groups containing 1 to 4 nitrogen atoms, including for example, quinolinyl, isoquinolinyl, quinazolinyl, isoquinazolinyl, azaquinazolinyl, and the like; unsaturated 5- to 6-membered heteromonocyclic group containing an oxygen atom, for example, pyranyl, 2-furyl, 3-furyl, benzofuryl, etc.; unsaturated 5 to 6-membered heteromonocyclic group containing a sulfur atom, for example, 2-thienyl, 3-thienyl, benzothienyl, etc.; unsaturated 5- to 6-membered heteromonocyclic group containing 1 to 2 oxygen atoms and 1 to 3 nitrogen atoms, for example, oxazolyl, isoxazolyl, oxadiazolyl [e.g., 1,2,4-oxadiazolyl, 1,3,4-oxadiazolyl, 1,2,5-oxadiazolyl]; unsaturated 5 to 6-membered heteromonocyclic group containing 1 to 2 sulfur atoms and 1 to 3 nitrogen atoms, for example, thiazolyl, isothiazolyl, thiadiazolyl [e.g., 1,2,4-thiadiazolyl, 1,3,4-thiadiazolyl, 1,2,5-thiadiazolyl].

The term "heterocyclic", when used alone or in combination, means a partially or fully saturated ring moiety containing one, two or even three rings wherein such rings may be attached together in a fused manner, formed from carbon atoms and including one or more heteroatoms selected from N, O or S. Examples of saturated heterocyclic radicals include saturated 3 to 6-membered heteromonocyclic groups containing 1 to 4 nitrogen atoms [e.g. pyrrolidinyl, imidazolidinyl, piperidinyl, pyrrolinyl, piperazinyl]; saturated 3 to 6-membered heteromonocyclic group containing 1 to 2 oxygen atoms and 1 to 3 nitrogen atoms [e.g. morpholinyl]; saturated 3 to 6-membered heteromonocyclic group containing 1 to 2 sulfur atoms and 1 to 3 nitrogen atoms [e.g., thiazolidinyl]. Examples of partially saturated heterocyclyl radicals include dihydrothienyl, dihydropyranyl, dihydrofuryl and dihydrothiazolyl.

The term "heterocycle" also embraces radicals where heterocyclic radicals are fused/condensed with aryl radicals: unsaturated condensed heterocyclic group containing 1 to 5 nitrogen atoms, for example, indolyl, isoindolyl, indolizinyl, benzimidazolyl, quinolyl, isoquinolyl, indazolyl, benzotriazolyl, tetrazolopyridazinyl [e.g., tetrazolo[1,5-b]pyridazinyl]; unsaturated condensed heterocyclic group containing 1 to 2 oxygen atoms and 1 to 3 nitrogen atoms [e.g. benzoxazolyl, benzoxadiazolyl]; unsaturated condensed heterocyclic group containing 1 to 2 sulfur atoms and 1 to 3 nitrogen atoms [e.g., benzothiazolyl, benzothiadiazolyl]; and saturated, partially unsaturated and unsaturated condensed heterocyclic group containing 1 to 2 oxygen or sulfur atoms [e.g. benzofuryl, benzothienyl, 2,3-dihydro-benzo[1,4]dioxinyl and dihydrobenzofuryl]. Examples of heterocyclic radicals include five to ten membered fused or unfused radicals.

Examples of partially saturated and fully saturated heterocyclyls include, without limitation, pyrrolidinyl, imidazolidinyl, piperidinyl, pyrrolinyl, pyrazolidinyl, piperazinyl, morpholinyl, tetrahydropyranyl, dihydropyranyl, dihydrofuranyl and dihydrothiazolyl, and the like.

The term "alkylamino" includes "N-alkylamino" where amino radicals are independently substituted with one alkyl radical. Preferred alkylamino radicals are "lower alkylamino" radicals having one to six carbon atoms. Even more preferred are lower alkylamino radicals having one to three carbon atoms. Examples of such lower alkylamino radicals include N-methylamino, and N-ethylamino, N-propylamino, N-isopropylamino and the like.

The term "dialkylamino" includes "N,N-dialkylamino" where amino radicals are independently substituted with two alkyl radicals. Preferred alkylamino radicals are "lower alkylamino" radicals having one to six carbon atoms. Even more preferred are lower alkylamino radicals having one to three carbon atoms. Examples of such lower alkylamino radicals include N,N-dimethylamino, N,N-diethylamino, and the like.

The term "carbonyl", whether used alone or with other terms, such as "aminocarbonyl", denotes —(C=O)—. "Carbonyl" is also used herein synonymously with the term "oxo".

The term "aminocarbonyl" denotes an amide group of the formula —C(=O)NH$_2$.

The term "alkylthio" or "thioalkoxy" embraces radicals containing a linear or branched alkyl radical, of one to ten carbon atoms, attached to a divalent sulfur atom. An example of "alkylthio" or "thioalkoxy" is methylthio, (CH$_3$S—).

The term "Formula I" includes any sub formulas, such as Formulas I-A, I-B, I-C and I-D.

The term "pharmaceutically-acceptable" when used with reference to a compound of Formulas I-V is intended to refer to a form of the compound that is safe for administration. For example, a salt form, a solvate, a hydrate, a prodrug or derivative form of a compound of Formulas I-V, which has been approved for mammalian use, via oral ingestion or other routes of administration, by a governing body or regulatory agency, such as the Food and Drug Administration (FDA) of the United States, is pharmaceutically acceptable.

Included in the compounds of Formulas I-V are the pharmaceutically acceptable salt forms of the free-base compounds. The term "pharmaceutically-acceptable salts" embraces salts commonly used to form alkali metal salts and to form addition salts of free acids or free bases. As appreciated by those of ordinary skill in the art, salts may be formed from ionic associations, charge-charge interactions, covalent bonding, complexation, coordination, etc. The nature of the salt is not critical, provided that it is pharmaceutically acceptable.

Suitable pharmaceutically acceptable acid addition salts of compounds of Formulas I-V may be prepared from an inorganic acid or from an organic acid. Examples of such inorganic acids are hydrochloric, hydrobromic, hydroiodic, hydrofluoric, nitric, carbonic, sulfuric and phosphoric acid. Appropriate organic acids may be selected from aliphatic, cycloaliphatic, aromatic, arylaliphatic, heterocyclic, carboxylic and sulfonic classes of organic acids, examples of which include, without limitation, formic, acetic, adipic, butyric, propionic, succinic, glycolic, gluconic, lactic, malic, tartaric, citric, ascorbic, glucuronic, maleic, fumaric, pyruvic, aspartic, glutamic, benzoic, anthranilic, mesylic, 4-hydroxybenzoic, phenylacetic, mandelic, embonic (pamoic), methanesulfonic (mesylate), ethanesulfonic, ethanedisulfonic, benzenesulfonic (besylate), pantothenic, 2-hydroxyethanesulfonic, toluenesulfonic, sulfanilic, cyclohexylaminosulfonic, camphoric, camphorsulfonic, digluconic, cyclopentanepropionic, dodecylsulfonic, glucoheptanoic, glycerophosphonic, heptanoic, hexanoic, 2-hydroxy-ethanesulfonic, nicotinic, 2-naphthalenesulfonic, oxalic, palmoic, pectinic, persulfuric, 2-phenylpropionic, picric, pivalic propionic, succinic, thiocyanic, undecanoic, stearic, algenic, β-hydroxybutyric, salicylic, galactaric and galacturonic acid.

Suitable pharmaceutically-acceptable base addition salts of compounds of Formulas I-V include metallic salts, such as salts made from aluminum, calcium, lithium, magnesium, potassium, sodium and zinc, or salts made from organic bases including, without limitation, primary, secondary and tertiary amines, substituted amines including cyclic amines, such as caffeine, arginine, diethylamine, N-ethyl piperidine, histidine, glucamine, isopropylamine, lysine, morpholine, N-ethyl morpholine, piperazine, piperidine, triethylamine, diisopropylethylamine and trimethylamine. All of these salts may be prepared by conventional means from the corresponding compound of the invention by reacting, for example, the appropriate acid or base with the compound of Formulas I-V.

Also, the basic nitrogen-containing groups can be quaternized with such agents as lower alkyl halides, such as methyl, ethyl, propyl, and butyl chloride, bromides and iodides; dialkyl sulfates like dimethyl, diethyl, dibutyl, and diamyl sulfates, long chain halides such as decyl, lauryl, myristyl and stearyl chlorides, bromides and iodides, aralkyl halides like benzyl and phenethyl bromides, and others. Water or oil-soluble or dispersible products are thereby obtained. Nitrogen atoms may also be oxidized to form the corresponding N-oxide. Such oxidized compounds are also within the scope of the invention.

Additional examples of such salts can be found in Berge et al., J. Pharm. Sci., 66:1 (1977). Conventional methods may be used to form the salts. For example, a phosphate salt of a compound of the invention may be made by combining the desired compound free base in a desired solvent, or combination of solvents, with phosphoric acid in a desired stoichiometric amount, at a desired temperature, typically under heat (depending upon the boiling point of the solvent). The salt can be precipitated upon cooling (slow or fast) and may crystallize (i.e., if crystalline in nature), as appreciated by those of ordinary skill in the art. Further, hemi-, mono-, di, tri- and poly-salt forms of the compounds of the present invention are also contemplated herein. Similarly, hemi-, mono-, di, tri- and poly-hydrated forms of the compounds, salts and derivatives thereof, are also contemplated herein.

The term "derivative" is intended to encompass any salt of a compound of this invention, any ester of a compound of this invention, or any other compound, which upon administration to a patient is capable of providing (directly or indirectly) a compound of this invention, or a metabolite or residue thereof, characterized by the ability to the ability to modulate an enzyme.

The term "pharmaceutically-acceptable derivative" as used herein, denotes a derivative which is pharmaceutically acceptable.

The term "prodrug", as used herein, denotes a compound which upon administration to a subject or patient is capable of providing (directly or indirectly) a compound of this invention. Examples of prodrugs would include esterified or hydroxylated compounds where the ester or hydroxyl groups would cleave in vivo, such as in the gut, to produce a compound according to Formula I-V. A "pharmaceutically-acceptable prodrug" as used herein, denotes a prodrug which is pharmaceutically acceptable. Pharmaceutically acceptable modifications to the compounds of Formula I-V are readily appreciated by those of ordinary skill in the art.

The compound(s) of Formulas I-V may be used to treat a subject by administering the compound(s) as a pharmaceutical composition. To this end, the compound(s) can be combined with one or more excipients, including without limitation, carriers, diluents or adjuvants to form a suitable composition, which is described in more detail herein.

The term "excipient", as used herein, denotes any pharmaceutically acceptable additive, carrier, adjuvant, or other suitable ingredient, other than the active pharmaceutical ingredient (API), which is typically included for formulation and/or administration purposes. "Diluent" and "adjuvant" are defined hereinafter.

The terms "treat", "treating," "treatment," and "therapy" as used herein refer to therapy, including without limitation, curative therapy, prophylactic therapy, and preventative therapy. Prophylactic treatment generally constitutes either preventing the onset of disorders altogether or delaying the onset of a pre-clinically evident stage of disorders in individuals.

The phrase "effective dosage amount" is intended to quantify the amount of each agent, which will achieve the goal of improvement in disorder severity and the frequency of incidence over treatment of each agent by itself, while avoiding adverse side effects typically associated with alternative therapies. Accordingly, this term is not limited to a single dose, but may comprise multiple dosages required to bring about a therapeutic or prophylactic response in the subject. For example, "effective dosage amount" is not limited to a single capsule or tablet, but may include more than one capsule or tablet, which is the dose prescribed by a qualified physician or medical care giver to the subject.

The term "leaving group" (also denoted as "LG") generally refers to groups that are displaceable by a nucleophile. Such leaving groups are known in the art. Examples of leaving groups include, but are not limited to, halides (e.g., I, Br, F, Cl), sulfonates (e.g., mesylate, tosylate), sulfides (e.g., $SCH_3$), N-hydroxsuccinimide, N-hydroxybenzotriazole, and the like. Nucleophiles are species that are capable of attacking a molecule at the point of attachment of the leaving group causing displacement of the leaving group. Nucleophiles are known in the art. Examples of nucleophilic groups include, but are not limited to, amines, thiols, alcohols, Grignard reagents, anionic species (e.g., alkoxides, amides, carbanions) and the like.

General Synthetic Procedures

The present invention further comprises procedures for the preparation of compounds of Formulas I-V, intermediates and/or starting materials to prepare compounds of Formulas I-V. The compounds of Formulas I-V can be synthesized according to the procedures described in the following Schemes 1 and 2, wherein the substituents are as defined for Formulas I-V above, except where further noted. Compounds of Formulas I-V may also be synthesized via the various Methods taught in the Examples described herein. Further, compounds of Formulas I-V, and intermediates to prepare the same, may be synthesized by methods, and form intermediates, described in published PCT patent application WO20100030954. The synthetic methods described below are merely exemplary, and the compounds of the invention may also be synthesized by alternate routes utilizing alternative synthetic strategies, as appreciated by persons of ordinary skill in the art.

The following list of abbreviations used throughout the specification represent the following and should assist in understanding the invention:

ACN, MeCN—acetonitrile
Aq., aq.—aqueous
Ar—argon (gas)
BOP—benzotriazol-1-yl-oxy Hexafluorophosphate
BuLi—Butyllithium
$Cs_2CO_3$—cesium carbonate
$CHCl_3$—chloroform
$CH_2Cl_2$, DCM—dichloromethane, methylene chloride
Cu(1)I—copper(1) iodide
DCC—dicyclohexylcarbodiimide
DIC—1,3-diisopropylcarbodiimide
DIEA, DIPEA—diisopropylethylamine
DIPA—diisopropylamine
DCE—dichloroethane
DME—dimethoxyethane
DMF—dimethylformamide
DMAP—4-dimethylaminopyridine
DMS—dimethylsulfide
DMSO—dimethylsulfoxide
EDC, EDCI—1-(3-dimethylaminopropyl)-3-ethylcarbodiimide
$Et_2O$—diethyl ether
EtOAc—ethyl acetate
FBS—fetal bovine serum
G, gm—gram
h, hr—hour
$H_2$—hydrogen
$H_2O$—water
HATU O—(7-azabenzotriazol-1-yl)-N,N,N',N'-tetramethyluroniumhexafluorophosphate
HBr—hydrobromic acid
HCl—hydrochloric acid
HOBt—1-hydroxybenzotriazole hydrate
HOAc—acetic acid
HPLC—high pressure liquid chromatography
IPA, IpOH—isopropyl alcohol
$K_2CO_3$—potassium carbonate
KI—potassium iodide
LG—leaving group
LDA—Lithium diisopropylamide
LiOH—lithium hydroxide
$MgSO_4$—magnesium sulfate
MS—mass spectrum
MeOH—methanol
$N_2$—nitrogen
$NaCNBH_3$—sodium cyanoborohydride
$Na_2CO_3$—sodium carbonate
$NaHCO_3$—sodium bicarbonate
NaH—sodium hydride
NaI—sodium iodide
$NaBH_4$—sodium borohydride
NaOH—sodium hydroxide
$Na_2SO_4$—sodium sulfate
$NH_4Cl$—ammonium chloride
$NH_4OH$—ammonium hydroxide
P(t-bu)$_3$—tri(tert-butyl)phosphine
PBS—phosphate buffered saline
Pd/C—palladium on carbon
Pd(PPh$_3$)$_4$—palladium(0)triphenylphosphine tetrakis
Pd(dppf)Cl$_2$—palladium(1,1-bisdiphenylphosphinoferrocene) II chloride
Pd(PhCN)$_2$Cl$_2$—palladium di-cyanophenyl dichloride
Pd(OAc)$_2$—palladium acetate
Pd$_2$(dba)$_3$—tris(dibenzylideneacetone) dipalladium
PyBop—benzotriazol-1-yl-oxy-tripyrrolidino-phosphonium hexafluorophosphate
RT, rt—room temperature
RBF, rbf—round bottom flask
TLC, tlc—thin layer chromatography
TBAF—Tetrabutylammonium flouride
TBTU—O-benzotriazol-1-yl-N,N,N,N'-tetramethyluronium tetrafluoroborate
TEA, Et$_3$N—triethylamine
TFA—trifluoroacetic acid
THF—tetrahydrofuran
UV—ultraviolet light

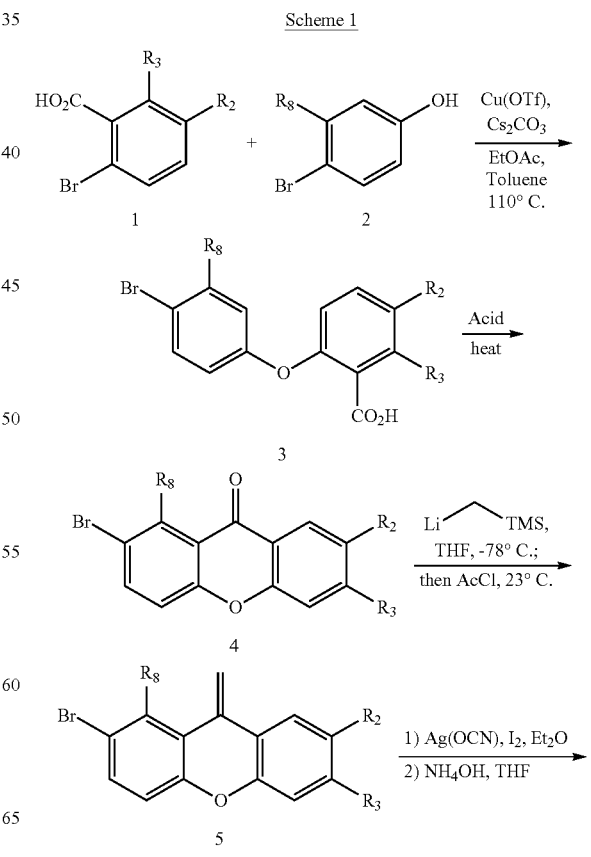

Scheme 1

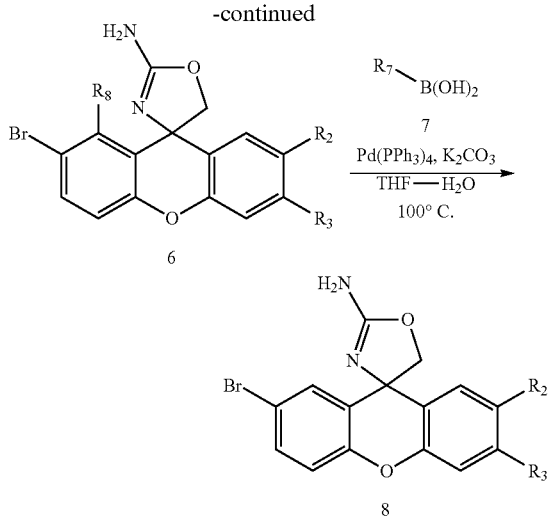

Scheme 1 describes an exemplary method for preparing compounds 8 of Formulas I-II, wherein X is O, one of Y and Z is O while the other of Y and Z is absent, $A^1$ is $CR^6$ and $R^1$, $R^4$, $R^5$, $R^6$ and $R^8$ are each H, respectively. As shown, a bromo-benzoic acid 1 can be coupled to a bromo-phenol 2 using a copper reagent in conjunction with a suitable base, such cesium carbonate, under suitable conditions. The coupled ether 3 can then be treated with an acid, such as sulfuric acid, to effect ring closure to the corresponding bromo-xanthene 4. The ketone of xanthene 4 can be converted to the corresponding ene group as shown under suitable conditions, such as using TMS-methyllithuim or triphenylphosphoniummethyl bromide under suitable reaction conditions, respectively, such as in the presence of a suitable base to afford the ene compound 5. Intermediate 5 can be reacted with cyanotosilver in the presence of iodine and ammonium hydroxide to provide the amino-oxazoline intermediate 6. The bromide of compound 6 can then be converted to desired compounds 8 via coupling at the site of the bromide, such as by a Suzuki or Suzuki-like aromatic-halogen exchange reaction, which reaction generally employs a boronic acid moiety, a phosphine reagent and a base.

The boronic ester intermediates 7 may be prepared by methods described in the following references: (1) PCT Int. Patent Appl. No. WO 2005073189, titled "Preparation of fused heteroaryl derivatives as p38 kinase inhibitors" or (2) PCT Int. Patent Appl. No. WO 2006094187, titled "Preparation of phthalazine, aza- and diaza-phthalazine compounds as protein kinase, especially p38 kinase, inhibitors for treating inflammation and related conditions". Also, desired boronic acids may be purchases commercially in catalogs, or specially made by the vendor.

The Suzuki method is a reaction using a borane reagent, such as a boronic acid 7 or ester such as a dioxaborolane (not shown), and a suitable leaving group containing reagent, such as the Br-xanthene 6 (Br is a suitable halogen leaving group "LG"). As appreciated to one of ordinary skill in the art, Suzuki reactions also utilize a palladium catalyst. Suitable palladium catalysts include, without limitation, $Pd(PPh_3)_4$, $Pd(OAc)_2$ or $Pd(dppf)Cl_2$. Where LG is a halide, the halide may be an iodide, a bromide or even a chloride. Chloropyridyl rings (where $A^1=N$) undergo Suzuki reactions in the presence of $Pd(OAc)_2$. Other LGs are also suitable. For example, Suzuki couplings are known to occur with a sulfonate, such as trifluoromethanesulfonate, as the leaving group.

The Suzuki reaction conditions may vary. For example, Suzuki reactions are generally run in the presence of a suitable base such as a carbonate base, bicarbonate or an acetate base, in a suitable solvent such as toluene, acetonitrile, DMF or an aqueous-organic solvent combination or a biphasic system of solvents. Further, the reaction may require heat depending upon the particular bromide 6 and/or boronic acid or ester 7, as appreciated by those skilled in the art. In addition, where the bromide is an aromatic moiety, such as phenyl, the reaction may be complete in a short period of time with heat.

Other methods of installing the boronate on a desired aromatic ring are known. For example metal coupling chemistry, such Stille, Kumada, Negishi coupling methods, and the like, may be employed to the xanthene cores 6 prepare desired cyclic products 8.

Scheme 2

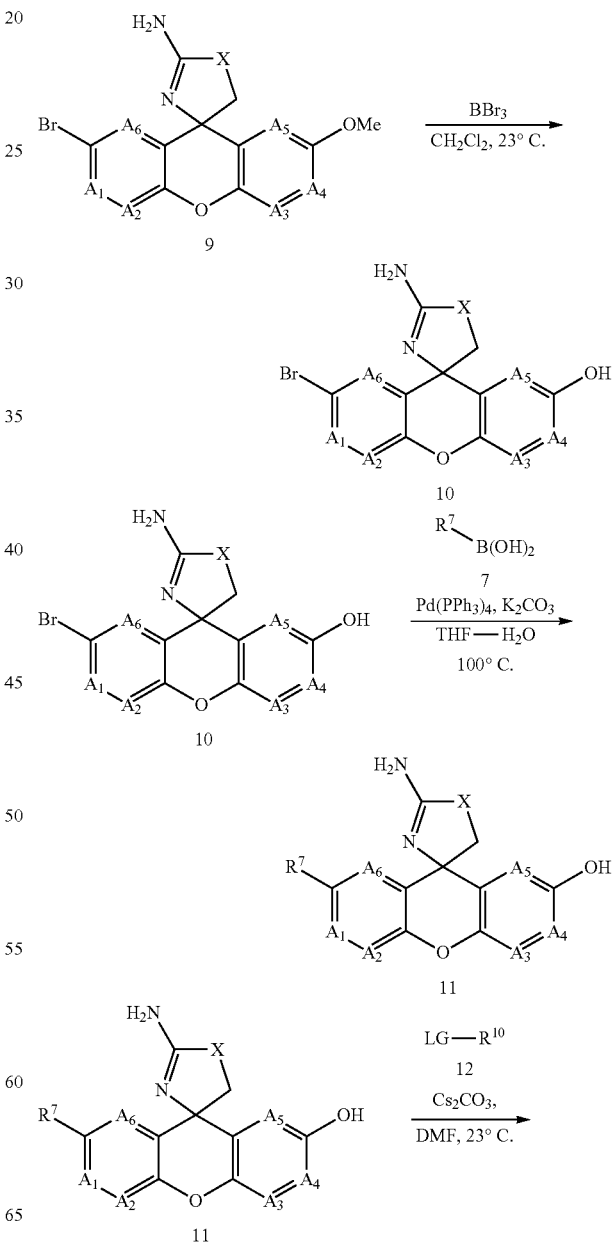

-continued

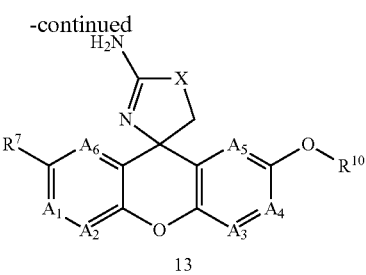

13

Desired compounds 13 of Formulas I, II, II, III, IV and V, wherein the $R^2$ group is —$OR^{10}$ may be made as generally described in Scheme 2. As shown, bromo-methoxy intermediate 9 can be O-demethylate using known reagents, such as borontribromide to afford the alcohol adduct 10. The bromide of alcohol 10 can be coupled as described above in scheme 2 to provide the desired $R^7$ group intermediate 11. The alcohol of intermediate 11 can be functionalized as desired, such as by alkylation as shown, by reaction with an alkyl halide in the presence of a suitable base, such as cesium carbonate as shown, under solvent conditions to afford the finally desired product 13.

"LG" in this instance is a "leaving group" which may be a halide such as an iodide, bromide or chloride. LG may also be a non-halide moiety such as an alkylsulfonate or other known groups which generally form an electrophilic species ($E^+$). Coupling reactions generally occur more readily in one or a combination of solvents and a base. Suitable solvents include, without limitation, generally non-nucleophilic, anhydrous solvents such as toluene, $CH_2Cl_2$, THF, DMF, N,N-dimethylacetamide and the like. The solvent may range in polarity, as appreciated by those skilled in the art. Suitable bases include, for example, tertiary amine bases such as DIEA, TEA, carbonate bases such as $Na_2CO_3$, $K_2CO_3$, $Cs_2CO_3$, hydrides such as NaH, KH, borohydrides, cyanoborohydrides and the like, alkoxides such as $NaOCH_3$, and the like. The base itself may also serve as a solvent. These coupling reactions are generally fast and conversion occurs typically in ambient conditions. However, depending upon the particular substrate, such reactions may require heat, as appreciated by those skilled in the art.

EXAMPLES

The Examples, described herein below, represent various exemplary starting materials, intermediates and compounds of Formulas I-IV, which should assist in a better understanding and appreciation of the scope of the present invention and of the various methods which may be used to synthesize compounds of Formulas I-IV. Starting materials and intermediates used in the Examples herein may also be prepared using the procedures described in co-pending U.S. patent application Ser. No. 12/558,426, filed Sep. 11, 2009, which specification and disclosure is hereby incorporated herein by reference in its entirety. It should be appreciated that the general methods above and specific examples below are illustrative only, for the purpose of assistance and of understanding the present invention, and should not be construed as limiting the scope of the present invention in any manner.

Chromatography: Unless otherwise indicated, crude product-containing residues were purified by passing the crude material or concentrate through an ISCO brand silica gel column (pre-packed or individually packed with $SiO_2$) and eluting the product off the column with a solvent gradient as indicated. For example a description of (330 g $SiO_2$, 0-40% EtOAc/Hexane) means the product was obtained by elution from the column packed with 330 gms of silica, with a solvent gradient of 0% to 40% EtOAc in Hexanes.

Preparative HPLC Method:

Unless otherwise indicated, the compounds described herein were purified via reverse phase HPLC using one of the following instruments: Shimadzu, varian, Gilson; utilizing one of the following two HPLC columns: (a) a Phenomenex Luna or (b) a Gemini column (5 micron or 10 micron, C18, 150×50 mm)

A typical run through the instrument included: eluting at 45 ml/min with a linear gradient of 10% (v/v) to 100% MeCN (0.1% v/v TFA) in water (0.1% TFA) over 10 minutes; conditions can be varied to achieve optimal separations.

Proton NMR Spectra:

Unless otherwise indicated, all $^1$H NMR spectra were run on a Bruker series 300 MHz instrument or a Bruker series 400 MHz instrument. Where so characterized, all observed protons are reported as parts-per-million (ppm) downfield from tetramethylsilane (TMS) or other internal reference in the appropriate solvent indicated.

Mass Spectra (MS)

Unless otherwise indicated, all mass spectral data for starting materials, intermediates and/or exemplary compounds are reported as mass/charge (m/z), having an ($M+H^+$) molecular ion. The molecular ion reported was obtained by electrospray detection method (commonly referred to as an ESI MS) utilizing a PE SCIEX API 150EX MS instrument instrument or an Agilent 1100 series LC/MSD system. Compounds having an isotopic atom, such as bromine and the like, are generally reported according to the detected isotopic pattern, as appreciated by those skilled in the art.

The compounds disclosed and described herein have been named using either (1) the naming convention provided with Chem-Draw Ultra 8.0 software, available in Chem Office, or (2) by the ISIS database software (Advanced Chemistry Design Labs or ACD software).

Example 1

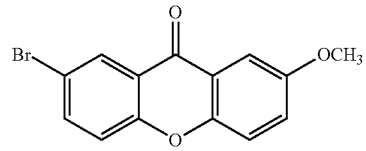 [SMILES: COc1ccc2oc3ccc(Br)cc3c(=O)c2c1]

Synthesis of 2-Bromo-7-methoxy-9H-xanthen-9-one

Step 1: 2-(4-Bromophenoxy)-5-methoxybenzoic acid

4-Bromophenol (8.7 g, 50 mmol), $Cs_2CO_3$ (16 g, 50 mmol), CuOTf toluene complex (2:1) (0.625 mmol, 5 mol % Cu, 150 mg), ethyl acetate (0.25 ml, 2.5 mmol) were added to a solution of 2-bromo-5-methoxybenzoic acid (11.6 g, 50 mmol) in toluene (40 mL) in a sealed tube. The reaction mixture was purged with $N_2$, and was heated to 110° C. until the aryl halide was consumed as determined by LC-MS (48 h). After cooling to rt, the mixture was filtered through a Celite plug. The Celite plug was washed with EtOAc. The mixture was acidified by 1N HCl, and extracted w/EtOAc. The combined organic phases were washed with brine, dried over anhydrous sodium sulfate, filtered, and concentrated. This residue was purified via column chromatography on silica gel (gradient elution with 0-10% MeOH/DCM) to afford 2-(4-bromophenoxy)-5-methoxybenzoic acid. MS m/z=324.9 [M+H]⁺. Calc'd for $C_{14}H_{11}BrO_4$: 323.1.

Step 2: 2-Bromo-7-methoxy-9H-xanthen-9-one

Sulfuric acid (41 ml, 765 mmol) was added to 2-(4-bromophenoxy)-5-methoxybenzoic acid (3750 mg, 12 mmol) at RT. The reaction mixture was stirred at 60° C. for 60 min. LCMS showed complete reaction. The reaction mixture was cooled to rt and poured slowly over stirred mixture of ice and water (100 ml). The tan precipitate was filtered and washed with water (3×30 ml), twice with 30 ml of 0.5N NaOH, and with water again. The residue was recrystallized from 40 ml THF to give the title compound. MS m/z=307.2 [M+H]⁺. Calc'd for $C_{14}H_9BrO_3$: 305.1.

Example 2

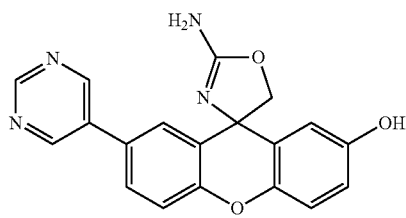 [SMILES: NC1=NC2(CO1)c1cc(O)ccc1Oc1ccc(-c3cncnc3)cc12]

Synthesis of 2'-Hydroxy-7'-(5-pyrimidinyl)spiro[1,3-oxazole-4,9'-xanthen]-2-amine Step 1:
2-Bromo-7-methoxy-9-methylene-9H-xanthene A solution of 2-bromo-7-methoxy-9H-xanthen-9-one (2.035 g, 6.7 mmol) in THF (67 ml) contained in a 250-mL RBF was cooled in a dry ice/acetone bath for 10 min to give a milky-white mixture. Trimethylsilyl methyllithium (10 ml of a 1.0 M solution in pentane, 10 mmol) was added dropwise over 5 min to give a clear orange solution. The mixture was stirred for 15 min, then acetyl chloride (0.76 ml, 11 mmol) was added dropwise, resulting in the formation of a clear, bright-yellow solution. The mixture was warmed to RT for 3 h, then an additional portion of acetyl chloride (0.25 mL) was added. The mixture was stirred for an additional 30 min before being diluted with saturated aqueous sodium bicarbonate solution (100 mL). The biphasic mixture was extracted with EtOAc (2×50 mL), and the combined organic extracts were dried over sodium sulfate, filtered, and evaporated to give a yellow solid that was used without further purification. MS m/z=303.0 [M+H]⁺. Calc'd for $C_{15}H_{12}BrO_2$: 303.0.

Step 2: 2'-Bromo-7'-methoxyspiro[1,3-oxazole-4,9'-xanthen]-2-amine

Crude 2-bromo-7-methoxy-9-methylene-9H-xanthene was suspended in ether (33 ml). silver cyanate (3.0 g, 20 mmol) and iodine (1.7 g, 6.7 mmol) were added in sequence, resulting in a brown mixture. After stirring for 40 min at RT, the reaction mixture was filtered through celite with the aid of ether, and the filtrate was evaporated. The residue was dissolve in a mixture of THF (26 mL) and ammonium hydroxide (2.6 mL) and stirred for 15 h. The reaction mixture was partitioned between water (100 mL) and DCM (70 mL). The layers were separated, and the aqueous layer was extracted with DCM (2×70 mL). The combined organic extracts were dried over sodium sulfate, filtered, and evaporated. The residue was purified by chromatography on silica gel (eluting with 0-40% of a 90:10:1 DCM/MeOH/NH₄OH in DCM) to give 2'-bromo-7'-methoxyspiro[1,3-oxazole-4,9'-xanthen]-2-amine as a pale yellow foam. MS m/z=361.2 [M+H]⁺. Calc'd for $C_{16}H_{14}BrN_2O_3$: 361.2.

Step 3: 2'-Bromo-7'-hydroxyspiro[1,3-oxazole-4,9'-xanthen]-2-amine

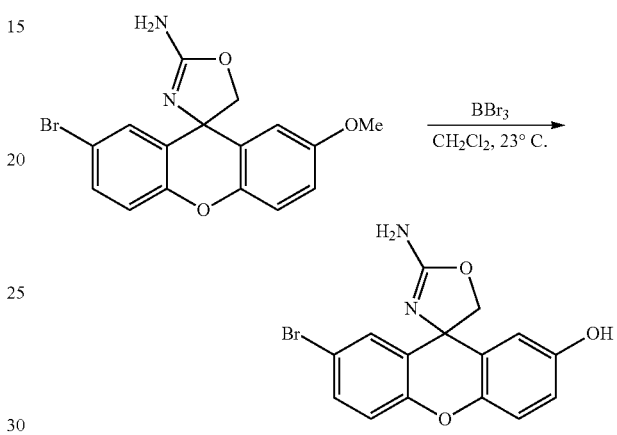

A solution of 2'-bromo-7'-methoxyspiro[1,3-oxazole-4,9'-xanthen]-2-amine (1.034 g, 2863 μmol) in DCM (29 mL) contained in a 100-mL RBF was cooled in an ice-bath for 15 min. A solution of boron tribromide (8.5 mL of a 1.0 M solution in DCM, 8588 μmol) was added dropwise over 5 min, resulting in a dark brown solution at The ice-bath was removed, and the mixture was stirred for 1.5 h. The reaction mixture was carefully quenched with saturated aqueous sodium bicarbonate solution (30 mL). The mixture was partitioned between water (50 mL) and DCM (50 mL). The aqueous layer was extracted with DCM (2×25 mL), and the combined organic extracts were dried over sodium sulfate. The solution was filtered, and the filter cake was washed successively with 10% MeOH/DCM. The combined filtrates were concentrated in vacuo. The residue was purified by chromatography on silica gel (eluting with 0-70% of a 90:10:1 DCM/MeOH/NH₄OH solution in DCM) to give 2'-bromo-7'-hydroxyspiro[1,3-oxazole-4,9'-xanthen]-2-amine. MS m/z=347.0 [M+H]⁺. Calc'd for $C_{15}H_{12}BrN_2O_3$: 347.0.

Step 4: 2'-Hydroxy-7'-(5-pyrimidinyl)spiro[1,3-oxazole-4,9'-xanthen]-2-amine

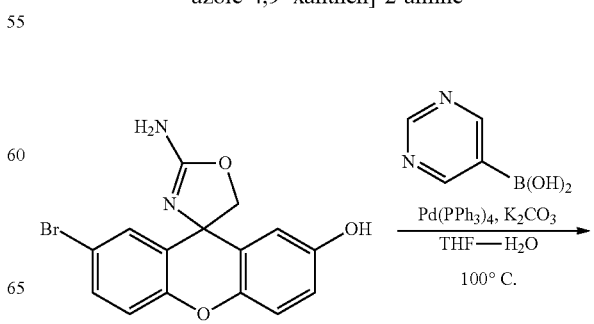

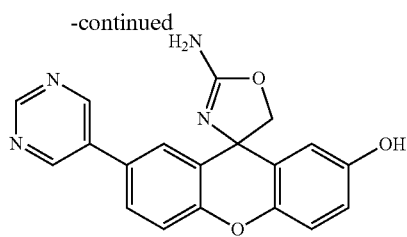

A 150-mL pressure vessel was charged with 2'-bromo-7'-hydroxyspiro[1,3-oxazole-4,9'-xanthen]-2-amine (845 mg, 2434 µmol) in THF (24 mL), pyrimidin-5-ylboronic acid (754 mg, 6085 µmol), tetrakis(triphenylphosphine)palladium(0) (281 mg, 243 µmol), and potassium carbonate (10.1 mL of a 1.2 M aqueous solution, 12.1 mmol). The vessel was sealed and placed in a 100° C. oil bath at for 4 h. The reaction mixture was cooled to RT and partitioned between EtOAc (50 mL) and water (50 mL). The aqueous layer was extracted with EtOAc (50 mL), and the combined organic extracts were dried over sodium sulfate, filtered, and evaporated. The crude material was purified by chromatography on silica gel (eluting with 30-100% of a 90:10:1 DCM/MeOH/NH$_4$OH solution in DCM) to give 2'-hydroxy-7'-(5-pyrimidinyl)spiro[1,3-oxazole-4,9'-xanthen]-2-amine as an off-white solid. MS m/z=347.2 [M+H]$^+$. Calc'd for $C_{19}H_{15}N_4O_3$: 347.1.

Example 3

Synthesis of 2'-Bromo-7'-chlorospiro[1,3-oxazole-4,9'-xanthen]-2-amine

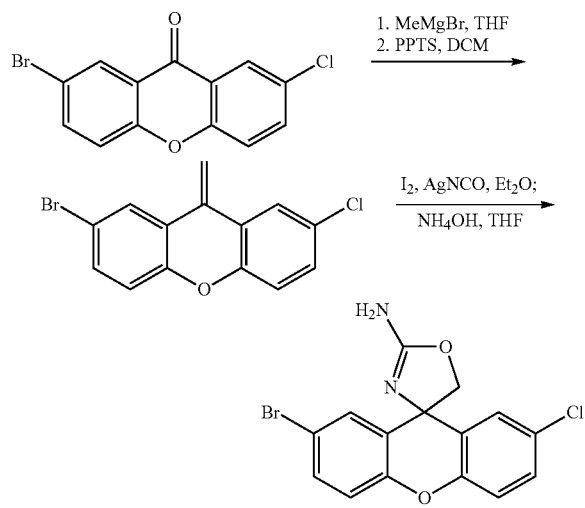

Step 1: Synthesis of 2'-Bromo-7'-chlorospiro[1,3-oxazole-4,9'-xanthen]-2-amine

2-Bromo-7-chloro-9H-xanthen-9-one (prepared as described in example 1 using 4-bromophenol and 2-bromo-5-chlorobenzoic acid) (12.78 g, 41 mmol) was treated with 100 ml of dry THF. The mixture was stirred for 10 min at room temperature and the resulting suspension was placed in water-ice bath for another 10 min. MeMgBr (23 ml, 70 mmol) (3M in THF) was added dropwise under argon using syringe. As addition progressed major amount of solid dissolved to form red solution. The mixture was stirred another 5 min at 0° C. then was removed from the bath and allowed to reach room temperature. The flask was recooled to 0° C. and ~20 ml of saturated ammonium chloride solution was added dropwise slowly (CAREFUL: gas evolution!). The mixture was diluted with ether, organic layer was separated, washed with brine, dried and concentrated to afford an oil. The oil was dissolved in 100 ml of DCM, PPTS (0.2 g, 0.8 mmol) was added and the mixture was heated to reflux for 5 min and left overnight at room temperature. The precipitate was filtered and rinsed with ether, the filtrate was concentrated in vacuo and treated with hot methanol (~30 ml) and allowed to crystallize at room temperature. The crystalline material was filtered off and dried in vacuo. These two batches gave 2-bromo-7-chloro-9-methylene-9H-xanthene (8.69 g, 68% yield). m/z=307.5 [M+H]$^+$. Calc'd for $C_{14}H_8BrClO$: 307.5

Step 2: 2'-Bromo-7'-chlorospiro[1,3-oxazole-4,9'-xanthen]-2-amine

A suspension of 2-bromo-7-chloro-9-methylene-9H-xanthene (244.0 mg, 793 µmol) in ether (7.9 mL) was treated sequentially with silver cyanate (357 mg, 2380 µmol) and iodine (201 mg, 793 µmol). The mixture was stirred for 6 h, then filtered through celite with the aid of ether. The filtrate was evaporated, and the residue was dissolved in THF (4.0 mL) and ammonium hydroxide (0.4 mL). The resulting mixture, which quickly developed a thick precipitate, was stirred for 1 h. Silica gel was added, and the solvent was evaporated to adsorb the crude product. The silica gel was loaded into a silica gel column and eluted with 0-40% of a 90:10:1 DCM/MeOH/NH$_4$OH mixture in DCM to give 2'-bromo-7'-chlorospiro[1,3-oxazole-4,9'-xanthen]-2-amine as an off-white solid. MS m/z=365.0 [M+H]$^+$. Calc'd for $C_{15}H_{11}BrClN_2O_2$: 365.0.

Example 4 (Method A)

Synthesis of 2'-Propoxy-7'-(5-pyrimidinyl)spiro[1,3-oxazole-4,9'-xanthen]-2-amine

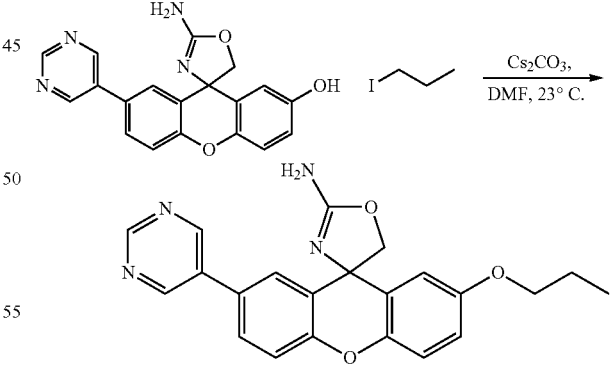

Step 1: 2'-Propoxy-7'-(5-pyrimidinyl)spiro[1,3-oxazole-4,9'-xanthen]-2-amine

A glass vial was charged with 2'-hydroxy-7'-(5-pyrimidinyl)spiro[1,3-oxazole-4,9'-xanthen]-2-amine (prepared as described in Example 2; 53.68 mg, 155 µmol), cesium carbonate (75.7 mg, 232 µmol), DMF (0.62 mL), and 1-iodopropane (16.6 µl, 170 µmol). The mixture was stirred at RT for 18 h, then poured into water (10 mL) and extracted with EtOAc (3×7 mL). The combined organic extracts were dried over sodium sulfate, filtered, and evaporated. The residue was purified by chromatography on silica gel (eluting with 0-80% of a 90:10:1 DCM/MeOH/NH₄OH solution in DCM) to give 2'-(1-propyloxy)-7'-(5-pyrimidinyl)spiro[1,3-oxazole-4,9'-xanthen]-2-amine as a white solid. MS m/z=389.2 [M+H]⁺. Calc'd for $C_{22}H_{21}N_4O_3$: 389.2.

Step 2: Chiral separation of racemic 2'-propoxy-7'-(5-pyrimidinyl)-spiro[1,3-oxazole-4,9'-xanthen]-2-amine 2'-Propoxy-7'-(5-pyrimidinyl)spiro[1,3-oxazole-4,9'-xanthen]-2-amine (40 mg) was subjected to chromatography using 15:85:0.2 MeOH:CO₂:DEA at 80 ml/min on a 20×250 mm, 5 μm ChiralPak AS-H column and 100-bar system pressure. The first peak (RT=3.5 min) provided (R)-2'-propoxy-7'-(5-pyrimidinyl)spiro[1,3-oxazole-4,9'-xanthen]-2-amine (13.0 mg, >99% ee), and the second peak (RT=4.3 min) provided (S)-2'-propoxy-7'-(5-pyrimidinyl)spiro[1,3-oxazole-4,9'-xanthen]-2-amine (12.8 mg, >99% ee).

Example 5

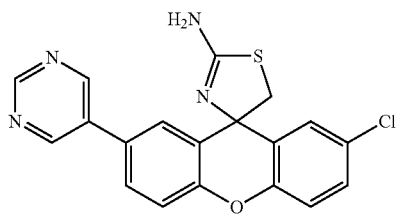 [SMILES: NC1=NC2(CS1)c1cc(Cl)ccc1Oc1ccc(-c3cncnc3)cc12]

Synthesis of Racemic 2'-chloro-7'-(5-pyrimidinyl)spiro[1,3-thiazole-4,9'-xanthen]-2-amine Step 1: Racemic-N-tert-butyl-2'-bromo-7'-chloro-spiro[1,3-thiazole-4,9'-xanthen]-2-amine A mixture of 2-bromo-7-chloro-9-methylene-9H-xanthene (950 mg, 3089 μmol) and silver thiocyanate (1538 mg, 9266 μmol) in ether (30887 μl, 3089 μmol) was treated with iodine (784 mg, 3089 μmol). After stirring for 3 h, the mixture was filtered through celite with the aid of ether. The filtrate was evaporated, and the residue was dissolved in THF (20 mL) and tert-butylamine (649 μl, 6177 μmol). The resulting mixture was stirred for 5 h, concentrated onto silica gel, and purified by chromatography on a 120-g Redi-Sep column, eluting with 0-40% EtOAc/Hexane to give racemic-N-tert-butyl-2'-bromo-7'-chloro-spiro[1,3-thiazole-4,9'-xanthen]-2-amine as a bright yellow foam. MS m/z=437.0 [M+H]+. Calc'd for $C_{19}H_{19}HrClN_2OS$: 437.0.

Step 2: Racemic-N-tert-butyl-2'-chloro-7'-(5-pyrimidinyl)-spiro[1,3-thiazole-4,9'-xanthen]-2-amine A 10-20 mL microwave vial was charged with racemic-N-tert-butyl-2'-bromo-7'-chloro-spiro[1,3-thiazole-4,9'-xanthen]-2-amine (363 mg, 829 μmol), pyrimidin-5-ylboronic acid (257 mg, 2073 μmol), tetrakis(triphenylphosphine)palladium(0) (95.8 mg, 82.9 μmol), THF (8292 μl, 829 μmol), and potassium carbonate (3455 μl of a 1.2 M aqueous solution, 4146 μmol). The vial was covered with a blanket of Ar (g), capped, and heated in a Biotage Initiator microwave reactor for 1 h at 100° C. The organic layer was separated, dried over sodium sulfate, filtered, and evaporated. The residue was purified by chromatography on an 80-g Redi-Sep column, eluting with 0-50% EtOAc/Hexane to give rac-N-tert-butyl-2'-chloro-7'-(5-pyrimidinyl)spiro[1,3-thiazole-4, 9'-xanthen]-2-amine as an orange-yellow solid. MS m/z=437.2 [M+H]+. Calc'd for $C_{23}H_{22}ClN_4OSS$: 437.1.

Step 3: Racemic-2'-chloro-7'-(5-pyrimidinyl)spiro[1,3-thiazole-4,9'-xanthen]-2-amine A vial was charged with rac-N-tert-butyl-2'-chloro-7'-(5-pyrimidinyl)spiro[1,3-thiazole-4,9'-xanthen]-2-amine (63.0 mg, 144 μmol) and TFA (1111 μl, 14418 μmol) resulting in a dark orange mixture. The vial was capped and placed in a 150° C. oil bath for 2 d. The reaction mixture cooled to RT, poured into 6N NaOH (aq.), and extracted with DCM (3×). The combined organic extracts were dried over sodium sulfate, filtered, and evaporated. The residue was purified by chromatography on a 12-g Redi-Sep column, eluting with 0-50% of a 90:10:1 mix of DCM/MeOH/NH₄OH in DCM to give racemic-2'-chloro-7'-(5-pyrimidinyl)spiro[1,3-thiazole-4,9'-xanthen]-2-amine as an off-white solid. MS m/z=381.0 [M+H]+. Calc'd for $C_{19}H_{14}ClN_4OS$: 381.1.

Step 4: Chiral separation of racemic 2'-Chloro-7'-(5-pyrimidinyl)spiro[1,3-oxazole-4,9'-xanthen]-2-amine 2'-Chloro-7'-(5-pyrimidinyl)spiro[1,3-oxazole-4,9'-xanthen]-2-amine (440 mg) was subjected to chromatography using 20:80:0.2 MeOH:CO₂:DEA at 70 ml/min on a 20×150 mm, 5 m ChiralPak AD-H column and 100-bar system pressure. The first peak (RT=6.31 min) provided (4R)-2'-Chloro-7'-(5-pyrimidinyl)spiro[1,3-oxazole-4,9'-xanthen]-2-amine (98% ee), and the second peak (RT=15.7 min) provided (4S)-2'-Chloro-7'-(5-pyrimidinyl)spiro[1,3-oxazole-4,9'-xanthen]-2-amine (>99% ee).

Example 6 (Method N)

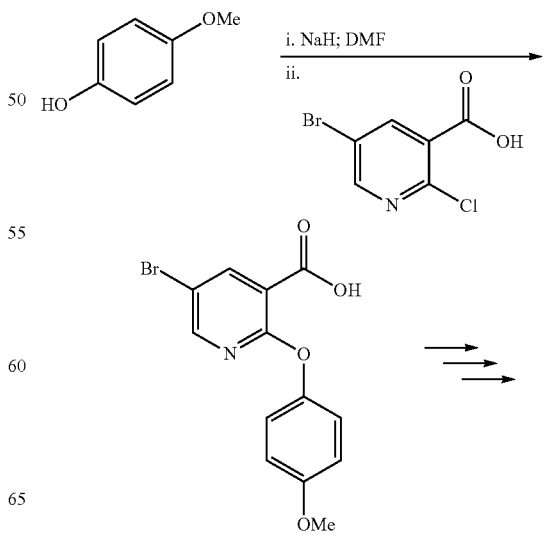

-continued

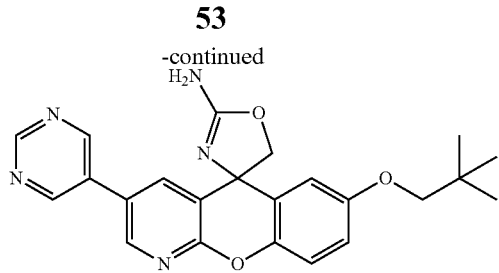

Synthesis of 7-(2,2-Dimethylpropoxy)-3-(5-pyrimidinyl)-spiro[chromeno[2,3-b]pyridine]-5,4'-[1,3]oxazole]-2'-amine Step 1: 5-Bromo-2-(4-methoxyphenoxy)nicotinic acid To a 500 mL RB flask charged with sodium hydride (60% dispersion in mineral oil) (5.33 g, 133 mmol) was added DMF (127 ml, 63.4 mmol). To this slurry at 0° C. was added 4-methoxyphenol (7.88 g, 63.4 mmol) portion wise over 1 minute resulting in the evolution of large amounts of hydrogen gas. The mixture was removed from the ice batch and allowed to stir for 5 minutes, before 5-bromo-2-chloronicotinic acid (15.00 g, 63.4 mmol) was introduced portion wise over 2 minutes. The resulting green slurry was stirred at rt for 10 minutes at which point the reaction become homogeneous. The solution was then heated at 140° C. for 1 hour. The reaction was cooled to rt and diluted with 800 mL of water. The water was washed twice with ether (300 mL). The aqueous layer was acidified with acetic acid (18.2 ml, 317 mmol) and allowed to stir at rt for 12 hours to provide a fine off white solid. Filtered to provide 5-bromo-2-(4-methoxyphenoxy) nicotinic acid as an off white solid. MS m/z=324.0 [M+H]$^+$. Calc'd for $C_{13}H_{11}BrNO_4$: 324.0.

Step 2: 3-Bromo-7-methoxy-5H-chromeno[2,3-b]pyridin-5-one

A slurry of 5-bromo-2-(4-methoxyphenoxy)nicotinic acid (12.20 g, 37.6 mmol) and polyphosphoric acid (200 g) was heated at 135° C. for 1.5 hours. The reaction was cooled to rt and poured onto 300 g of ice before being basified to pH 12 with 50% aq. KOH (1.5 L). The resulting yellow slurry was filtered and washed with 100 mL of ether. The wet solid was then partitioned between water and DCM (1:1; 2000 mL). The layers were separated and the aqueous layer was extracted with DCM 5×500 mL. The combined organics were washed with brine, dried over sodium sulfate, filtered and concentrated to provide 3-bromo-7-methoxy-5H-chromeno[2,3-b]pyridin-5-one as a yellow solid. MS m/z=306.2 [M+H]$^+$. Calc'd for $C_{13}H_9BrNO_3$: 306.0.

Step 3: 3-bromo-7-methoxy-5-methylene-5H-chromeno[2,3-b]pyridine

To a solution of 3-bromo-7-methoxy-5H-chromeno[2,3-b]pyridin-5-one (4.50 g, 14.7 mmol) in THF (294 ml, 14.7 mmol) at 5° C. was added methylmagnesium bromide (1 M in butyl ether) (36.8 ml, 36.8 mmol). The reaction was removed from the ice bath and stirred for an additional 1 hour. TLC showed complete conversion to a lower Rf material. The reaction mixture was quenched with saturated ammonium chloride (250 mL) and to it DCM (100 mL) was added. The mixture was stirred vigorously for 30 minutes before being poured into a separatory funnel containing 300 mL of DCM. The layers were separated and the aqueous layer was extracted with DCM 2×100 mL. The combined organic layers were washed with brine, dried over $Na_2SO_4$ and filtered. TLC revealed tertiary alcohol and no olefin. The organics were concentrated under reduced pressure at 60° C. Flask was maintained at 60° C. on the rotovap for 1 hour at which point TLC and NMR show clean conversion to 3-bromo-7-methoxy-5-methylene-5H-chromeno[2,3-b]pyridine. MS m/z=304.2 [M+H]$^+$. Calc'd for $C_{14}H_{11}BrNO_2$: 304.0.

Step 4: 3-Bromo-7-methoxy-spiro[chromeno[2,3-b]pyridine]-5,4'-[1,3]oxazole]-2'-amine A 500 mL RBF containing iodine (3067 mg, 12083 μmol) and 60 mL of THF was cooled to −15° C. Silver cyanate (5175 mg, 34524 μmol) was added in one portion, and the mixture was stirred at −15 to −20° C. for 20 minutes, after which a solution of 3-bromo-7-methoxy-5-methylene-5H-chromeno [2,3-b]pyridine (3500 mg, 11508 μmol) in 10 mL of THF was added to the mixture followed by a 2 mL THF wash. The resulting yellow slurry was maintained at −20° C. to −10° C. for 1 hour at which point LCMS indicated the complete consumption of the starting material. The mixture was diluted with 20 mL of ether and filtered through a pad of celite. The filter cake was washed with ether and concentrated with minimal heating to provide an orange residue. This residue was taken up in 70 mL of THF and cooled to 0° C. and treated with ammonia (2 M in propanol) (17262 μl, 34524 μmol). The mixture was stirred at 0° C. for 5 minutes then removed from ice bath, warmed to rt and stirred overnight. The reaction was quenched with 10% $Na_2S_2O_3$ 250 mL and poured into ethyl acetate 250 mL. The layers were separated and the aqueous layer was extracted with ethyl acetate 2×250 mL. The combined organic layers were washed with brine, dried over $Na_2SO_4$ and filtered. The resulting crude material was purified by flash chromatography eluting with 0-100% EA in hexanes to provide 3-bromo-7-methoxy-spiro[chromeno[2,3-b]pyridine]-5,4'-[1,3]oxazole]-2'-amine as a tan foam. MS m/z=362.1 [M+H]$^+$. Calc'd for $C_{15}H_{13}BrN_3O_3$: 362.0.

Step 5: 3-Bromo-7-hydroxy-spiro[chromeno[2,3-b]pyridine]-5,4'-[1,3]oxazole]-2'-amine To a solution of 3-bromo-7-methoxy-spiro[chromeno[2,3-b]pyridine]-5,4'-[1,3]oxazole]-2'-amine (2300 mg, 6350 μmol) in DCM (127009 μl, 6350 μmol) at 0° C. was added tribromoborane (1801 μl, 19051 μmol). Immediately a thick precipitate formed. The resulting red slurry was stirred at 0° C. for 10 minutes at which point the ice bath was removed and the mixture was allowed to warm to rt and stirred at rt for 1 hour. Added another 1 mL of tribromoborane at rt and the mixture was stirred for another hour. The reaction was cooled to 0° C. and carefully quenched with saturated sodium bicarbonate 250 mL and poured into DCM 250 mL. The layers were separated and the aqueous layer was extracted with DCM 3×300 mL. The organic layers were washed with brine, dried over $Na_2SO_4$ and filtered. The extraction process was repeated with DCM. All organic layers were combined and concentrated under reduced pressure to provide 3-bromo-7-hydroxy-spiro[chromeno[2,3-b]pyridine]-5,4'-[1,3]oxazole]-2'-amine as a brown solid. MS m/z=348.0 [M+H]$^+$. Calc'd for $C_{14}H_{11}BrN_3O_3$: 348.0.

Step 6: 3-Bromo-7-(2,2-dimethylpropoxy)-spiro [chromeno[2,3-b]pyridine]-5,4'-[1,3]oxazole]-2'-amine To a solution of 3-bromo-7-hydroxy-spiro[chromeno[2,3-b]pyridine]-5,4'-[1,3]oxazole]-2'-amine (650 mg, 1867 μmol) and DMF (7468 μl, 1867 μmol) in a microwave vial were added cesium carbonate (1521 mg, 4668 μmol) and 1-iodo-2,2-dimethylpropane (495 μl, 3734 μmol). The mixture was heated in a microwave at 100° C. for 1 hour and to it was added another 400 mL of 1-iodo-2,2-dimethylpropane and heated in the microwave at 100° C. for another 1 hour. The reaction was diluted with 5 mL of water and 5 mL of ethyl acetate and stirred for 5 minutes until homogeneous. The resulting mixture was poured into 10 mL of ethyl acetate and 25 mL of saturated ammonium chloride the layers were separated. The aqueous layer was extracted with ethyl acetate 3×20 mL. The aqueous layer was then extracted with DCM 3×15 mL. The organic layers were each washed with brine, combined, dried over sodium sulfate, filtered and concentrated. The resulting oil was purified by silica gel chromatography (12 g RediSep) 0-100% EA in hexanes then repurified 0-100% EA in hexanes to provide 3-bromo-7-(2,2-dimethylpropoxy)-spiro[chromeno[2,3-b]pyridine]-5,4'-[1,3]oxazole]-2'-amine as a yellow solid. MS m/z=418.2 [M+H]$^+$. Calc'd for $C_{19}H_{21}BrN_3O_3$: 418.1.

Step 7: 7-(2,2-Dimethylpropoxy)-3-(5-pyrimidinyl)-spiro[chromeno[2,3-b]pyridine]-5,4'-[1,3]oxazole]-2'-amine A sealable tube was charged with 3-bromo-7-(2,2-dimethylpropoxy)-spiro[chromeno[2,3-b]pyridine]-5,4'-[1,3]oxazole]-2'-amine (0.120 g, 287 μmol), pyrimidin-5-ylboronic acid (98 mg, 789 μmol), Pd(Ph$_3$P)$_4$ (33 mg, 29 μmol) 8 mL of THF and a solution of potassium carbonate (1 M) (1434 μl, 1434 μmol). The tube was sealed and heated at 90° C. for 2.5 hours. The reaction was cooled to RT and diluted with 15 mL of water. The organics were removed and the aqueous layer was extracted with ethyl acetate 3×45 mL. The combined organics were washed with brine, dried over sodium sulfate, filtered and concentrated to provide a residue which was purified by chromatography on silica gel (40 g; 0-10% MeOH in DCM) to provide 7-(2,2-dimethylpropoxy)-3-(5-pyrimidinyl)-spiro[chromeno[2,3-b]pyridine]-5,4'-[1,3]oxazole]-2'-amine as a yellow solid. MS m/z=418.2 [M+H]$^+$. Calc'd for $C_{23}H_{24}N_5O_3$: 418.2.

Step 8: Chiral separation of racemic 7-(2,2-dimethylpropoxy-3-(5-pyrimidinyl)-spiro[chromeno[2,3-b]pyridine]-5,4'-[1,3]oxazole]-2'-amine Racemic 7-(2,2-dimethylpropoxy)-3-(5-pyrimidinyl)-spiro[chromeno[2,3-b]pyridine]-5,4'-[1,3]oxazole]-2'-amine (69 mg) was subjected to chromatography using 15:85:0.1 MeOH:CO$_2$:DEA at 70 ml/min on a 2×15 cm, 5 μm ChiralPak AD-H column and 100-bar system pressure. The first peak (RT=3.2 min) provided (S)-7-(2,2-dimethylpropoxy)-3-(5-pyrimidinyl)-spiro[chromeno[2,3-b]pyridine]-5,4'-[1,3]oxazole]-2'-amine (29 mg, >99% ee), and the second peak (RT=6.8 min) provided (R)-7-(2,2-dimethylpropoxy)-3-(5-pyrimidinyl)-spiro[chromeno[2,3-b]pyridine]5,4'-[1,3]oxazole]-2'-amine (>99% ee).

Example 7

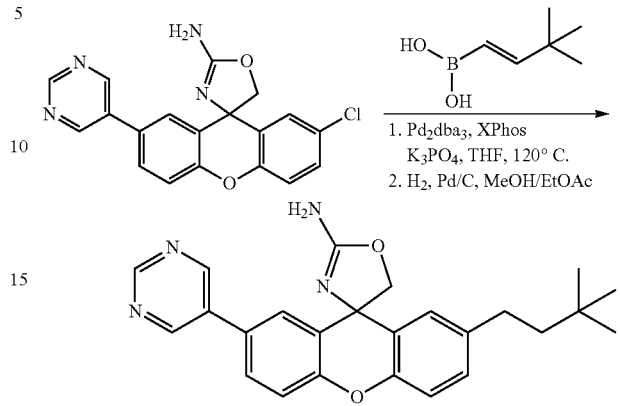

Synthesis of (rac)-2'-(3,3-dimethylbutyl)-7'-(5-pyrimidinyl)spiro[1,3-oxazole-4,9'-xanthen]-2-amine A microwave vial was charged with (rac)-2'-Chloro-7'-(5-pyrimidinyl)spiro[1,3-oxazole-4,9'-xanthen]-2-amine (90 mg, 247 μmol), Pd$_2$dba$_3$ (11 mg, 12 μmol), X-Phos (12 mg, 25 μmol), (E)-3,3-dimethylbut-1-enylboronic acid (63 mg, 493 μmol) and potassium phosphate (157 mg, 740 μmol). THF (2 mL) was added and the mixture was heated at 120° C. in microwave reactor for 2 hrs. The mixture was diluted with ethyl acetate and filtered through plug of Celite. After removal of the solvents the residue was purified by flash chromatography on silica gel (12 g Redi-Sep column, 20-100% DCM/MeOH/NH$_4$OH 90:10:1 in DCM) to give 2'-(3,3-dimethylbut-1-enyl)-7'-(pyrimidin-5-yl)-5H-spiro[oxazole-4,9'-xanthen]-2-amine (65 mg, 64% yield). This product was hydrogenated at 1 atm of H$_2$ in MeOH/EtOAc mixture using 10% palladium on carbon (53 mg, 49 μmol) for 60 hrs. The reaction mixture was filtered and concentrated in vacuo and was further purified by reverse-phase HPLC (10-90% CH$_3$CN/H$_2$O with 0.1% TFA). The fractions containing product were combined and dried overnight under high vacuum to give 2'-(3,3-dimethylbutyl)-7'-(pyrimidin-5-yl)-5H-spiro[oxazole-4,9'-xanthen]-2-amine as its TFA salt.

Step 2: Chiral separation of racemic 2'-(3,3-dimethylbutyl)-7'-(pyrimidin-5-yl)-5H-spiro[oxazole-4,9'-xanthen]-2-amine Racemic 2'-(3,3-dimethylbutyl)-7'-(pyrimidin-5-yl)-5H-spiro[oxazole-4,9'-xanthen]-2-amine (490 mg) from step 1 was subjected to chromatography using 20:80:0.1 MeOH:CO$_2$:DEA at 70 ml/min on a 20×150 mm ChiralPak AD-H column and 100-bar system pressure. The first peak (RT=1.97 min) provided (4S)-2'-(3,3-dimethylbutyl)-7'-(pyrimidin-5-yl)-5H-spiro[oxazole-4,9'-xanthen]-2-amine (210 mg, 99% ee), and the second peak (RT=4.43 min) provided (4R)-2'-(3,3-dimethylbutyl)-7'-(pyrimidin-5-yl)-5H-spiro[oxazole-4,9'-xanthen]-2-amine (>99% ee).

Example 8

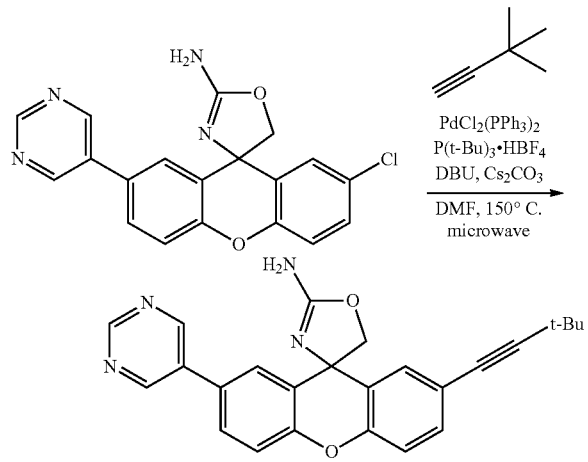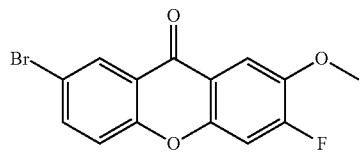 [SMILES: COc1cc2c(=O)c3cc(Br)ccc3oc2cc1F]

Synthesis of 2'-(3,3-dimethylbut-1-ynyl)-7'-(pyrimidin-5-yl)-5H-spiro[oxazole-4,9'-xanthen]-2-amine A microwave vial was charged with (racemic)-2'-Chloro-7'-(5-pyrimidinyl)spiro[1,3-oxazole-4,9'-xanthen]-2-amine (100 mg, 274 μmol), cesium carbonate (134 mg, 411 μmol), bis(triphenylphosphine)palladium(II) chloride (19 mg, 27 μmol) and tri-tert-butylphosphonium tetrafluoroborate (16 mg, 55 DMF (1 ml), DBU (21 μl, 137 μmol) and 3,3-dimethylbut-1-yne (167 μl, 1371 μmol) were added. The vial was sealed and heated at 150° C. in Biotage microwave oven for 60 min. The mixture was diluted with 5 ml of EtOAc, filtered through Celite and concentrated in vacuo to give brown oil, which was re-dissolved in 7 ml of EtOAc and shaken with 10 ml of 2N HCl. Acidic aqueous layer was basified with 30% ammonium hydroxide and precipitated brown oil was extracted twice with EtOAc. The organic layers were washed with brine, concentrated, dissolved in 1.5 ml of DMF, filtered through Nalgene PTFE 0.2 mkm filter and subjected to preparative reverse phase HPLC (15-90% ACN in 0.1% aq TFA). The fractions containing product were concentrated in vacuo in order to remove ACN, saturated NaHCO$_3$ was added and the mixture was extracted with EtOAc (15 ml). The organic layer was washed with brine, dried over MgSO$_4$ and concentrated to give (rac)-2'-(3,3-dimethylbut-1-ynyl)-7'-(pyrimidin-5-yl)-5H-spiro[oxazole-4,9'-xanthen]-2-amine (49% yield).

Step 2: Chiral separation of racemic 2'-(3,3-dimethylbut-1-ynyl)-7'-(pyrimidin-5-yl)-5H-spiro[oxazole-4,9'-xanthen]-2-amine Racemic 2'-(3,3-dimethylbut-1-ynyl)-7'-(pyrimidin-5-yl)-5H-spiro[oxazole-4,9'-xanthen]-2-amine (490 mg) was subjected to chromatography using 20:80:0.1 MeOH:CO$_2$:DEA at 65 ml/min on a 20×150 mm ChiralPak AD-H column and 100-bar system pressure. The first peak (RT=3.51 min) provided (4S)-2'-(3,3-dimethylbut-1-ynyl)-7'-(pyrimidin-5-yl)-5H-spiro[oxazole-4,9'-xanthen]-2-amine (204 mg, 99% ee), and the second peak (RT=5.44 min) provided (4R)-2'-(3,3-dimethylbut-1-ynyl)-7'-(pyrimidin-5-yl)-5H-spiro[oxazole-4,9'-xanthen]-2-amine (>99% ee).

Example 9

Synthesis of 7-Bromo-3-fluoro-2-methoxy-9H-xanthen-9-one

The titled compound was prepared in a manner similar to the procedure described in Example 1, but using 2-bromo-4-fluoro-5-methoxybenzoic acid as the starting material, which starting material was prepared as follows:

Step 1: 4-Bromo-2-fluoro-5-methylphenol 2-fluoro-5-methylphenol (23.8 g, 0.19 mol) and bromine (9.7 ml, 0.19 mol) are combined in 50 ml of glacial acetic acid and stirred at RT for one hour. Acetic acid was removed under vacuum. The liquid was diluted with ethyl acetate and washed with water. The organic layer was washed with brine, dried over anhydrous sodium sulfate, filtered and concentrated to afford 4-bromo-2-fluoro-5-methylphenol (38 g, 98% yield) as a colorless liquid. No [M+H] peak by LCMS. 1H NMR (400 MHz, CHLOROFORM-d) ppm 1.98 (s, 1 H) 2.22 (s, 3 H) 6.81 (dd, J=9.15, 0.54 Hz, 1 H) 7.17 (d, J=9.88 Hz, 1 H)

Step 2: 1-Bromo-5-fluoro-4-methoxy-2-methylbenzene

4-Bromo-2-fluoro-5-methylphenol (40 g, 0.19 mol), cesium carbonate (75 g, 0.23 mol), and iodomethane (15 ml, 0.23 mol) were combined in 100 ml of DMF and stirred at RT for one hour (exothermic). The solution was diluted with ethyl acetate and filtered. The solution was washed with water twice, dried with anhydrous sodium sulfate, filtered, and concentrated. The product was purified via silica gel column chromatography (RediSep 330 g column) using 0-50% ethyl acetate in hexane to afford 1-bromo-5-fluoro-4-methoxy-2-methylbenzene (38 g, 89% yield) as a colorless liquid. No [M+H] peak by LCMS. 1H NMR (400 MHz, CHLOROFORM-d) δ ppm 2.24 (s, 3 H) 3.76 (s, 3 H) 6.73 (d, J=8.80 Hz, 1 H) 7.13 (d, J=10.56 Hz, 1 H)

Step 3: 2-Bromo-4-fluoro-5-methoxybenzoic acid

Potassium permanganate (53 g, 3.4 mol) was added to a solution of 1-bromo-5-fluoro-4-methoxy-2-methylbenzene (37 g, 1.7 mol) in 75 ml of pyridine and 150 ml of water at 60° C. The solution was stirred at 60° C. degrees for 24 hours. The solution was filtered and the solids were washed with a solution of water/methanol (50:50). The filtrate was concentrated to approximately 100 ml, then acidified (pH 1) with concentrated HCl. The solid was collected by filtration and dried under vacuum to afford 2-bromo-4-fluoro-5-methoxybenzoic acid as an off white solid. MS m/z=248.9 [M+H].

Example 10

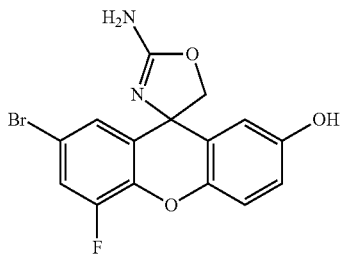 [SMILES: NC1=NC2(CO1)c1cc(O)ccc1Oc1c(F)cc(Br)cc12]

Synthesis of 2-Amino-2'-bromo-4'-fluoro-5H-spiro[oxazole-4,9'-xanthen]-7'-ol

The titled compound was prepared in a manner similar to the procedures described in scheme 1 and Examples 1 and 2, but using a 3-fluoro-4-bromo-phenol (see scheme 1) as starting material 2.

Example 11

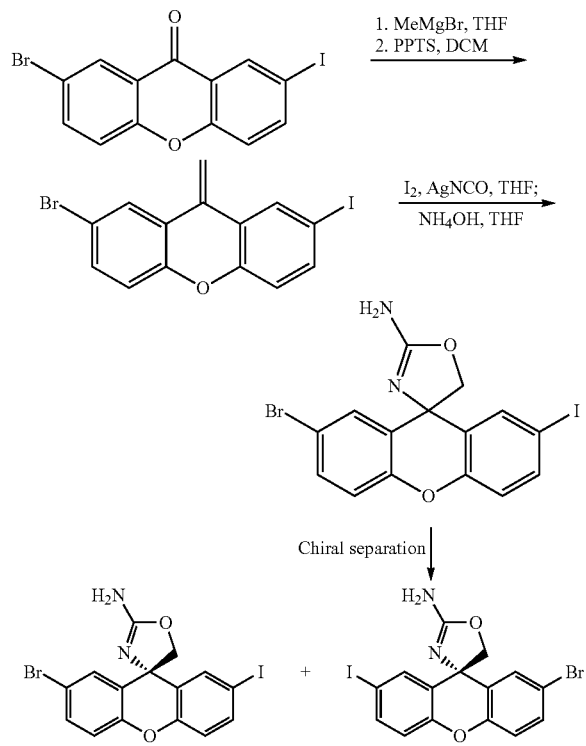

Synthesis of S)-2'-Bromo-7'-iodo-5H-spiro[1,3-oxazole-4,9'-xanthen]-2-amine and (R)-2'-Bromo-7'-iodo-5H-spiro[1,3-oxazole-4,9'-xanthen]-2-amine Step 1: Synthesis of 2-bromo-7-iodo-9-methylene-9H-xanthene 1-L RBF was charged with 2-bromo-7-iodo-9H-xanthen-9-one (42 g, 105 mmol) (prepared as described in Example 1 from 2,5-diiodobenzoic acid and 4-bromophenol) and THF (350 mL) and the suspension was stirred for 30 min at RT. The mixture was cooled to 0° C. (water-ice bath) and methylmagnesium bromide (62.4 mL, 187 mmol) was added at 0° C. dropwise through syringe. The mixture was stirred for 30 min at 0° C. Saturated $NH_4Cl$ solution was carefully added dropwise to quench the reaction. Ether (~100 ml) was added followed by water in order to achieve a clean phase separation. The organic layer was separated and washed with brine, dried over $MgSO_4$ and concentrated to give brown oil. DCM (150 mL) and PPTS (0.526 g, 2.095 mmol) were added and the resulting mixture was refluxed for 3 hrs. Upon cooling to RT the mixture crystallized. The solid was filtered, washed with DCM and dried to give 6.12 g (~15%) of the product. DCM filtrate was washed with $NaHCO_3$ and brine and concentrated. The residue was treated with 150 ml of dry ether. The precipitate was filtered off and dried to give 2-bromo-7-iodo-9-methylene-9H-xanthene as a yellowish solid. The filtrate yielded more of 2-bromo-7-iodo-9-methylene-9H-xanthene.

Step 2: 2'-Bromo-7'-iodo-5H-spiro[1,3-oxazole-4,9'-xanthen]-2-amine 500 mL RBF was charged with iodine (7.04 g, 27.7 mmol) and 210 ml of dry THF. The mixture was cooled to −20-15° C. (methanol-ice bath) and silver cyanate (11.9 g, 79 mmol) was added in one portion. The resulting brown slurry was stirred for 1 hr, then 2-bromo-7-iodo-9-methylene-9H-xanthene (10.55 g, 26.4 mmol) was added portion-wise. The mixture was then stirred at 0° C. for 1 hr and filtered through Celite with the aid of THF (50 ml). To the filtrate, ammonia (39.6 ml, 79.3 mmol) (2M in i-PrOH) was added at RT the reaction mixture was stirred overnight. The resulting brown solution was diluted with 5% solution of $Na_2S_2O_3$ (15 ml) and sodium bicarbonate (15 ml), then 50 ml of EtOAc was added. The organic extract was washed with saturated NaCl (2×50 mL) and dried over $MgSO_4$. The solution was filtered, concentrated in vacuo and purified by chromatography through a Redi-Sep pre-packed silica gel column (120 g), eluting with a gradient of 10% to 80% DCM/MeOH/NH4OH (90:10:1) in DCM, to provide a crude product as brown glass which crystallized overnight. This crystalline material was treated with 20 ml of DCM and solid was filtered and dried to afford 3.3 g of 2'-Bromo-7'-iodo-5H-spiro[1,3-oxazole-4,9'-xanthen]-2-amine as a white solid. The filtrate was purified by chromatography through a Redi-Sep pre-packed silica gel column (80 g), eluting with a gradient of 5% to 40% DCM/MeOH/$NH_4OH$ (90:10:1) in DCM, to provide additional 2'-Bromo-7'-iodo-5H-spiro[1,3-oxazole-4,9'-xanthen]-2-amine as a tan glass crystalline material.

Step 3: (S)-2'-Bromo-7'-iodo-5H-spiro[1,3-oxazole-4,9'-xanthen]-2-amine and (R)-2'-Bromo-7'-iodo-5H-spiro[1,3-oxazole-4,9'-xanthen]-2-amine Racemic 2'-Bromo-7'-iodo-5H-spiro[1,3-oxazole-4,9'-xanthen]-2-amine was purified by chromatography using a elution gradient of 20:80:0.2 MeOH:$CO_2$:DEA at 80 ml/min on a 20×250 mm ChiralPak AD-H column and 100-bar system pressure. The first peak (RT=3.4 min) provided (S)-2'-Bromo-7'-iodo-5H-spiro[1,3-oxazole-4,9'-xanthen]-2-amine (99% ee), and the second peak (RT=4.7 min) provided (R)-2'-Bromo-7'-iodo-5H-spiro[1,3-oxazole-4,9'-xanthen]-2-amine (>99% ee).

Example 12 (Method AA66)

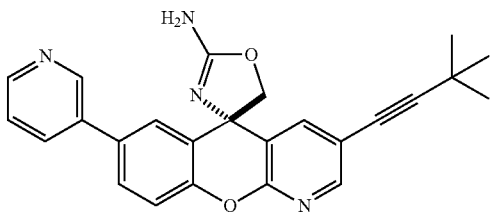

Synthesis of (5S)-3-(3,3-dimethyl-1-butyn-1-yl)-7-(3-pyridinyl)spiro[chromeno[2,3-b]pyridine-5,4'-[1,3]oxazol]-2'-amine Step 1: (5S)-3-bromo-7-(3-pyridinyl)spiro[chromeno[2,3-b]pyridine-5,4'-[1,3]oxazol]-2'-amine A sealable tube was charged with (5S)-7-iodo-3-bromo-spiro[chromeno[2,3-b]pyridine-5,4'-[1,3]oxazol]-2'-amine (350 mg, 0.764 mmol), pyridin-3-ylboronic acid (94 mg, 0.764 mmol), tetrakis(triphenylphosphine)palladium (20.04 mg, 0.076 mmol) and THF (7641 µL, 0.764 mmol). The mixture was purged with Ar for 2 minutes then a solution of potassium carbonate (1.5 M) (1019 µL, 1.528 mmol) was added and the reaction vessel was sealed and heated at 110° C. for 6 hours. The reaction was diluted with water (100 mL) and poured into a separatory funnel containing ethyl acetate (50 mL). The layers were separated and the aqueous layer was extracted with ethyl acetate (4×50 mL). The combined organic layers were washed with brine, dried over sodium sulfate, filtered and concentrated in vacuo to provide a brown oil that was purified by silica gel chromatography (Redi-Sep pre-packed silica gel column (40 g), 0-10% methanol in methylenechloride with 0.1% ammonium hydroxide) to provide (5S)-3-bromo-7-(3-pyridinyl)spiro[chromeno[2,3-b]pyridine-5,4'-[1,3]oxazol]-2'-amine (175 mg, 0.428 mmol, 56.0% yield) as a brown foam. MS m/z=409.0 [M+H]+. Calc'd for $C_{19}H_{14}BrN_4O_2$: 409.0.

Step 2: (5S)-3-(3,3-dimethyl-1-butyn-1-yl)-7-(3-pyridinyl)spiro[chromeno[2,3-b]pyridine-5,4'-[1,3]oxazol]-2'-amine (5S)-3-Bromo-7-(3-pyridinyl)spiro[chromeno[2,3-b]pyridine-5,4'-[1,3]oxazol]-2'-amine (170 mg, 0.415 mmol), diisopropyl amine (2911 µL, 20.77 mmol), copper iodide (15.82 mg, 0.083 mmol), tetrakis(triphenylphosphine)palladium (48.0 mg, 0.042 mmol), 3,3-dimethylbut-1-yne (171 mg, 2.082 mmol) and DMF (2769 µL, 0.415 mmol) were combined in a sealable tube, which was then flushed with argon and heated at 90° C. for 5 hours. After cooling to room temperature the reaction in the tube was diluted with water (25 mL) and poured into a separatory funnel containing ethyl acetate (25 mL). The layers were separated and the aqueous layer was extracted with ethyl acetate (4×50 mL). The combined organic layers were washed with brine, dried over sodium sulfate, filtered and concentrated in vacuo to provide a brown oil that was purified by silica gel chromatography (Redi-Sep pre-packed silica gel column (40 g), 0-10% methanol in methylenechloride with 0.1% ammonium hydroxide) to provide (5S)-3-(3,3-dimethyl-1-butyn-1-yl)-7-(3-pyridinyl)spiro[chromeno[2,3-b]pyridine-5,4'-[1,3]oxazol]-2'-amine (110 mg, 0.268 mmol, 64.5% yield) as a brown foam. MS m/z=411.2 [M+H]+. Calc'd for $C_{25}H_{23}N_4O_3$: 411.2.

Example 13

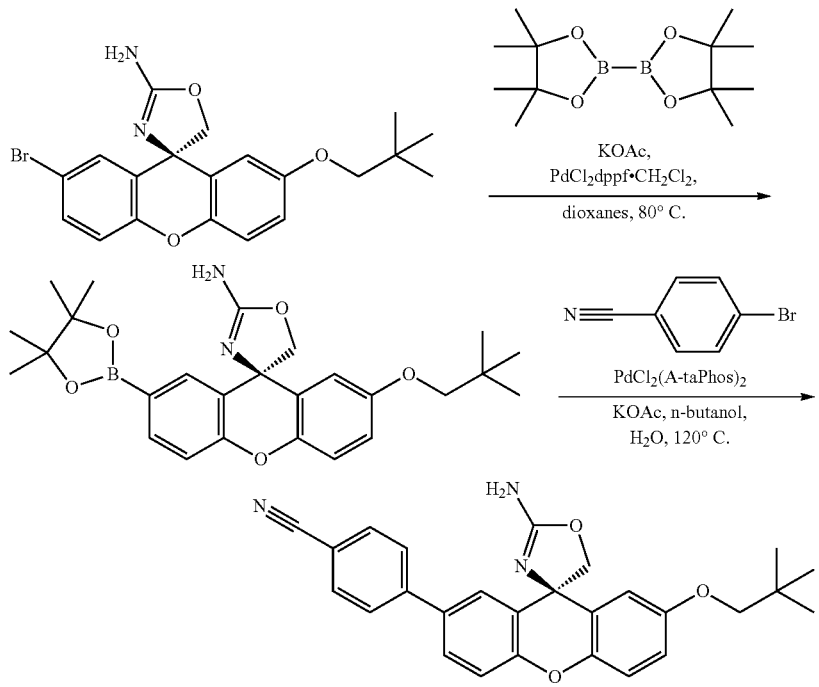

Synthesis of (R)-4-(2-amino-2'-(neopentyloxy)-5H-spiro[oxazole-4,9'-xanthene]-7'-yl)benzonitrile Step 1: (R)-2'-(Neopentyloxy)-7'-(4,4,5,5-tetramethyl-1,3,2-dioxaborolan-2-yl)-5H-spiro[oxazole-4,9'-xanthen]-2-amine A 250 mL RBF was charged with (S)-2'-bromo-7'-(neopentyloxy)-5H-spiro[oxazole-4,9'-xanthen]-2-amine (3 g, 7.2 mmol), Bis(pinacolate)diboron (3.65 g, 14.4 mmol), and potassium acetate (1.4 g, 14.4 mmol). Anhydrous dioxane (40 mL) was added and the mixture was purged with Ar. [1,1'-Bis(diphenylphosphino)-ferrocene]dichloropalladium (II) complex with dichloromethane (1:1) (587 mg, 719 μmol) was added and the reaction mixture was stirred under a reflux condenser under Ar in an 80° C. oil bath for 3 h followed by 3 h at 110° C. The reaction mixture was allowed to cool to RT and concentrated in vacuo to give a dark brown solid. The solid was resuspended between EtOAc (200 mL) and water (200 mL). The organic phase was washed with saturated aqueous sodium bicarbonate (100 mL) and brine (100 mL). The organic phase was then dried over magnesium sulfate, treated with decolorizing carbon, filtered through a pad of Celite, and concentrated in vacuo to give a brown residue. The residue was suspended in dichloromethane (30 mL), sonicated for 30 s, and then added to hexane (120 mL). The resulting precipitate was collected by suction filtration and air-dried to afford the crude desired product as a tan solid which was taken directly without further purification. MS m/z=464.8 [M+H]$^+$. Calc'd for $C_{26}H_{33}BN_2O_5$: 464.25

Step 2: (R)-4-(2-amino-2'-(neopentyloxy)-5H-spiro[oxazole-4,9'-xanthene]-7'-ylbenzonitrile A 2-mL microwave vial was charged with (R)-2'-(neopentyloxy)-7'-(4,4,5,5-tetramethyl-1,3,2-dioxaborolan-2-yl)-5H-spiro[oxazole-4,9'-xanthen]-2-amine (100 mg, 0.215 mmol) in n-butanol (1723 μL), 4-bromobenzonitrile (78 mg, 0.431 mmol), and potassium acetate (63.4 mg, 0.646 mmol) in water (431 μL). The vessel was purged with Argon gas. Bis(di-tert-butyl(4-dimethylaminophenyl)phosphine(dichloropalladium (II) (3.1 mg, 4.3 μmol) was added and the reaction was heated to 120° C. for 15 min in a Biotage microwave initiator. The reaction was then cooled to room temperature and purified by reverse-phase preparative HPLC using a Gemini NX C18 column (150×30 mm, 5 um), 0.1% trifluoroacetic acid in acetonitrile/water, gradient 10% to 70% over 10 min to give the desired product as the trifluoroacetic acid salt. MS m/z=440.0 [M+H]$^+$. Calc'd for $C_{27}H_{25}N_3O_3$: 439.19.

Example 14

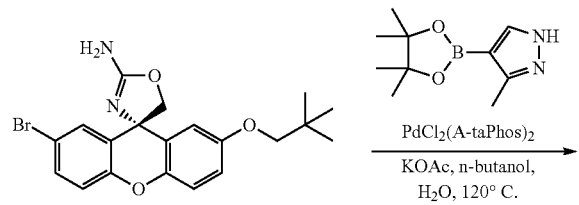

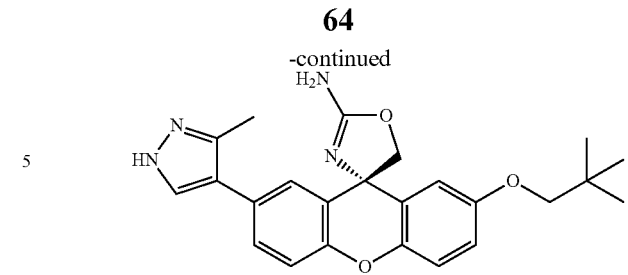

Synthesis of (S)-2'-(3-methyl-1H-pyrazol-4-yl)-7'-(neopentyloxy)-5H-spiro[oxazole-4,9'-xanthen]-2-amine 2,2,2-trifluoroacetate A 2-mL microwave vial was charged with (R)-2'-bromo-7'-(neopentyloxy)-5H-spiro[oxazole-4,9'-xanthen]-2-amine (50 mg, 120 μmol) in n-butanol (959 μL), 3-methyl-4-(4,4,5,5-tetramethyl-1,3,2-dioxaborolan-2-yl)-1H-pyrazole (49.9 mg, 240 μmol), and potassium acetate (35.3 mg, 359 μmol) in water (240 μL). The vessel was purged with Ar. Bis(di-tert-butyl(4-dimethylaminophenyl)phosphine(dichloropalladium (II) (1.7 mg, 2.4 μmol) was added and the reaction was heated to 120° C. for 30 min in a Biotage microwave initiator. The reaction was then cooled to room temperature and loaded an AccuBOND II SCX cartridge, washed with methanol (3 ml) and eluted with 2N ammonia in methanol (6 ml) to give the crude product. The crude mixture was then purified by reverse-phase preparative HPLC using a Gemini NX C18 column (150×30 mm, 5 um), 0.1% TFA in acetonitrile/water, gradient 10% to 90% over 10 min to give the desired product as the TFA salt. MS m/z=419.0 [M+H]$^+$. Calc'd for $C_{24}H_{26}N_4O_3$: 418.20.

Example 15

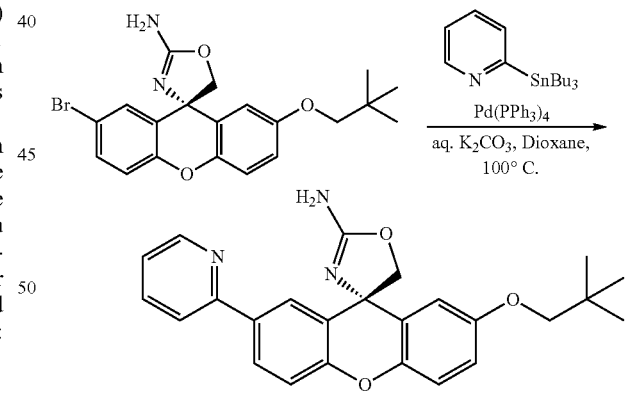

A vial was charged with (R)-2'-bromo-7'-(neopentyloxy)-5H-spiro[oxazole-4,9'-xanthen]-2-amine (0.050 g, 0.120 mmol), tetrakis(triphenylphosphine)palladium (0) (0.014 g, 0.012 mmol), 2-(tributylstannyl)pyridine (0.132 g, 0.359 mmol), and dioxane (0.6 mL). The reaction was stirred overnight at 100° C. The mixture was diluted with DMSO and filtered through a syringe filter, which was flushed with additional DMSO. The material was purified via Gilson HPLC (10-90% MeCN:H2O). The clean product fractions were partitioned between DCM and saturated sodium bicarbonate solution. The aqueous layer was extracted with DCM, and the combined organic layers were dried with sodium sulfate, filtered, and concentrated to afford (S)-2'-(neopentyloxy)-7'-(pyridin-2-yl)-5H-spiro[oxazole-4,9'-xanthen]-2-amine as a white solid. MS MH+ 416.4

Example 16

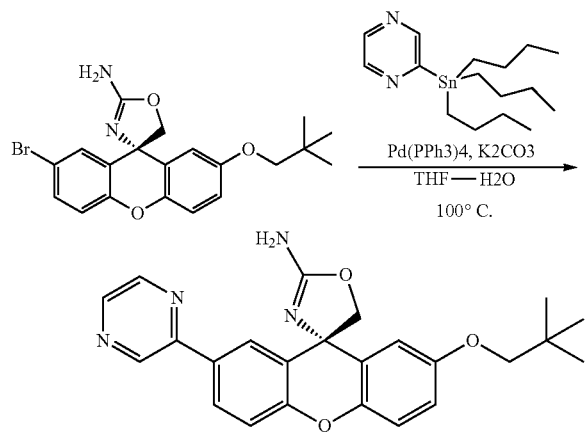

Synthesis of (S)-2'-(neopentyloxy)-7'-(pyrazin-2-yl)-5H-spiro[oxazole-4,9'-xanthen]-2-amine A vial was charged with (R)-2'-bromo-7'-(neopentyloxy)-5H-spiro[oxazole-4,9'-xanthen]-2-amine (55.6 mg, 0.133 mmol), tetrakis(triphenylphosphine)palladium (0) (15.40 mg, 0.013 mmol), 2-(tributylstannyl)pyrazine (148 mg, 0.400 mmol), and dioxane (0.7 mL). The vial was sealed under a blanket of Ar gas and placed in a 100° C. oil for 16 h. The mixture was then cooled and filtered through celite. The filtrate was evaporated, and the residue was purified by chromatography on a 12-g Redi-Sep column, eluting with 0-10% MeOH/DCM to give a brown oil. This oil was dissolved in MeOH and filtered through a 2 micron filter, then purified further by reverse-phase HPLC (10-90% $CH_3CN/H_2O$ with 0.1% TFA). The product containing fractions were combined in saturated aqueous sodium bicarbonate solution with the aid of MeOH. The mixture was extracted with DCM (2×), and the combined organic extracts were dried over sodium sulfate, filtered, and evaporated to give (S')-2'-(neopentyloxy)-7'-(pyrazin-2-yl)-5H-spiro[oxazole-4,9'-xanthen]-2-amine as a white solid. MS m/z=417.2 $[M+H]^+$. Calc'd for $C_{24}H_{25}N_4O_3$: 417.19.

Examples 17a & 17b

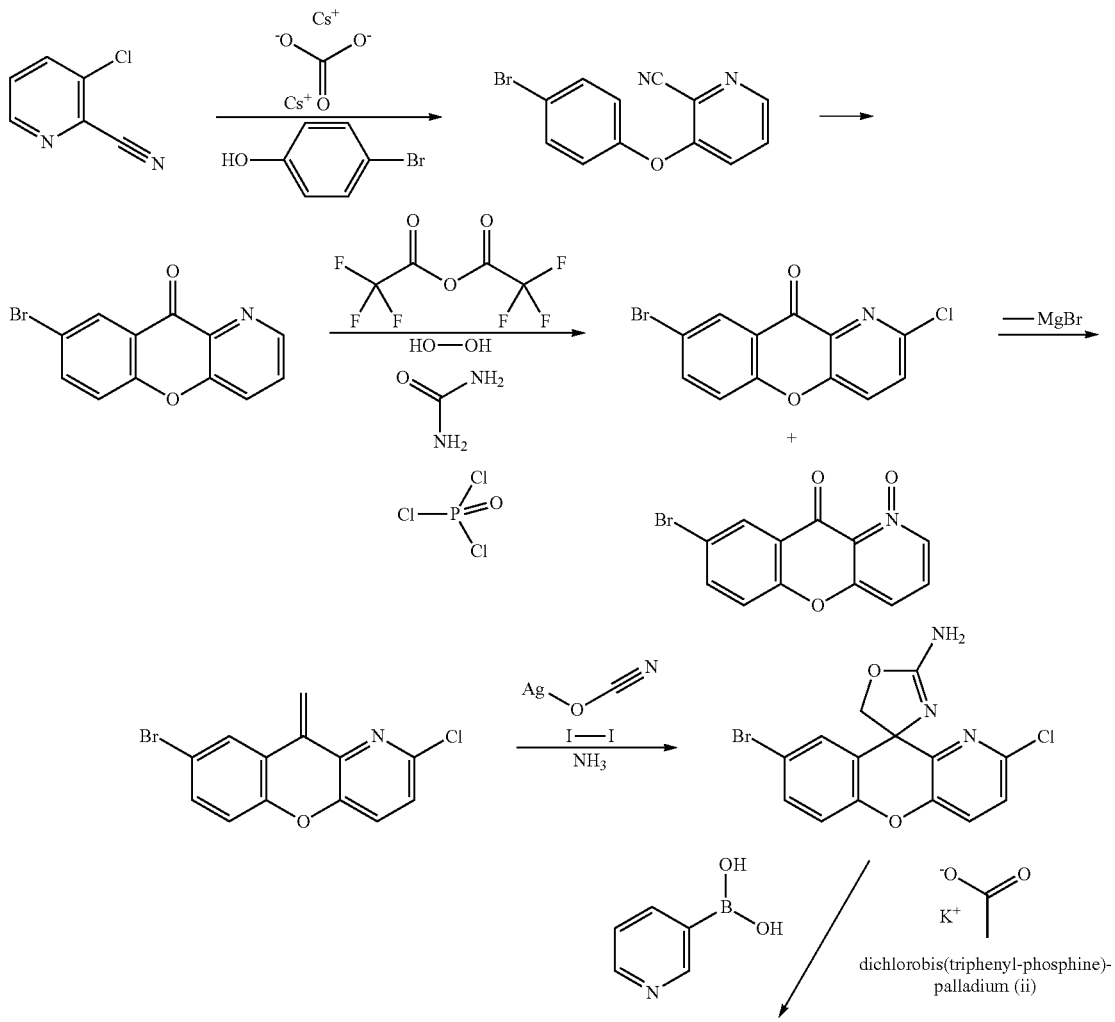

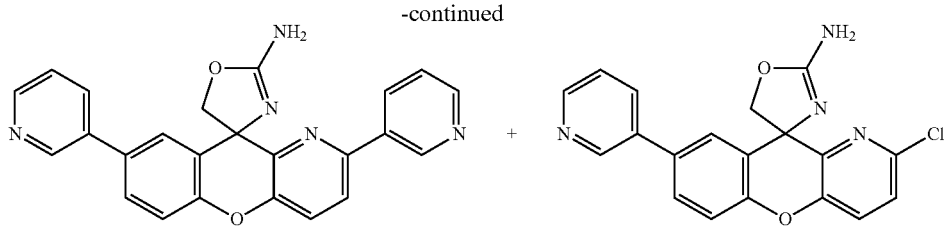

Synthesis of 2,8-di(pyridin-3-yl)-5'H-spiro[chromeno[3,2-b]pyridine-10,4'-oxazol]-2'-amine (17b) and 2-chloro-8-(pyridin-3-yl)-5'H-spiro[chromeno[3,2-b]pyridine-10,4'-oxazol]-2'-amine (17a)

Step 1: A RBF was charged with 3-chloro-2-cyanopyridine (40 g, 289 mmol), 4-bromophenol (49.9 g, 289 mmol) and cesium carbonate (113 g, 346 mmol). The reactants were suspended in 50 mL of DMSO and allowed to stir at 85 C overnight. The reaction was cooled to RT and to it was added 600 mL of water. The reaction was filtered and the solid washed with water, air dried to provide 3-(4-bromophenoxy)picolinonitrile as a tan solid.

Step 2: A mixture of 3-(4-bromophenoxy)picolinonitrile (57 g, 207 mmol) and 300 g of PPA was stirred at 190° C. for 2 h, followed by 180° C. overnight. After cooling to RT, the reaction mixture was poured into 500 g of ice water. After the PH was adjusted to 7 with KOH, the suspension was filtered. The solid was washed with large excess of water, followed by washing with methanol and acetone. The resulting solid was air dried to give 8-bromo-10H-chromeno[3,2-b]pyridin-10-one as a tan solid with >90% purity. The material was carried on to the next step.

Step 3: To a solution of 8-bromo-10H-chromeno[3,2-b]pyridin-10-one (60 g, 217 mmol) and urea peroxide (42.9 g, 456 mmol) in 120 mL of DCM at 0° C. was added dropwise trifluoroacetic anhydride (63.9 mL, 456 mmol). The resulting reaction was stirred for 2 h. The reaction was quenched with 10% $Na_2S_2O_3$, extracted with DCM, dried over $Na_2SO_4$ and evaporated to dryness to give crude 8-bromo-10-oxo-10H-chromeno[3,2-b]pyridine 1-oxide as a pale yellow solid.

Step 4: To a suspension of 8-bromo-10-oxo-10H-chromeno[3,2-b]pyridine 1-oxide in 100 mL of toluene at 0° C. was added dropwise phosphorus oxychloride (35.8 mL, 391 mmol) followed by 2 mL of DMF and the mixture was stirred at RT overnight. The solvent was evaporated under vacuum and the residue which crashed out of water, was filtered and washed with water, methanol and acetone in sequence. The solid was air dried to give 8-bromo-2-chloro-10H-chromeno[3,2-b]pyridin-10-one as a tan solid.

Step 5: To a suspension of 8-bromo-2-chloro-10H-chromeno[3,2-b]pyridin-10-one (20 g, 64.4 mmol) in 500 mL of THF at −78° C. was added dropwise methylmagnesium bromide 3.0 M in diethyl ether (13.82 mL, 116 mmol). The reaction was allowed to slowly warmed up to 0° C. in about 2 h. The reaction was quenched with $NH_4Cl$ solution, extracted with EtOAc, dried over $Na_2SO_4$, filtered and evaporated to give the corresponding crude tertiary alcohol. This solid residue was re-dissolved in 100 mL of THF and treated with 30 mL of chloroform and the resulting solution was evaporated on a 75° C. water bath for 10 min to give crude 8-bromo-2-chloro-10-methylene-10H-chromeno[3,2-b]pyridine as a brownish solid.

Step 6: A solution of iodine (12.96 g, 51.0 mmol) in THF at −25° C. was treated with silver cyanate (21.86 g, 146 mmol). After 30 min, a solution of 8-bromo-2-chloro-10-methylene-10H-chromeno[3,2-b]pyridine (15 g, 48.6 mmol) in THF was added dropwise. The slurry was maintained at −25° C. for 2 h until LCMS showed complete consumption of starting material. The slurry was filtered through celite with ether. The brown solution was concentrated to dryness, taken up in THF, cooled to 0° C. and treated with ammonia, 2 m solution in 2-propanol (4.22 mL, 194 mmol) (100 mL). The reaction was allowed to slowly warm to RT and stirred overnight. The solvents were evaporated and the residue was diluted with water, extracted with EtOAc and purified by column chromatography (SiO2, DCM to DCM/EA=3:1 to DCM/MeOH=100:2 to 100:5) to provide 8-bromo-2-chloro-5'H-spiro[chromeno[3,2-b]pyridine-10,4'-oxazol]-2'-amine (impure) as a brownish solid. MS (M+1): 365.9.

Step 7: A mixture of the 8-bromo-2-chloro-5'H-spiro[chromeno[3,2-b]pyridine-10,4'-oxazol]-2'-amine (from step 6, 40.0 mg, 0.109 mmol), potassium acetate (27.3 μL, 0.436 mmol), dichlorobis(triphenyl-phosphine)palladium (ii) (3.83 mg, 5.46 μmol) and 3-pyridylboronic acid (40.2 mg, 0.327 mmol) in 1.5 ml of dioxane/water=2:1 was heated at 110° C. under microwave irradiation for 15 min. LCMS and TLC showed incomplete conversion after 15 min. The reaction was re-heated in the microwave at 130° C. for 20 additional min. After cooling, the reaction mixture was purified by column chromatography (SiO2, DCM to DCM/MeOH=100:1 to 100:5 to 100:10 to 100:20) to afford 2,8-di(pyridin-3-yl)-5'H-spiro[chromeno[3,2-b]pyridine-10,4'-oxazol]-2'-amine as a gum. MS (M+1): 408.0; and 2-chloro-8-(pyridin-3-yl)-5'H-spiro[chromeno[3,2-b]pyridine-10,4'-oxazol]-2'-amine also as a gum. MS (M+1): 365.0.

The following are procedures for preparing intermediates, which were used to prepare Examplary compounds, representative of the present invention. The procedures and Methods hereforth were used to prepare the compounds in Tables I herein.

Example 18 (Method AA1)

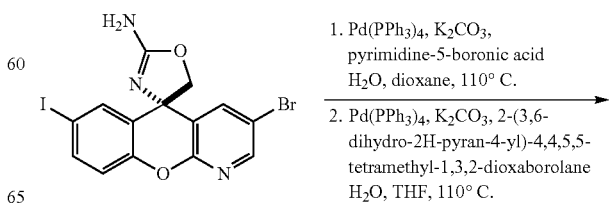

1. Pd(PPh₃)₄, K₂CO₃, pyrimidine-5-boronic acid H₂O, dioxane, 110° C.

2. Pd(PPh₃)₄, K₂CO₃, 2-(3,6-dihydro-2H-pyran-4-yl)-4,4,5,5-tetramethyl-1,3,2-dioxaborolane H₂O, THF, 110° C.

-continued

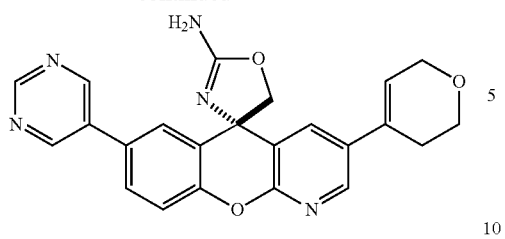

Synthesis of (S)-3-(3,6-dihydro-2H-pyran-4-yl)-7-(pyrimidin-5-yl)-5'H-spiro[chromeno[2,3-b]pyridine-5,4'-oxazol]-2'-amine Step 1: A 10-20 mL microwave vial was charged with (S)-3-bromo-7-iodo-5'H-spiro[chromeno[2,3-b]pyridine-5,4'-oxazol]-2'-amine (503 mg, 1.098 mmol), pyrimidin-5-ylboronic acid (143 mg, 1.153 mmol), pd(ph3p)4 (127 mg, 0.110 mmol). The vial was flushed with Ar(g), then THF (5489 µL, 1.098 mmol) and potassium carbonate (1.5 M) (1464 µL, 2.195 mmol) (aq. solution) were added in sequence. The vial was sealed and heated at 110° C. for 2 hours. The mixture was diluted with water and extracted with 10% i-PrOH/EtOAc (3×). The combined organic extracts were dried over sodium sulfate, filtered, and evaporated. The residue was purified by chromatography on a 100-g SNAP column, eluting with 0-100% of a 90:10:1 mixture of DCM/MeOH/NH$_4$OH in DCM to provide (S)-3-bromo-7-(pyrimidin-5-yl)-5'H-spiro[chromeno[2,3-b]pyridine-5,4'-oxazol]-2'-amine as an off-white solid.

Step 2: A vial was charged with (S)-3-bromo-7-(pyrimidin-5-yl)-5'H-spiro[chromeno[2,3-b]pyridine-5,4'-oxazol]-2'-amine (68.1 mg, 0.166 mmol), 2-(3,6-dihydro-2H-pyran-4-yl)-4,4,5,5-tetramethyl-1,3,2-dioxaborolane (105 mg, 0.498 mmol), tetrakis(triphenylphosphine)palladium (19.18 mg, 0.017 mmol), THF (830 µL), and potassium carbonate (415 µL, 0.830 mmol) (as a 2.0 M aq. solution). The vial was sealed and placed in a 110° C. for 5 hours. The layers were separated, and the aqueous layer was extracted with EtOAc (2×). The combined organic extracts were dried over sodium sulfate, filtered, and evaporated. The residue was purified by chromatography on a 25-g SNAP column, eluting with 0-60% of a 90:10:1 mixture of DCM/MeOH/NH$_4$OH in DCM to give (S)-3-(3,6-dihydro-2H-pyran-4-yl)-7-(pyrimidin-5-yl)-5'H-spiro[chromeno[2,3-b]pyridine-5,4'-oxazol]-2'-amine as a white solid Example 19 (Method AA2)

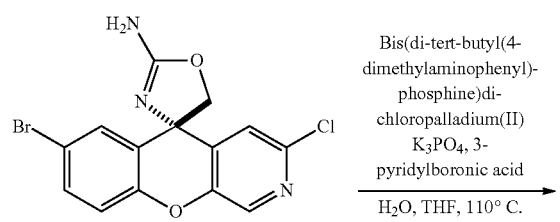

Synthesis of (S)-3,7-di(pyridin-3-yl)-5'H-spiro[chromeno[2,3-c]pyridine-5,4'-oxazol]-2'-amine

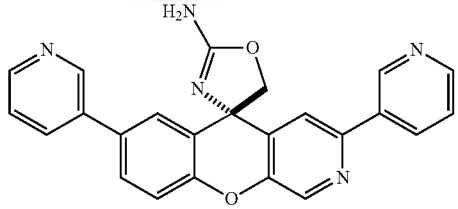

A glass microwave reaction vessel was charged with (S)-7-bromo-3-chloro-5'H-spiro[chromeno[2,3-c]pyridine-5,4'-oxazol]-2'-amine (32 mg, 0.087 mmol), potassium phosphate (55.6 mg, 0.262 mmol), Amphos (1.525 mg, 2.153 µmol) and 3-pyridylboronic acid (32.2 mg, 0.262 mmol) in dioxane (0.6 mL) and water (0.200 mL). The reaction mixture was stirred and heated in a microwave at 100° C. for 30 min. The reaction mixture was diluted with water (mL) and extracted with EtOAc (2×5 mL). The organic extract was washed with saturated NH$_4$Cl (2×5 mL) and dried over MgSO4. The solution was filtered and concentrated in vacuo to give the crude material as a yellow solid. The crude material was absorbed onto a plug of silica gel and purified by silica gel chromatography (0-10% MeOH in DCM) to provide (S)-3,7-di(pyridin-3-yl)-5'H-spiro[chromeno[2,3-c]pyridine-5,4'-oxazol]-2'-amine as white solid.

Example 20 (Method AA3)

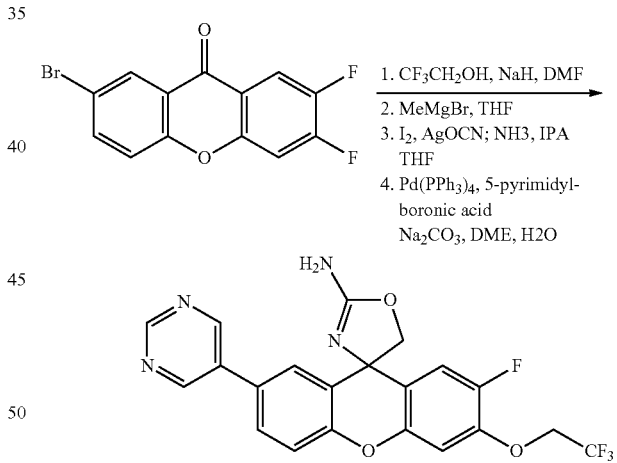

Step 1: To a solution of 7-bromo-2,3-difluoro-9H-xanthen-9-one (3.1 g, 9.97 mmol) and 2,2,2-trifluoroethanol (1.445 mL, 19.93 mmol) in DMF (33 mL) at 0° C. was added sodium hydride (0.598 g, 14.95 mmol) slowly in portions. After addition, the mixture was stirred at RT for overnight. Then, H$_2$O (100 mL) was added slowly and the mixture was extracted with EtOAc (1×100 mL). The organic layer was collected, dried over MgSO$_4$, and concentrated. The residue was then washed with hexane (1×100 mL) to give 2.76 g of 7-bromo-2-fluoro-3-(2,2,2-trifluoroethoxy)-9H-xanthen-9-one as a light yellow solid. MS (ESI, positive ion) m/z: 390.9, 392.9 (M+1).

Step 2: To a solution of 7-bromo-2-fluoro-3-(2,2,2-trifluoroethoxy)-9H-xanthen-9-one (2.00 g, 5.11 mmol) in THF (25 mL) at 0° C. was added methylmagnesium bromide 3.0 M in diethyl ether (3.41 mL, 10.23 mmol) slowly. After addition, the mixture was stirred at RT for overnight. Then, the mixture was cooled to 0° C. and saturated ammonium chloride (50 mL) was added slowly. The mixture was then stirred at RT for 15 min. Then, the organic layer was collected and the aqueous layer was extracted with EtOAc (1×50 mL). The combined organic extracts were dried over MgSO₄, concentrated, and dried in vacuo to give 7-bromo-2-fluoro-9-methylene-3-(2,2,2-trifluoroethoxy)-9H-xanthene as a brown solid. MS (ESI, positive ion) m/z: 388.9, 390.9 (M+1).

Step 3: To a solution of iodine (0.254 mL, 4.93 mmol) in THF (25 mL) at −20° C. was added silver cyanate (0.616 mL, 16.45 mmol). After addition, the mixture was stirred at −20° C. for 1 h. Then, a solution of 7-bromo-2-fluoro-9-methylene-3-(2,2,2-trifluoroethoxy)-9H-xanthene (1.600 g, 4.11 mmol) in THF (1.5 mL) was added and the mixture was stirred at 0° C. for 2 h. Then, the mixture was filtered through celite with the aid of THF (15 mL). Then, ammonia (6.17 mL, 12.33 mmol) (2 M in i-PrOH) was added dropwise to the filtrate. The resulting mixture was stirred at RT for overnight. Then, saturated Na₂O₃S₂ (5 mL) was added followed by saturated NaHCO₃ (5 mL). The mixture was stirred at room temperature for 5 min. The organic layer was collected, dried over MgSO₄, and concentrated. The residue was then mixed with silica gel and the solid mixture was purified by silica gel column chromatography using ISCO instrument (solid loading, 0%-20% MeOH/DCM) to give 7'-bromo-2'-fluoro-3'-(2,2,2-trifluoroethoxy)-5H-spiro[oxazole-4,9'-xanthen]-2-amine as a light yellow solid.

MS (ESI, positive ion) m/z: 446.9, 448.9 (M+1).

Step 4: To a solution of 7'-bromo-2'-fluoro-3'-(2,2,2-trifluoroethoxy)-5H-spiro[oxazole-4,9'-xanthen]-2-amine (0.250 g, 0.559 mmol) in 1,2-Dimethoxyethane (2.5 mL) at RT was added sodium carbonate monohydrate crystals (0.070 mL, 1.677 mmol), 5-pyrimidinylboronic acid (0.104 g, 0.839 mmol), tetrakis(triphenylphosphine)palladium (0.052 g, 0.045 mmol), and H₂O (0.5 mL). The resulting mixture was then heated to 90° C. for 5 h. Then, the mixture was cooled to RT and EtOAc (5 mL) was added. The mixture was stirred at RT for 1 min. The organic layer was collected, dried over MgSO₄, and concentrated. The residue was then dissolved in DMSO (2 mL) and the solution mixture was then purified by preparative HPLC (0%-100% MeCN 0.1% TFA/H₂O 0.1% TFA) to give a desired product in a solution of MeCN 0.1% TFA/H₂O 0.1% TFA. Then, solution mixture was neutralized by saturated NaHCO₃ and MeCN was removed in vacuo. Then saturated NaHCO₃ (2 mL) was added and the mixture was extracted with EtOAc (2×15 mL). The combined organic extracts were dried over MgSO₄, concentrated, and dried in vacuo to give the product depicted above as a colorless solid. MS (ESI, positive ion) m/z: 447 (M+1).

Example 21 (Method AA4)

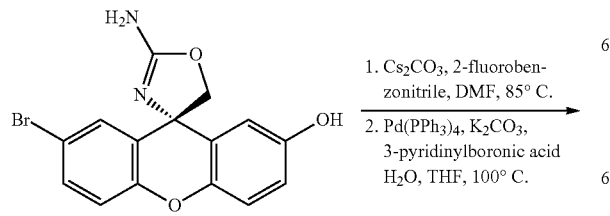

-continued

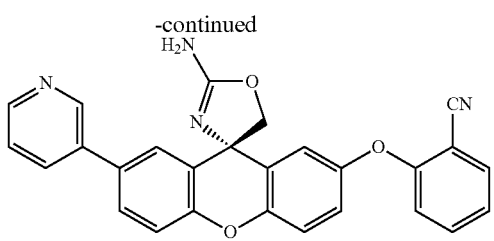

Synthesis of (S)-2-(2-amino-2'-(pyridin-3-yl)-5H-spiro[oxazole-4,9'-xanthene]-7'-yloxy)benzonitrile Step 1: A vial was charged with (R)-2-amino-2'-bromo-5H-spiro[oxazole-4,9'-xanthen]-7'-ol (210 mg, 0.605 mmol), cesium carbonate (237 mg, 0.726 mmol), and DMF (4033 μL). The mixture was stirred for 15 min, then 2-fluorobenzonitrile (81 μL, 0.665 mmol) was added. The mixture was heated at 85° C. overnight. The reaction was diluted with water and EtOAc. The aqueous layer was extracted with EtOAc (2×). The combined organic extracts were dried over sodium sulfate, filtered, and evaporated. The residue was chromatographed on a 40-g Redi-Sep column, eluting with 0-100% of a 90:10:1 mix of DCM/MeOH/NH₄OH in DCM. The product isolated this way was impure, so the material was resubjected to chromatography on a 40-g Redi-Sep column, this time eluting with 0-100% EtOAc/Hexane. This gave (R)-2-(2-amino-2'-bromo-5H-spiro[oxazole-4,9'-xanthene]-7'-yloxy)benzonitrile as 94% pure by HPLC. It was a yellow solid after evaporation from DCM/hexane.

Step 2: A vial was charged with (R)-2-(2-amino-2'-bromo-5H-spiro[oxazole-4,9'-xanthene]-7'-yloxy)benzonitrile (75 mg, 0.167 mmol), pyridin-3-ylboronic acid (51.4 mg, 0.418 mmol), tetrakis(triphenylphosphine)palladium(0) (9.67 mg, 8.37 μmol), THF (837 μL), and potassium carbonate (418 μL, 0.837 mmol) (as a 2.0 M aq. solution). The vial was sealed and heated to 100° C. in a shaker overnight. The mixture was diluted with EtOAc and the layers were separated. The aqueous layer was extracted with EtOAc (2×). The combined organic extracts were evaporated, and the residue was chromatographed on a 25-g SNAP column, eluting with 0-80% of a 90:10:1 mix of DCM/MeOH/NH₄OH in DCM to give (S)-2-(2-amino-2'-(pyridin-3-yl)-5H-spiro[oxazole-4,9'-xanthene]-7'-yloxy)benzonitrile as a pale-yellow solid.

Example 22 (Method AA5)

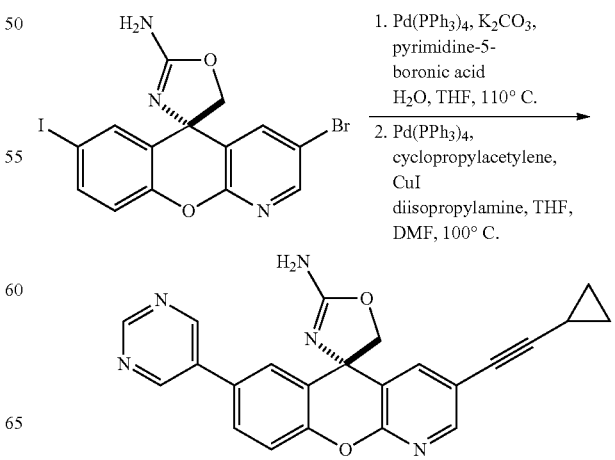

Synthesis of (S)-3-(3,3-dimethylbut-1-ynyl)-7-(pyrimidin-5-yl)-5'H-spiro[chromeno[2,3-b]pyridine-5,4'-oxazol]-2'-amine Step 1: A sealable tube was charged with (S)-3-bromo-7-iodo-5'H-spiro[chromeno[2,3-b]pyridine-5,4'-oxazol]-2'-amine (2.000 g, 4.37 mmol), pd(ph3p)4 (0.504 g, 0.437 mmol), pyrimidin-5-ylboronic acid (0.568 g, 4.58 mmol) and THF (21.83 mL, 4.37 mmol). The mixture was flushed with Ar then a solution of potassium carbonate (1.5 M) (5.82 mL, 8.73 mmol) was added. The reaction was heated at 110° C. for 2 hours before being diluted with water 50 mL and poured into a separatory funnel containing EtOAc 50 mL. The layers were separated and the aqueous layer was extracted with EtOAc 3×100 mL. The aqeuous layer was then extracted with DCM (3×100 mL). The combined organic layers were washed with brine, dried over sodium sulfate, filtered and concentrated in vacuo to provide a brown oil that was purified by silica gel chromatography (Redi-Sep pre-packed silica gel column (80 g), 0-10% methanol in methylenechloride with 0.1% ammonium hydroxide) to provide (S)-3-bromo-7-(pyrimidin-5-yl)-5'H-spiro[chromeno[2,3-b]pyridine-5,4'-oxazol]-2'-amine as a light yellow foam.

Step 2: Combined (S)-3-bromo-7-(pyrimidin-5-yl)-5'H-spiro[chromeno[2,3-b]pyridine-5,4'-oxazol]-2'-amine (75 mg, 0.183 mmol), tetrakis(triphenylphosphine)palladium (21.13 mg, 0.018 mmol), copper iodide (3.48 mg, 0.018 mmol), THF (366 μL, 0.183 mmol) and DMF (366 μL, 0.183 mmol) in a reaction vial. To the mixture was added diisopropyl amine (512 μL, 3.66 mmol) then ethynylcyclopropane (60.4 mg, 0.914 mmol). The reaction vial was sealed and heated at 110° C. for 1.5 hours. The reaction was allowed to cool to RT before being diluted with water (15 mL) and poured into a separatory funnel containing ethyl acetate (50 mL). The layers were separated and the aqueous layer was extracted with ethyl acetate (1×25 mL). The combined organic layers were washed with water and then brine, dried over sodium sulfate, filtered and concentrated in vacuo to provide a brown foam that was purified by silica gel chromatography (Redi-Sep pre-packed silica gel column (12 g), 0-10% methanol in methylenechloride with 0.1% ammonium hydroxide) to provide (S)-3-(3,3-dimethylbut-1-ynyl)-7-(pyrimidin-5-yl)-5'H-spiro[chromeno[2,3-b]pyridine-5,4'-oxazol]-2'-amine as an orange solid.

Example 23 (Method AA6)

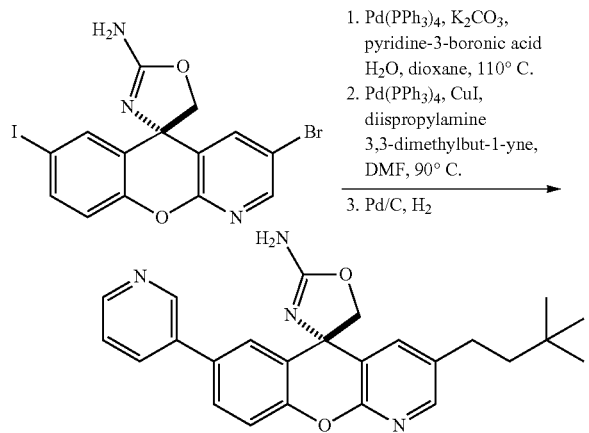

Synthesis of (S)-3-(3,3-dimethylbutyl)-7-(pyridin-3-yl)-5'H-spiro[chromeno[2,3-b]pyridine-5,4'-oxazol]-2'-amine Step 1: A sealable tube was charged with (S)-3-bromo-7-iodo-5'H-spiro[chromeno[2,3-b]pyridine-5,4'-oxazol]-2'-amine (600 mg, 1.310 mmol), Pd(PPh$_3$)$_4$ (151 mg, 0.131 mmol), pyridin-3-ylboronic acid (161 mg, 1.310 mmol) and THF (6550 μL, 1.310 mmol). The mixture was purged with Ar for 2 minutes then a solution of potassium carbonate (1747 μL, 2.62 mmol) was added. The tube was sealed and heated at 110° C. for 2 hours. The reaction was diluted with water 50 mL and poured into a separatory funnel containing EtOAc 50 mL. The layers were separated and the aqueous layer was extracted with EtOAc 4×50 mL. The combined organic layers were washed with brine, dried over sodium sulfate, filtered and concentrated in vacuo to provide a brown oil that was purified by silica gel chromatography (Redi-Sep pre-packed silica gel column (40 g), 0-10% methanol in DCM with 0.1% ammonium hydroxide) to provide (S)-3-bromo-7-(pyridin-3-yl)-5'H-spiro[chromeno[2,3-b]pyridine-5,4'-oxazol]-2'-amine as a light yellow foam.

Step 2: Combined (S)-3-bromo-7-(pyridin-3-yl)-5'H-spiro[chromeno[2,3-b]pyridine-5,4'-oxazol]-2'-amine (250 mg, 0.611 mmol), Pd(PPh$_3$)$_4$ (70.6 mg, 0.061 mmol), copper(i) iodide (23.27 mg, 0.122 mmol) and DMF (4073 μL, 0.611 mmol) in a sealable tube. Added (201 mg, 2.444 mmol) and DIPA (4353 μL, 30.5 mmol), flushed with argon, sealed and heated at 90° C. overnight. The reaction was diluted with water (25 mL) and poured into a separatory funnel containing ethyl acetate (50 mL). The layers were separated and the aqueous layer was extracted with ethyl acetate (1×100 mL). The combined organic layers were washed with water, dried over sodium sulfate, filtered and concentrated in vacuo to provide a brown foam that was purified by silica gel chromatography (Redi-Sep pre-packed silica gel column (12 g), 0-10% methanol in methylenechloride with 0.1% ammonium hydroxide) to provide (S)-3-(3,3-dimethylbut-1-ynyl)-7-(pyridin-3-yl)-5'H-spiro[chromeno[2,3-b]pyridine-5,4'-oxazol]-2'-amine as a brown solid Step 3: To a solution of (S)-3-(3,3-dimethylbut-1-ynyl)-7-(pyridin-3-yl)-5'H-spiro[chromeno[2,3-b]pyridine-5,4'-oxazol]-2'-amine (60 mg, 0.146 mmol) in 5 mL of methanol was added Pd/C (5%) (156 mg, 1.462 mmol). The mixture was maintained under an atmosphere of hydrogen gas for 20 hours before being filtered through a celite plug, washing well with methanol. The filtrate was concentrated and the derived residue was purified by silical gel chromatography (12 g, 0-10% methanol in methylenechloride with 0.1% ammonium hydroxide) to provide (S)-3-(3,3-dimethylbutyl)-7-(pyridin-3-yl)-5'H-spiro[chromeno[2,3-b]pyridine-5,4'-oxazol]-2'-amine as a white solid.

Example 24 (Method AA7)

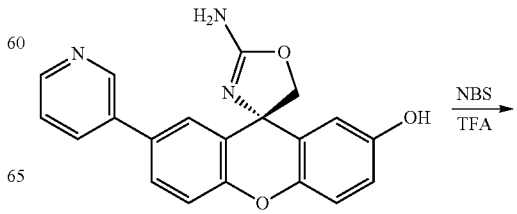

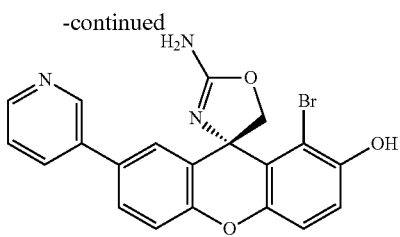

A vial was charged with (S)-2-amino-7'-(pyridin-3-yl)-5H-spiro[oxazole-4,9'-xanthen]-2'-ol (106 mg, 0.308 mmol) and TFA (1540 µL) to give an orange solution. The vial was submerged in an ice-bath for 15 min, and n-bromosuccinimide (54.8 mg, 0.308 mmol) was added in a single portion. Stirred the mixture for 1 hour, then it was diluted with methanol and evaporated under reduced pressure. The residue was dissolved in methanol and loaded onto a 2-g SCX-2 acidic column. The column was first eluted with methanol to remove impurities, then with 2 M ammonia in methanol to elute the product. The filtrate was evaporated in vacuo to give a brown oil. This oil was chromatographed on a 40-g HP (high performance) Redi-Sep column, eluting with 0-100% of a 90:10:1 mix of DCM/MeOH/DCM in DCM to provide the depicted compound as a yellow solid.

Example 25 (Method AA8)

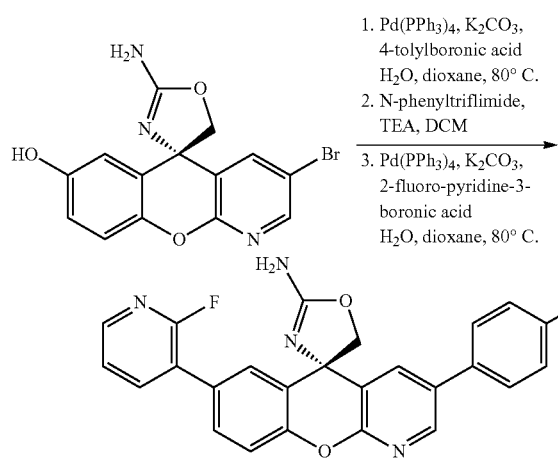

Synthesis of (S)-7-(2-fluoropyridin-3-yl)-3-p-tolyl-5'H-spiro[chromeno[2,3-b]pyridine-5,4'-oxazol]-2'-amine Step 1: A vial was charged (S)-2'-amino-3-bromo-5'H-spiro[chromeno[2,3-b]pyridine-5,4'-oxazol]-7-ol (282 mg, 0.809 mmol), p-tolylboronic acid (220 mg, 1.618 mmol), potassium carbonate (559 mg, 4.04 mmol), Pd(PPh₃)₄ (46.7 mg, 0.040 mmol). The vial was flushed with Ar (g), then Dioxane (4044 µL) and water (2 mL) were added in sequence. The vial was sealed and placed in an 80° C. oil bath. After stirring for 50 minutes, the mixture was partitioned between brine and 10% iPrOH/EtOAc. The layers were separated, and the aq. layer was extracted with EtOAc. The combined organic extracts were dried over sodium sulfate, filtered, and evaporated. The residue was chomatographed on an 80-g Redi-Sep column, eluting with 0-80% of a 90:10:1 mix of DCM/MeOH/NH₄OH in DCM to give (S)-2'-amino-3-p-tolyl-5'H-spiro[chromeno[2,3-b]pyridine-5,4'-oxazol]-7-ol (259.36 mg, 0.722 mmol, 89% yield) as an orange solid.

Step 2: A 25-mL flask was charged with (S)-2'-amino-3-p-tolyl-5'H-spiro[chromeno[2,3-b]pyridine-5,4'-oxazol]-7-ol (259.36 mg, 0.722 mmol) in DCM (7217 µL) to give an clear, orange solution. triethylamine (201 µL, 1.443 mmol) and 1,1,1-trifluoro-N-phenyl-N-(trifluoromethylsulfonyl)methanesulfonamide (271 mg, 0.758 mmol) were added in sequence. The mixture was stirred for 4 hours before being loaded directly onto a 25-g silica gel loading column with the aid of DCM. The column was eluted onto a prequilibrated 40-g Redi-Sep column with 0-5% MeOH/DCM to give (S)-2'-amino-3-p-tolyl-5'H-spiro[chromeno[2,3-b]pyridine-5,4'-oxazole]-7-yl trifluoromethanesulfonate (317.34 mg, 0.646 mmol, 89% yield) as a cream-colored solid Step 3: A vial was charged with (S)-2'-amino-3-p-tolyl-5'H-spiro[chromeno[2,3-b]pyridine-5,4'-oxazole]-7-yl trifluoromethanesulfonate (45.0 mg, 0.092 mmol), 2-fluoropyridin-3-ylboronic acid (38.7 mg, 0.275 mmol), potassium carbonate (229 µL, 0.458 mmol), and Pd(PPh₃)₄ (5.29 mg, 4.58 µmol). The vial was flushed with Ar (g), then dioxane (458 µL) (actual amount as 1 mL) and water (0.5 mL) were added in sequence. The vial was selaed and placed in an 80° C. oil bath for 2 hours. The mixture was diluted with EtOAc, washed with brine, dried over sodium sulfate, filtered, and evaporated. The residue was chromatographed on a 12-g Redi-Sep column with 0-5% MeOH/DCM to give (S)-7-(2-fluoropyridin-3-yl)-3-p-tolyl-5'H-spiro[chromeno[2,3-b]pyridine-5,4'-oxazol]-2'-amine (29.53 mg, 0.067 mmol, 73.6% yield) as a tan solid.

Example 26 (Method AA9)

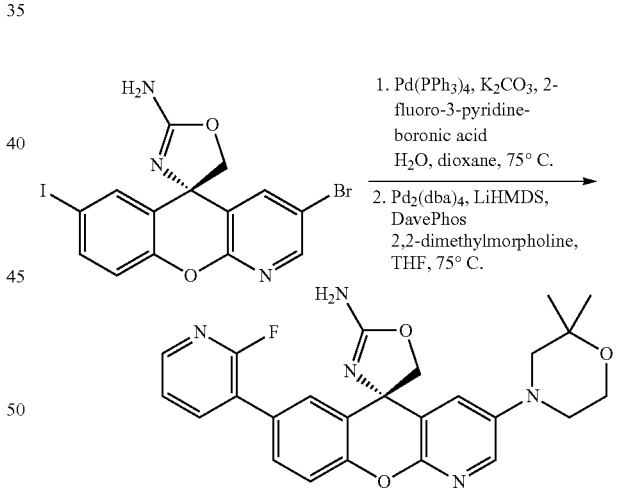

Synthesis of (S)-3-(2,2-dimethylmorpholino)-7-(2-fluoropyridin-3-yl)-5'H-spiro[chromeno[2,3-b]pyridine-5,4'-oxazol]-2'-amine Step 1: A vial was charged with (S)-3-bromo-7-iodo-5'H-spiro[chromeno[2,3-b]pyridine-5,4'-oxazol]-2'-amine (302.9 mg, 0.661 mmol), 2-fluoro-3-pyridineboronic acid (102 mg, 0.727 mmol), potassium carbonate (457 mg, 3.31 mmol), and tetrakis(triphenylphosphine)palladium(0) (38.2 mg, 0.033 mmol). The vial was flushed with Ar (g), then dioxane (3306 µL) and water (1.7 mL) were added in sequence. The vial was sealed and placed in a 75° C. oil bath for 2 hours. The mixture was diluted with EtOAc (15 mL) and brine (15 mL). The layers were separated, and the aq. layer was extracted with EtOAc (2×15 mL). The combined organic extracts were dried over sodium sulfate, filtered, and evaporated. The residue was purified by chromatography on a 40-g Redi-Sep column, eluting with 0-60% of a 90:10:1 mix of DCM/MeOH/NH$_4$OH in DCM to give (S)-3-bromo-7-(2-fluoropyridin-3-yl)-5'H-spiro[chromeno[2,3-b]pyridine-5,4'-oxazol]-2'-amine as an off-white solid.

Step 2: A vial was charged with (S)-3-bromo-7-(2-fluoropyridin-3-yl)-5'H-spiro[chromeno[2,3-b]pyridine-5,4'-oxazol]-2'-amine (110 mg, 0.257 mmol), DavePhos (12.16 mg, 0.031 mmol), and tris(dibenzylideneacetone)dipalladium(0) (11.79 mg, 0.013 mmol). The vessel was flushed with Ar(g), then lithium bis(trimethylsilyl)amide (772 µL, 0.772 mmol) (1.0 M solution in THF) and 2,2-dimethylmorpholine (61.8 µL, 0.515 mmol) were added in sequence. The vial was sealed and placed in a 75° C. oil bath for two hours. The mixture was diluted with saturated aq. ammonium chloride solution (20 mL) and water (10 mL). The mixture was extracted with DCM (3×20 mL), leaving behing a dark oily solid. The combined organic extracts were dried over sodium sulfate, filtered, and evaporated. The residue was chromatographed on an 24-g Redi-Sep Gold column with 0-70% of a 90:10:1 mix of DCM/MeOH/NH$_4$OH in DCM to give (S)-3-(2,2-dimethylmorpholino)-7-(2-fluoropyridin-3-yl)-5'H-spiro[chromeno[2,3-b]pyridine-5,4'-oxazol]-2'-amine as a yellow solid.

Example 27 (Method AA10)

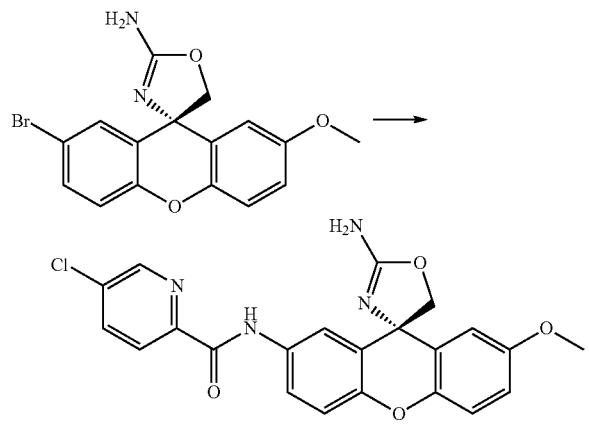

Synthesis of N-((4S)-2-amino-7'-methoxyspiro[1,3-oxazole-4,9'-xanthen]-2'-yl)-5-chloro-2-pyridinecarboxamide Step 1: A 5 mL smith synthesizer vial was charged with (R)-2'-bromo-7'-methoxy-5H-spiro[oxazole-4,9'-xanthen]-2-amine (1.248 g, 3.46 mmol), sodium azide (0.684 g, 10.52 mmol), L-ascorbic acid sodium salt (0.057 g, 0.288 mmol), copper(I) iodide (0.131 g, 0.688 mmol), and (1R,2R)—N1,N2-dimethylcyclohexane-1,2-diamine (0.116 mL, 0.736 mmol) in EtOH (6.0 mL), water (2.6 mL) and the reaction was heated to 100° C. in the microwave for 35 minutes. The reaction vial was cooled to RT and concentrated on the rotary evaporator and the resulting residue was taken up in ethyl acetate (125 mL), water (50 mL) the organic layer was separated. The organic layer was dried over sodium sulfate and concentrated to yield the crude product which was purified by silica gel flash column chromatography (using a 40 G ISCO silica gel cartridge), and eluted using hexanes/ethyl acetate gradient. The fractions were combined and concentrated to yield (S)-2'-azido-7'-methoxy-5H-spiro[oxazole-4,9'-xanthen]-2-amine as a yellowish solid. MS (ESI pos. ion) m/z: 324 (M+1).

Step 2: A solution of (S)-2'-azido-7'-methoxy-5H-spiro[oxazole-4,9'-xanthen]-2-amine (1.162 g, 3.59 mmol) in dichloromethane (25 mL) was treated with pyridine (0.775 mL, 9.50 mmol) followed by trifluoroaceticacid anhydride (0.9 mL, 6.43 mmol) at RT. The reaction was allowed to stir for 2 hours during which formation of desired product was detected (M+H~420) along with traces of unreacted starting material. The reaction was allowed to stir for another 6 hours and diluted with DCM (75 mL), water (20 mL), and separated the organic layer. The organic layer was dried over anhydrous sodium sulfate, and concentrated to yield (S)—N-(2'-azido-7'-methoxy-5H-spiro[oxazole-4,9'-xanthene]-2-yl)-2,2,2-trifluoroacetamide as a yellowish solid. MS (ESI pos. ion) m/z: 420 (M+1).

Step 3: A solution of (S)—N-(2'-azido-7'-methoxy-5H-spiro[oxazole-4,9'-xanthene]-2-yl)-2,2,2-trifluoroacetamide (0.410 g, 0.978 mmol) in ethanol (12 mL) and THF (8 mL) was stirred with palladium hydroxide, 20 wt % pd (dry basis) on carbon, wet, degussa type e101 ne/w (0.136 g, 0.978 mmol) under hydrogen at atmospheric pressure and RT for 2 hours. The catalyst was removed by filtration over a celite-pad, washed with EtOH (15 mL). The combined filtrates were concentrated to yield the crude product (104584-37-2). The product (S)—N-(2'-amino-7'-methoxy-5H-spiro[oxazole-4,9'-xanthene]-2-yl)-2,2,2-trifluoroacetamide was obtained as an off-white solid. MS (ESI pos. ion) m/z: 394 (M+1).

Step 4: A 25 mL RBF containing a solution of (S)—N-(2'-amino-7'-methoxy-5H-spiro[oxazole-4,9'-xanthene]-2-yl)-2,2,2-trifluoroacetamide (0.058 g, 0.147 mmol), 5-chloropyridine-2-carboxylic acid (0.030 g, 0.190 mmol), 1-(3-dimethylaminopropyl)-3-ethylcarbodiimide hydrochloride (0.045 g, 0.235 mmol) in DCM (4 mL) and DMF (0.25 mL) was treated with 1-hydroxy-1H-benzotriazole (0.014 g, 0.104 mmol) and stirred for 1.5 hrs at RT. The reaction was diluted with DCM (50 mL) and water (15 mL). The DCM layer was separated, dried over anhydrous sodium sulfate, and concentrated to dryness to yield (S)-5-chloro-N-(2'-methoxy-2-(2,2,2-trifluoroacetamido)-5H-spiro[oxazole-4,9'-xanthene]-7'-yl)picolinamide as a brownish solid. MS (ESI pos. ion) m/z: 533 (M+1).

Step 5: A solution of (S)-5-chloro-N-(2'-methoxy-2-(2,2,2-trifluoroacetamido)-5H-spiro[oxazole-4,9'-xanthene]-7'-yl)picolinamide (0.054 g, 0.101 mmol) in methanol (3.5 mL) was treated with potassium carbonate anhydrous (0.045 g, 0.326 mmol) and stirred at RT for 30 minutes. The catalyst was removed by filtration and the filtrate was concentrated to yield the crude product as a yellowish gummy solid. The crude product was purified by preparative HPLC [gradient 10-90% MeCN (0.1% TFA)/H$_2$O (0.1% TFA)] to give pure product which was dissolved in methanol (5 mL) and neutralized by passing the solution through a Polymer Lab-HCO$_3$ macroporous resin cartridge, and the filtrate was concentrated to give N-((4S)-2-amino-7'-methoxyspiro[1,3-oxazole-4,9'-xanthen]-2'-yl)-5-chloro-2-pyridinecarboxamide as an off-white solid. MS (ESI pos. ion) m/z: 437 (M+1).

Example 28 (Method AA11)

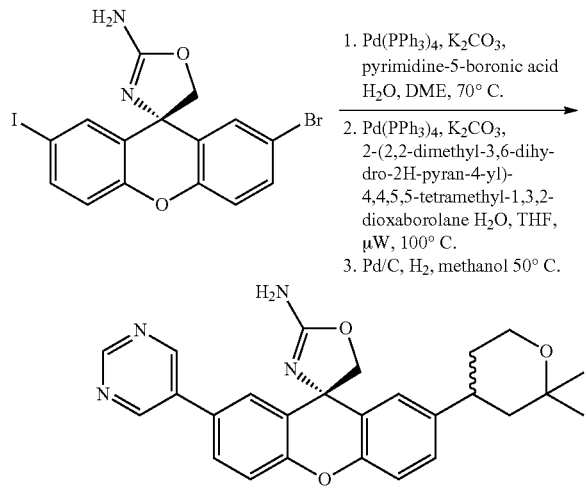

Synthesis of R)-2'-(2,2-dimethyltetrahydro-2H-pyran-4-yl)-7'-(pyrimidin-5-yl)-5H-spiro[oxazole-4,9'-xanthen]-2-amine Step 1: A 100 ml RBF was charged with (R)-2'-bromo-7'-iodo-5H-spiro[oxazole-4,9'-xanthen]-2-amine (3.3 g, 7.22 mmol), pyrimidin-5-ylboronic acid (1.163 g, 9.39 mmol), and tetrakis(triphenylphosphine)palladium(0) (0.834 g, 0.722 mmol). To this were added DME (51.6 mL) followed by sodium carbonate (10.83 mL, 21.66 mmol) (2M solution) and the mixture was heated at 70° C. for 24 hrs. The mixture was diluted with water and ethyl acetate, filtered and organic layer was separated and concentrated. The crude material was purified by FC on 80 g RediSep column using 5-70% gradient of DCM/MeOH/NH4OH in DCM to give (S)-2'-bromo-7'-(pyrimidin-5-yl)-5H-spiro[oxazole-4,9'-xanthen]-2-amine).

Step 2: A 15 ml resealable vial was charged with (S)-2'-bromo-7'-(pyrimidin-5-yl)-5H-spiro[oxazole-4,9'-xanthen]-2-amine (700 mg, 1.711 mmol), 2-(2,2-dimethyl-3,6-dihydro-2H-pyran-4-yl)-4,4,5,5-tetramethyl-1,3,2-dioxaborolane (652 mg, 2.74 mmol), 1.5:1 mixture of regioisomers of the double bond, major shown, which contains significant amount of bis-pinaclborane. Potassium carbonate (709 mg, 5.13 mmol) and AmPhos (60.6 mg, 0.086 mmol), 1,4-Dioxane (9978 µL) and Water (1425 µL) were added, the vial was sealed and heated in microwave reactor for 1 hr at 100° C. The mixture was diluted with ethyl acetate, filtered through celite and concentrated, the residue was purified by flash chromatography (20-60% gradient of DCM/MeOH/NH4OH (90:10:1) in DCM) to afford a 450 mg (60% yield) of 1:1 mixture of (R)-2'-(6,6-dimethyl-3,6-dihydro-2H-pyran-4-yl)-7'-(pyrimidin-5-yl)-5H-spiro[oxazole-4,9'-xanthen]-2-amine and (R)-2'-(2,2-dimethyl-3,6-dihydro-2H-pyran-4-yl)-7'-(pyrimidin-5-yl)-5H-spiro[oxazole-4,9'-xanthen]-2-amine.

Step 3: To a solution of (R)-2'-(2,2-dimethyl-3,6-dihydro-2H-pyran-4-yl)-7'-(pyrimidin-5-yl)-5H-spiro[oxazole-4,9'-xanthen]-2-amine (55 mg, 0.125 mmol) in MeOH (2 mL) palladium on carbon (66.4 mg, 0.062 mmol) was added and the mixture was hydrogenated at 50° C. (1 atm of hydrogen gas) for 30 min. Another 20 mg of Pd/C was added and hydrogenation was continued for 1.5 hr at 50° C. The mixture was filtered through a plug of celite and purified by silica gel chromatography (10-80% DCM/MeOH/NH4OH in DCM) to afford (R)-2'-(2,2-dimethyltetrahydro-2H-pyran-4-yl)-7'-(pyrimidin-5-yl)-5H-spiro[oxazole-4,9'-xanthen]-2-amine.

Example 29 (Method AA12)

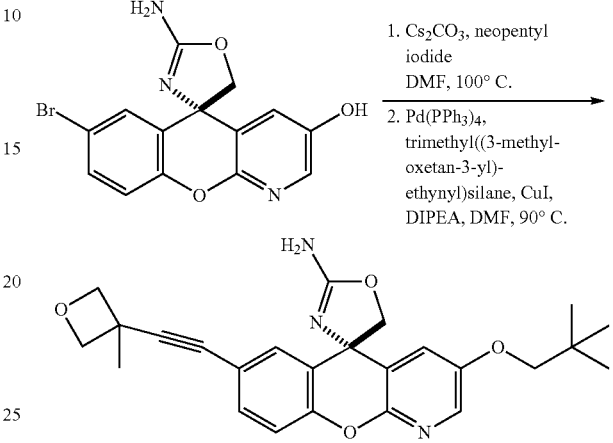

Synthesis of (S)-7-((3-methyloxetan-3-yl)ethynyl)-3-(neopentyloxy)-5'H-spiro[chromeno[2,3-b]pyridine-5,4'-oxazol]-2'-amine Step 1: To a solution of (S)-2'-amino-7-bromo-5'H-spiro[chromeno[2,3-b]pyridine-5,4'-oxazol]-3-ol (390 mg, 1.120 mmol) in DMF (4481 µL, 1.120 mmol) in a sealed tube was added cesium carbonate (912 mg, 2.80 mmol). After stirring for 1 minute neopentyl iodide (223 µL, 1.680 mmol) was added, the reaction vessel was sealed and heated at 100° C. for 2.5 hours. Reaction was cooled to RT to prevent over alkylation. The reaction was diluted with water (25 mL) and 10 mL of ethyl acetate and stirred for 30 minutes before being poured into a separatory funnel containing ethyl acetate (100 mL) and water (250 mL). The layers were separated and the aqueous layer was extracted with ethyl acetate (3×50 mL). The aqueous layer was then extracted with DCM (3×50 mL). The organic layers were each washed with water and then brine, at which point all the organics were combined, dried over sodium sulfate, filtered and concentrated in vacuo to provide a brown foam that was purified by silica gel chromatography (Redi-Sep pre-packed silica gel column (40 g), 0-10% methanol in methylenechloride with 0.1% ammonium hydroxide) to provide (S)-7-bromo-3-(neopentyloxy)-5'H-spiro[chromeno[2,3-b]pyridine-5,4'-oxazol]-2'-amine as a yellow solid.

Step 2: A sealable tube was charged with (S)-7-bromo-3-(neopentyloxy)-5'H-spiro[chromeno[2,3-b]pyridine-5,4'-oxazol]-2'-amine (75 mg, 0.179 mmol), copper iodide (3.38 mg, 0.018 mmol), tetrakis(triphenylphosphine)palladium (20.53 mg, 0.018 mmol). To this mixture was added DMF (355 µL, 0.178 mmol), diisopropylamine (498 µL, 3.55 mmol) and trimethyl((3-methyloxetan-3-yl)ethynyl)silane (90 mg, 0.533 mmol). The tube was flushed with argon, sealed and heated to 90° C. for 12 hours. The reaction was diluted with water (100 mL) and poured into a separatory funnel containing ethyl acetate (50 mL). The layers were separated and the aqueous layer was extracted with ethyl acetate (2×50 mL). The combined organic layers were washed with water and then brine, dried over sodium sulfate, filtered and concentrated in vacuo to provide a brown oil that was purified by silica gel chromatography (Redi-Sep pre-packed silica gel column (12 g), 0-10% methanol in methylenechloride with 0.1% ammonium hydroxide) to provide (S)-7-((3-methyloxetan-3-yl)ethynyl)-3-(neopentyloxy)-5'H-spiro[chromeno[2,3-b]pyridine-5,4'-oxazol]-2'-amine as a yellow solid.

Example 30 (Method AA13)

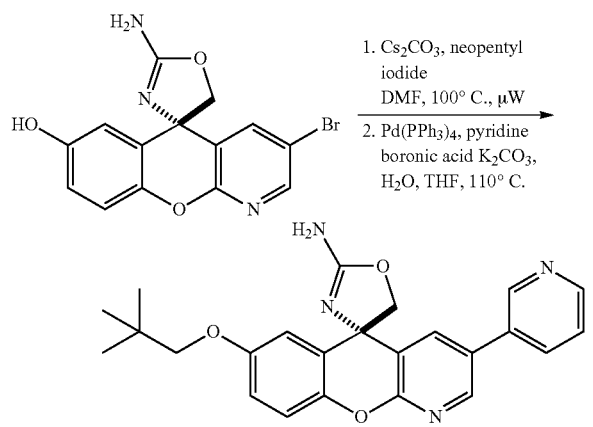

Synthesis of (R)-7-(neopentyloxy)-3-(pyridin-3-yl)-5'H-spiro[chromeno[2,3-b]pyridine-5,4'-oxazol]-2'-amine Step 1: A 350 mL sealable flask was charged with (R)-2'-amino-3-bromo-5'H-spiro[chromeno[2,3-b]pyridine-5,4'-oxazol]-7-ol (12.10 g, 34.8 mmol) and DMF (99 mL, 34.8 mmol). To this solution was added cesium carbonate (28.3 g, 87 mmol). The resulting brown slurry was stirred at rt for 3 minutes before neopentyl iodide (9.21 mL, 69.5 mmol) was added in one portion. The reaction vessel was sealed and heated at 100° C. After heating for 4 hours another 1 mL of neopentyl iodide was added and heating at 100° C. was continued for another 1 hour at which point the reaction was allowed to cool to room temperature. The reaction was diluted with ethyl acetate (500 mL) and poured into water (2000 mL) before being transferred into a separatory funnel containing ethyl acetate (500 mL). The layers were separated and the aqueous layer was extracted with ethyl acetate (3×500 mL). The combined organic layers were washed with water and then brine. The aqeuous layer was combined with the above brined wash and was then extracted with DCM (2×500 mL). The organic layers were washed with water and then brine. All of the organigs were combined, dried over sodium sulfate, filtered and concentrated in vacuo to provide a brown foam that was purified by silica gel chromatography (Redi-Sep pre-packed silica gel column (330 g), 0-10% methanol in DCM with 0.1% ammonium hydroxide) to provide (R)-3-bromo-7-(neopentyloxy)-5'H-spiro[chromeno[2,3-b]pyridine-5,4'-oxazol]-2'-amine as a light yellow solid.

Step 2: Combined (R)-3-bromo-7-(neopentyloxy)-5'H-spiro[chromeno[2,3-b]pyridine-5,4'-oxazol]-2'-amine (9.15 g, 21.88 mmol), tetrakis(triphenylphosphine)palladium (2.53 g, 2.188 mmol) and 3-pyridylboronic acid (6.72 g, 54.7 mmol). Added THF (146 mL, 21.88 mmol) followed by potassium carbonate (1.5 M) (58.3 mL, 88 mmol). Flushed reaction tube with argon, sealed and heated at 110° C. for 2.5 hours. The reaction was allowed to cool to RT before being poured into a separatory funnel containing ethyl acetate (500 mL). Water (1000 mL) was added and, the layers were separated and the aqueous layer was extracted with ethyl acetate (3×500 mL). The combined organic layers were washed with brine, dried over sodium sulfate, filtered and concentrated in vacuo to provide a brown foam. This foam was purified by silica gel chromatography (Redi-Sep pre-packed silica gel column (330 g), 0-10% methanol in methylenechloride with 0.1% ammonium hydroxide) to provide (R)-7-(neopentyloxy)-3-(pyridin-3-yl)-5'H-spiro[chromeno[2,3-b]pyridine-5,4'-oxazol]-2'-amine as a light yellow solid.

Example 31 (Method AA14)

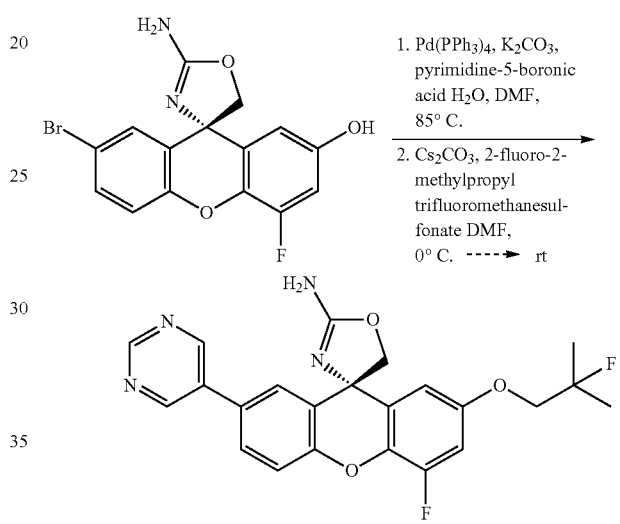

Synthesis of (S)-4'-fluoro-2'-(2-fluoro-2-methylpropoxy)-7'-(pyrimidin-5-yl)-5H-spiro[oxazole-4,9'-xanthen]-2-amine Step 1: A 25 ml RBF was charged with (S)-2-amino-7'-bromo-4'-fluoro-5H-spiro[oxazole-4,9'-xanthen]-2'-ol (629 mg, 1.723 mmol), tetrakis(triphenylphosphine)palladium (199 mg, 0.172 mmol), and pyrimidin-5-ylboronic acid (320 mg, 2.58 mmol). DMF (8613 µL) and sodium carbonate (2M solution) (2584 µL, 5.17 mmol) were added and the mixture was stirred at 85° C. for 2.5 hrs. The mixture was cooled to RT, water (~5 ml) was added and stirring was continued for 10 min. The precipitate was filtered out, washed with water (3×5 mL), 1:1 i-PrOH/water to remove color and dried in vacuo to afford (S)-2-amino-4'-fluoro-7'-(pyrimidin-5-yl)-5H-spiro[oxazole-4,9'-xanthen]-2'-ol as yellow solid.

Step 2: A vial was charged with (S)-2-amino-4'-fluoro-7'-(pyrimidin-5-yl)-5H-spiro[oxazole-4,9'-xanthen]-2'-ol (61.0 mg, 0.167 mmol), cesium carbonate (82 mg, 0.251 mmol), and DMF (670 µL). The resulting mixture was stirred vigorously for 10 min, then the vial was placed in large ice-bath for 10 min and 2-fluoro-2-methylpropyl trifluoromethanesulfonate (33.3 µL, 0.201 mmol) was added dropwise. The ice bath was removed after 5 minutes and the mixture was stirred at RT for 6 hours before being diluted with water (10 mL) and extracted with EtOAc (3×5 mL). The combined organic extracts were dried over sodium sulfate, filtered, and evaporated. The residue was chromatographed on a 12 g Redi-Sep column, eluting with 5-60% gradient of DCM/MeOH/NH4OH (90:10:1) in DCM to give (S)-4'-fluoro-2'-(2-fluoro-2-methylpropoxy)-7'-(pyrimidin-5-yl)-5H-spiro[oxazole-4,9'-xanthen]-2-amine as an off-white solid.

Example 32 (Method AA16)

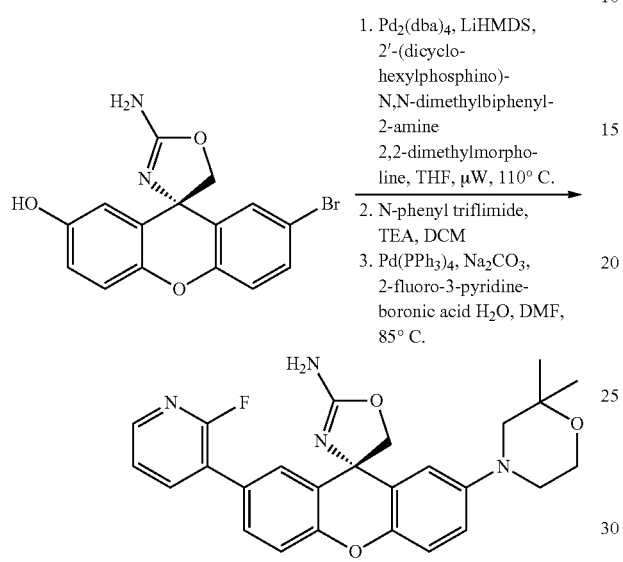

Synthesis of (S)-2'-(2,2-dimethylmorpholino)-7'-(2-fluoropyridin-3-yl)-5H-spiro[oxazole-4,9'-xanthen]-2-amine Step 1: A 2-5 ml microwave vial was charged with (S)-2-amino-2'-bromo-5H-spiro[oxazole-4,9'-xanthen]-7'-ol (300 mg, 0.864 mmol) (104780-26-0), Pd$_2$dba$_3$ (39.6 mg, 0.043 mmol), 2'-(dicyclohexylphosphino)-N,N-dimethylbiphenyl-2-amine (40.8 mg, 0.104 mmol) and 2,2-dimethylmorpholine (299 mg, 2.59 mmol). The mixture was capped with argon and LiHMDS (1M in THF) (4321 µL, 4.32 mmol) was added and the vial was sealed and heated at 110° C. in microwave reactor for 1 hr. The reaction mixture was quenched by addition of 2 ml water and EtOAc, then saturated NH$_4$Cl was added. The organic layer was filterd through Celite, concentrated in vacuo and purified on a 40 g RediSep column using 15-80% DCM/MeOH/NH4OH in DCM to afford (R)-2-amino-2'-(2,2-dimethylmorpholino)-5H-spiro[oxazole-4,9'-xanthen]-7'-ol.

Step 2: To a solution of (R)-2-amino-2'-(2,2-dimethylmorpholino)-5H-spiro[oxazole-4,9'-xanthen]-7'-ol (370 mg, 0.970 mmol) in DCM (4850 µL), were added triethylamine (270 µL, 1.940 mmol) and 1,1,1-trifluoro-N-phenyl-N-(trifluoromethylsulfonyl)methanesulfonamide (520 mg, 1.455 mmol). After stirring at room temperature for 60 hours the mixture was directly loaded onto 12 g RediSep column and purified using 15-60% DCM/MeOH/NH4OH to afford (R)-2-amino-2'-(2,2-dimethylmorpholino)-5H-spiro[oxazole-4,9'-xanthene]-7'-yl trifluoromethanesulfonate.

Step 3: A 25 mL RB flask was charged with (R)-2-amino-2'-(2,2-dimethylmorpholino)-5H-spiro[oxazole-4,9'-xanthene]-7'-yl trifluoromethanesulfonate (270 mg, 0.526 mmol), tetrakis(triphenylphosphine)palladium(0) (60.8 mg, 0.053 mmol), 2-fluoropyridin-3-ylboronic acid (119 mg, 0.841 mmol), DMF (2629 µL) and sodium carbonate (2M solution) (789 µL, 1.577 mmol). The mixture was stirred under argon for 2 hrs at 85° C. The mixture was diluted with water (2 ml) and extracted with 10 ml of EtOAc. Organic layer was washed with water, brine, passed through plug of Celite and concentrated. The dark residue was purified by silica gel chromatography (5-70% DCM/MeOH/NH4OH in DCM) to afford (S)-2'-(2,2-dimethylmorpholino)-7'-(2-fluoropyridin-3-yl)-5H-spiro[oxazole-4,9'-xanthen]-2-amine.

Example 33

Method AA17

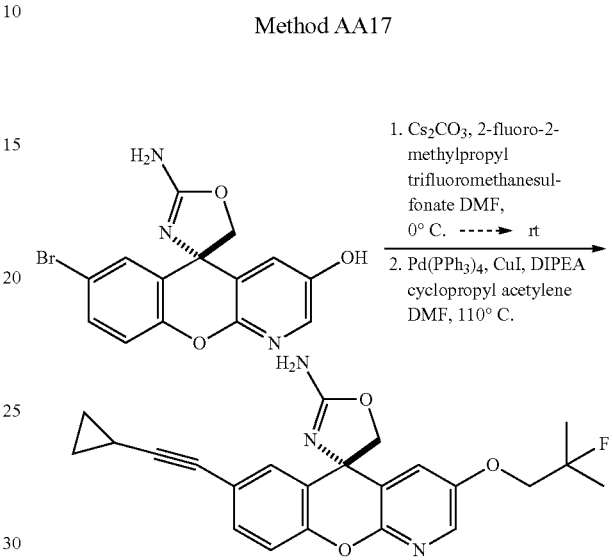

Synthesis of (S)-7-(cyclopropylethynyl)-3-(2-fluoro-2-methylpropoxy)-5'H-spiro[chromeno[2,3-b]pyridine-5,4'-oxazol]-2'-amine Step 1: A vial was charged with (S)-2'-amino-7-bromo-5'H-spiro[chromeno[2,3-b]pyridine-5,4'-oxazol]-3-ol (750 mg, 2.154 mmol), DMF (8617 µL, 2.154 mmol) and cesium carbonate (2106 mg, 6.46 mmol). The mixture was cooled to 0° C. and 2-fluoro-2-methylpropyl trifluoromethanesulfonate (966 mg, 4.31 mmol) was added. The reaction was removed from the ice bath and stirred at RT for 45 minutes. The reaction was diluted with water (250 mL) and poured into a separatory funnel containing ethyl acetate (250 mL). The layers were separated and the aqueous layer was extracted with ethyl acetate (3×100 mL). The combined organic layers were washed with water and then brine, dried over sodium sulfate, filtered and concentrated in vacuo to provide a light yellow solid that was purified by silica gel chromatography (Redi-Sep pre-packed silica gel column (40 g), 0-10% methanol in methylenechloride with 0.1% ammonium hydroxide) to provide (S)-7-bromo-3-(2-fluoro-2-methylpropoxy)-5'H-spiro[chromeno[2,3-b]pyridine-5,4'-oxazol]-2'-amine as a light yellow solid.

Step 2: A sealable tube was charged with (S)-7-bromo-3-(2-fluoro-2-methylpropoxy)-5'H-spiro[chromeno[2,3-b]pyridine-5,4'-oxazol]-2'-amine (75 mg, 0.178 mmol), copper(i) iodide (3.38 mg, 0.018 mmol), tetrakis(triphenylphosphine) palladium (20.53 mg, 0.018 mmol). Added DMF (355 µL, 0.178 mmol), diisopropylamine (498 µL, 3.55 mmol) and cyclopropylacetylene (75 µL, 0.888 mmol) and the tube was flushed with argon, sealed and heated to 110° C. for 2 hours. More copper iodide (3.38 mg, 0.018 mmol), tetrakis(triphenylphosphine)palladium (20.53 mg, 0.018 mmol), diisopropylamine (498 µL, 3.55 mmol) and cyclopropylacetylene (75 µL, 0.888 mmol) were added and the black mixture was heated at 110° C. for 3 hours. The reaction was diluted with water (100 mL) and poured into a separatory funnel containing ethyl acetate (50 mL). The layers were separated and the aqueous layer was extracted with ethyl acetate (2×50 mL). The combined organic layers were washed with water and then brine, dried over sodium sulfate, filtered and concentrated in vacuo to provide a brown oil that was purified by silica gel chromatography (Redi-Sep pre-packed silica gel column (12 g), 0-10% methanol in methylenechloride with 0.1% ammonium hydroxide) to provide (S)-7-(cyclopropylethynyl)-3-(2-fluoro-2-methylpropoxy)-5'H-spiro[chromeno[2,3-b]pyridine-5,4'-oxazol]-2'-amine as a tan solid.

Example 34

Method AA18

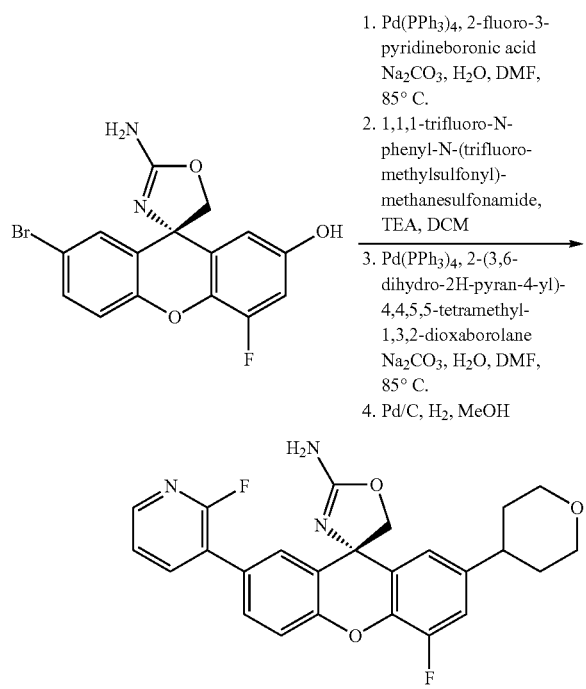

Synthesis of (S)-4'-fluoro-7'-(2-fluoropyridin-3-yl)-2'-(tetrahydro-2H-pyran-4-yl)-5H-spiro[oxazole-4,9'-xanthen]-2-amine Step 1: A RBF was charged with sodium carbonate (2 M, 2 mL), tetrakis(triphenylphosphine)palladium (0.237 g, 0.205 mmol), (S)-2-amino-7'-bromo-4'-fluoro-5H-spiro[oxazole-4,9'-xanthen]-2'-ol (0.75 g, 2.054 mmol), and 2-fluoro-3-pyridineboronic acid (0.579 g, 4.11 mmol) and DMF (5 ml). The solution was heated at 85° C. overnight. The solution was diluted with water (25 ml) and filtered. The solids were triturated with methanol and dried under vacuum to afford (S)-2-amino-4'-fluoro-7'-(2-fluoropyridin-3-yl)-5H-spiro[oxazole-4,9'-xanthen]-2'-ol as a tan solid.

Step 2: A flask was charged with (S)-2-amino-4'-fluoro-7'-(2-fluoropyridin-3-yl)-5H-spiro[oxazole-4,9'-xanthen]-2'-ol (300 mg, 0.787 mmol), TEA (0.219 ml, 1.573 mmol), DCM (5 mL) and 1,1,1-trifluoro-N-phenyl-N-(trifluoromethylsulfonyl)methanesulfonamide (337 mg, 0.944 mmol). The solution was stirred at RT overnight. The solution was loaded directly on a silica column. The product was purified via silica gel column chromatography (RediSep 12 g column) using 5-25% 90/10/1 (DCM/MeOH/ammonia) in DCM to afford (S)-2-amino-5'-fluoro-2'-(2-fluoropyridin-3-yl)-5H-spiro[oxazole-4,9'-xanthene]-7'-yl trifluoromethanesulfonate as a yellow solid.

Step 3: A flask was charged with tetrakis(triphenylphosphine)palladium (29.3 mg, 0.025 mmol), 2-(3,6-dihydro-2H-pyran-4-yl)-4,4,5,5-tetramethyl-1,3,2-dioxaborolane (106 mg, 0.506 mmol), (S)-2-amino-5'-fluoro-2'-(2-fluoropyridin-3-yl)-5H-spiro[oxazole-4,9'-xanthene]-7'-yl trifluoromethanesulfonate (130 mg, 0.253 mmol), sodium carbonate (saturated) (0.253 mL, 1.266 mmol) and DMF (2 ml). The solution was heated at 85° C. for 18 hours. The product was purified via Gilson HPLC (gradient elution 20-90% MeCN/H₂O, 0.1% TFA) to afford (S)-2'-(3,6-dihydro-2H-pyran-4-yl)-4'-fluoro-7'-(2-fluoropyridin-3-yl)-5H-spiro[oxazole-4,9'-xanthen]-2-amine.

Step 4: (S)-2'-(3,6-dihydro-2H-pyran-4-yl)-4'-fluoro-7'-(2-fluoropyridin-3-yl)-5H-spiro[oxazole-4,9'-xanthen]-2-amine (30 mg, 0.067 mmol) and palladium on carbon (7.14 mg, 0.067 mmol) were combined in 10 ml of MeOH and stirred under an atmosphere of hydrogen overnight. The solution was filtered and concentrated to afford (S)-4'-fluoro-7'-(2-fluoropyridin-3-yl)-2'-(tetrahydro-2H-pyran-4-yl)-5H-spiro[oxazole-4,9'-xanthen]-2-amine as a white solid.

Example 35

Method AA19

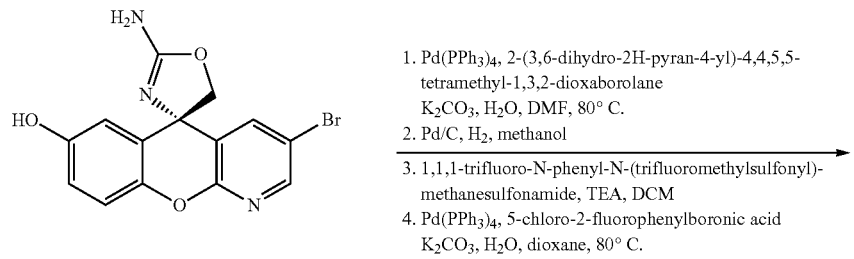

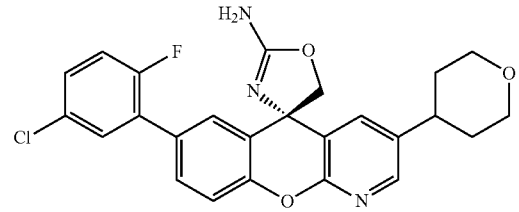

Synthesis of (S)-7-(5-chloro-2-fluorophenyl)-3-(tetrahydro-2H-pyran-4-yl)-5'H-spiro[chromeno[2,3-b]pyridine-5,4'-oxazol]-2'-amine Step 1: A vial was charged with (S)-2'-amino-3-bromo-5'H-spiro[chromeno[2,3-b]pyridine-5,4'-oxazol]-7-ol (380 mg, 1.091 mmol), potassium carbonate (754 mg, 5.46 mmol), 2-(3,6-dihydro-2H-pyran-4-yl)-4,4,5,5-tetramethyl-1,3,2-dioxaborolane (688 mg, 3.27 mmol), pd(ph3p)4 (126 mg, 0.109 mmol), DMF (5457 µL), and water (2.5 mL). The vial was sealed, placed in 80° C. and heated overnight. The mixture was diluted with water (35 mL) and extracted with EtOAc (3×15 mL). The combined organic extract was dried over sodium sulfate, filtered, and evaporated. The residue was purified by chromatography on a 80-g Redi-Sep column, eluting with 0-100% of a 90:10:1 mix of DCM/MeOH/NH$_4$OH in DCM to give (S)-2'-amino-3-(3,6-dihydro-2H-pyran-4-yl)-5'H-spiro[chromeno[2,3-b]pyridine-5,4'-oxazol]-7-ol as an orange solid.

Step 2: A 25-mL flask was charged with (S)-2'-amino-3-(3,6-dihydro-2H-pyran-4-yl)-5'H-spiro[chromeno[2,3-b]pyridine-5,4'-oxazol]-7-ol (211 mg, 0.601 mmol) and MeOH (75070 µL). The mixture was sonicated for 1 min to give an opaque mixture. Palladium on carbon (63.9 mg, 0.060 mmol) was added, and H$_2$ (g) was bubbled through the mixture for 1 min. The mixture was stirred further under a balloon of H$_2$ (g) for 60 hours. The mixture was filtered through celite with the aid of methanol. The filtrate was evaporated, and the residue was chromatographed on a 40-g Redi-Sep column with 0-100% of a 90:10:1 mix of DCM/MeOH/NH$_4$OH to give (S)-2'-amino-3-(tetrahydro-2H-pyran-4-yl)-5'H-spiro[chromeno[2,3-b]pyridine-5,4'-oxazol]-7-ol as an off-white solid.

Step 3: A 25-mL RBF was charged with [Reactants] and triethylamine (194 µL, 1.392 mmol) in DCM (2.5 mL) to give an opaque mixture. n-phenyltrifluoromethanesulfonimide (261 mg, 0.731 mmol) was added, and the mixture was stirred for 2 hours before an additional portion of triflimide (50 mg) was added. After an additional 2 hours the mixture was diluted with DCM (20 mL) and saturated aq. sodium bicarbonate solution (20 mL). The layers were separated, and the aq. layer was extracted with DCM (2×10 mL). The combined organic extracts were dried over sodium sulfate, filtered, and evaporated. The residue was chromatographed on a 40-g Redi-Sep column with 0-70% MeOH/DCM to give (S)-2'-amino-3-(tetrahydro-2H-pyran-4-yl)-5'H-spiro[chromeno[2,3-b]pyridine-5,4'-oxazole]-7-yl trifluoromethanesulfonate as a white solid.

Step 4: A vial was charged with (S)-2'-amino-3-(tetrahydro-2H-pyran-4-yl)-5'H-spiro[chromeno[2,3-b]pyridine-5,4'-oxazole]-7-yl trifluoromethanesulfonate (70.0 mg, 0.144 mmol), 5-chloro-2-fluorophenylboronic acid (75 mg, 0.433 mmol), potassium carbonate (100 mg, 0.721 mmol), and Pd(PPh$_3$)$_4$ (8.33 mg, 7.21 µmol). The vial was flushed with Ar (g), then Dioxane (721 µL) and water (0.3 mL) were added in sequence. The vial was sealed and placed in an 80° C. for 1.5 hours. The mixture was diluted with brine (20 mL) and extracted with EtOAc (2×15 mL). The combined organic extracts were dried over sodium sulfate, filtered, and evaporated. The residue was chromatographed on a 24-g Redi-Sep Gold column with 0-60% of a 90:10:1 mix of DCM/MeOH/NH$_4$OH in DCM to give (S)-7-(5-chloro-2-fluorophenyl)-3-(tetrahydro-2H-pyran-4-yl)-5'H-spiro[chromeno[2,3-b]pyridine-5,4'-oxazol]-2'-amine Example 36

Method AA20

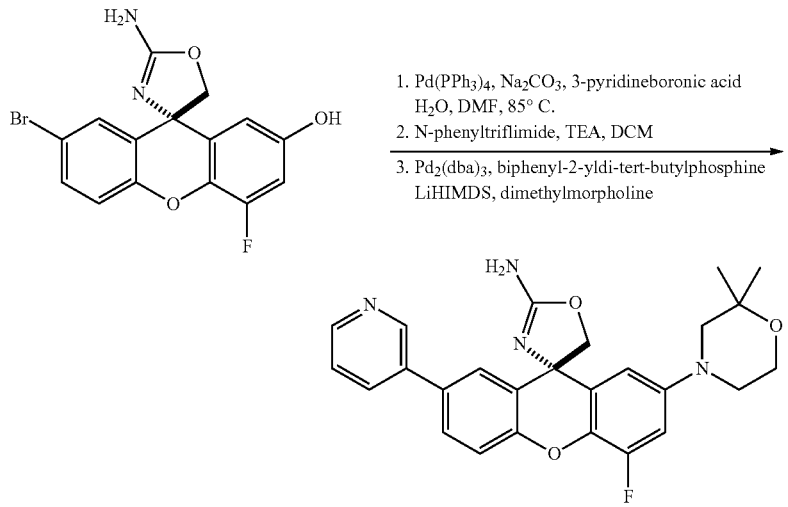

Synthesis of (S)-2'-(2,2-dimethylmorpholino)-4'-fluoro-7'-(pyridin-3-yl)-5H-spiro[oxazole-4,9'-xanthen]-2-amine 2,2,2-trifluoroacetate Step 1: A 25 ml RB flask was charged with (S)-2-amino-7'-bromo-4'-fluoro-5H-spiro[oxazole-4,9'-xanthen]-2'-ol (629 mg, 1.723 mmol), tetrakis(triphenylphosphine)palladium(0) (199 mg, 0.172 mmol), and pyrimidin-5-ylboronic acid (320 mg, 2.58 mmol). DMF (8613 µL) and sodium carbonate (2 M solution) (2584 µL, 5.17 mmol) were added and the mixture was stirred at 85° C. for 2.5 hrs The mixture was cooled to room temperature, water (~5 ml) was added and stirring was continued for 10 min. The precipitate was filtered out, washed with water (3×5 mL), 1:1 i-PrOH/water to remove color and dried in vacuo to afford (S)-2-amino-4'-fluoro-7'-(pyrimidin-5-yl)-5H-spiro[oxazole-4,9'-xanthen]-2'-ol as yellow solid.

Step 2: To a solution of (S)-2-amino-4'-fluoro-7'-(pyrimidin-5-yl)-5H-spiro[oxazole-4,9'-xanthen]-2'-ol (374 mg, 1.027 mmol) in DCM (51330 µL), triethylamine (286 µL, 2.053 mmol) and 1,1,1-trifluoro-N-phenyl-N-(trifluoromethylsulfonyl)methanesulfonamide (550 mg, 1.540 mmol) were added and the mixture was stirred overnight at room temperature. Additional N-phenyltriflimide (100 mg) and TEA (0.1 ml) were added and the stirring continued for 4 hrs. The mixture was directly loaded onto 12 g RediSep column and purified using 15-60% DCM/MeOH/NH4OH to afford (S)-2-amino-5'-fluoro-2'-(pyrimidin-5-yl)-5H-spiro[oxazole-4,9'-xanthene]-7'-yl trifluoromethanesulfonate.

Step: A 0.5-2 ml microwave vial was charged with $Pd_2 dba_3$ (7.39 mg, 8.07 μmol), biphenyl-2-yldi-tert-butylphosphine (5.78 mg, 0.019 mmol) and. The solids were capped with argon and 2,2-dimethylmorpholine (55.8 mg, 0.484 mmol) and LiHMDS (1 M in THF) (0.646 mL, 0.646 mmol) were added and the vial sealed and heated at 110° C. in microwave reactor for 1 hr. The mixture was quenched with 1 ml of water, diluted with EtOAc and saturated $NH_4Cl$. The organic layer was filtered through Celite and concentrated. The residue was purified by Prep HPLC (Gilson, 15-90% MeCN in 0.1% aq. TFA) to afford (S)-2'-(2,2-dimethylmorpholino)-4'-fluoro-7'-(pyridin-3-yl)-5H-spiro[oxazole-4,9'-xanthen]-2-amine 2,2,2-trifluoroacetate.

Example 37

Method AA21

Synthesis of (S)-5-(2'-amino-3-(3,3-dimethylbut-1-ynyl)-5'H-spiro[chromeno[2,3-b]pyridine-5,4'-oxazole]-7-yl)nicotinonitrile Step 1: A vial charged with (S)-2'-amino-3-bromo-5'H-spiro[chromeno[2,3-b]pyridine-5,4'-oxazol]-7-ol (0.250 g, 0.718 mmol), $Pd(PPh_3)_4$ (0.083 g, 0.072 mmol), and copper (i) iodide (0.014 g, 0.072 mmol), was treated with 1 mL THF followed by diisopropylamine (1.535 mL, 10.77 mmol). The solution was degassed with argon and 3,3-dimethylbut-1-yne (0.295 g, 3.59 mmol) was added and the vial heated to 80° C. overnight. The reaction mixture was purified directly by column chromatography yielding (S)-2'-amino-3-(3,3-dimethylbut-1-ynyl)-5'H-spiro[chromeno[2,3-b]pyridine-5,4'-oxazol]-7-ol.

Step 2: A vial charged with (S)-2'-amino-3-(3,3-dimethylbut-1-ynyl)-5'H-spiro[chromeno[2,3-b]pyridine-5,4'-oxazol]-7-ol (0.200 g, 0.572 mmol) and potassium carbonate (0.087 g, 0.630 mmol) was treated with 2 mL DMF and was allowed to stir for 15 minutes. The reaction mixture was cooled to 0° C. and n-phenyltriflamide (0.245 g, 0.630 mmol) was added. After stirring for one hour the reaction mixture was poured into water and extracted with EtOAc. The organics were dried over MgSO4 and concentrated. Purification of the crude residue by column chromatography gave (S)-2'-amino-3-(3,3-dimethylbut-1-ynyl)-5'H-spiro[chromeno[2,3-b]pyridine-5,4'-oxazole]-7-yl trifluoromethanesulfonate (0.183 g, 0.380 mmol, 66.4% yield)

Step 3: A vial charged with 5-cyanopyridin-3-ylboronic acid (0.030 g, 0.206 mmol), palladiumtetrakis (10.80 mg, 9.35 μmol), potassium carbonate (0.129 g, 0.935 mmol), and (S)-2'-amino-3-(3,3-dimethylbut-1-ynyl)-5'H-spiro[chromeno[2,3-b]pyridine-5,4'-oxazole]-7-yl trifluoromethanesulfonate (0.090 g, 0.187 mmol) was treated with 1 mL of dioxane followed by 0.4 mL water. The vial was flushed with argon and was heated to 80° C. for 4 hours. The reaction mixture was diluted with EtOAc and dried over MgSO4. The organics were then concentrated, and the crude residue was purified by column chromatography yielding (S)-5-(2'-amino-3-(3,3-dimethylbut-1-ynyl)-5'H-spiro[chromeno[2,3-b]pyridine-5,4'-oxazole]-7-yl)nicotinonitrile.

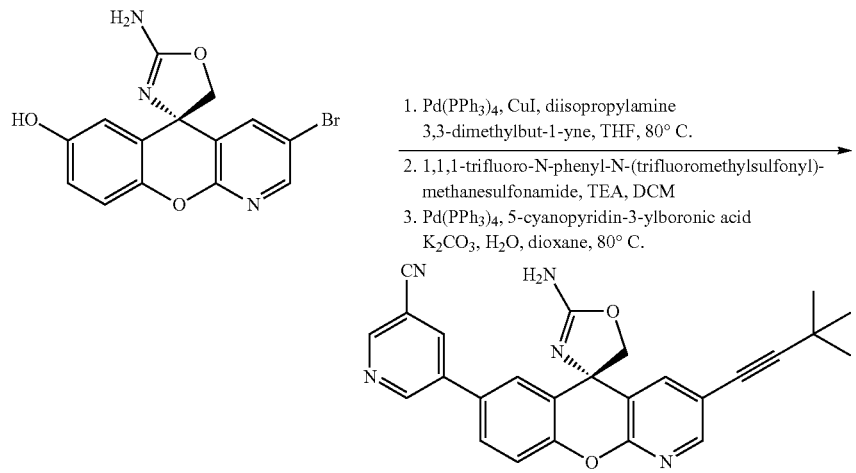

Example 38

Method AA22

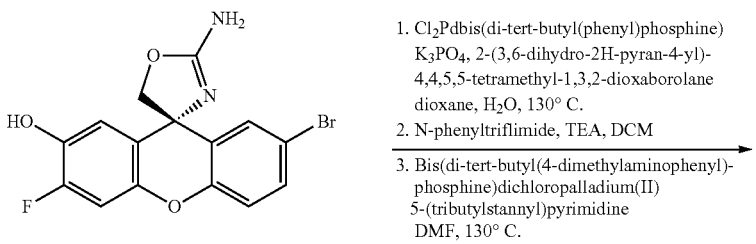

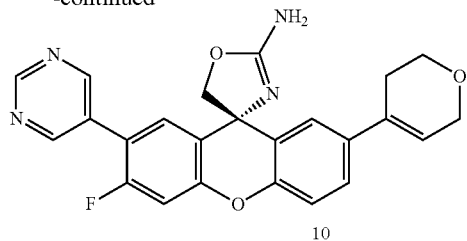

Synthesis of (R)-7'-(3,6-dihydro-2H-pyran-4-yl)-3'-fluoro-2'-(pyrimidin-5-yl)-5H-spiro[oxazole-4,9'-xanthen]-2-amine Step 1: A mixture of 2-(3,6-dihydro-2H-pyran-4-yl)-4,4,5,5-tetramethyl-1,3,2-dioxaborolane (276 mg, 1.315 mmol), (S)-2-amino-7'-bromo-3'-fluoro-5H-spiro[oxazole-4,9'-xanthen]-2'-ol (300 mg, 0.822 mmol), potassium phosphate (523 mg, 2.465 mmol) and Cl₂Pdbis(di-tert-butyl(phenyl)phosphine) (15.28 mg, 0.025 mmol) in 3 ml of dioxane/water=2:1 was heated at 110° C. microwave for 30 min. The reaction mixture was purified by silica gel chromatography (DCM to DCM/MeOH=100:1 to 100:6) to give (R)-2-amino-7'-(3,6-dihydro-2H-pyran-4-yl)-3'-fluoro-5H-spiro[oxazole-4,9'-xanthen]-2'-ol as a white solid.

Step 2: To a suspension of (R)-2-amino-7'-(3,6-dihydro-2H-pyran-4-yl)-3'-fluoro-5H-spiro[oxazole-4,9'-xanthen]-2'-ol (150 mg, 0.407 mmol) and n-phenyltrifluoromethanesulfonimide (218 mg, 0.611 mmol) in 15 mL of dry DCM was added TEA (142 μL, 1.018 mmol). After stirring at RT overnight the solution was evaporated to dryness and the residue was purified by silica gel chromatography (DCM to DCM/EA=4:1 to 3:1 to 2:1 to 1:1) to give (R)-2-amino-2'-(3,6-dihydro-2H-pyran-4-yl)-6'-fluoro-5H-spiro[oxazole-4,9'-xanthene]-7'-yl trifluoromethanesulfonate as a white solid.

Step 3: A mixture of 5-(tributylstannyl)pyrimidine (73.8 mg, 0.200 mmol), AmPhos (4.24 mg, 5.99 μmol) and (R)-2-amino-2'-(3,6-dihydro-2H-pyran-4-yl)-6'-fluoro-5H-spiro[oxazole-4,9'-xanthene]-7'-yl trifluoromethanesulfonate (50 mg, 0.100 mmol) in 0.3 mL of DMF was heated at 130° C. for 1 hour. After cooling and evaporation of the solvent under high vacuum, the mixture was purified by silica gel chromatography (DCM to DCM/EA=1:1 to 1:2 to pure EA to EA/MeOH=100:5 to 100:10) to provide (R)-7'-(3,6-dihydro-2H-pyran-4-yl)-3'-fluoro-2'-(pyrimidin-5-yl)-5H-spiro[oxazole-4,9'-xanthen]-2-amine as an off-white solid.

Example 39

Method AA23

Synthesis of (S)-4-(2'-amino-7-phenyl-5'H-spiro[chromeno[2,3-b]pyridine-5,4'-oxazole]-3-yl)-2-methylbut-3-yn-2-ol Step 1: A 25-mL flask was charged with (S)-2'-amino-3-bromo-5'H-spiro[chromeno[2,3-b]pyridine-5,4'-oxazol]-7-ol (1.012 g, 2.91 mmol), copper(i) iodide (0.055 g, 0.291 mmol), and tetrakis(triphenylphosphine)palladium (0.034 g, 0.029 mmol). The vial was flushed with Ar(g), then a septum was attached. DMF (5.81 mL), diisopropylamine (6.11 mL, 43.6 mmol), and 2-methylbut-3-yn-2-ol (1.137 mL, 11.63 mmol) were added in sequence to give a clear, brown solution. A reflux condenser was attached, and the flask was placed in a 75° C. oil bath for 4 hours. The mixture was diluted with water (35 mL) and extracted with DCM (4×20 mL). The combined organic extracts were dried over sodium sulfate, filtered, and evaporated. The residue, which contained a considerable amount of DMF, was loaded onto a 10-g SCX-2 column with the aid of methanol. The column was eluted with methanol to remove impurities, then with 2M ammonia in methanol to elute the product. The filtrate was evaporated, and the residue was chromatographed on an 80-g Redi-Sep column, eluting with 0-10% MeOH/DCM to give (S)-2'-amino-3-(3-hydroxy-3-methylbut-1-ynyl)-5'H-spiro[chromeno[2,3-b]pyridine-5,4'-oxazol]-7-ol.

Step 2: A 10-mL pear flask was charged with (S)-2'-amino-3-(3-hydroxy-3-methylbut-1-ynyl)-5'H-spiro[chromeno[2,3-b]pyridine-5,4'-oxazol]-7-ol (111 mg, 0.316 mmol), cesium carbonate (113 mg, 0.348 mmol), and DMF (1580 μL). The resulting mixture was stirred for 5 min, then placed in an ice-bath for 5 min. 1,1,1-trifluoro-N-phenyl-N-(trifluoromethylsulfonyl)methanesulfonamide (124 mg, 0.348 mmol) was added, the ice-bath was removed and stirring was continued for 1 hour. The mixture was partitioned between water (15 mL) and EtOAc (15 mL), with a small amount of brine to break up an emulsion. The layers were separated, and the aqueous layer was extracted with EtOAc (15 mL). The combined organic extracts were dried over sodium sulfate, filtered, and evaporated. The residue was chromatographed

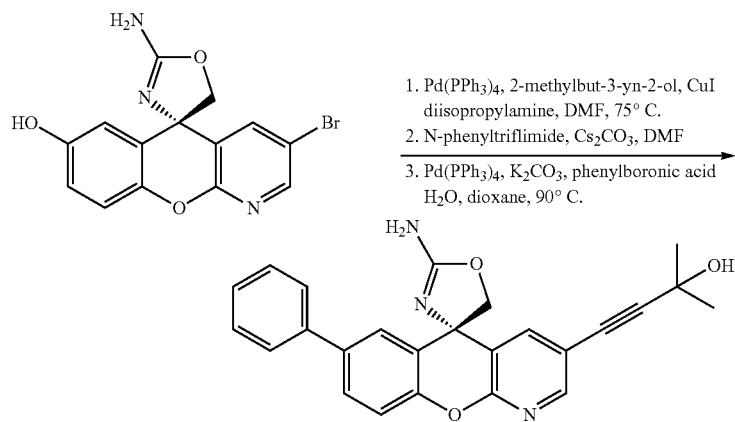

on a 12-g Redi-Sep column eluting with 0-6% MeOH/DCM to give (S)-2'-amino-3-(3-hydroxy-3-methylbut-1-ynyl)-5'H-spiro[chromeno[2,3-b]pyridine-5,4'-oxazole]-7-yl trifluoromethanesulfonate as a feathery-white solid.

Step: A 0.5-2 mL vial was charged with (S)-2'-amino-3-(3-hydroxy-3-methylbut-1-ynyl)-5'H-spiro[chromeno[2,3-b]pyridine-5,4'-oxazole]-7-yl trifluoromethanesulfonate (72.4 mg, 0.150 mmol), phenylboronic acid (54.8 mg, 0.449 mmol), potassium carbonate (103 mg, 0.748 mmol), and tetrakis(triphenylphosphine)palladium (8.64 mg, 7.48 µmol). The vial was purged with Ar(g), then Dioxane (748 µL) and water (0.37 mL) were added in sequence. The vial was sealed and placed in a 90° C. oil bath for 1 hour. The mixture was diluted with water (15 mL), and extracted with EtOAc (3×10 mL). The combined organic extracts were dried over sodium sulfate, filtered, and evaporated. The residue was chromatographed on a 40-g Redi-Sep column eluting with 0-6% MeOH/DCM to give (S)-4-(2'-amino-7-phenyl-5'H-spiro[chromeno[2,3-b]pyridine-5,4'-oxazole]-3-yl)-2-methylbut-3-yn-2-ol as a slightly tan solid Example 40

Method AA24

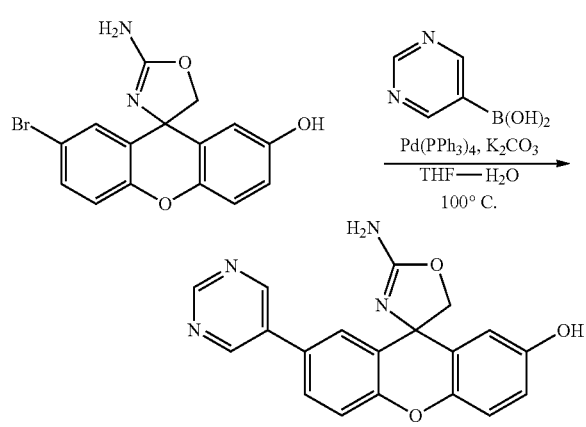

A 150-mL pressure vessel was charged with 2'-bromo-7'-hydroxyspiro[1,3-oxazole-4,9'-xanthen]-2-amine (845 mg, 2434 µmol) in THF (24 mL), pyrimidin-5-ylboronic acid (754 mg, 6085 µmol), tetrakis(triphenylphosphine)palladium(0) (281 mg, 243 µmol), and potassium carbonate (10.1 mL of a 1.2 M aqueous solution, 12.1 mmol). The vessel was sealed and placed in a 100° C. oil bath at for 4 h. The reaction mixture was cooled to RT and partitioned between EtOAc (50 mL) and water (50 mL). The aqueous layer was extracted with EtOAc (50 mL), and the combined organic extracts were dried over sodium sulfate, filtered, and evaporated. The crude material was purified by chromatography on silica gel (eluting with 30-100% of a 90:10:1 DCM/MeOH/NH₄OH solution in DCM) to give 2'-hydroxy-7'-(5-pyrimidinyl)spiro[1,3-oxazole-4,9'-xanthen]-2-amine as an off-white solid.

Example 41

Method AA25

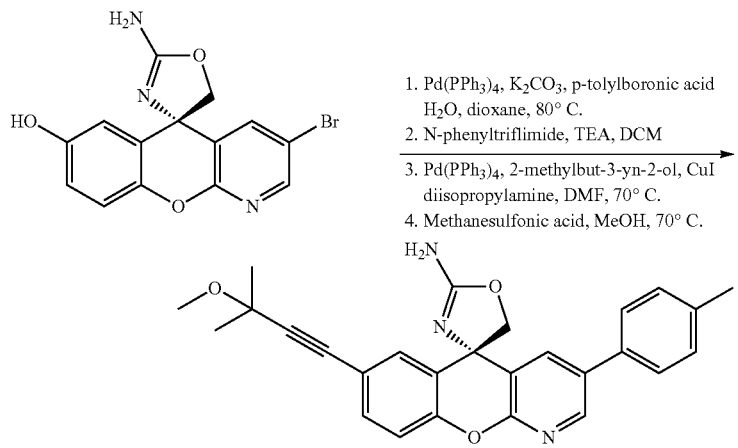

Synthesis of (S)-7-(3-methoxy-3-methylbut-1-ynyl)-3-p-tolyl-5'H-spiro[chromeno[2,3-b]pyridine-5,4'-oxazol]-2'-amine Step 1: A vial was charged (S)-2'-amino-3-bromo-5'H-spiro[chromeno[2,3-b]pyridine-5,4'-oxazol]-7-ol (282 mg, 0.809 mmol), p-tolylboronic acid (220 mg, 1.618 mmol), potassium carbonate (559 mg, 4.04 mmol), tetrakis(triphenylphosphine)palladium (46.7 mg, 0.040 mmol). The vial was flushed with Ar (g), then Dioxane (4044 µL) and water (2 mL) were added in sequence. The vial was sealed and placed in an 80° C. oil bath for 1 hour. The mixture was partitioned between brine and 10% iPrOH/EtOAc. The layers were separated, and the aq. layer was extracted with EtOAc. The combined organic extracts were dried over sodium sulfate, filtered, and evaporated. The residue was chromatographed on an 80-g Redi-Sep column, eluting with 0-80% of a 90:10:1 mix of DCM/MeOH/NH₄OH in DCM to give (S)-2'-amino-3-p-tolyl-5'H-spiro[chromeno[2,3-b]pyridine-5,4'-oxazol]-7-ol as an orange solid.

Step 2: A 25-mL flask was charged with (S)-2'-amino-3-p-tolyl-5'H-spiro[chromeno[2,3-b]pyridine-5,4'-oxazol]-7-ol (259.36 mg, 0.722 mmol) in DCM (7217 µL) to give an clear, orange solution. triethylamine (201 µL, 1.443 mmol) and 1,1,1-trifluoro-N-phenyl-N-(trifluoromethylsulfonyl)methanesulfonamide (271 mg, 0.758 mmol) were added in sequence and stirred for 4 hours. The reaction mixture was loaded directly onto a 25-g silica gel loading column with the aid of DCM. The column was eluted onto a prequilibrated 40-g Redi-Sep column with 0-5% MeOH/DCM to give (S)-2'-amino-3-p-tolyl-5'H-spiro[chromeno[2,3-b]pyridine-5,4'-oxazole]-7-yl trifluoromethanesulfonate as a cream-colored solid.

Step 3: A vial was charged with (S)-2'-amino-3-p-tolyl-5'H-spiro[chromeno[2,3-b]pyridine-5,4'-oxazole]-7-yl trifluoromethanesulfonate (209 mg, 0.426 mmol), copper(i) iodide (8.11 mg, 0.043 mmol), and tetrakis(triphenylphosphine)palladium (49.2 mg, 0.043 mmol). The vial was flushed with Ar (g), then DMF (1704 μL, 0.426 mmol), diisopropylamine (1194 μL, 8.52 mmol), and 2-methylbut-3-yn-2-ol (208 μL, 2.130 mmol) were added in sequence. The vial was sealed and placed in a 70° C. oil bath for 2 hours. The mixture was diluted with EtOAc (15 mL), washed with water (10 mL), washed with brine (15 mL), dried over sodium sulfate, filtered, and evaporated. The residue was taken up in DCM/MeOH (not completely soluble) and chromatographed on a 40-g Redi-Sep column, eluting with 0-8% MeOH/DCM (product came out in a streak) to give (S)-4-(2'-amino-3-p-tolyl-5'H-spiro[chromeno[2,3-b]pyridine-5,4'-oxazole]-7-yl)-2-methylbut-3-yn-2-ol as a light yellow solid Step 4: A vial was charged with (S)-4-(2'-amino-3-p-tolyl-5'H-spiro[chromeno[2,3-b]pyridine-5,4'-oxazole]-7-yl)-2-methylbut-3-yn-2-ol (134.5 mg, 0.316 mmol), MeOH (3161 μL), and methanesulfonic acid (103 μL, 1.581 mmol). The vial was sealed and placed in a 70° C. oil bath for 4 hours. The mixture was poured into saturated aq. sodium bicarbonate solution (30 mL) and extracted with EtOAc (2×25 mL). The combined organic extracts were dried over sodium sulfate, filtered, and evaporated. The residue was chromatographed on a 40-g Redi-Sep column to give a impure material that was dissolved in methanol and purified by reverse-phase HPLC (10-90% $CH_3CN/H_2O$ with 0.1% TFA). The fractions containing product were combined in saturated aq. sodium bicarbonate solution with the aid of methanol, and the mixture was extracted with DCM (3×). The combined organic extracts were dried over sodium sulfate, filtered, and evaporated to give (S)-7-(3-methoxy-3-methylbut-1-ynyl)-3-p-tolyl-5'H-spiro[chromeno[2,3-b]pyridine-5,4'-oxazol]-2'-amine.

Example 42

Method AA26

Synthesis of (S)-3-(3-methoxy-3-methylbut-1-ynyl)-7-(pyridin-3-yl)-5'H-spiro[chromeno[2,3-b]pyridine-5,4'-oxazol]-2'-amine Step 1: Combined (S)-2'-amino-3-bromo-5'H-spiro[chromeno[2,3-b]pyridine-5,4'-oxazol]-7-ol (1.260 g, 3.62 mmol), tetrakis(triphenylphosphine)palladium (0.418 g, 0.362 mmol), copper(i) iodide (0.069 g, 0.362 mmol) and THF (14.48 mL, 3.62 mmol) and DMF (14.48 mL, 3.62 mmol) in a sealable reaction tube. Added diisopropylamine (10.14 mL, 72.4 mmol) then 2-methylbut-3-yn-2-ol (1.768 mL, 18.10 mmol) and flushed the reaction tube with argon. Sealed and heated at 110° C. for 3 hours. The mixture was diluted with water (150 mL) and 10% iPrOH/EtOAc (50 mL). The layers were separated, and the aqueous layer was extracted with 10% iPrOH/EtOAc (2×50 mL). The organic layers were combined, washed with water (60 mL), washed with brine (60 mL), dried over sodium sulfate, filtered, and evaporated. The residue was purified by chromatography on a 100-g SNAP column, eluting with 0-100% of a 90:10:1 mixture of DCM/MeOH/NH$_4$OH in DCM to (S)-2'-amino-3-(3-hydroxy-3-methylbut-1-ynyl)-5'H-spiro[chromeno[2,3-b]pyridine-5,4'-oxazol]-7-ol as a brown solid.

Step 2: A vessel was charged with (S)-2'-amino-3-(3-hydroxy-3-methylbut-1-ynyl)-5'H-spiro[chromeno[2,3-b]pyridine-5,4'-oxazol]-7-ol (0.512 g, 1.457 mmol) in methanol (17.73 mL, 437 mmol). Methane sulfonic acid (0.945 mL, 14.57 mmol) was added, and the vial was sealed and placed in a 55° C. oil bath overnight. Potassium carbonate was added to quench the acid, and the mixture was filtered with the aid of DCM. The filtrate was evaporated, and the residue was soluble in MeOH/DCM, but some potassium carbonate still came through. The residue was purified by chromatography on a 50-g SNAP column, eluting with 0-100% of a 90:10:1 mixture of DCM/MeOH/NH$_4$OH in DCM. The material thus obtained was rechromatographed to under the same conditions to give (S)-2'-amino-3-(3-methoxy-3-methylbut-1-ynyl)-5'H-spiro[chromeno[2,3-b]pyridine-5,4'-oxazol]-7-ol as a pale-yellow solid.

Step 3: A 15-mL RBF was charged with cesium carbonate (358 mg, 1.099 mmol) and (S)-2'-amino-3-(3-methoxy-3-methylbut-1-ynyl)-5'H-spiro[chromeno[2,3-b]pyridine-5,4'-oxazol]-7-ol (365.01 mg, 0.999 mmol) in DMF (4995 μL). The resulting mixture was stirred for 10 min, then the flask was submerged in an ice-bath for 5 min. n-phenyltrifluoromethanesulfonimide (393 mg, 1.099 mmol) was added as a single portion. The mixture was stirred for 2 min, then the

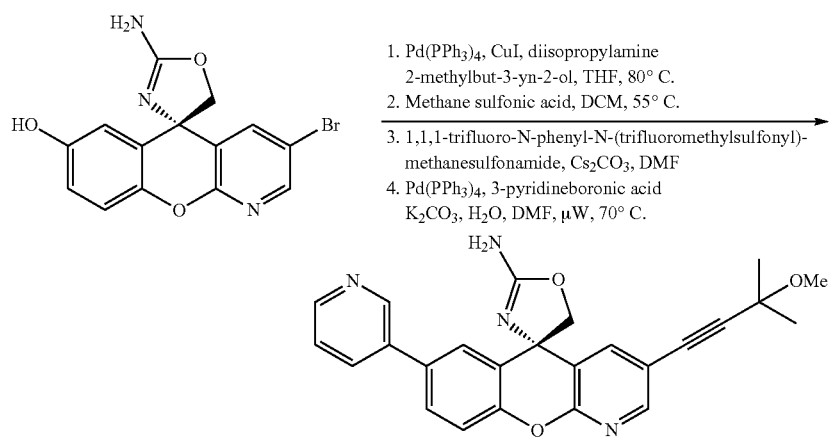

1. Pd(PPh$_3$)$_4$, CuI, diisopropylamine
   2-methylbut-3-yn-2-ol, THF, 80° C.
2. Methane sulfonic acid, DCM, 55° C.
3. 1,1,1-trifluoro-N-phenyl-N-(trifluoromethylsulfonyl)-methanesulfonamide, Cs$_2$CO$_3$, DMF
4. Pd(PPh$_3$)$_4$, 3-pyridineboronic acid
   K$_2$CO$_3$, H$_2$O, DMF, μW, 70° C.

ice-bath was removed and stirring was continued for 1 hour. The mixture was diluted with water (and a small amount of brine to clear an emulsion) and extracted with EtOAc (3×). The combined organic extracts were dried over sodium sulfate, filtered, and evaporated. The residue was purified by chromatography on a 50-g SNAP column, eluting with 0-60% of a 90:10 mixture of DCM/MeOH in DCM. The obtained residue was taken up in water (total 20 mL) and extracted with EtOAc (2×15 mL). The combined organic extracts were dried over sodium sulfate, filtered, and evaporated to give (S)-2'-amino-3-(3-methoxy-3-methylbut-1-ynyl)-5'H-spiro[chromeno[2,3-b]pyridine-5,4'-oxazole]-7-yl trifluoromethanesulfonate.

Step 4: A vial was charged with (S)-2'-amino-3-(3-methoxy-3-methylbut-1-ynyl)-5'H-spiro[chromeno[2,3-b]pyridine-5,4'-oxazole]-7-yl trifluoromethanesulfonate (104 mg, 0.210 mmol), pyridin-3-ylboronic acid (77 mg, 0.629 mmol), and tetrakis(triphenylphosphine)palladium (24.22 mg, 0.021 mmol). The vial was purged with Ar (g), then DMF (1048 µL) and potassium carbonate (524 µL, 1.048 mmol) (as a 2.0 M aq. solution) were added in sequence. The vial was capped and heated in a Biotage Initiator microwave reactor for 1.5 h at 70° C. The mixture was diluted with water (10 mL) and extracted with EtOAc (2×10 mL). The combined organic extracts were dried over sodium sulfate, filtered, and evaporated. The residue was purified by chromatography on a 25-g SNAP column, eluting with 0-60% of a 90:10:1 mixture of DCM/MeOH/NH$_4$OH in DCM to give (S)-3-(3-methoxy-3-methylbut-1-ynyl)-7-(pyridin-3-yl)-5'H-spiro[chromeno[2,3-b]pyridine-5,4'-oxazol]-2'-amine.

Example 43

Method AA27

(3×30 mL). The aq. layer was extracted with ethyl acetate and 10% iPrOH/EtOAc, and the solid was taken with the organic layer. The different organic layers were combined, dried over sodium sulfate, filtered, and evaporated. The material was purified via column chromatography (RediSep 40 g, gradient elution 0-10% MeOH:DCM w/1% NH4OH) to afford (S)-2'-amino-3-morpholino-5'H-spiro[chromeno[2,3-b]pyridine-5,4'-oxazol]-7-ol as an orange solid.

Step 2: A 25-mL RBF was charged with cesium carbonate (0.371 g, 1.138 mmol) and (S)-2'-amino-3-morpholino-5'H-spiro[chromeno[2,3-b]pyridine-5,4'-oxazol]-7-ol (0.336 g, 0.948 mmol) in DMF (4.74 mL). The resulting mixture was stirred for 10 min, then the flask was submerged in an ice-bath for 5 min. n-phenyltrifluoromethanesulfonimide (0.373 g, 1.043 mmol) was added as a single portion and the reaction was allowed to warm to RT overnight. The reaction was cooled in an ice bath and 150 mg of cesium carbonate was added. The reaction was stirred for 10 minutes, then 40 mg of n-phenyltrifluoromethanesulfonimide was added and the reaction was stirred for one hour. The mixture was diluted with water and extracted twice with EtOAc (a little brine was added to help with emulsion). The combined organic extracts were dried over sodium sulfate, filtered, and evaporated. The material was purified via column chromatography (RediSep 40 g, gradient elution 0-7% MeOH:DCM w/1% NH4OH) to afford (S)-2'-amino-3-morpholino-5'H-spiro[chromeno[2,3-b]pyridine-5,4'-oxazole]-7-yl trifluoromethanesulfonate as an off-white solid.

Step 3: A vial was charged with (S)-2'-amino-3-morpholino-5'H-spiro[chromeno[2,3-b]pyridine-5,4'-oxazole]-7-yl trifluoromethanesulfonate (0.120 g, 0.247 mmol), tetrakis(triphenylphosphine)palladium (2.85 mg, 2.467 µmol), and copper(i) iodide (4.70 mg, 0.025 mmol). The vial was flushed with Ar (g), then DMF (0.987 mL), diisopropylamine (0.692 mL, 4.93 mmol), and ethynylcyclopropane (0.104 mL, 1.233 mmol) were added in sequence to give a yellow solu-

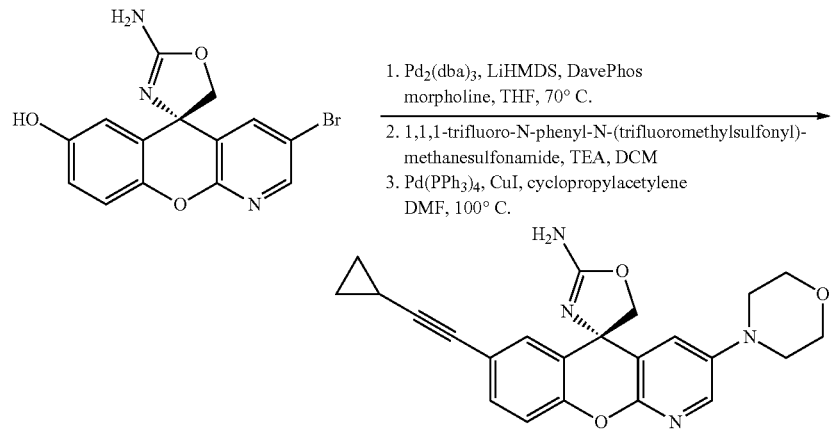

Synthesis of (S)-3-(3,3-dimethylbut-1-ynyl)-7-(pyrazin-2-yl)-5'H-spiro[chromeno[2,3-b]pyridine-5,4'-oxazol]-2'-amine Step 1: A vial was charged with (S)-2'-amino-3-bromo-5'H-spiro[chromeno[2,3-b]pyridine-5,4'-oxazol]-7-ol (0.647 g, 1.858 mmol), DavePhos (0.088 g, 0.223 mmol), and tris(dibenzylideneacetone)dipalladium(0) (0.085 g, 0.093 mmol). The vessel was flushed with Ar(g), then lithium bis(trimethylsilyl)amide (1.0 M in THF) (9.29 mL, 9.29 mmol) and morpholine (0.486 mL, 5.58 mmol) were added in sequence. The vial was sealed and heated at 70° C. for one hour at which point the mixture was diluted with water and saturated NH$_4$Cl. The mixture was extracted with DCM tion. The vial was sealed and heated to 70° C. for two hours at which point 8 mg of tetrakis(triphenylphosphine)palladium and 0.1 mL of cyclopropylacetylene were added and the reaction was heated to 100° C. and stirred for two hours. The vial was purged with Ar (g), then DMF (1.039 mL) and 2-(tributylstannyl)pyrazine (0.197 mL, 0.623 mmol) were added in sequence. The vial was sealed and heated to 110° C. for one hour. The mixture was loaded onto a 2-g SCX-2 column and eluted 4× with methanol to remove impurities. The product was then eluted with 2M ammonia in methanol. The filtrate was evaporated, and the residue was purified via column chromatography (RediSep 40 g, gradient elution 0-5% MeOH:DCM) to afford (S)-3-(3,3-dimethylbut-1-ynyl)-7-(pyrazin-2-yl)-5'H-spiro[chromeno[2,3-b]pyridine-5,4'-oxazol]-2'-amine as a white solid.

Example 44

Method AA30

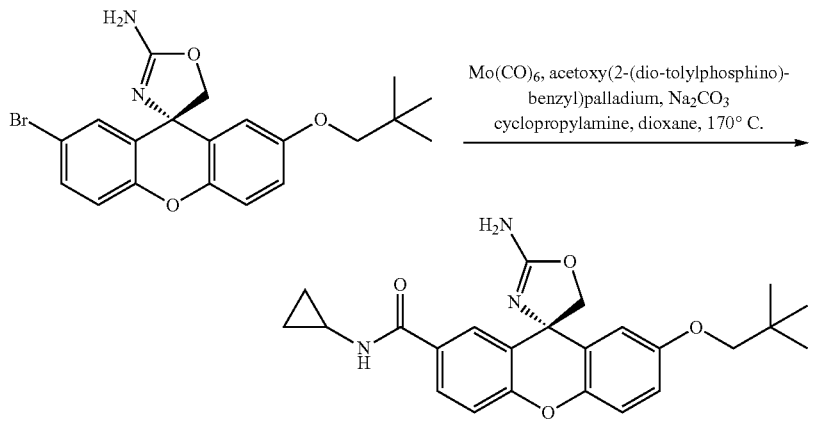

A 0.5-2 mL microwave vial charged with (R)-2'-bromo-7'-(neopentyloxy)-5H-spiro[oxazole-4,9'-xanthen]-2-amine (0.1000 g, 0.240 mmol), Mo(CO)$_6$ (0.063 g, 0.240 mmol), acetoxy(2-(dio-tolylphosphino)benzyl)palladium (0.011 g, 0.012 mmol), sodium carbonate (0.025 g, 0.240 mmol), cyclopropylamine (0.025 mL, 0.359 mmol), and 1,4-dioxane (0.443 mL, 5.03 mmol) was sealed and heated to 170° C. for 30 minutes. The mixture was diluted with EtOAc and water and filtered through celite. The celite was washed with EtOAc and MeOH. The aqueous phase was extracted with EtOAc three times. The organic layer was dried over Na$_2$SO$_4$ and concentrated in vacuo. The crude was purified by silica gel chromatography (2-10% MeOH—CH$_2$Cl$_2$, then 10% MeOH—CH$_2$Cl$_2$). The product was purified again by reverse phase prep HPLC: 10-55% CH3CN (0.1% TFA)-water (0.1% TFA) in 26 min. The fractions were combined and neutralized with solid Na$_2$CO$_3$, extracted three times with DCM. The organic layer was concentrated to provide (S)-2-amino-N-cyclopropyl-7'-(neopentyloxy)-5H-spiro[oxazole-4,9'-xanthene]-2'-carboxamide.

Example 45

Method AA31

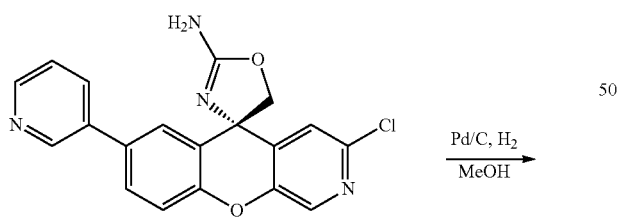

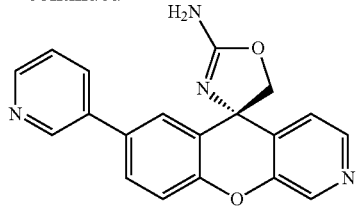

To the solution of (S)-3-chloro-7-(pyridin-3-yl)-5'H-spiro[chromeno[2,3-c]pyridine-5,4'-oxazol]-2'-amine (23 mg, 0.063 mmol) in MeOH (2 mL) was added 10% Pd on Carbon (10 mg, 0.073 mmol). The mixture was hydrogenated under 1 atm of H$_2$ for 24 h. After filtration and concentration, the crude material was absorbed onto a plug of silica gel and purified by chromatography through a Redi-Sep pre-packed silica gel column (12 g), eluting with isocratic % to 20% MeOH in CH2CL2, to provide (S)-7-(pyridin-3-yl)-5'H-spiro[chromeno[2,3-c]pyridine-5,4'-oxazol]-2'-amine as white solid.

Example 46

Method AA32

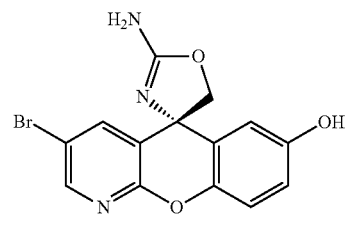

1. Pd(PPh$_3$)$_4$, 2-methylbut-3-yn-2-ol, CuI diisopropylamine, DMF, 85° C.
2. Methanesulfonic acid, MeOH, 70° C.
3. Nonafluorobutanesulfonyl fluoride Cs$_2$CO$_3$, DMF
4. Pd(PPh$_3$)$_4$, 4-(tributylstannyl)pyridazine CuI, LiCl, DMF, 110° C.

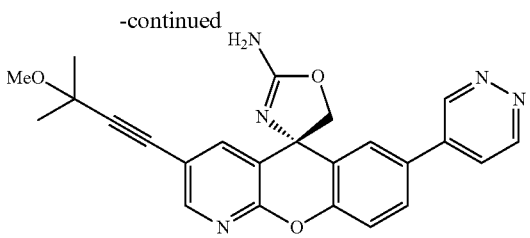

Synthesis of (R)-3-(3-methoxy-3-methylbut-1-ynyl)-7-(pyridazin-4-yl)-5'H-spiro[chromeno[2,3-b]pyridine-5,4'-oxazol]-2'-amine Step 1: Combined (R)-2'-amino-3-bromo-5'H-spiro[chromeno[2,3-b]pyridine-5,4'-oxazol]-7-ol (2.259 g, 6.49 mmol), tetrakis(triphenylphosphine)palladium (0.750 g, 0.649 mmol), copper(i) iodide (0.124 g, 0.649 mmol) and THF (26.0 mL, 6.49 mmol) and DMF (26.0 mL, 6.49 mmol) in a reaction tube. Added diisopropylamine (18.19 mL, 130 mmol) then 2-methylbut-3-yn-2-ol (3.17 mL, 32.4 mmol) and flushed the reaction tube with argon. Sealed and heated at 85° C. for 3 hours. The mixture was diluted with water (100 mL) and extracted with DCM (1×100 mL, 2×50 mL). The combined organic extracts were dried over sodium sulfate, filtered, and evaporated. The resuling liquid was poured onto a 25-g SCX-2 column and eluted with methanol. The product was then eluted with 2M ammonia in methanol. The filtrate was evaporated and purified by chromatography on a 120-g Redi-Sep column, eluting with 0-100% of a 90:10:1 mixture of DCM/MeOH/NH₄OH in DCM to give (R)-2'-amino-3-(3-hydroxy-3-methylbut-1-ynyl)-5'H-spiro[chromeno[2,3-b]pyridine-5,4'-oxazol]-7-ol as a tan solid.

Step 2: A vessel was charged with (S)-2'-amino-3-(3-hydroxy-3-methylbut-1-ynyl)-5'H-spiro[chromeno[2,3-b]pyridine-5,4'-oxazol]-7-ol (0.679 g, 1.933 mmol) in methanol (23.51 mL, 580 mmol). methane sulfonic acid (0.627 mL, 9.66 mmol) was added, and the vial was sealed and placed in a 70° C. oil bath for 5 hours. The volatiles were evaporated, and the residue was loaded onto a silica gel cartridge in MeOH/DCM. The column was eluted onto an 80-g Redi-Sep column with 30-100% of a 90:10:1 mixture of DCM/MeOH/NH₄OH in DCM. The fractions containing product were evaporated to give (S)-2'-amino-3-(3-methoxy-3-methylbut-1-ynyl)-5'H-spiro[chromeno[2,3-b]pyridine-5,4'-oxazol]-7-ol as an off-white solid.

Step 3: A 25-mL flask was charged with (R)-2'-amino-3-(3-methoxy-3-methylbut-1-ynyl)-5'H-spiro[chromeno[2,3-b]pyridine-5,4'-oxazol]-7-ol (577.53 mg, 1.581 mmol), cesium carbonate (566 mg, 1.739 mmol), and DMF (7903 µL). The resulting mixture was stirred for 10 min, then the vial was submerged in an ice-bath for 10 min. nonafluorobutanesulfonyl fluoride (306 µL, 1.739 mmol) was added dropwise over 2 minutes. The mixture was stirred for 2 hours, then quenched with saturated aqueous ammonium chloride (10 mL), and partitioned between water (15 mL) and EtOAc (15 mL). The layers were separated, and the aqueous layer was extracted with EtOAc (15 mL). The combined organic layers were washed with brine, dried over sodium sulfate, filtered, and evaporated. The residue was purified by chromatography on an 80-g Redi-Sep column, eluting with 0-50% of a 90:10 mixture of DCM/MeOH in DCM to give (R)-2'-amino-3-(3-methoxy-3-methylbut-1-ynyl)-5'H-spiro[chromeno[2,3-b]pyridine-5,4'-oxazole]-7-yl 1,1,2,2,3,3,4,4,4-nonafluorobutane-1-sulfonate as a white solid.

Step 4: A vial was charged with (R)-2'-amino-3-(3-methoxy-3-methylbut-1-ynyl)-5'H-spiro[chromeno[2,3-b]pyridine-5,4'-oxazole]-7-yl-1,1,2,2,3,3,4,4,4-nonafluorobutane-1-sulfonate (102 mg, 0.158 mmol), copper(i) iodide (3.01 mg, 0.016 mmol), tetrakis(triphenylphosphine)palladium (18.24 mg, 0.016 mmol), and lithium chloride (10.96 mg, 1.579 mmol). The vial was purged with Ar (g), then DMF (790 µL) and 4-(tributylstannyl)pyridazine (146 µL, 0.474 mmol) were added in sequence. The vial was sealed and placed in a 110° C. oil bath for 4 hours. The mixture loaded onto a 2-g SCX-2 column and eluted 4× with methanol to remove impurities. The product was then eluted with 2M ammonia in methanol. The filtrate was evaporated, and the residue was chromatographed on a 40-g Redi-Sep column, eluting with 0-100% EtOAc/Hexane, then with 0-10% MeOH/DCM. Ther resulting material was still impure, so the material was dissolved in methanol and purified by reverse-phase HPLC (15-80% CH₃CN/H₂O with 0.1% TFA). The fractions containing product were combined in saturated aq. sodium bicarbonate solution with the aid of methanol and extracted with DCM (3×). The combined organic extracts were dried over sodium sulfate, filtered, and evaporated to give (R)-3-(3-methoxy-3-methylbut-1-ynyl)-7-(pyridazin-4-yl)-5'H-spiro[chromeno[2,3-b]pyridine-5,4'-oxazol]-2'-amine as a white solid.

Example 47

Method AA33

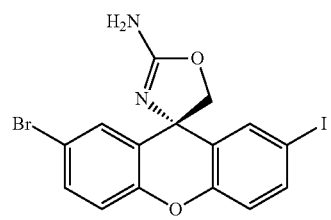

1. Cl₂Pd(PPh₃)₂, 1-ethynylcyclobutanol, CuI
   diisopropylamine, THF, rt

2. Pd(PPh₃)₄, CuI, Na₂CO₃
   3-pyridylboronic acid, DME, 90° C.

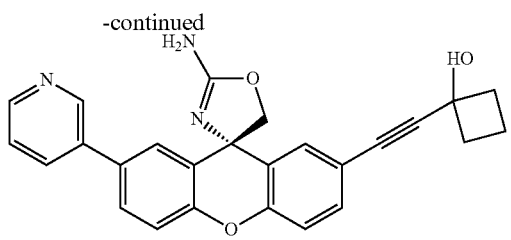

Step 1: To a solution of (S)-2'-bromo-7'-iodo-5H-spiro[oxazole-4,9'-xanthen]-2-amine (0.250 g, 0.547 mmol) in THF (4.5 mL) was added dichlorobis(triphenylphosphine)palladium (ii) (0.077 g, 0.109 mmol), 1-ethynylcyclobutanol (0.079 g, 0.820 mmol), copper(i) iodide (3.71 μL, 0.109 mmol), and diisopropyl amine (0.613 mL, 4.38 mmol). The resulting mixture was then stirred at RT for 2 h. EtOAc (7 mL) was added and the mixture was filtered. The solid was washed with EtOAc (1×5 mL). The combined filtrates were concentrated. The residue was mixed with silica gel and the solid mixture was purifed by silica gel column chromatography (solid loading, 0%-20% MeOH/DCM) to give the alkynylated product as a brown solid.

Step 2: To a solution of (R)-1-((2-amino-2'-bromo-5H-spiro[oxazole-4,9'-xanthene]-7'-yl)ethynyl)cyclobutanol (0.290 g, 0.682 mmol) in DME (5.5 mL) was added 3-pyridylboronic acid (0.084 g, 0.682 mmol), tetrakis(triphenylphosphine)palladium(0) (0.063 g, 0.055 mmol), sodium carbonate monohydrate crystals (0.217 g, 2.046 mmol), and H₂O (1.0 mL). The resulting mixture was then heated to 90° C. for 5 h. Then, the mixture was cooled to room temperature and EtOAc (10 mL) was added. The mixture was stirred at room temperature for 2 min. The organic layer was collected, dried over MgSO4, and concentrate. The residue was mixed with silica gel and the solid mixture was purified by silica gel column chromatography (solid loading, 0%-20% MeOH/DCM) to give the depicted product as a brown solid.

Example 48

Method AA34

Synthesis of (S)-4-(2'-amino-7-(cyclopropylethynyl)-5'H-spiro[chromeno[2,3-b]pyridine-5,4'-oxazole]-3-yl)-2-methylbut-3-yn-2-ol Step 1: Combined (R)-2'-amino-3-bromo-5'H-spiro[chromeno[2,3-b]pyridine-5,4'-oxazol]-7-ol (2.259 g, 6.49 mmol), tetrakis(triphenylphosphine)palladium (0.750 g, 0.649 mmol), copper(i) iodide (0.124 g, 0.649 mmol) and THF (26.0 mL, 6.49 mmol) and DMF (26.0 mL, 6.49 mmol). Added diisopropylamine (18.19 mL, 130 mmol) then 2-methylbut-3-yn-2-ol (3.17 mL, 32.4 mmol) and flushed the reaction tube with argon. Sealed and heated at 85° C. for 3 hours. The mixture was diluted with water (100 mL) and extracted with DCM (1×100 mL, 2×50 mL). (DCM was used because this product is partially soluble in water and EtOAc is not as good a solvent for it). The combined organic extracts were dried over sodium sulfate, filtered, and evaporated. The resuling liquid was poured onto a 25-g SCX-2 column and eluted with methanol. The product was then eluted with 2M ammonia in methanol. The filtrate was evaporated and purified by chromatography on a 120-g Redi-Sep column, eluting with 0-100% of a 90:10:1 mixture of DCM/MeOH/NH₄OH in DCM to give (R)-2'-amino-3-(3-hydroxy-3-methylbut-1-ynyl)-5'H-spiro[chromeno[2,3-b]pyridine-5,4'-oxazol]-7-ol as a tan solid.

Step 2: A 25-mL flask was charged with (S)-2'-amino-3-(3-hydroxy-3-methylbut-1-ynyl)-5'H-spiro[chromeno[2,3-b]pyridine-5,4'-oxazol]-7-ol (437.24 mg, 1.244 mmol), cesium carbonate (446 mg, 1.369 mmol), and DMF (6222

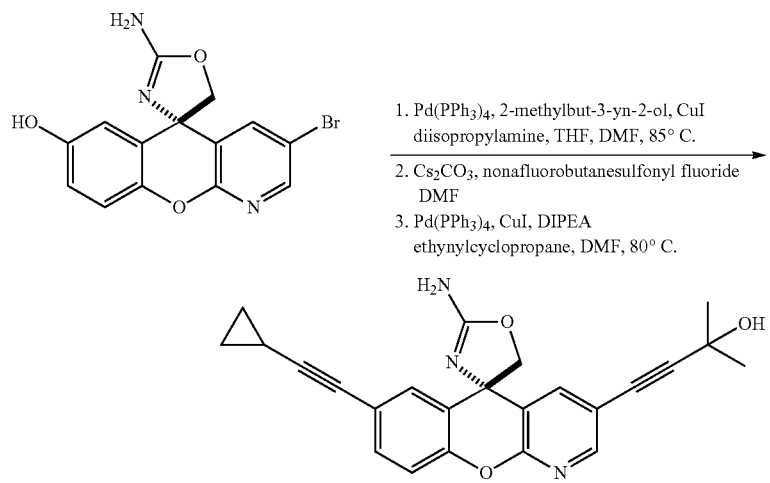

μL). The resulting mixture was stirred for 10 min, then the vial was submerged in an ice-bath for 10 min. nonafluorobutane-sulfonyl fluoride (241 μL, 1.369 mmol) was added dropwise over 1 min. The mixture was stirred for 3 hours before being diluted with water (20 mL) and a small amount of brine. This mixture was extracted with EtOAc (2×20 mL). The combined organic extracts were washed with brine, dried over sodium sulfate, filtered, and evaporated. The residue was purified by chromatography on an 80-g Redi-Sep column, eluting with 0-60% of a 90:10 mixture of DCM/MeOH in DCM to give (S)-2'-amino-3-(3-hydroxy-3-methylbut-1-ynyl)-5'H-spiro[chromeno[2,3-b]pyridine-5,4'-oxazole]-7-yl 1,1,2,2,3,3,4,4,4-nonafluorobutane-1-sulfonate as a white solid.

Step 3: A 0.5-2 mL vial was charged with (S)-2'-amino-3-(3-hydroxy-3-methylbut-1-ynyl)-5'H-spiro[chromeno[2,3-b]pyridine-5,4'-oxazole]-7-yl-1,1,2,2,3,3,4,4,4-nonafluorobutane-1-sulfonate (106 mg, 0.167 mmol), and copper(i) iodide (3.19 mg, 0.017 mmol). The vial was flushed with Ar (g), then DMF (669 μL, 0.167 mmol), diisopropylamine (469 μL, 3.35 mmol), and ethynylcyclopropane (70.8 μL, 0.836 mmol) were added in sequence to give a yellow solution. The vial was sealed and heated overnight in at 80° C. The mixture was diluted with water (15 mL) and extracted with EtOAc (3×10 mL). The combined organic extracts were washed with brine, dried over sodium sulfate, filtered, and evaporated. The residue was purified by chromatography on a 40-g Redi-Sep column, eluting with 0-50% of a 90:10:1 mixture of DCM/MeOH/NH$_4$OH in DCM to give (S)-4-(2'-amino-7-(cyclopropylethynyl)-5'H-spiro[chromeno[2,3-b]pyridine-5,4'-oxazole]-3-yl)-2-methylbut-3-yn-2-ol as a tan solid after evaporation from DCM/hexanes.

Example 49

Method AA36

Synthesis of (S)-2'-(1H-imidazol-2-yl)-7'-(neopentyloxy)-5H-spiro[oxazole-4,9'-xanthen]-2-amine Step 1: (R)-2'-Bromo-7'-(neopentyloxy)-5H-spiro[oxazole-4,9'-xanthen]-2-amine (1170 mg, 2.80 mmol), Bis(pinacolate)diboron (1780 mg, 7.01 mmol), Potassium acetate (550 mg, 5.61 mmol) and PdCl$_2$dppf with DCM (229 mg, 0.280 mmol) were combined in a 20 ml microwave vial. Dioxane (14 ml) was added, Ar gas was bubbled through, and the vial was sealed and heated to 90° C. After 3 days, the reaction mixture was concentrated and brought up in DMF (~10 ml). To the dark brown solution was added H$_2$O and a precipitate formed. The solution was filtered to give a brown solid. The filtrate was diluted with DCM and washed with sat'd aqueous NaHCO$_3$. The precipitate was brought up in DCM (1 ml) and sonicated for 30 s. Addition of hexanes crashed out minimal amounts of the desired product and the precipitate and solution were combined with the organic layer from before and concentrated. The crude mixture was diluted with H$_2$O and filtered to give the crude product as a brown solid that was brought up in minimal DCM, sonicated for 20 s, diluted with hexanes, filtered and washed with hexanes to provide (S)-2'-(neopentyloxy)-7'-(4,4,5,5-tetramethyl-1,3,2-dioxaborolan-2-yl)-5H-spiro[oxazole-4,9'-xanthen]-2-amine as a brown solid.

Step 2: A solution of (S)-2'-(neopentyloxy)-7'-(4,4,5,5-tetramethyl-1,3,2-dioxaborolan-2-yl)-5H-spiro[oxazole-4,9'-xanthen]-2-amine (50 mg, 0.108 mmol) in BuOH (861 μL), 2-bromo-1H-imidazole (0.129 mmol), and KOAc (31.7 mg, 0.323 mmol) in Water (215 μL) was purged with Ar in a sealed tube. AmPhos (1.525 mg, 2.153 μmol) was added and the reaction was heated to 120° C. for 30 min in the microwave. The reaction was cooled to rt, diluted with MeOH (3 ml), loaded onto an AccuBOND II SCX cartridge, washed with MeOH (3 ml) and eluted with 2N NH3 in MeOH (6 ml) to give the crude product which was purified by reverse-phase preparative HPLC using a Gemini NX c!8 column (150*30 mm, 5 um), 0.1% TFA in CH3CN/H2O, gradient 0% to 70% over 10 min to provide (S)-2'-(1H-imidazol-2-yl)-7'-(neopentyloxy)-5H-spiro[oxazole-4,9'-xanthen]-2-amine.

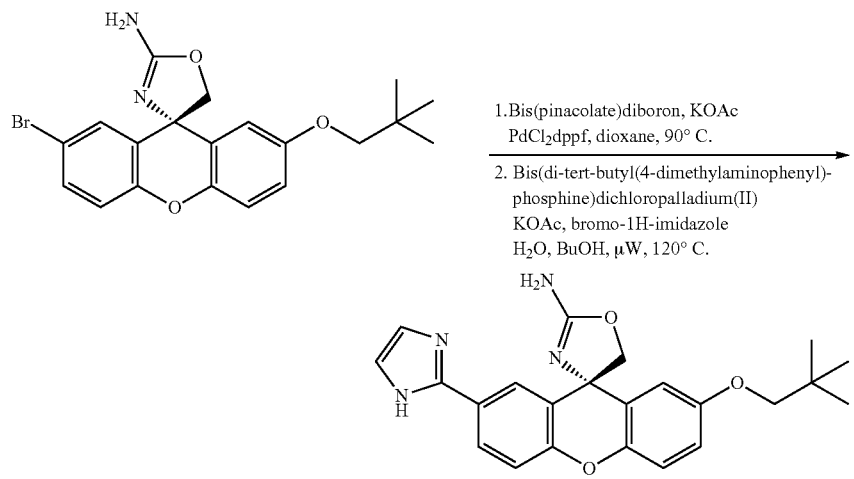

Example 50

Method AA37

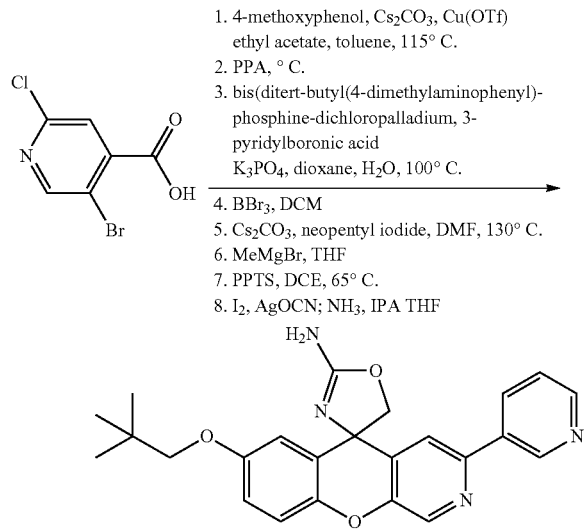

Step 1: To a solution of 5-bromo-2-chloroisonicotinic acid (14.0 g, 59.2 mmol) in toluene (200 mL) was added 4-methoxyphenol (6.16 mL, 77 mmol), and cesium carbonate (38.6 g, 118 mmol). The resulting mixture was stirred at RT and was flushed with $N_2$. Then, copper (trifluoromethane) (0.919 g, 1.776 mmol) and EtOAc (0.6 mL) were added. The mixture was then heated to 115° C. for 17 h. Then, the mixture was cooled to RT and was concentrated to ⅒th of the original volume. The residue was then dissolved in EtOAc (400 mL) and water (400 mL). The organic layer was separated and the aqueous layer was collected. The aqueous layer was carefully adjusted to pH=4.0 using concentrated HCl at 0° C. Then, EtOAc (400 mL) was added and the mixture was stirred at RT for 15 min. A brown precipitation (not product) was observed. The mixture was filtered and the filtrate was collected and concentrated. Then, MeOH (200 mL) was added to the residue and a light brown precipitation was observed. The mixture was filtered and the solid was collected. Then, the solid was dissolved in DCM (1000 mL).

The mixture was filtered and the filtrate was concentrated to give the product as light yellow solid. MS (ESI, positive ion) m/z: 280, 282 (M+1).

Step 2: To a RBF was added 2-chloro-5-(4-methoxyphenoxy)isonicotinic acid (1.1 g, 3.93 mmol) and polyphosphoric acid (56 g). The resulting mixture was then heated to 150° C. for 1 h. Then, the mixture was carefully poured to a beaker containing ice and water. Then, the mixture was adjusted to pH=7 using $NaHCO_3$ (s). Then, the mixture was extracted with EtOAc (2×200 mL). The combined organic extracts were dried over $MgSO_4$, concentrated, and dried in vacuo to give the product as a yellow solid. MS (ESI, positive ion) m/z: 262, 264 (M+1).

Step 3: To a solution of 3-chloro-7-methoxy-5H-chromeno[2,3-c]pyridin-5-one (0.410 g, 1.567 mmol) in 1,4-Dioxane (7.0 mL) and Water (2.333 mL) was added 3-pyridylboronic acid (0.289 g, 2.350 mmol), potassium phosphate (0.998 g, 4.70 mmol), and bis(ditert-butyl(4-dimethylaminophenyl)phosphinedichloropalladium II (0.111 g, 0.157 mmol). The resulting mixture was then subjected to a microwave irradiation at 100° C. for 15 min. Then, DCM (10 mL) and $H_2O$ (5 mL) were added to the mixture. The mixture was then stirred at RT for 5 min. The organic layer was collected and the aqueous layer was extracted with DCM (1×10 mL). The combined organic extracts were dried over $MgSO_4$ and concentrated. Then, MeOH (5 mL) was added to the residue. A yellow precipitation was observed. The mixture was filtered, and the yellow solid was collected and dried in vacuo to give the product as a light yellow solid. MS (ESI, positive ion) m/z: 305 (M+1).

Step 4: To a solution of 7-methoxy-3-(pyridin-3-yl)-5H-chromeno[2,3-c]pyridin-5-one (363 mg, 1.193 mmol) in DCM (6 mL) was added boron tribromide, 1.0M in DCM (2.98 mL, 2.98 mmol) drop wise. After addition, the mixture was stirred at RT for overnight. Then, the mixture was carefully quenched with MeOH (50 mL). The mixture was then concentrated and DCM (10 mL) was added. A yellow precipitation was observed. The mixture was filtered and the yellow solid was collected. Then, MeOH (200 mL) was added to the yellow solid and the mixture was stirred at RT for 2 h. The mixture was filtered and the yellow solid was collected and dried in vacuo to the product as a yellow solid. MS (ESI, positive ion) m/z: 291 (M+1).

Step 5: To a microwave vial was added 7-hydroxy-3-(pyridin-3-yl)-5H-chromeno[2,3-c]pyridin-5-one (0.312 g, 1.075 mmol), DMF (7.5 mL), cesium carbonate (0.525 g, 1.612 mmol), and neopentyl iodide (0.513 mL, 3.87 mmol). The resulting mixture was then subjected to a microwave irradiation at 130° C. for 15 min. Then, EtOAc (30 mL) and $H_2O$ (30 mL) were added. The mixture was then stirred at RT for 5 min. A yellow precipitation was observed. The mixture was filtered, and the yellow solid was collected and dried in vacuo to give the product as a yellow solid. MS (ESI, positive ion) m/z: 361 (M+1).

Step 6: To a solution of 7-(neopentyloxy)-3-(pyridin-3-yl)-5H-chromeno[2,3-c]pyridin-5-one (0.230 g, 0.638 mmol) in THF (4 mL) at 0° C. was added methylmagnesium chloride, 3.0M solution in THF (0.425 mL, 1.276 mmol). After addition, the mixture was stirred at RT for 4 h. Then, saturated ammonium chloride (10 mL) and EtOAc (20 mL) were added. The mixture was stirred at RT for 5 min. Then, the organic layer was collected, dried over $MgSO_4$, and concentrated to give 240 mg of the product as a light brown solid. MS (ESI, positive ion) m/z: 377 (M+1).

Step 7: A solution of 5-methyl-7-(neopentyloxy)-3-(pyridin-3-yl)-5H-chromeno[2,3-c]pyridin-5-ol (0.240 g, 0.638 mmol) in 1,2-dichloroethane (2.0 mL) was added pyridinium 4-toluenesulfonate (6.41 mg, 0.026 mmol). The resulting mixture was then heated to 65° C. for 6 h. Then, saturated $NaHCO_3$ (5 mL) was added to the mixture and the mixture was extracted with DCM (2×10 mL). The combined organic extracts were dried over $MgSO_4$ and concentrated. The residue was then dissolved in a solution of EtOAc/hexane. A light brown precipitation was observed. The mixture was filtered and the light brown solid was washed with hexane (2×5 mL) to give the desired product, which was used in the next step. MS (ESI, positive ion) m/z: 359 (M+1).

Step 8: To a solution of iodine (0.178 g, 0.703 mmol) in THF (4 mL) at −20° C. was added silver cyanate (0.287 g, 1.917 mmol). After addition, the mixture was stirred at −20° C. for 1 h. Then, 5-methylene-7-(neopentyloxy)-3-(pyridin-3-yl)-5H-chromeno[2,3-c]pyridine (0.229 g, 0.639 mmol) was added and the mixture was stirred at 0° C. for 2 h. Then, the mixture was filtered through celite with the aid of THF (7 mL). Then, ammonia (0.958 mL, 1.917 mmol) (2 M in i-PrOH) was added drop wise to the filtrate at 0° C. The resulting mixture was stirred at RT for overnight. Then, saturated Na$_2$S$_2$O$_3$ (1.0 mL) was added followed by saturated NaHCO$_3$ (1.0 mL). The mixture was stirred at RT for 15 min. The organic layer was collected, dried over MgSO$_4$, and concentrated. The residue was mixed with silica gel and the solid mixture was purified by silica gel column chromatography using ISCO instrument (solid loading, 0%-20% MeOH/DCM) to give the depicted product as a brown solid, which was then purified by preparative HPLC (0%-100% MeCN 0.1% TFA/H$_2$O 0.1% TFA) to give a desired product in a solution of MeCN 0.1% TFA/H$_2$O. The solvent, MeCN was removed and saturated NaHCO$_3$ (4 mL) was added. The mixture was then extracted with EtOAc (2×10 mL). The combined organic extracts were then dried over MgSO$_4$, concentrated, and dried in vacuo to give the depicted product as a white solid. MS (ESI, positive ion) m/z: 417 (M+1).

Example 51

Method AA39

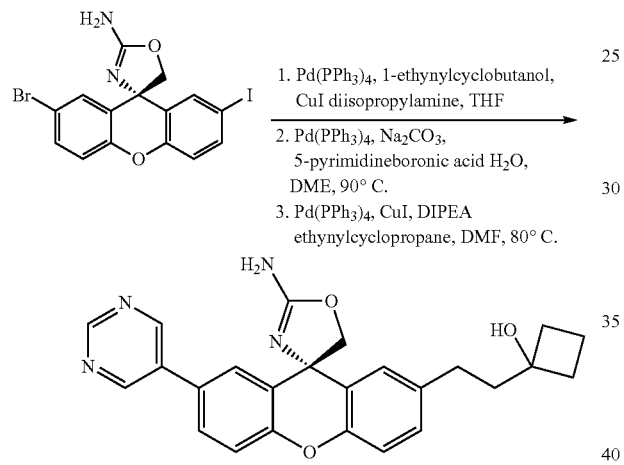

Step 1: To a solution of (S)-2'-bromo-7'-iodo-5H-spiro[oxazole-4,9'-xanthen]-2-amine (1.070 g, 2.341 mmol) in THF (20 mL) was added 1-ethynylcyclobutanol (0.338 g, 3.51 mmol), copper(i) iodide (0.016 mL, 0.468 mmol), dichlorobis(triphenyl-phosphine)palladium (ii) (0.329 g, 0.468 mmol), and DIPA (2.62 mL, 18.73 mmol). The resulting mixture was then stirred at RT overnight. EtOAc (30 mL) was added and the mixture was filtered. The solid was washed with EtOAc (1×5 mL). The combined filtrates were concentrated. The residue was mixed with silica gel and the solid mixture was purifed by silica gel column chromatography (solid loading, 0%-20% MeOH/DCM) to give the product as a light brown solid Step 2: To a solution of (R)-1-((2-amino-2'-bromo-5H-spiro[oxazole-4,9'-xanthene]-7'-yl)ethynyl)cyclobutanol (883 mg, 2.076 mmol) in DME (7 mL) and H$_2$O (2.333 mL) was added tetrakis(triphenylphosphine)palladium(0) (192 mg, 0.166 mmol), 5-pyrimidinylboronic acid (283 mg, 2.284 mmol), and sodium carbonate (0.087 mL, 2.076 mmol). The resulting mixture was then heated to 90° C. for 5 h. The mixture was cooled to RT and EtOAc (20 mL) was added. The mixture was stirred at RT for 5 min. The organic layer was collected, dried over MgSO$_4$, and concentrated. The residue was then dissolved in a solution of DMSO (2 mL) and MeOH (2 mL). The solution was then purified by preparative HPLC (0%-100% MeCN 0.1% NH$_4$OH/H$_2$O 0.1% NH$_4$OH) to give the product as a light yellow solid Step 3: To a solution of (R)-1-((2-amino-2'-(pyrimidin-5-yl)-5H-spiro[oxazole-4,9'-xanthene]-7'-yl)ethynyl)cyclobutanol (0.134 g, 0.316 mmol) in MeOH (2 mL) was added palladium hydroxide (20 mg). The resulting mixture was then stirred at RT under H$_2$ overnight. The mixture was filtered through celite and washed with MeOH (2×5 mL). The combined filtrates were concentrated and the residue was dissolved in MeOH (2 mL).

The solution was then purified by preparative HPLC (0%-90% MeCN 0.1% NH$_4$OH/H$_2$O 0.1% NH$_4$OH) to give the title compound as a white solid.

Example 52

Method AA40

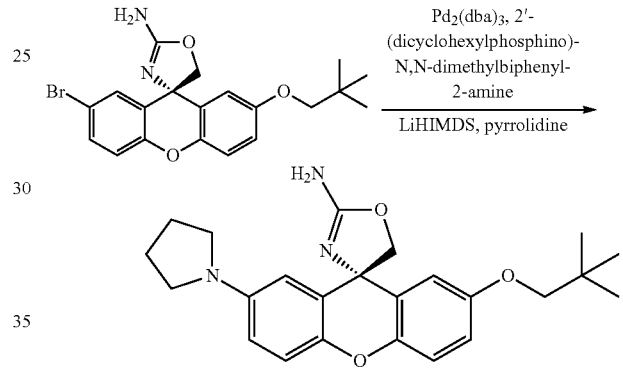

Synthesis of (S)-2'-(neopentyloxy)-7'-(pyrrolidin-1-yl)-5H-spiro[oxazole-4,9'-xanthen]-2-amine A vial was charged with (R)-2'-bromo-7'-(neopentyloxy)-5H-spiro[oxazole-4,9'-xanthen]-2-amine (0.100 g, 0.240 mmol), 2'-(dicyclohexylphosphino)-N,N-dimethylbiphenyl-2-amine (1.132 mg, 2.88 µmol), Pd$_2$(dba)$_3$ (1.097 mg, 1.198 µmol), LiHMDS (1.0 M in THF) (0.959 mL, 0.959 mmol), and pyrrolidine (0.059 mL, 0.719 mmol). The vial was sealed and heated to 100° C. overnight. Additional Pd$_2$(dba)$_3$ (1.097 mg, 1.198 µmol), 2'-(dicyclohexylphosphino)-N,N-dimethylbiphenyl-2-amine (1.132 mg, 2.88 µmol), LiHMDS (1.0 M in THF) (0.480 mL, 0.480 mmol) and pyrrolidine (0.059 mL, 0.719 mmol) were added and the reaction was at 100° C. for 2 hours. The reaction mixture was diluted with a saturated aqueous ammonium chloride solution (10 mL) and extracted three times with DCM. The combined organic extracts were dried over sodium sulfate, filtered, and evaporated. The material was purified via Gilson HPLC (20-90% MeCN:H$_2$O). The product fractions were partitioned between DCM and saturated sodium bicarbonate solution. The aqueous layer was extracted with DCM, and the combined organic layers were dried with sodium sulfate, filtered, and concentrated to afford (S)-2'-(neopentyloxy)-7'-(pyrolidin-1-yl)-5H-spiro[oxazole-4,9'-xanthen]-2-amine as a white solid.

Example 53

Method AA41

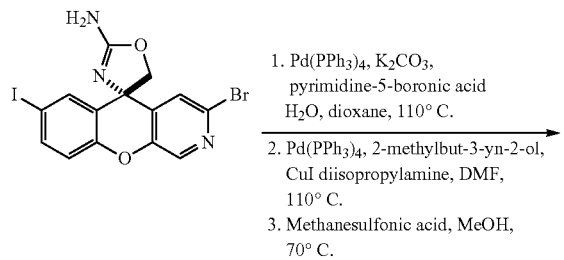

1. Pd(PPh₃)₄, K₂CO₃, pyrimidine-5-boronic acid H₂O, dioxane, 110° C.
2. Pd(PPh₃)₄, 2-methylbut-3-yn-2-ol, CuI diisopropylamine, DMF, 110° C.
3. Methanesulfonic acid, MeOH, 70° C.

Synthesis of (S)-3-(3-methoxy-3-methylbut-1-ynyl)-7-(pyrimidin-5-yl)-5'H-spiro[chromeno[2,3-b]pyridine-5,4'-oxazol]-2'-amine Step 1: A 10-20 mL microwave vial was charged with (S)-3-bromo-7-iodo-5'H-spiro[chromeno[2,3-b]pyridine-5,4'-oxazol]-2'-amine (503 mg, 1.098 mmol), pyrimidin-5-yl-boronic acid (143 mg, 1.153 mmol), tetrakis(triphenylphosphine)palladium (127 mg, 0.110 mmol). The vial was flushed with Ar(g), then THF (5489 μL, 1.098 mmol) and potassium carbonate (1.5 M) (1464 μL, 2.195 mmol) (aq. solution) were added in sequence. The vial was sealed and heated at 110° C. for 2 hours. The mixture was diluted with water and extracted with 10% i-PrOH/EtOAc (3×). The combined organic extracts were dried over sodium sulfate, filtered, and evaporated. The residue was purified by chromatography on a 100-g SNAP column, eluting with 0-100% of a 90:10:1 mixture of DCM/MeOH/NH₄OH in DCM to provide (S)-3-bromo-7-(pyrimidin-5-yl)-5'H-spiro[chromeno[2,3-b]pyridine-5,4'-oxazol]-2'-amine as an off-white solid.

Step 2: Combined (S)-3-bromo-7-(pyrimidin-5-yl)-5'H-spiro[chromeno[2,3-b]pyridine-5,4'-oxazol]-2'-amine (99 mg, 0.242 mmol), tetrakis(triphenylphosphine)palladium (28.0 mg, 0.024 mmol), copper(i) iodide (4.61 mg, 0.024 mmol) and THF (969 μL, 0.242 mmol) and DMF (969 μL, 0.242 mmol). Added DIPA (679 μL, 4.85 mmol) then 2-methylbut-3-yn-2-ol (118 μL, 1.211 mmol) and flushed the reaction tube with argon. Sealed and heated at 110° C. for 2 hours. The mixture was diluted with water and extracted with EtOAc (3×). The combined organic extracts were dried over sodium sulfate, filtered, and evaporated. The residue was purified by chromatography on a 25-g SNAP column, eluting with 0-100% of a 90:10:1 mixture of DCM/MeOH/NH₄OH to give (S)-4-(2'-amino-7-(pyrimidin-5-yl)-5'H-spiro[chromeno[2,3-b]pyridine-5,4'-oxazole]-3-yl)-2-methylbut-3-yn-2-ol as a white solid after evaporation from DCM/hexane.

Step 3: To a solution of (S)-4-(2'-amino-7-(pyrimidin-5-yl)-5'H-spiro[chromeno[2,3-b]pyridine-5,4'-oxazole]-3-yl)-2-methylbut-3-yn-2-ol (58 mg, 0.140 mmol) in MeOH (1703 μL, 42.1 mmol) was added methane sulfonic acid (91 μL, 1.403 mmol) in a vial. The vial was sealed and placed in a 70° C. oil bath for 3 hours. The mixture was poured into saturated aqueous sodium bicarbonate solution (20 mL) and extracted with DCM (3×10 mL). The combined organic extracts were dried over sodium sulfate, filtered, and evaporated. The residue was purified by chromatography on a 25-g SNAP column, eluting with 0-70% of a 90:10:1 mixture of DCM/MeOH/NH₄OH in DCM to give (S)-3-(3-methoxy-3-methylbut-1-ynyl)-7-(pyrimidin-5-yl)-5'H-spiro[chromeno[2,3-b]pyridine-5,4'-oxazol]-2'-amine as a white solid after evaporation from DCM/hexane.

Example 54

Method AA42

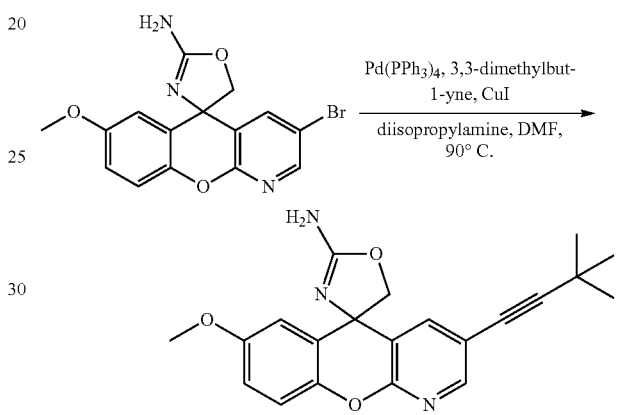

Synthesis of 3-(3,3-dimethylbut-1-ynyl)-7-methoxy-5'H-spiro[chromeno[2,3-b]pyridine-5,4'-oxazol]-2'-amine 3-Bromo-7-methoxy-5'H-spiro[chromeno[2,3-b]pyridine-5,4'-oxazol]-2'-amine (104186-10-peak 1) (500 mg, 1.381 mmol), tetrakis(triphenylphosphine)palladium (160 mg, 0.138 mmol), copper(i) iodide (52.6 mg, 0.276 mmol) were combined, and to the mixture was added DMF (6903 μL, 1.381 mmol), 3,3-dimethylbut-1-yne (340 mg, 4.14 mmol) and DIPA (4837 μL, 34.5 mmol). The reaction was flushed with argon, sealed and heated at 90° C. for 2 hours. The reaction mixture was diluted with water (100 mL) and poured into a separatory funnel containing EtOAc (100 mL). The layers were separated and the aqueous layer was extracted with EtOAc (3×50 mL). The combined organic layers were washed with water and then brine, dried over sodium sulfate, filtered and concentrated in vacuo to provide a brown oil that was purified by silica gel chromatography (Redi-Sep prepacked silica gel column (40 g), 0-10% methanol in methylenechloride with 0.1% ammonium hydroxide) to provide the desired product contaminated with triphenylphosphine. The yellow solid was suspended in 25 mL of ether, resulting in the formation of a fine white precipitate. Decanted ether and washed the solid with 10 mL of ether. Dried under reduced pressure to provide 3-(3,3-dimethylbut-1-ynyl)-7-methoxy-5'H-spiro[chromeno[2,3-b]pyridine-5,4'-oxazol]-2'-amine as a white solid.

Example 55

Method AA43

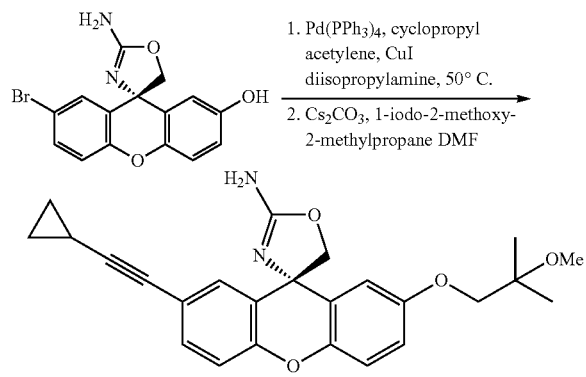

Synthesis of (S)-2'-(cyclopropylethynyl)-7'-(2-methoxy-2-methylpropoxy)-5H-spiro[oxazole-4,9'-xanthen]-2-amine Step 1: A vial was charged with (R)-2-amino-2'-bromo-5H-spiro[oxazole-4,9'-xanthen]-7'-ol (1.00 g, 2.88 mmol), cyclopropyl acetylene (0.732 mL, 8.64 mmol), copper(i) iodide (0.110 g, 0.576 mmol), and DIPA (14.40 mL). Tetrakis(triphenylphosphine)palladium(0) (0.333 g, 0.288 mmol) was added, the vial was flushed with argon, and the reaction was heated to 50° C. and stirred overnight. The reaction was diluted with ethyl acetate and filtered through Celite. The solution was concentrated and purified via column chromatography (RediSep 40 g, gradient elution 0-10% MeOH:DCM) to afford (S)-2-amino-2'-(cyclopropylethynyl)-5H-spiro[oxazole-4,9'-xanthen]-7'-ol as a tan solid.

Step 2: A 2-5 mL microwave vial was charged with (S)-2-amino-2'-(cyclopropylethynyl)-5H-spiro[oxazole-4,9'-xanthen]-7'-ol (0.250 g, 0.752 mmol), cesium carbonate (0.980 g, 3.01 mmol), and DMF (3.01 mL). The mixture was stirred vigorously for 5 min, then 1-iodo-2-methoxy-2-methylpropane (0.303 mL, 2.257 mmol) was added via syringe. The vial was sealed and the reaction was microwaved at 110° C. for two hours. The mixture was diluted with water and EtOAc and the layers were separated, and the aqueous layer was extracted twice with EtOAc. The combined organic extracts were dried over sodium sulfate, filtered, and evaporated. The residue was purified by chromatography on a 12-g Redi-Sep column, eluting with 0-10% MeOH/DCM to provide (S)-2'-(cyclopropylethynyl)-7'-(2-methoxy-2-methylpropoxy)-5H-spiro[oxazole-4,9'-xanthen]-2-amine as an off-white solid.

Example 56

Method AA44

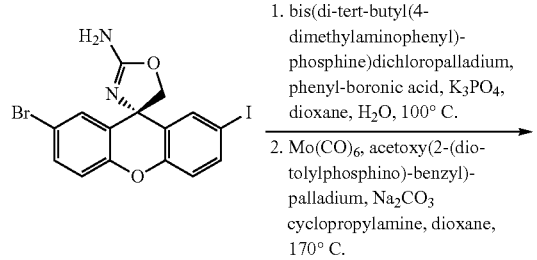

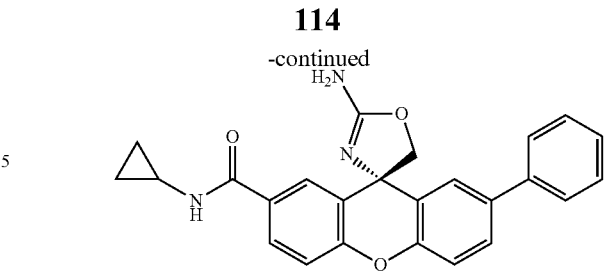

Step 1: A 100 ml RBF vial was charged with (S)-2'-bromo-7'-iodo-5H-spiro[oxazole-4,9'-xanthen]-2-amine (3.37 g, 7.37 mmol) in dioxane (30 mL), water (15 mL), phenylboronic acid (0.965 g, 7.91 mmol), bis(di-tert-butyl(4-dimethylaminophenyl)phosphine)dichloropalladium(II) (0.106 g, 0.150 mmol), and potassium phosphate-tribasic (3.17 g, 14.93 mmol). The reaction was heated to 100° C. in an oil-bath for 8 hours. The reaction was diluted with ethyl acetate (100 mL), water (25 mL), and the ethyl acetate layer was separated and dried over anhydrous sodium sulfate. Concentration and purification by silica gel flash column chromatography (hexanes/ethyl acetate) provided (R)-2'-bromo-7'-phenyl-5H-spiro[oxazole-4,9'-xanthen]-2-amine Step 2: A 0.5-2 mL microwave vial charged with (R)-2'-bromo-7'-phenyl-5H-spiro[oxazole-4,9'-xanthen]-2-amine (0.1000 g, 0.246 mmol), Mo(CO)$_6$ (0.065 g, 0.246 mmol), acetoxy(2-(dio-tolylphosphino)benzyl)palladium (0.012 g, 0.012 mmol), sodium carbonate (0.026 g, 0.246 mmol), cyclopropanamine (0.026 mL, 0.368 mmol), and 1,4-dioxane (0.541 mL, 6.14 mmol) was sealed and heated to 170° C. for 30 min. The mixture was diluted with EtOAc and water. The aqueous phase was extracted with EtOAc three times. The organic layer was dried over Na$_2$SO$_4$ and concentrated in vacuo. The crude was purified by silica gel chromatography (12 g, 2-10% MeOH—CH$_2$Cl$_2$, then 10-20% MeOH (2 M NH$_3$)—CH$_2$Cl$_2$). The product was purified again by reverse phase prep HPLC: 15-60% CH$_3$CN (0.1% TFA)-water (0.1% TFA) in 26 min. The fractions were combined and neutralized with solid Na$_2$CO$_3$, extracted three times with CH$_2$Cl$_2$. The organic layer was dried over Na$_2$SO$_4$ and concentrated in vacuo. The depicted product was obtained as a white solid.

Example 57

Method AA45

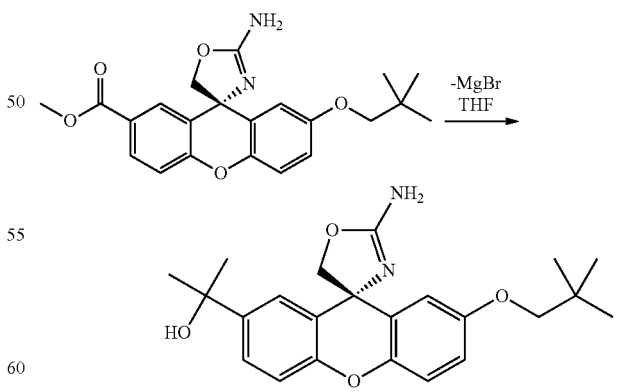

Synthesis of (S)-2-(2-amino-2'-(neopentyloxy)-5H-spiro[oxazole-4,9'-xanthene]-7'-yl)propan-2-ol To a solution of (S)-methyl 2-amino-7'-(neopentyloxy)-5H-spiro[oxazole-4,9'-xanthene]-2'-carboxylate (50 mg, 0.13 mmol) in THF (1 mL) was added methylmagnesium bromide (Aldrich, 0.76 mL, 0.76 mmol) at 0° C. The cooling bath was removed after the addition. After 1 h, the reaction was quenched with saturated NH₄Cl. The mixture was extracted with EtOAc three times. The organic phase was dried over Na₂SO₄, and concentrated in vacuo. The residue was purified by silica gel chromatography (12 g, 2-10% in 10 min, then 10% MeOH—CH₂Cl₂). The product was obtained as a white solid. MS: 397 (M+1).

Example 58

Method AA46

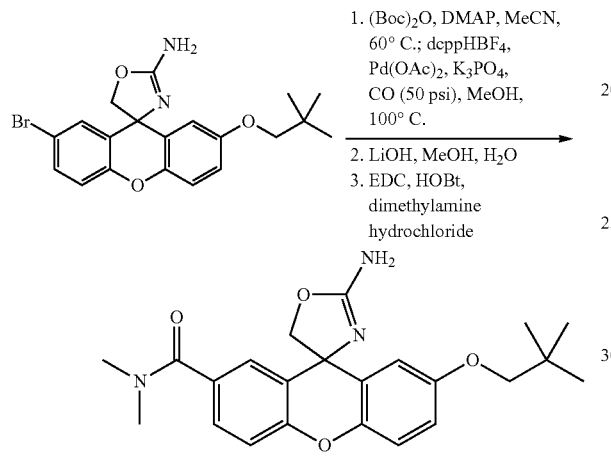

Step 1: The mixture of 2'-bromo-7'-(neopentyloxy)-5H-spiro[oxazole-4,9'-xanthen]-2-amine (1.00 g, 2.4 mmol), CH₃CN (15 mL), di-tert-butyl dicarbonate (Aldrich, 0.63 g, 2.9 mmol), and DMAP (Aldrich, 0.015 g, 0.12 mmol) was heated to 60° C. overnight. LCMS showed the product. di-tert-butyl dicarbonate (70 mg) was added and the reaction was continued overnight. LC didn't show further improvement in conversion. The mixture was diluted with EtOAc and washed with saturated Na₂CO₃, water and brine. The organic layer was dried over Na₂SO₄ and concentrated in vacuo. The residue was purified by silica gel chromatography (40 g, 0-10%, then 10% MeOH—CH₂Cl₂). The Boc-protected 2'-bromo-7'-(neopentyloxy)-5H-spiro[oxazole-4,9'-xanthen]-2-amine was obtained as a white solid. MS: 517, 519, 462 (M+1). The mixture of the above product (70 mg, 0.14 mmol, potassium phosphate (115 mg, 0.54 mmol), dcppHBF₄ (0.41 mg, 0.68 µmol), palladium acetate (0.12 mg, 0.54 µmol), and MeOH (3 mL) was pressurized with carbon monoxide, purged twice with CO gas (40 psi) and then heated to 100° C. (50 psi) overnight. The reaction mixture was concentrated in vacuo. The residue was diluted with EtOAc and water. The aqueous phase was extracted with EtOAc three times. The organic layer was dried over Na₂SO₄ and concentrated in vacuo. The crude was purified by prep TLC: 8% MeOH—CH₂Cl₂. The product was obtained as a white solid. MS: 397 (M+1).

Step 2: To a mixture of methyl 2-amino-7'-(neopentyloxy)-5H-spiro[oxazole-4,9'-xanthene]-2'-carboxylate (33 mg, 83 µmol) and lithium hydroxide hydrate (Aldrich, 7 mg, 166 µmol) was added THF:MeOH:water (3:2:1, 1 mL). The mixture was stirred at RT for 5 h, then at 40° C. for 2 h. The mixture was concentrated in vacuo. The residue was neutralized with 1N HCl (2 mL). Ether was added to the mixture and stirred at RT for 10 min. The solid was filtered, washed with ether and dried in vacuum oven. The product was obtained as a white solid. MS: 383 (M+1).

Step 3: A mixture of 2-amino-7'-(neopentyloxy)-5H-spiro[oxazole-4,9'-xanthene]-2'-carboxylic acid (17 mg, 44 µmol), EDC (Aldrich, 13 mg, 67 µmol), HOBt (Ana Spec, 3 mg, 22 µmol), TEA (Aldrich, 37 µL, 267 µmol), dimethylamine.HCl (Alfa Aesar, 33 mg, 400 µmol) and DMF (0.5 mL) was stirred at RT overnight. The mixture was diluted with EtOAc and washed with saturated Na₂CO₃. The organic layer was dried over Na₂SO₄ and concentrated in vacuo. The crude was purified by silica gel chromatography (4 g, 0-10% MeOH—CH₂Cl₂). The depicted product was obtained as colorless film. MS: 410 (M+1).

Example 59

Method AA47

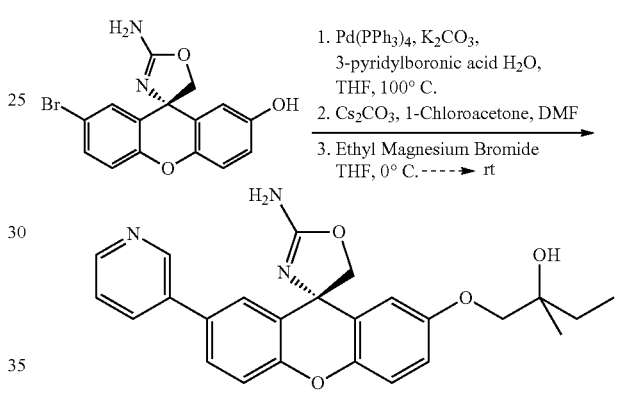

Synthesis of 1-((S)-2-amino-2'-(pyridin-3-yl)-5H-spiro[oxazole-4,9'-xanthene]-7'-yloxy)-2-methylbutan-2-ol Step 1: A 350-mL pressure vessel was charged with (R)-2-amino-2'-bromo-5H-spiro[oxazole-4,9'-xanthen]-7'-ol (4.00 g, 11.52 mmol), 3-pyridylboronic acid (3.54 g, 28.8 mmol), tetrakis(triphenylphosphine)palladium(0) (1.331 g, 1.152 mmol), THF (57.6 mL), and potassium carbonate (2.0M aq. solution) (28.8 mL, 57.6 mmol). The vessel was sealed and heated to 100° C. and stirred for 2 hours. The layers were partitioned between EtOAc (20 mL) and water (20 mL). The layers were separated, and the aqueous layer was extracted with EtOAc (2×20 mL). The combined organic layers were washed with brine (emulsion!), dried over sodium sulfate and filtered with the aid of 10% MeOH/DCM. The filtrate was evaporated to give a yellow solid. This solid was taken up in minimal DCM and sonicated for 5 min. The solid was filtered and washed with DCM (30 mL). Filtering and washing with DCM afforded (S)-2-amino-7'-(pyridin-3-yl)-5H-spiro[oxazole-4,9'-xanthen]-2'-ol as a pale-yellow solid Step 2: A vial was charged with (S)-2-amino-7'-(pyridin-3-yl)-5H-spiro[oxazole-4,9'-xanthen]-2'-ol (0.300 g, 0.869 mmol), cesium carbonate (0.425 g, 1.303 mmol). DMF (3.47 mL) was added, the vial was sonicated for 30 s, and the mixture was stirred vigorously for 20 min, at which time some white solid still remained. The vial was cooled in an ice-bath for 10 min, then 1-chloroacetone (0.083 mL, 1.042 mmol) was added dropwise and the reaction was stirred over the weekend, during which the bath warmed to RT. The reaction was cooled back to 0° C. and 1-chloroacetone (0.083 mL, 1.042 mmol) was added. The reaction was stirred for two hours before 0.5 equivalents of cesium carbonate and chloroacetone were added at one hour intervals until the reaction was complete. The mixture was partitioned between water and EtOAc. The layers were separated, and the aqueous layer was extracted with EtOAc (2×). The combined organic extracts were dried over sodium sulfate, filtered, and evaporated. The material was purified via column chromatography (RediSep 40 g, gradient elution 0-5% MeOH:DCM) to afford (S)-1-(2-amino-2'-(pyridin-3-yl)-5H-spiro[oxazole-4,9'-xanthene]-7'-yloxy)propan-2-one as a white solid. The remaining fractions were combined and concentrated to afford impure material as an off-white solid.

Step 3: (S)-1-(2-amino-2'-(pyridin-3-yl)-5H-spiro[oxazole-4,9'-xanthene]-7'-yloxy)propan-2-one (0.050 g, 0.125 mmol) was dissolved in THF (1.246 mL) and cooled to 0° C. ethylmagnesium bromide 1.0 M solution in THF (0.374 mL, 0.374 mmol) was added and the reaction was stirred for one hour. Additional ethylmagnesium bromide 1.0 M solution in THF (0.374 mL, 0.374 mmol) was added again and the reaction was stirred overnight at RT. The reaction was diluted with ethyl acetate and washed with water. The aqueous layer was extracted with ethyl acetate, and the combined organic layers were dried with sodium sulfate, filtered, and concentrated. The material was purified via Gilson HPLC (25-90% MeCN:H₂O). The product fractions were partitioned between DCM and saturated sodium bicarbonate solution. The aqueous layer was extracted with DCM, and the combined organic layers were dried with sodium sulfate, filtered, and concentrated to afford 1-((S)-2-amino-2'-(pyridin-3-yl)-5H-spiro[oxazole-4,9'-xanthene]-7'-yloxy)-2-methylbutan-2-ol as a white solid.

over MgSO4, and concentrated. The residue was mixed silica gel and the solid mixture was purified by silica gel column chromatography (solid loading, 0%-100% ammonia in methanol 2M/DCM) to give the product as a brown solid.

Step 2: To a solution of (R)-tert-butyl 2-(2-amino-2'-bromo-5H-spiro[oxazole-4,9'-xanthene]-7'-yl)acetate (0.505 g, 1.134 mmol) in 1,2-Dimethoxyethane (7 mL) was added 5-pyrimidinylboronic acid (0.155 g, 1.247 mmol), sodium carbonate monohydrate (0.142 mL, 3.40 mmol), tetrakis(triphenylphosphine)palladium(0) (0.105 g, 0.091 mmol), and H₂O (1.4 mL). The resulting mixture was then heated to 90° C. for 10 h. The mixture was cooled to room temperature, EtOAc (20 mL) and sat. NaHCO₃ (5 mL) were added. The mixture was stirred at room temperature for 5 minutes then the organic layer was collected, dried over MgSO₄, and concentrated. The residue was then dissolved in a solution of DMSO (1 mL) and MeOH (1 mL). The solution mixture was then purified by preparative HPLC (0%-90% MeCN 0.1% NH₄OH/H₂O 0.1% NH₄OH) to give the product as a light yellow solid.

Step 3: A solution of (R)-tert-butyl 2-(2-amino-2'-(pyrimidin-5-yl)-5H-spiro[oxazole-4,9'-xanthene]-7'-yl)acetate (14 mg, 0.031 mmol) in 30% TFA in DCM (0.5 mL) was stirred at room temperature for 1 h. A saturated NaHCO₃ solution was added slowly to the mixture at 0° C. to adjust the pH to 7. Then, solvents were removed and the residue was dissolved in a solution of MeOH (0.5 mL), H₂O (0.1 mL), and DMF (0.3 mL). The solution mixture was then purified by preparative HPLC (0%-100% MeCN 0.1% NH₄OH/H₂O 0.1% NH₄OH) to give the depicted product as a white solid.

Example 60

Method AA48

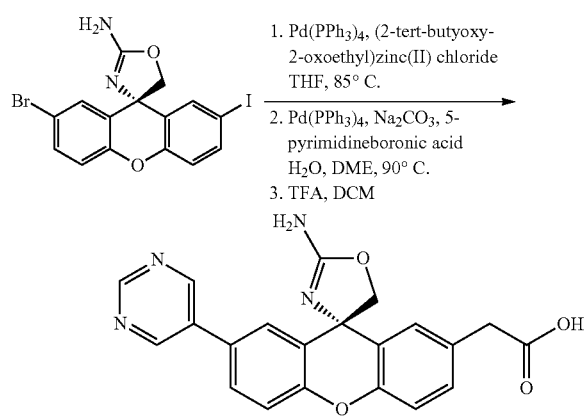

Step 1: To a solution of (S)-2'-bromo-7'-iodo-5H-spiro[oxazole-4,9'-xanthen]-2-amine (0.978 g, 2.140 mmol) in THF (5 mL) was added (2-tert-butoxy-2-oxoethyl)zinc(II) chloride (17.12 mL, 8.56 mmol) and tetrakis(triphenylphosphine)palladium(0) (0.124 g, 0.107 mmol). The resulting mixture was then heated to 85° C. overnight. Saturated ammonium chloride (50 mL) and EtOAc (100 mL) were added and the mixture was stirred at room temperature overnight. The mixture was filtered and the organic layer was collected, dried Example 61

Method AA49

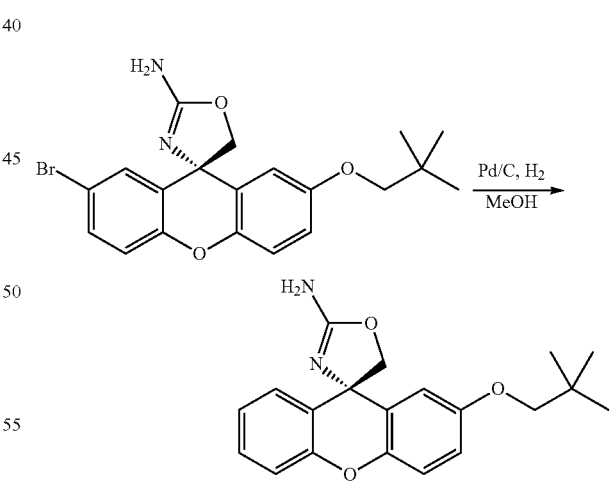

A mixture of (R)-2'-bromo-7'-(neopentyloxy)-5H-spiro[oxazole-4,9'-xanthen]-2-amine (0.0500 g, 0.120 mmol), ethanol (2 mL), and palladium 10% on activated carbon (0.013 g, 0.012 mmol) was stirred under 1 atm of H₂ gas overnight. The catalyst was filtered through celite and the filtrate was concentrated in vacuo to provide (S)-2'-(neopentyloxy)-5H-spiro[oxazole-4,9'-xanthen]-2-amine as a white solid.

Example 62

Method AA50

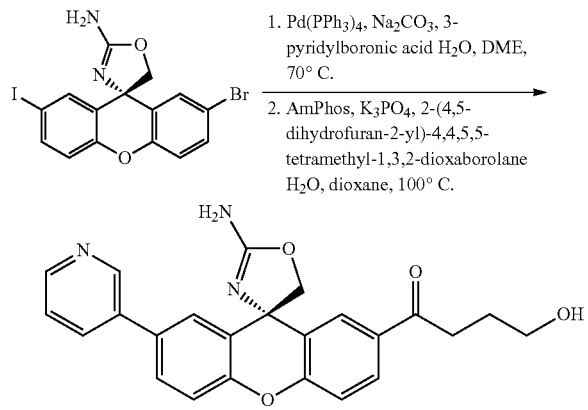

Synthesis of (S)-1-(2-amino-2'-(pyridin-3-yl)-5H-spiro[oxazole-4,9'-xanthene]-7'-yl)-4-hydroxybutan-1-one Step 1: A 250 ml RB flask was charged with (R)-2'-bromo-7'-iodo-5H-spiro[oxazole-4,9'-xanthen]-2-amine (4.06 g, 8.88 mmol), pyridin-3-ylboronic acid (1.419 g, 11.55 mmol), tetrakis(triphenylphosphine)palladium(0) (1.026 g, 0.888 mmol). DME (63.4 mL) and sodium carbonate (13.32 mL, 26.6 mmol) (2M solution) were added and the mixture was heated at 70° C. for 15 hrs. The mixture was diluted with water and ethyl acetate, filtered and organic layer was separated and concentrated. The crude material was purified by silica gel chromatography (0-50% gradient of 90/10/1 DCM/MeOH/NH4OH in DCM) to give (S)-2'-bromo-7'-(pyridin-3-yl)-5H-spiro[oxazole-4,9'-xanthen]-2-amine as an off-white solid.

Step: A 2-5 ml microwave vial was charged with (S)-2'-bromo-7'-(pyridin-3-yl)-5H-spiro[oxazole-4,9'-xanthen]-2-amine (96 mg, 0.235 mmol), potassium phosphate (150 mg, 0.705 mmol), 2-(4,5-dihydrofuran-2-yl)-4,4,5,5-tetramethyl-1,3,2-dioxaborolane (92 mg, 0.470 mmol) and AmPhos (16.65 mg, 0.024 mmol). 1,4-Dioxane (1176 μL) and water (392 μL) were added and the vial was sealed and heated in microwave reactor for 1 hr at 100° C. The mixture was diluted with ethyl acetate, filtered through celite, and concentrated on 2 g of silica gel. Purification by flash chromatography on 12 g rediSep column using 5-50% gradient of DCM/MeOH/NH4OH (90:10:1) in DCM provided (S)-1-(2-amino-2'-(pyridin-3-yl)-5H-spiro[oxazole-4,9'-xanthene]-7'-yl)-4-hydroxybutan-1-one as an off-white solid.

Example 63

Method AA51

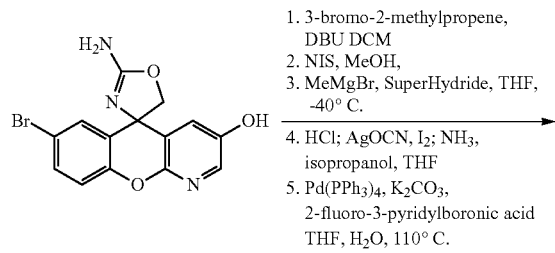

1. 3-bromo-2-methylpropene, DBU DCM
2. NIS, MeOH,
3. MeMgBr, SuperHydride, THF, -40° C.
4. HCl; AgOCN, I2; NH3, isopropanol, THF
5. Pd(PPh3)4, K2CO3, 2-fluoro-3-pyridylboronic acid THF, H2O, 110° C.

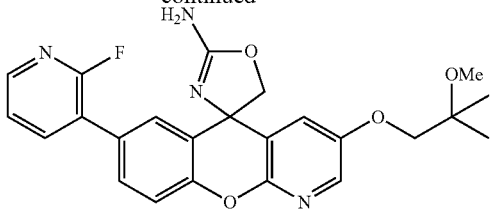

Synthesis of 7-(2-fluoropyridin-3-yl)-3-(2-methoxy-2-methylpropoxy)-5'H-spiro[chromeno[2,3-b]pyridine-5,4'-oxazol]-2'-amine Step 1: A solution of 2'-amino-7-bromo-5'H-spiro[chromeno[2,3-b]pyridine-5,4'-oxazol]-3-ol (15.00 g, 51.4 mmol) in 100 mL DCM was treated with DBU (9.68 mL, 64.2 mmol) and was allowed to stir for 10 minutes. 3-Bromo-2-methylpropene (5.44 mL, 53.9 mmol) was added, and the reaction mixture was allowed to stir at RT for an additional 1 hour. The reaction mixture was quenched with 200 mL 0.5 N citric acid and was concentrated to remove the organics. The resulting solid was filtered, washed with 1:1 water/acetone, and was dried. The solid was purified by column chromatography yielding 7-bromo-3-(2-methylallyloxy)-5H-chromeno[2,3-b]pyridin-5-one.

Step 2: A suspension of 7-bromo-3-(2-methylallyloxy)-5H-chromeno[2,3-b]pyridin-5-one (4.50 g, 13.00 mmol) in 100 mL MeOH was treated with NIS (5.85 g, 26.0 mmol) and was allowed to stir at room temperature for 48 hours. The reaction mixture was poured into 1:1 water/brine and was extracted with ether and then DCM. The organics were dried over MgSO4 and concentrated. Purification of the crude residue by column chromatography gave 7-bromo-3-(3-iodo-2-methoxy-2-methylpropoxy)-5H-chromeno[2,3-b]pyridin-5-one as a yellow solid.

Step: A solution of 7-bromo-3-(3-iodo-2-methoxy-2-methylpropoxy)-5H-chromeno[2,3-b]pyridin-5-one (4.10 g, 8.13 mmol) in 100 mL THF was cooled to -40° C. and was treated with methylmagnesium chloride (5.42 mL, 16.27 mmol). After stirring for two hours, the reaction mixture was allowed to warm to room temperature and superhydride (40.7 mL, 40.7 mmol) was added. After stirring for an additional 2 hours the reaction mixture was cooled to 0° C. and was quenched with MeOH. The reaction mixture was poured into saturated NH4Cl solution and was extracted with EtOAc. The organics were washed with waer, brine, dried over MgSO4 and concentrated yielding 7-bromo-3-(2-methoxy-2-methylpropoxy)-5-methyl-5H-chromeno[2,3-b]pyridin-5-ol.

Step 4: A solution of 7-bromo-3-(2-methoxy-2-methylpropoxy)-5-methyl-5H-chromeno[2,3-b]pyridin-5-ol (1.780 g, 4.51 mmol) in 50 mL THF was treated with HCl 4N in dioxane (0.113 mL, 0.451 mmol) and was heated to 50° C. for one hour. The reaction mixture was cooled to 0° C. and added to the mixture below. A separate solution of iodine (1.260 g, 4.97 mmol) in 50 mL THF was prepared and cooled to -40° C. Silver cyanate (1.692 g, 11.29 mmol) was added, and the reaction mixture was allowed to stir for one hour. The above solution was then added via cannula and the reaction mixture was allowed to stir for an additional hour before ammonia 2N in IPA (13.54 mL, 27.1 mmol) was added, and the reaction mixture was allowed to warm to room temperature and stir 3 hours. The reaction mixture was quenched with 10% sodium thiosulfate solution, and was allowed to stir at room temperature for one hour. The organics were separated, washed with water, brine, dried over MgSO4 and concentrated. Purification of the crude residue by column chromatography gave 7-bromo-3-(2-methoxy-2-methylpropoxy)-5'H-spiro[chromeno[2,3-b]pyridine-5,4'-oxazol]-2'-amine.

Step 5: A vial charged with 2-fluoropyridin-3-ylboronic acid (0.156 g, 1.105 mmol), palladiumtetrakis (0.043 g, 0.037 mmol), potassium carbonate (0.255 g, 1.842 mmol), and 7-bromo-3-(2-methoxy-2-methylpropoxy)-5'H-spiro[chromeno[2,3-b]pyridine-5,4'-oxazol]-2'-amine (0.160 g, 0.368 mmol) was dissolved in 3 mL THF and 0.5 mL water and was heated to 110° C. 2 hours. The reaction mixture was diluted with EtOAc and dried over $MgSO_4$. The organcis were concentrated then purified directly by column chromatography yielding 7-(2-fluoropyridin-3-yl)-3-(2-methoxy-2-methylpropoxy)-5'H-spiro[chromeno[2,3-b]pyridine-5,4'-oxazol]-2'-amine.

Example 64

Method AA52

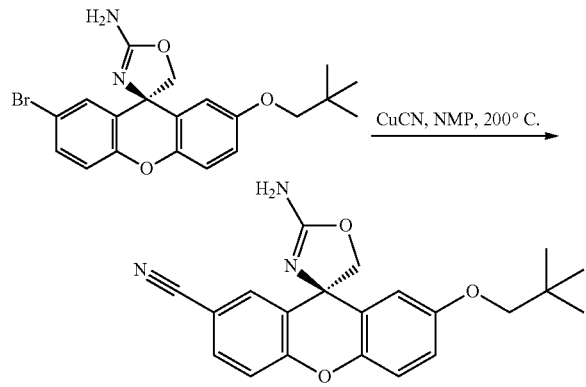

Synthesis of (R)-2-amino-7'-(neopentyloxy)-5H-spiro[oxazole-4,9'-xanthene]-2'-carbonitrile (S)-2'-bromo-7'-(neopentyloxy)-5H-spiro[oxazole-4,9'-xanthen]-2-amine (250 mg, 0.599 mmol) and CuCN (268 mg, 3.00 mmol) were brought up in NMP (1997 µL) and heated to 200° C. in the microwave. The reactions were cooled to rt, filtered and purified by reverse-phase preparative HPLC using a Gemini NX c!8 column (150*30 mm, 5 um), 0.1% TFA in $CH_3CN/H_2O$, gradient 0% to 70% over 10 min to provide the product. Solvent was removed by evaporation and the product was brought up in sat's aqueous $NaHCO_3$ and DCM and extracted with DCM. The organic washes were combined, dried over $Na_2SO_4$, filtered and concentrated to give (R)-2-amino-7'-(neopentyloxy)-5H-spiro[oxazole-4,9'-xanthene]-2'-carbonitrile.

Example 65

Method AA54

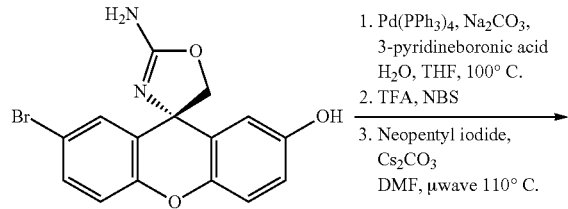

1. Pd(PPh₃)₄, Na₂CO₃, 3-pyridineboronic acid H₂O, THF, 100° C.
2. TFA, NBS
3. Neopentyl iodide, Cs₂CO₃ DMF, µwave 110° C.

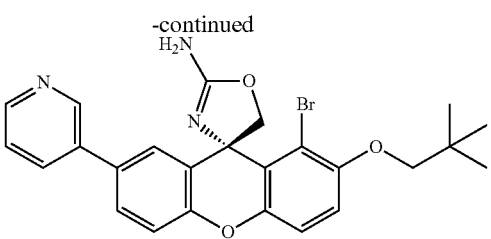

Synthesis of (S)-1'-bromo-2'-(neopentyloxy)-7'-(pyridin-3-yl)-5H-spiro[oxazole-4,9'-xanthen]-2-amine Step 1: A 75-mL pressure vessel was charged with starting material (3.25 g, 9.36 mmol), pyridin-3-ylboronic acid (2.88 g, 23.40 mmol), tetrakis(triphenylphosphine)palladium(0) (1.081 g, 0.936 mmol), THF (46.8 mL), and potassium carbonate (23.40 mL, 46.8 mmol) (as a 2.0 M aq. solution). The vessel was sealed and placed in a 100° C. oil bath for 5 hours. The mixture was partitioned between EtOAc (50 mL) and water (50 mL). The layers were separated, and the aqueous layer was extracted with EtOAc (2×30 mL). The combined mixture was dried over sodium sulfate and filtered with the aid of 10% MeOH/DCM. The filtrate was evaporated to give a yellow solid. This solid was taken up in DCM (80 mL) and sonicated for 5 min. The solid was filtered and washed with DCM (2×40 mL), then air-dried on the filter. The filtrate was evaporated and again taken up in DCM (80 mL). The mixture was sonicated for 10 min, then filtered and washed with DCM (30 mL). The solid was air-dried and combined with the first solid to give (S)-2-amino-7'-(pyridin-3-yl)-5H-spiro[oxazole-4,9'-xanthen]-2'-ol.

Step 2: A 50-mL RBF was charged with (S)-2-amino-7'-(pyridin-3-yl)-5H-spiro[oxazole-4,9'-xanthen]-2'-ol (1.426 g, 4.13 mmol) and TFA (20.65 mL). The mixture was stirred for 30 min and sonicated for 2 min, but it did not become a clear solution. An additional portion of TFA (5 mL) was added, giving an orange mixture. The flask was cooled in an ice-bath for 15 min. n-bromosuccinimide (0.735 g, 4.13 mmol) was added in one portion. After stirring for 2 hour the mixture was diluted with methanol and evaporated in vacuo. The residue was dissolved in methanol and loaded onto a 10-g SCX-2 column. The column was eluted with methanol to remove impurities, then with 2M ammonia in methanol to give the product. The filtrate was evaporated, and the residue was purified by chromatography on a 100-g SNAP column, eluting with 0-100% of a 90:10:1 mix of a DCM/MeOH/NH₄OH in DCM. The product came out in two peaks which were combined to give (S)-2-amino-1'-bromo-7'-(pyridin-3-yl)-5H-spiro[oxazole-4,9'-xanthen]-2'-ol as an off-white powder. NMR matched that of the product.

Step 3: A vial was charged with (S)-2-amino-1'-bromo-7'-(pyridin-3-yl)-5H-spiro[oxazole-4,9'-xanthen]-2'-ol (163 mg, 0.384 mmol), cesium carbonate (375 mg, 1.152 mmol), and DMF (2.0 mL). The mixture was stirred for 10 min, then 1-iodo-2,2-dimethylpropane (102 µL, 0.768 mmol) was added. The vial was sealed and heated in a Biotage Initiator microwave reactor for 2 h at 110° C. LCMS at this time shows no starting material and mainly desired product. The mixture was partitioned between water and EtOAc. Brine was added to break up the emulsioon that formed and this was partially successful. The aqueous layer was extracted with EtOAc (2×), and the combined organic extracts were dried over sodium sulfate, filtered, and evaporated. The residue was chromatographed on a 50-g SNAP column, eluting with 0-70% of a 90:10:1 mix of DCM/MeOH/NH₄OH in DCM to give (S)-1'-bromo-2'-(neopentyloxy)-7'-(pyridin-3-yl)-5H-spiro[oxazole-4,9'-xanthen]-2-amine as an off-white solid after evaporation from DCM/hexane.

Example 66

Method AA55

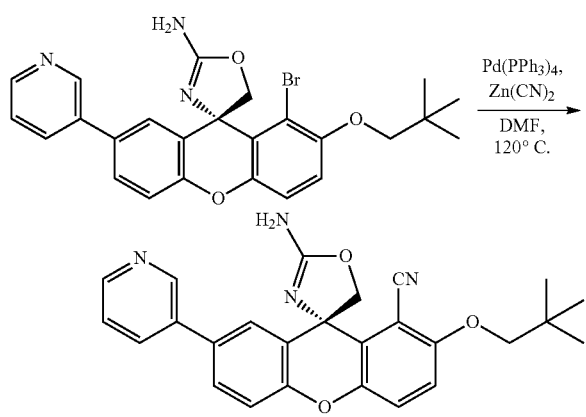

Synthesis of (S)-2-amino-2'-(neopentyloxy)-7'-(pyridin-3-yl)-5H-spiro[oxazole-4,9'-xanthene]-1'-carbonitrile A vial was charged with (S)-1'-bromo-2'-(neopentyloxy)-7'-(pyridin-3-yl)-5H-spiro[oxazole-4,9'-xanthen]-2-amine (68.1 mg, 0.138 mmol), dicyanozinc (81 mg, 0.689 mmol), tetrakis(triphenylphosphine)palladium(0) (31.8 mg, 0.028 mmol), and DMF (689 µL). The vial was sealed and placed in a 120° C. oil bath for 12 hours. The mixture was diluted with water and extracted with DCM (3×). The combined organic extracts were dried over sodium sulfate, filtered, and evaporated. The residue was chromatographed on a 25-g SNAP column, eluting with a 90:10:1 mix of DCM/MeOH/NH$_4$OH in DCM. This gave ca. 40 mg of a white powder that was impure by HPLC. The solid was combined with 104487-6-2 in DMSO/MeOH and purified by reverse-phase HPLC (10-90% CH$_3$CN/H$_2$O with 0.1% TFA). The fractions containing product were combined in saturated aq. sodium bicarbonate solution with the aid of methanol and extracted with DCM (3×). The combined organic extracts were dried over sodium sulfate, filtered, and evaporated to give (S)-2-amino-2'-(neopentyloxy)-7'-(pyridin-3-yl)-5H-spiro[oxazole-4,9'-xanthene]-1'-carbonitrile as an off-white powder after evaporation from DCM/hexane.

Example 67

Method AA56

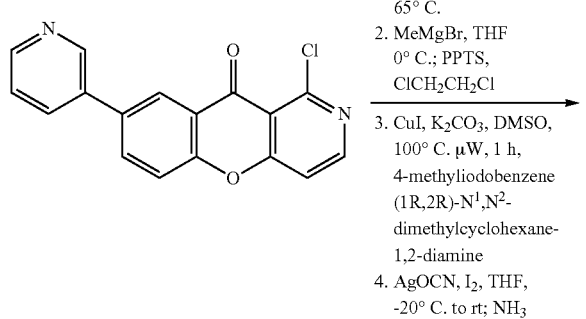

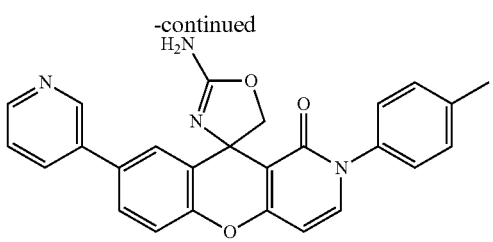

Step 1: A resealable tube was charged with 1-chloro-8-(pyridin-3-yl)-10H-chromeno[3,2-c]pyridin-10-one (0.500 g, 1.620 mmol) and acetic acid (12.5 mL). Ammonium acetate (1.248 g, 16.20 mmol) was added, the system was purged with argon, and the tube was sealed. The mixture stirred at 65° C. for 20 h. The reaction mixture was filtered and washed with water. The filter cake was concentrated down from heptanes to afford 8-(pyridin-3-yl)-1H-chromeno[3,2-c]pyridine-1,10(2H)-dione as an off-white solid. MS m/z=291.0 [M+H]$^+$. Calcd for C$_{17}$H$_{10}$N$_2$O$_3$: 290.07.

Step 2: A solution of 8-(pyridin-3-yl)-1H-chromeno[3,2-c]pyridine-1,10(2H)-dione (0.100 g, 0.345 mmol) in THF (3.00 mL) was cooled to 0° C. and methylmagnesium bromide (3.0 M in diethyl ether) (0.345 mL, 1.034 mmol) was added dropwise. The mixture stirred at 0° C. for 1 h. The mixture was quenched at 0° C. with saturated aqueous ammonium chloride solution and diluted with ethyl acetate. The aqueous phase was separated and extracted with ethyl acetate. The combined organic phases were washed with brine, dried over anhydrous sodium sulfate, filtered, and concentrated to afford a tan solid. The material was dissolved in 1,2-dichloroethane (3.00 mL), pyridinium p-toluenesulfonate (8.66 mg, 0.034 mmol) was added, and the mixture was heated at reflux for 2 h to afford a tan suspension. This mixture was filtered, and the solids were washed with 1,2 dichloroethane and dried to afford 10-methylene-8-(pyridin-3-yl)-2,10-dihydro-1H-chromeno[3,2-c]pyridin-1-one as a tan solid. MS m/z=289.0 [M+H]$^+$. Calcd for C$_{18}$H$_{12}$N$_2$O$_2$: 288.1.

Step 3: A resealable tube was charged with (1R,2R)-diaminomethylcyclohexane (9.77 mg, 0.069 mmol), copper(I) iodide (8.72 mg, 0.046 mmol), 10-methylene-8-(pyridin-3-yl)-2,10-dihydro-1H-chromeno[3,2-c]pyridin-1-one (0.066 g, 0.229 mmol), 4-iodotoluene (0.055 g, 0.252 mmol), potassium carbonate (0.063 g, 0.458 mmol), and DMSO (2.5 mL). The system was purged with argon and the tube was sealed. The mixture stirred in an Initiator microwave reactor (Personal Chemistry, Biotage AB, Inc., Upssala, Sweden) at 100° C. for 2 h. The reaction mixture was diluted with dichloromethane and filtered through a pad of celite. The filtrate was concentrated and partitioned between dichloromethane and water. The aqueous phase was separated and extracted with dichloromethane. The combined organic phases were washed with brine, dried over anhydrous sodium sulfate, filtered, and concentrated to afford 10-methylene-8-(pyridin-3-yl)-2-p-tolyl-2,10-dihydro-1H-chromeno[3,2-c]pyridin-1-one. MS m/z=379.0 [M+H]$^+$. Calcd for C$_{25}$H$_{18}$N$_2$O$_2$: 378.4.

Step 4: A solution of iodine (0.061 g, 0.239 mmol) in THF (2.5 mL) was cooled to −25° C. and silver cyanate (0.102 g, 0.682 mmol) was added. The mixture stirred at −25° C. for 30 min and then a −25° C. solution of 10-methylene-8-(pyridin-3-yl)-2-p-tolyl-2,10-dihydro-1H-chromeno[3,2-c]pyridin-1-one (0.086 g, 0.227 mmol) in THF (2.5 mL) was added via cannula. The mixture stirred at −20° C. for 1 h. The reaction mixture was cooled to −40° C. and ammonia, 2.0 M in 2-propanol (0.568 mL, 1.136 mmol) was added dropwise. The reaction mixture was allowed to warm to RT overnight. The reaction mixture was filtered through celite and washed with ethyl acetate. The filtrate was partitioned between ethyl acetate and saturated aqueous sodium thiosulfate solution. The aqueous phase was separated and extracted with ethyl acetate. The combined organic phases were washed with brine, dried over anhydrous sodium sulfate, filtered, and concentrated to afford a yellow solid. This material was purified via column chromatography on silica gel (RediSep 40 g column, gradient elution with 50-100% ((90:10:1, dichloromethane/methanol/ammonium hydroxide)-dichloromethane) to afford 2'-amino-8-(pyridin-3-yl)-2-p-tolyl-5'H-spiro[chromeno[3,2-c]pyridine-10,4'-oxazol]-1(2H)-one. MS m/z=437.0 [M+H]⁺. Calcd for $C_{26}H_{20}N_4O_3$: 436.2.

Example 68

Method AA57

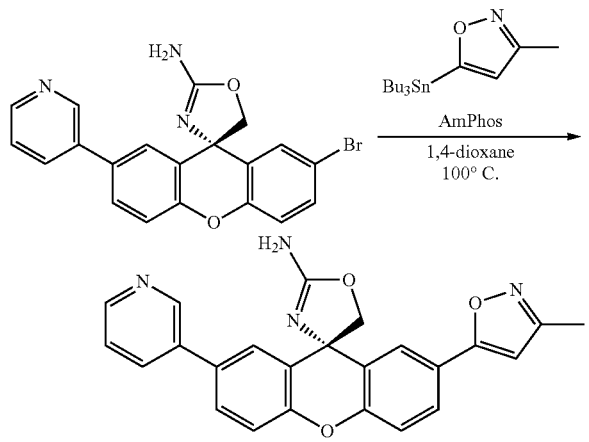

Synthesis of (S)-2'-(2-fluoropyridin-3-yl)-7'-(3-methylisoxazol-5-yl)-5H-spiro[oxazole-4,9'-xanthen]-2-amine A resealable was charged with (S)-2'-bromo-7'-(2-fluoropyridin-3-yl)-5H-spiro[oxazole-4,9'-xanthen]-2-amine (300 mg, 0.704 mmol), 3-methyl-5-(tributylstannyl)isoxazole (786 mg, 2.111 mmol), amphos (18.68 mg, 0.070 mmol) and argon purged dry dioxane (3 mL). The tube was purged with argon, sealed and heated with microwave at 100° C. for 1 h. The solution was concentrated. The crude product was purified via silica gel column chromatography (RediSep 12 g column) using 10-50% 90/10/1 DCM/MeOH/ammonia in DCM to afford (S)-2'-(2-fluoropyridin-3-yl)-7'-(3-methylisoxazol-5-yl)-5H-spiro[oxazole-4,9'-xanthen]-2-amine as a white solid. MS m/z=429.2 [M+H]+. Calcd for $C_{24}H_{17}FN_4O_3$: 428.42.

Example 69

Method AA60

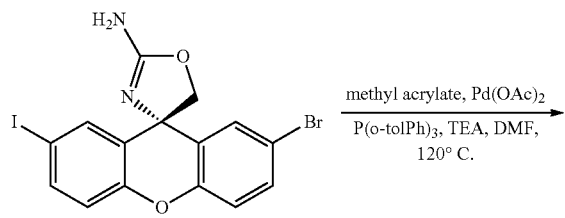

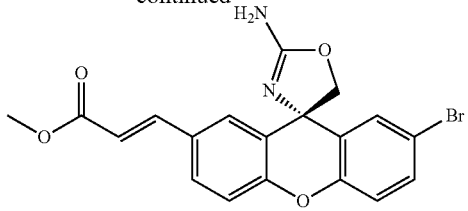

Synthesis of (S,E)-methyl 3-(2-amino-2'-bromo-5H-spiro[oxazole-4,9'-xanthene]-7'-yl)acrylate A mixture of (R)-2'-bromo-7'-iodo-5H-spiro[oxazole-4,9'-xanthen]-2-amine (3.00 g, 6.56 mmol), methyl acrylate (0.621 mL, 6.89 mmol), phosphine, tri-o-tolyl (0.400 g, 1.313 mmol), palladium(ii) acetate (0.295 g, 1.313 mmol), and triethylamine 99.5% (1.826 mL, 13.13 mmol) in DMF (12 mL) in a microwave vial was purged with argon for 5 min, capped, and heated to 120° C. for 40 min in a microwave. The reaction mixture was diluted with EtOAc (100 mL) and washed with water, dried over Na2SO4, and concentrated. The product was purified with ISCO using 0-70% EtOAc in hexanes to give (S,E)-methyl 3-(2-amino-2'-bromo-5H-spiro[oxazole-4,9'-xanthene]-7'-yl)acrylate. MS (ESI pos. ion) m/z: 416.9 (M+1).

Example 70

Method AA62

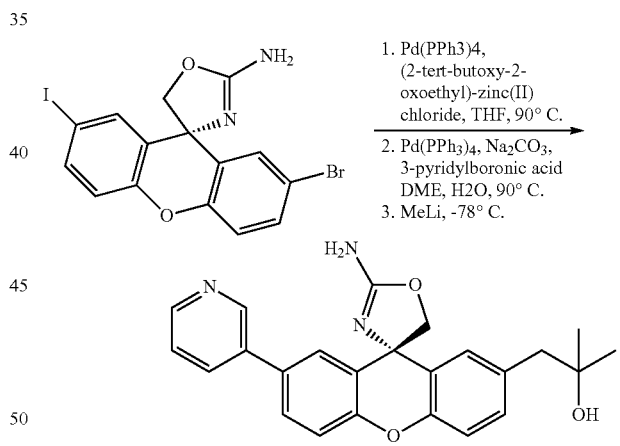

Step 1: To a solution of (R)-2'-bromo-7'-iodo-5H-spiro[oxazole-4,9'-xanthen]-2-amine (1.5 g, 3.28 mmol) in THF (7.5 mL) was added (2-tert-butoxy-2-oxoethyl)zinc(II) chloride (21.00 mL, 10.50 mmol) (0.5 M in diethyl ether) and tetrakis(triphenylphosphine)palladium(0) (0.190 g, 0.164 mmol). The resulting mixture was then heated to 85-90° C. for overnight. Then, the mixture was cooled to RT and saturated NaHCO₃ solution (50 mL) was added. The mixture was then extracted with EtOAc (2×50 mL). The combined organic extracts were dried over MgSO₄ and concentrated. The residue was then dissolved in DCM. The solution mixture was then purified by silica gel column chromatography using ISCO instrument (solid loading, 0%-30% MeOH/DCM) to give the product as a light brown solid. MS (ESI, positive ion) m/z: 444.9, 446.9 (M+1).

Step 2: To a solution of (R)-tert-butyl 2-(2-amino-2'-bromo-5H-spiro[oxazole-4,9'-xanthene]-7'-yl)acetate (0.663 g, 1.489 mmol) in 1,2-dimethoxyethane (7 mL) was added 3-pyridineboronic acid (0.220 g, 1.787 mmol), tetrakis(triphenylphosphine)palladium(o) (0.138 g, 0.119 mmol), bisodium carbonate (0.062 mL, 1.489 mmol), and water (2.333 mL). The resulting mixture was then heated to 85-90° C. for 5 h. Then, the mixture was cooled to room temperature and was diluted with EtOAc (10 mL). Then, saturated NaHCO₃ (3 mL) was added and the mixture was stirred at room temperature for 5 min. The organic layer was collected, dried over MgSO₄, and concentrated. The residue was then dissolved in a solution of DMSO (1 mL) and MeOH (2 mL). The solution mixture was then purified by preparative HPLC (0%-100% MeCN 0.1% TFA/H₂O 0.1% TFA) to give a desired product in a solution of MeCN/H₂O 0.1% TFA. The solution mixture was neutralized by saturated NaHCO₃. The solvent, MeCN was removed and saturated NaHCO₃ (10 mL) was added and the mixture was extracted with EtOAc (2×20 mL). The combined organic extracts were dried over MgSO₄, concentrated, and dried in vacuo to give the product both as a white solid and as an orange solid (<95% pure). MS (ESI, positive ion) m/z: 444 (M+1).

Step 3: To a solution of (R)-tert-butyl 2-(2-amino-2'-(pyridin-3-yl)-5H-spiro[oxazole-4,9'-xanthene]-7'-yl)acetate (95 mg, 0.214 mmol) in THF (1 mL) at −78° C. was added methyllithium, 1.6M solution in diethyl ether (0.669 mL, 1.071 mmol). The resulting mixture was then stirred at −78° C. for 2 h. Then, the mixture was quenched with saturated ammonium chloride (1 mL). Then, saturated NaHCO₃ (5 mL) and EtOAc (10 mL) were added. The mixture was then extracted with EtOAc (2×10 mL). The combined organic extracts were dried over MgSO₄ and concentrated. The residue was then dissolved in a solution of DMSO (1 mL) and MeOH (1 mL). The solution mixture was then purified by preparative HPLC (0%-100% MeCN 0.1% TFA/H₂O 0.1% TFA) to give two products: R)-1-(2-amino-2'-(pyridin-3-yl)-5H-spiro[oxazole-4,9'-xanthene]-7'-yl)-2-methylpropan-2-ol and (R)-1-(2-amino-2'-(pyridin-3-yl)-5H-spiro[oxazole-4,9'-xanthene]-7'-yl)propan-2-one in a solution of MeCN/H₂O 0.1% TFA. The solution was then neutralized by saturated NaHCO₃. Then, the solvents were removed, and saturated NaHCO₃ (2 mL) and EtOAc (5 mL) were added. The mixture was then stirred at RT for 15 min. The organic layer was collected, dried over MgSO₄, concentrated, and dried in vacuo to give the depicted product as a white solid. MS (ESI, positive ion) m/z: 402 (M+1).

Example 71

Method AA63

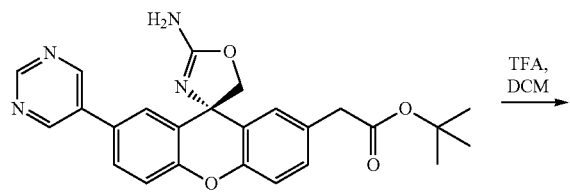

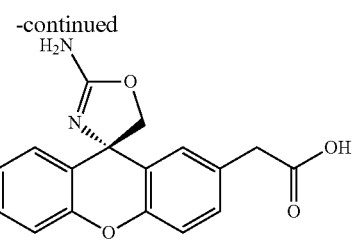

A solution of (R)-tert-butyl 2-(2-amino-2'-(pyrimidin-5-yl)-5H-spiro[oxazole-4,9'-xanthene]-7'-yl)acetate (14 mg, 0.031 mmol) in 30% TFA in DCM (0.5 mL) was stirred at RT for 1 h. Then, saturated NaHCO₃ solution was added slowly to the mixture at 0° C. until pH=7.0. Then, solvents were removed and the residue was dissolved in a solution of MeOH (0.5 mL), H₂O (0.1 mL), and DMF (0.3 mL). The solution mixture was then purified by preparative HPLC (0%-100% MeCN 0.1% NH₄OH/H₂O 0.1% NH₄OH) to give the acid adduct as a white solid. MS (ESI, positive ion) m/z: 389 (M+1).

Example 72

Method AA64

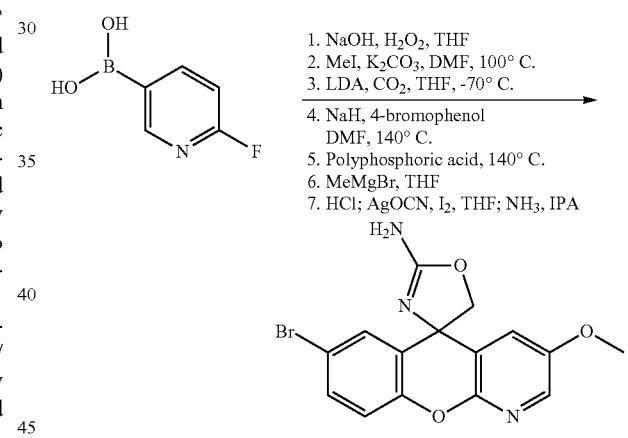

Step 1: A three neck 3-L flask equipped with an overhead stirred was charged with 6-fluoropyridin-3-ylboronic acid (105 g, 745 mmol) and 1 L of THF. The mixture was cooled to 0° C. and NaOH 6N (373 mL, 2235 mmol) was added. To the resulting mixture was added hydrogen peroxide 30% (126 mL, 4098 mmol), dropwise via an addition funnel over the course of 30 minutes. After stirring at 0° C. for 2 hours the mixture was removed from the ice bath and maintained at RT for 30 minutes. The reaction was acidified to pH 7 with 6 N HCl (ca. 300 mL) and diluted with 500 mL of ether. The aqueous layer was extracted with ether (2×1 L) and the combined organic layers were washed with water (1.5 L) then brine before being dried over sodium sulfate. Filtration and concentration of the crude material provided a white solid that was dried on high vac overnight to provide 6-fluoropyridin-3-ol.

Step 2: To a solution of 6-fluoropyridin-3-ol (75 g, 663 mmol) in DMF (265 mL, 663 mmol) were added potassium carbonate (59.7 g, 995 mmol) and iodomethane (108 g, 763 mmol). The resulting slurry was heated at 100° C. for 3 hours. The reaction was diluted with water (1000 mL) and poured into a separatory funnel containing diethyl ether (1000 mL). The layers were separated and the aqueous layer was extracted with diethyl ether (4×500 mL). The combined organic layers were washed with water and then brine, dried over sodium sulfate, filtered and concentrated in vacuo to provide a yellow oil. This oil was diluted with 500 mL of DCM and concentrated to provide a yellow oil with a large amount of an off white precipitate. The mixture was filtered and the derived solid was washed well with DCM. The filtrate was concentrate to provide a mixture consisting of a yellow oil and an off white solid. The solid eas filtered, washing with DCM. Repeat this procedure again and then concentrated the filtrate to provide a yellow oil. The oil was taken up in 100 mL of ether and flashed through a plug of silica gel with 10:1 hexanes:ether to provide 2-fluoro-5-methoxypyridine as a yellow oil.

Step 3: To a solution of DIPA (54.0 mL, 385 mmol) in THF (1101 mL, 385 mmol) at −60° C. was added BuLi, 2.5 M in hexanes (154 mL, 385 mmol) over 5 minutes such that the internal temperature was maintained below −60° C. After stirring for 45 minutes at −65° C. a solution of 2-fluoro-5-methoxypyridine (49 g, 385 mmol) in 200 mL of THF was added over the course of 2 minutes maintaining an internal temperature <−65° C. The reaction was stirred at −70° C. for 1.5 hours then reaction was poured into a 3 L flask containing 1200 g of crushed dry ice. The reaction was allowed to warm to 0° C. and then poured into 1000 mL of water. The organics were removed under reduced pressure and the aqueuous layer was acidified with 1100 mL of 2 N HCl. The resulting thick white slurry was stirred for 1 hour then filtered to provide 2-fluoro-5-methoxynicotinic acid as a white solid.

Step 4: To a slurry of sodium hydride (60% dispersion) (21.74 g, 543 mmol) in DMF (351 mL, 175 mmol) at 0° C. was added 4-bromophenol (60.7 g, 351 mmol) over the course of 5 minutes. Stirred at 0° C. for two minutes then removed from the ice bath and stirred for an additional 5 minutes at room temperature. Added 2-fluoro-5-methoxynicotinic acid (30 g, 175 mmol) portionwise over 10 minutes and heated the resulting slurry at 140° C. After cooling to room temperature the mixture was then poured onto 1 kg of ice and was quenched with acetic acid (50.2 mL, 877 mmol) and then 75 mL of 6 N HCl. Stirred vigorously for 1 hour, leading to the formation of a red slurry containing a very fine white precipitate. Filtered the slurry to provide 2-(4-bromophenoxy)-5-methoxynicotinic acid.

Step 5: A 2 L flask charged with polyphosphoric acid (115% $H_3PO_4$) (300 g, 89 mmol) was heated to 140° C. at which point 2-(4-bromophenoxy)-5-methoxynicotinic acid (29 g, 89 mmol) was introduced. The thick viscous mixture is slowly stirred while heating at 140° C. After heating for 2.5 hours the solution was cooled to 100° C. and then poured onto 1 kg of ice, leading to the formation of a yellow taffy mixture. The slurry was vigorously stirred for 1 hour leading to the formation of a fine white precipitate. Filtration of this mixture proceeded slowly to provide an off white solid. This solid was washed well with DCM. The filtrate, which contained the desired product, was washed with brine and concentrated to provide 7-bromo-3-methoxy-5H-chromeno[2,3-b]pyridin-5-one as an off-white solid.

Step 6: To a slurry of 7-bromo-3-methoxy-5H-chromeno[2,3-b]pyridin-5-one (23 g, 75 mmol) in THF (751 mL, 75 mmol) at −40° C. was added methylmagnesium chloride, 3.0 M solution in THF (88 mL, 263 mmol) over 2 minutes such that the temperature did not rise above −35° C. The resulting red slurry was maintained at −30° C. After 1 hour the reaction, which was now homogeneous, was quenched with 50 mL of ethyl acetate. The solution was then carefully quenched with 800 mL of 50% ammonium chloride. The mixture was poured into a separatory funnel containing ethyl acetate (100 mL). The layers were separated and the organics were washed with brined, dried over sodium sulfate, filtered and concentrated. The aqueous layer was extracted with ethyl acetate (3×500 mL). The combined organic layers were washed with water and then brine, dried over sodium sulfate, filtered, and combined with the above derived oil. This organic solution was washed with brined, dried over sodium sulfate, fitlered and concentrated to provide 7-bromo-3-methoxy-5-methyl-5H-chromeno[2,3-b]pyridin-5-ol as a yellow solid.

Step 7: To a solution of 7-bromo-3-methoxy-5-methyl-5H-chromeno[2,3-b]pyridin-5-ol (23.5 g, 72.9 mmol) in THF (729 mL, 72.9 mmol) was added HCl (1 M in ether) (0.729 mL, 0.729 mmol). The resulting solution was heated at 45° C. for 1 hour. The light yellow solution was cooled to −25° C. and added to the slurry below.

In a separate 2 L flask was added iodine (20.37 g, 80 mmol) and 400 mL of THF. This solution was cooled to −15° C. and silver cyanate (32.8 g, 219 mmol) was added. The resulting slurry was maintained at −40° C. for 25 minutes before the above solution was added via cannula over 15 minutes maintaining the temperature below −35° C. The derived slurry was maintained at −30° C. for 1 hour at which it was filtered through a pad of celite, washing well with 200 mL of THF. The derived brown solution was cooled to −20° C. and treated with ammonia, 2.0 M solution in 2-propanol (219 mL, 438 mmol). The resulting solution was allowed to slowly warm to rt overnight. To the reaction was added 700 mL of 10% sodium thiosulfate and the resulting light orange solution was stirred for 10 minutes before being poured into a separatory funnel containing 250 mL of ethyl acetate. The layers were separated and the organics were washed with brine and then concentrated in vacuo. This mixture was combined with the organic extracts obtained below.

The aqueous layer was extracted with ethyl acetate (2×500 mL). These organics were combined with the organics obtained and poured into a separatory funnel. The layers were separated and the aqueous layer was extracted with ethyl acetate (2×100 mL). The combined organic layers were washed with brine, dried over sodium sulfate, filtered and concentrated in vacuo to provide 25 g of 7-bromo-3-methoxy-5'H-spiro[chromeno[2,3-b]pyridine-5,4'-oxazol]-2'-amine as a brown solid.

Example 73

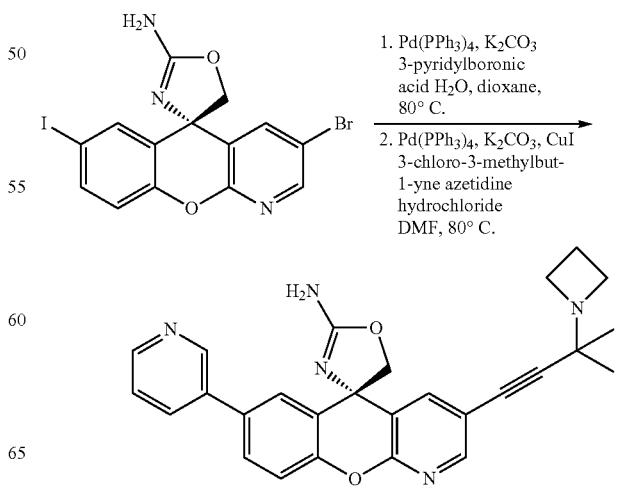

Synthesis of (S)-3-(3-(azetidin-1-yl)-3-methylbut-1-ynyl)-7-(pyridin-3-yl)-5'H-spiro[chromeno[2,3-b]pyridine-5,4'-oxazol]-2'-amine Step 1: A vial charged with pyridin-3-ylboronic acid (0.295 g, 2.401 mmol), palladiumtetrakis (0.126 g, 0.109 mmol), potassium carbonate (1.509 g, 10.92 mmol), and (S)-3-bromo-7-iodo-5'H-spiro[chromeno[2,3-b]pyridine-5,4'-oxazol]-2'-amine (1.000 g, 2.183 mmol) was treated with 11 mL dioxane followed by 4.5 mL water. The vial was flushed with argon and was heated to 80° C. for 4 hours. The reaction mixture was diluted with EtOAc and dried over MgSO$_4$. The organics were then concentrated, and the crude residue was purified by column chromatography yielding (S)-3-bromo-7-(pyridin-3-yl)-5'H-spiro[chromeno[2,3-b]pyridine-5,4'-oxazol]-2'-amine Step 2: A vial charged with potassium carbonate (0.338 g, 2.444 mmol), (S)-3-bromo-7-(pyridin-3-yl)-5'H-spiro[chromeno[2,3-b]pyridine-5,4'-oxazol]-2'-amine (0.100 g, 0.244 mmol), azetidine hydrochloride (0.209 g, 3.67 mmol), copper(i) iodide (4.65 mg, 0.024 mmol), and palladiumtetrakistriphenylphosphine (0.028 g, 0.024 mmol) was treated with 2 mL DMF and was thoroughly degassed with argon gas. 3-chloro-3-methylbut-1-yne (0.125 g, 1.222 mmol) was added, the vial was placed under argon, and was heated to 80° C. for 4 hours. The reaction mixture was poured into water and was extracted with EtOAc. The organics were washed with brine, dried over MgSO$_4$ and concentrated. Purification of the crude residue by column chromatography gave (S)-3-(3-(azetidin-1-yl)-3-methylbut-1-ynyl)-7-(pyridin-3-yl)-5'H-spiro[chromeno[2,3-b]pyridine-5,4'-oxazol]-2'-amine Example 74

Method AA65

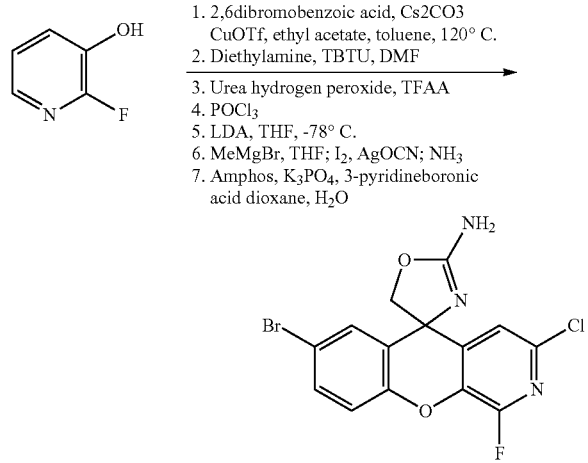

Synthesis of 1-fluoro-3,7-di(pyridin-3-yl)-5'H-spiro[chromeno[2,3-c]pyridine-5,4'-oxazol]-2'-amine Step 1: A 500 mL RBF was charged with 2-fluoro-3-hydroxypyridine (3487 mg, 30.8 mmol), 2,5-dibromobenzoic acid (8630 mg, 30.8 mmol), copper (I) trifluoromethanesulfonate toluene complex (2:1) (399 mg, 0.771 mmol) and cesium carbonate (2.01E+04 mg, 61.7 mmol). To this was added 100 mL of toluene and the mixture was azeotroped to remove about 20 mL of toluene under reduced pressure. Reaction mixture was then flushed with N2 and was heated to 120° C. for 2 hours. LC-MS analysis showed formation of the desired product along with significant impurities. The reaction mixture was cooled to RT and concentrated to give a gummy residue. The residue was taken up in ethyl acetate (100 mL) and water (75 mL). The aqueous layer was neutralized with 1N HCl to pH ~2.0-3.0. The aqueous layer was extracted with ethyl acetate (2×150 mL), separated, dried over anhydrous sodium sulfate, and concentrated to yield the crude product as a brown solid which was used directly in the next step.

Step 2: A mixture of crude 5-bromo-2-(2-fluoropyridin-3-yloxy)benzoic acid (8.00 g, 25.6 mmol), diethylamine (6.63 mL, 64.1 mmol) and TBTU (8.23 g, 25.6 mmol) in 8 mL of DMF was stirred overnight. The reaction was quenched with Sat. NaHCO3, extracted with EA/H=2:1, washed with brine, dried over Na2SO4, filtered and evaporated to dryness. CC (DCM to DCM/EA 100:5 to 100:10 to 100:20 to 3:1) gave 5-bromo-N,N-diethyl-2-(2-fluoropyridin-3-yloxy)benzamide as a yellow solid.

Step 3: To a solution of 5-bromo-N,N-diethyl-2-(2-fluoropyridin-3-yloxy)benzamide (1.4 g, 3.81 mmol) and urea peroxide (1.076 g, 11.44 mmol) in 10 mL of DCM at 0 C was added dropwise trifluoroacetic anhydride (1.601 mL, 11.44 mmol) and the resulting reaction was stirred overnight. LCMS showed only less than 50% of desired conversion. The mixture was evaporated to dryness, quenched with Sat. NaHCO$_3$, extracted with EA, dried over Na$_2$SO$_4$, filtered and evaporated to dryness. CC (DCM to DCM/EA=3:1 to DCM/MeOH=100:2 to 100:5 to 100:10) gave 3-(4-bromo-2-(diethylcarbamoyl)phenoxy)-2-fluoropyridine 1-oxide as an off-white solid.

Step 4: To a solution of 3-(4-bromo-2-(diethylcarbamoyl)phenoxy)-2-fluoropyridine 1-oxide (420 mg, 1.096 mmol) in 15 mL of DCM was added dropwise phosphorus oxychloride (301 µL, 3.29 mmol) followed by 2 drops of DMF. After stirring at rt for 1 h, the reaction was quenched with sat. NaHCO$_3$, extracted with EA, dried over Na2SO4, filtered and evaporated to dryness. CC (DCM to DCM/EA=10:1 to 5:1 to 3:1) gave 5-bromo-2-(6-chloro-2-fluoropyridin-3-yloxy)-N,N-diethylbenzamide as a colorless gum.

Step 5: To a solution of 5-bromo-2-(6-chloro-2-fluoropyridin-3-yloxy)-N,N-diethylbenzamide (120 mg, 0.299 mmol) in 5 mL of dry THF at −78 C was added dropwise lithium diisopropylamide, 2.0 m heptane/tetrahydrofuran/ethylbenzene (158 µL, 1.195 mmol) (0.6 mL of 2M solution) and the reaction was stirred at −78 C for 3 h. The reaction was quenched at −78 C with sat. NH$_4$Cl and was allowed to warm up to RT. The reaction was extracted with EA, dried over Na$_2$SO$_4$, filtered and evaporated to dryness. CC (hexane to H/DCM=1:1 to DCM) gave 7-bromo-3-chloro-1-fluoro-5H-chromeno[2,3-c]pyridin-5-one as an offwhite solid. MS (M+1): 328.

Step 6: To a solution of 7-bromo-3-chloro-1-fluoro-5H-chromeno[2,3-c]pyridin-5-one (50 mg, 0.152 mmol) in 5 mL of dry THF at −78 C was added methylmagnesium chloride, 3.0 m solution in tetrahydrofuran (16.87 µL, 0.228 mmol) (0.07 mL) and the reaction was slowly warmed up to −30 C. Only half of conversion was detected. To this was added another batch of methylmagnesium chloride, 3.0 m solution in THF (16.87 µL, 0.228 mmol) (0.07 mL). The reaction was quenched at −30 C with sat. NH$_4$Cl, extracted with EA, dried over Na$_2$SO$_4$, filtered and evaporated to dryness. It was then treated with 1 mg of PPTS in DCM at 25 C for 0.5 h. After cooling, 0.1 g of NaHCO$_3$ was added the solvent was evaporated to dryness to give crude 7-bromo-3-chloro-1-fluoro-5-methylene-5H-chromeno[2,3-c]pyridine which was directly used in the next step.

A solution of iodine (8.23 µL, 0.160 mmol) in THF at −25 C was treated with silver cyanate (22.81 µL, 0.609 mmol). After 30 min, a solution of crude 7-bromo-3-chloro-1-fluoro-5-methylene-5H-chromeno[2,3-c]pyridine in THF was added dropwise. The slurry was maintained at −25 C for 2 h until LCMS showed complete consumption of starting material. The slurry was filtered through celite with ether. The brown solution was concentrated to dryness, taken up in THF, cooled to 0 C and treated with ammonia, 2 m solution in 2-propanol (13.21 µL, 0.609 mmol) (0.4 mL). The reaction was allowed to slowly warm to RT and stirred overnight. Half the solvent was evaporated and the residue was diluted with water, extracted with EA, dried over $Na_2SO_4$, filtered and evaporated to dryness. The residue was filtered, washed with DCM and air dried to give 7-bromo-3-chloro-1-fluoro-5'H-spiro[chromeno[2,3-c]pyridine-5,4'-oxazol]-2'-amine as a yellow solid. MS (M+1): 384.

Step 7: A mixture of 7-bromo-3-chloro-1-fluoro-5'H-spiro[chromeno[2,3-c]pyridine-5,4'-oxazol]-2'-amine (40.0 mg, 0.104 mmol), pyridin-3-ylboronic acid (21.73 mg, 0.177 mmol), bis-(di-tert-butyl(4-dimethylaminophenyl)phosphine)dichloropalladium(ii) (2.95 mg, 4.16 µmol) and potassium phosphate (66.2 mg, 0.312 mmol) in 1.5 ml of dioxane/water=2:1 was heated at 120 C microwave for 20 min. LCMS showed mostly conversion to the mono coupling product. 10 mg of pyridin-3-ylboronic acid (21.73 mg, 0.177 mmol) was added and the reaction was heated at 140 C under microwave for 20 min. The reaction mixture was directly loaded to CC (SiO2, DCM to DCM/MeOH=100:1 to 100:6) to give crude final product which was further purified by prep TLC (DCM/MeOH) to give 1-fluoro-3,7-di(pyridin-3-yl)-5'H-spiro[chromeno[2,3-c]pyridine-5,4'-oxazol]-2'-amine as a white solid. MS (M+1): 426.

Example 75

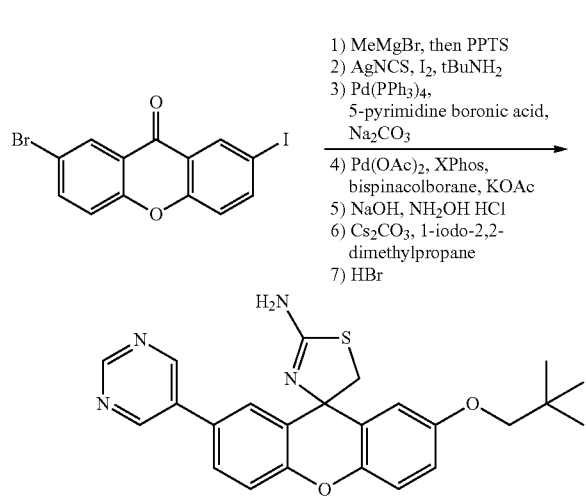

1) MeMgBr, then PPTS
2) AgNCS, I$_2$, tBuNH$_2$
3) Pd(PPh$_3$)$_4$, 5-pyrimidine boronic acid, Na$_2$CO$_3$
4) Pd(OAc)$_2$, XPhos, bispinacolborane, KOAc
5) NaOH, NH$_2$OH HCl
6) Cs$_2$CO$_3$, 1-iodo-2,2-dimethylpropane
7) HBr Synthesis of (R) and (S)-2'-(neopentyloxy)-7'-(pyrimidin-5-yl)-5H-spiro[thiazole-4,9'-xanthen]-2-amine Step 1: A 500 ml RB flask was charged with 2-bromo-7-iodo-9H-xanthen-9-one (16.030 g, 40.0 mmol) and THF (150 mL). The mixture was stirred for 10 min at RT and the resulting suspension was placed in water-ice bath for another 10 min. Methylmagnesium bromide, 3.0 M in Et$_2$O (20.0 ml, 60.0 mmol) was added dropwise. After 1 hr, the mixture was carefully quenched with sat NH$_4$Cl (150 mL) at 0° C. and diluted with EtOAc. The organic layer was washed with brine, dried with sodium sulfate, and concentrated in vacuo. The material was dissolved in 100 mL of methylene chloride, treated with PPTS (0.201 g, 0.800 mmol), and heated to reflux for 2 hr. The mixture was cooled to RT, diluted with methylene chloride, and washed with saturated sodium bicarbonate and brine. The organic fraction was dried over sodium sulfate and concentrated in vacuo to afford crude 2-bromo-7-iodo-9-methylene-9H-xanthene as a light orange solid that was advanced without further purification. MS: MH+=399.0/401.0.

Step 2: A 100 mL flask was charged with iodine (1.002 g, 3.95 mmol) and THF (30 mL) and the resulting solution was cooled to −20° C. in a methanol-ice bath. Thiocyanatosilver (1.872 g, 11.28 mmol) was added in one portion and the resulting mixture was stirred for 0.5 hr at ca. −15° C. Crude 2-bromo-7-iodo-9-methylene-9H-xanthene (1.500 g, 3.76 mmol) was added as a solid in one portion and the resulting mixture was stirred for 5 min @-15° C., then at 0° C. for 1 hr. The yellow mixture was filtered through celite with the aid of THF (5 ml) and to the filtrate was dropwise added 2-methylpropan-2-amine (1.195 mL, 11.28 mmol) at RT. After 20 hrs, the solution was concentrated in vacuo, taken up in CH2Cl2, and adsorbed onto silica gel. The material was purified by silica gel chromatography using 15-30% Hexanes:EtOAc to afford 2'-bromo-N-tert-butyl-7'-iodo-5H-spiro[thiazole-4,9'-xanthen]-2-amine as a yellow solid. MH+=529.8/530.8.

Step 3: To a mixture of sodium carbonate (1.562 g, 14.74 mmol), palladium tetrakistriphenylphosphine (0.454 g, 0.393 mmol), pyrimidin-5-ylboronic acid (0.791 g, 6.39 mmol) and 2'-bromo-N-tert-butyl-7'-iodo-5H-spiro[thiazole-4,9'-xanthen]-2-amine (2.600 g, 4.91 mmol) in a resealable pressure tube, was added DME (15 mL) and water (5 mL) at RT. The tube was sealed and heated to 80° C. After 24 hrs, the mixture was cooled to RT, diluted with EtOAc, and washed with water and brine. The organic fraction was adsorbed onto silica gel and purified by silica gel chromatography using 40% hexanes:EtOAc to afford 2'-bromo-N-tert-butyl-7'-(pyrimidin-5-yl)-5H-spiro[thiazole-4,9'-xanthen]-2-amine MS: MH+=481.0/483.0.

Step 4: A pressure tube was charged with 2'-bromo-N-tert-butyl-7'-(pyrimidin-5-yl)-5H-spiro[thiazole-4,9'-xanthen]-2-amine (0.150 g, 0.312 mmol), 4,4,4',4',5,5,5',5'-octamethyl-2,2'-bi(1,3,2-dioxaborolane) (0.237 g, 0.935 mmol), potassium acetate (0.092 g, 0.935 mmol), XPhos (0.030 g, 0.062 mmol), diacetoxypalladium (7.00 mg, 0.031 mmol), and 1,4-dioxane (3.0 mL, 0.312 mmol). The tube was purged with Argon, sealed, and heated to 100° C. After 18 hrs the dark mixture was filtered over celite with EtOAc. The filtrate was concentrated in vacuo and purified by silica gel chromatography using 25-50% Hexanes:EtOAc to afford N-tert-butyl-2'-(pyrimidin-5-yl)-7'-(4,4,5,5-tetramethyl-1,3,2-dioxaborolan-2-yl)-5H-spiro[thiazole-4,9'-xanthen]-2-amine as a white foam. MH+=529.2.

Step 5: To a mixture of N-tert-butyl-2'-(pyrimidin-5-yl)-7'-(4,4,5,5-tetramethyl-1,3,2-dioxaborolan-2-yl)-5H-spiro[thiazole-4,9'-xanthen]-2-amine (0.475 g, 0.899 mmol), NaOH solid (0.062 mL, 3.33 mmol), and hydroxyammonium chloride (0.120 mL, 2.88 mmol) was added Ethanol (8 mL). The mixture was stirred at RT. After 48 hrs, the mixture was concentrated in vacuo and the residue partioned between DCM and water. The aqueous layer was acidified to ca. pH=7 and extracted with CH$_2$Cl$_2$. The combined organic fractions

135 were adsorbed onto silica gel and purified by silica gel chromatography using 40-80% Hexanes:EtOAc to give 2-(tert-butylamino)-7'-(pyrimidin-5-yl)-5H-spiro[thiazole-4,9'-xanthen]-2'-ol as an off-white solid. MS: MH+=419.2.

Step 6: To a solution of 2-(tert-butylamino)-7'-(pyrimidin-5-yl)-5H-spiro[thiazole-4,9'-xanthen]-2'-ol (0.075 g, 0.179 mmol) in DMF (2 mL) was added cesium carbonate (0.175 g, 0.538 mmol) followed by 1-iodo-2,2-dimethylpropane (0.048 mL, 0.358 mmol). The mixture was heated to 100° C. After 6 hrs the mixture was cooled to RT, diluted with EtOAc, and washed with water and brine. The organic fraction was concentrated in vacuo and purified by silica gel chromatography using 40-60% Hexanes:EtOAc to afford N-tert-butyl-2'-(neopentyloxy)-7'-(pyrimidin-5-yl)-5H-spiro[thiazole-4,9'-xanthen]-2-amine as an off-white foam. MS: MH+=489.2.

Step 7: A resealable tube charged with a solution of N-tert-butyl-2'-(neopentyloxy)-7'-(pyrimidin-5-yl)-5H-spiro[thiazole-4,9'-xanthen]-2-amine (0.033 g, 0.068 mmol) in 48% HBr (1.00 mL, 18.42 mmol) was heated to 80° C. After 3 hrs, the solution was cooled and evaporated to dryness with a stream of N2. The residue was treated with CH2Cl2 (2 mL) and TEA (0.1 mL). The solution was loaded onto a silica gel column and purified with 1-5% MeOH:CH2Cl2 w/1% NH4OH (Rf=0.5 in 10% MeOH:CH2Cl2 w/1% NH4OH) to afford racemic material that was resolved by chiral chromatography to give both (R) and (S)-2'-(neopentyloxy)-7'-(pyrimidin-5-yl)-5H-spiro[thiazole-4,9'-xanthen]-2-amine MS Found: MH+=433.2.

Example 76

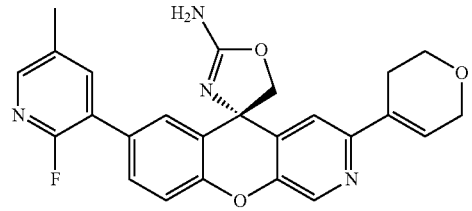

A glass microwave reaction vessel was charged with (S)-3-chloro-7-(2-fluoro-5-methylpyridin-3-yl)-5'H-spiro[chromeno[2,3-c]pyridine-5,4'-oxazol]-2'-amine (0.100 g, 0.252 mmol), potassium phosphate (0.160 g, 0.756 mmol), 2-(3,6-dihydro-2H-pyran-4-yl)-4,4,5,5-tetramethyl-1,3,2-dioxaborolane (0.106 g, 0.504 mmol) and Bis(di-tert-butyl(4-dimethylaminophenyl)phosphine)dichloropalladium (II) (8.92 mg, 0.013 mmol) in dioxane (1.2 mL) and water (0.40 mL). The reaction mixture was stirred and heated in microwave at 120° C. for 30 minutes before being diluted with EtOAc and saturated Na2CO3. The organic layer was washed twice with saturated Na2CO3, dried over Na2SO4 and concentrated in vacuo. The crude was purified by silica gel chromatography (2-10% MeOH—CH2Cl2), followed by preparative HPLC (15-60% CH3CN (with 0.1% TFA)-water (with 0.1% TFA) in 20 min) to provide (S)-3-(3,6-dihydro-2H-pyran-4-yl)-7-(2-fluoro-5-methylpyridin-3-yl)-5'H-spiro[chromeno[2,3-c]pyridine-5,4'-oxazol]-2'-amine as a white solid (MS: MH+=445).

136

Example 77

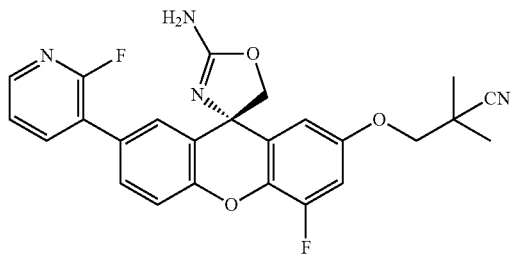 [SMILES: CC(C)(C#N)COc1cc(F)c2c(c1)[C@]1(COC(N)=N1)c1cc(-c3cccnc3F)ccc1O2]

A vial was charged with (S)-2-amino-4'-fluoro-7'-(2-fluoropyridin-3-yl)-5H-spiro[oxazole-4,9'-xanthen]-2'-ol (45.0 mg, 0.118 mmol), cesium carbonate (57.7 mg, 0.177 mmol), and DMF (787 μL). The mixture was stirred vigorously for 15 min, then 2-cyano-2-methylpropyl trifluoromethanesulfonate (22.56 μL, 0.130 mmol) was added via syringe. The resulting mixture was stirred at room temperature for 19 hours before being diluted with water (10 mL) and EtOAc (10 mL). The layers were separated, and the aqueous layer was extracted with EtOAc (2×10 mL). The combined organic extracts were dried over sodium sulfate, filtered, and evaporated. The residue was purified by chromatography on a 12 g Redi-Sep column, eluting with 5-60% MeOH/DCM to give (S)-3-(2-amino-5'-fluoro-2'-(2-fluoropyridin-3-yl)-5H-spiro[oxazole-4,9'-xanthene]-7'-yloxy)-2,2-dimethylpropanenitrile as an off-white solid. (MS: MH+=463).

Example 78

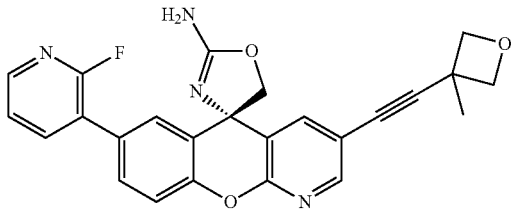 [SMILES: CC1(C#Cc2cnc3c(c2)[C@]2(COC(N)=N2)c2cc(-c4cccnc4F)ccc2O3)COC1]

A vial was charged with (S)-2'-amino-3-((3-methyloxetan-3-yl)ethynyl)-5'H-spiro[chromeno[2,3-b]pyridine-5,4'-oxazole]-7-yl trifluoromethanesulfonate (50.0 mg, 0.101 mmol), 2-fluoropyridin-3-ylboronic acid (21.33 mg, 0.151 mmol), potassium carbonate (69.7 mg, 0.505 mmol), and Pd(PPh3)4 (11.66 mg, 10.09 μmol). The vial was flushed with Ar (g), then dioxane (505 μL) and water (0.25 mL) were added in sequence. The vial was sealed and placed in a 70° C. oil for 1 hour. The mixture was diluted with EtOAc and washed with brine. The organic layer was dried over sodium sulfate, filtered, and evaporated. The residue was chromatographed on a 12-g Redi-Sep column with 0-60% of a 90:10:1 mix of DCM/MeOH/NH4OH in DCM to give a pink solid. The solid was dissolved in MeOH and loaded onto a 500-mg SCX-2 column. The column was first eluted with methanol, then with 2N ammonia in methanol to remove the product. The filtrate was evaporated to give (S)-7-(2-fluoropyridin-3-yl)-3-(3-methyloxetan-3-yl)ethynyl)-5'H-spiro[chromeno[2,3-b]pyridine-5,4'-oxazol]-2'-amine as pale yellow solid. Found MS: MH+=443.0.

Example 79

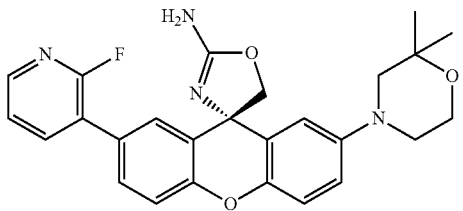 [SMILES: CC1(C)CN(c2ccc3c(c2)[C@]2(COC(N)=N2)c2cc(-c4cccnc4F)ccc2O3)CCO1]

A 25 mL RB flask was charged with (R)-2-amino-2'-(2,2-dimethylmorpholino)-5H-spiro[oxazole-4,9'-xanthene]-7'-yl trifluoromethanesulfonate (270 mg, 0.526 mmol), tetrakis(triphenylphosphine)palladium(0) (60.8 mg, 0.053 mmol), 2-fluoropyridin-3-ylboronic acid (119 mg, 0.841 mmol), DMF (2629 μL) and sodium carbonate (2M solution) (789 μL, 1.577 mmol). The mixture was stirred under argon for 2 hrs at 85° C.

The mixture was diluted with water (2 ml) and extracted with 10 ml of EtOAc. The organic layer was washed with water, brine, passed through plug of Celite and concentrated. Dark residue was purified by silica gel chromatography on a 12 g RediSep column using 5-70% DCM/MeOH/NH4OH in DCM to afford (S)-2'-(2,2-dimethylmorpholino)-7'-(2-fluoropyridin-3-yl)-5H-spiro[oxazole-4,9'-xanthen]-2-amine Found MS: MH+=461.

Example 80

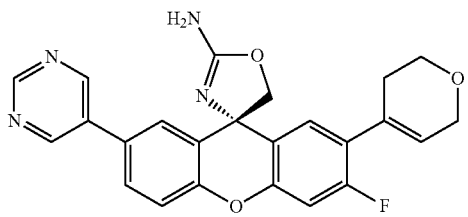 [SMILES: NC1=N[C@@]2(CO1)c1cc(-c3cncnc3)ccc1Oc1cc(F)c(C3=CCOCC3)cc12]

Synthesis of (S)-2'-(3,6-dihydro-2H-pyran-4-yl)-3'-fluoro-7'-(pyrimidin-5-yl)-5H-spiro[oxazole-4,9'-xanthen]-2-amine A 0.5-2 ml microwave vial was charged with tetrakis(triphenylphosphine)palladium(0) (27.9 mg, 0.024 mmol), 2-(3,6-dihydro-2H-pyran-4-yl)-4,4,5,5-tetramethyl-1,3,2-dioxaborolane (86 mg, 0.411 mmol). A solution of (S)-2-amino-6'-fluoro-2'-(pyrimidin-5-yl)-5H-spiro[oxazole-4,9'-xanthene]-7'-yl trifluoromethanesulfonate (120 mg, 0.242 mmol) in DMF (1612 μL) was added followed by sodium carbonate (2M solution) (363 μL, 0.725 mmol). The vial was sealed and heated in microwave reactor at 85° C. for 1 hr. The mixture was diluted with water and extracted with EtOAc. The organic layer was washed with water, brine, filtered through celite and concentrated to leve brown oil. The crude material was purified by silica gel chromatography on 12 g RediSep column using (15-60% DCM/MeOH/NH4OH 90:10:1 in DCM) to afford (S)-2'-(3,6-dihydro-2H-pyran-4-yl)-3'-fluoro-7'-(pyrimidin-5-yl)-5H-spiro[oxazole-4,9'-xanthen]-2-amine Found MS: MH+=431.

Example 81

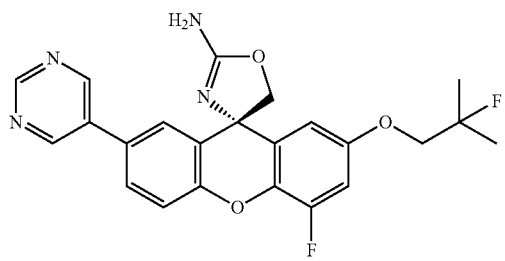 [SMILES: CC(C)(F)COc1cc(F)c2c(c1)[C@]1(COC(N)=N1)c1cc(-c3cncnc3)ccc1O2]

Synthesis of (S)-4'-fluoro-2'-(2-fluoro-2-methylpropoxy)-7'-(pyrimidin-5-yl)-5H-spiro[oxazole-4,9'-xanthen]-2-amine A vial was charged with (S)-2-amino-4'-fluoro-7'-(pyrimidin-5-yl)-5H-spiro[oxazole-4,9'-xanthen]-2'-ol (61.0 mg, 0.167 mmol), cesium carbonate (82 mg, 0.251 mmol), and DMF (670 μL). The resulting mixture was stirred vigorously for 10 min, then the vial was placed in large ice-bath for 10 min. 2-fluoro-2-methylpropyl trifluoromethanesulfonate (33.3 μL, 0.201 mmol) was added dropwise and the ice-bath was removed after 5 minutes. The mixture was stirred at for 6 hours, then the mixture was diluted with water (10 mL) and extracted with EtOAc (3×5 mL). The combined organic extracts were dried over sodium sulfate, filtered, and evaporated. The residue was chromatographed on a 12 g Redi-Sep column, eluting with 5-60% gradient of DCM/MeOH/NH4OH (90:10:1) in DCM to give (S)-4'-fluoro-2'-(2-fluoro-2-methylpropoxy)-7'-(pyrimidin-5-yl)-5H-spiro[oxazole-4,9'-xanthen]-2-amine as an off-white solid. Found MS: MH+=439.

Example 82

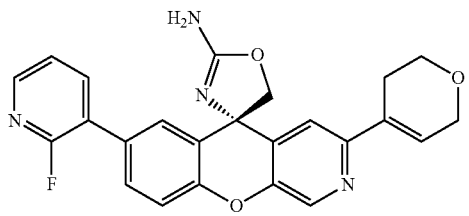 [SMILES: NC1=N[C@@]2(CO1)c1cc(-c3cccnc3F)ccc1Oc1cnc(C3=CCOCC3)cc12]

Synthesis of (S)-3-(3,6-dihydro-2H-pyran-4-yl)-7-(2-fluoropyridin-3-yl)-5'H-spiro[chromeno[2,3-c]pyridine-5,4'-oxazol]-2'-amine A glass microwave reaction vessel was charged with (S)-3-chloro-7-(2-fluoropyridin-3-yl)-5'H-spiro[chromeno[2,3-c]pyridine-5,4'-oxazol]-2'-amine (0.075 g, 0.196 mmol), potassium phosphate (0.125 g, 0.588 mmol), 2-(3,6-dihydro-2H-pyran-4-yl)-4,4,5,5-tetramethyl-1,3,2-dioxaborolane (0.082 g, 0.392 mmol) and Bis(di-tert-butyl(4-dimethylaminophenyl)phosphine)dichloropalladium (II) (0.014 g, 0.020 mmol) in dioxane (1.2 mL) and water (0.40 mL). The reaction mixture was stirred and heated in microwave at 120° C. for 30 min. The mixture was diluted with EtOAc and saturated Na₂CO₃. The organic layer was washed twice with saturated Na₂CO₃, dried over Na₂SO₄ and concentrated in vacuo. The crude was purified by silica gel chromatography (12 g, 2-10% MeOH-DCM, then 10% MeOH-DCM) provided (S)-3-(3,6-dihydro-2H-pyran-4-yl)-7-(2-fluoropyridin-3-yl)-5'H-spiro[chromeno[2,3-c]pyridine-5,4'-oxazol]-2'-amine as a grey solid. Found MS: MH+=431.

Example 83

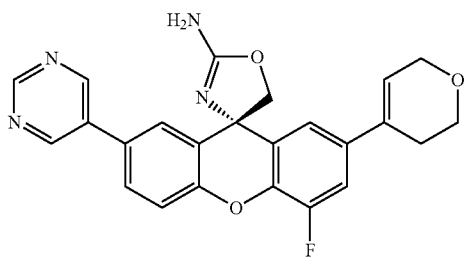 [SMILES: NC1=N[C@@]2(CO1)c1cc(-c3cncnc3)ccc1Oc1c(F)cc(C3=CCOCC3)cc12]

Synthesis of (R)-2'-(3,6-dihydro-2H-pyran-4-yl)-4'-fluoro-7'-(pyrimidin-5-yl)-5H-spiro[oxazole-4,9'-xanthen]-2-amine A vial was charged with 2-amino-2'-(3,6-dihydro-2H-pyran-4-yl)-4'-fluoro-5H-spiro[oxazole-4,9'-xanthene]-7'-yl trifluoromethanesulfonate (150 mg, 0.300 mmol), pyrimidin-5-ylboronic acid (111 mg, 0.899 mmol), and Pd(PPh₃)₄ (34.6 mg, 0.030 mmol). The vial was purged with Ar (g), then DMF (2 mL) and potassium carbonate (0.749 mL, 1.499 mmol) (as a 2.0 M aq. solution) were added in sequence. The vial was capped and heated in a Biotage Initiator microwave reactor for 1.5 h at 75° C. The product was purified via Gilson HPLC (gradient elution 20-90% MeCN/H₂O, 0.1% TFA) to afford (R)-2'-(3,6-dihydro-2H-pyran-4-yl)-4'-fluoro-7'-(pyrimidin-5-yl)-5H-spiro[oxazole-4,9'-xanthen]-2-amine as an off white solid. Found MS: MH+=431.

Example 84

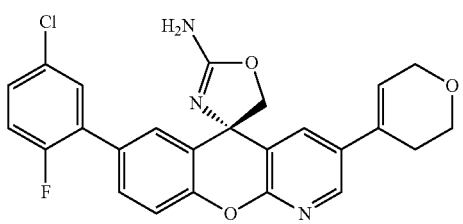 [SMILES: NC1=N[C@@]2(CO1)c1cc(-c3cc(Cl)ccc3F)ccc1Oc1ncc(C3=CCOCC3)cc12]

Synthesis of (S)-7-(5-chloro-2-fluorophenyl)-3-(3,6-dihydro-2H-pyran-4-yl)-5'H-spiro[chromeno[2,3-b]pyridine-5,4'-oxazol]-2'-amine A vial was charged with (S)-2'-amino-3-(3,6-dihydro-2H-pyran-4-yl)-5'H-spiro[chromeno[2,3-b]pyridine-5,4'-oxazole]-7-yl trifluoromethanesulfonate (0.050 g, 0.103 mmol), 5-chloro-2-fluorophenylboronic acid (0.054 g, 0.310 mmol), and Pd(PPh₃)₄ (5.97 mg, 5.17 μmol). The vial was purged with Ar (g). Then, DMF (0.517 mL) and potassium carbonate (0.259 mL, 0.517 mmol) (as a 2.0 M aq. solution) were added in sequence. The vial was sealed and stirred at 70° C. for one hour. The reaction was diluted with ethyl acetate and washed with water. The aqueous layer was extracted with ethyl acetate, and the combined organic layers were dried with sodium sulfate, filtered, and concentrated. The material was purified via column chromatography (RediSep 40 g, gradient elution 0-7% MeOH in DCM) to afford (S)-7-(5-chloro-2-fluorophenyl)-3-(3,6-dihydro-2H-pyran-4-yl)-5'H-spiro[chromeno[2,3-b]pyridine-5,4'-oxazol]-2'-amine as a white solid. Found MS: MH+=464.

Example 85

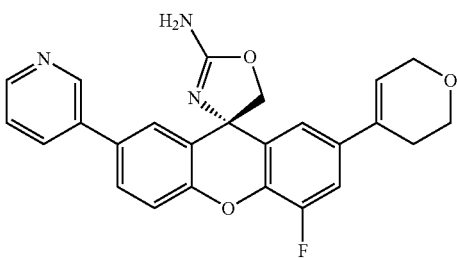 [SMILES: NC1=N[C@@]2(CO1)c1cc(-c3cccnc3)ccc1Oc1c(F)cc(C3=CCOCC3)cc12]

Synthesis of (R)-2'-(3,6-dihydro-2H-pyran-4-yl)-4'-fluoro-7'-(pyridin-3-yl)-5H-spiro[oxazole-4,9'-xanthen]-2-amine A vial was charged with 2-amino-2'-(3,6-dihydro-2H-pyran-4-yl)-4'-fluoro-5H-spiro[oxazole-4,9'-xanthene]-7'-yl trifluoromethanesulfonate (150 mg, 0.300 mmol), pyridin-3-ylboronic acid (111 mg, 0.899 mmol), and Pd(PPh₃)₄ (34.6 mg, 0.030 mmol). The vial was purged with Ar (g), then DMF (2 mL) and potassium carbonate (0.749 mL, 1.499 mmol) (as a 2.0 M aq. solution) were added in sequence. The vial was capped and heated in a Biotage Initiator microwave reactor for 1.5 h at 75° C. The product was purified via Gilson HPLC (gradient elution 20-90% MeCN/H₂O, 0.1% TFA) to afford (R)-2'-(3,6-dihydro-2H-pyran-4-yl)-4'-fluoro-7'-(pyridin-3-yl)-5H-spiro[oxazole-4,9'-xanthen]-2-amine as an off white solid. Found MS: MH+=430.

Example 86

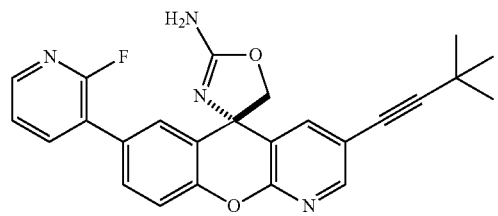

Synthesis of (S)-3-(3,3-dimethylbut-1-ynyl)-7-(2-fluoropyridin-3-yl)-5'H-spiro[chromeno[2,3-b]pyridine-5,4'-oxazol]-2'-amine Combined (S)-3-bromo-7-(2-fluoropyridin-3-yl)-5'H-spiro[chromeno[2,3-b]pyridine-5,4'-oxazol]-2'-amine (80 mg, 0.187 mmol), tetrakis(triphenylphosphine)palladium (21.64 mg, 0.019 mmol), copper(i) iodide (3.57 mg, 0.019 mmol) and THF (749 µL, 0.187 mmol) and DMF (749 µL, 0.187 mmol) in a reaction tube. Added DIPA (525 µL, 3.75 mmol) then 3,3-dimethylbut-1-yne (115 µL, 0.936 mmol) and flushed the reaction tube with argon. Sealed and heated at 110° C. for 3 hours. The mixture was partioned between water (10 mL) and EtOAc (10 mL). The layers were separated, and the aqueous layer was extracted with EtOAc (2×10 mL). The combined organic extracts were dried over sodium sulfate, filtered, and evaporated. The residue was purified by chromatography on a 25-g SNAP column, eluting with 0-70% of a 90:10:1 mixture of DCM/MeOH/NH$_4$OH in DCM. The derived residue was then purified by reverse-phase HPLC (10-90% CH$_3$CN/H$_2$O with 0.1% TFA) to give (S)-3-(3,3-dimethylbut-1-ynyl)-7-(2-fluoropyridin-3-yl)-5'H-spiro [chromeno[2,3-b]pyridine-5,4'-oxazol]-2'-amine as a white powder after evaporation from DCM/hexane. Found MS: MH+=429.

The following examples in Table I were prepared by methods and Steps analogous to those described in Examples 1-86 above. Provided also is the mass spectral data and BACE enzyme and cell-based assay data (IC$_{50}$'s in uM ranges) for each example, where available. Where the name of the exemplified compound, in each of the Tables herein, does not designate a specific (S) or (R) stereoisomer, then the Example was tested as a racemic mixture. Racemic mixture Examples were in many cases, found to be generally close to a 1:1 stereoisomer mixture.

The following are procedures for preparing intermediates, which were used to prepare Examplary compounds, representative of the present invention. The procedures and Methods hereforth were used to prepare the compounds in Table I herein.

Example 87

Method BB1

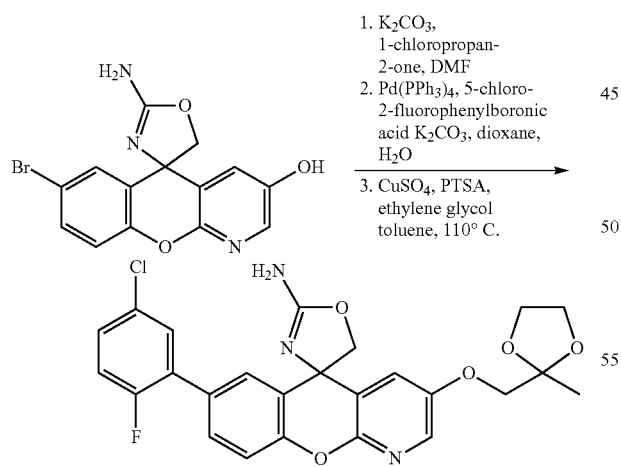

Synthesis of 7-(5-chloro-2-fluorophenyl)-3-((2-methyl-1,3-dioxolan-2-yl)methoxy)-5'H-spiro [chromeno[2,3-b]pyridine-5,4'-oxazol]-2'-amine Step 1: A solution of 2'-amino-7-bromo-5'H-spiro [chromeno[2,3-b]pyridine-5,4'-oxazol]-3-ol (0.570 g, 1.637 mmol) in 5 mL DMF was treated with potassium carbonate (0.283 g, 2.047 mmol) and was allowed to stir at RT for 15 minutes. The reaction mixture was then cooled to 0° C. and 1-chloropropan-2-one (0.151 g, 1.637 mmol) was added as a solution in 1 mL THF. After stirring for one hour the reaction mixture was allowed to warm to RT and stir for 4 hours. The reaction mixture was poured into 1:1 water/brine, extracted with EtOAc (3×25 mL). The combined organics were dried over MgSO$_4$ and concentrated. Purification of the crude residue by column chromatography provided 1-(2'-amino-7-bromo-5'H-spiro[chromeno[2,3-b]pyridine-5,4'-oxazole]-3-yloxy)propan-2-one. MS m/z=404.0 [M+H].

Step 2: A vial charged with 5-chloro-2-fluorophenylboronic acid (0.431 g, 2.474 mmol), palladiumtetrakis (0.057 g, 0.049 mmol), potassium carbonate (0.684 g, 4.95 mmol), and 1-(2'-amino-7-bromo-5'H-spiro[chromeno[2,3-b]pyridine-5,4'-oxazole]-3-yloxy)propan-2-one (0.400 g, 0.990 mmol) was treated with 5 mL dioxane followed by 1 mL water. The vial was flushed with argon and was heated to 80° C. for 3 hours. The reaction mixture was diluted with EtOAc (25 mL) and dried over MgSO$_4$. The organic layers were combined and concentrated, and the crude residue was purified by column chromatography yielding 1-(2'-amino-7-(5-chloro-2-fluorophenyl)-5'H-spiro[chromeno[2,3-b]pyridine-5,4'-oxazole]-3-yloxy)propan-2-one. MS m/z=454.0 [M+H].

Step 3: To a vial charged with 1-(2'-amino-7-(5-chloro-2-fluorophenyl)-5'H-spiro[chromeno[2,3-b]pyridine-5,4'-oxazole]-3-yloxy)propan-2-one (0.140 g, 0.308 mmol), p-toluenesulfonic acid (0.159 g, 0.925 mmol), and 4 Angstrom molecular seives was added 3 mL toluene. The resulting mixture was treated with ethylene glycol (0.022 mL, 0.401 mmol) and was heated to reflux. After stirring for 10 hours, copper(ii) sulfate (0.059 g, 0.617 mmol) was added followed by an additional portion of ethylene glycol (0.022 mL, 0.401 mmol). The reaction mixture was heated to reflux for an additional 4 hours before being allowed to cool to RT. The mixture was poured into saturated NaHCO$_3$ (25 mL) solution and extracted with EtOAc (3×25 mL). The organics were washed with brine, dried over MgSO$_4$ and concentrated. Purification of the crude residue by column chromatography gave 7-(5-chloro-2-fluorophenyl)-3-((2-methyl-1,3-dioxolan-2-yl)methoxy)-5'H-spiro[chromeno[2,3-b]pyridine-5,4'-oxazol]-2'-amine. MS m/z=498.0 [M+H].

Example 88

Method BB2

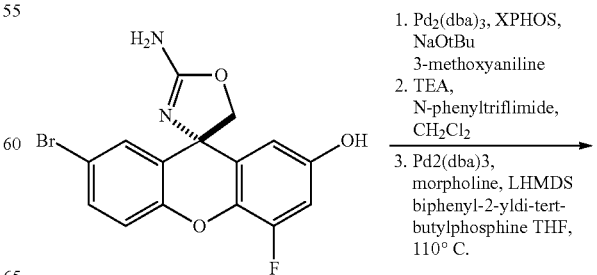

143

-continued

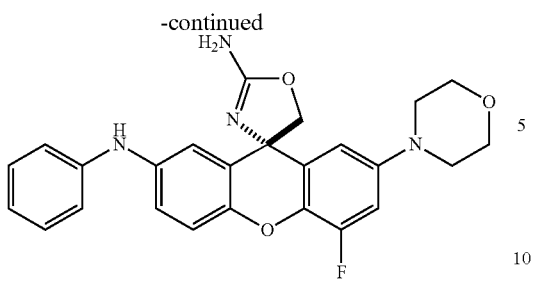

Synthesis of (S)-4'-fluoro-N7'-(3-methoxyphenyl)-2'-morpholino-5H-spiro[oxazole-4,9'-xanthene]-2,7'-diamine Step 1: A vial was charged with (S)-2-amino-7'-bromo-4'-fluoro-5H-spiro[oxazole-4,9'-xanthen]-2'-ol (400 mg, 1.095 mmol), di-tert-butyl(2',4',6'-triisopropylbiphenyl-2-yl)phosphine (81 mg, 0.192 mmol), $Pd_2 dba_3$ (50.2 mg, 0.055 mmol), sodium tert-butoxide (316 mg, 3.29 mmol) and 3-methoxyaniline (245 μL, 2.191 mmol). Toluene (2191 μL) was added and the vial was flushed with argon, sealed and shaken to combine all the components. The resulting dark mixture was heated at 100° C. for 16 hrs. The mixture was diluted with water (5 ml) and ethyl acetate (15 ml) and neutralized with saturated $NH_4Cl$ solution. The organic layer was loaded onto a 5 g SCX column and washed with EtOAc and MeOH. The material was recovered from the column by washing with 2M $NH_3$ in MeOH. Concentration and separated by silica gel chromatography (10-80% $CH_2Cl_2$/MeOH/$NH_4OH$ in $CH_2CO$ provided (S)-2-amino-4'-fluoro-7'-(3-methoxyphenylamino)-5H-spiro[oxazole-4,9'-xanthen]-2'-ol (230 mg, 0.565 mmol, 51.5% yield). MS m/z=408.0 [M+H].

Step 2: To a solution of (S)-2-amino-4'-fluoro-7'-(3-methoxyphenylamino)-5H-spiro[oxazole-4,9'-xanthen]-2'-ol (230 mg, 0.565 mmol) in $CH_2Cl_2$ (2823 μL), triethylamine (157 μL, 1.129 mmol) and 1,1,1-trifluoro-N-phenyl-N-(trifluoromethylsulfonyl)methanesulfonamide (323 mg, 0.903 mmol) were added and the mixture was left at RT for 1 hr. The mixture was directly loaded to 12 g RediSep column and purified by silica gel chromatography using 0-50% $CH_2Cl_2$/MeOH/$NH_4OH$ in $CH_2Cl_2$ to afford (S)-2-amino-5'-fluoro-2'-(3-methoxyphenylamino)-5H-spiro[oxazole-4,9'-xanthene]-7'-yl trifluoromethanesulfonate. MS m/z=540.0 [M+H].

Step 3: A vial was charged with morpholine (0.062 mL, 0.706 mmol), (S)-2-amino-5'-fluoro-2'-(3-methoxyphenylamino)-5H-spiro[oxazole-4,9'-xanthene]-7'-yl trifluoromethanesulfonate (127 mg, 0.235 mmol), $Pd_2 dba_3$ (10.78 mg, 0.012 mmol), (8.43 mg, 0.028 mmol). The tube was flushed with argon and LiHMDS (1M in THF) (0.942 mL, 0.942 mmol) was added and the vial sealed and heated at 110° C. in microwave reactor for 1 hr. The mixture was quenched with 1 ml of water, diluted with EtOAc, and loaded onto 2 g SCX-2 column. The column was washed with EtOAc and MeOH. The material was flushed from the column using 2M ammonia in MeOH. The derived solution was purified by silica gel chromatography to afford (S)-4'-fluoro-N7'-(3-methoxyphenyl)-2'-morpholino-5H-spiro[oxazole-4,9'-xanthene]-2,7'-diamine MS m/z=477.0 [M+H].

144

Example 89

Method BB3

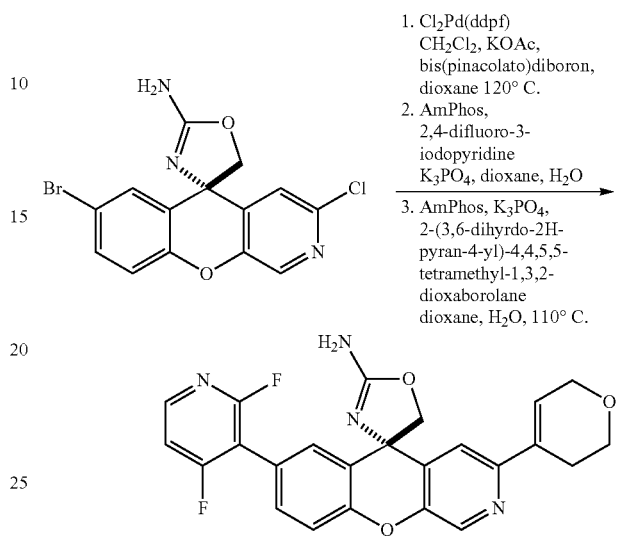

Synthesis of (5S)-7-(2,4-difluoro-3-pyridinyl)-3-(3,6-dihydro-2H-pyran-4-yl)spiro[chromeno[2,3-c]pyridine-5,4'-[1,3]oxazol]-2'-amine Step 1: A mixture (S)-7-bromo-3-chloro-5'H-spiro[chromeno[2,3-c]pyridine-5,4'-oxazol]-2'-amine (1.00 g, 2.73 mmol, prepared as described in Method BB41), bis(pinacolato)diboron (0.831 g, 3.27 mmol), dichloro(1,1-bis(diphenylphosphinoferrocene))palladium(ii) complex with DCM (0.111 g, 0.136 mmol), and KOAc (0.512 mL, 8.18 mmol) of in dioxane (10 mL) was purged with nitrogen for 10 minutes and heated in a microwave at 120° C. for 1 h. The reaction was diluted with water and extracted with EtOAc (2×25 mL). The organic phase was washed with brine, dried over $NaSO_4$, and concentrated under vacuum to give the desired product (S)-3-chloro-7-(4,4,5,5-tetramethyl-1,3,2-dioxaborolan-2-yl)-5'H-spiro[chromeno[2,3-c]pyridine-5,4'-oxazol]-2'-amine (0.42 g, 1.015 mmol, 37.2% yield) which was carried on without further purification.

Step 2: A 20 mL glass microwave reaction vessel was charged with (S)-3-chloro-7-(4,4,5,5-tetramethyl-1,3,2-dioxaborolan-2-yl)-5'H-spiro[chromeno[2,3-c]pyridine-5,4'-oxazol]-2'-amine (0.251 g, 0.608 mmol), potassium phosphate (0.269 g, 1.266 mmol), 2,4-difluoro-3-iodopyridine (0.122 g, 0.506 mmol) and bis(di-tert-butyl(4-dimethylaminophenyl)phosphine)dichloropalladium (II) (0.036 g, 0.051 mmol) in dioxane (3.2 mL) and water (0.8 mL). The reaction mixture was heated at 100° C. for 30 min in microwave reactor. After cooling the rt the mixture was diluted with EtOAc and water. The aqueous layer was washed twice with saturated $Na_2CO_3$. The organic layer was dried over $Na_2SO_4$ and concentrated in vacuo. The crude residue was purified by silica gel chromatography (2-10% MeOH—$CH_2Cl_2$) to provide the desired product as a brown residue.

Step 3: A glass microwave reaction vessel was charged with (S)-3-chloro-7-(2,4-difluoropyridin-3-yl)-5'H-spiro[chromeno[2,3-c]pyridine-5,4'-oxazol]-2'-amine (0.190 g, 0.474 mmol), potassium phosphate (0.302 g, 1.422 mmol), 2-(3,6-dihydro-2H-pyran-4-yl)-4,4,5,5-tetramethyl-1,3,2-dioxaborolane (0.169 g, 0.806 mmol) and bis(di-tert-butylphenylphosphine)dichloropalladium (II) (0.029 g, 0.047 mmol) in dioxane (4 mL) and water (1.2 mL). The reaction mixture was heated in microwave at 110° C. for 30 min. The mixture was diluted with EtOAc and saturated $Na_2CO_3$. The organic layer was washed twice with saturated $Na_2CO_3$, dried over $Na_2SO_4$ and concentrated in vacuo. The crude residue was purified by silica gel chromatography (2-10% MeOH—$CH_2Cl_2$) to provide a residue that was purified by HPLC to provide the titled compound as a white solid. MS m/z=449.2 [M+H]$^+$. Calculated for $C_{24}H_{18}F_2N_4O_3$: 448.13.

$^1$H NMR (400 MHz, CHLOROFORM-d) δ ppm 2.54-2.75 (m, 2 H) 3.95 (t, J=5.38 Hz, 2 H) 4.36-4.43 (m, 4 H) 4.63-4.81 (m, 1 H) 6.63 (br. s., 1 H) 7.07 (dd, J=8.02, 5.67 Hz, 1H) 7.29 (s, 1 H) 7.39 (s, 1 H) 7.46 (d, J=8.02 Hz, 1 H) 7.56 (s, 1 H) 8.16 (dd, J=7.82, 5.67 Hz, 1 H) 8.49 (s, 1 H)

Example 90

Method BB4

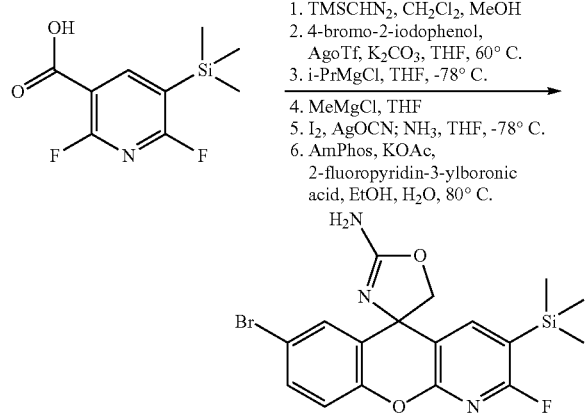

Synthesis of (5S)-7-bromo-2-fluoro-3-(trimethylsilyl)spiro[chromeno[2,3-b]pyridine-5,4'-[1,3]oxazol]-2'-amine Step 1: 2,6-Difluoro-5-(trimethylsilyl)pyridine-3-carboxylic acid (1.17 g, 5.05 mmol) was dissolved in a mixture of DCM (20 mL) and MeOH (5 mL) and treated with (trimethylsilyl)diazomethane (2.0 m in diethyl ether, 5.0 mL, 10.00 mmol). [2,6-Difluoro-5-(trimethylsilyl)pyridine-3-carboxylic acid was synthesized according to M. Schlosser and T. Rausis, Eur. J. Org. Chem., 2004, pp 1018-1024]. The derived solution was maintained at rt for 1 hour. Evaporation under reduced pressure and purification using the by silica gel chromatography (hexane to ethyl actetate gradient) gave the desired methyl 2,6-difluoro-5-(trimethylsilyl)nicotinate.

Step 2: Methyl 2,6-difluoro-5-(trimethylsilyl)nicotinate (1.19 g, 4.85 mmol), 4-bromo-2-iodophenol (1.450 g, 4.85 mmol), and silver trifluoromethanesulfonate (1.496 g, 5.82 mmol) were dissolved in dry THF (40 mL) and treated with potassium carbonate (1.006 g, 7.28 mmol). The mixture was heated to 60° C. for 10 hours before being cooled to rt and filtered through a pad of celite. Water (100 mL) and diethyl ether (100 mL) were added to the filtrate and the phases were separated. The organics were dried with magnesium sulfate, filtered and evaporated to dryness under reduced pressure. Purification using silica chromatography (hexane to DCM gradient) gave the desired methyl 2-(4-bromo-2-iodophenoxy)-6-fluoro-5-(trimethylsilyl)nicotinate.

Step 3: Methyl 2-(4-bromo-2-iodophenoxy)-6-fluoro-5-(trimethylsilyl)nicotinate (2.04 g, 3.89 mmol) was dissolved in dry THF (80 mL) and cooled in a dry ice bath to −78° C. Isopropylmagnesium chloride (2.0 M solution in diethyl ether, 3.89 mL (7.78 mmol) was added and the solution stirred for 15 minutes. The mixture was removed from the cold bath and allowed to slowly warm to RT. Water (100 mL), saturated ammonium chloride (10 mL), and EtOAc (200 mL) were added and the phases mixed and separated. The organics were dried with magnesium sulfate and evaporated to dryness under reduced pressure. The crude was purified using silica chromatography (hexane to ethyl acetate gradient) to give 7-bromo-2-fluoro-3-(trimethylsilyl)-5H-chromeno[2,3-b]pyridin-5-one.

Step 4: 7-bromo-2-fluoro-3-(trimethylsilyl)-5H-chromeno[2,3-b]pyridin-5-one (1.05 g, 2.9 mmol) was dissolved in dry THF (30 mL) and treated with methylmagnesium bromide (3.0 M in diethyl ether, 2.0 mL, 6.00 mmol). After 15 minutes 5N HCl (30 mL) was added followed by EtOAc (100 mL) and water (100 mL). The phases were mixed and separated and the organics were dried with magnesium sulfate before evaporating to dryness under reduced pressure. Purification using silica chromatography (hexane to dichloromethane gradient) gave the desired 7-bromo-2-fluoro-5-methylene-3-(trimethylsilyl)-5H-chromeno[2,3-b]pyridine.

Step 5: Iodine (0.364 g, 1.435 mmol) was dissolved in dry THF (30 mL) under nitrogen and cooled to −78° C. Silver cyanate (0.615 g, 4.10 mmol) was added in one portion and the mixture was stirred for 5 minutes. This slurry was transferred to a −30° C. bath and it was stirred for another 10 minutes. A solution of 7-bromo-2-fluoro-5-methylene-3-(trimethylsilyl)-5H-chromeno[2,3-b]pyridine (0.498 g, 1.367 mmol) in dry tetrahydrofuran (10 mL) was added and the reaction stirred for 1 hour maintaining the bath temperature between −25 and −15° C. The reaction was diluted with diethyl ether (10 mL) and filtered through a pad of celite. The solids were washed with 1:1 THF:ether (20 mL) then the filtrate was cooled in a −20° C. bath under nitrogen. Ammonia (2.0 M solution in MeOH, 3.5 mL, 7.00 mmol) was added and the flask sealed. The solution was allowed to warm slowly over the next 10 hours. The reaction mixture was evaporated to dryness under reduced pressure and the crude purified using silica chromatography (0-10% methanol in dichloromethane gradient) to give 7-bromo-2-fluoro-3-(trimethylsilyl)-5'H-spiro[chromeno[2,3-b]pyridine-5,4'-oxazol]-2'-amine Step 6: 7-Bromo-2-fluoro-3-(trimethylsilyl)-5'H-spiro[chromeno[2,3-b]pyridine-5,4'-oxazol]-2'-amine (0.137 g, 0.324 mmol), bis-(di-tert-butyl(4-dimethylaminophenyl)phosphine)dichloropalladium(ii) (0.011 g, 0.016 mmol), 2-fluoropyridin-3-ylboronic acid (0.055 g, 0.389 mmol), and potassium acetate (0.127 g, 1.298 mmol) were suspended in a mixture of ethanol (30 mL) and water (5 mL) and heated to 80° C. After 20 minutes the solution was cooled to rt and concentrated under reduced pressure to ~10 mL. This solution was then diluted with water (100 mL) and EtOAc (100 mL). The phases were mixed and separated and the organics were dried with magnesium sulfate before filtered and evaporated to dryness under reduced pressure. Purification using silica chromatography (0-10% methanol in DCM gradient followed by a second column using dichloromethane to EtOAc gradient) gave the desired 2-fluoro-7-(2-fluoropyridin-3-yl)-3-(trimethylsilyl)-5'H-spiro[chromeno[2,3-b]pyridine-5,4'-oxazol]-2'-amine Example 91

Method BB5

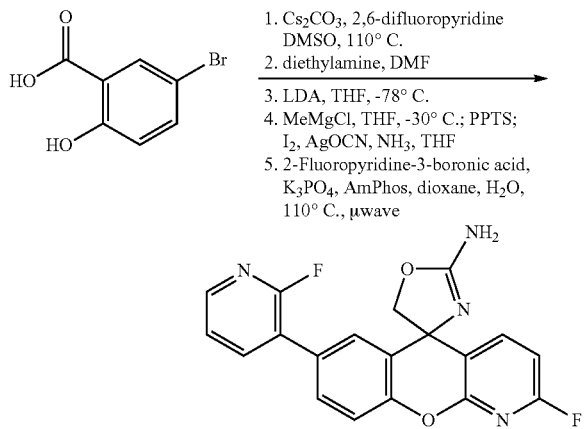

Step 1: A mixture of cesium carbonate (3.20 mL, 40.0 mmol), 5-bromosalicylic acid (4.34 g, 20.00 mmol) and 2,6-difluoropyridine (5.52 g, 48.0 mmol) in 8 mL of DMSO was stirred at 110° C. for 3 h. After cooling to rt, the reaction mixture was dissolved in water and the pH was adjusted to ~3 with 1 N HCl. The reaction mixture was extracted with EtOAC (3×25 mL), washed with brine and evaporated to dryness to give crude 5-bromo-2-(6-fluoropyridin-2-yloxy)benzoic acid which was used directly in the next step.

Step 2: To mixture of 5-bromo-2-(6-fluoropyridin-2-yloxy)benzoic acid (16 g, 51.3 mmol) and TBTU (16.46 g, 51.3 mmol) in 15 mL of DMF was added diethylamine (13.26 mL, 128 mmol). The resulting solution was allowed to stir at rt overnight. The reaction was quenched with saturated NaHCO$_3$, extracted with a 2:1 mixture of EtOAc and hexanes (3×50 mL). The combined organics were washed with brine, and evaporated to dryness. Purification by silica gel chromatography (hexane to CH$_2$Cl$_2$ to CH$_2$Cl$_2$/EA=20:1 to 10:1 to 5:1) provided 5-bromo-N,N-diethyl-2-(6-fluoropyridin-2-yloxy)benzamide as a off-white solid.

Step 3: To a solution of 5-bromo-N,N-diethyl-2-(6-fluoropyridin-2-yloxy)benzamide (2.90 g, 7.90 mmol) in 50 mL of dry THF at −78° C. was added dropwise lithium diisopropylamide (2.0 M heptane/THF/ethylbenzene, 11.8 mL, 23.69 mmol) and the reaction was stirred at −78° C. for 2 hours. The reaction quenched at −78° C. with 30 mL of 1 N HCl in ether. After warming to rt, the reaction was further quenched with saturated NH$_4$Cl (250 mL) extracted with ethyl acetate (3×250 mL). The combined organics were washed with brine, and evaporated to dryness. Purification by silica gel chromatography (hexane to hexane/CH$_2$Cl$_2$=1:1 to CH$_2$Cl$_2$ to CH$_2$Cl$_2$/EA=10:1) gave 7-bromo-2-fluoro-5H-chromeno[2,3-b]pyridin-5-one as a white solid and 7-bromo-2-(diethylamino)-5H-chromeno[2,3-b]pyridin-5-one as a white solid.

Step 4: A solution of 7-bromo-2-fluoro-5H-chromeno[2,3-b]pyridin-5-one (150 mg, 0.510 mmol) in 5 mL of dry THF at −78° C. was added to methylmagnesium chloride, 3.0 M solution in THF (0.33 mL, 1.020 mmol) (0.33 mL) and the reaction was slowly warmed up to −30 C. At this temperature additional methylmagnesium chloride 3.0 M solution in THF (0.3 mL, 1.020 mmol) was added and stirring was continued for 1 hour. The reaction was quenched at −30° C. with saturated NH$_4$Cl (150 mL) and extracted with EtOAc (3×150 mL). The combined organics were dried over sodium sulfate, filtered and evaporated to dryness. The derived residue was treated with 1 mg of PPTS in CH$_2$Cl$_2$ at 25° C. for 0.5 h. This mixture was quenched with 0.1 g of NaHCO$_3$ and the solvent was evaporated to dryness to give crude 7-bromo-2-fluoro-5-methylene-5H-chromeno[2,3-b]pyridine which was directly used in the next step. A solution of iodine (27.6 µL, 0.536 mmol) in THF at −25° C. was treated with silver cyanate (76 µL, 2.040 mmol). After 30 min, a solution of the above derived olefin (7-bromo-2-fluoro-5-methylene-5H-chromeno[2,3-b]pyridine) in 20 mL of THF was added dropwise. The slurry was maintained at −25° C. for 2 h at which point the slurry was filtered through celite, washing well with ether. The brown filtrate was concentrated to dryness, taken up in THF (10 mL), cooled to 0° C. and treated with ammonia (2 M solution in 2-propanol, 1.1 mL, 2.040 mmol). The reaction was allowed to slowly warm to rt and stirred overnight. Half of the solvent was evaporated in vacuo and the residue was diluted with water (50 mL) and extracted with ethyl acetate (3×50 mL). The combined organics were dried over sodium sulfate, filtered and evaporated to dryness. Purification by silica gel chromatography (CH$_2$Cl$_2$ to CH$_2$Cl$_2$/EA=3:1 to 2:1 to 1:1 to 1:2) afforded 7-bromo-2-fluoro-5'H-spiro[chromeno[2,3-b]pyridine-5,4'-oxazol]-2'-amine as a yellow solid.

Step 5: A mixture of 7-bromo-2-fluoro-5'H-spiro[chromeno[2,3-b]pyridine-5,4'-oxazol]-2'-amine (26.0 mg, 0.074 mmol), 2-fluoro-3-pyridineboronic acid (16.74 mg, 0.119 mmol), bis-(di-tert-butyl(4-dimethylaminophenyl)phosphine)dichloropalladium(ii) (2.103 mg, 2.97 µmol) and potassium phosphate (47.3 mg, 0.223 mmol) in a 2:1 mixture of dioxane and water (1.5 ml) was heated at 110° C. in the microwave for 20 minutes. The reaction mixture was subjected to purification by silica gel chromatography (SiO2, CH$_2$Cl$_2$ to CH$_2$Cl$_2$/MeOH=100:1 to 100:6) to give 2-fluoro-7-(2-fluoropyridin-3-yl)-5'H-spiro[chromeno[2,3-b]pyridine-5,4'-oxazol]-2'-amine as a white solid. MS m/z=367.0 [M+H].

Example 92

Method BB6

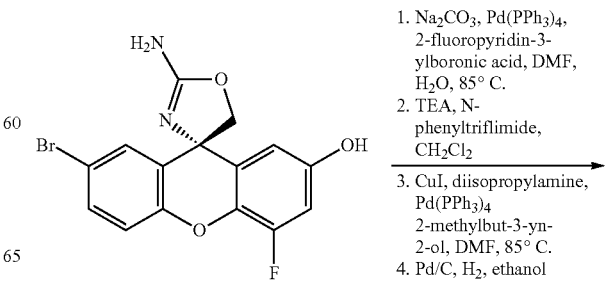

-continued

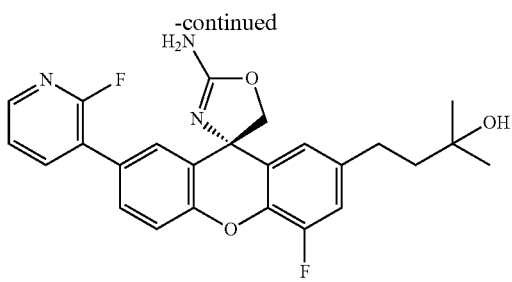

Synthesis of (S)-4-(2-amino-5'-fluoro-2'-(2-fluoropyridin-3-yl)-5H-spiro[oxazole-4,9'-xanthene]-7'-yl)-2-methylbutan-2-ol Step 1: A 500 mL RBF was charged with (S)-2-amino-7'-bromo-4'-fluoro-5H-spiro[oxazole-4,9'-xanthen]-2'-ol (20.00 g, 54.8 mmol), 2-fluoropyridin-3-ylboronic acid (13.89 g, 99 mmol) and sodium carbonate (23.22 g, 219 mmol). DMF (130 mL) was added and the mixture was stirred for 1 minute before tetrakis(triphenylphosphine) palladium (4.43 g, 3.83 mmol) and water (52.2 mL) were added. The mixture was capped with argon, equipped with a reflux condenser and heated at 85° C. for 16 hrs. The mixture was cooled to RT and the resulting yellow precipitate was filtered. The filtrate was diluted with water (200 mL) and saturated ammonium chloride (200 mL), leading to the formation of a white precipitate and a brown semisolid. The precipitate was filtered and the semisolid was triturated with water (~200 mL) to provide a brown solid which was also filtered and washed with water. The combined solids were washed excessively with water and dried overnight under a stream of air to afford (S)-2-amino-4'-fluoro-7'-(2-fluoropyridin-3-yl)-5H-spiro[oxazole-4,9'-xanthen]-2'-ol as tan solid which was used without further purification. MS m/z=382.0 [M+H].

Step 2: To a suspension of (S)-2-amino-4'-fluoro-7'-(2-fluoropyridin-3-yl)-5H-spiro[oxazole-4,9'-xanthen]-2'-ol (1.2 g, 3.15 mmol) in $CH_2Cl_2$ (15.73 mL) were added triethylamine (0.877 mL, 6.29 mmol) and 1,1,1-trifluoro-N-phenyl-N-(trifluoromethylsulfonyl)methanesulfonamide (1.799 g, 5.03 mmol). The mixture was maintained at RT for 48 hours, to afford clear yellow solution LCMS 110110-4-2 showed ~90% conversion. The mixture was diluted with $CH_2Cl_2$ (15 mL) and washed sequentially with $NaHCO_3$ (25 mL) and brine. Filtration and concentration provided a solid that was purified by silica gel chromatography (0-40% $CH_2Cl_2$/MeOH/$NH_4OH$ in $CH_2Cl_2$) to afford (S)-2-amino-5'-fluoro-2'-(2-fluoropyridin-3-yl)-5H-spiro[oxazole-4,9'-xanthene]-7'-yl trifluoromethanesulfonate as yellow foam. MS m/z=514.0 [M+H].

Step 3: A 15 ml resealable tube was charged with (S)-2-amino-5'-fluoro-2'-(2-fluoropyridin-3-yl)-5H-spiro[oxazole-4,9'-xanthene]-7'-yl trifluoromethanesulfonate (300 mg, 0.584 mmol), tetrakis(triphenylphosphine)palladium(0) (67.5 mg, 0.058 mmol), copper(i) iodide (11.13 mg, 0.058 mmol), DMF (2922 μL), 2-methylbut-3-yn-2-ol (114 μL, 1.169 mmol) and diisopropylamine (416 μL, 2.92 mmol). The mixture was capped with argon, sealed and heated at 85° C. for 1 hr. Concentration and purification of the crude residue by silica gel chromatography (10-60% $CH_2Cl_2$/MeOH/$NH_4OH$ 90:10:1 in $CH_2Cl_2$) afforded (S)-4-(2-amino-5'-fluoro-2'-(2-fluoropyridin-3-yl)-5H-spiro[oxazole-4,9'-xanthene]-7'-yl)-2-methylbut-3-yn-2-ol. MS m/z=448.0 [M+H].

Step 4: A 100 ml flask was charged with (S)-4-(2-amino-5'-fluoro-2'-(2-fluoropyridin-3-yl)-5H-spiro[oxazole-4,9'-xanthene]-7'-yl)-2-methylbut-3-yn-2-ol (120 mg, 0.268 mmol) ethanol (4 ml). Palladium on carbon (86 mg, 0.080 mmol) was added under argon and the resulting mixture was hydrogenated under 1 atm of hydrogen gas for 1 hr. The mixture was filtered through celite and concentrated in vacuo to provide (S)-4-(2-amino-5'-fluoro-2'-(2-fluoropyridin-3-yl)-5H-spiro[oxazole-4,9'-xanthene]-7'-yl)-2-methylbutan-2-ol. MS m/z=454.0 [M+H].

Example 93

Method BB7

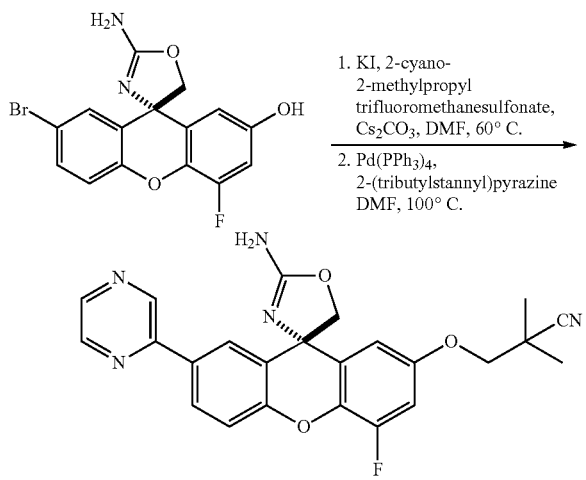

Synthesis of (S)-3-(2-amino-5'-fluoro-2'-(pyrazin-2-yl)-5H-spiro[oxazole-4,9'-xanthene]-7'-yloxy)-2,2-dimethylpropanenitrile Step 1: To a flask charged with potassium iodide (273 mg, 1.643 mmol), 2-cyano-2-methylpropyl trifluoromethanesulfonate (1140 mg, 4.93 mmol), cesium carbonate (3212 mg, 9.86 mmol), and (S)-2-amino-7'-bromo-4'-fluoro-5H-spiro[oxazole-4,9'-xanthen]-2'-ol (1200 mg, 3.29 mmol) was added 10 ml of DMF. The resulting slurry was heated for 1 hour at 60° C. The solution was quenched with water (20 mL). The aqueous layer was extracted with $CH_2Cl_2$ (3×25 mL) and the combined organic layers were washed with brine and dried over anhydrous sodium sulfate. After being filtered and concentrated, the derived residue was purified via silica gel column chromatography using 15-70% 90/10/1 ($CH_2Cl_2$/MeOH/ammonia) in $CH_2Cl_2$ to afford (S)-3-(2-amino-2'-bromo-5'-fluoro-5H-spiro[oxazole-4,9'-xanthene]-7'-yloxy)-2,2-dimethylpropanenitrile as a brown solid. MS m/z=446.0 [M+H].

Step 2: To a flask charged with Pd(PPh_3)_4 (8.82 mg, 0.034 mmol), 2-(tributylstannyl)pyrazine (248 mg, 0.672 mmol), and (S)-3-(2-amino-2'-bromo-5'-fluoro-5H-spiro[oxazole-4,9'-xanthene]-7'-yloxy)-2,2-dimethylpropanenitrile (150 mg, 0.336 mmol) was added 3 ml of DMF. The resulting mixture was heated in the microwave at 100° C. for one hour. The solution was concentrated in vacuo and the derived residue was purified by HPLC (gradient elution 10-90% $MeCN/H_2O$, 0.1% TFA) to afford (S)-3-(2-amino-5'-fluoro-2'-(pyrazin-2- yl)-5H-spiro[oxazole-4,9'-xanthene]-7'-yloxy)-2,2-dimethylpropanenitrile as a white solid. MS m/z=446.0 [M+H].

Example 94

Method BB8

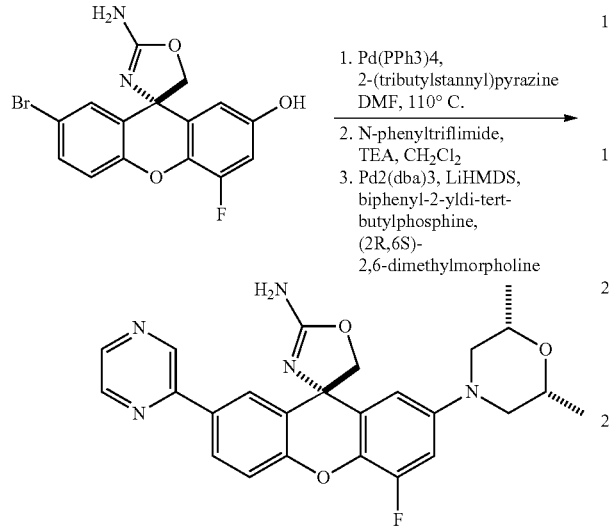

Synthesis of (S)-2'-((2R,6S)-2,6-dimethylmorpholino)-4'-fluoro-7'-(pyrazin-2-yl)-5H-spiro[oxazole-4,9'-xanthen]-2-amine Step 1: Pd(PPh$_3$)$_4$ (0.506 g, 0.438 mmol), (S)-2-amino-7'-bromo-4'-fluoro-5H-spiro[oxazole-4,9'-xanthen]-2'-ol (1.6 g, 4.38 mmol), and 2-(tributylstannyl)pyrazine (2.426 g, 6.57 mmol) were combined in 10 ml of DMF and heated in the microwave at 110° C. for two hours. The solution was diluted with ethyl acetate (50 mL) and washed twice with water. The organic layer was washed with brine and dried over anhydrous sodium sulfate, filtered and concentrated. The product was purified via silica gel column chromatography (RediSep 40 g column) using 10-100% 90/10/1 (CH$_2$Cl$_2$/MeOH/ammonia) in CH$_2$Cl$_2$ to afford (S)-2-amino-4'-fluoro-7'-(pyrazin-2-yl)-5H-spiro[oxazole-4,9'-xanthen]-2'-ol as a white solid. MS m/z=365.0 [M+H].

Step 2: (S)-2-amino-4'-fluoro-7'-(pyrazin-2-yl)-5H-spiro [oxazole-4,9'-xanthen]-2'-ol (600 mg, 1.647 mmol) and TEA (0.459 ml, 3.29 mmol) were combined in 25 ml of CH$_2$Cl$_2$, and 1,1,1-trifluoro-N-phenyl-N-(trifluoromethylsulfonyl) methanesulfonamide (706 mg, 1.976 mmol) was added. The resulting solution was stirred at RT overnight. The solution was loaded directly on a silica gel column. The product was purified via silica gel column chromatography (RediSep 40 g column) using 10-70% 90/10/1 (CH$_2$Cl$_2$/MeOH/ammonia) in CH$_2$Cl$_2$ to afford (S)-2-amino-5'-fluoro-2'-(pyrazin-2-yl)-5H-spiro[oxazole-4,9'-xanthene]-7'-yl trifluoromethanesulfonate as a yellow solid solid. MS m/z=496.9 [M+H].

Step 3: A microwave vial was charged with (S)-2-amino-5'-fluoro-2'-(pyrazin-2-yl)-5H-spiro[oxazole-4,9'-xanthene]-7'-yl trifluoromethanesulfonate (150 mg, 0.302 mmol), Pd$_2$(dba)$_3$ (13.84 mg, 0.015 mmol), biphenyl-2-yldi-tert-butylphosphine (10.82 mg, 0.036 mmol) and (2R,6S)-2, 6-dimethylmorpholine (104 mg, 0.907 mmol) and capped under argon. LiHMDS (1 M in THF) (1.511 mL, 1.511 mmol) was added and the mixture was heated in the microwave at 110° C. for 1 hr. To the reaction was added 1 ml of water and the mixture was concentrated in vacuo. The product was purified via Gilson HPLC (gradient elution 20-70% MeCN/H$_2$O, 0.1% TFA) and freebased with sodium bicarbonte to afford (S)-2'-((2R,6S)-2,6-dimethylmorpholino)-4'-fluoro-7'-(pyrazin-2-yl)-5H-spiro[oxazole-4,9'-xanthen]-2-amine as an off white solid. MS m/z=462.0 [M+H].

Example 95

Method BB9

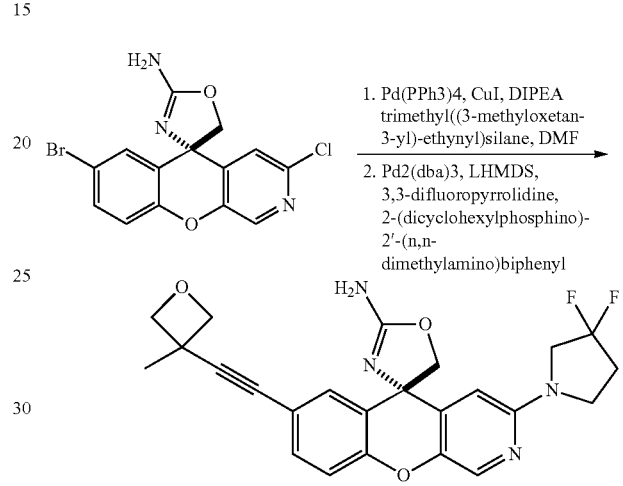

Synthesis of (5S)-3-(3,3-difluoro-1-pyrrolidinyl)-7-((3-methyl-3-oxetanyl)ethynyl)spiro[chromeno[2,3-c]pyridine-5,4'-[1,3]oxazol]-2'-amine Step 1: Pd(PPh$_3$)$_4$ (0.315 g, 0.273 mmol), copper(i) iodide (0.055 mL, 1.637 mmol) and (S)-7-bromo-3-chloro-5'H-spiro[chromeno[2,3-c]pyridine-5,4'-oxazol]-2'-amine (1.00 g, 2.73 mmol) were combined in a heating tube which was degassed with argon gas. Sequential addition of DMF (10 mL), DIPA (5.73 mL, 40.9 mmol) and trimethyl ((3-methyloxetan-3-yl)ethynyl)silane (0.505 g, 3.00 mmol) to the mixture provided a brown slurry. The reaction vessel was sealed and heated at 90° C. for 24 h. The reaction mixture was poured into water and extracted with EtOAc (3×25 mL). The combined organic layers were washed with water, brine, dried over sodium sulfate, filtered and concentrated. The crude material ws purified by column chromatography with 30-70% EA/HX to give the desired product.

Step 2: Tris(dibenzylideneacetone)dipalladium (0) (0.012 g, 0.013 mmol), 2-(dicyclohexylphosphino)-2'-(n,n-dimethylamino)biphenyl (0.015 g, 0.039 mmol), 3,3-difluoropyrolidine HCl, 98% (0.113 g, 0.786 mmol) and (S)-3-chloro-7-((3-methyloxetan-3-yl)ethynyl)-5'H-spiro[chromeno[2,3-c]pyridine-5,4'-oxazol]-2'-amine (0.100 g, 0.262 mmol) were combined and degassed with nitrogen. LHMDS (1.06 m solution in THF) (1.571 mL, 1.571 mmol) was added and the mixture was stirred at 90° C. overnight. The solvent was removed and the crude material was purified by column chromatography with 0-5% 2M NH$_3$ in MeOH/CH$_2$Cl$_2$ to provide the desired product as an off white solid. MS m/z=452.9 [M+H].

Example 96

Method BB10

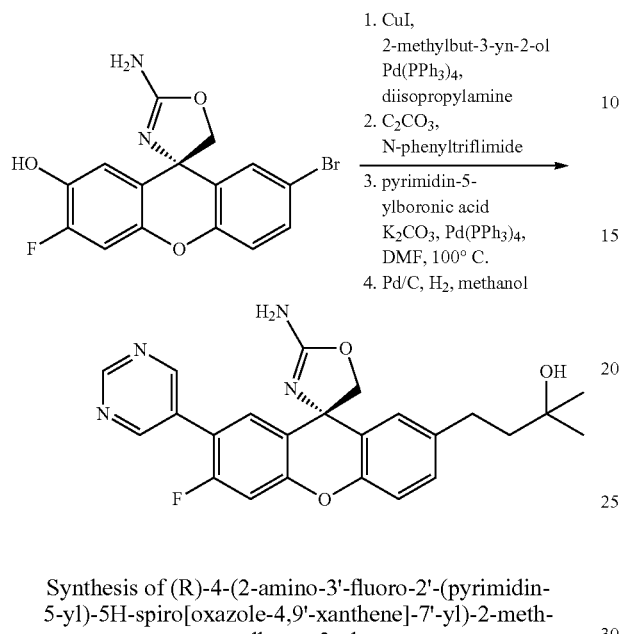

Synthesis of (R)-4-(2-amino-3'-fluoro-2'-(pyrimidin-5-yl)-5H-spiro[oxazole-4,9'-xanthene]-7'-yl)-2-methylbutan-2-ol Step 1: A vial charged with (S)-2-amino-7'-bromo-3'-fluoro-5H-spiro[oxazole-4,9'-xanthen]-2'-ol (0.225 g, 0.616 mmol), Pd(PPh$_3$)$_4$ (0.071 g, 0.062 mmol), and copper(i) iodide (0.012 g, 0.062 mmol), was treated with 3 mL DMF followed by DIPA (1.317 mL, 9.24 mmol). The solution was purged with argon for 2 minutes then 2-methylbut-3-yn-2-ol (0.301 mL, 3.08 mmol) was added and the vial was sealed and heated to 80° C. overnight. The reaction mixture was poured into saturated NH$_4$Cl (50 mL) and was extracted with EtOAc (3×25 mL). The combined organics were washed with brine, dried over MgSO$_4$ and concentrated. Purification of the crude residue by column chromatography [0-100% (9:1:0.1—CH$_2$Cl$_2$:MeOH:NH4OH)/CH$_2$Cl$_2$] provided (R)-2-amino-3'-fluoro-7'-(3-hydroxy-3-methylbut-1-ynyl)-5H-spiro[oxazole-4,9'-xanthen]-2'-ol. MS m/z=369.3 [M+H].

Step 2: A solution of (R)-2-amino-3'-fluoro-7'-(3-hydroxy-3-methylbut-1-ynyl)-5H-spiro[oxazole-4,9'-xanthen]-2'-ol (0.240 g, 0.652 mmol) in 6 mL DMF was treated with cesium carbonate (0.318 g, 0.977 mmol). The resulting slurry was allowed to stir for 15 minutes before being cooled to −10° C. and treated with 1,1,1-trifluoro-N-phenyl-N-(trifluoromethylsulfonyl)methanesulfonamide (0.244 g, 0.684 mmol). After stirring for an additional hour the reaction mixture was loaded directly only a column and purified by column chromatography [0-100% (9:1:0.1—CH$_2$Cl$_2$:MeOH:NH4OH)/CH$_2$Cl$_2$] to provide (R)-2-amino-6'-fluoro-2'-(3-hydroxy-3-methylbut-1-ynyl)-5H-spiro[oxazole-4,9'-xanthene]-7'-yl trifluoromethanesulfonate. MS m/z=501.0 [M+H].

Step 3: A solution of (R)-2-amino-6'-fluoro-2'-(3-hydroxy-3-methylbut-1-ynyl)-5H-spiro[oxazole-4,9'-xanthene]-7'-yl trifluoromethanesulfonate (0.317 g, 0.633 mmol), pyrimidin-5-ylboronic acid (0.157 g, 1.267 mmol), Pd(PPh$_3$)$_4$ (0.037 g, 0.032 mmol), and potassium carbonate (0.438 g, 3.17 mmol) in 1.5 mL dioxane was treated with 0.5 mL water and was heated to 100° C. overnight. The reaction mixture was cooled to rt and diluted with EtOAc. The layers were separated and the organic layer was dried over MgSO$_4$ filtered and concentrated. Purification of the crude residue by column chromatography [0-80% (9:1:0.1—CH$_2$Cl$_2$:MeOH:NH4OH)/CH$_2$Cl$_2$] gave (R)-4-(2-amino-3'-fluoro-2'-(pyrimidin-5-yl)-5H-spiro[oxazole-4,9'-xanthene]-7'-yl)-2-methylbut-3-yn-2-ol. MS m/z=431.0 [M+H].

Step 4: A vial charged with (R)-4-(2-amino-3'-fluoro-2'-(pyrimidin-5-yl)-5H-spiro[oxazole-4,9'-xanthene]-7'-yl)-2-methylbut-3-yn-2-ol (0.050 g, 0.116 mmol) and 10% Pd/C (1.236 mg, 0.012 mmol) was taken up in 5 mL MeOH thoroughly degassed then placed under 50 psi H$_2$ overnight. The reaction mixture was filtered through celite and concentrated in vacuo to provide an off white solid. Purification of the crude residue by column chromatography [0-80% (9:1:0.1—CH$_2$Cl$_2$:MeOH:NH$_4$OH)/CH$_2$Cl$_2$] gave (R)-4-(2-amino-3'-fluoro-2'-(pyrimidin-5-yl)-5H-spiro[oxazole-4,9'-xanthene]-7'-yl)-2-methylbutan-2-ol. MS m/z=435.0 [M+H].

Example 97

Method BB12

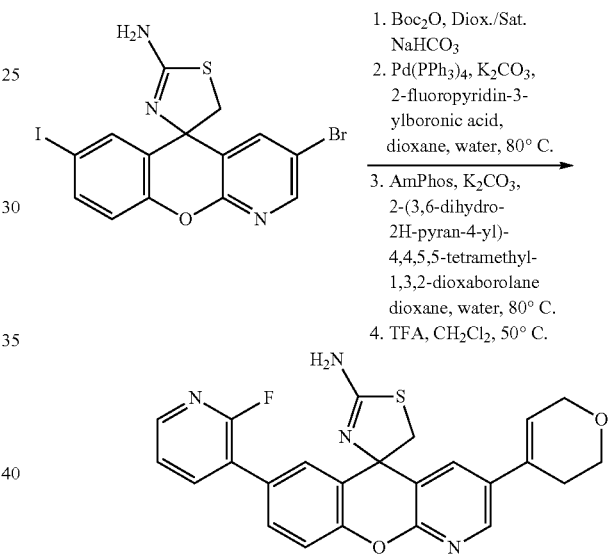

Synthesis of (S)-3-(3,6-dihydro-2H-pyran-4-yl)-7-(2-fluoropyridin-3-yl)-5'H-spiro[chromeno[2,3-b]pyridine-5,4'-thiazol]-2'-amine Step 1: 3-bromo-7-iodo-5'H-spiro[chromeno[2,3-b]pyridine-5,4'-thiazol]-2'-amine (0.770 g, 1.624 mmol; prepared as described in Method BB26) was dissolved in dioxane (8 mL). 8 mL of saturated sodium bicarbonate solution was added, followed by boc-anhydride (3.77 mL, 16.24 mmol). The reaction was stirred overnight at RT. The reaction was diluted with EtOAc and washed with water. The aqueous layer was extracted with EtOAc, and the combined organic layers were dried with sodium sulfate, filtered, and concentrated. The material was purified via silica gel chromatography (gradient elution 0-25% EtOAc:Hex) to afford tert-butyl 3-bromo-7-iodo-5'H-spiro[chromeno[2,3-b]pyridine-5,4'-thiazole]-2'-ylcarbamate as a yellow solid. MS m/z=576.0. Calc'd for C$_{19}$H$_{17}$BrIN$_3$O$_3$S: 574.23.

Step 2: A vial was charged with tert-butyl 3-bromo-7-iodo-5'H-spiro[chromeno[2,3-b]pyridine-5,4'-thiazole]-2'-ylcarbamate (0.454 g, 0.791 mmol), 2-fluoropyridin-3-ylboronic acid (0.167 g, 1.186 mmol), potassium carbonate (0.546 g, 3.95 mmol), and tetrakis(triphenylphosphine)palladium(0)

(0.091 g, 0.079 mmol). The vial was flushed with Ar (g), then Dioxane (5.27 mL) and water (2.64 mL) were added in sequence. The vial was sealed and heated at 80° C. for one hour. The reaction was diluted with EtOAc and washed with water. The aqueous layer was extracted with EtOAc, and the combined organic layers were dried with sodium sulfate, filtered, and concentrated. The material was purified via silica gel chromatography (gradient elution 0-50% EtOAc:Hex) to afford tert-butyl 3-bromo-7-(2-fluoropyridin-3-yl)-5'H-spiro[chromeno[2,3-b]pyridine-5,4'-thiazole]-2'-ylcarbamate as a light yellow solid. MS m/z=545.1. Calc'd for $C_{24}H_{20}BrFN_4O_3S$: 543.41

Step 3: A vial was charged with tert-butyl 3-bromo-7-(2-fluoropyridin-3-yl)-5'H-spiro[chromeno[2,3-b]pyridine-5,4'-thiazole]-2'-ylcarbamate (0.105 g, 0.193 mmol), 2-(3,6-dihydro-2H-pyran-4-yl)-4,4,5,5-tetramethyl-1,3,2-dioxaborolane (0.122 g, 0.580 mmol), potassium carbonate (0.134 g, 0.966 mmol), and bis(di-tert-butyl(4-dimethylaminophenyl)phosphine)dichloropalladium(II) (0.014 g, 0.019 mmol). The vial was flushed with Ar (g), then dioxane (1.288 mL) and water (0.644 mL) were added in sequence. The vial was sealed and heated at 80° C. overnight. The reaction was diluted with ethyl acetate and washed with water. The aqueous layer was extracted with ethyl acetate, and the combined organic layers were dried with sodium sulfate, filtered, and concentrated. The material was purified via silica gel chromatography (gradient elution 0-100% EtOAc:Hex) to afford tert-butyl 3-(3,6-dihydro-2H-pyran-4-yl)-7-(2-fluoropyridin-3-yl)-5'H-spiro[chromeno[2,3-b]pyridine-5,4'-thiazole]-2'-ylcarbamate as an off-white solid. MS m/z=547.2. Calc'd for $C_{29}H_{27}FN_4O_4S$: 546.61.

Step 4: A RBF was charged with tert-butyl 3-(3,6-dihydro-2H-pyran-4-yl)-7-(2-fluoropyridin-3-yl)-5'H-spiro[chromeno[2,3-b]pyridine-5,4'-thiazole]-2'-ylcarbamate (0.091 g, 0.166 mmol). The material was dissolved in 0.5 mL of $CH_2Cl_2$ and TFA (0.149 mL, 1.932 mmol) was added. The reaction was heated to 50° C. and stirred for one hour. The reaction was concentrated, diluted with $CH_2Cl_2$ and washed with saturated sodium bicarbonate solution. The aqueous layer was extracted with $CH_2Cl_2$, and the combined organic layers were washed with brine, dried with sodium sulfate, filtered, and concentrated to afford (S)-3-(3,6-dihydro-2H-pyran-4-yl)-7-(2-fluoropyridin-3-yl)-5'H-spiro[chromeno[2,3-b]pyridine-5,4'-thiazol]-2'-amine as an off-white solid. MS m/z=447.3 [M+H]$^+$. Calculated for $C_{24}H_{19}FN_4O_2S$: 446.12.

$^1$H NMR (400 MHz, DMSO-d$_6$) δ=8.40 (d, J=2.5 Hz, 1 H), 8.28-8.21 (m, 1 H), 8.14-8.04 (m, 1 H), 7.83 (d, J=2.5 Hz, 1 H), 7.66-7.61 (m, 2 H), 7.49 (ddd, J=1.8, 5.0, 7.3 Hz, 1 H), 7.42 (d, J=9.1 Hz, 1 H), 7.06 (s, 2 H), 6.29 (td, J=1.3, 2.7 Hz, 1 H), 4.25 (q, J=2.6 Hz, 2 H), 3.85 (t, J=5.5 Hz, 2 H), 3.48-3.41 (m, 2 H), 2.48-2.42 (m, 2 H)

Example 98

Method BB13

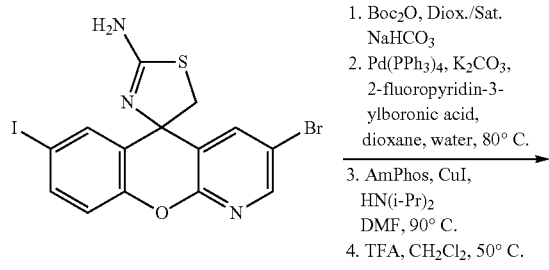

1. Boc$_2$O, Diox./Sat. NaHCO$_3$
2. Pd(PPh$_3$)$_4$, K$_2$CO$_3$, 2-fluoropyridin-3-ylboronic acid, dioxane, water, 80° C.
3. AmPhos, CuI, HN(i-Pr)$_2$ DMF, 90° C.
4. TFA, CH$_2$Cl$_2$, 50° C.

-continued

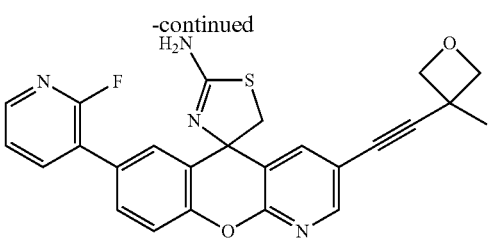

Synthesis of (S)-tert-butyl 7-(2-fluoropyridin-3-yl)-3-((3-methyloxetan-3-yl)ethynyl)-5'H-spiro[chromeno[2,3-b]pyridine-5,4'-thiazole]-2'-ylcarbamate Step 1: 3-bromo-7-iodo-5'H-spiro[chromeno[2,3-b]pyridine-5,4'-thiazol]-2'-amine (770 g, 1.624 mmol) was dissolved in dioxane (8 mL). 8 mL of saturated sodium bicarbonate solution was added, followed by boc-anhydride (3.77 mL, 16.24 mmol). The reaction was stirred overnight at RT. The reaction was diluted with EtOAc and washed with water. The aqueous layer was extracted with EtOAc, and the combined organic layers were dried with sodium sulfate, filtered, and concentrated. The material was purified via silica gel chromatography (gradient elution 0-25% EtOAc:Hex) to afford tert-butyl 3-bromo-7-iodo-5'H-spiro[chromeno[2,3-b]pyridine-5,4'-thiazole]-2'-ylcarbamate as a yellow solid. MS m/z=576.0. Calc'd for $C_{19}H_{17}BrIN_3O_3S$: 574.23.

Step 2: A vial was charged with tert-butyl 3-bromo-7-iodo-5'H-spiro[chromeno[2,3-b]pyridine-5,4'-thiazole]-2'-ylcarbamate (0.454 g, 0.791 mmol), 2-fluoropyridin-3-ylboronic acid (0.167 g, 1.186 mmol), potassium carbonate (0.546 g, 3.95 mmol), and tetrakis(triphenylphosphine)palladium(0) (0.091 g, 0.079 mmol). The vial was flushed with Ar (g), then dioxane (5.27 mL) and water (2.64 mL) were added in sequence. The vial was sealed and heated at 80° C. for one hour. The reaction was diluted with EtOAc and washed with water. The aqueous layer was extracted with EtOAc, and the combined organic layers were dried with sodium sulfate, filtered, and concentrated. The material was purified via silica gel chromatography (gradient elution 0-50% EtOAc:Hex) to afford tert-butyl 3-bromo-7-(2-fluoropyridin-3-yl)-5'H-spiro[chromeno[2,3-b]pyridine-5,4'-thiazole]-2'-ylcarbamate as a light yellow solid. MS m/z=545.1. Calc'd for $C_{24}H_{20}BrFN_4O_3S$: 543.41.

Step 3: A vial was charged with (5)-tert-butyl 3-bromo-7-(2-fluoropyridin-3-yl)-5'H-spiro[chromeno[2,3-b]pyridine-5,4'-thiazole]-2'-ylcarbamate (0.181 g, 0.333 mmol), copper (i) iodide (0.013 g, 0.067 mmol), and bis(di-tert-butyl(4-dimethylaminophenyl)phosphine)dichloropalladium(II) (0.024 g, 0.033 mmol). The vial was flushed with Ar (g), then DMF (1.665 mL), DIPA (0.712 mL, 5.00 mmol), and trimethyl((3-methyloxetan-3-yl)ethynyl)silane (0.201 mL, 0.999 mmol) were added in sequence. The reaction was heated to 90° C. and stirred for three hours. The reaction was diluted with EtOAc and washed with water. The aqueous layer was extracted with EtOAc, and the combined organic layers were dried with sodium sulfate, filtered, and concentrated. The material was purified via silica gel chromatography (gradient elution 0-50% EtOAc:Hex) to afford (S)-tert-butyl 7-(2-fluoropyridin-3-yl)-3-((3-methyloxetan-3-yl)ethynyl)-5'H-spiro[chromeno[2,3-b]pyridine-5,4'-thiazole]-2'-ylcarbamate as a yellow solid. MS m/z=559.2. Calc'd for $C_{30}H_{27}FN_4O_4S$: 558.62.

Step 4: A RBF was charged with (5)-tert-butyl 7-(2-fluoropyridin-3-yl)-3-((3-methyloxetan-3-yl)ethynyl)-5'H-spiro[chromeno[2,3-b]pyridine-5,4'-thiazole]-2'-ylcarbamate (0.101 g, 0.181 mmol). The material was dissolved in 1.5 mL of $CH_2Cl_2$ and TFA (0.256 mL, 3.33 mmol) was added. The reaction was heated to 40° C. and stirred for four hours. The reaction was diluted with $CH_2Cl_2$ and washed with saturated sodium bicarbonate solution. The aqueous layer was extracted with $CH_2Cl_2$, and the combined organic layers were dried with sodium sulfate, filtered, and concentrated. The material was purified via column chromatography (gradient elution 0-5% MeOH:$CH_2Cl_2$) to afford (S)-tert-butyl 7-(2-fluoropyridin-3-yl)-3-((3-methyloxetan-3-yl)ethynyl)-5'H-spiro[chromeno[2,3-b]pyridine-5,4'-thiazole]-2'-ylcarbamate as a white solid. MS m/z=459.3. Calc'd for $C_{25}H_{19}FN_4O_2S$: 458.51.

Example 99

Method BB14

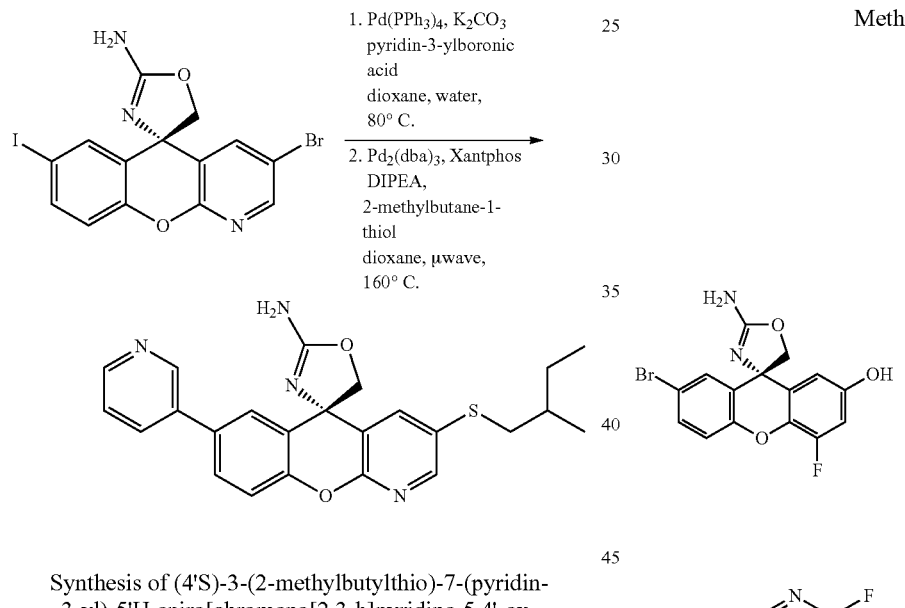

Synthesis of (4'S)-3-(2-methylbutylthio)-7-(pyridin-3-yl)-5'H-spiro[chromeno[2,3-b]pyridine-5,4'-oxazol]-2'-amine Step 1: A vial was charged with (S)-3-bromo-7-iodo-5'H-spiro[chromeno[2,3-b]pyridine-5,4'-oxazol]-2'-amine (906 mg, 1.978 mmol), pyridin-3-ylboronic acid (267 mg, 2.176 mmol), potassium carbonate (1367 mg, 9.89 mmol), and tetrakis(triphenylphosphine)palladium(0) (114 mg, 0.099 mmol). The vial was flushed with argon and dioxane (9.89 mL) and water (5.1 mL) were added in sequence. The vial was sealed and placed in an 80° C. oil bath for 4 h. The mixture was cooled to rt, diluted with EtOAc (45 mL), and brine (45 mL). The layers were separated, and the aq. layer was extracted with EtOAc (2×35 mL). The combined organic extracts were dried over sodium sulfate, filtered, and concentrated. The residue was purified by chromatography on a 40-g Redi-Sep column, eluting with 0-60% of a 90:10:1 mix of $CH_2Cl_2$/MeOH/$NH_4OH$ in $CH_2Cl_2$ to give (S)-3-bromo-7-(pyridin-3-yl)-5'H-spiro[chromeno[2,3-b]pyridine-5,4'-oxazol]-2'-amine as an off-white solid.

Step: A mixture of (S)-3-bromo-7-(pyridin-3-yl)-5'H-spiro[chromeno[2,3-b]pyridine-5,4'-oxazol]-2'-amine (53 mg, 0.130 mmol), 2-methylbutane-1-thiol (14.21 mg, 0.130 mmol), tris(dibenzylideneacetone)dipalladium (5.93 mg, 6.48 µmol), (9,9-dimethyl-9H-xanthene-4,5-diyl)bis(diphenylphosphine) (3.75 mg, 6.48 µmol), N,N-diethyl-N-isopropylpropan-2-amine (45.1 µL, 0.259 mmol), and dry 1,4-dioxane (0.5 mL) was irradiated in microwave glass vessel at 160° C. for 35 minutes. The whole was cooled to rt and the resulting solid was filtered off and washed with MeOH (3 mL). The filtrates were combined, concentrated, and purified with reverse phase HPLC. Fractions containing the product were combined, and concentrated. TFA was removed using catch and release with strong cation exchange with 2 g SCX columns. First, the material was loaded in the column with MeOH. The column washed with MeOH to remove the TFA, then with 2M $NH_3$ in MeOH to collect the product. The basic wash was collected and dried to afford (4'S)-3-(2-methylbutylthio)-7-(pyridin-3-yl)-5'H-spiro[chromeno[2,3-b]pyridine-5,4'-oxazol]-2'-amine as a white solid.

Example 100

Method BB15

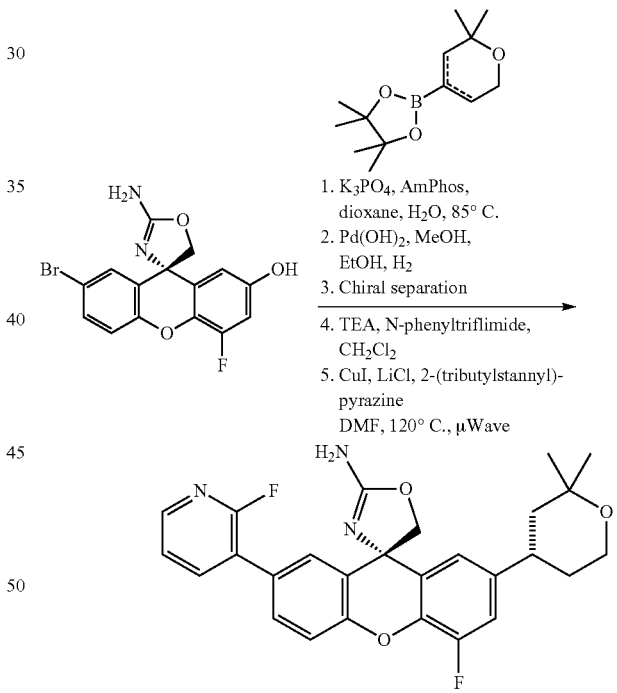

Step 1: To a solution of (S)-2-amino-2'-bromo-4'-fluoro-5H-spiro[oxazole-4,9'-xanthen]-7'-ol (1.0 g, 2.74 mmol) in 1,4-dioxane (13.5 mL) and water (4.50 mL) were added potassium phosphate (1.744 g, 8.22 mmol), and bis(di-tert-butyl(4-dimethylaminophenyl)phosphine)dichloropalladium(II) (0.097 g, 0.137 mmol). A 2:1 mixture of 2-(6,6-dimethyl-3,6-dihydro-2H-pyran-4-yl)-4,4,5,5-tetramethyl-1,3,2-dioxaborolane and 2-(2,2-dimethyl-3,6-dihydro-2H-pyran-4-yl)-4,4,5,5-tetramethyl-1,3,2-dioxaborolane (652 mg, 2.74 mmol) was added and the resulting mixture was heated to 85° C. for 4 hours. The mixture was cooled to RT and diluted with EtOAc (25 mL). The layers were separated and the aqueous layer was extracted with EtOAc (2×100 mL). The combined organic extracts were dried over MgSO₄ and silica gel was added. The solvents were removed and the solid mixture was purified by silica gel column chromatography using (solid loading, 0%-20% MeOH/CH₂Cl₂) to provide a mixture of (S)-2-amino-2'-(6,6-dimethyl-3,6-dihydro-2H-pyran-4-yl)-4'-fluoro-5H-spiro[oxazole-4,9'-xanthen]-7'-ol and (S)-2-amino-2'-(2,2-dimethyl-3,6-dihydro-2H-pyran-4-yl)-4'-fluoro-5H-spiro[oxazole-4,9'-xanthen]-7'-ol as a light yellow solid. MS m/z=576.0 [M+H].

Step 2: To a solution of (S)-2-amino-2'-(6,6-dimethyl-3,6-dihydro-2H-pyran-4-yl)-4'-fluoro-5H-spiro[oxazole-4,9'-xanthen]-7'-ol and (S)-2-amino-2'-(2,2-dihydro-2H-pyran-4-yl)-4'-fluoro-5H-spiro[oxazole-4,9'-xanthen]-7'-ol (0.760 g, 1.917 mmol) in EtOH (6 mL) and MeOH (1 mL) was added palladium hydroxide (100 mg). The mixture was stirred at RT under H₂ (42 psi) overnight. The mixture was filtered through celite, washing well with methanol. The combined filtrates were concentrated and the residue was dissolved in MeOH (20 mL). Silica gel was added and the solvent was removed in vacuo. The derived solid mixture was purified by silica gel column chromatography using (solid loading, 0%-100% EtOAc/hexane, then 5%-20% MeOH/CH₂Cl₂) to provide a mixture of 1:1 mixture of (S)-2-amino-2'-((S)-2,2-dimethyltetrahydro-2H-pyran-4-yl)-4'-fluoro-5H-spiro[oxazole-4,9'-xanthen]-7'-ol and (S)-2-amino-2'-((R)-2,2-dimethyltetrahydro-2H-pyran-4-yl)-4'-fluoro-5H-spiro[oxazole-4,9'-xanthen]-7'-ol as a light yellow solid.

Step 3: Individual diastereomers (S)-2-amino-2'-((S)-2,2-dimethyltetrahydro-2H-pyran-4-yl)-4'-fluoro-5H-spiro[oxazole-4,9'-xanthen]-7'-ol and (S)-2-amino-2'-((R)-2,2-dimethyltetrahydro-2H-pyran-4-yl)-4'-fluoro-5H-spiro[oxazole-4,9'-xanthen]-7'-ol were separated by SFC and each were processed individually.

Step 4: To a solution of (S)-2-amino-2'-((S)-2,2-dimethyltetrahydro-2H-pyran-4-yl)-4'-fluoro-5H-spiro[oxazole-4,9'-xanthen]-7'-ol (0.143 g, 0.359 mmol) in CH₂Cl₂ (2.5 mL) at 0° C. was added n-phenyltrifluoromethanesulfonimide (0.192 g, 0.538 mmol) and triethylamine (0.100 mL, 0.718 mmol). After the addition was complete, the mixture was stirred at RT for 5 h. The mixture was loading directly onto a column and was purified by silica gel column chromatography (0%-20% MeOH/CH₂Cl₂) to give the product of step 3 as a yellow solid.

Step 5: To a solution of (S)-2-amino-2'-((S)-2,2-dimethyltetrahydro-2H-pyran-4-yl)-4'-fluoro-5H-spiro[oxazole-4,9'-xanthene]-7'-yl trifluoromethanesulfonate (0.152 g, 0.287 mmol) in DMF (1.9 mL) was added copper(i) iodide (0.971 µL, 0.029 mmol), lithium chloride (0.059 mL, 2.87 mmol), tetrakis(triphenylphosphine)palladium(0) (0.033 g, 0.029 mmol), and 2-(tributylstannyl)pyrazine (0.271 mL, 0.860 mmol). The resulting mixture was then subjected to a microwave irradiation at 120° C. for 20 min. The solution was cooled to rt filtered through a plug of celite. The filtrate was purified by preparative HPLC (0%-100% MeCN 0.1% TFA/H₂O 0.1% TFA) to give a desired product as TFA salt. The derived salt was dissolved in MeOH (4 mL) and passed through a PL-HCO3 MP resin 200 mg/6 mL tube and the resin was washed with MeOH (2×5 mL). The filtrate was concentrated and dried in vacuo to give the depicted compound as a light yellow solid.

Example 101

Method BB16

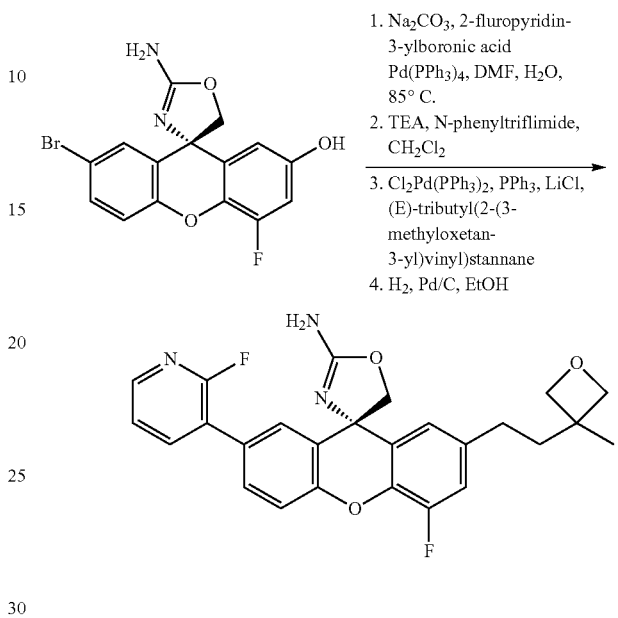

1. Na₂CO₃, 2-fluropyridin-3-ylboronic acid Pd(PPh₃)₄, DMF, H₂O, 85° C.
2. TEA, N-phenyltriflimide, CH₂Cl₂
3. Cl₂Pd(PPh₃)₂, PPh₃, LiCl, (E)-tributyl(2-(3-methyloxetan-3-yl)vinyl)stannane
4. H₂, Pd/C, EtOH Synthesis of (S)-4'-fluoro-7'-(2-fluoropyridin-3-yl)-2'-(2-(3-methyloxetan-3-yl)ethyl)-5H-spiro[oxazole-4,9'-xanthen]-2-amine Step 1: A 500 mL RBF was charged with (S)-2-amino-7'-bromo-4'-fluoro-5H-spiro[oxazole-4,9'-xanthen]-2'-ol (20.00 g, 54.8 mmol), 2-fluoropyridin-3-ylboronic acid (13.89 g, 99 mmol) and sodium carbonate (23.22 g, 219 mmol). DMF (130 mL) was added and the mixture was stirred for 1 minute before tetrakis(triphenylphosphine) palladium (4.43 g, 3.83 mmol) and water (52.2 mL) were added. The mixture was capped with argon, equipped with a reflux condenser and heated at 85° C. for 16 hrs. The mixture was cooled to room temperature and the resulting yellow precipitate was filtered. The filtrate was diluted with water (200 mL) and saturated ammonium chloride (200 mL), leading to the formation of a white precipitate and a brown semisolid. The precipitate was filtered and the semisolid was triturated with water (~200 mL) to provide a brown solid which was also filtered and washed with water. The combined solids were washed excessively with water and dried overnight under a stream of air to afford (S)-2-amino-4'-fluoro-7'-(2-fluoropyridin-3-yl)-5H-spiro[oxazole-4,9'-xanthen]-2'-ol as tan solid which was used without further purification.

Step 2: To a reaction vessel charged with (S)-2-amino-4'-fluoro-7'-(2-fluoropyridin-3-yl)-5H-spiro[oxazole-4,9'-xanthen]-2'-ol (365 mg, 0.957 mmol) in dry CH₂Cl₂ (2.5 mL) was added TEA (0.266 mL, 1.914 mmol). The resulting solution was stirred for several minutes at room temperature before 1,1,1-trifluoro-N-phenyl-N-(trifluoromethylsulfonyl)methanesulfonamide (513 mg, 1.436 mmol) was added in one portion. The mixture was maintained at rt for 1 hour before being washed sequentially with saturated NaHCO₃, water and brine. The organics were filtered through the pad of celite and concentrated in vacuo. The crude material was absorbed onto a plug of silica gel and purified by silica gel chromatography (40-50% EtOAc in hexane then 50% CH₂Cl₂:MeOH: NH4OH (90:10:1) in EtOAc to provide (S)-2-amino-5'-fluoro-2'-(2-fluoropyridin-3-yl)-5H-spiro[oxazole-4,9'-xanthene]-7'-yl trifluoromethanesulfonate as off white solid. MS m/z=513.8 [M+H].

Step 3: A glass microwave reaction vessel was charged with (S)-2-amino-5'-fluoro-2'-(2-fluoropyridin-3-yl)-5H-spiro[oxazole-4,9'-xanthene]-7'-yl trifluoromethanesulfonate (120 mg, 0.234 mmol), trans-dichlorobis(triphenylphosphine)palladium (19.69 mg, 0.028 mmol), triphenylphosphine (36.8 mg, 0.140 mmol), lithium chloride (0.041 mL, 1.987 mmol) and (E)-tributyl(2-(3-methyloxetan-3-yl)vinyl)stannane (136 mg, 0.351 mmol). DMF (2.5 mL) was added and the reaction mixture was purged with argon for several minutes. The vessel was sealed and heated in a Initiator microwave reactor (Personal Chemistry, Biotage AB, Inc., Upssala, Sweden) at 120° C. for 10 mins. The mixture was cooled to rt and portioned between saturated KF (7 mL) and CH₂Cl₂ (20 mL). The organics were washed with brine, dried over sodium sulfate filtered and concentrated. The crude material was absorbed onto a plug of silica gel and purified by chromatography through a Redi-Sep pre-packed silica gel column (40 g; 0-50% ethyl acetate in hexanes then 50% CH₂Cl₂: MeOH: NH₄OH in EtOAc) to provide (S,E)-4'-fluoro-7'-(2-fluoropyridin-3-yl)-2'-(2-(3-methyloxetan-3-yl)vinyl)-5H-spiro[oxazole-4,9'-xanthen]-2-amine as light-yellow solid. MS m/z=462.2 [M+H].

Step 4: To a reaction vessel charged with (S,E)-4'-fluoro-7'-(2-fluoropyridin-3-yl)-2'-(2-(3-methyloxetan-3-yl)vinyl)-5H-spiro[oxazole-4,9'-xanthen]-2-amine (38 mg, 0.082 mmol) and Pd/C (5%) (30 mg, 0.082 mmol) was added EtOH (1.5 mL). The reaction mixture was purged with hydrogen gas for 5 minutes and then maintained under 1 atm of hydrogen gas for 4 hours. The mixture was filtered through celite and the derived filtrate concentrated to provide (S)-4'-fluoro-7'-(2-fluoropyridin-3-yl)-2'-(2-(3-methyloxetan-3-yl)ethyl)-5H-spiro[oxazole-4,9'-xanthen]-2-amine as white solid. MS m/z=464.2 [M+H].

Example 102

Method BB17

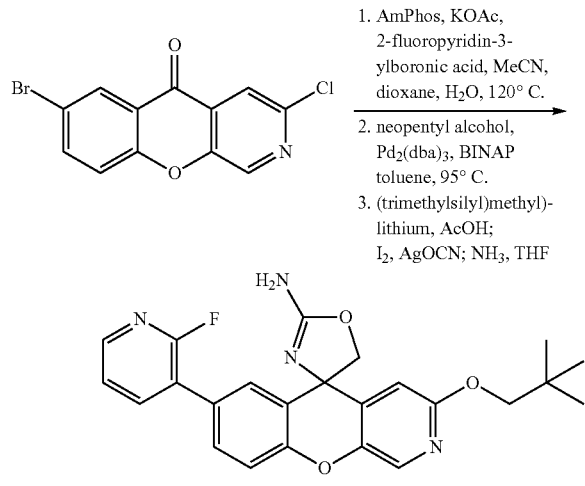

Synthesis of 7-(2-fluoropyridin-3-yl)-3-(neopentyloxy)-5'H-spiro[chromeno[2,3-c]pyridine-5,4'-oxazol]-2'-amine 2,2,2-trifluoroacetate Step 1: A vial was charged with 7-bromo-3-chloro-5H-chromeno[2,3-c]pyridin-5-one (3 g, 9.66 mmol), 2-fluoropyridin-3-ylboronic acid (1.497 g, 10.63 mmol), bis(di-tert-butyl(4-dimethylaminophenyl)phosphine) dichloropalladium(II) (0.684 g, 0.966 mmol), and KOAc (1.510 mL, 24.15 mmol). The vial was evacuated and back-filled with nitrogen (this procedure was repeated twice). ACN (20 mL), dioxane (30 mL) and water (3 mL) were added, and the vial was sealed and the reaction mixture was heated to 120° C. for 4 h. The reaction mixture was cooled to RT. Upon addition of EtOAc, a solid precipitated which was filtered off and dried under vacuum to provide 3-Chloro-7-(2-fluoropyridin-3-yl)-5H-chromeno[2,3-c]pyridin-5-one as a tan solid.

Step 2: A vial was charged with 3-chloro-7-(2-fluoropyridin-3-yl)-5H-chromeno[2,3-c]pyridin-5-one (275 mg, 0.842 mmol), neopentyl alcohol (297 mg, 3.37 mmol), Pd₂ dba₃ (38.5 mg, 0.042 mmol), racemic-2-(di-t-butylphosphino)-1,1'-binaphthyl (67.1 mg, 0.168 mmol) and cesium carbonate (686 mg, 2.104 mmol). The vial was evacuated and backfilled with nitrogen (procedure was repeated twice). Toluene (1.7 mL) was added, the vial was sealed and the reaction mixture was heated to 95° C. in an oilbath overnight. The reaction mixture was cooled to RT and partitioned between EtOAc and water. The organic phase was separated and dried over MgSO₄. The solvent was removed under reduced pressure and the residue was purified by flash chromatography (10-100% EtOAc/hexanes). 7-(2-Fluoropyridin-3-yl)-3-(neopentyloxy)-5H-chromeno[2,3-c]pyridin-5-one (60 mg) was obtained as a yellow powder.

Step 3: A solution of 7-(2-fluoropyridin-3-yl)-3-(neopentyloxy)-5H-chromeno[2,3-c]pyridin-5-one (60 mg, 0.159 mmol) in THF (2 mL) was cooled to −78° C. and ((trimethylsilyl)methyl)lithium (1.0 M solution in pentane, 0.634 mL, 0.634 mmol) was added dropwise. After 15 minutes, aqueous diluted acetic acid was added. The cold bath was removed and the reaction mixture was allowed to warm to RT. The reaction mixture was quenched with aqueous saturated bicarbonate solution and extracted with EtOAc. The organic phase was washed with saturated ammonium chloride solution and dried over MgSO₄. The solvent was removed under reduced pressure and the yellow residue was dissolved in THF (1 mL). This solution was added to a mixture of iodine (44.3 mg, 0.174 mmol) and silver cyanate (71.3 mg, 0.476 mmol) in THF (1 mL) which was prestirred for 1 h at −20° C. The reaction was allowed to warm to 0° C. After 2 h at room temperature the reaction mixture was filtered through a pad of celite. The celite was washed with THF. Ammonia (2.0M solution in isopropanol; 3.17 mL, 6.34 mmol) was added dropwise and the reaction mixture was allowed to stir overnight. The solvent was removed under reduced pressure and the remaining residue was purified by preparative HPLC. The combined fractions were concentrated to afford 7-(2-fluoropyridin-3-yl)-3-(neopentyloxy)-5'H-spiro[chromeno[2,3-c]pyridine-5,4'-oxazol]-2'-amine 2,2,2-trifluoroacetate as a light-yellow solid. (ESI, pos. ion) m/z: 435.2 [M+H].

Example 103

Method BB18

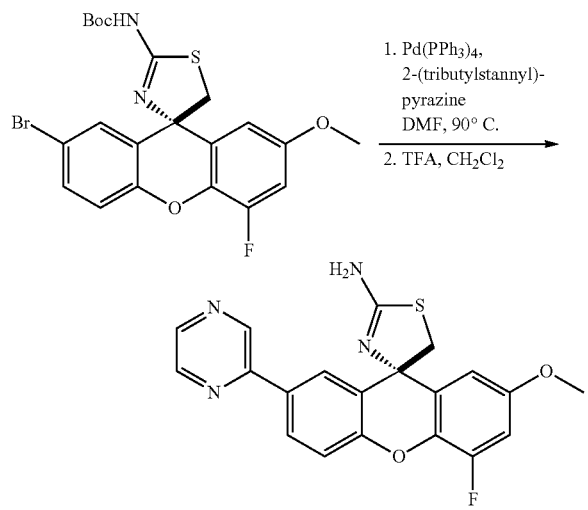

Synthesis of 4'-fluoro-2'-methoxy-7'-(pyrazin-2-yl)-5H-spiro[thiazole-4,9'-xanthen]-2-amine Step 1: A 10 ml resealable tube was charged with tert-butyl 7'-bromo-4'-fluoro-2'-methoxy-5H-spiro[thiazole-4,9'-xanthene]-2-ylcarbamate (300 mg, 0.606 mmol), tetrakis(triphenylphosphine)palladium (70.0 mg, 0.061 mmol) and DMF (3.03 ml) and 2-(tributylstannyl)pyrazine (402 mg, 1.090 mmol). The mixture was stirred for 3 hr at 110° C. The mixture was partitioned between EtOAc and water. The organic layer was washed twice with water, filtered through celite and concentrated under reduced pressure. The solids were triturated with hexane to remove excess tin residue before being filtered. Purification by silica gel chromatography (10-80% $CH_2Cl_2$/MeOH/$NH_4OH$ in $CH_2Cl_2$) to provide tert-butyl 4'-fluoro-2'-methoxy-7'-(pyrazin-2-yl)-5H-spiro[thiazole-4,9'-xanthene]-2-ylcarbamate.

Step 2: A solution of the derived carbamate in 3 mL of $CH_2Cl_2$ was treated with TFA (1 ml, 12.98 mmol). The solution was allowed to stir at RT overnight before being concentrated in vacuo. The derived material was neutralized with $NaHCO_3$ (25 mL) and extracted with EtOAc (3×25 mL). The combined organic layers were combined, filtered through celite and concentrated to afford 4'-fluoro-2'-methoxy-7'-(pyrazin-2-yl)-5H-spiro[thiazole-4,9'-xanthen]-2-amine. MS m/z=395.0 [M+H].

Example 104

Method BB19

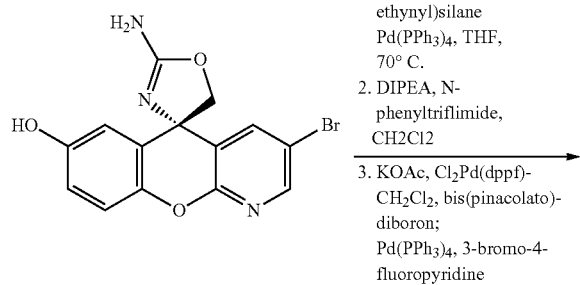

1. CuI, TBAF, trimethyl-((3-methyloxetan-3-yl)ethynyl)silane Pd(PPh$_3$)$_4$, THF, 70° C.
2. DIPEA, N-phenyltriflimide, CH2Cl2
3. KOAc, Cl$_2$Pd(dppf)-CH$_2$Cl$_2$, bis(pinacolato)diboron; Pd(PPh$_3$)$_4$, 3-bromo-4-fluoropyridine

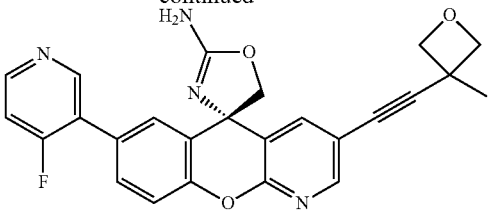

Synthesis of (S)-7-(4-fluoropyridin-3-yl)-3-((3-methyloxetan-3-yl)ethynyl)-5'H-spiro[chromeno[2,3-b]pyridine-5,4'-oxazol]-2'-amine Step 1: A sealable tube was charged with (S)-2'-amino-3-bromo-5'H-spiro[chromeno[2,3-b]pyridine-5,4'-oxazol]-7-ol (3.00 g, 8.62 mmol), tetrakis(triphenylphosphine)palladium (0.996 g, 0.862 mmol), copper(i) iodide (0.164 g, 0.862 mmol). To this was added trimethyl((3-methyloxetan-3-yl)ethynyl)silane (2.90 g, 17.23 mmol) followed by tetra-n-butylammonium fluoride (1 M in THF) (25.9 mL, 25.9 mmol). The resulting brown solution was flushed with argon and heated at 70° C. for 5 hours. The reaction was cooled to rt and diluted with 250 mL of water. The slurry was poured into a separatory funnel containing EtOAc (500 mL). The layers were separated and the aqueous layer was extracted with EtOAc (3×250 mL). In the first extraction a slight emulsion formed, this was cleared upon the addition of 50 mL of brine. The aqueous layer was then extracted with $CH_2Cl_2$ (3×200 mL). The organic layers were washed with brine, dried over sodium sulfate, filtered and concentrated in vacuo to provide a brown foam that was purified by silica gel chromatography (Redi-Sep pre-packed silica gel column (330 g), 0-100% $CH_2Cl_2$ to 10:1 methanol in methylenechloride with 0.1% ammonium hydroxide) to provide (S)-2'-amino-3-((3-methyloxetan-3-yl)ethynyl)-5'H-spiro[chromeno[2,3-b]pyridine-5,4'-oxazol]-7-ol as a brown foam.

Step 2: A solution of the derived alcohol was taken up in 85 mL of $CH_2Cl_2$ and treated sequentially with DIPEA (2.402 mL, 17.23 mmol) and n-phenyltrifluoromethane-sulfonimide (3.08 g, 8.62 mmol). The resulting solution was maintained at rt for 1.5 hours. The mixture was cooled to room temperature and concentrated to a brown oil that was purified by silica gel chromatography (Redi-Sep pre-packed silica gel column (330 g), 0-100% ethyl acetate in hexanes) to provide (S)-2'-amino-3-((3-methyloxetan-3-yl)ethynyl)-5'H-spiro[chromeno[2,3-b]pyridine-5,4'-oxazole]-7-yl trifluoromethanesulfonate as a yellow solid. MS m/z=495.9 [M+H].

Step 3: A solution of potassium acetate (0.210 g, 2.140 mmol), $PdCl_2$(dppf)-$CH_2Cl_2$ adduct (0.022 g, 0.027 mmol), (S)-2'-amino-3-((3-methyloxetan-3-yl)ethynyl)-5'H-spiro[chromeno[2,3-b]pyridine-5,4'-oxazole]-7-yl trifluoromethanesulfonate (0.265 g, 0.535 mmol), and bis(pinacolato)diboron (0.143 g, 0.562 mmol) in 5 mL DMF was heated to 100° C. for 3 hours. Pd(PPh$_3$)$_4$ (0.031 g, 0.027 mmol) was added, followed by 3-bromo-4-fluoropyridine (0.141 g, 0.802 mmol), potassium carbonate (0.296 g, 2.140 mmol), and 2 mL water. The reaction mixture was capped with argon and was heated to 100° C. for 2 hours. After cooling to RT, the reaction mixture was diluted with EtOAc and was washed sequentially with water and brine. The organics were dried over $MgSO_4$ and concentrated. Purification of the crude residue by column chromatography [0-100% (9:1 $CH_2Cl_2$:MeOH)/$CH_2Cl_2$] then HPLC (10-90% MeCN/$H_2O$) provided (S)-7-(4-fluoropyridin-3-yl)-3-(3-methyloxetan-3-yl)

ethynyl)-5'H-spiro[chromeno[2,3-b]pyridine-5,4'-oxazol]-2'-amine. MS m/z=443.0 [M+H].

Example 105

Method BB20

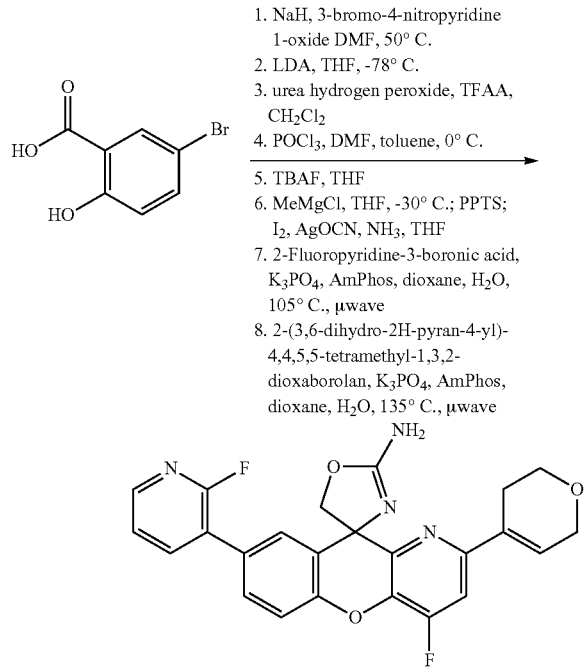

1. NaH, 3-bromo-4-nitropyridine 1-oxide DMF, 50° C.
2. LDA, THF, -78° C.
3. urea hydrogen peroxide, TFAA, CH$_2$Cl$_2$
4. POCl$_3$, DMF, toluene, 0° C.
5. TBAF, THF
6. MeMgCl, THF, -30° C.; PPTS; I$_2$, AgOCN, NH$_3$, THF
7. 2-Fluoropyridine-3-boronic acid, K$_3$PO$_4$, AmPhos, dioxane, H$_2$O, 105° C., μwave
8. 2-(3,6-dihydro-2H-pyran-4-yl)-4,4,5,5-tetramethyl-1,3,2-dioxaborolan, K$_3$PO$_4$, AmPhos, dioxane, H$_2$O, 135° C., μwave Synthesis of 2-(3,6-dihydro-2H-pyran-4-yl)-4-fluoro-8-(2-fluoropyridin-3-yl)-5'H-spiro[chromeno[3,2-b]pyridine-10,4'-oxazol]-2'-amine Step 1: To a solution of methyl 5-bromosalicylate (5.78 g, 25.00 mmol) in 30 mL of dry THF was added slowly sodium hydride (0.600 g, 25.00 mmol, 60 wt %) and the solution was stirred at rt for 15 minutes. The solvent was evaporated and the residue was dissolved in 10 mL of dry DMF. To this was added 3-bromo-4-nitropyridine 1-oxide (4.38 g, 20.00 mmol) and the reaction mixture was stirred at 50° C. for 4 h and 40° C. overnight. Water was added and the resulting solid was washed with water, filtered and dried under vacuum. Purification of the crude residue by column chromatography (CH$_2$Cl$_2$ to CH$_2$Cl$_2$/EA=10:1 to 5:1 to 3:1 to 1:1 to pure EA) gave 3-(4-bromo-2-(methoxycarbonyl)phenoxy)-4-nitropyridine 1-oxide as a yellow solid.

Step 2: To a solution of 3-(4-bromo-2-(methoxycarbonyl)phenoxy)-4-nitropyridine 1-oxide (369 mg, 1.000 mmol) in 20 mL of dry THF at −78° C. was added dropwise lithium diisopropylamide (2M, 1.99 mL, 1.999 mmol) and the reaction was stirred at −78° C. for 3 h. The reaction was quenched at this temperature with 15 mL of 1 M HCl in ether and the whole was allowed to warm up to rt. The reaction was extracted with ethyl acetate (3×100 mL). The combined organics were dried over sodium sulfate, filtered and evaporated to dryness. Purification of the crude residue by column chromatography (hexane to H/CH$_2$Cl$_2$=1:1 to CH$_2$Cl$_2$) gave 8-bromo-4-nitro-10-oxo-10H-chromeno[3,2-b]pyridine 1-oxide (20 mg, 0.059 mmol, 5.94% yield) as an offwhite solid and 8-bromo-4-nitro-10H-chromeno[3,2-b]pyridin-10-one as an light yellow solid.

Step 3: To a suspension of urea hydrogen peroxide (58.6 mg, 0.623 mmol) in 5 mL of CH$_2$Cl$_2$ at 0° C. was added dropwise trifluoroacetic anhydride (87 μL, 0.623 mmol). After stirring for 5 min at 0° C., a solution of 8-bromo-4-nitro-10H-chromeno[3,2-b]pyridin-10-one (80 mg, 0.249 mmol) in CH$_2$Cl$_2$ (5 mL) was added and the resulting reaction was stirred at rt for 1.5 h. The mixture was carefully quenched with saturated NaHCO$_3$ and extracted with ethyl acetate (5×5 mL). The combined organics were dried over sodium sulfate, filtered and evaporated to dryness. Purification of the crude residue by column chromatography (CH$_2$Cl$_2$ to CH$_2$Cl$_2$/EA=10:1 to 5:1) gave 8-bromo-4-nitro-10-oxo-10H-chromeno[3,2-b]pyridine 1-oxide as an light yellow solid.

Step 4: A suspension of 8-bromo-4-nitro-10-oxo-10H-chromeno[3,2-b]pyridine 1-oxide (90 mg, 0.267 mmol) in 1 mL of dry DMF was added dropwise to a solution of phosphorus oxychloride (44.0 μL, 0.481 mmol) in 0.2 mL of DMF and 0.5 mL of toluene at 0° C. After stirring at 0° C. for 0.5 h, the reaction was quenched with saturated NaHCO$_3$ and extracted with ethyl acetate (5×5 mL). The combined organics were dried over sodium sulfate, filtered and evaporated to dryness. Purification of the crude residue by column chromatography (CH$_2$Cl$_2$ to CH$_2$Cl$_2$/EA=100:3) gave 8-bromo-2-chloro-4-nitro-10H-chromeno[3,2-b]pyridin-10-one as a light yellow solid.

Step 5: To a solution of 8-bromo-2-chloro-4-nitro-10H-chromeno[3,2-b]pyridin-10-one (80 mg, 0.225 mmol) in 0.8 mL of DMF at 0° C. was added tetrabutylammonium fluoride (1M in THF, 0.45 mL, 0.450 mmol) dropwise. After 15 minutes, the reaction was quenched with saturated NH$_4$Cl (20 mL) and extracted with ethyl acetate (2×10 mL). The combined organics were dried over sodium sulfate, filtered and evaporated to dryness. Purification of the crude residue by column chromatography (SiO2, CH$_2$Cl$_2$ to CH$_2$Cl$_2$/EA=100:3) gave 8-bromo-2-chloro-4-fluoro-10H-chromeno[3,2-b]pyridin-10-one as an off white solid.

Step 6: To a solution of 8-bromo-2-chloro-4-fluoro-10H-chromeno[3,2-b]pyridin-10-one (44 mg, 0.134 mmol) in 10 mL of dry THF was added dropwise methylmagnesium chloride (3M in THF, 0.12 mL, 0.335 mmol) in at −78° C. The reaction was slowly warmed up to 0° C. over 2 hours. The reaction was quenched at 0° C. with saturated NH$_4$Cl (20 mL) and extracted with EtOAc (2×10 mL). The combined organics were dried over sodium sulfate, filtered and evaporated to dryness. The derived tertiary alcohol was taken up in 10 mL of CH$_2$Cl$_2$ treated with 1 mg of PPTS. After stirring for 30 minutes the mixture was cooled to 0° C. and 0.1 g of NaHCO$_3$ was added. The solvent was evaporated to dryness to give crude 8-bromo-2-chloro-4-fluoro-10-methylene-10H-chromeno[3,2-b]pyridine which was directly used in the next step. A solution of iodine (7.24 μL, 0.141 mmol) in THF at −25° C. was treated with silver cyanate (20.07 μL, 0.536 mmol). After stirring for 30 minutes, a solution of the derived olefin (8-bromo-2-chloro-4-fluoro-10-methylene-10H-chromeno[3,2-b]pyridine) in THF (10 mL) was added dropwise. The slurry was maintained at −25° C. for 2 h at which point the slurry was filtered through celite. The brown solution was concentrated to dryness, taken up in 10 mL THF, cooled to 0° C. and treated with ammonia (2M in 2-propanol (0.3 mL, 0.536 mmol). The reaction was allowed to slowly warm to rt and stirred overnight. The solvent was evaporated and the residue was purified by flash column (CH$_2$Cl$_2$ to CH$_2$Cl$_2$/EA=2:1 to 1:1 to CH$_2$Cl$_2$/MeOH=100:5) to give 8-bromo-2-chloro-4-fluoro-5'H-spiro[chromeno[3,2-b]pyridine-10,4'-oxazol]-2'-amine as an off white solid.

Step 7: A mixture of 8-bromo-2-chloro-4-fluoro-5'H-spiro[chromeno[3,2-b]pyridine-10,4'-oxazol]-2'-amine (27.0 mg, 0.070 mmol), bis-(di-tert-butyl(4-dimethylaminophenyl)phosphine)dichloropalladium(ii) (2.486 mg, 3.51 μmol), 2-fluoropyridine-3-boronic acid (10.8 mg, 0.077 mmol) and potassium phosphate (29.8 mg, 0.140 mmol) in a 2:1 mixture of dioxane and water (1.2 mL) was heated at 105° C. in the microwave for 35 min. The reaction mixture was purified by column chromatography (SiO2, $CH_2Cl_2$ to $CH_2Cl_2$/EA=2:1 to 1:1 to 3:4 to 1:2 to 1:3 to pure EA) to give 2-chloro-4-fluoro-8-(2-fluoropyridin-3-yl)-5'H-spiro[chromeno[3,2-b]pyridine-10,4'-oxazol]-2'-amine as an off white solid.

Step 8: A mixture of 2-chloro-4-fluoro-8-(2-fluoropyridin-3-yl)-5'H-spiro[chromeno[3,2-b]pyridine-10,4'-oxazol]-2'-amine (19.00 mg, 0.047 mmol), 2-(3,6-dihydro-2H-pyran-4-yl)-4,4,5,5-tetramethyl-1,3,2-dioxaborolane (24.90 mg, 0.119 mmol), bis-(di-tert-butyl(4-dimethylaminophenyl)phosphine)dichloropalladium(ii) (1.678 mg, 2.370 μmol) and potassium phosphate (22.14 mg, 0.104 mmol) in a 2:1 mixture of dioxane and water (1.5 mL was heated at 135° C. in the microwave for 25 minutes. The reaction mixture was purified by column chromatography (SiO2, $CH_2Cl_2$ to $CH_2Cl_2$/EA=3:1 to 2:1 to 1:1 to pure EA to EA/MeOH=100:5) to give 2-(3,6-dihydro-2H-pyran-4-yl)-4-fluoro-8-(2-fluoropyridin-3-yl)-5'H-spiro[chromeno[3,2-b]pyridine-10,4'-oxazol]-2'-amine as a off white solid.

Example 106

Method BB21

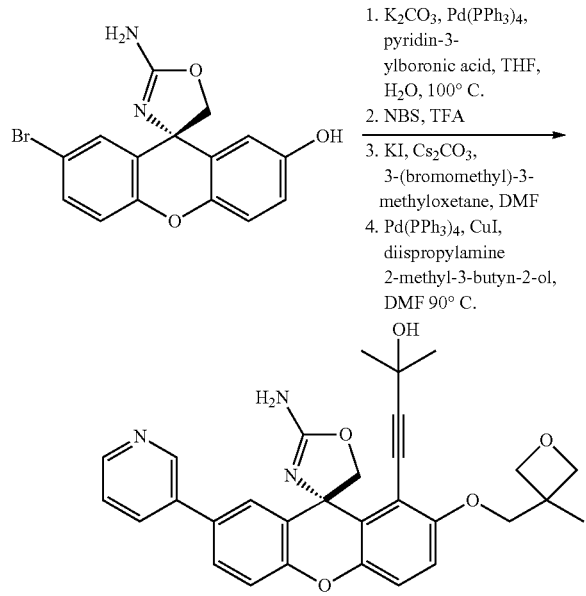

Synthesis of (S)-4-(2-amino-2'-((3-methyloxetan-3-yl)methoxy)-7'-(pyridin-3-yl)-5H-spiro[oxazole-4,9'-xanthene]-1'-yl)-2-methylbut-3-yn-2-ol Step 1: A 75-mL pressure vessel was charged with (R)-2-amino-2'-bromo-5H-spiro[oxazole-4,9'-xanthen]-7'-ol (3.25 g, 9.36 mmol), pyridin-3-ylboronic acid (2.88 g, 23.40 mmol), tetrakis(triphenylphosphine)palladium(0) (1.081 g, 0.936 mmol), THF (46.8 mL), and potassium carbonate (23.40 mL, 46.8 mmol) (as a 2.0 M aq. solution). The vessel was sealed and placed in a 100° C. oil bath for 6 hours. The mixture was partitioned between EtOAc (50 mL) and water (50 mL). The layers were separated, and the aqueous layer was extracted with EtOAc (2×30 mL. The combined mixture was dried over sodium sulfate and filtered with the aid of 10% MeOH/$CH_2Cl_2$. The filtrate was evaporated to give a yellow solid. This solid was taken up in $CH_2Cl_2$ (80 mL) and sonicated for 5 min. The solid was filtered and washed with $CH_2Cl_2$ (2×40 mL), then air-dried on the filter. The filtrate was evaporated and again taken up in $CH_2Cl_2$ (80 mL). The mixture was sonicated for 10 min, then filtered and washed with $CH_2Cl_2$ (30 mL). The solid was air-dried and combined with the first solid to give (S)-2-amino-7'-(pyridin-3-yl)-5H-spiro[oxazole-4,9'-xanthen]-2'-ol. MS m/z=346.0 [M+H].

Step 2: A 100-mL round-bottom flask was charged with (S)-2-amino-7'-(pyridin-3-yl)-5H-spiro[oxazole-4,9'-xanthen]-2'-ol (1100 mg, 3.19 mmol) and TFA (1.59E+04 μL). The mixture was sonicated for 1 minute and then the flask was submerged in an ice-bath and the resulting red solution was treated with n-bromosuccinimide (567 mg, 3.19 mmol). After stirring at 0° C. for 15 minutes the mixture was diluted with 15 mL of MeOH and evaporated in vacuo. The residue was dissolved in methanol and loaded onto a 10-g SCX-2 column. The column was eluted with methanol to remove impurities, then with 2M ammonia in methanol to give the product as a light yellow solid that was carried on without further purification. MS m/z=424.0 [M+H].

Step 3: To a slurry of (S)-2-amino-1'-bromo-7'-(pyridin-3-yl)-5H-spiro[oxazole-4,9'-xanthen]-2'-ol (710 mg, 1.674 mmol), cesium carbonate (1091 mg, 3.35 mmol) and potassium iodide (306 mg, 1.841 mmol) in DMF (6694 μL, 1.674 mmol) at 0° C. was added 3-(bromomethyl)-3-methyloxetane (304 mg, 1.841 mmol). The reaction was removed from the ice bath and allowed to warm to rt. Reaction was allowed to stir at rt overnight before being diluted with water (250 mL) and poured into a separatory funnel containing ethyl acetate (100 mL). The layers were separated and the aqueous layer was extracted with ethyl acetate (2×100 mL). The combined organic layers were washed with brine, dried over sodium sulfate, filtered and concentrated in vacuo to provide a red oil that was purified by silica gel chromatography (Redi-Sep pre-packed silica gel column (40 g), 0-100% $CH_2Cl_2$ to 10:1 methanol in methylenechloride with 0.1% ammonium hydroxide) to provide (S)-1'-bromo-2'-((3-methyloxetan-3-yl)methoxy)-7'-(pyridin-3-yl)-5H-spiro[oxazole-4,9'-xanthen]-2-amine as an off white solid. MS m/z=508.0 [M+H].

Step 4: A resealable tube was charged with (S)-1'-bromo-2'-((3-methyloxetan-3-yl)methoxy)-7'-(pyridin-3-yl)-5H-spiro[oxazole-4,9'-xanthen]-2-amine (300 mg, 0.590 mmol), 2-methyl-3-butyn-2-ol (248 mg, 2.95 mmol), tetrakis(triphenylphosphine)palladium (68.2 mg, 0.059 mmol) and copper (i) iodide (22.48 mg, 0.118 mmol). To this were added DMF (1180 μL, 0.590 mmol) and diisopropylamine (1241 μL, 8.85 mmol). The reaction was flushed with argon, sealed and heated at 90° C. for 1.5 hours. The reaction was diluted with water (100 mL) and poured into a separatory funnel containing EtOAc (50 mL). The layers were separated and the aqueous layer was extracted with ethyl acetate (3×25 mL). The combined organic layers were washed with brine, dried over sodium sulfate, filtered and concentrated in vacuo to provide a brown oil that was purified by silica gel chromatography (Redi-Sep pre-packed silica gel column (40 g), 0-100% $CH_2Cl_2$ to 10:1 methanol in methylenechloride with 0.1% ammonium hydroxide) to provide (S)-4-(2-amino-2'-((3-methyloxetan-3-yl)methoxy)-7'-(pyridin-3-yl)-5H-spiro[oxazole-4,9'-xanthene]-1'-yl)-2-methylbut-3-yn-2-ol as a light yellow solid. MS m/z=512.2 [M+H].

Example 107

Method BB22

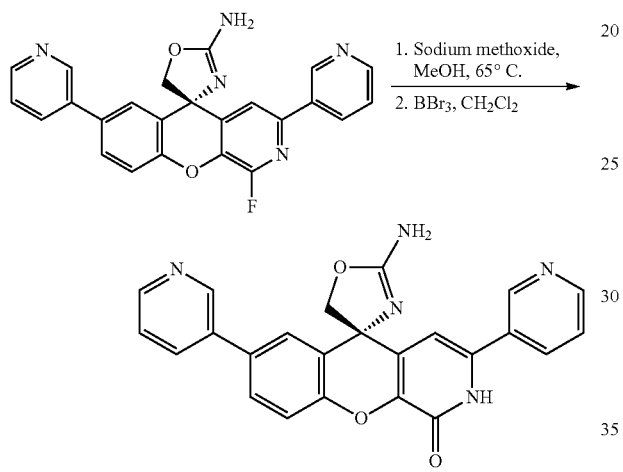

Synthesis of (S)-2'-amino-3,7-di(pyridin-3-yl)-5'H-spiro[chromeno[2,3-c]pyridine-5,4'-oxazol]-1(2H)-one Step 1: A solution of (S)-1-fluoro-3,7-di(pyridin-3-yl)-5'H-spiro[chromeno[2,3-c]pyridine-5,4'-oxazol]-2'-amine (40 mg, 0.094 mmol) and sodium methoxide (52.4 μL, 0.940 mmol) in 15 mL of MeOH was heated to 65° for 5 h. After cooling to rt, the reaction was evaporated to dryness and was partitioned between water (100 mL) and EtOAc (100 mL). The layers were separated and the organics were dried over sodium sulfate, filtered and evaporated to dryness. Flash column ($CH_2Cl_2$ to $CH_2Cl_2$/MeOH=100:5 to 100:10 to 100:20) gave (S)-1-methoxy-3,7-di(pyridin-3-yl)-5'H-spiro[chromeno[2,3-c]pyridine-5,4'-oxazol]-2'-amine as an off white solid.

Step 2: To a solution of (S)-1-methoxy-3,7-di(pyridin-3-yl)-5'H-spiro[chromeno[2,3-c]pyridine-5,4'-oxazol]-2'-amine (15 mg, 0.034 mmol) in 5 mL of dry $CH_2Cl_2$ at rt was added boron tribromide (1 M in $CH_2Cl_2$, 1.0 m in DCM (0.34 mL, 0.343 mmol) and the resulting suspension was stirred at rt for 2 h. The reaction was quenched with half saturated $NaHCO_3$ (50 mL) and extracted with EtOAc (3×25 mL). The combined organics were dried over sodium sulfate, filtered and evaporated to dryness. Purification by silica gel chromatography ($CH_2Cl_2$/MeOH=100:10 to 100:12 to 100:15 to 4:1) gave (S)-2'-amino-3,7-di(pyridin-3-yl)-5'H-spiro[chromeno[2,3-c]pyridine-5,4'-oxazol]-1(2H)-one.

Example 108

Method BB24

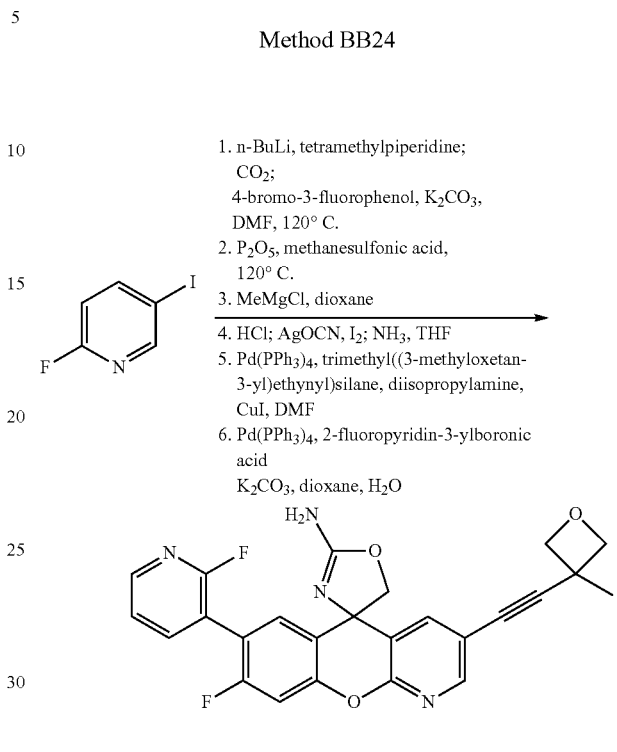

Synthesis of (4'R)-8-fluoro-7-(2-fluoropyridin-3-yl)-3-((3-methyloxetan-3-yl)ethynyl)-5'H-spiro[chromeno[2,3-b]pyridine-5,4'-oxazol]-2'-amine; and (4'S)-8-fluoro-7-(2-fluoropyridin-3-yl)-3-((3-methyloxetan-3-yl)ethynyl)-5'H-spiro[chromeno[2,3-b]pyridine-5,4'-oxazol]-2'-amine Step 1: A solution of n-butyllithium (150 mL, 375 mmol) in 950 mL THF was cooled to −10° C. and treated with a solution of 2,2,6,6-tetramethylpiperidine (72.7 mL, 428 mmol) in 50 mL THF. After stirring for 15 min, the solution was cooled to −78° C. and 2-fluoro-5-iodopyridine (80 g, 357 mmol) was added as a solution in 400 mL THF dropwise via addition funnel over 60 minutes. After stirring for an additional 30 min, $CO_2$ was bubbled through the red solution for 10 minutes. The cooling bath was removed, and $CO_2$ was bubbled through the reaction mixture for an additional hour. The reaction mixture was concentrated in vacuo, triturated with hexanes and again concentrated in vacuo. The crude residue was taken up in 360 mL DMF and was treated with 4-bromo-3-fluorophenol (68.1 g, 357 mmol) followed by potassium carbonate (61.6 g, 446 mmol). The resulting mixture was heated to 120° C. for 18 h. The reaction mixture was cooled to rt and filtered through celite. The filtrate was diluted with EtOAc (500 mL) and was acidified to pH 3 with 6 N HCl. The organics were washed with water, brine, dried over $MgSO_4$ and concentrated in vacuo. The crude residue was triturated with ether/hexanes, and the derived solid was dried under a stream of nitrogen to provide 2-(4-bromo-3-fluorophenoxy)-5-iodonicotinic acid (108.93 g, 249 mmol) as a brown solid.

Step 2: A flask charged with 2-(4-bromo-3-fluorophenoxy)-5-iodonicotinic acid (109 g, 249 mmol) and phosphorus pentoxide (70.6 g, 497 mmol) was treated with methanesulfonic acid (484 mL, 7460 mmol). After stirring for 30 minutes at room temperature, the reaction mixture was heated to 120° C. for 18 h. The reaction mixture was allowed to cool to room temperature and was poured into 1 L of ice water. After stirring for one hour, the resulting solid was filtered and subsequently washed sequentially with water and MeOH. The solid was dried to provide a 1:4 mixture of 7-bromo-6-fluoro-3-iodo-5H-chromeno[2,3-b]pyridin-5-one and 7-bromo-8-fluoro-3-iodo-5H-chromeno[2,3-b]pyridin-5-one (81.92 g, 195 mmol, 78% yield) as an off white solid.

Step 3: A suspension of 7-bromo-6-fluoro-3-iodo-5H-chromeno[2,3-b]pyridin-5-one and 7-bromo-8-fluoro-3-iodo-5H-chromeno[2,3-b]pyridin-5-one (1:4 mixture) (76 g, 182 mmol) in 1 L dioxane was placed under argon and was heated with a heat gun until it became a homogenous solution. The solution was allowed to cool to room temperature and stir 72 hours. The reaction mixture was then cooled to −10° C. and was treated with methylmagnesium chloride (106 mL, 319 mmol) dropwise with stirring over 30 min. After stirring for an additional 60 min, the reaction mixture was quenched with MeOH (25 mL). Water (250 mL) was added, followed by concentrated NH$_4$Cl solution (250 mL). The reaction mixture was concentrated in vacuo to remove most of the organics. The remaining aqueous solution was extracted with EtOAc (3×500 mL). The organics were washed with brine, dried over MgSO$_4$ and concentrated. The crude residue was taken up in ~300 mL CH$_2$Cl$_2$ and was again concentrated. This process was repeated 3×. The crude black solid was triturated with MeOH and was again dried to provide a 1:10 mixture of 7-bromo-6-fluoro-3-iodo-5-methylene-5H-chromeno[2,3-b]pyridine and 7-bromo-8-fluoro-3-iodo-5-methylene-5H-chromeno[2,3-b]pyridine (59.200 g, 142 mmol, 78% yield). This material was used without purification.

Step 4: A solution of 7-bromo-8-fluoro-3-iodo-5-methylene-5H-chromeno[2,3-b]pyridine (59.2 g, 136 mmol) in 500 mL THF was treated with HCl 4 N in dioxane (3.39 mL, 13.57 mmol) and was allowed to stir at RT for one hour at which point the reaction mixture was cooled to 0° C. A separate flask charged with a solution of iodine (37.9 g, 149 mmol) in 500 mL THF was cooled to −40° C. and treated with silver cyanate (50.8 g, 339 mmol). This mixture was allowed to stir for one hour before being treated with the solution of 7-bromo-8-fluoro-3-iodo-5-methylene-5H-chromeno[2,3-b]pyridine (59.2 g, 136 mmol) in 500 mL THF. The resulting orange slurry was maintained at 0° C. for 1 hour at which point ammonia 2 N in IPA (407 mL, 814 mmol) was added, and the reaction mixture was allowed to warm to room temperature and stir for 18 hours. The reaction mixture was filtered through celite, washing well with THF. The filtrate was quenched with saturated sodium thiosulfate solution (500 mL) and was allowed to stir for 72 hours. The reaction mixture was diluted with water (500 mL) and extracted with EtOAc (5×250 mL). The organics were washed with water then brine. The organics were dried over MgSO$_4$ and concentrated in vacuo. The crude residue was triturated with EtOAc and filtered. The remaining solid was triturated with CH$_2$Cl$_2$ and again filtered. The resulting tan solid was collected and dried under a stream of nitrogen to provide 7-bromo-8-fluoro-3-iodo-5'H-spiro[chromeno[2,3-b]pyridine-5,4'-oxazol]-2'-amine (37.90 g, 80 mmol).

Step 5: A vial charged with Pd(PPh$_3$)$_4$ (0.73 g, 0.63 mmol), copper(I) iodide (0.48 g, 2.52 mmol), 7-bromo-8-fluoro-3-iodo-5'H-spiro[chromeno[2,3-b]pyridine-5,4'-oxazol]-2'-amine (3.0 g, 6.30 mmol), trimethyl((3-methyloxetan-3-yl)ethynyl)silane (1.06 g, 6.30 mmol) and 13 mL DMF was degassed with argon and treated with DIPA (4.49 mL, 31.5 mmol). The resulting slurry was allowed to stir at RT for 18 h at which point an additional portion of copper(I) iodide (0.48 g, 2.52 mmol) was added. After stirring for an additional 4 h the reaction mixture was poured into water (50 mL) and was extracted with EtOAc (3×100 mL). The resulting suspension was filtered through a glass frit and the filtrate was dried over MgSO$_4$ and concentrated in vacuo. Purification of the crude residue by column chromatography [0-50% (9:1 CH$_2$Cl$_2$:MeOH)/CH$_2$Cl$_2$] provided 7-bromo-8-fluoro-3-((3-methyloxetan-3-yl)ethynyl)-5'H-spiro[chromeno[2,3-b]pyridine-5,4'-oxazol]-2'-amine (1.18 g, 2.66 mmol).

Step 6: A solution of Pd(PPh$_3$)$_4$ (0.077 g, 0.066 mmol), 2-fluoropyridin-3-ylboronic acid (0.19 g, 1.33 mmol), 7-bromo-8-fluoro-3-((3-methyloxetan-3-yl)ethynyl)-5'H-spiro[chromeno[2,3-b]pyridine-5,4'-oxazol]-2'-amine (0.30 g, 0.66 mmol), and potassium carbonate (0.46 g, 3.32 mmol) in 4.5 mL dioxane was treated with 1.8 mL water and was heated to 80° C. overnight. The reaction mixture cooled to rt and diluted with EtOAc (50 mL). The layers were separated and the organics were dried over MgSO$_4$, and concentrated in vacuo. Purification of the crude residue by column chromatography [0-80% (9:1 CH$_2$Cl$_2$:MeOH)/CH$_2$Cl$_2$] gave 8-fluoro-7-(2-fluoropyridin-3-yl)-3-((3-methyloxetan-3-yl)ethynyl)-5'H-spiro[chromeno[2,3-b]pyridine-5,4'-oxazol]-2'-amine (0.067 g, 0.146 mmol). Chiral separation provided (4'R)-8-fluoro-7-(2-fluoropyridin-3-yl)-3-((3-methyloxetan-3-yl)ethynyl)-5'H-spiro[chromeno[2,3-b]pyridine-5,4'-oxazol]-2'-amine (0.022 g, 0.048 mmol, peak 1) and (4'S)-8-fluoro-7-(2-fluoropyridin-3-yl)-3-((3-methyloxetan-3-yl)ethynyl)-5'H-spiro[chromeno[2,3-b]pyridine-5,4'-oxazol]-2'-amine (0.022 g, 0.048 mmol, peak 2).

Example 109

Method BB25

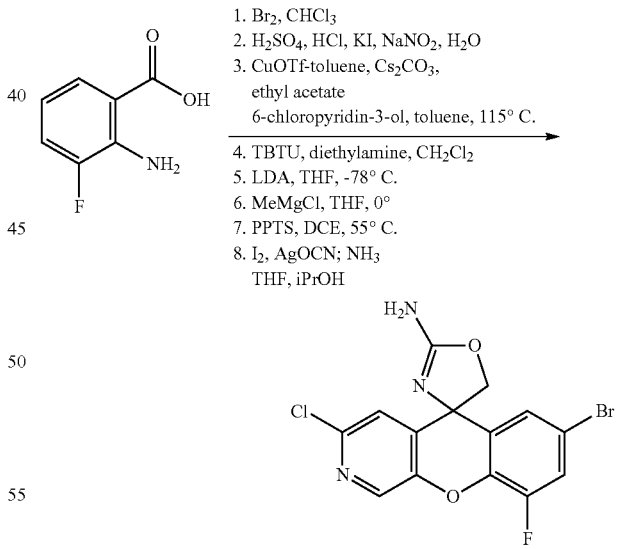

Synthesis of 7-bromo-3-chloro-9-fluoro-5'H-spiro[chromeno[2,3-c]pyridine-5,4'-oxazol]-2'-amine Step 1: Bromine (3.65 mL, 70.9 mmol) in Chloroform (250 mL) was added dropwise via an addition funnel to a suspension of 2-amino-3-fluorobenzoic acid (10 g, 64.5 mmol) in chloroform (400 mL) at RT. The solution was stirred for 12 hours at which point the resulting slurry was filtered. The solid was washed well with CH$_2$Cl$_2$ and dried under a stream of nitrogen to afford 2-amino-5-bromo-3-fluorobenzoic acid HBr.

MS m/z=233.9 [M+H].

Step 2: Sulfuric acid (47.0 mL, 882 mmol) was added to a mixture of 2-amino-5-bromo-3-fluorobenzoic acid hydrobromide (16.34 g, 51.9 mmol) and HCl (12.45 mL, 156 mmol) at 0° C. The resulting slurry was stirred at 0° C. and sodium nitrite (3.58 g, 51.9 mmol) in water (20 mL) was added dropwise over 10 minutes. The reaction was stirred 40 minutes at 0° C. before a solution of potassium iodide (17.23 g, 104 mmol) in water (20.00 mL) was added dropwise. The solution was stirred allowed to warm to RT, leading to the formation of a viscous mixture. After 1 hour at ambient temperature, the reaction was poured into ice water (500 mL) and the resulting precipitate was filtered. The black solid was washed with well water to give a dark brown solid which was dried in a vacuum oven at 50° C. for 12 hours to afford 5-bromo-3-fluoro-2-iodobenzoic acid as an orange/tan solid. MS m/z=344.8 [M+H].

Step 3: A flask was charged with 5-bromo-3-fluoro-2-iodobenzoic acid (25.5 g, 73.9 mmol), 6-chloropyridin-3-ol (11.51 g, 88.9 mmol), and cesium carbonate (48.2 g, 148 mmol). The flask was evacuated and flushed with nitrogen twice before copper (i) trifluoromethanesulfonate toluene complex (0.488 g, 0.942 mmol) was added. Toluene (181 mL) (degassed 10 minutes by bubbling nitrogen through the solution prior to use) and ethyl acetate (0.263 mL, 2.68 mmol) were added and the mixture was heated at 115° C. for 12 hrs. The reaction was cooled to rt and poured into water (250 mL). The layers are separated and the organic layer was extracted with water (3×100 mL). The combined aqueous layers are washed with diethyl ether and then the pH of the aqueous layer was brought to a pH=3-4 with 1 N HCl. The aqueous layer was then extracted with ethyl acetate (3×250 mL). The combined organic extracts were washed with saturated aqueous sodium chloride and dried over sodium sulfate. The solution was filtered and concentrated in vacuo to provide the desired product which was used directly for the next reaction without further purification. MS m/z=348.1 [M+H].

Step 4: (N,N,N',N'-tetramethyl-o-(1H-benzotriazol-1-yl) uronium tetrafluoroborate (53.1 g, 165 mmol) was added to a solution of 5-bromo-2-(6-chloropyridin-3-yloxy)-3-fluorobenzoic acid (38.2 g, 110 mmol) and diethylamine (63.3 mL, 606 mmol) in CH$_2$Cl$_2$ (500 mL) at 0° C. After stirring 5 hours at RT, the reaction was quenched with saturated aqueous sodium bicarbonate (250 mL) at RT and diluted with water (100 mL) and the organics was removed in vacuo. The mixture was diluted with EtOAc (250 mL) and the layers were separated and the aqueous layer was extracted with EtOAc (3×100 mL). The combined organic extracts were washed with saturated aqueous sodium bicarbonate, water, 1N HCl, water, brine, and dried over sodium sulfate. The solution was filtered and concentrated in vacuo to provide a residue that was purified by filtering through a pad of silica gel by eluting with 1:2 EtOAc in hexane to provide 5-bromo-2-(6-chloropyridin-3-yloxy)-N,N-diethyl-3-fluorobenzamide.

Step 5: n-Butyllithium, 2.5 M (44.8 mL, 112 mmol) was added slowly to a solution of diisopropylamine (19.16 mL, 134 mmol) in THF (400 mL) at −78° C. The resulting solution was stirred at 0° C. for 15 minutes before cooling to −78° C. A solution of 5-bromo-2-(6-chloropyridin-3-yloxy)-N,N-diethyl-3-fluorobenzamide (30 g, 74.7 mmol) in THF (400 mL), cooled to −78° C., was added dropwise via cannula under positive pressure. The resulting solution was stirred 3 hours at −78° C. before being quenched with saturated ammonium chloride (200 mL). The reaction mixture was diluted with water (20 mL) and extracted with EtOAc (3×250 mL). The combined organic extracts were washed with saturated aqueous ammonium chloride, water, saturated aqueous sodium chloride, and dried over sodium sulfate. The solution was filtered and concentrated in vacuo to provide an off white solid that was triturated with methanol. The derived solid was dried under a stream of nitrogen to provide 7-bromo-3-chloro-9-fluoro-5H-chromeno[2,3-c]pyridin-5-one. MS m/z=330.1 [M+H].

Step 6: Methyl magnesium chloride, 22 wt % in tetrahydrofuran (6.14 mL, 18.26 mmol) was added to a solution of 7-bromo-3-chloro-9-fluoro-5H-chromeno[2,3-c]pyridin-5-one (3.0 g, 9.13 mmol) in THF (40 mL) at 0° C. After 2 hours, the reaction was quenched with saturated aqueous ammonium chloride (250 mL) and diluted with water (100 mL) and extracted with EtOAc (3×200 mL). The combined organic extracts were washed with saturated aqueous ammonium chloride, water, saturated aqueous sodium chloride, and dried over sodium sulfate. The solution was filtered and concentrated in vacuo to give the crude product 7-bromo-3-chloro-9-fluoro-5-methyl-5H-chromeno[2,3-c]pyridin-5-ol which was used directly in the next reaction. MS m/z=346.0 [M+H].

Step 7: Pyridinium p-toluene-sulfonate (2.53 g, 10.06 mmol) was added to a solution of 7-bromo-3-chloro-9-fluoro-5-methyl-5H-chromeno[2,3-c]pyridin-5-ol (3.15 g, 9.14 mmol) in DCE (91 mL) at 55° C. The reaction was stirred 2.5 hours at which time TLC analysis (10:1 Hex/EtOAc) showed the reaction to be complete. The reaction was poured into saturated aqueous sodium bicarbonate (150 mL) and the layers were separated. The aqueous layer was extracted with CH$_2$Cl$_2$ (4×150 mL). The combined organic extracts were washed with saturated aqueous sodium chloride, and dried over sodium sulfate. The solution was filtered and concentrated in vacuo to give the crude product 7-bromo-3-chloro-9-fluoro-5-methylene-5H-chromeno[2,3-c]pyridine which was concentrated and used without further purification. MS m/z=327.9 [M+H].

Step 8: To a solution of iodine (2.56 g, 10.07 mmol) in THF (23 mL) at −20° C. was added silver cyanate (4.12 g, 27.5 mmol) and the mixture was stirred at −20° C. for 1 hour. To this slurry was added a solution of 7-bromo-3-chloro-9-fluoro-5-methylene-5H-chromeno[2,3-c]pyridine (2.99 g, 9.16 mmol) in THF (23.00 mL) dropwise over 5 minutes. The reaction was maintained at 0° C. for 2.5 hours at which point it was filtered through a bed of celite. The filtrate was cooled to 20° C. and treated with a 2 M solution of ammonia in i-PrOH (13.73 mL, 27.5 mmol). The resulting dark solution was allowed to warm to rt and stir for 12 hours. The reaction mixture was diluted with saturated aqueous sodium bicarbonate (200 mL) and saturated aqueous sodium thiosulfate (200 mL) and extracted with CH$_2$Cl$_2$ (3×250 mL). The combined organic extracts were washed with water, saturated aqueous sodium chloride, and dried over sodium sulfate. The solution was filtered and concentrated in vacuo to provide a residue that was purified by silica gel chromatography (100% CH$_2$Cl$_2$ followed by 1:20 MeOH in CH$_2$Cl$_2$ to provide 7-bromo-3-chloro-9-fluoro-5'H-spiro[chromeno[2,3-c]pyridine-5,4'-oxazol]-2'-amine. MS m/z=386.0 [M+H].

Example 110

Method BB26

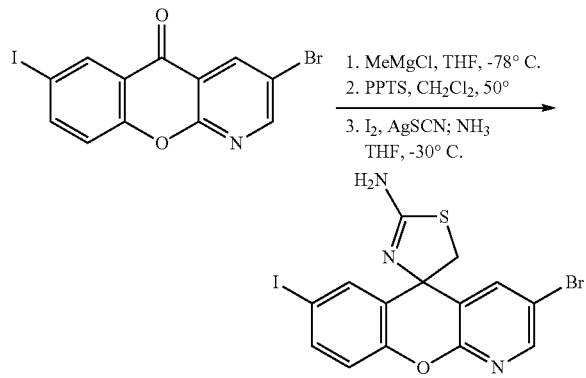

Synthesis of 3-bromo-7-iodo-5'H-spiro[chromeno[2,3-b]pyridine-5,4'-thiazol]-2'-amine Step 1: A RBF was charged with 3-bromo-7-iodo-5H-chromeno[2,3-b]pyridin-5-one (12 g, 29.9 mmol) and THF (149 mL). The mixture was cooled to −78° C. using an acetone/dry ice bath. Methylmagnesium chloride (3.0M in THF) (21.89 mL, 65.7 mmol) was added dropwise and the reaction was stirred for two hours at −78° C. The reaction was quenched with saturated ammonium chloride solution (150 mL) and warmed to RT.

The biphasic solution was extracted three times with EtOAc, and the combined organic layers were dried with sodium sulfate, filtered, and concentrated to afford crude 3-bromo-7-iodo-5-methyl-5H-chromeno[2,3-b]pyridin-5-ol as a light yellow solid. MS m/z=420.0. Calc'd for $C_{13}H_9BrINO_2$: 418.02.

Step 2: 3-bromo-7-iodo-5-methyl-5H-chromeno[2,3-b]pyridin-5-ol (12.09 g, 28.9 mmol) was taken up in $CH_2Cl_2$ (116 mL) and ppts (0.100 g, 0.578 mmol) was added. The reaction was heated to 55° C. and stirred for two hours. The reaction was concentrated to afford crude 3-bromo-7-iodo-5-methylene-5H-chromeno[2,3-b]pyridine as an orange solid. The material was used immediately in the next step.

Step 3: A RBF was charged with iodine (7.71 g, 30.4 mmol), which was dissolved in 150 mL of THF and cooled to −40° C. in a dry ice/acetonitrile bath. Silver thiocyanate (14.40 g, 87 mmol) was added and the slurry was stirred for 30 minutes. In a separate flask, 3-bromo-7-iodo-5-methylene-5H-chromeno[2,3-b]pyridine (11.57 g, 28.9 mmol, 100% yield) was dissolved in minimal THF. The olefin solution was added dropwise to the iodine slurry via cannula, maintaining the internal temperature below −30° C. The reaction was stirred for 30 minutes. Ammonia (2.0 M in IPA) (72.3 mL, 145 mmol) was added and the reaction was stirred for 18 hours, during which the reaction warmed to RT. The reaction was filtered and the solids were washed with ethyl acetate and THF. The filtrate was diluted with ethyl acetate and saturated sodium thiosulfate solution was added. The biphasic solution was stirred for ten minutes, after which the layers were separated and the aqueous layer was extracted with ethyl acetate. The combined organic layers were dried with sodium sulfate, filtered, and concentrated. The material was purified via silica gel chromatography (gradient elution 0-10% EtOAc:$CH_2Cl_2$) to afford 3-bromo-7-iodo-5'H-spiro[chromeno[2,3-b]pyridine-5,4'-thiazol]-2'-amine as a light yellow solid. MS m/z=476.1. Calc'd for $C_{14}H_9BrIN_3OS$: 474.11.

Example 111

Method BB27

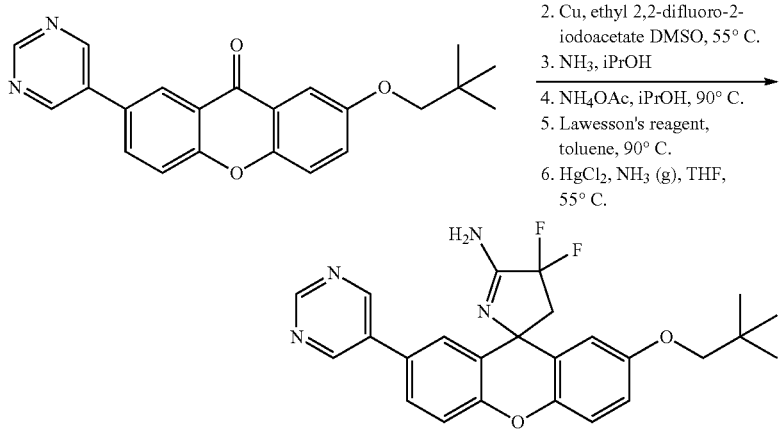

Synthesis of 4,4-difluoro-2'-(neopentyloxy)-7'-(pyrimidin-5-yl)-3,4-dihydrospiro[pyrrole-2,9'-xanthen]-5-amine Step 1: Methyl magnesium chloride, 22 wt % in THF (5.0 mL, 14.88 mmol), was added to a solution of 2-(neopentyloxy)-7-(pyrimidin-5-yl)-9H-xanthen-9-one (2.2 g, 6.10 mmol) in THF (61.0 mL) at 0° C. After 2 hours, the reaction mixture was quenched with saturated aqueous ammonium chloride (200 mL) and extracted with EtOAc (3×200 mL). The combined organic extracts were washed with saturated aqueous ammonium chloride, water, saturated aqueous sodium chloride, and dried over sodium sulfate. The solution was filtered and concentrated in vacuo to afford 9-methyl-2-

(neopentyloxy)-7-(pyrimidin-5-yl)-9H-xanthen-9-ol which used directly for the next reaction without further purification. Pyridinium p-toluene-sulfonate (0.140 g, 0.558 mmol) was added to a solution of 9-methyl-2-(neopentyloxy)-7-(pyrimidin-5-yl)-9H-xanthen-9-ol (0.200 g, 0.531 mmol) in DCE (2 mL) at 65° C. The reaction was monitored by and TLC analysis (1:1 Hex/EtOAc) and after 2 hours the solution was allowed to cool and was poured into saturated aqueous sodium bicarbonate (25 mL) and the layers were separated. The aqueous layer was extracted with $CH_2Cl_2$ (3×15 mL). The combined organic extracts were washed with saturated aqueous sodium chloride, and dried over sodium sulfate. The solution was filtered and concentrated in vacuo to give the crude material which was taken up in toluene and concentrated twice to remove residual pyridine. The product was used without further purification. MS m/z=359.2 [M+H].

Step 2: Ethyl 2,2-difluoro-2-iodoacetate (0.062 mL, 0.418 mmol) was added to a mixture of copper (0.013 g, 0.209 mmol) and 5-(9-methylene-7-(neopentyloxy)-9H-xanthen-2-yl)pyrimidine (0.150 g, 0.418 mmol) in DMSO (4 mL) (degassed 10 minutes with nitrogen prior to use) at 55° C. The reaction was stirred over 12 hours. After cooling, the reaction mixture was diluted with water and a 10:1 mixture of saturated aqueous ammonium chloride/ammonium hydroxide and extracted with $CH_2Cl_2$ (3×15 mL). The combined organic extracts were washed with a 10:1 mixture of saturated aqueous ammonium chloride/ammonium hydroxide, water, saturated aqueous sodium chloride, and dried over sodium sulfate. The solution was filtered and concentrated in vacuo to provide a residue that was purified by silica gel chromatography (1:1.5 EtOAc in hexane) to provide ethyl 2,2-difluoro-3-(9-hydroxy-2-(neopentyloxy)-7-(pyrimidin-5-yl)-9H-xanthen-9-yl). The procedure of step 2 is also described in Yang et al, *J. Org. Chem.*, Vol. 56, No. 17, 1991 pp. 5125-5132.

Step 3: Ammonia, as a 2 M solution in iPrOH (15 mL, 30.0 mmol), was added to ethyl 2,2-difluoro-3-(9-hydroxy-2-(neopentyloxy)-7-(pyrimidin-5-yl)-9H-xanthen-9-yl)propanoate (0.100 g, 0.201 mmol) at room temperature. After 30 minutes of stirring at RT the solution was concentrated to afford 2,2-difluoro-3-(9-hydroxy-2-(neopentyloxy)-7-(pyrimidin-5-yl)-9H-xanthen-9-yl)propanamide. M=470.3 [M+H].

Step 4: Ammonium acetate (0.131 g, 1.704 mmol) was added to a solution of 2,2-difluoro-3-(9-hydroxy-2-(neopentyloxy)-7-(pyrimidin-5-yl)-9H-xanthen-9-yl)propanamide (0.04 g, 0.085 mmol) in 2-Propanol (0.852 mL) and the reaction was heated to 90° C. After 30 minutes the reaction was diluted with water and saturated aqueous sodium bicarbonate (50 mL) and extracted with $CH_2Cl_2$ (3×25 mL). The combined organic extracts were washed with water, saturated aqueous sodium chloride, and dried over sodium sulfate. The solution was filtered and concentrated in vacuo to afford a residue that was purified by silica gel chromatography (1:1 EtOAc in hexane) to provide 4,4-difluoro-2'-(neopentyloxy)-7'-(pyrimidin-5-yl)spiro[pyrrolidine-2,9'-xanthen]-5-one. M=452.1 [M+H].

Step 5: Lawesson's reagent (6.72 mg, 0.017 mmol) was added to a solution of 4,4-difluoro-2'-(neopentyloxy)-7'-(pyrimidin-5-yl)spiro[pyrrolidine-2,9'-xanthen]-5-one (0.015 g, 0.033 mmol) in toluene (0.665 mL) and the reaction was heated at 90° C. for 2.5 hours before being concentrated. The crude material was purified by dissolving in a minimal amount of $CH_2Cl_2$ and filtering through a pad of silica gel eluting with 1:4 EtOAc in hexane followed by 1:1 EtOAc in hexane, to provide 4,4-difluoro-2'-(neopentyloxy)-7'-(pyrimidin-5-yl)spiro[pyrrolidine-2,9'-xanthene]-5-thione. M=468.1 [M+H].

Step 6: Ammonia gas was bubbled through a solution of 4,4-difluoro-2'-(neopentyloxy)-7'-(pyrimidin-5-yl)spiro[pyrrolidine-2,9'-xanthene]-5-thione (0.013 g, 0.028 mmol) in THF (0.350 mL) at 55° C. for 2 minutes. Mercury(II) chloride (0.011 g, 0.042 mmol) was added in one portion and ammonia gas was bubbled through for 3 more minutes while heating at 55° C. (THF solution replenished as necessary to maintain a volume of ~0.2-0.3 mL). The resulting reaction was stirred at 55° C. under nitrogen atmosphere for 14 hours. After cooling, the reaction was partitioned between $CH_2Cl_2$ (25 mL) and water (10 mL). The reaction mixture was diluted with a 10:1 mixture of saturated aqueous ammonium chloride/ammonium hydroxide, the layers were separated and the aqueous layer was extracted with $CH_2Cl_2$ (3×25 mL). The combined organic extracts were washed with a 10:1 mixture of saturated aqueous ammonium chloride/ammonium hydroxide, water, saturated aqueous sodium chloride, and dried over sodium sulfate. The solution was filtered and concentrated in vacuo to provide a residue that was purified by filtering through a pad of silica gel by eluting with 1:10 MeOH 2 M ammonia solution in $CH_2Cl_2$ followed by further purification by preparative thin layer chromatography (20:1 $CHCl_3$/MeOH) to provide 4,4-difluoro-2'-(neopentyloxy)-7'-(pyrimidin-5-yl)-3,4-dihydrospiro[pyrrole-2,9'-xanthen]-5-amine as a white solid after triturating with pentane. MS m/z=451.2 [M+H]. This procedure is analogous to that described in Foloppe et al, *Tetrahedron Letters*, 33, 20, pp. 2803-2804, 1992.

Example 112

Method BB28

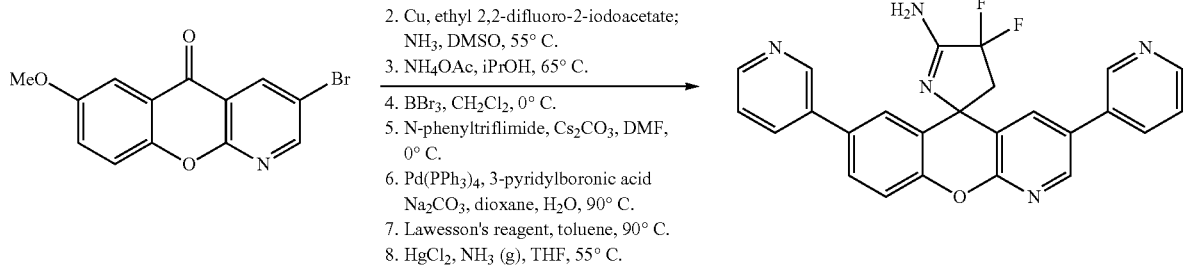

1. MeMgCl, THF, 0° C.; PPTS, DCE, 50° C.
2. Cu, ethyl 2,2-difluoro-2-iodoacetate; $NH_3$, DMSO, 55° C.
3. $NH_4OAc$, iPrOH, 65° C.
4. $BBr_3$, $CH_2Cl_2$, 0° C.
5. N-phenyltriflimide, $Cs_2CO_3$, DMF, 0° C.
6. $Pd(PPh_3)_4$, 3-pyridylboronic acid $Na_2CO_3$, dioxane, $H_2O$, 90° C.
7. Lawesson's reagent, toluene, 90° C.
8. $HgCl_2$, $NH_3$ (g), THF, 55° C.

Synthesis of (5S)-4',4'-difluoro-3,7-di-3-pyridinyl-3',4'-dihydrospiro[chromeno[2,3-b]pyridine-5,2'-pyrrol]-5'-amine Step 1: Methyl magnesium chloride, 22 wt % in THF (4.67 mL, 13.90 mmol) was added to a solution of 3-bromo-7-methoxy-5H-chromeno[2,3-b]pyridin-5-one (2.66 g, 8.69 mmol) in THF (100 mL) at 0° C. After 2 hours, the reaction was quenched with saturated aqueous ammonium chloride (200 mL) and diluted with water and extracted with EtOAc (3×150 mL). The combined organic extracts were washed with saturated aqueous ammonium chloride, water, saturated aqueous sodium chloride, and dried over sodium sulfate. The solution was filtered and concentrated in vacuo to give the crude material which was used directly for the next reaction. MS m/z=324.0 [M+H]. Pyridinium p-toluene-sulfonate (0.078 g, 0.310 mmol) was added to a solution of 3-bromo-7-methoxy-5-methyl-5H-chromeno[2,3-b]pyridin-5-ol (0.100 g, 0.310 mmol) in DCE (3 mL) at 55° C. The reaction was stirred 60 minutes before LC/MS analysis showed the reaction to be complete and the reaction was poured into saturated aqueous sodium bicarbonate (100 mL) and the layers were separated. The aqueous layer was extracted with $CH_2Cl_2$ (3×50 mL). The combined organic extracts were washed with saturated aqueous sodium chloride, and dried over sodium sulfate. The solution was filtered and concentrated in vacuo to give the crude material which was dried under vacuum and then used directly for the next reaction. MS m/z=306.1 [M+H].

Step 2: This procedure was followed in accordance with that described in Yang et al, *J. Org. Chem.*, Vol. 56, No. 17, 1991 pp. 5125-5132.

Copper (0.303 g, 4.77 mmol) and ethyl 2,2-difluoro-2-iodoacetate (0.771 mL, 5.24 mmol) were added to a solution of 3-bromo-7-methoxy-5-methylene-5H-chromeno[2,3-b]pyridine (1.45 g, 4.77 mmol) in DMSO (50 mL) (degassed 10 minutes by bubbling in nitrogen through the solvent prior to use) and the reaction was heated to 55° C. After 6 hours the reaction was allowed to cool to RT. The reaction was diluted with diethyl ether (50 mL) and washed with 10:1 saturated aqueous ammonium chloride/aqueous ammonium hydroxide, water, saturated aqueous sodium chloride, and dried over magnesium sulfate. The solution was filtered and concentrated in vacuo to give the crude material which was dissolved in ammonia, 2 M solution in i-PrOH (40 mL, 80 mmol), and stirred 12 hours before being concentrated. The crude material was purified by silica gel chromatography (1:1 EtOAc in hexanes followed by 1:20 MeOH in $CH_2Cl_2$) to provide 3-(3-bromo-5-hydroxy-7-methoxy-5H-chromeno[2,3-b]pyridin-5-yl)-2,2-difluoropropanamide. MS m/z=417.2 [M+H].

Step 3: 3-(3-bromo-5-hydroxy-7-methoxy-5H-chromeno[2,3-b]pyridin-5-yl)-2,2-difluoropropanamide (0.120 g, 0.289 mmol) was added to a saturated solution of ammonium acetate (2.228 g, 28.9 mmol) in 2-propanol (20 mL) and the mixture was heated to reflux. After 2.5 hours the reaction was allowed to cool to rt and the 2-propanol was removed in vacuo. The derived residue was partitioned between $CH_2Cl_2$ (50 mL) and water (50 mL). The layers were separated and the aqueous layer was extracted with $CH_2Cl_2$ (3×25 mL) and EtOAc (3×25 mL). The combined organic layers were washed with saturated sodium bicarbonate, water, brine, dried over sodium sulfate, and concentrated. The product was precipitated from 1:1 chloroform and diethyl ether to afford 3-bromo-4',4'-difluoro-7-methoxyspiro[chromeno[2,3-b]pyridine-5,2'-pyrrolidin]-5'-one as a gold solid. MS m/z=397.1 [M+H].

Step 4: Tribromoborane, as a 1 M solution in DCM (1.057 mL, 1.057 mmol) was added to a solution of 3-bromo-4',4'-difluoro-7-methoxyspiro[chromeno[2,3-b]pyridine-5,2'-pyrrolidin]-5'-one (0.070 g, 0.176 mmol) at 0° C. After stirring 1.5 hours at 0° C. the reaction was allowed to warm to RT and stir for an additional 1.5 hours. At this point the reaction was cooled to 0° C. and quenched with 9:1 saturated aqueous ammonium chloride/ammonium hydroxide. This mixture was diluted with water and extracted with $CH_2Cl_2$ (3×25 mL) and the EtOAc (3×25 mL). The combined organic extracts were washed with 9:1 saturated aqueous ammonium chloride/ammonium hydroxide, water, saturated aqueous sodium chloride, and dried over sodium sulfate. The solution was filtered and concentrated in vacuo to give the crude material which was used directly for the next reaction. MS m/z=383.0 [M+H].

Step 5: N-phenyltrifluoromethanesulfonimide (0.045 g, 0.125 mmol) was added to a mixture of 3-bromo-4',4'-difluoro-7-hydroxyspiro[chromeno[2,3-b]pyridine-5,2'-pyrrolidin]-5'-one (0.040 g, 0.104 mmol) and cesium carbonate (0.041 g, 0.125 mmol) in DMF (0.522 mL) at 0° C. The reaction was stirred at RT for 1.5 hours when LC/MS analysis showed the reaction to be nearly complete. The reaction was poured into water (20 mL) and extracted with EtOAc (3×15 mL). The combined organic extracts were washed with water, saturated aqueous sodium chloride, and dried over sodium sulfate. The solution was filtered and concentrated in vacuo to give the crude material. The crude material was purified by dissolving in a minimal amount of DCM and filtering through a pad of silica gel eluting with 100% $CH_2Cl_2$ followed by 1:10 MeOH in $CH_2Cl_2$, to provide 3-bromo-4',4'-difluoro-5'-oxospiro[chromeno[2,3-b]pyridine-5,2'-pyrrolidine]-7-yl trifluoromethanesulfonate. MS m/z=516.9 [M+H].

Step 6: $Pd(PPh_3)_4$ (10.77 mg, 9.32 mmol) was added to a degassed (nitrogen) solution of 3-bromo-4',4'-difluoro-5'-oxospiro[chromeno[2,3-b]pyridine-5,2'-pyrrolidine]-7-yl trifluoromethanesulfonate (0.048 g, 0.093 mmol) and 3-pyridylboronic acid (0.034 g, 0.279 mmol) in dioxane (0.900 mL) and a 2 M sodium carbonate aqueous solution (0.300 mL, 0.600 mmol). The reaction was heated at 90° C. for 1.5 hours before being cooled to rt and diluted with water (10 mL) and 9:1 saturated aqueous ammonium chloride/ammonium hydroxide (10 mL) and extracted with EtOAc (3×20 mL). The combined organic extracts were washed with 9:1 saturated aqueous ammonium chloride/ammonium hydroxide, water, saturated aqueous sodium chloride, and dried over sodium sulfate. The solution was filtered and concentrated in vacuo to give the crude material which was used directly for the next reaction without further purification. MS m/z=443.1 [M+H].

Step 7: 4',4'-difluoro-3,7-di(pyridin-3-yl)spiro[chromeno[2,3-b]pyridine-5,2'-pyrrolidin]-5'-one (0.041 g, 0.093 mmol) as the crude product from the previous reaction was dissolved in toluene (1.5 mL) along with enough $CH_2Cl_2$ to form a homogenous solution. The solution was placed in an oil bath at 90° C. and the $CH_2Cl_2$ was allowed to boil off before the reaction was capped with a septum and placed under a nitrogen atmosphere. Lawesson's reagent (0.019 g, 0.046 mmol) was added and the reaction was stirred at 90° C. for 4 hours. After cooling to rt, the reaction was poured into water (10 mL) and extracted with $CH_2Cl_2$ (3×25 mL) and a 2:1 chloroform/i-PrOH mixture (2×10 mL).

The combined organic extracts were washed with saturated aqueous sodium chloride and concentrated in vacuo to provide a residue that was purified by silica gel chromatography (1:20 followed by 1:10 MeOH in $CH_2Cl_2$) to provide 4',4'- difluoro-3,7-di(pyridin-3-yl)spiro[chromeno[2,3-b]pyridine-5,2'-pyrrolidine]-5'-thione as a orange solid. MS m/z=459.1 [M+H].

Step 8: Ammonia gas was bubbled through a solution of 4',4'-difluoro-3,7-di(pyridin-3-yl)spiro[chromeno[2,3-b]pyridine-5,2'-pyrrolidine]-5'-thione (0.019 g, 0.041 mmol) in THF (0.691 mL) at 55° C. for 2 minutes. Mercuric chloride (0.019 g, 0.070 mmol) was added in one portion and ammonia gas was bubbled through for 5 more minutes while heating at 55° C. (THF solution replenished as necessary to maintain a volume of ~0.6 mL). The resulting reaction was stirred at 55° C. under nitrogen atmosphere for 12 hours to completion. After cooling, the reaction was filtered with $CH_2Cl_2$, MeOH, and 2:1 mixture of $CHCl_3$/i-PrOH. The filtrate was diluted with a 10:1 mixture of saturated aqueous ammonium chloride/ammonium hydroxide (10 mL), the layers were separated and the aqueous layer was extracted with a 2:1 mixture of $CHCl_3$/i-PrOH (3×20 mL). The combined organic extracts were washed with a 10:1 mixture of saturated aqueous ammonium chloride/ammonium hydroxide, water, saturated aqueous sodium chloride, and dried over sodium sulfate. The solution was filtered and concentrated in vacuo to afford a residue that was purified by silica gel chromatography (1:20 MeOH in $CH_2Cl_2$, followed by 1:10 2 M ammonia MeOH solution in $CH_2Cl_2$) to provide 4',4'-difluoro-3,7-di(pyridin-3-yl)-3',4'-dihydrospiro[chromeno[2,3-b]pyridine-5,2'-pyrrol]-5'-amine as an off-white solid after triturating with diethyl ether and pentane. MS m/z=442.0 [M+H].

Example 113 (Method BB29)

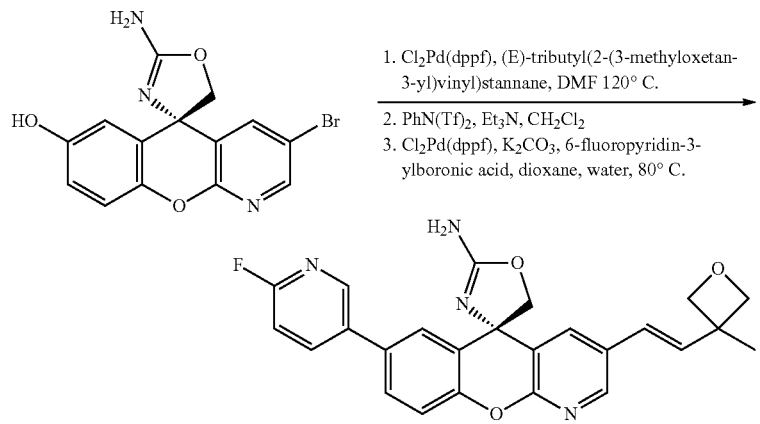

Synthesis of (S,E)-7-(6-fluoropyridin-3-yl)-3-(2-(3-methyloxetan-3-yl)vinyl)-5'H-spiro[chromeno[2,3-b]pyridine-5,4'-oxazol]-2'-amine Step 1: A vial was charged with (S)-2'-amino-3-bromo-5'H-spiro[chromeno[2,3-b]pyridine-5,4'-oxazol]-7-ol (715 mg, 2.054 mmol) and dichloro 1,1'-bis(diphenylphosphino)ferrocene palladium(II) (168 mg, 0.205 mmol). The vial was flushed with Ar (g), then DMF (1 mL) and (E)-tributyl(2-(3-methyloxetan-3-yl)vinyl)stannane (1080 µL, 3.08 mmol) were added in sequence. The vial was sealed and heated in a Biotage Initiator microwave reactor for 2.5 h at 120° C. The mixture was loaded onto a 25-g SCX-2 ion exchange column and eluted with methanol to remove impurities. The product was then eluted with 2N ammonia in MeOH. The filtrate was concentrated under vacuum, and the residue was purified by chromatography on silica gel with 0-100% of a 90:10:1 mixture of $CH_2Cl_2$/MeOH/$NH_4OH$ in $CH_2Cl_2$ to give (S,E)-2'-amino-3-(2-(3-methyloxetan-3-yl)vinyl)-5'H-spiro[chromeno[2,3-b]pyridine-5,4'-oxazol]-7-ol as a brown oil. MS m/z=366.2. Calc'd for $C_{20}H_{20}N_3O_4$: 366.2.

Step 2: A 100-mL RBF was charged with (S,E)-2'-amino-3-(2-(3-methyloxetan-3-yl)vinyl)-5'H-spiro[chromeno[2,3-b]pyridine-5,4'-oxazol]-7-ol (355 mg, 0.972 mmol), $CH_2Cl_2$ (9.7 mL), triethylamine (271 µL, 1.943 mmol), resulting in a clear, pale brown solution. 1,1,1-Trifluoro-N-phenyl-N-(trifluoromethylsulfonyl)methanesulfonamide (364 mg, 1.020 mmol) was added, and the resulting mixture was stirred for 16 h. An additional portion of 1,1,1-trifluoro-N-phenyl-N-(trifluoromethylsulfonyl)methanesulfonamide (40 mg) was added, and the mixture was stirred for an additional 2 h. The mixture was concentrated under vacuum, and the residue was purified by chromatography on an silica gel, eluting with 0-5% MeOH/$CH_2Cl_2$ to give (S,E)-2'-amino-3-(2-(3-methyloxetan-3-yl)vinyl)-5'H-spiro[chromeno[2,3-b]pyridine-5,4'-oxazole]-7-yl trifluoromethanesulfonate as an off-white solid. MS m/z=498.0. Calc'd for $C_{21}H_{19}F_3N_3O_6S$: 498.1.

Step 3: Similar to a Suzuki reaction, a vial was charged with (S,E)-2'-amino-3-(2-(3-methyloxetan-3-yl)vinyl)-5'H-spiro[chromeno[2,3-b]pyridine-5,4'-oxazole]-7-yl trifluoromethanesulfonate (80 mg, 0.161 mmol), 6-fluoropyridin-3-ylboronic acid (68.0 mg, 0.482 mmol), potassium carbonate (111 mg, 0.804 mmol), and dichloro 1,1'-bis(diphenylphosphino)ferrocene palladium(II) (1.313 mg, 1.608 µmol). The vial was flushed with Ar (g), then dioxane (1 mL) and water (0.5 mL) were added. The vial was sealed and heated to 80° C. for 4 h. The reaction mixture was cooled to RT, partitioned between water and EtOAc, and the aq. layer was extracted with EtOAc (2×). The combined organic extracts were dried over sodium sulfate, filtered, and concentrated under vacuum. The residue was purified by chromatography on silica gel eluting with 0-80% of a 90:10:1 mixture of $CH_2Cl_2$/MeOH/$NH_4OH$ in $CH_2Cl_2$ to give ca. 55 mg of an light orange solid. The solid was dissolved in MeOH and purified by reverse-phase HPLC (10-70% $CH_3CN$/$H_2O$ with 0.1% TFA). The fractions containing product were poured onto a 2-g SCX-2 ion exchange column and eluted with methanol to remove impurities.

The product was eluted with 2N ammonia in MeOH. The filtrate was concentrated under vacuum to give 29 mg of a white solid. The solid was repurified by chromatography on silica gel as before to give (S,E)-7-(6-fluoropyridin-3-yl)-3-(2-(3-methyloxetan-3-yl)vinyl)-5'H-spiro[chromeno[2,3-b]pyridine-5,4'-oxazol]-2'-amine as a white solid. MS m/z=445.2. Calc'd for $C_{25}H_{22}FN_4O_3$: 445.2.

Example 114 (Method BB30)

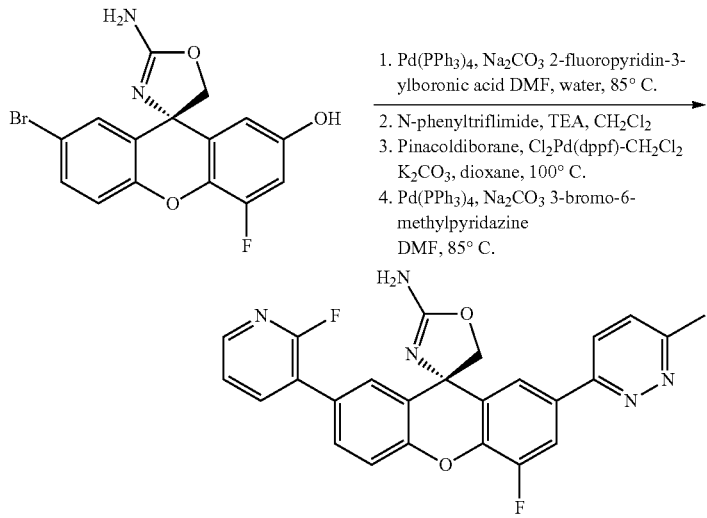

Synthesis of (S)-4'-fluoro-7'-(2-fluoropyridin-3-yl)-2'-(6-methylpyridazin-3-yl)-5H-spiro[oxazole-4,9'-xanthen]-2-amine Step 1: Sodium carbonate (saturated, 2 mL), Pd(PPh₃)₄ (0.237 g, 0.205 mmol), (S)-2-amino-7'-bromo-4'-fluoro-5H-spiro[oxazole-4,9'-xanthen]-2'-ol (0.75 g, 2.054 mmol), and 2-fluoropyridine-3-boronic acid (310 mg, 2.18 mmol) were combined in DMF (5 mL). The solution was heated at 85° C. overnight before being cooled to rt. The solution was diluted with water (25 ml) and filtered. The solids were triturated with MeOH and dried under vacuum to afford (S)-2-amino-4'-fluoro-7'-(2-fluoropyridin-3-yl)-5H-spiro[oxazole-4,9'-xanthen]-2'-ol as a tan solid. MS m/z=382.0 [M+H].

Step 2: (S)-2-amino-4'-fluoro-7'-(2-fluoropyridin-3-yl)-5H-spiro[oxazole-4,9'-xanthen]-2'-ol (900 mg, 2.360 mmol) and TEA (0.658 ml, 4.72 mmol) were combined in 25 ml of CH₂Cl₂, and 1,1,1-trifluoro-N-phenyl-N-(trifluoromethylsulfonyl)methanesulfonamide (1012 mg, 2.83 mmol) was added. The derived solution was stirred at RT overnight. The solution was loaded directly on a silica column. The product was purified via silica gel column chromatography (RediSep 40 g column) eluting with 10-70% 90/10/1 (CH₂Cl₂/MeOH/ammonia) in CH₂Cl₂ to afford (S)-2-amino-5'-fluoro-2'-(2-fluoropyridin-3-yl)-5H-spiro[oxazole-4,9'-xanthene]-7'-yl trifluoromethanesulfonate as a yellow solid solid. MS m/z=514.0 [M+H].

Step 3: A 15 mL resealable tube was charged with (S)-2-amino-5'-fluoro-2'-(2-fluoropyridin-3-yl)-5H-spiro[oxazole-4,9'-xanthene]-7'-yl trifluoromethanesulfonate (1.07 g, 2.084 mmol), Cl₂Pd(dppf)-CH₂Cl₂ complex (0.170 g, 0.208 mmol), bis-pinacolatodiboron (0.900 g, 3.54 mmol), KOAc (0.614 g, 6.25 mmol) and dioxane (6.95 mL). The vial was sealed and heated at 100° C. overnight. The mixture was cooled to rt and filtered through celite. The filtrate was partitioned between ethyl acetate (50 mL) and water (25 mL). The organic layer was washed with brine, filtered through celite and concentrated in vacuo. The derived residue was redissolved in EtOAc (6 mL) and ~10 ml of hexane was added. The resulting light yellow solution was decanted from the black oil and concentrated in vacuo to give a tan solid. This solid was then triturated with 200 mL hexane and the resulting precipitate was filtered and dried in vacuo to afford (S)-4'-fluoro-7'-(2-fluoropyridin-3-yl)-2'-(4,4,5,5-tetramethyl-1,3,2-dioxaborolan-2-yl)-5H-spiro[oxazole-4,9'-xanthen]-2-amine as a beige solid.

Step 4: Sodium carbonate (saturated, 1 mL), Pd(PPh₃)₄ (23.52 mg, 0.020 mmol), (S)-4'-fluoro-7'-(2-fluoropyridin-3-yl)-2'-(4,4,5,5-tetramethyl-1,3,2-dioxaborolan-2-yl)-5H-spiro[oxazole-4,9'-xanthen]-2-amine (200 mg, 0.407 mmol), and 3-bromo-6-methylpyridazine (141 mg, 0.814 mmol) were combined in DMF (5 mL). The solution was heated at 85° C. overnight. The solution was filtered through celite and the derived residue was purified via Gilson HPLC (gradient elution 25-65% MeCN/H₂O, 0.1% TFA) to afford (S)-4'-fluoro-7'-(2-fluoropyridin-3-yl)-2'-(6-methylpyridazin-3-yl)-5H-spiro[oxazole-4,9'-xanthen]-2-amine as an off white solid. MS m/z=458.0 [M+H].

Example 115a & 115b (Method BB31)

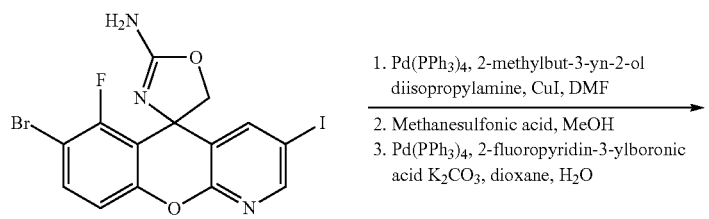

-continued

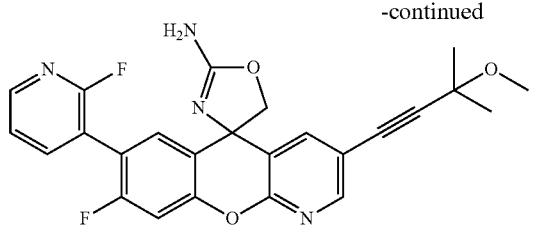

Synthesis of (4'R)-8-fluoro-7-(2-fluoropyridin-3-yl)-3-(3-methoxy-3-methylbut-1-ynyl)-5'H-spiro[chromeno[2,3-b]pyridine-5,4'-oxazol]-2'-amine (115a) and (4'S)-8-fluoro-7-(2-fluoropyridin-3-yl)-3-(3-methoxy-3-methylbut-1-ynyl)-5'H-spiro[chromeno[2,3-b]pyridine-5,4'-oxazol]-2'-amine (115b)

Step 1: A vial charged with Pd(PPh$_3$)$_4$ (0.485 g, 0.420 mmol), copper(i) iodide (0.080 g, 0.420 mmol), 7-bromo-8-fluoro-3-iodo-5'H-spiro[chromeno[2,3-b]pyridine-5,4'-oxazol]-2'-amine (2.000 g, 4.20 mmol), 2-methylbut-3-yn-2-ol (0.353 g, 4.20 mmol) and 9 mL DMF was degassed with argon and treated with DIPA (2.99 mL, 21.01 mmol). The resulting black mixture was allowed to stir at RT for 3 hours. The reaction mixture was then poured into water (25 mL) and extracted with EtOAc (3×30 mL). The organics were dried over MgSO$_4$ and concentrated in vacuo. Purification of the crude residue by column chromatography [0-50% (9:1 CH$_2$Cl$_2$:MeOH)/CH$_2$Cl$_2$] provided 4-(2'-amino-7-bromo-8-fluoro-5'H-spiro[chromeno[2,3-b]pyridine-5,4'-oxazole]-3-yl)-2-methylbut-3-yn-2-ol.

Step 2: A solution of 4-(2'-amino-7-bromo-8-fluoro-5'H-spiro[chromeno[2,3-b]pyridine-5,4'-oxazole]-3-yl)-2-methylbut-3-yn-2-ol (0.580 g, 1.342 mmol) in 10 mL MeOH was treated with methanesulfonic acid (0.871 mL, 13.42 mmol). The resulting solution was allowed to stir at RT for 72 hours and was then heated at 85° C. for 3 hours. The reaction mixture was poured into saturated NaHCO$_3$ (50 mL) and was extracted with EtOAc (3×25 mL). The organics were washed with brine, dried over MgSO$_4$ and concentrated in vacuo. Purification of the crude residue by column chromatgraphy [0-100% (95:5 EtOAc/MeOH)/CH$_2$Cl$_2$] afforded 7-bromo-8-fluoro-3-(3-methoxy-3-methylbut-1-ynyl)-5'H-spiro[chromeno[2,3-b]pyridine-5,4'-oxazol]-2'-amine Step 3: A solution of Pd(PPh$_3$)$_4$ (0.064 g, 0.055 mmol), 2-fluoropyridin-3-ylboronic acid (0.155 g, 1.102 mmol), 7-bromo-8-fluoro-3-(3-methoxy-3-methylbut-1-ynyl)-5'H-spiro[chromeno[2,3-b]pyridine-5,4'-oxazol]-2'-amine (0.246 g, 0.551 mmol), and potassium carbonate (0.381 g, 2.76 mmol) in 5 mL dioxane was treated with 2 mL water and was heated to 80° C. overnight. The reaction mixture was cooled to rt and diluted with EtOAc (25 mL). The mixture was dried over MgSO$_4$ and concentrated. Purification of the crude residue by column chromatography [0-80% (9:1 CH$_2$Cl$_2$:MeOH)/CH$_2$Cl$_2$] provided a mixture of (4'R)-8-fluoro-7-(2-fluoropyridin-3-yl)-3-(3-methoxy-3-methylbut-1-ynyl)-5'H-spiro[chromeno[2,3-b]pyridine-5,4'-oxazol]-2'-amine and (4'S)-8-fluoro-7-(2-fluoropyridin-3-yl)-3-(3-methoxy-3-methylbut-1-ynyl)-5'H-spiro[chromeno[2,3-b]pyridine-5,4'-oxazol]-2'-amine (0.132 g, 0.285 mmol). Chiral separation of this material provided (4'R)-8-fluoro-7-(2-fluoropyridin-3-yl)-3-(3-methoxy-3-methylbut-1-ynyl)-5'H-spiro[chromeno[2,3-b]pyridine-5,4'-oxazol]-2'-amine (peak 1) and (4'S)-8-fluoro-7-(2-fluoropyridin-3-yl)-3-(3-methoxy-3-methylbut-1-ynyl)-5'H-spiro[chromeno[2,3-b]pyridine-5,4'-oxazol]-2'-amine (peak 2).

Example 116 (Method BB32)

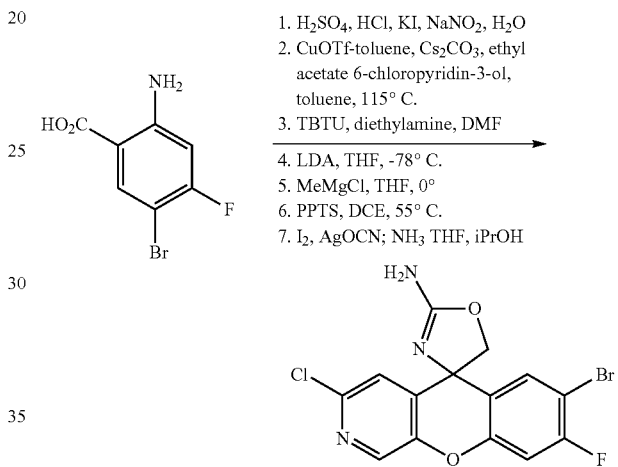

Synthesis of -bromo-3-chloro-8-fluoro-5'H-spiro[chromeno[2,3-c]pyridine-5,4'-oxazol]-2'-amine Step 1: Sulfuric acid (19.36 mL, 363 mmol) was added to a solution of 2-amino-5-bromo-4-fluorobenzoic acid (5.00 g, 21.37 mmol) in concentrated HCl (5.13 mL, 64.1 mmol) at 0° C. To this was added a solution of sodium nitrate (1.816 g, 21.37 mmol) in water (9 mL). The reaction was stirred for 40 minutes at 0° C. before potassium iodide (7.09 g, 42.7 mmol) in water (9.00 mL) was added dropwise. The solution was stirred at rt for 1 hour, at which point it had become a viscous oil. The mixture was poured into a mixture of ice water (250 mL) with EtOAc (200 mL). The layers were separated and the aqueous layer was extracted with EtOAc (3×100 mL). The combined organic extracts were washed with 1N HCl, 1 N aqueous sodium sulfite, and dried over sodium sulfate. The solution was filtered and concentrated in vacuo to give 5-bromo-4-fluoro-2-iodobenzoic acid.

Step 2: A flask was charged with 5-bromo-4-fluoro-2-iodobenzoic acid (4.00 g, 11.60 mmol), 6-chloropyridin-3-ol (1.803 g, 13.92 mmol), and cesium carbonate (7.56 g, 23.19 mmol). The flask was evacuated and flushed with nitrogen twice before copper (I) trifluoromethanesulfonate toluene complex (0.156 g, 0.302 mmol) was added. Toluene (58.0 mL) (degassed 10 minutes by bubbling nitrogen through the solution prior to use) and ethyl acetate (0.084 mL, 0.858 mmol) were added and the mixture was heated at 115° C. After 2 hours, the reaction was allowed to cool to RT and the mixture was diluted with water (50 mL) and stirred vigorously for 15 minutes. After diluting with ether (200 mL), the layers were separated and the organic layer was extracted with 10% sodium carbonate. The pH of the combined aqueous layers was adjusted to pH ~2 and extracted with ethyl acetate. The combined organic layers were washed with saturated sodium chloride, dried over sodium sulfate, filtered, and concentrated to afford 5-bromo-2-(6-chloropyridin-3-yloxy)-4-fluorobenzoic acid as a solid. MS m/z=347.9 [M+H].

Step 3: (N,N,N',N'-Tetramethyl-o-(1h-benzotriazol-1-yl) uronium tetrafluoroborate (6.95 g, 21.64 mmol) was added to a solution of 5-bromo-2-(6-chloropyridin-3-yloxy)-4-fluorobenzoic acid (5.00 g, 14.43 mmol) and diethylamine (8.00 mL, 77 mmol) in DMF (70 mL) at 0° C. The reaction was stirred 1.5 hours before being quenched with saturated sodium bicarbonate (100 mL). The reaction mixture was diluted with water (50 mL) and extracted with EtOAc (3×50 mL). The combined organic extracts were washed with saturated aqueous ammonium chloride, water, 10% aqueous sodium carbonate, saturated aqueous sodium chloride, and dried over sodium sulfate. The solution was filtered and concentrated in vacuo to provide a residue that was purified by silica gel chromatography (1:2 EtOAc in hexane) to provide 5-bromo-2-(6-chloropyridin-3-yloxy)-N,N-diethyl-4-fluorobenzamide. MS m/z=403.0 [M+H].

Step 4: n-Butyl lithium (3.14 mL, 7.84 mmol) was added to a solution of diisopropylamine (1.341 mL, 9.41 mmol) in THF (40 mL) at −78° C. The resulting solution was stirred at 0° C. for 15 minutes before being added dropwise via cannula to a solution of 5-bromo-2-(6-chloropyridin-3-yloxy)-N,N-diethyl-4-fluorobenzamide (2.1 g, 5.23 mmol) in THF (40.0 mL) cooled to −78° C. under positive pressure. The resulting solution was stirred 3 hours at −78° C. before being quenched with saturated ammonium chloride (100 mL). The reaction mixture was diluted with water (50 mL) and extracted with EtOAc (3×75 mL). The combined organic extracts were washed with saturated aqueous $NH_4Cl$, water, saturated aqueous NaCl, and dried over sodium sulfate. The solution was filtered and concentrated in vacuo to give the crude material. The crude material was purified by dissolving in a minimal amount of $CH_2Cl_2$ and filtering through a pad of silica gel by eluting with 1:10 EtOAc in hexane, to provide 7-bromo-3-chloro-8-fluoro-5H-chromeno[2,3-c]pyridin-5-one as a off-white solid. MS m/z=330.0 [M+H].

Step 5: Methylmagnesium chloride, 3.0 M solution in THF (0.958 mL, 2.87 mmol) was added to a solution of 7-bromo-3-chloro-8-fluoro-5H-chromeno[2,3-c]pyridin-5-one (0.590 g, 1.796 mmol) in THF (6 mL) at 0° C. After 1.5 hours the reaction was quenched with saturated aqueous ammonium chloride (50 mL) and extracted with EtOAc (2×50 mL). The combined organic extracts were washed with water, saturated aqueous sodium chloride, and dried over sodium sulfate. The solution was filtered and concentrated in vacuo to give the crude material which was used directly for the next reaction without further purification.

Step 6: Pyridinium p-toluenesulfonate (0.023 g, 0.090 mmol) was added to a solution of 7-bromo-3-chloro-8-fluoro-5-methyl-5H-chromeno[2,3-c]pyridin-5-ol (0.619 g, 1.796 mmol) in DCE (7.19 mL) at 65° C. After 1.5 hours, the reaction was judged complete by LC/MS analysis and the solution was allowed to cool to rt and was poured into saturated sodium bicarbonate (50 mL). The layers were separated and the aqueous layer was extracted with $CH_2Cl_2$ (3×25 mL). The combined organic extracts were washed with saturated aqueous sodium chloride, and dried over sodium sulfate. The solution was filtered and concentrated in vacuo to afford 7-bromo-3-chloro-8-fluoro-5-methylene-5H-chromeno[2,3-c]pyridine which was used directly for the next reaction without further purification. MS m/z=327.9 [M+H].

Step 7: To a solution of iodine (0.502 g, 1.977 mmol) in THF (4 mL) at −20° C. was added silver cyanate (0.202 mL, 5.39 mmol) and the mixture was stirred at −20° C. for 1 hour. 7-bromo-3-chloro-8-fluoro-5-methylene-5H-chromeno[2,3-c]pyridine (0.587 g, 1.798 mmol) as a solution in THF (5.00 mL) was added slowly by syringe and the mixture was stirred at 0° C. for 2.5 hours. The whole was then filtered through Celite with the aid of THF (~6 mL). A 2 M ammonia solution in i-PrOH (2.70 mL, 5.39 mmol) was added slowly to the filtrate and the resulting solution was stirred at RT for 3.5 hours. The reaction mixture was diluted with saturated aqueous sodium bicarbonate and saturated aqueous $NaHSO_3$ (25 mL) and extracted with $CH_2Cl_2$ (3×25 mL). The combined organic extracts were washed with water, saturated aqueous sodium chloride, and dried over sodium sulfate. The solution was filtered and concentrated in vacuo to afford 7-bromo-3-chloro-8-fluoro-5'H-spiro[chromeno[2,3-c]pyridine-5,4'-oxazol]-2'-amine. MS m/z=386.0 [M+H].

Example 117 (Method BB33)

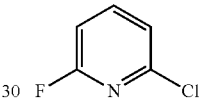

1. LDA, B(OPr)₃, -78° C.; NaOH, H₂O₂; MOMCl, K₂CO₃, acetone
2. LDA, 5-bromo-2-fluorobenzaldehyde THF, -78° C.
3. NMO, TPAP; BBr₃, CH₂Cl₂
4. MeMgBr, THF, -30° C.; HCl; I₂, AgOCN, NH₃, THF

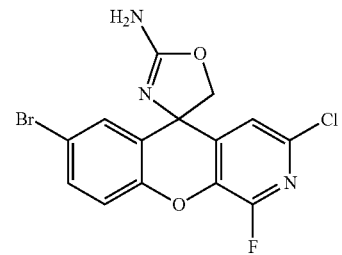

Synthesis of 7-bromo-3-chloro-1-fluoro-5'H-spiro[chromeno[2,3-c]pyridine-5,4'-oxazol]-2'-amine Step 1: DIPA (6.0 mL, 42.8 mmol) was dissolved in dry THF (20 mL) and cooled under nitrogen in a dry ice bath. n-Butyllithium solution (2.5 M in hexanes, 17 mL, 42.5 mmol) was added and after stirring for a few minutes a solution of 2-chloro-6-fluoropyridine (5.0 g, 38.0 mmol) in dry THF (20 mL) was added dropwise. The solution was stirred for 50 minutes then a solution of triisopropyl borate (8.72 mL, 38.0 mmol) in dry tetrahydrofuran (10 mL) was added dropwise. The reaction was stirred for 10 minutes. Water (80 mL) was added and the reaction concentrated under reduced pressure until water began to distill. The solution was treated with aqueous sodium hydroxide (10.0 N, 11.40 mL, 114 mmol) and hydrogen peroxide (30% by wt, 4.66 mL, 45.6 mmol) and stirred at RT for 90 minutes. Additional hydrogen peroxide (0.75 mL) was added. After stirring for 30 minutes, ice (~100 mL), water (100 mL) and HCl (2N, 60 mL) were added followed by EtOAc (200 ml). The phases were mixed and separated and the organic dried with magnesium sulfate before evaporating to dryness under reduced pressure. The crude intermediate was dissolved in acetone (100 mL) and treated with potassium carbonate (6.30 g, 45.6 mmol) and chloromethyl methyl ether (2.89 mL, 38.0 mmol). The mixture was heated in a 60° C. oil bath and monitored by TLC. The reaction was complete within 2 hours and was concentrated under reduced pressure to ~30 mL. Water (100 mL) and diethyl ether (100 ml) were added and the phases mixed and separated. The organic was dried with magnesium sulfate and evaporated to dryness under reduced pressure. The crude oil was found to be 6-chloro-2-fluoro-3-(methoxymethoxy)pyridine and did not required purification.

Step 2: DIPA (0.750 mL, 5.35 mmol) was dissolved in dry THF (20 mL) under nitrogen and cooled in a dry ice bath to −78° C. Butyllithium solution (2.5 M in hexanes, 2.0 mL, 5.00 mmol) was added and the solution was stirred for a few minutes. A solution of 6-chloro-2-fluoro-3-(methoxymethoxy)pyridine (0.864 g, 4.51 mmol) in dry THF (10 mL) was added slowly and the resulting solution stirred for 40 minutes. A solution of 5-bromo-2-fluorobenzaldehyde (1.02 g, 5.05 mmol) in dry THF (1 mL) was added dropwise. After 10 minutes saturated ammonium chloride (10 mL), water (100 mL) and EtOAc (100 mL) were added and the phases mixed and separated. The organic was dried with magnesium sulfate and evaporated to dryness under reduced pressure. Purification using silica chromatography (hexane to EtOAc gradient) gave the desired (5-bromo-2-fluorophenyl)(6-chloro-2-fluoro-3-(methoxymethoxy)pyridin-4-yl)methanol.

Step 3: (5-Bromo-2-fluorophenyl)(6-chloro-2-fluoro-3-(methoxymethoxy)pyridin-4-yl)methanol (1.008 g, 2.55 mmol) and 4-methylmorpholine n-oxide (0.898 g, 7.66 mmol) were dissolved in DCM (60 mL) and treated with tetrapropylammonium perruthenate (0.045 g, 0.128 mmol). When the oxidation was complete by TLC (EA/hexane) it was passed through a short silica column using 1:1 EtOAc: DCM to wash off the desired ketone. Evaporation under reduced pressure gave the intermediate as a clear oil that crystallized on standing. It was dissolved in DCM (60 mL) under nitrogen and cooled in an ice bath. Boron tribromide (0.5 mL, 5.29 mmol) was added and the solution turned red. After 5 minutes additional DCM (80 mL) was added followed by ice (~50 mL) and water (100 mL). The phases were mixed and separated and the organic dried with magnesium sulfate before evaporating to dryness under reduced pressure. The crude material was dissolved in dioxane (50 mL) and treated with cesium carbonate (0.246 mL, 3.07 mmol). The reaction was heated to reflux for 30 minutes. It was cooled and water (100 mL) and EtOAc (100 mL) were added. The phases were mixed and separated and the organic dried with magnesium sulfate before evaporating to dryness under reduced pressure. The crude product was purified using silica chromatography (hexane to ethyl acetate gradient) to give 7-bromo-3-chloro-1-fluoro-5H-chromeno[2,3-c]pyridin-5-one as a white solid.

Step 4: 7-Bromo-3-chloro-1-fluoro-5H-chromeno[2,3-c]pyridin-5-one (21.5 g, 65.4 mmol) was suspended in dry THF (300 mL) under nitrogen in an ice bath. Methylmagnesium bromide (3.0 M in diethyl ether, 36 mL, 108 mmol) was added in ~12 mL portions allowing 10-15 minutes between additions. The mixture was stirred for a 15 minutes after the final addition. Saturated ammonium chloride (50 mL) was added carefully followed by diethyl ether (200 mL), ethyl aceate (200 mL), water (400 mL) and 2 N HCl (50 mL). The phases were mixed and separated and the organic dried with magnesium sulfate before evaporating to dryness under reduced pressure. The crude alcohol was dissolved in dry THF (300 mL) and treated with HCl (4.0 M solution in 1,4-dioxane, 16 mL, 64.0 mmol). The mixture was heated to 50° C. and stirred for 30 minutes. The crude reaction mixture was evaporated to dryness under reduced pressure. The crude tar was triturated with diethyl ether (200 mL) and stirred in an ice bath. A cream coloured solid precipitated within a few minutes. After 10 minutes the mixture was filtered through a sintered glass frit and dried under high vacuum to give the desired 7-bromo-3-chloro-1-fluoro-5-methylene-5H-chromeno[2,3-c]pyridine.

Step 5: 7-Bromo-3-chloro-1-fluoro-5-methylene-5H-chromeno[2,3-c]pyridine (14.2 g, 43.5 mmol) was dissolved in dry THF (400 mL) under nitrogen and cooled in an ice bath. Silver cyanate (19.55 g, 130 mmol) was added followed by slow addition of a solution of iodine (11.04 g, 43.5 mmol) in dry THF (80 mL) over 30 minutes. It was stirred for another 30 minutes then it was filtered through a pad of celite. The filtrate was treated with ammonia (2.0 M solution in MeOH, 250 mL, 500 mmol) and capped. The solution was stirred for 10 hours. The crude reaction was concentrated under reduced pressure to ~100 mL then diluted with DCM (300 mL). The solution was washed with aqueous sodium sulfite to remove iodine then evaporated to dryness under reduced pressure. DCM/MeOH (60:40, 300 mL) were added to the solids and the crude was triturated for 10 minutes before filtering through a pad of celite. The solution was evaporated to dryness under reduced pressure to give 7-bromo-3-chloro-1-fluoro-5'H-spiro[chromeno[2,3-c]pyridine-5,4'-oxazol]-2'-amine.

Chiral separation of the racemic mixture provides the individual (R) and (S) enantiomers, which may be used to prepare compounds of the invention.

Example 118 (Method BB34)

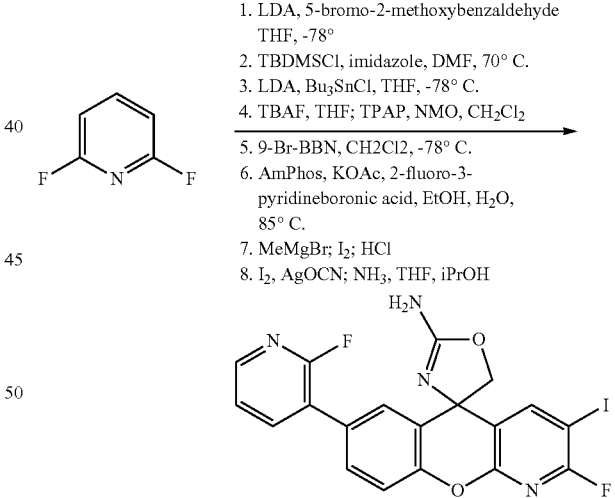

1. LDA, 5-bromo-2-methoxybenzaldehyde THF, -78°
2. TBDMSCl, imidazole, DMF, 70° C.
3. LDA, Bu₃SnCl, THF, -78° C.
4. TBAF, THF; TPAP, NMO, CH₂Cl₂
5. 9-Br-BBN, CH2Cl2, -78° C.
6. AmPhos, KOAc, 2-fluoro-3-pyridineboronic acid, EtOH, H₂O, 85° C.
7. MeMgBr; I₂; HCl
8. I₂, AgOCN; NH₃, THF, iPrOH Synthesis of 2-fluoro-7-(2-fluoropyridin-3-yl)-3-iodo-5'H-spiro[chromeno[2,3-b]pyridine-5,4'-oxazol]-2'-amine Step 1: DIPA (8.0 mL, 56.6 mmol) was dissolved in dry THF (40 mL) under nitrogen and cooled in a dry ice bath to −78°. n-Butyllithium solution, 2.5 m in hexanes (23.0 mL, 57.5 mmol) was added and the solution stirred for a few minutes prior to dropwise addition of 2,6-difluoropyridine (5.0 mL, 55.1 mmol) in dry THF (10 mL) via an addition funnel over 10 minutes. The pale yellow solution was stirred for 30 minutes then additional dry THF (70 mL) was added dropwise via an addition funnel. Solid 5-bromo-2-methoxybenzaldehyde (11.85 g, 55.1 mmol) was added in one portion and the reaction stirred for 5 minutes. Additional dry THF (100 mL) was added dropwise to keep the mixture stirring freely. After 15 minutes saturated ammonium chloride (20 mL) was added to quench followed by ethyl acetate (200 mL) and water (200 mL). The phases were mixed and separated and the organic dried with magnesium sulfate before evaporating to dryness under reduced pressure. Purification using silica chromatography (hexane to DCM gradient) gave (5-bromo-2-methoxyphenyl)(2,6-difluoropyridin-3-yl)methanol.

Step 2: (5-Bromo-2-methoxyphenyl)(2,6-difluoropyridin-3-yl)methanol (13.77 g, 41.7 mmol) and imidazole (3.41 g, 50.1 mmol) were dissolved in dry DMF (20 mL) under nitrogen. t-Butyl(chloro)dimethylsilane (6.92 g, 45.9 mmol) was added and the solution heated to 70° C. After 1 hour the mixture was cooled to RT. Water (200 mL) and diethyl ether (200 mL) were added and the phases mixed and separated. The organic was washed with water (200 mL) one more time then dried with magnesium sulfate and evaporated to dryness under reduced pressure. Purification using silica chromatography (hexane to 1:1 DCM: hexane gradient) gave 3-((5-bromo-2-methoxyphenyl)(tert-butyldimethylsilyloxy)methyl)-2,6-difluoropyridine as a thick oil that solidified on standing.

Step 3: DIPA (1.2 mL, 8.49 mmol) (freshly distilled) was dissolved in dry THF (40 mL) under nitrogen and cooled in a dry ice bath to −78°. N-butyllithium solution (2.5 m in hexanes, 3.0 mL, 7.50 mmol) was added and the solution stirred for a few minutes. A solution of 3-((5-bromo-2-methoxyphenyl)(tert-butyldimethylsilyloxy)methyl)-2,6-difluoropyridine (3.20 g, 7.20 mmol) in dry THF (20 mL) was added dropwise via an addition funnel and the solution stirred for 1 hour. Tributyltin chloride (2.0 mL, 7.37 mmol) was added to the pale yellow solution and it was stirred for 10 minutes. The reaction was quenched by addition of saturated ammonium chloride (10 mL). Water (100 mL) and diethyl ether (200 mL) were added and the phases mixed and separated. The organic was dried with magnesium sulfate and evaporated to dryness under reduced pressure. Purification using silica chromatography (2-15% diethyl ether in hexane gradient) gave 3-((5-bromo-2-methoxyphenyl)(tert-butyldimethylsilyloxy)methyl)-2,6-difluoro-5-(tributylstannyl)pyridine.

Step 4: 3-((5-Bromo-2-methoxyphenyl)(tert-butyldimethylsilyloxy)methyl)-2,6-difluoro-5-(tributylstannyl)pyridine (1.17 g, 1.595 mmol) was dissolved in dry THF (10 mL). Tetrabutylammonium fluoride (2.2 mL, 2.200 mmol) was added and the reaction stirred for 5 minutes. Water (100 mL), diethyl ether (100 mL) and saturated ammonium chloride (10 mL) were added. The phases were mixed and separated and the organic dried with magnesium sulfate before evaporating to dryness under reduced pressure. The crude alcohol was dissolved in DCM (50 mL) and treated with 4-methylmorpholine n-oxide (0.467 g, 3.99 mmol) followed by tetrapropylammonium perruthenate (0.056 g, 0.160 mmol). The dark yellow solution was stirred for 15 minutes until it turned black. The solution was diluted with DCM (50 mL) and water (100 mL). The phases were mixed, filtered through a pad of celite and separated and the organic dried with magnesium sulfate before evaporating to dryness under reduced pressure. The crude was purified using silica chromatography (hexane to DCM gradient) to give (5-bromo-2-methoxyphenyl)(2,6-difluoro-5-(tributylstannyl)pyridin-3-yl)methanone.

Step 5: (5-Bromo-2-methoxyphenyl)(2,6-difluoro-5-(tributylstannyl)pyridin-3-yl)methanone (6.48 g, 10.50 mmol) was dissolved in DCM (60 mL) under nitrogen and cooled in a dry ice bath to −78° C. 9-Bromo-9-borabicyclo[3.3.1]nonane, (1 M in DCM, 11.02 mL, 11.02 mmol) was added dropwise over 5 minutes and the reaction stirred for another 5 minutes. The flask was removed from the cold bath and stirred at ambient temperature for 20 minutes then saturated sodium bicarbonate (50 mL) was added to quench. Water (200 mL) and dichloromethane (100 mL) were added and the phases mixed and separated. The organic was dried with magnesium sulfate and evaporated to dryness under reduced pressure. Purification using silica chromatography (hexane to dichloromethane gradient) gave 7-bromo-2-fluoro-3-(tributylstannyl)-5H-chromeno[2,3-b]pyridin-5-one.

Step 6: 7-Bromo-2-fluoro-3-(tributylstannyl)-5H-chromeno[2,3-b]pyridin-5-one (0.240 g, 0.412 mmol), AmPhos (0.015 g, 0.021 mmol), potassium acetate (0.077 mL, 1.235 mmol), and 2-fluoro-3-pyridineboronic acid (0.070 g, 0.494 mmol) were suspended in a mixture of EtOH (20 mL) and water (2 mL) and heated to 85° C. After 30 minutes water (250 mL) and ethyl acetate (200 mL) were added and the phases mixed and separated. The organic was washed with 10% saturated sodium bicarbonate (100 mL) then dried with magnesium sulfate and evaporated to dryness under reduced pressure. The crude was purified using silica chromatography (hexane to ethyl acetate gradient) to give 2-fluoro-7-(2-fluoropyridin-3-yl)-3-(tributylstannyl)-5H-chromeno[2,3-b]pyridin-5-one.

Step 7: 2-Fluoro-7-(2-fluoropyridin-3-yl)-3-(tributylstannyl)-5H-chromeno[2,3-b]pyridin-5-one (1.79 g, 2.99 mmol) was dissolved in dry THF (50 mL) and cooled in an ice bath under nitrogen to 0°. Methylmagnesium bromide (3.0 M in diethyl ether, 3.2 mL, 9.60 mmol) was added slowly. After 15 minutes saturated ammonium chloride was added carefully to quench followed by diethyl ether (200 mL) and water (200 mL). The phases were mixed and separated and the organic dried with magnesium sulfate before evaporating to dryness under reduced pressure. The crude alcohol was dissolved in acetonitrile (100 mL) and treated with iodine (0.154 mL, 2.99 mmol). It was stirred for 30 minutes at RT. Water (200 mL) and ethyl acetate (200 mL) were added and the phases mixed and separated. The organic was washed with aqueous sodium sulfite then dried with magnesium sulfate and evaporated to dryness under reduced pressure. The crude was purified using column chromatography (hexane to EtOAc gradient). The purified alcohol was dissolved in dry THF (200 mL) and treated with a catalytic amount of hydrogen chloride in dioxane (4 M, 0.25 mL). It was stirred for 15 minutes. Saturated sodium bicarbonate (30 mL), water (200 mL) and ethyl acetate (300 mL) were added and the phases mixed and separated. The organic was dried with magnesium sulfate and evaporated to dryness under reduced pressure. The crude 2-fluoro-7-(2-fluoropyridin-3-yl)-3-iodo-5-methylene-5H-chromeno[2,3-b]pyridine (1.14 g, 2.63 mmol, 88% yield) was used without purification.

Step 8: 2-Fluoro-7-(2-fluoropyridin-3-yl)-3-iodo-5-methylene-5H-chromeno[2,3-b]pyridine (1.14 g, 2.63 mmol) was dissolved in ACN (50 mL) and treated with silver cyanate (1.181 g, 7.88 mmol). The suspension was stirred under nitrogen in an ice bath and a solution of iodine (0.666 g, 2.63 mmol) in dry THF (10 mL) was added dropwise. After stirring for 15 minutes, the reaction was filtered through a pad of celite and the filtrate treated with ammonia (2.0 M solution in methanol, 10 mL, 20.00 mmol). The reaction was sealed and stirred for 10 hours then it was concentrated under reduced pressure. The crude was partitioned between water (200 mL) and ethyl acetate (200 mL). The organic was dried with magnesium sulfate and evaporated to dryness under reduced pressure. Purification using silica chromatography (0-6% methanol in DCM gradient) gave 2-fluoro-7-(2-fluoropyridin-3-yl)-3-iodo-5'H-spiro[chromeno[2,3-b]pyridine-5,4'-oxazol]-2'-amine

Example 119 (Method BB35)

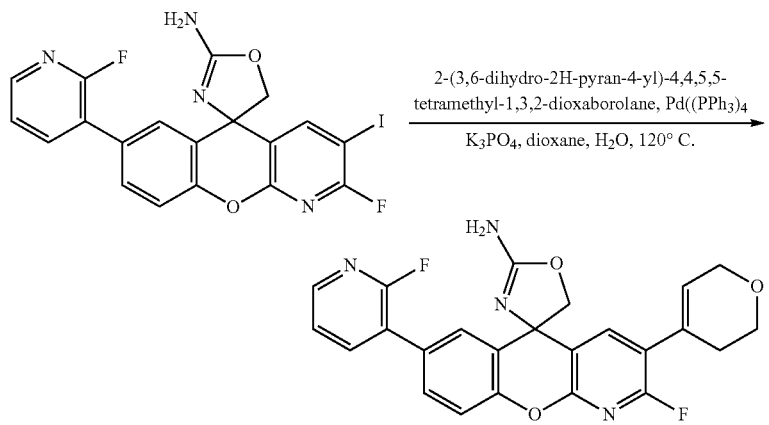

Synthesis of 3-(3,6-dihydro-2H-pyran-4-yl)-2-fluoro-7-(2-fluoropyridin-3-yl)-5'H-spiro[chromeno[2,3-b]pyridine-5,4'-oxazol]-2'-amine Step 1: 2-Fluoro-7-(2-fluoropyridin-3-yl)-3-iodo-5'H-spiro[chromeno[2,3-b]pyridine-5,4'-oxazol]-2'-amine (0.151 g, 0.307 mmol), 2-(3,6-dihydro-2H-pyran-4-yl)-4,4,5,5-tetramethyl-1,3,2-dioxaborolane (0.150 g, 0.71 mmol), tetrakis(triphenylphosphine)palladium (0.177 g, 0.153 mmol), and potassium phosphate (0.102 mL, 1.227 mmol) were suspended in dioxane (2 mL) and water (0.5 mL) and sealed in a microwave vessel under argon. The mixture was heated to 120° C. for 20 minutes. The reaction mixture was concentrated under reduced pressure and partitioned between water (80 mL) and ethyl acetate (80 mL). The organic was dried with magnesium sulfate and evaporated to dryness under reduced pressure. Purification using silica chromatography (1-4% methanol in dichloromethane gradient) gave 3-(3,6-dihydro-2H-pyran-4-yl)-2-fluoro-7-(2-fluoropyridin-3-yl)-5'H-spiro[chromeno[2,3-b]pyridine-5,4'-oxazol]-2'-amine.

Example 120 (Method BB36)

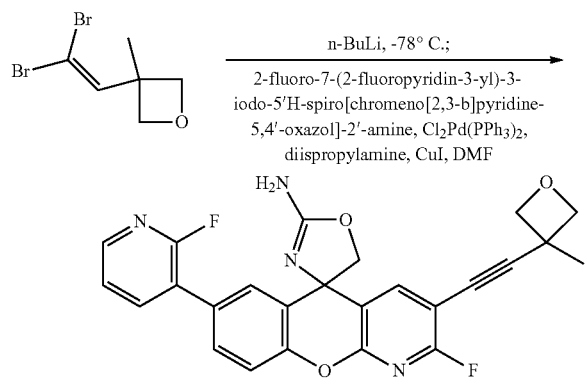

Synthesis of 2-Fluoro-7-(2-fluoropyridin-3-yl)-3-((3-methyloxetan-3-yl)ethynyl)-5'H-spiro[chromeno[2,3-b]pyridine-5,4'-oxazol]-2'-amine Step 1: 3-(2,2-dibromovinyl)-3-methyloxetane (0.156 g, 0.609 mmol) was dissolved in a mixture of diethyl ether (10 mL) and dry THF (10 mL) and cooled in a dry ice bath under nitrogen. Butyllithium solution, 2.5 m in hexanes (0.528 mL, 1.321 mmol) was added dropwise and the mixture stirred for 40 minutes before removing from the cold bath and quenching with saturated ammonium chloride. Water (100 mL) and diethyl ether (100 mL) were added and the phases mixed and separated. The organic layer was dried with magnesium sulfate and concentrated to ~20 mL under reduced pressure using a 40° C. water bath. The crude alkyne was combined with 2-fluoro-7-(2-fluoropyridin-3-yl)-3-iodo-5'H-spiro[chromeno[2,3-b]pyridine-5,4'-oxazol]-2'-amine (0.250 g, 0.508 mmol), copper(i) iodide (0.097 g, 0.508 mmol), trans-dichlorobis(triphenyl-phosphine)palladium (ii) (7.13 mg, 10.16 μmol), and diisopropylethylamine (1.00 mL, 5.75 mmol) in dry dimethylformamide (5 mL) and heated to 90° C. After 2 hours DIPA (2 mL) was added and it was stirred at 60° C. overnight.

Another equivalent of the alkyne was prepared and added. After sealing and heating at 80° C. for another 3 hours the mixture was cooled to rt and partitioned between water (100 mL) and ethyl acetate (100 mL). The organic was dried with magnesium sulfate and evaporated to dryness under reduced pressure. Purification by silica gel chromatography (0-5% methanol in DCM gradient) followed by reverse phase HPLC and free basing gave the desired 2-fluoro-7-(2-fluoropyridin-3-yl)-3-((3-methyloxetan-3-yl)ethynyl)-5'H-spiro[chromeno[2,3-b]pyridine-5,4'-oxazol]-2'-amine

Example 121 (Method BB37)

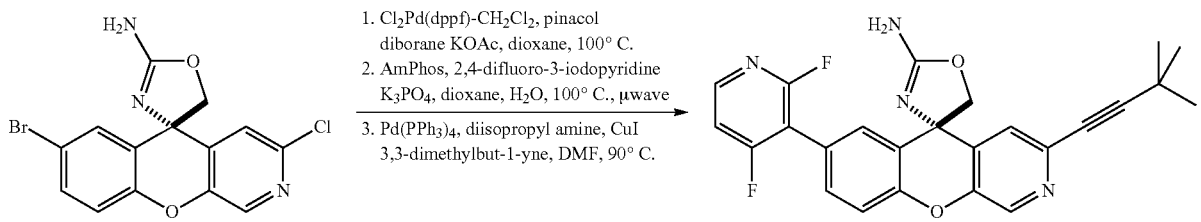

Synthesis of (5S)-7-(2,4-difluoro-3-pyridinyl)-3-(3,3-dimethyl-1-butyn-1-yl)spiro[chromeno[2,3-c]pyridine-5,4'-[1,3]oxazol]-2'-amine Step 1: A mixture of (S)-7-bromo-3-chloro-5'H-spiro[chromeno[2,3-c]pyridine-5,4'-oxazol]-2'-amine (2.03 g, 5.54 mmol), 4,4,4',4',5,5,5',5'-octamethyl-2,2'-bi(1,3,2-dioxaborolane) (2.81 g, 11.07 mmol), Cl₂Pd(dppf)-CH₂Cl₂ adduct (0.452 g, 0.554 mmol) and potassium acetate (1.630 g, 16.61 mmol) were combined a reaction vessel. To this mixture was added dioxane (26 mL) and the resulting slurry was purged with nitrogen, sealed and heated at 100° C. overnight. The mixture was filtered through a pad of celite. The filtrate was concentrated, diluted with water (50 mL) and extracted with EtOAc (3×50 mL). The combined organic layers were washed with brine, dried over magnesium sulfate, filtered and concentrated. The crude material was purified by column chromatography with 0-10% MeOH/DCM, then purified again with 30-60% EtOAc/DCM to provide the desired product.

Step 2: A 20 mL glass microwave reaction vessel was charged with (S)-3-chloro-7-(4,4,5,5-tetramethyl-1,3,2-dioxaborolan-2-yl)-5'H-spiro[chromeno[2,3-c]pyridine-5,4'-oxazol]-2'-amine (0.506 g, 1.223 mmol), potassium phosphate tribasic (0.230 mL, 2.78 mmol), 2,4-difluoro-3-iodopyridine (0.2680 g, 1.112 mmol), dioxane (4.8 mL) and water (1.2 mL). The vessel was flushed with argon, sealed and heated at 100° C. in a microwave for 30 minutes. The mixture was partitioned between EtOAc (50 mL) and water (50 mL). The aqueous layer was washed twice with saturated Na₂CO₃. The organic layer was dried over sodium sulfate and concentrated in vacuo. The crude residue was purified by silica gel chromatography (100% EtOAc) to provide the desired product.

Step 3: Tetrakis(triphenylphosphine)palladium (0.029 g, 0.025 mmol), copper(i) iodide (5.50 µL, 0.162 mmol) and (S)-3-chloro-7-(2,4-difluoropyridin-3-yl)-5'H-spiro[chromeno[2,3-c]pyridine-5,4'-oxazol]-2'-amine (0.100 g, 0.250 mmol) were combined in a heating tube that was subsequently purged with argon. DMF (1.5 mL), DIPA (0.533 mL, 3.74 mmol) and 3,3-dimethylbut-1-yne (0.031 g, 0.374 mmol) were added in sequence and the reaction vessel was sealed and heated at 90° C. for 16 h. The reaction mixture was poured into water (25 mL) and extracted with EtOAc (3×20 mL).

The combined organic layers were washed with water and then brine, dried over sodium sulfate, filtered and concentrated. The crude material was purified by column chromatography with 80-100% EtOAc/hexanes, then 5% 2M NH₃ in MeOH/CH₂Cl₂ to provide the desired product. MS m/z=458.0 [M+H].

Example 122 (Method BB38)

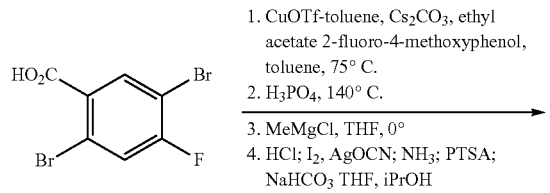

1. CuOTf-toluene, Cs₂CO₃, ethyl acetate 2-fluoro-4-methoxyphenol, toluene, 75° C.
2. H₃PO₄, 140° C.
3. MeMgCl, THF, 0°
4. HCl; I₂, AgOCN; NH₃; PTSA; NaHCO₃ THF, iPrOH

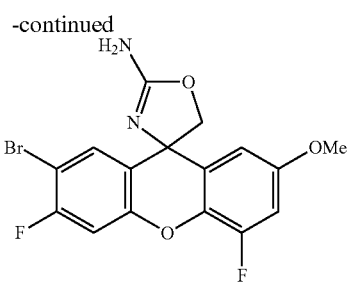

Synthesis of (S)-2'-bromo-3',5'-difluoro-7'-methoxy-5H-spiro[oxazole-4,9'-xanthen]-2-amine and (R)-2'-bromo-3',5'-difluoro-7'-methoxy-5H-spiro[oxazole-4,9'-xanthen]-2-amine Step 1: A 2 L RB flask was charged with 2-fluoro-4-methoxyphenol (49.6 g, 349 mmol), 2,5-dibromo-4-fluorobenzoic acid (80 g, 269 mmol), ethyl acetate (1.316 mL, 13.43 mmol), cesium carbonate (192 g, 591 mmol) and toluene (1200 mL). To the mixture at was added copper(I) triflate toluene complex (2:1) (1.713 g, 8.06 mmol) and it was stirred at room temperature for 20 minutes. The solution was then heated to 75° C. for 16 hours at which point the toluene was removed under reduced pressure. The solution was dissolved in 1.5 liters of water and washed with 250 ml of EtOAc. The aqeuous layer was acidified to pH 1 with concentrated HCl and the resulting precipitate was collected by filtration and washed with water. The derived solid was washed with a 1:1 solution of ethyl acetate and hexane, then dried under vacuum to afford 5-bromo-4-fluoro-2-(2-fluoro-4-methoxyphenoxy)benzoic acid as a light brown solid. MS m/z=358.8 [M+H].

Step 2: To a flaske charged with polyphosphoric acid (396 g, 4038 mmol) was added 5-bromo-4-fluoro-2-(2-fluoro-4-methoxyphenoxy)benzoic acid (58 g, 162 mmol) and the viscous mixture was heated at 140° C. for 2 hours. The viscous solution was cooled slightly and diluted with ice-water (1 L). After 15 min of stirring, EtOAc (1 L) was added and the aqueous fraction extracted with EtOAc (3×200 mL). The combined organic fractions were dried over sodium sulfate and concentrated. The solids were washed with 6 N NaOH, then water. The solids were then sequentially triturated with methanol and ethyl acetate. The resulting solid was dried under vacuum to afford 2-bromo-3,5-difluoro-7-methoxy-9H-xanthen-9-one (41 g, 120 mmol, 74.4% yield).

Step 3: A mixture of 2-bromo-3,5-difluoro-7-methoxy-9H-xanthen-9-one (40 g, 117 mmol) and THF (300 mL) was cooled to 0° C. and treated with methylmagnesium chloride (58.6 mL, 176 mmol) (3M in THF). After stirring at this temperature for 20 minutes, the reaction was quenched by the addition of sataturated NH₄Cl (500 mL). Brine was added and the mixture was extracted with EtOAc (3×100 mL). The combined organic extracts were dried with sodium sulfate, filtered and concentrated in vacuo to afford crude 2-bromo-3,5-difluoro-7-methoxy-9-methyl-9H-xanthen-9-ol as a brown solid that was carried on without further purification. MS m/z=339.0 [M+1−H₂O].

Step 4: To a 1000 mL RBF charged with 2-bromo-3,5-difluoro-7-methoxy-9-methyl-9H-xanthen-9-ol (38 g, 106 mmol) and THF (200 mL) was added HCl (4 M in dioxane) (1.330 mL, 5.32 mmol). This solution was stirred at rt for 15 minutes before being added to the mixture below.

Separately, to a mixture of iodine (28.4 g, 112 mmol) in 300 mL of THF at −30° C. was added silver cyanate (9.97 mL, 266 mmol) and the slurry was stirred for 30 minutes. To this mixture was added the solution of the olefin derived above. The mixture was stirred for one hour at −30° C. at which point ammonia (2M in isopropanol, 266 mL, 532 mmol) was then added and the black mixture was stirred at room temperature for 24 hours. The mixture was filtered through celine and concentrated in vacuo. The solution was diluted with CH$_2$Cl$_2$ (300 mL) and 10 ml of MeOH and filtered. The filtrated was treated with p-toluenesulfonic acid monohydrate (24.29 g, 128 mmol). After 20 min of stirring, the resulting precipitate was collected by filtration. The solid was stirred with saturated NaHCO$_3$ (500 mL) and EtOAc (500 mL). The organic fraction was washed with brine, dried with sodium sulfate, filtered and concentrated in vacuo to afford (S)-2'-bromo-3', 5'-difluoro-7'-methoxy-5H-spiro[oxazole-4,9'-xanthen]-2-amine as an off-white/tan solid. MS m/z=398.8 [M+H].

Chiral separation provided (S)-2'-bromo-3',5'-difluoro-7'-methoxy-5H-spiro[oxazole-4,9'-xanthen]-2-amine and (R)-2'-bromo-3',5'-difluoro-7'-methoxy-5H-spiro[oxazole-4,9'-xanthen]-2-amine, both as off white solids. MS m/z=398.8 [M+H].

Example 123 (Method BB39)

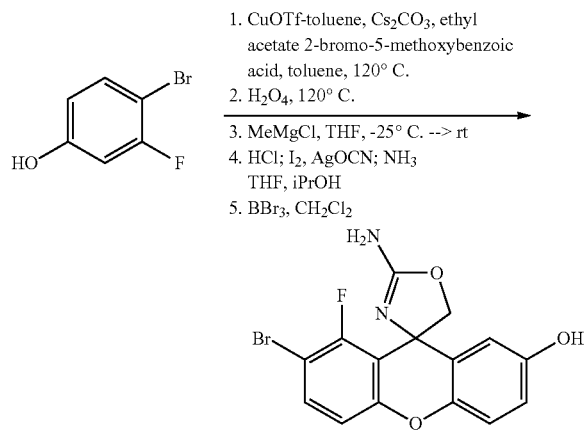

Synthesis of (R)-2-amino-2'-bromo-1'-fluoro-5H-spiro[oxazole-4,9'-xanthen]-7'-ol and (S)-2-amino-2'-bromo-1'-fluoro-5H-spiro[oxazole-4,9'-xanthen]-7'-ol Step 1: A 1 L 3-neck flask equipped with a reflux condenser and overhead stirrer was charged with cesium carbonate (99 g, 303 mmol), 4-bromo-3-fluorophenol (34.7 g, 182 mmol), 2-bromo-5-methoxybenzoic acid (35 g, 151 mmol) and 100 mL of toluene. To this slurry were added EtOAc (0.741 mL, 7.57 mmol) and copper (i) trifluoromethanesulfonate toluene complex (1.959 g, 3.79 mmol). The resulting blue slurry was then heated at 120° C. After heating for 10 minutes the slurry went from blue to a greenish color. The reaction was maintained at 120° C. for 20 hours before being cooled rt and poured into 1 L of water. 1 L of ethyl acetate was added and the mixture was acidified to pH 2 with 3 N HCl. The layers were separated and the aqueous layer was extracted with EtOAc (3×500 mL). The combined organics were washed with brine, dried over sodium sulfate, filtered and concentrated to provide a light brown solid that was carried on without further purification.

Step 2: To a 1 L flask charged with 2-(4-bromo-3-fluorophenoxy)-5-methoxybenzoic acid (100 g, 293 mmol) was added sulfuric acid (391 mL, 7329 mmol). The resulting slurry was heated to 80° C. for 2 hours. The reaction was removed from the oil bath, cooled to rt and poured into a 3 L flask containing 2 L of ice water. The derived slurry was vigorously stirred for 2 hours before being filtered. The derived solid was washed well with water (3×500 mL), 3 N NaOH (2×500 mL) and water (2×500 mL). The wet solid was then washed with ether (2×250 mL) and dried under a vacuum at 50° C. overnight. The solid was then azeotropped from toluene (3×100 mL) to provide 41 g of a 4:1 mixture of 2-bromo-1-fluoro-7-methoxy-9H-xanthen-9-one:2-bromo-3-fluoro-7-methoxy-9H-xanthen-9-one (40.0 g, 123.9 mmol, 42.2% yield). A portion of this material (10 g) was slurried in hot IPA (200 mL) and placed in the refrigerator overnight. The derived solid was filtered and purified by silica gel chromatography (100% CH$_2$Cl$_2$) to provide 2-bromo-1-fluoro-7-methoxy-9H-xanthen-9-one (4.1 g) and 2-bromo-3-fluoro-7-methoxy-9H-xanthen-9-one (0.95 g) both as light white solids.

Step 3: To a solution of 2-bromo-1-fluoro-7-methoxy-9H-xanthen-9-one (0.79 g, 2.445 mmol) in THF (30.6 mL, 2.445 mmol) at −25° C. was added methylmagnesium chloride, (3.0 M solution in THF, 0.937 mL, 2.81 mmol). After stirring for 5 minutes at −25° C. the reaction was removed from the cold bath and allowed to warm to rt. Once at rt another 1 equivalent of methylmagnesium chloride was added to the reaction mixture and stirring was continued for another 1 hour. TLC showed complete conversion to a lower Rf product (eluent 100% CH$_2$Cl$_2$). The reaction was diluted with water (50 mL; reaction became colorless) and poured into a separatory funnel containing EtOAc (100 mL). The layers were separated and the aqueous layer was extracted with EtOAc (3×50 mL). The combined organic layers were washed with brine, dried over sodium sulfate, filtered and concentrated in vacuo to provide the desired alcohol as a colorless oil. MS m/z=321.0 [M+H−H$_2$O].

Step 4: To a solution of 2-bromo-1-fluoro-7-methoxy-9-methyl-9H-xanthen-9-ol (0.85 mg, 2.44 mmol) in 20 mL of THF was added HCl (4.0 M solution in 1,4-dioxane, 0.031 mL, 0.122 mmol). After stirring for 10 minutes at rt, TLC showed complete conversion to a higher Rf spot (10% EA in hexanes). This solution was added directly to the slurry below.

To a solution of iodine (0.621 g, 2.445 mmol) in 10 mL of THF at −25° C. was added silver cyanate (1.099 g, 7.33 mmol). This mixture was stirred at −25° C. for 20 minutes then a solution of the above derived olefin was added in one portion. The resulting orange mixture was maintained at −20° C. for 1 hour before being filtered through celite. The filtrate was cooled to −10° C. and treated with ammonia (2.0 M solution in 2-propanol, 2.445 mL, 4.89 mmol). Once the addition was compete, the reaction was removed from cold bath and allowed reaction to warm to rt overnight. The reaction was diluted with 10% sodium thiosulfate (100 mL) and poured into a separatory funnel containing EtOAc (100 mL). The layers were separated and the aqueous layer was extracted with EtOAc (2×100 mL). The combined organic layers were washed with brine, dried over sodium sulfate, filtered and concentrated in vacuo to provide a light yellow solid. The solid was suspended in 50 mL of EtOAc and filtered. The filtrate was concentrated and purified by silica gel chromatography (0-100% CH$_2$Cl$_2$ to 10:1 MeOH in CH$_2$Cl$_2$ with 0.1% ammonium hydroxide) to provide 2'-bromo-1'-fluoro-7'-methoxy-5H-spiro[oxazole-4,9'-xanthen]-2-amine as a light yellow foam. MS m/z=378.8 [M+H].

Step 5: To a solution of 2'-bromo-1'-fluoro-7'-methoxy-5H-spiro[oxazole-4,9'-xanthen]-2-amine (0.575 g, 1.516 mmol) in 15 mL of CH$_2$Cl$_2$ at −15° C. was added boron tribromide (1.0 M in CH$_2$Cl$_2$, 4.55 mL, 4.55 mmol). The mixture was slowly allowed to warm to 0° C. over the course of 1.25 hours at which point the reaction was carefully quenched with 2 mL of MeOH and saturated sodium bicarbonate (100 mL). This mixture was poured into a separatory funnel containing EtOAc (100 mL). The layers were separated and the aqueous layer was extracted with EtOAc (2×100 mL). The combined organic layers were washed with brine, dried over sodium sulfate, filtered and concentrated in vacuo to provide 2-amino-2'-bromo-1'-fluoro-5H-spiro[oxazole-4,9'-xanthen]-7'-ol as a glassy red solid. MS m/z=365.1 [M+H].

Chiral separation provided (R)-2-amino-2'-bromo-1'-fluoro-5H-spiro[oxazole-4,9'-xanthen]-7'-ol and (S)-2-amino-2'-bromo-1'-fluoro-5H-spiro[oxazole-4,9'-xanthen]-7'-ol, both as off white solids. MS m/z=365.1 [M+H].

Example 124 (Method BB40)

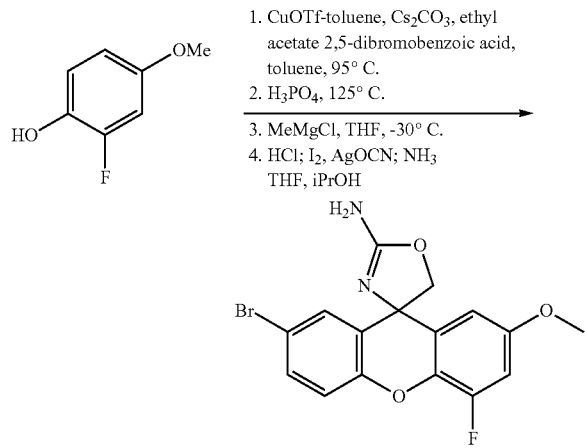

Synthesis of (S)-7'-bromo-4'-fluoro-2'-methoxy-5H-spiro[oxazole-4,9'-xanthen]-2-amine and (R)-7'-bromo-4'-fluoro-2'-methoxy-5H-spiro[oxazole-4,9'-xanthen]-2-amine Step 1: A three-neck RBF equipped with a reflux condenser and overhead stirrer was charged with 2-fluoro-4-methoxyphenol (14.24 g, 100 mmol), 2,5-dibromobenzoic acid (25.5 g, 91 mmol), EtOAc (0.446 mL, 4.55 mmol), copper (I) triflate toluene complex (2:1) (0.484 g, 2.27 mmol) and toluene (300 mL). Cesium carbonate (59.4 g, 182 mmol) was carefully added portion-wise. The mixture was stirred for 10 minutes at RT then heated at 95° C. for 3 hours. The toluene was cooled to RT then extracted twice with 300 ml of water. The combined water extracts were acidified with 6 N HCl at which time a precipitate formed. The mixture was extracted with EtOAc (3×500 mL) and the combined organic fractions were dried over sodium sulfate and concentrated in vacuo. The resulting solid was triturated with minimal 1:1 Hexanes:EtOAc and filtered. The collected solid was dried in vacuo to afford 5-bromo-2-(2-fluoro-4-methoxyphenoxy)benzoic acid as a grey solid. The mother liquors were set aside for later recrystallizatio. MS m/z=341.0 [M+H].

Step 2: 5-bromo-2-(2-fluoro-4-methoxyphenoxy)benzoic acid (28.5 g, 84 mmol) and polyphosphoric acid (205 g, 2089 mmol) were combined and heated at 125° C. for two hours. The solution was diluted with water (1 L) and filtered. The solids were washed well with 2N NaOH, then with water. The solids were then dried under vacuum to afford 7-bromo-4-fluoro-2-methoxy-9H-xanthen-9-one as an off white solid. MS m/z=323.0 [M+H].

Step 3: 7-bromo-4-fluoro-2-methoxy-9H-xanthen-9-one (22 g, 68.1 mmol) was dissolved in 300 ml of THF and cooled to −30° C. in a dry ice ACN bath. Methylmagnesium chloride (34.0 mL, 102 mmol) (3M in THF) was added to the slurry maintaining temperature less than −15° C. The solution was allowed to warm to RT (undissolved solids went into solution), then quenched with saturated NH$_4$Cl (250 mL). The aqueous layer was extracted with EtOAc (3×200 mL) and the combined organic layers were washed with brine and dried over anhydrous sodium sulfate, filtered and concentrated to afford 7-bromo-4-fluoro-2-methoxy-9-methyl-9H-xanthen-9-ol as a brown liquid that was used without further purification.

Step 4: 7-Bromo-4-fluoro-2-methoxy-9-methyl-9H-xanthen-9-ol (24 g, 70.8 mmol) was slurried in THF (100 mL) and HCl (4 M in dioxane) (0.354 mL, 1.415 mmol) was added. The solution was warmed to 50° C. for 1.5 hours. In a separate RB charged with a mixture of iodine (18.86 g, 74.3 mmol) and 300 ml of THF at −30° C. was added silver cyanate (7.95 mL, 212 mmol). This mixture was maintained for 30 minutes, at which point the ofefin derived above was added in one portion. The solution was stirred for another 30 minutes at −30° C. at which time ammonia (2M in iPrOH, 177 mL, 354 mmol) was added. The dark mixture was allowed to warm to rt and stir for 20 hours. The solution was filtered and 200 ml of saturated aqueous sodium thiosulfate was added and the solution was stirred for 30 minutes. The aqueous layer was separated and the organics were washed with water, brine, then dried over sodium sulfate and concentrated. The solids were triturated with IPA, filtered, and dried under vacuum to give 10 g of the desired product as a first crop. The filtrate was concentrated and purified via silica gel column chromatography (0-100% ethyl acetate in hexane). The solid obtained was triturated with IPA, filtered, then dried under vacuum to give 2 g of a second crop which was combined with the first crop to afford 7'-bromo-4'-fluoro-2'-methoxy-5H-spiro[oxazole-4,9'-xanthen]-2-amine as an off white solid. MS m/z=379.0 [M+H].

Chiral separation provided (S)-7'-bromo-4'-fluoro-2'-methoxy-5H-spiro[oxazole-4,9'-xanthen]-2-amine and (R)-7'-bromo-4'-fluoro-2'-methoxy-5H-spiro[oxazole-4,9'-xanthen]-2-amine, both as off white solids. MS m/z=379.0 [M+H].

Example 125 (Method BB41)

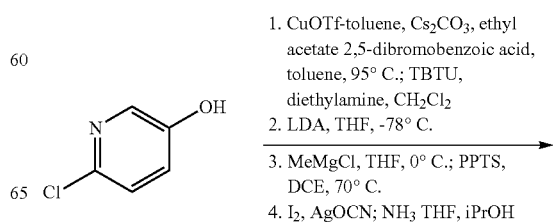

-continued

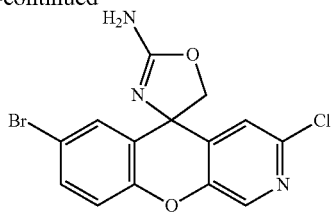

Synthesis of (S)-7-bromo-3-chloro-5'H-spiro[chromeno[2,3-c]pyridine-5,4'-oxazol]-2'-amine and (R)-7-bromo-3-chloro-5'H-spiro[chromeno[2,3-c]pyridine-5,4'-oxazol]-2'-amine Step 1: To a 5 L of three necks bottle was charged 200 g (0.715 mol) of 2,5-dibromobenzoic acid, 111.07 g (0.857 mol) of 5-hydroxyl-2-chloropyridine and 469.52 g (1.43 mol) of cesium carbonate. (The solid was fleshed for 20 min with nitrogen gas then Copper (I) trifloromethanesulfonate toluene complex (9.62 g, 18.59 mmol) and 2500 mL of toluene and 5.24 mL (53.62 mmol) of ethyl acetate were added. The resulting suspension was heated to 105° C. (oil-bath: 115° C.) stirred for 1.5 hrs. Cooled to RT and the toluene was removed by simple poured. To this residue, was added 1.5 L of water and 500 mL of EtOAc and stirred until whole solid was dissolved. The EtOAc was separate and the aqueous was neutralized with 6N HCl till the pH2-3. Extracted with EtOAc (800 mL×3) and combined organic layers was dried on $Na_2SO_4$. Filtered and concentrated to get the brown solid which did not purify and used to next step reaction directly. The above derived 5-bromo-2-(6-chloropyridin-3-yloxy)benzoic acid obtained above was dissolved in 2.5 L of DCM and then 229.6 g (0.715 mol) of TBTU was added. 148.6 mL (1.43 mol) of diethylamine was added dropwise. The resulting dark solution was stirred at RT for overnight. 500 mL of sat. $NH_4Cl$ and 500 mL of water was added. After stirred for 15 min, the aqueous layer was separated. The organic layer was washed one time with 1000 mL of sat. $NaCO_2$ solution then dried on $Na_2SO_4$. Filtered and 400 g of silica gel was added. Concentrated the organic layers to a crude material, which was loaded on a column (Column size: 7"×16", Silica gel: 3 kg) and eluted with hexane/EtOAc (20:1 to 5:1, Rf of product: 0.6, TLC solvent: hexane: EtOAc/3:1) to give the desired product.

Step 2: 5-Bromo-2-(6-chloropyridin-3-yloxy)-N,N-diethylbenzamide (290 g, 0.756 mol) of was dissolved in dry THF (2000 mL) and cooled to −78 C. To this solution was added a solution of LDA (preparation with 392.6 ml (2.778 mol) of diisopropylamine and 1058 mL of BuLi (2.5 M in hexane) 700 mL of dry THF). After the addition was complete the solution was stirred for 30 min at −78° C., then the dry ice acetone bath was removed and the reaction was quenched slowly with 2 L of Sat $NH_4Cl$. Separated the layers and the aqueous layer was extracted with ethyl acetate (2×500 mL). The combined organic layers were dried and past through a pad of silica gel to provide the desired product as a light yellow solid (110 g, 50% yield, three steps).

Step 3: To a solution of compound 7-bromo-3-chloro-5H-chromeno[2,3-c]pyridin-5-one (400 g, 1.288 mol) in dry THF (5 L) was added drop wise a solution of methylmagnesium chloride (2M in THF, 1.5 L) at 0° C. After the addition was complete the reaction was stirred at rt overnight. The mixture was cooled to 0° C. and quenched with saturated $NH_4Cl$ (3 L). 2 L of ethyl acetate were added, the phases were separated and the aqueous layer was extracted one time with EtOAc (1 L). The combined organic layers were past through a pad of silica gel to provide the desire product as a light yellow solid.

Step 3: To a solution of 7-bromo-3-chloro-5-methyl-5H-chromeno[2,3-c]pyridin-5-ol (450 g, 1.28 mol) in dichloroethane (5.5 L) at rt was added PPTS (18 g, 71.6 mmol). The resulting solution was heated to 70° C. for 6 hours and was then allowed to cool to rt. The mixture was concentrated to 10% of the original volume and was then purified by silica gel chromatography (Column size: 7"×16", Silica gel: 2.5 kg, DCM) to provide the desired product as a light pink solid (46%, two steps).

Step 4: To a solution of iodine (181.2 g, 0.714 mol) in dry THF (5 L) was added silver cyanate (291.48 g, 1.95 mol) at −20° C. The resulting slurry was maintained at this temperature for 1 hr. To this suspension was added a solution of 7-bromo-3-chloro-5-methylene-5H-chromeno[2,3-c]pyridine (200 g, 0.6482 mol) in 1 L of THF and the mixture was stirred at 0° C. for 3 hours. The mixture was then filtered through a pad of celite, washing well with THF. The filtrate was cooled to 10° C. and treated with a solution of ammonia in i-PrOH (2M, 972.3 mL). The resulting dark solution was stirred at rt overnight at which point 1 L of saturated sodium thio sulfate and 1.5 L of saturated sodium bicarbonate were added. The mixture was stirred 1 hour then the phases were separated and the aqueous phase was extracted with ethyl acetate (1 L). The combined organic layers were dried over sodium sulfate, filtered and evaporated. The derived solid was triturated with 1 L of DCM and 1 L of water before being filtered to provide 7-bromo-3-chloro-5'H-spiro[chromeno[2,3-c]pyridine-5,4'-oxazol]-2'-amine as yellow solid.

Chiral separation provided (S)-7-bromo-3-chloro-5'H-spiro[chromeno[2,3-c]pyridine-5,4'-oxazol]-2'-amine and (R)-7-bromo-3-chloro-5'H-spiro[chromeno[2,3-c]pyridine-5,4'-oxazol]-2'-amine, both as light yellow solids.

Example 126 (Method BB42)

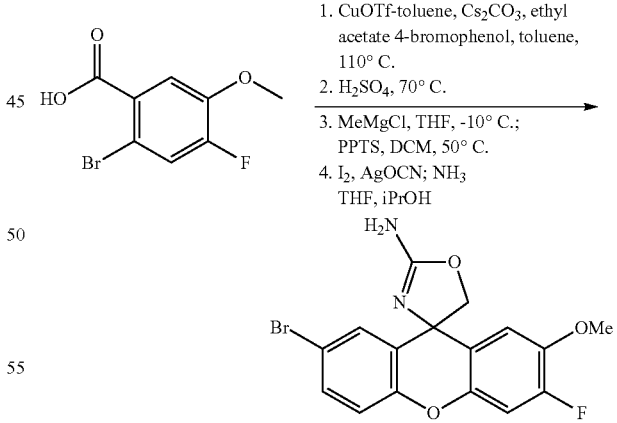

Synthesis of (R)-7'-bromo-3'-fluoro-2'-methoxy-5H-spiro[oxazole-4,9'-xanthen]-2-amine and (S)-7'-bromo-3'-fluoro-2'-methoxy-5H-spiro[oxazole-4,9'-xanthen]-2-amine Step 1: A mixture of 2-bromo-4-fluoro-5-methoxybenzoic acid 1 (1.0 kg, 4.02 mol), 4-bromophenol (4.41 mol, 1.05 equiv, 729.5 g) and $Cs_2CO_3$ (12.06 mol, 3 equiv. 3.92 kg) in anhydrous DMF (12 L) was degassed with N₂ for 30 min. To this mixture was added copper (I) triflate toluene complex (2:1) (0.04 equiv. 83.12 g) and the mixture was further degassed again with N₂ for 15 min. The resulting mixture was heated at 110° C. for 4 days. The reaction mixture was cooled to ambient temperature and poured onto 5 L of ice water. The pH was adjusted to 1 with concentrated HCl and the aqueous layer was extracted with EtOAc (3×4 L). The combined extracts were washed with brine (2×2 L). The organic layer was separated, dried over Na₂SO₄, filtered and concentrated under reduced pressure to provide a thick brown oil. The brown oil was triturated with a 5% IPA/water mixture (5 L) at ambient temp to obtain a brown solid. The solid was filtered, washed with water and hexane and dried overnight under vacuum to afford 2-(4-bromophenoxy)-4-fluoro-5-methoxybenzoic acid (1.3 kg, 95% yield) as a brown solid.

Step 2: A 3 neck 22 L RBF equipped with a mechanical stirrer, temperature probe and N₂ inlet was charged with concentrated H₂SO₄ (2.7 L) and heated to 60° C. To this mixture was added 2-(4-bromophenoxy)-4-fluoro-5-methoxybenzoic acid (1.3 kg, 3.81 mol) in portions such that the internal temp remained below 70° C. The resulting mixture was stirred at 60° C. for 1 hour at which point the reaction mixture was cooled to 0° C. and slowly poured onto ice water. The resulting solids were removed by filtration, washed with water and triturated with EtOAc (3 L). The solid was then washed with EtOAc, hexane and dried under vacuum at 30° C. to afford 7-bromo-3-fluoro-2-methoxy-9H-xanthen-9-one as an off white solid.

Step 3: To a suspension of 7-bromo-3-fluoro-2-methoxy-9H-xanthen-9-one (25 g, 73.4 mmol) in THF (500 mL) was added MeMgCl (2.0 equiv. 146.75 mmol, 48.9 mL, 3.0 M solution in THF) at −20° C. (internal temp) slowly over 30 minutes. The resulting mixture was allowed to reach ambient temperature where it was maintained for 12 hours. The reaction was quenched by adding saturated NH₄Cl. The phases were separated and the aqueous layer was extracted with EtOAc (2×300 mL). The combined organic extracts were washed with brine, dried over Na₂SO₄, filtered and concentrated to afford 25 g of 7-bromo-3-fluoro-2-methoxy-9-methyl-9H-xanthen-9-ol that was used in the next step without further purification. A solution of the derived alcohol (25 g) was dissolved in DCM (300 mL) and pPTS (250 mg, 0.995 mmol) was added. The mixture was heated to reflux for 2 hours at which time the reaction was cooled to rt and washed with NaHCO₃ (100 mL). The layers were separated and the organic layer was washed with brine, dried over Na₂SO₄, filtered and concentrated. The resulting residue was purified via chromatography (hexanes/DCM, 3:1) to provide 7-bromo-3-fluoro-2-methoxy-9-methylene-9H-xanthene as an orange solid.

Step 4: A solution of iodine (306 g, 1.20 mol, 1.05 eq) in THF (1.2 L) was cooled to −20° C. and treated with silver cyanate (515 g, 3.48 mol, 3.0 eq). The mixture was stirred for 30 minutes at −10° C. and then cooled down to −30° C. Once at this temperature a solution of 7-bromo-3-fluoro-2-methoxy-9-methylene-9H-xanthene as an orange solid (368 g, 1.146 mol) in THF (4.0 L) was added over to the above mixture, keeping the internal temperature, <−10° C. (~20 min). The reaction mixture was slowly warmed up to 0° C. and stirred for 30 minutes. The reaction mixture was cooled down again to −30° C. and a solution of ammonium in IPA (2.0M) was added slowly, keeping internal temperature <−10° C. After the addition, the mixture was stirred for overnight at room temperature. The mixture was filtered through a pad of celite, washed with THF. The filtrate was diluted with EtOAc (~4 L) and washed sequentially with aqueous Na₂S₂O₄ (2 L) and brine. Thd solution was dried over Na₂SO₄, filtered and concentrated to provide a residue was triturated with ethyl ether. The resulting solid was filtered and washed with cold ether to afford 7'-bromo-3'-fluoro-2'-methoxy-5H-spiro[oxazole-4,9'-xanthen]-2-amine (260 g) as a white solid. The filtrate was concentrated and purified via chromatography (ethyl acetate/hexanes (1:3) to (1:1)) to afford 180 g of 7'-bromo-3'-fluoro-2'-methoxy-5H-spiro[oxazole-4,9'-xanthen]-2-amine.

Chiral separation provided (R)-7'-bromo-3'-fluoro-2'-methoxy-5H-spiro[oxazole-4,9'-xanthen]-2-amine and (S)-7'-bromo-3'-fluoro-2'-methoxy-5H-spiro[oxazole-4,9'-xanthen]-2-amine, both as off white solids.

Example 89

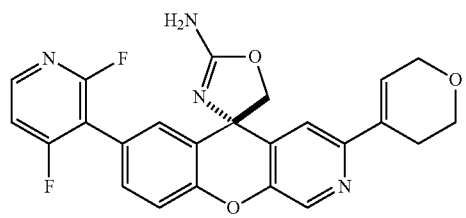

A glass microwave reaction vessel was charged with (S)-3-chloro-7-(2,4-difluoropyridin-3-yl)-5'H-spiro[chromeno[2,3-c]pyridine-5,4'-oxazol]-2'-amine (0.567 g, 1.415 mmol), potassium phosphate (0.751 g, 3.54 mmol), 2-(3,6-dihydro-2H-pyran-4-yl)-4,4,5,5-tetramethyl-1,3,2-dioxaborolane (0.594 g, 2.83 mmol) and bis(di-tert-butylphenylphosphine)dichloropalladium (II) (0.088 g, 0.141 mmol). Dioxane (9 mL) and water (3 mL) were added and the reaction vessel was flushed with argon and sealed. The reaction mixture was heated in microwave at 105° C. for 30 min. The mixture was diluted with EtOAc (25 mL) and saturated Na₂CO₃ (50 mL). The organic layer was washed twice with saturated Na₂CO₃, dried over Na₂SO₄ and concentrated in vacuo. The crude residue was purified by silica gel chromatography (2-10% MeOH—CH₂Cl₂ to afford an off white solid that was further purified by reverse phase HPLC: (15-55% CH₃CN—H₂O with 0.1% TFA in 20 min) to provide the depicted product above as a TFA salt. MS m/z=449.0 [M+H].

Example 127

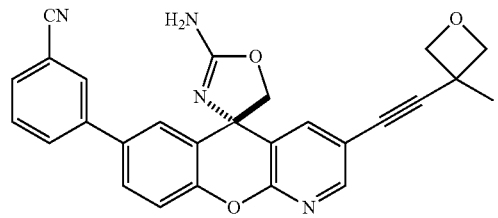

A vial was charged with (S)-2'-amino-3-((3-methyloxetan-3-yl)ethynyl)-5'H-spiro[chromeno[2,3-b]pyridine-5,4'-oxazole]-7-yl trifluoromethanesulfonate (92 mg, 0.186 mmol, prepared from the alcohol as described in Method CC6), 3-cyanophenylboronic acid (82 mg, 0.557 mmol), potassium carbonate (128 mg, 0.928 mmol), and Cl₂Pd(dppf) (1.516 mg, 1.857 µmol). The vial was flushed with argon, then dioxane (928 µL) and water (0.5 mL) were added. The vial was sealed and placed in an 80° C. oil bath for 1.5 hours. An additional portion of catalyst (3 mg) was added and the mixture was returned to the 80° C. oil bath. Heating was continued for an additional 2 hours. The mixture was cooled to rt and was diluted with EtOAc (15 mL) and brine (20 mL). The layers were separated, and the aqueous layer was extracted with EtOAc (15 mL). The combined organic layers were dried over sodium sulfate, filtered, and evaporated. The residue was chromatographed on a 40-g Redi-Sep column, eluting with 0-50% of a 90:10:1 mix of $CH_2Cl_2/MeOH/NH_4OH$ in $CH_2Cl_2$ to give (S)-3-(2'-amino-3-((3-methyloxetan-3-yl) ethynyl)-5'H-spiro[chromeno[2,3-b]pyridine-5,4'-oxazole]-7-yl)benzonitrile as a pale, tan solid.

MS m/z=449.2 $[M+H]^{-1}$. Calculated for $C_{27}H_{21}N_4O_3$: 449.2.

$^1$H NMR (400 MHz, DMSO-$d_6$) δ 1.66 (s, 3 H), 4.34-4.42 (m, 2 H), 4.45 (d, J=5.58 Hz, 2 H), 4.78 (d, J=5.48 Hz, 2 H), 6.66 (br. s, 2 H), 7.35 (d, J=8.61 Hz, 1 H), 7.64-7.71 (m, 2 H), 7.74-7.79 (m, 2 H), 7.81-7.86 (m, 1 H), 7.98 (d, J=8.12 Hz, 1 H), 8.12-8.18 (m, 1 H), 8.31-8.42 (m, 1H).

Example 128

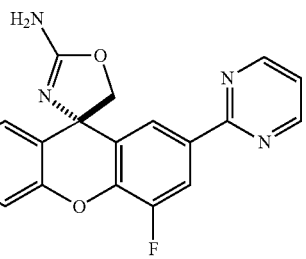

A microwave vial was charged with (S)-2-amino-5'-fluoro-2'-(2-fluoropyridin-3-yl)-5H-spiro[oxazole-4,9'-xanthene]-7'-yl trifluoromethanesulfonate (100 mg, 0.195 mmol), tetrakis(triphenylphosphine)palladium(0) (22.51 mg, 0.019 mmol), copper(i) iodide (3.71 mg, 0.019 mmol), 2-(tributylstannyl)pyrimidine (216 mg, 0.584 mmol) and DMF (974 μL). Lithium chloride (83 mg, 1.948 mmol) was added, the vial was flushed with argon, sealed and heated at 85° C. for 4 hrs. The mixture was cooled to the room temperature, diluted with water (1 ml) and ethyl acetate (3 ml). The organic layer was loaded onto 2 g SCX-2 column and washed with ethyl acetate and methanol. The material was released from the column using 2 M ammonia in MeOH solution. The filtrated was concentrated and purified by silica gel chromatography (10-80% $CH_2Cl_2/MeOH/NH4OH$ in $CH_2Cl_2$) to afford (S)-4'-fluoro-7'-(2-fluoropyridin-3-yl)-2'-(pyrimidin-2-yl)-5H-spiro[oxazole-4,9'-xanthen]-2-amine (40 mg, 0.090 mmol).

MS m/z=426.0 $[M+H]^+$. Calculated for $C_{24}H_{16}FN_5O_2$: 425.13.

$^1$H NMR (400 MHz, DMSO-$d_6$) ppm 4.29 (s, 2 H), 6.49-6.66 (m, 2 H), 7.47 (m, 3 H), 7.60-7.68 (m, 2 H), 8.08-8.28 (m, 4 H), 8.30-8.36 (m, 1 H), 8.93 (d, J=4.8 Hz, 2H)

Example 129

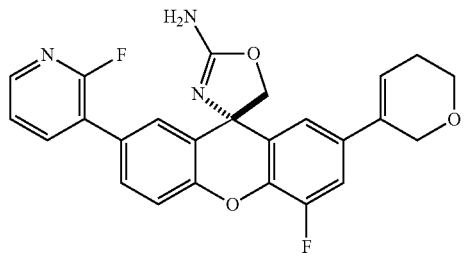

Sodium carbonate (saturated) (1 ml), Pd(PPh$_3$)$_4$ (53.5 mg, 0.046 mmol), (S)-2-amino-5'-fluoro-2'-(2-fluoropyridin-3-yl)-5H-spiro[oxazole-4,9'-xanthene]-7'-yl trifluoromethanesulfonate (475 mg, 0.925 mmol; prepared from the alcohol by steps analogous to those described in Method BB40 and Example 2), and 2-(5,6-dihydro-2H-pyran-3-yl)-4,4,5,5-tetramethyl-1,3,2-dioxaborolane (389 mg, 1.850 mmol) were combined in DMF (5 ml). The solution was heated at 85° C. for three hours before being cooled to rt. The solution was concentrated and the derived residue was purified via silica gel column chromatography (RediSep 40 g column) using 20-70% 90/10/1 ($CH_2Cl_2$/MeOH/ammonia) in $CH_2Cl_2$ to afford (S)-2'-(5,6-dihydro-2H-pyran-3-yl)-4'-fluoro-7'-(2-fluoropyridin-3-yl)-5H-spiro[oxazole-4,9'-xanthen]-2-amine as a white solid. MS m/z=448.0 $[M+H]^+$. Chemical Formula: $C_{25}H_{19}F_2N_3O_3$. Exact Mass: 447.14. $^1$H NMR (400 MHz, DMSO-$d_6$) δ ppm 2.18-2.36 (m, 2 H) 3.75 (t, J=5.5 Hz, 2 H) 4.24 (m, 2 H) 4.30-4.48 (m, 2 H) 6.22-6.36 (m, 1 H) 6.52 (s, 2 H) 7.07-7.15 (m, 1 H) 7.38 (m, J=8.5 Hz, 2 H) 7.50 (ddd, J=7.4, 4.9, 1.9 Hz, 1 H) 7.53-7.66 (m, 2 H) 8.12 (ddd, J=10.4, 7.5, 1.9 Hz, 1 H) 8.20-8.30 (m, 1 H)

Example 130

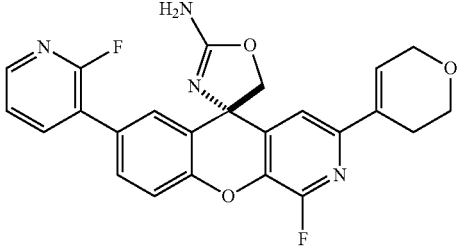

A reaction vessel charged with (S)-3-chloro-1-fluoro-7-(2-fluoropyridin-3-yl)-5'H-spiro[chromeno[2,3-c]pyridine-5,4'-oxazol]-2'-amine (95 mg, 0.237 mmol; prepared as described in Method BB33) 2-(3,6-dihydro-2H-pyran-4-yl)-4,4,5,5-tetramethyl-1,3,2-dioxaborolane (100 mg, 0.474 mmol), bis-(di-tert-butyl(4-dimethylaminophenyl)phosphine)dichloropalladium(II) (8.39 mg, 0.012 mmol) and potassium phosphate (111 mg, 0.522 mmol) in 1.5 ml of a 2:1 mixture of dioxane and was heated at 135° C. microwave for 25 minutes. The reaction mixture was loaded directly onto a silica gel column and purified ($CH_2Cl_2$ to $CH_2Cl_2$/ethyl acetate=3:1 to 2:1 to 1:1 to 100% ethyl acetate to ethyl acetate/MeOH=100:5) to provide (S)-3-(3,6-dihydro-2H-pyran-4-yl)-1-fluoro-7-(2-fluoropyridin-3-yl)-5'H-spiro[chromeno[2,3-c]pyridine-5,4'-oxazol]-2'-amine as a off-white solid. MS m/z=449.0 $[M+H]^+$. Calculated for $C_{24}H_{18}F_2N_4O_3$: 448.42.

$^1$H NMR (400 MHz, CHLOROFORM-d)=8.18 (d, J=4.7 Hz, 1 H), 7.87 (ddd, J=1.8, 7.7, 9.7 Hz, 1 H), 7.64 (s, 1 H), 7.53 (d, J=8.6 Hz, 1 H), 7.33 (d, J=8.6 Hz, 1 H), 7.30-7.25 (m, 1 H), 7.22 (s, 1 H), 6.68 (br. s., 1 H), 4.47-4.29 (m, 4 H), 3.92 (t, J=5.5 Hz, 2 H), 2.56 (d, J=2.2 Hz, 2 H)

Example 131

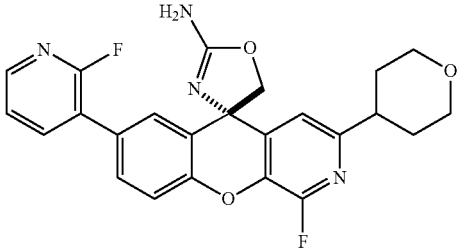

A suspension of (S)-3-(3,6-dihydro-2H-pyran-4-yl)-1-fluoro-7-(2-fluoropyridin-3-yl)-5'H-spiro[chromeno[2,3-c]pyridine-5,4'-oxazol]-2'-amine (60 mg, 0.134 mmol; prepared as described in Method BB33) and 10% Pd/C (60 mg) was stirred at rt under 1 atm of H₂ gas for 12 hours. The suspension was filtered through a pad of silica gel washing with a 1:1 mixture of CH₂Cl₂/MeOH. The filtrate was evaporated to dryness and purified by silica gel chromatography (EtOAc to EtOAc/MeOH=100:5 to 100:7) to provide (S)-1-fluoro-7-(2-fluoropyridin-3-yl)-3-(tetrahydro-2H-pyran-4-yl)-5'H-spiro[chromeno[2,3-c]pyridine-5,4'-oxazol]-2'-amine as an off-white solid.

MS m/z=451.0 [M+H]⁺. Calculated for $C_{24}H_{18}F_2N_4O_3$: 450.44.

¹H NMR (400 MHz, CHLOROFORM-d) δ=8.18 (d, J=4.7 Hz, 1 H), 7.87 (ddd, J=1.9, 7.6, 9.7 Hz, 1 H), 7.63 (t, J=1.7 Hz, 1 H), 7.54 (d, J=8.4 Hz, 1 H), 7.32 (d, J=8.4 Hz, 1H), 7.30-7.24 (m, 1 H), 7.08 (s, 1 H), 4.44-4.32 (m, 2 H), 4.11-4.05 (m, 2 H), 3.52 (dt, J=3.0, 11.4 Hz, 2 H), 2.95-2.82 (m, 1 H), 1.94-1.81 (m, 4 H), 1.99-1.80 (m, 4 H)

Example 132

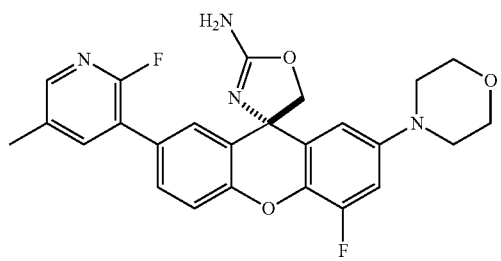

A resealable vial was charged with (S)-2-amino-4'-fluoro-2'-morpholino-5H-spiro[oxazole-4,9'-xanthene]-7'-yl trifluoromethanesulfonate (130 mg, 0.258 mmol; prepared as described in Method BB40), tetrakis(triphenylphosphine)palladium(0) (29.8 mg, 0.026 mmol), 2-fluoro-5-methylpyridin-3-ylboronic acid (64.0 mg, 0.413 mmol), DMF (1.3 mL) and 2 M aqueous sodium carbonate (387 μL, 0.775 mmol). The vial was sealed and the mixture stirred for 2 hr at 85° C. The mixture was cooled and diluted with EtOac (6 mL) and water (2 ml). The organic layer was filtered through celite, concentrated, and purified by reverse phase HPLC (Gilson, 15-90% MeCN in 0.1% aq. TFA). The fractions containing product were concentrated in vacuo, neutralized with saturated sodium bicarbonage and extracted with ethyl acetate. Organic layer was washed with brine, and concentrated. The residue was redissoved in ~1 mL 1:1 MeCN/water and liophilized to afford (S)-4'-fluoro-7'-(2-fluoro-5-methylpyridin-3-yl)-2'-morpholino-5H-spiro[oxazole-4,9'-xanthen]-2-amine.

MS m/z=465.0 [M+H]⁺. Calculated for $C_{25}H_{22}F_2N_4O_3$: 464.17.

¹H NMR (400 MHz, DMSO-d₆) ppm 2.36 (s, 3 H), 3.07 (dd, J=5.7, 4.0 Hz, 4 H), 3.74 (t, J=4.7 Hz, 4 H), 4.20 (s, 2 H), 6.41-6.58 (m, 2 H), 6.61-6.66 (m, 1 H), 6.99 (dd, J=13.8, 2.8 Hz, 1 H), 7.31 (dd, J=8.2, 0.5 Hz, 1 H), 7.55 (s, 2 H), 7.92 (dd, J=9.9, 1.9 Hz, 1 H), 8.03 (s, 1 H).

Example 133

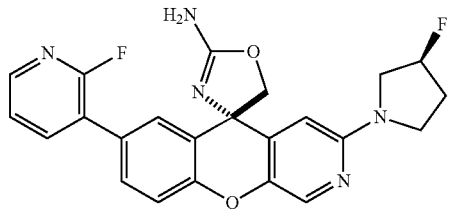

To a resealed tube charged with a mixture of (S)-3-chloro-7-(2-fluoropyridin-3-yl)-5'H-spiro[chromeno[2,3-c]pyridine-5,4'-oxazol]-2'-amine (0.20 g, 0.522 mmol), pd2(dba)₃ (0.024 g, 0.026 mmol), 2-(dicyclohexylphosphino)-2'-(n,n-dimethylamino)biphenyl (0.031 g, 0.078 mmol) and(S)-3-fluoropyrrolidine hydrochloride (0.197 g, 1.567 mmol) was added 1.0 M lithium bis(trimethylsilyl)amide (3.13 mL, 3.13 mmol) in THF and the resulting mixture was heated at 90° C. for 24 h. The mixture was cooled, concentrated and purified by reverse phase HPLC to afford (S)-7-(2-fluoropyridin-3-yl)-3-((S)-3-fluoropyrrolidin-1-yl)-5'H-spiro[chromeno[2,3-c]pyridine-5,4'-oxazol]-2'-amine.

Example 134

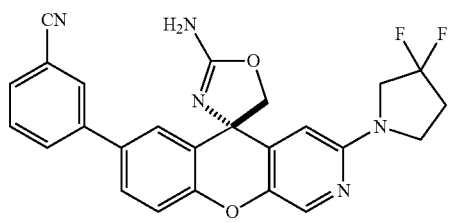

To a mixture of (S)-3-(2'-amino-3-chloro-5'H-spiro[chromeno[2,3-c]pyridine-5,4'-oxazole]-7-yl)benzonitrile (0.10 g, 0.257 mmol), 3,3-difluoropyrrolidine hydrochloride (0.111 g, 0.772 mmol), pd2(dba)₃ (0.012 g, 0.013 mmol), and 2'-(dicyclohexylphosphino)-N,N-dimethylbiphenyl-2-amine (0.015 g, 0.039 mmol) in a resealed tube was added THF (1 mL) and 1.0 M lithium bis(trimethylsilyl)amide (1.543 mL, 1.543 mmol). The resulting mixture was heated at 90° C. for 17 h. The mixture was cooled, concentrated and purified by reverse phase HPLC to afford (S)-3-(2'-amino-3-(3,3-difluoropyrolidin-1-yl)-5'H-spiro[chromeno[2,3-c]pyridine-5,4'-oxazole]-7-yl)benzonitrile.

Example 135

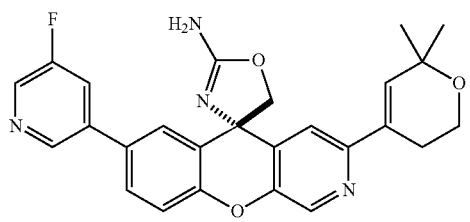

A glass microwave reaction vessel was charged with (S)-3-chloro-7-(5-fluoropyridin-3-yl)-5'H-spiro[chromeno[2,3-c]pyridine-5,4'-oxazol]-2'-amine (0.250 g, 0.653 mmol; prepared as described in Method BB41), 2-(6,6-dimethyl-3,6-dihydro-2H-pyran-4-yl)-4,4,5,5-tetramethyl-1,3,2-dioxaborolane (0.311 g, 1.306 mmol), bis(di-tert-butylphenylphosphine)dichloropalladium (II) (0.041 g, 0.065 mmol), dioxane (3 mL) and water (0.8 mL). The reaction mixture was exposed to MW radiation at 105° C. for 30 min in a microwave reactor. The mixture was diluted with EtOAc and water. The organic layer was washed with saturated sodium carbonate and dried over sodium sulfate. The crude material was initially purified by silica gel chromatography using 2-10% MeOH (2M NH3)-CH2Cl2) followed by further purification by SFC chromatography to give (S)-3-(6,6-dimethyl-3,6-dihydro-2H-pyran-4-yl)-7-(5-fluoropyridin-3-yl)-5'H-spiro[chromeno[2,3-c]pyridine-5,4'-oxazol]-2'-amine MS m/z=459.0 [M+H]⁺. Calculated for C26H23FN4O3: 458.18

¹H NMR (400 MHz, CHLOROFORM-d) ppm 1.38 (d, J=3.13 Hz, 6 H) 2.57 (dd, J=5.28, 1.37 Hz, 2 H) 3.96 (t, J=5.38 Hz, 2 H) 4.36 (d, J=5.48 Hz, 2 H) 4.64 (br. s., 2 H) 6.56 (s, 1 H) 7.29 (d, J=8.41 Hz, 1 H) 7.38 (s, 1 H) 7.54 (dd, J=8.51, 2.25 Hz, 1 H) 7.56-7.60 (m, 1 H) 7.60 (d, J=2.35 Hz, 1 H) 8.46 (d, J=2.54 Hz, 1 H) 8.50 (s, 1 H) 8.67 (t, J=1.66 Hz, 1 H)

Example 136

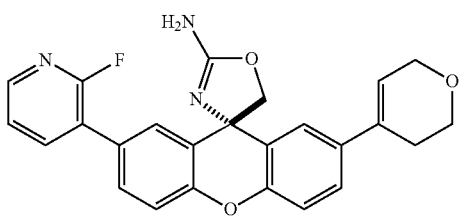

A resealable vial was charged with (R)-2-amino-2'-(3,6-dihydro-2H-pyran-4-yl)-5H-spiro[oxazole-4,9'-xanthene]-7'-yl trifluoromethanesulfonate (100 mg, 0.207 mmol; prepared by method AA1 as described in Example 2), tetrakis(triphenylphosphine)palladium (23.95 mg, 0.021 mmol) and 2-fluoropyridin-3-ylboronic acid (0.332 mmol). DMF (1036 µL) was added followed by 2 M aqueous sodium carbonate (311 µL, 0.622 mmol) and the vial was sealed and heated at 85° C. for 1 hr. The mixture was cooled to the RT, diluted with water (2 ml) and EtOAc (5 ml). The organic layer was loaded onto 2 g SCX-2 column and washed with ethyl acetate and MeOH. The material was released from the column using 2M ammonia in MeOH solution, concentrated and purified by reverse phase HPLC (Gilson, 15-90% MeCN in 0.1% aq. TFA) to afford (R)-2'-(3,6-dihydro-2H-pyran-4-yl)-7'-(2-fluoropyridin-3-yl)-5H-spiro[oxazole-4,9'-xanthen]-2-amine 2,2,2-trifluoroacetate.

MS m/z=430.8 [M+H]⁺. Calculated for C25H20FN3O3: 429.15.

¹H NMR (400 MHz, DMSO-d₆) ppm 3.85 (t, J=5.9 Hz, 2 H), 4.20-4.30 (m, 2 H), 5.12 (s, 2 H), 6.29-6.36 (m, 1 H), 7.30 (d, J=8.6 Hz, 1 H), 7.42 (d, J=8.6 Hz, 1 H), 7.52 (ddd, J=7.3, 5.0, 1.9 Hz, 1 H), 7.58-7.67 (m, 2 H), 7.76 (dt, J=8.6, 1.8 Hz, 1 H), 7.88 (s, 1 H), 8.20 (ddd, J=10.4, 7.4, 2.0 Hz, 1 H), 8.26-8.32 (m, 1 H), 9.29-9.75 (m, 2 H), 11.15-11.37 (m, 1 H).

Example 137

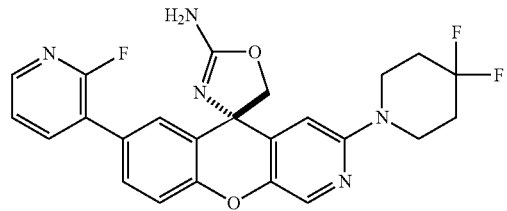

To a resealable tube charged with a mixture of (S)-3-chloro-7-(2-fluoropyridin-3-yl)-5'H-spiro[chromeno[2,3-c]pyridine-5,4'-oxazol]-2'-amine (0.20 g, 0.522 mmol), pd2(dba)3 (0.024 g, 0.026 mmol), 2-(dicyclohexylphosphino)-2'-(n,n-dimethylamino)biphenyl (0.031 g, 0.078 mmol) and 4,4-difluoropiperidine HCl (0.247 g, 1.567 mmol) was added 1.0 M lithium bis(trimethylsilyl)amide (3.13 mL, 3.13 mmol) in THF and the resulting mixture was heated at 90° C. for 24 h. The mixture was concentrated and purified on silica gel using 0-6% MeOH/DCM to afford (S)-3-(4,4-difluoropiperidin-1-yl)-7-(2-fluoropyridin-3-yl)-5'H-spiro[chromeno[2,3-c]pyridine-5,4'-oxazol]-2'-amine.

Example 138

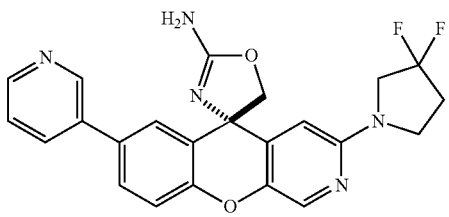

To a resealable tube charged with a mixture of (S)-3-chloro-7-(pyridin-3-yl)-5'H-spiro[chromeno[2,3-c]pyridine-5,4'-oxazol]-2'-amine (0.085 g, 0.233 mmol), 3,3-difluoropyrrolidine HCl (0.100 g, 0.699 mmol), pd2(dba)₃ (10.67 mg, 0.012 mmol), and 2-(dicyclohexylphosphino)-2'-(n,n-dimethylamino)biphenyl (0.014 g, 0.035 mmol) was added 1.0 M lithium bis(trimethylsilyl)amide (1.398 mL, 1.398 mmol) in THF and the resulting mixture was heated at 90° C. for 17 h. The mixture was concentrated and purified by reverse phase HPLC to afford (S)-3-(3,3-difluoropyrrolidin-1-yl)-7-(pyridin-3-yl)-5'H-spiro[chromeno[2,3-c]pyridine-5,4'-oxazol]-2'-amine.

Example 139

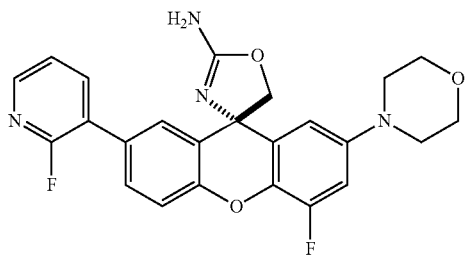

A resealable vial was charged with (S)-2-amino-4'-fluoro-2'-morpholino-5H-spiro[oxazole-4,9'-xanthene]-7'-yl trifluoromethanesulfonate (125 mg, 0.248 mmol; prepared by steps analogous to those described in Method BB40 and Example 2), tetrakis(triphenylphosphine)palladium(0) (28.7 mg, 0.025 mmol), 2-fluoropyridin-3-ylboronic acid (56.0 mg, 0.397 mmol), DMF (1.2 mL) and 2 M aqueous sodium carbonate (372 μL, 0.745 mmol). The vial was sealed and the mixture was stirred for 2 hr at 85° C. The mixture was cooled and diluted with ethyl acetate (6 mL) and water (2 ml). The organic layer was loaded onto 2 g SCX column and washed with EtOAc and MeOH/DCM 1:1. The material was recovered from the column with 2 M ammonia in MeOH, concentrated and purified by silica gel chromatography using 15-60% DCM/MeOH/NH4OH 90:10:1 in DCM to give a solid that was sonicated with 2 mL of DCM, then filtered and dried to afford (S)-4'-fluoro-7'-(2-fluoropyridin-3-yl)-2'-morpholino-5H-spiro[oxazole-4,9'-xanthen]-2-amine MS m/z=451.0 [M+H]+. Chemical Formula: $C_{24}H_{20}F_2N_4O_3$. Exact Mass: 450.15.

$^1$H NMR (400 MHz, DMSO-$d_6$) δ ppm 3.06-3.18 (m, 4 H) 3.81 (m, J=9.5 Hz, 4 H) 4.20-4.29 (m, 2 H) 6.55 (s, 2 H) 6.67-6.73 (m, 1 H) 7.05 (dd, J=13.9, 2.9 Hz, 1 H) 7.38 (d, J=8.4 Hz, 1 H) 7.50-7.58 (m, 1 H) 7.58-7.70 (m, 2 H) 8.11-8.21 (m, 1 H) 8.26-8.34 (m, 1 H)

Example 139-A (Method BB100)

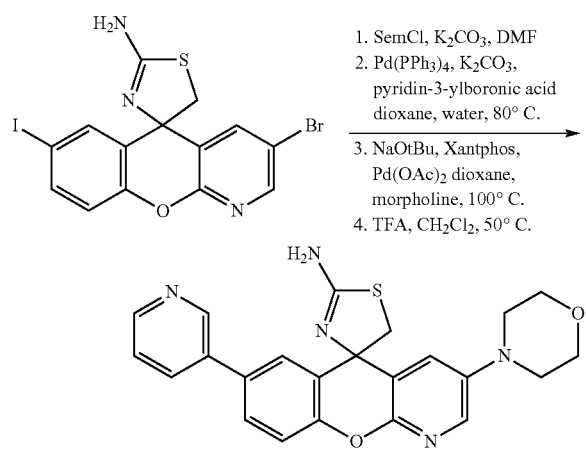

Synthesis of (S)-3-morpholino-7-(pyridin-3-yl)-5'H-spiro[chromeno[2,3-b]pyridine-5,4'-thiazol]-2'-amine (Example 581) and (R)-3-morpholino-7-(pyridin-3-yl)-5'H-spiro[chromeno[2,3-b]pyridine-5,4'-thiazol]-2'-amine (Example 580)

Step 1: 3-Bromo-7-iodo-5'H-spiro[chromeno[2,3-b]pyridine-5,4'-thiazol]-2'-amine (500 g, 1.055 mmol) and potassium carbonate (0.729 g, 5.27 mmol) were dissolved in DMF (7.03 mL) and stirred for 5 min. The reaction was cooled to 0° C. and SEM-Cl (0.561 mL, 3.16 mmol) was added slowly dropwise. The reaction was warmed to RT and stirred overnight. The mixture was poured into a separatory funnel containing water (25 mL) and EtOAc (15 mL). The aqueous layer was extracted with EtOAc (3×20 mL), and the combined organic layers were washed with brine, dried with sodium sulfate, filtered, and concentrated. The material was purified via column chromatography (0-50% EtOAc:Hex) to afford 3-bromo-7-iodo-N,N-bis((2-(trimethylsilyl)ethoxy)methyl)-5'H-spiro[chromeno[2,3-b]pyridine-5,4'-thiazol]-2'-amine, isolated as a pink solid.

Step 2: A vial was charged with 3-bromo-7-iodo-N,N-bis ((2-(trimethylsilyl)ethoxy)methyl)-5'H-spiro[chromeno[2,3-b]pyridine-5,4'-thiazol]-2'-amine (0.114 g, 0.155 mmol), pyridin-3-ylboronic acid (0.029 g, 0.233 mmol), potassium carbonate (0.107 g, 0.776 mmol), and tetrakis(triphenylphosphine)palladium(0) (0.018 g, 0.016 mmol). The vial was flushed with Ar (g), then dioxane (1.035 mL) and water (0.517 mL) were added in sequence. The vial was sealed and heated at 80° C. for 2 hrs. After cooling to RT the reaction was diluted with EtOAc (25 mL) and washed with water (25 mL). The aqueous layer was extracted with EtOAc (3×15 mL), and the combined organic layers were washed with brine, dried with sodium sulfate, filtered, and concentrated. The material was purified via column chromatography (RediSep 40 g, gradient elution 0-5% MeOH:DCM) to afford 3-bromo-7-(pyridin-3-yl)-N,N-bis((2-(trimethylsilyl)ethoxy)methyl)-5'H-spiro[chromeno[2,3-b]pyridine-5,4'-thiazol]-2'-amine as a white solid.

Step 3: A vial was charged with 3-bromo-7-(pyridin-3-yl)-N,N-bis((2-(trimethylsilyl)ethoxy)methyl)-5'H-spiro [chromeno[2,3-b]pyridine-5,4'-thiazol]-2'-amine (0.080 g, 0.117 mmol), palladium diacetate (2.62 mg, 0.012 mmol), sodium tert-butoxide (0.071 ml, 0.583 mmol), and xantphos (0.013 g, 0.023 mmol). Dioxane (1.166 ml) and morpholine (0.030 ml, 0.350 mmol) were added sequentially and the reaction was stirred at 100° C. for 24 hours. The mixture was cooled to RT and was diluted with EtOAc (20 mL) and washed with water. The aqueous layer was extracted with EtOAc (3×15 mL), and the combined organic layers were, dried with sodium sulfate, filtered, and concentrated. The material was purified via column chromatography (RediSep 12 g, gradient elution 0-100% EtOAc:Hex) to afford 3-morpholino-7-(pyridin-3-yl)-N,N-bis((2-(trimethylsilyl)ethoxy) methyl)-5'H-spiro[chromeno[2,3-b]pyridine-5,4'-thiazol]-2'-amine as an off-white solid.

Step 4: A solution of 3-morpholino-7-(pyridin-3-yl)-N,N-bis((2-(trimethylsilyl)ethoxy)methyl)-5'H-spiro[chromeno [2,3-b]pyridine-5,4'-thiazol]-2'-amine (0.066 g, 0.095 mmol) in 5 mL of DCM was treated with TFA (0.5 ml, 6.49 mmol). The reaction was stirred for 3 hrs at 50° C. The mixture was cooled to RT and was diluted with DCM (25 mL). The derived solution was washed with saturated sodium bicarbonate (50 mL). The aqueous layer was extracted with DCM (3×15 mL) and the combined organic layers were washed with brine, dried with sodium sulfate, filtered, and concentrated. The material was purified by column chromatography (RediSep 12 g, gradient elution 0-100% DCM: 100:10:1 DCM, MeOH, NH4OH) to provide 3-morpholino-7-(pyridin-3-yl)-5'H-spiro[chromeno[2,3-b]pyridine-5,4'-thiazol]-2'-amine as a racemic mixture. Chiral separation provided (S)-3-morpholino-7-(pyridin-3-yl)-5'H-spiro[chromeno[2,3-b]pyridine-5,4'-thiazol]-2'-amine and (R)-3-morpholino-7-(pyridin-3-yl)-5'H-spiro[chromeno[2,3-b]pyridine-5,4'-thiazol]-2'-amine, both isomers as a white solid. MS m/z=432.3.

Example 140

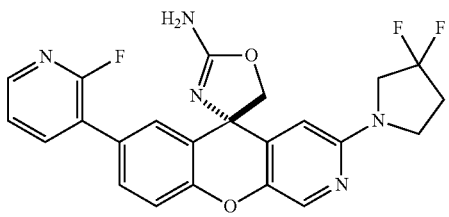

To a resealable tube charged with a mixture of (S)-3-chloro-7-(2-fluoropyridin-3-yl)-5'H-spiro[chromeno[2,3-c]pyridine-5,4'-oxazol]-2'-amine (0.25 g, 0.653 mmol), pd2(dba)3 (0.030 g, 0.033 mmol), 2-(dicyclohexylphosphino)-2'-(n,n-dimethylamino)biphenyl (0.039 g, 0.098 mmol), and 3,3-difluoropyrrolidine hydrochloride (0.281 g, 1.959 mmol) was added 1.0 M lithium bis(trimethylsilyl)amide (3.92 mL, 3.92 mmol) in THF and the resulting mixture was heated at 90° C. for 24 h. The mixture was concentrated and purified by reverse phase HPLC to afford (S)-3-(3,3-difluoropyrrolidin-1-yl)-7-(2-fluoropyridin-3-yl)-5'H-spiro[chromeno[2,3-c]pyridine-5,4'-oxazol]-2'-amine.

The following compounds in Table I are additional representative examples of compounds of Formulas I, I-A, I-B, I-C, I-D, II, II-A, III, IV and V, and sub-formulas thereof, provided by the present invention. The methods which were used to prepare each exemplary compound are also included in the Table, along with the mass found and biological data (average nM $IC_{50}$'s for the enzyme and cell assays) where available.

TABLE I

| Ex. No. | Compound Name | Observed Mass | Method | BACE 1 FRET assay (uM) | HEK cell assay (uM) |
|---|---|---|---|---|---|
| 141 | 4-((5S)-2'-amino-7-(5-methyl-3-pyridinyl)spiro[chromeno[2,3-c]pyridine-5,4'-[1,3]oxazol]-3-yl)-2-pyridinecarbonitrile | 447 | AA1 | 0.0174 | 0.1135 |
| 142 | (5S)-3,7-diphenylspiro[chromeno[2,3-c]pyridine-5,4'-[1,3]oxazol]-2'-amine | 406.1 | AA2 | 0.0158 | 0.5318 |
| 143 | 3-((5S)-2'-amino-3-(3,6-dihydro-2H-pyran-4-yl)spiro[chromeno[2,3-c]pyridine-5,4'-[1,3]oxazol]-7-yl)benzonitrile | 437 | AA1 | 0.0011 | 0.0094 |
| 144 | (5S)-3-(3,6-dihydro-2H-pyran-4-yl)-7-(5-methoxy-3-pyridinyl)spiro[chromeno[2,3-c]pyridine-5,4'-[1,3]oxazol]-2'-amine | 443 | AA1 | 0.0016 | 0.0088 |
| 145 | (5S)-3-(3,6-dihydro-2H-pyran-4-yl)-7-(3-(trifluoromethyl)phenyl)spiro[chromeno[2,3-c]pyridine-5,4'-[1,3]oxazol]-2'-amine | 479.9 | AA1 | 0.0022 | 0.0819 |
| 89 | (5S)-7-(2,4-difluoro-3-pyridinyl)-3-(3,6-dihydro-2H-pyran-4-yl)spiro[chromeno[2,3-c]pyridine-5,4'-[1,3]oxazol]-2'-amine | 449 | BB3 | 0.0007 | 0.0047 |
| 90 | (5S)-7-bromo-2-fluoro-3-(trimethylsilyl)spiro[chromeno[2,3-b]pyridine-5,4'-[1,3]oxazol]-2'-amine | 423.8 | BB4 | 0.8616 | 10 |
| 146 | (5S)-2-fluoro-7-(2-fluoro-3-pyridinyl)-3-(trimethylsilyl)spiro[chromeno[2,3-b]pyridine-5,4'-[1,3]oxazol]-2'-amine | 439 | BB4 | 0.0123 | 0.1691 |
| 147 | 2-fluoro-3,7-bis(2-fluoro-3-pyridinyl)spiro[chromeno[2,3-b]pyridine-5,4'-[1,3]oxazol]-2'-amine | 461.9 | BB35 | 0.0223 | 0.1238 |
| 148 | 3-(3,3-dimethyl-1-butyn-1-yl)-2-fluoro-7-(2-fluoro-3-pyridinyl)spiro[chromeno[2,3-b]pyridine-5,4'-[1,3]oxazol]-2'-amine | 447 | AA33 | 0.0007 | 0.0214 |
| 149 | 2-fluoro-7-(2-fluoro-3-pyridinyl)-3-((3-methyl-3-oxetanyl)ethynyl)spiro[chromeno[2,3-b]pyridine-5,4'-[1,3]oxazol]-2'-amine | 461 | BB36 | 0.0008 | 0.0076 |
| 150 | 3-(3,6-dihydro-2H-pyran-4-yl)-2-fluoro-7-(2-fluoro-3-pyridinyl)spiro[chromeno[2,3-b]pyridine-5,4'-[1,3]oxazol]-2'-amine | 449 | BB35 | 0.0026 | 0.0482 |
| 151 | 2-fluoro-7-(2-fluoro-3-pyridinyl)-3-(2-fluoro-4-pyridinyl)spiro[chromeno[2,3-b]pyridine-5,4'-[1,3]oxazol]-2'-amine | 461.9 | BB35 | 0.0013 | 0.0508 |
| 152 | (5S)-1-fluoro-7-(2-fluoro-3-pyridinyl)-3-(2-fluoro-4-pyridinyl)spiro[chromeno[2,3-c]pyridine-5,4'-[1,3]oxazol]-2'-amine | 461.9 | AA1 | 0.002 | |
| 153 | (5S)-7-(5-fluoro-3-pyridinyl)-3-((3-methyl-3-oxetanyl)ethynyl)spiro[chromeno[2,3-c]pyridine-5,4'-[1,3]oxazol]-2'-amine | 443 | AA5 | 0.0092 | 0.0462 |
| 154 | (5S)-3-((3-methyl-3-oxetanyl)ethynyl)-7-(3-pyridinyl)spiro[chromeno[2,3-c]pyridine-5,4'-[1,3]oxazol]-2'-amine | 425 | AA5 | 0.0014 | 0.0065 |
| 155 | (5S)-3-((3-methyl-3-oxetanyl)ethynyl)-7-phenylspiro[chromeno[2,3-c]pyridine-5,4'-[1,3]oxazol]-2'-amine | 424 | AA5 | 0.0173 | 0.1731 |
| 156 | (5S)-7-(6-fluoro-3-pyridinyl)-3-((3-methyl-3-oxetanyl)ethynyl)spiro[chromeno[2,3-c]pyridine-5,4'-[1,3]oxazol]-2'-amine | 443 | AA5 | 0.0109 | 0.0459 |
| 157 | (5S)-7-(3-chlorophenyl)-3-((3-methyl-3-oxetanyl)ethynyl)spiro[chromeno[2,3-c]pyridine-5,4'-[1,3]oxazol]-2'-amine | 457.9 | AA5 | 0.0008 | 0.0302 |
| 158 | (5S)-7-(5-chloro-2-fluoro-3-pyridinyl)-3-((3-methyl-3-oxetanyl)ethynyl)spiro[chromeno[2,3-c]pyridine-5,4'-[1,3]oxazol]-2'-amine | 476.9 | AA5 | 0.001 | 0.0116 |
| 159 | (5S)-7-(cyclopropylethynyl)-3-(3,6-dihydro-2H-pyran-4-yl)spiro[chromeno[2,3-c]pyridine-5,4'-[1,3]oxazol]-2'-amine | 400 | AA5 | 0.0049 | 0.084 |

TABLE I-continued

| Ex. No. | Compound Name | Observed Mass | Method | BACE 1 FRET assay (uM) | HEK cell assay (uM) |
|---|---|---|---|---|---|
| 160 | (5S)-3-(3,6-dihydro-2H-pyran-4-yl)-7-((3-methyl-3-oxetanyl)ethynyl)spiro[chromeno[2,3-c]pyridine-5,4'-[1,3]oxazol]-2'-amine | 430 | AA33 | 0.022 | 0.091 |
| 161 | (5S)-3-(3,6-dihydro-2H-pyran-4-yl)-7-(3,3-dimethyl-1-butyn-1-yl)spiro[chromeno[2,3-c]pyridine-5,4'-[1,3]oxazol]-2'-amine | 416 | AA33 | 0.0097 | 0.1084 |
| 162 | (5S)-7-(3,3-dimethyl-1-butyn-1-yl)-3-(2-fluoro-4-pyridinyl)spiro[chromeno[2,3-c]pyridine-5,4'-[1,3]oxazol]-2'-amine | 428.9 | AA33 | 0.023 | 0.775 |
| 163 | (5S)-3-(3,3-difluoro-1-pyrrolidinyl)-7-((3-methyl-3-oxetanyl)ethynyl)spiro[chromeno[2,3-c]pyridine-5,4'-[1,3]oxazol]-2'-amine | 452.9 | AA33 | 0.0174 | 0.1242 |
| 164 | 3-((5S)-2'-amino-3-((3-methyl-3-oxetanyl)ethynyl)spiro[chromeno[2,3-c]pyridine-5,4'-[1,3]oxazol]-7-yl)benzonitrile | 449 | BB9 | 0.0023 | 0.0189 |
| 165 | (5S)-7-(2,4-difluoro-3-pyridinyl)-3-(3,3-dimethyl-1-butyn-1-yl)spiro[chromeno[2,3-c]pyridine-5,4'-[1,3]oxazol]-2'-amine | 447 | BB37 | 0.002 | |
| 166 | (5S)-7-(3-chlorophenyl)-3-(2-pyrazinyl)spiro[chromeno[2,3-b]pyridine-5,4'-[1,3]oxazol]-2'-amine | 441.8 | AA57 | 0.0018 | 0.0177 |
| 167 | (5S)-7-(6-fluoro-3-pyridinyl)-3-((3-methyl-3-oxetanyl)ethynyl)spiro[chromeno[2,3-b]pyridine-5,4'-[1,3]oxazol]-2'-amine | 443 | AA23 | 0.0026 | 0.0139 |
| 168 | (5S)-3-((3-methyl-3-oxetanyl)ethynyl)-7-(2-pyrazinyl)spiro[chromeno[2,3-b]pyridine-5,4'-[1,3]oxazol]-2'-amine | 426.2 | AA66 | 0.0033 | 0.0145 |
| 169 | 3-((5S)-2'-amino-3-(3,6-dihydro-2H-pyran-4-yl)spiro[chromeno[2,3-b]pyridine-5,4'-[1,3]oxazol]-7-yl)benzonitrile | 437.2 | AA1 | 0.0013 | 0.0045 |
| 127 | 3-((5S)-2'-amino-3-((3-methyl-3-oxetanyl)ethynyl)spiro[chromeno[2,3-b]pyridine-5,4'-[1,3]oxazol]-7-yl)benzonitrile | 449.2 | AA23 | 0.0011 | 0.005 |
| 170 | (5S)-7-(3-chloro-2-fluorophenyl)-3-(3,6-dihydro-2H-pyran-4-yl)spiro[chromeno[2,3-b]pyridine-5,4'-[1,3]oxazol]-2'-amine | 464 | AA1 | 0.0015 | 0.0183 |
| 171 | (5S)-3-(5,6-dihydro-2H-pyran-3-yl)-7-(2-fluoro-3-pyridinyl)spiro[chromeno[2,3-b]pyridine-5,4'-[1,3]oxazol]-2'-amine | 431 | AA1 | 0.0012 | 0.0052 |
| 172 | (5S)-7-(5-chloro-2-fluorophenyl)-3-(5,6-dihydro-2H-pyran-3-yl)spiro[chromeno[2,3-b]pyridine-5,4'-[1,3]oxazol]-2'-amine | 464 | AA1 | 0.0004 | 0.0053 |
| 173 | (5S)-7-(3-chlorophenyl)-3-(5,6-dihydro-2H-pyran-3-yl)spiro[chromeno[2,3-b]pyridine-5,4'-[1,3]oxazol]-2'-amine | 446 | AA1 | 0.0006 | 0.005 |
| 174 | (5S)-7-(2-fluoro-3-pyridinyl)-3-((3S)-tetrahydro-2H-pyran-3-yl)spiro[chromeno[2,3-b]pyridine-5,4'-[1,3]oxazol]-2'-amine | 433.2 | AA19 | 0.0121 | 0.04 |
| 175 | (5S)-7-(2-fluoro-3-pyridinyl)-3-((E)-2-(3-methyl-3-oxetanyl)ethenyl)spiro[chromeno[2,3-b]pyridine-5,4'-[1,3]oxazol]-2'-amine | 445.2 | AA57 | 0.0005 | 0.001 |
| 176 | (5S)-7-(6-fluoro-3-pyridinyl)-3-((E)-2-(3-methyl-3-oxetanyl)ethenyl)spiro[chromeno[2,3-b]pyridine-5,4'-[1,3]oxazol]-2'-amine | 445.2 | BB29 | 0.0012 | 0.0032 |
| 177 | (5S)-7-(5-chloro-2-fluorophenyl)-3-((E)-2-(3-methyl-3-oxetanyl)ethenyl)spiro[chromeno[2,3-b]pyridine-5,4'-[1,3]oxazol]-2'-amine | 478.2 | BB29 | 0.0004 | 0.0018 |
| 178 | (5S)-7-(cyclopropylethynyl)-3-(3,3-difluoro-1-pyrrolidinyl)spiro[chromeno[2,3-b]pyridine-5,4'-[1,3]oxazol]-2'-amine | 423.2 | BB9 | 0.0031 | 0.0143 |
| 179 | (5S)-7-(cyclopropylethynyl)-3-(2,2-dimethyl-4-morpholinyl)spiro[chromeno[2,3-b]pyridine-5,4'-[1,3]oxazol]-2'-amine | 431.2 | BB9 | 0.0111 | 0.0641 |
| 180 | (5S)-7-(3,3-dimethyl-1-butyn-1-yl)-3-(1-methyl-1H-pyrazol-3-yl)spiro[chromeno[2,3-b]pyridine-5,4'-[1,3]oxazol]-2'-amine | 414.2 | AA33 | 0.0495 | 0.1647 |
| 181 | (5S)-7-(cyclopropylethynyl)-3-(4,4-difluoro-1-piperidinyl)spiro[chromeno[2,3-b]pyridine-5,4'-[1,3]oxazol]-2'-amine | 437.1 | BB9 | 0.0057 | 0.0271 |
| 182 | (5S)-7-(cyclopropylethynyl)-3-(3,3-dimethyl-1-pyrrolidinyl)spiro[chromeno[2,3-b]pyridine-5,4'-[1,3]oxazol]-2'-amine | 415.2 | BB9 | 0.0031 | 0.022 |
| 183 | (5S)-7-(cyclopropylethynyl)-3-(1-methyl-1H-pyrazol-3-yl)spiro[chromeno[2,3-b]pyridine-5,4'-[1,3]oxazol]-2'-amine | 398.2 | AA33 | 0.0515 | 0.1893 |

TABLE I-continued

| Ex. No. | Compound Name | Observed Mass | Method | BACE 1 FRET assay (uM) | HEK cell assay (uM) |
|---|---|---|---|---|---|
| 184 | (5S)-3-((2-methylpropyl)sulfanyl)-7-(3-pyridinyl)spiro[chromeno[2,3-b]pyridine-5,4'-[1,3]oxazol]-2'-amine | 419.2 | BB14 | 0.0141 | 0.2938 |
| 185 | (5S)-3-(benzylsulfanyl)-7-methoxyspiro[chromeno[2,3-b]pyridine-5,4'-[1,3]oxazol]-2'-amine | 406.2 | BB14 | 5.0623 | 10 |
| 186 | (5S)-7-(5-chloro-3-pyridinyl)-3-((3-methyl-3-oxetanyl)ethynyl)spiro[chromeno[2,3-b]pyridine-5,4'-[1,3]oxazol]-2'-amine | 459 | AA5 | 0.0005 | 0.003 |
| 187 | (5S)-3-((3-methyl-3-oxetanyl)ethynyl)-7-(5-(trifluoromethyl)-3-pyridinyl)spiro[chromeno[2,3-b]pyridine-5,4'-[1,3]oxazol]-2'-amine | 493 | AA5 | 0.0029 | 0.0116 |
| 99 | (5S)-3-(2-methylbutyl)sulfanyl)-7-(3-pyridinyl)spiro[chromeno[2,3-b]pyridine-5,4'-[1,3]oxazol]-2'-amine | 433.2 | BB14 | 0.0173 | 0.3017 |
| 188 | (5S)-7-(3,4-difluorophenyl)-3-((3-methyl-3-oxetanyl)ethynyl)spiro[chromeno[2,3-b]pyridine-5,4'-[1,3]oxazol]-2'-amine | 460.2 | AA5 | 0.0045 | 0.0866 |
| 189 | (4S)-4'-fluoro-7'-(2-fluoro-3-pyridinyl)-2'-(2-oxa-7-azaspiro[3.5]non-7-yl)spiro[1,3-oxazole-4,9'-xanthen]-2-amine | 491.2 | AA20 | 0.0008 | 0.0078 |
| 136 | (4R)-2'-(3,6-dihydro-2H-pyran-4-yl)-7'-(2-fluoro-3-pyridinyl)spiro[1,3-oxazole-4,9'-xanthen]-2-amine | 430 | AA1 | 0.0026 | 0.0185 |
| 190 | 5-((4R)-2-amino-7'-(3,6-dihydro-2H-pyran-4-yl)spiro[1,3-oxazole-4,9'-xanthen]-2'-yl)-3-pyridinecarbonitrile | 437 | AA1 | 0.0103 | 0.0231 |
| 191 | (4R)-2'-(3,6-dihydro-2H-pyran-4-yl)-7'-(2-fluoro-5-methyl-3-pyridinyl)spiro[1,3-oxazole-4,9'-xanthen]-2-amine | 444 | AA1 | 0.0056 | 0.0356 |
| 192 | (4R)-2'-(3,6-dihydro-2H-pyran-4-yl)-7'-(2-pyrazinyl)spiro[1,3-oxazole-4,9'-xanthen]-2-amine | 413 | AA22 | 0.0131 | 0.035 |
| 193 | (4R)-2'-(3,6-dihydro-2H-pyran-4-yl)-7'-(5-fluoro-3-pyridinyl)spiro[1,3-oxazole-4,9'-xanthen]-2-amine | 430 | AA1 | 0.0075 | 0.018 |
| 194 | (4R)-2'-(3,6-dihydro-2H-pyran-4-yl)-7'-(5-methoxy-3-pyridinyl)spiro[1,3-oxazole-4,9'-xanthen]-2-amine | 442 | AA1 | 0.008 | 0.0274 |
| 195 | 3-((4R)-2-amino-7'-(3,6-dihydro-2H-pyran-4-yl)spiro[1,3-oxazole-4,9'-xanthen]-2'-yl)benzonitrile | 436 | AA1 | 0.0094 | 0.0631 |
| 196 | (4S)-4'-fluoro-7'-(2-fluoro-3-pyridinyl)-2'-(2-pyridinyl)spiro[1,3-oxazole-4,9'-xanthen]-2-amine | 443 | AA22 | 0.0012 | 0.0097 |
| 128 | (4S)-4'-fluoro-7'-(2-fluoro-3-pyridinyl)-2'-(2-pyrimidinyl)spiro[1,3-oxazole-4,9'-xanthen]-2-amine | 444 | AA22 | 0.0011 | 0.0082 |
| 197 | (4S)-7'-(3,6-dihydro-2H-pyran-4-yl)-5'-fluoro-N~2~'-(3-methoxyphenyl)spiro[1,3-oxazole-4,9'-xanthene]-2,2'-diamine | 474 | AA16 | 0.0368 | 0.6795 |
| 198 | (4S)-5'-fluoro-N~2~'-(3-methoxyphenyl)-7'-(4-morpholinyl)spiro[1,3-oxazole-4,9'-xanthene]-2,2'-diamine | 477 | BB2 | 0.0779 | 0.572 |
| 199 | 4-((4S)-2-amino-4'-fluoro-7'-(2-fluoro-3-pyridinyl)spiro[1,3-oxazole-4,9'-xanthen]-2'-yl)-2-methyl-3-butyn-2-ol | 448 | AA21 | 0.0008 | 0.0051 |
| 92 | 4-((4S)-2-amino-4'-fluoro-7'-(2-fluoro-3-pyridinyl)spiro[1,3-oxazole-4,9'-xanthen]-2'-yl)-2-methyl-2-butanol | 452 | BB6 | 0.001 | 0.0042 |
| 200 | 4-((4S)-2-amino-4'-fluoro-7'-(2-fluoro-3-pyridinyl)spiro[1,3-oxazole-4,9'-xanthen]-2'-yl)-6-methyl-2H-pyran-2-one | 474 | AA36 | 0.0006 | 0.0085 |
| 201 | (4S)-4'-fluoro-7'-(2-fluoro-3-pyridinyl)-2'-(3-pyridazinyl)spiro[1,3-oxazole-4,9'-xanthen]-2-amine | 444 | BB30 | 0.0018 | 0.0076 |
| 202 | (4S)-4'-fluoro-7'-(6-fluoro-3-pyridinyl)-2'-(4-morpholinyl)spiro[1,3-oxazole-4,9'-xanthen]-2-amine | 451 | AA16 | 0.0049 | 0.0118 |
| 132 | (4S)-4'-fluoro-7'-(2-fluoro-5-methyl-3-pyridinyl)-2'-(4-morpholinyl)spiro[1,3-oxazole-4,9'-xanthen]-2-amine | 465 | AA16 | 0.0015 | 0.006 |
| 203 | (4S)-4'-fluoro-7'-(2-fluoro-3-pyridinyl)-2'-(4-pyridinyl)spiro[1,3-oxazole-4,9'-xanthen]-2-amine | 443 | AA8 | 0.0011 | 0.0077 |
| 204 | 3-(((4S)-2-amino-7'-(5-chloro-3-pyridinyl)-4'-fluorospiro[1,3-oxazole-4,9'-xanthen]-2'-yl)oxy)-2,2-dimethylpropanenitrile | 479 | AA14 | 0.0005 | 0.0045 |

TABLE I-continued

| Ex. No. | Compound Name | Observed Mass | Method | BACE 1 FRET assay (uM) | HEK cell assay (uM) |
|---|---|---|---|---|---|
| 205 | (4S)-4'-fluoro-7'-(2-fluoro-3-pyridinyl)-2'-(2-pyrazinyl)spiro[1,3-oxazole-4,9'-xanthen]-2-amine | 444 | AA22 | 0.0016 | 0.0101 |
| 206 | (4S)-7'-(5-chloro-3-pyridinyl)-4'-fluoro-2'-((3-methyl-3-oxetanyl)methoxy)spiro[1,3-oxazole-4,9'-xanthen]-2-amine | 482 | AA14 | 0.0007 | 0.0024 |
| 207 | (4S)-4'-fluoro-7'-(2-fluoro-3-pyridinyl)-N~2~'-(2-methoxyethyl)-N~2~'-methylspiro[1,3-oxazole-4,9'-xanthene]-2,2'-diamine | 453.2 | AA20 | 0.0075 | 0.0314 |
| 208 | (4S)-7'-(5-chloro-3-pyridinyl)-4'-fluoro-2'-(4-morpholinyl)spiro[1,3-oxazole-4,9'-xanthen]-2-amine | 467.2 | AA20 | 0.0008 | 0.0038 |
| 209 | (4S)-4'-fluoro-2'-(4-morpholinyl)-7'-(5-(4-morpholinyl)-3-pyridinyl)spiro[1,3-oxazole-4,9'-xanthen]-2-amine | 518.2 | AA20 | 0.2491 | 0.2088 |
| 210 | (4S)-7'-(5-chloro-3-pyridinyl)-2'-(3,6-dihydro-2H-pyran-4-yl)-4'-fluorospiro[1,3-oxazole-4,9'-xanthen]-2-amine | 464 | AA8 | 0.0003 | 0.003 |
| 211 | (4S)-7'-(5-chloro-3-pyridinyl)-4'-fluoro-2'-(tetrahydro-2H-pyran-4-ylmethoxy)spiro[1,3-oxazole-4,9'-xanthen]-2-amine | 496.2 | AA14 | 0.0006 | 0.0082 |
| 212 | (4S)-4'-fluoro-7'-(2-fluoro-3-pyridinyl)-2'-(4-pyrimidinyl)spiro[1,3-oxazole-4,9'-xanthen]-2-amine | 444 | BB30 | 0.0014 | 0.0113 |
| 213 | (4S)-4'-fluoro-7'-(2-fluoro-3-pyridinyl)-2'-(2-methoxy-5-pyrimidinyl)spiro[1,3-oxazole-4,9'-xanthen]-2-amine | 474 | AA8 | 0.0027 | 0.0216 |
| 214 | (4S)-4'-fluoro-7'-(2-fluoro-3-pyridinyl)-2'-(5-pyrimidinyl)spiro[1,3-oxazole-4,9'-xanthen]-2-amine | 444 | AA8 | 0.0028 | 0.0187 |
| 215 | (4R)-4'-fluoro-2'-methoxy-7'-(5-pyrimidinyl)spiro[1,3-thiazole-4,9'-xanthen]-2-amine | 450 | AA18 | 0.0081 | 0.1134 |
| 216 | (4S)-4'-fluoro-2'-methoxy-7'-(5-pyrimidinyl)spiro[1,3-thiazole-4,9'-xanthen]-2-amine | 450 | AA18 |  | 0.045 |
| 217 | (4R)-4'-fluoro-2'-methoxy-7'-(5-pyrimidinyl)spiro[1,3-thiazole-4,9'-xanthen]-2-amine | 478 | BB30 |  | 1.5747 |
| 218 | (4S)-7'-bromo-4'-fluoro-2'-methoxyspiro[1,3-thiazole-4,9'-xanthen]-2-amine | 457 | AA8 |  | 0.1282 |
| 219 | (4S)-4'-fluoro-7'-(2-fluoro-3-pyridinyl)-2'-((2S)-tetrahydro-2H-pyran-2-yl)spiro[1,3-oxazole-4,9'-xanthen]-2-amine | 473 | AA8 | 0.0009 | 0.0062 |
| 220 | (4S)-4'-fluoro-7'-(2-fluoro-3-pyridinyl)-2'-((2R)-tetrahydro-2H-pyran-2-yl)spiro[1,3-oxazole-4,9'-xanthen]-2-amine | 395 | BB12 | 0.0016 | 0.0128 |
| 221 | (4S)-2'-(2-chloro-4-pyrimidinyl)-4'-fluoro-7'-(2-fluoro-3-pyridinyl)spiro[1,3-oxazole-4,9'-xanthen]-2-amine | 395 | BB12 | 0.0007 | 0.1293 |
| 222 | (4R)-4'-fluoro-2'-methoxy-7'-(2-pyrazinyl)spiro[1,3-thiazole-4,9'-xanthen]-2-amine | 395 | BB12 | 0.0414 | 1.0793 |
| 223 | (4S)-4'-fluoro-7'-(2-fluoro-3-pyridinyl)-2'-(6-methyl-3-pyridinyl)spiro[1,3-oxazole-4,9'-xanthen]-2-amine | 395 | BB26 | 0.002 |  |
| 224 | (4S)-4'-fluoro-7'-(2-fluoro-3-pyridinyl)-2'-(6-methoxy-3-pyridinyl)spiro[1,3-oxazole-4,9'-xanthen]-2-amine | 395 | BB12 | 0.002 |  |
| 225 | (4S)-4'-fluoro-7'-(2-fluoro-3-pyridinyl)-2'-(8-oxa-3-azabicyclo[3.2.1]oct-3-yl)spiro[1,3-oxazole-4,9'-xanthen]-2-amine | 477 | AA20 | 0.0003 | 0.0016 |
| 226 | (4S)-4'-fluoro-7'-(2-fluoro-3-pyridinyl)-2'-(2-methyl-5-pyrimidinyl)spiro[1,3-oxazole-4,9'-xanthen]-2-amine | 458 | AA8 | 0.0039 | 0.0272 |
| 227 | (5S)-7-(5-chloro-3-pyridinyl)-3-(6-methyl-3-pyridinyl)spiro[chromeno[2,3-c]pyridine-5,4'-[1,3]oxazole]-2'-amine | 455.9 | AA1 | 0.0014 | 0.0071 |
| 228 | (5S)-3-(3,6-dihydro-2H-pyran-4-yl)-7-(6-fluoro-5-methyl-3-pyridinyl)spiro[chromeno[2,3-c]pyridine-5,4'-[1,3]oxazol]-2'-amine | 445 | AA1 | 0.0025 | 0.014 |
| 229 | (5S)-7-(6-fluoro-5-methyl-3-pyridinyl)-3-(4-pyridinyl)spiro[chromeno[2,3-c]pyridine-5,4'-[1,3]oxazole]-2'-amine | 440 | AA1 | 0.0128 | 0.0604 |
| 230 | (5S)-7-(6-fluoro-5-methyl-3-pyridinyl)-3-(3-pyridinyl)spiro[chromeno[2,3-c]pyridine-5,4'-[1,3]oxazol]-2'-amine | 440 | AA1 | 0.0081 | 0.0363 |

TABLE I-continued

| Ex. No. | Compound Name | Observed Mass | Method | BACE 1 FRET assay (uM) | HEK cell assay (uM) |
|---|---|---|---|---|---|
| 231 | (5S)-3-(3,6-dihydro-2H-pyran-4-yl)-7-(5-(3,6-dihydro-2H-pyran-4-yl)-3-pyridinyl)spiro[chromeno[2,3-c]pyridine-5,4'-[1,3]oxazol]-2'-amine | 495 | AA1 | 0.034 | 0.106 |
| 232 | (5S)-7-(5-chloro-3-pyridinyl)-3-(1-methyl-1H-pyrazol-4-yl)spiro[chromeno[2,3-c]pyridine-5,4'-[1,3]oxazol]-2'-amine | 445 | AA1 | 0.0013 | 0.0074 |
| 233 | (5S)-3-(1-methyl-1H-pyrazol-4-yl)-7-(5-(1-methyl-1H-pyrazol-4-yl)-3-pyridinyl)spiro[chromeno[2,3-c]pyridine-5,4'-[1,3]oxazol]-2'-amine | 491 | AA1 | 0.028 | 0.092 |
| 234 | (5R)-7-(3-chlorophenyl)-3-(3,6-dihydro-2H-pyran-4-yl)spiro[chromeno[2,3-c]pyridine-5,4'-[1,3]oxazol]-2'-amine | 446.1 | AA1 | 0.4899 | 4.2783 |
| 235 | (5S)-7-(5-chloro-2-methoxy-3-pyridinyl)-3-(3,6-dihydro-2H-pyran-4-yl)spiro[chromeno[2,3-c]pyridine-5,4'-[1,3]oxazol]-2'-amine | 477.2 | AA1 | 0.0012 | 0.0147 |
| 236 | (5S)-3-(3,6-dihydro-2H-pyran-4-yl)-7-(2-fluoro-4-methyl-3-pyridinyl)spiro[chromeno[2,3-c]pyridine-5,4'-[1,3]oxazol]-2'-amine | 445.2 | AA1 | 0.0009 | 0.006 |
| 237 | (5S)-7-(2-fluoro-4-methyl-3-pyridinyl)-3-(2-fluoro-4-pyridinyl)spiro[chromeno[2,3-c]pyridine-5,4'-[1,3]oxazol]-2'-amine | 458.1 | AA1 | 0.0016 | 0.0224 |
| 238 | (5S)-7-phenyl-3-(tetrahydro-2H-pyran-4-yl)spiro[chromeno[2,3-c]pyridine-5,4'-[1,3]oxazol]-2'-amine | 414.2 | AA11 | 0.0407 | 0.1644 |
| 239 | (5S)-3-(2-fluoro-4-pyridinyl)-7-(2-methoxy-3-pyridinyl)spiro[chromeno[2,3-c]pyridine-5,4'-[1,3]oxazol]-2'-amine | 456.2 | AA1 | 0.0335 | 0.3889 |
| 240 | (5S)-3-(3,6-dihydro-2H-pyran-4-yl)-7-(2-methoxy-3-pyridinyl)spiro[chromeno[2,3-c]pyridine-5,4'-[1,3]oxazol]-2'-amine | 443.1 | AA1 | 0.0173 | 0.1081 |
| 241 | (5S)-7-(3-chlorophenyl)-3-(tetrahydro-2H-pyran-4-yl)spiro[chromeno[2,3-c]pyridine-5,4'-[1,3]oxazol]-2'-amine | 448.1 | AA11 | 0.0034 | 0.0629 |
| 242 | (5S)-7-(5-chloro-3-pyridinyl)-3-(tetrahydro-2H-pyran-4-yl)spiro[chromeno[2,3-c]pyridine-5,4'-[1,3]oxazol]-2'-amine | 449.1 | AA11 | 0.0031 | 0.0211 |
| 243 | (5S)-3-(3,6-dihydro-2H-pyran-4-yl)-7-(3-(1-methyl-1H-pyrazol-4-yl)phenyl)spiro[chromeno[2,3-c]pyridine-5,4'-[1,3]oxazol]-2'-amine | 492.2 | AA1 | 0.0195 | 0.2873 |
| 244 | (5S)-3-(3,6-dihydro-2H-pyran-4-yl)-7-(3-(1-ethyl-1H-pyrazol-4-yl)phenyl)spiro[chromeno[2,3-c]pyridine-5,4'-[1,3]oxazol]-2'-amine | 506.1 | AA1 | 0.0537 | 0.3264 |
| 245 | (5S)-3-(3,6-dihydro-2H-pyran-4-yl)-7-(3-(3,5-dimethyl-4-isoxazolyl)phenyl)spiro[chromeno[2,3-c]pyridine-5,4'-[1,3]oxazol]-2'-amine | 507.2 | AA1 | 0.023 | 0.5288 |
| 246 | (5S)-7-(2-fluoro-3-pyridinyl)-3-(3-methyl-4-pyridinyl)spiro[chromeno[2,3-c]pyridine-5,4'-[1,3]oxazol]-2'-amine | 440.2 | AA1 | 0.0542 | 0.2906 |
| 247 | (5S)-3-(3,6-dihydro-2H-pyran-4-yl)-7-(2-methyl-3-pyridinyl)spiro[chromeno[2,3-c]pyridine-5,4'-[1,3]oxazol]-2'-amine | 427.2 | AA1 | 0.0449 | 0.0455 |
| 248 | (5S)-3-(2-fluoro-4-pyridinyl)-7-(2-methyl-3-pyridinyl)spiro[chromeno[2,3-c]pyridine-5,4'-[1,3]oxazol]-2'-amine | 440.1 | AA1 | 0.0991 | 0.1909 |
| 249 | (5S)-3-(3,6-dihydro-2H-pyran-4-yl)-7-(5-(1-propyn-1-yl)-3-pyridinyl)spiro[chromeno[2,3-c]pyridine-5,4'-[1,3]oxazol]-2'-amine | 451.1 | AA1 | 0.0002 | 0.0013 |
| 250 | (5S)-3-(2-fluoro-4-pyridinyl)-7-(5-(1-propyn-1-yl)-3-pyridinyl)spiro[chromeno[2,3-c]pyridine-5,4'-[1,3]oxazol]-2'-amine | 464.1 | AA1 | 0.0004 | 0.0041 |
| 251 | (5S)-3-(3,6-dihydro-2H-pyran-4-yl)-7-(6-fluoro-2-methyl-3-pyridinyl)spiro[chromeno[2,3-c]pyridine-5,4'-[1,3]oxazol]-2'-amine | 445.1 | AA1 | 0.0268 | 0.2708 |
| 252 | (5S)-7-(6-fluoro-2-methyl-3-pyridinyl)-3-(2-fluoro-4-pyridinyl)spiro[chromeno[2,3-c]pyridine-5,4'-[1,3]oxazol]-2'-amine | 458.1 | AA1 | 0.0661 | 0.548 |
| 253 | (5S)-3-(3,6-dihydro-2H-pyran-4-yl)-7-(2-fluoro-6-methyl-3-pyridinyl)spiro[chromeno[2,3-c]pyridine-5,4'-[1,3]oxazol]-2'-amine | 445.1 | AA1 | 0.036 | 0.3204 |
| 254 | (5S)-7-(2-fluoro-6-methyl-3-pyridinyl)-3-(2-fluoro-4-pyridinyl)spiro[chromeno[2,3-c]pyridine-5,4'-[1,3]oxazol]-2'-amine | 458.1 | AA1 | 0.0545 | 1.0685 |

TABLE I-continued

| Ex. No. | Compound Name | Observed Mass | Method | BACE 1 FRET assay (uM) | HEK cell assay (uM) |
|---|---|---|---|---|---|
| 255 | (5S)-3-(3,6-dihydro-2H-pyran-4-yl)-7-(3-(1,3-dimethyl-1H-pyrazol-4-yl)phenyl)spiro[chromeno[2,3-c]pyridine-5,4'-[1,3]oxazol]-2'-amine | 506.1 | AA1 | 0.0223 | 0.5653 |
| 256 | (5S)-3-chloro-7-(5-(1-propyn-1-yl)-3-pyridinyl)spiro[chromeno[2,3-c]pyridine-5,4'-[1,3]oxazol]-2'-amine | 403.1 | AA24 | 0.0059 | |
| 257 | 3-(((4S)-2-amino-4'-fluoro-7'-(3-pyridinyl)spiro[1,3-oxazole-4,9'-xanthen]-2'-yl)oxy)-2,2-dimethylpropanenitrile | 445 | AA14 | 0.001 | 0.0063 |
| 258 | (4S)-4'-fluoro-7'-(6-fluoro-3-pyridinyl)-2'-(tetrahydro-2H-pyran-4-ylmethoxy)spiro[1,3-oxazole-4,9'-xanthen]-2-amine | 480 | AA14 | 0.006 | 0.0304 |
| 259 | (4S)-4'-fluoro-2'-(2-fluoro-2-methylpropoxy)-7'-(6-fluoro-3-pyridinyl)spiro[1,3-oxazole-4,9'-xanthen]-2-amine | 456 | AA14 | 0.0027 | 0.0198 |
| 260 | (4S)-2'-(3,6-dihydro-2H-pyran-4-yl)-4'-fluoro-7'-(6-fluoro-3-pyridinyl)spiro[1,3-oxazole-4,9'-xanthen]-2-amine | 448 | AA1 | 0.0019 | 0.0109 |
| 261 | (4S)-2'-(((1R)-2,2-difluorocyclopropyl)methoxy)-4'-fluoro-7'-(6-fluoro-3-pyridinyl)spiro[1,3-oxazole-4,9'-xanthen]-2-amine | 472 | AA14 | 0.0068 | 0.0718 |
| 262 | (4S)-4'-fluoro-7'-(6-fluoro-3-pyridinyl)-2'-(1-methyl-1H-pyrazol-4-yl)spiro[1,3-oxazole-4,9'-xanthen]-2-amine | 446 | AA1 | 0.0033 | 0.0126 |
| 263 | 3-(((4S)-2-amino-4'-fluoro-7'-(6-fluoro-3-pyridinyl)spiro[1,3-oxazole-4,9'-xanthen]-2'-yl)oxy)-2,2-dimethylpropanenitrile | 463 | AA14 | 0.0023 | 0.0133 |
| 264 | 3-(((4S)-2-amino-4'-fluoro-7'-(5-methoxy-3-pyridinyl)spiro[1,3-oxazole-4,9'-xanthen]-2'-yl)oxy)-2,2-dimethylpropanenitrile | 475 | AA13 | 0.001 | 0.0081 |
| 93 | 3-(((4S)-2-amino-4'-fluoro-7'-(2-pyrazinyl)spiro[1,3-oxazole-4,9'-xanthen]-2'-yl)oxy)-2,2-dimethylpropanenitrile | 446 | BB7 | 0.0028 | 0.0146 |
| 265 | 5-((4S)-2-amino-7'-(2-cyano-2-methylpropoxy)-5'-fluorospiro[1,3-oxazole-4,9'-xanthen]-2'-yl)-3-pyridinecarbonitrile | 470 | AA13 | 0.0008 | 0.0047 |
| 266 | (4S)-4'-fluoro-7'-(6-fluoro-3-pyridinyl)-2'-((3-methyl-3-oxetanyl)methoxy)spiro[1,3-oxazole-4,9'-xanthen]-2-amine | 466 | AA13 | 0.0022 | 0.0068 |
| 267 | (4S)-4'-fluoro-2'-((3-methyl-3-oxetanyl)methoxy)-7'-(2-pyrazinyl)spiro[1,3-oxazole-4,9'-xanthen]-2-amine | 449 | BB7 | 0.0031 | 0.012 |
| 94 | (4S)-2'-((2R,6S)-2,6-dimethyl-4-morpholinyl)-4'-fluoro-7'-(2-pyrazinyl)spiro[1,3-oxazole-4,9'-xanthen]-2-amine | 462 | BB8 | 0.0063 | 0.0197 |
| 268 | (4S)-4'-fluoro-2'-((1S,4S)-2-oxa-5-azabicyclo[2.2.1]hept-5-yl)-7'-(2-pyrazinyl)spiro[1,3-oxazole-4,9'-xanthen]-2-amine | 446 | BB8 | 0.0105 | 0.0261 |
| 269 | (4S)-4'-fluoro-2'-(4-morpholinyl)-7'-(2-pyrazinyl)spiro[1,3-oxazole-4,9'-xanthen]-2-amine | 434 | BB8 | 0.0052 | 0.0188 |
| 270 | (4S)-4'-fluoro-7'-(2-pyrazinyl)-2'-(tetrahydro-2H-pyran-4-ylmethoxy)spiro[1,3-oxazole-4,9'-xanthen]-2-amine | 463 | BB7 | 0.0054 | 0.0336 |
| 271 | (4S)-2'-(3,3-difluoro-1-pyrrolidinyl)-4'-fluoro-7'-(2-fluoro-3-pyridinyl)spiro[1,3-oxazole-4,9'-xanthen]-2-amine | 471 | AA9 | 0.0005 | 0.0041 |
| 272 | 3-(((4S)-2-amino-4'-fluoro-7'-(5-fluoro-3-pyridinyl)spiro[1,3-oxazole-4,9'-xanthen]-2'-yl)oxy)-2,2-dimethylpropanenitrile | 463 | AA14 | 0.0005 | 0.0059 |
| 273 | (4S)-4'-fluoro-7'-(5-fluoro-3-pyridinyl)-2'-((3-methyl-3-oxetanyl)methoxy)spiro[1,3-oxazole-4,9'-xanthen]-2-amine | 466 | AA14 | 0.0007 | 0.0031 |
| 274 | (4S)-2'-((2R,6S)-2,6-dimethyl-4-morpholinyl)-4'-fluoro-7'-(5-fluoro-3-pyridinyl)spiro[1,3-oxazole-4,9'-xanthen]-2-amine | 479 | AA20 | 0.0029 | 0.0104 |
| 275 | (4S)-4'-fluoro-7'-(2-fluoro-3-pyridinyl)-2'-(6-methoxy-3-pyridazinyl)spiro[1,3-oxazole-4,9'-xanthen]-2-amine | 474 | AA8 | 0.0007 | 0.008 |
| 276 | (4S)-4'-fluoro-7'-(5-fluoro-3-pyridinyl)-2'-((1S,4S)-2-oxa-5-azabicyclo[2.2.1]hept-5-yl)spiro[1,3-oxazole-4,9'-xanthen]-2-amine | 463 | AA20 | 0.0008 | 0.0033 |
| 277 | (4S)-4'-fluoro-7'-(5-fluoro-3-pyridinyl)-2'-(4-morpholinyl)spiro[1,3-oxazole-4,9'-xanthen]-2-amine | 451 | AA20 | 0.0015 | 0.0064 |

TABLE I-continued

| Ex. No. | Compound Name | Observed Mass | Method | BACE 1 FRET assay (uM) | HEK cell assay (uM) |
|---|---|---|---|---|---|
| 278 | (4S)-2'-(5,6-dihydro-2H-pyran-3-yl)-4'-fluoro-7'-(5-fluoro-3-pyridinyl)spiro[1,3-oxazole-4,9'-xanthen]-2-amine | 448 | AA8 | 0.0004 | 0.0039 |
| 279 | (4S)-4'-fluoro-7'-(2-fluoro-3-pyridinyl)-2'-((3R)-3-fluoro-1-pyrrolidinyl)spiro[1,3-oxazole-4,9'-xanthen]-2-amine | 453.2 | AA20 | 0.0015 | 0.0085 |
| 280 | (4S)-4'-fluoro-7'-(2-fluoro-3-pyridinyl)-2'-((3S)-3-fluoro-1-pyrrolidinyl)spiro[1,3-oxazole-4,9'-xanthen]-2-amine | 453.2 | AA20 | 0.0007 | 0.0069 |
| 281 | (4S)-4'-fluoro-7'-(2-fluoro-3-pyridinyl)-2'-(3-methoxy-1-azetidinyl)spiro[1,3-oxazole-4,9'-xanthen]-2-amine | 451 | AA20 | 0.002 | 0.0054 |
| 282 | (4S)-2'-(2,2-dimethyl-4-morpholinyl)-4'-fluoro-7'-(5-fluoro-3-pyridinyl)spiro[1,3-oxazole-4,9'-xanthen]-2-amine | 479 | AA20 | 0.002 | 0.0082 |
| 283 | (4S)-4'-fluoro-7'-(5-fluoro-3-pyridinyl)-2'-(8-oxa-3-azabicyclo[3.2.1]oct-3-yl)spiro[1,3-oxazole-4,9'-xanthen]-2-amine | 477 | AA20 | 0.0004 | 0.0032 |
| 114 | (4S)-4'-fluoro-7'-(2-fluoro-3-pyridinyl)-2'-(6-methyl-3-pyridazinyl)spiro[1,3-oxazole-4,9'-xanthen]-2-amine | 458 | BB30 | 0.0005 | 0.004 |
| 284 | (4S)-4'-fluoro-7'-(5-fluoro-3-pyridinyl)-2'-((3S)-tetrahydro-2H-pyran-3-yl)spiro[1,3-oxazole-4,9'-xanthen]-2-amine | 450 | AA18 | 0.0022 | 0.0135 |
| 285 | (4S)-4'-fluoro-7'-(5-fluoro-3-pyridinyl)-2'-((3R)-tetrahydro-2H-pyran-3-yl)spiro[1,3-oxazole-4,9'-xanthen]-2-amine | 450 | AA18 | 0.0024 | 0.0204 |
| 286 | (4S)-4'-fluoro-7'-(2-fluoro-3-pyridinyl)-2'-((3S)-tetrahydro-2H-pyran-3-yl)spiro[1,3-oxazole-4,9'-xanthen]-2-amine | 450 | AA18 | 0.0019 | 0.0158 |
| 287 | (4S)-4'-fluoro-7'-(2-fluoro-3-pyridinyl)-2'-((3R)-tetrahydro-2H-pyran-3-yl)spiro[1,3-oxazole-4,9'-xanthen]-2-amine | 450 | AA18 | 0.0017 | 0.0217 |
| 288 | (4S)-2'-(2,5-dihydro-3-furanyl)-4'-fluoro-7'-(5-fluoro-3-pyridinyl)spiro[1,3-oxazole-4,9'-xanthen]-2-amine | 434 | AA8 | 0.0003 | 0.0041 |
| 289 | (4S)-4'-fluoro-7'-(6-fluoro-3-pyridinyl)-2'-(2-pyrimidinyl)spiro[1,3-oxazole-4,9'-xanthen]-2-amine | 444 | AA22 | 0.0025 | 0.0146 |
| 290 | (4S)-4'-fluoro-7'-(5-fluoro-3-pyridinyl)-2'-(6-methoxy-3-pyridazinyl)spiro[1,3-oxazole-4,9'-xanthen]-2-amine | 474 | BB30 | 0.0008 | 0.0081 |
| 291 | (4S)-2'-(2,5-dihydro-3-furanyl)-4'-fluoro-7'-(2-fluoro-3-pyridinyl)spiro[1,3-oxazole-4,9'-xanthen]-2-amine | 434 | AA8 | 0.0006 | 0.008 |
| 292 | (4S)-4'-fluoro-7'-(5-fluoro-3-pyridinyl)-2'-(6-methyl-3-pyridazinyl)spiro[1,3-oxazole-4,9'-xanthen]-2-amine | 458 | BB30 | 0.002 | 0.0316 |
| 293 | (4S)-4'-fluoro-7'-(5-fluoro-3-pyridinyl)-2'-(2-methoxy-5-pyrimidinyl)spiro[1,3-oxazole-4,9'-xanthen]-2-amine | 474.1 | AA8 | 0.0075 | 0.0825 |
| 294 | (4S)-3',5'-difluoro-7'-((3-methyl-3-oxetanyl)methoxy)-2'-(3-pyridinyl)spiro[1,3-oxazole-4,9'-xanthen]-2-amine | 466 | AA14 | 0.0611 | 0.6124 |
| 295 | (4S)-7'-(3,6-dihydro-2H-pyran-4-yl)-3',5'-difluoro-2'-(3-pyridinyl)spiro[1,3-oxazole-4,9'-xanthen]-2-amine | 448.2 | AA1 | 0.1118 | |
| 296 | (4S)-4'-fluoro-7'-(5-fluoro-3-pyridinyl)-2'-((3R)-tetrahydro-3-furanyl)spiro[1,3-oxazole-4,9'-xanthen]-2-amine | 436.2 | AA18 | 0.0072 | |
| 297 | (4S)-4'-fluoro-7'-(5-fluoro-3-pyridinyl)-2'-((3S)-tetrahydro-3-furanyl)spiro[1,3-oxazole-4,9'-xanthen]-2-amine | 436.2 | AA18 | 0.0052 | |
| 298 | (4S)-7'-(5,6-dihydro-2H-pyran-3-yl)-3',5'-difluoro-2'-(3-pyridinyl)spiro[1,3-oxazole-4,9'-xanthen]-2-amine | 448 | AA1 | 0.0968 | |
| 299 | (4S)-4'-fluoro-7'-(2-fluoro-3-pyridinyl)-2'-((3R)-tetrahydro-3-furanyl)spiro[1,3-oxazole-4,9'-xanthen]-2-amine | 436.2 | AA18 | 0.0028 | |
| 300 | (4S)-4'-fluoro-7'-(2-fluoro-3-pyridinyl)-2'-((3S)-tetrahydro-3-furanyl)spiro[1,3-oxazole-4,9'-xanthen]-2-amine | 436.2 | AA18 | 0.0023 | |
| 139 | (4S)-4'-fluoro-7'-(2-fluoro-3-pyridinyl)-2'-(4-morpholinyl)spiro[1,3-oxazole-4,9'-xanthen]-2-amine | 451 | AA20 | 0.001 | 0.0052 |

TABLE I-continued

| Ex. No. | Compound Name | Observed Mass | Method | BACE 1 FRET assay (uM) | HEK cell assay (uM) |
|---|---|---|---|---|---|
| 301 | (4S)-4'-fluoro-7'-(6-fluoro-3-pyridinyl)-2'-(tetrahydro-2H-pyran-4-yl)spiro[1,3-oxazole-4,9'-xanthen]-2-amine | 450 | AA8 | 0.0048 | 0.0159 |
| 302 | (4S)-4'-fluoro-7'-(6-fluoro-3-pyridinyl)-2'-((1S,4S)-2-oxa-5-azabicyclo[2.2.1]hept-5-yl)spiro[1,3-oxazole-4,9'-xanthen]-2-amine | 463.2 | AA16 | 0.0031 | 0.0056 |
| 129 | (4S)-2'-(5,6-dihydro-2H-pyran-3-yl)-4'-fluoro-7'-(2-fluoro-3-pyridinyl)spiro[1,3-oxazole-4,9'-xanthen]-2-amine | 448 | AA8 | 0.0002 | 0.0032 |
| 303 | (4S)-2'-((2R,6S)-2,6-dimethyl-4-morpholinyl)-4'-fluoro-7'-(2-fluoro-3-pyridinyl)spiro[1,3-oxazole-4,9'-xanthen]-2-amine | 479 | AA20 | 0.002 | 0.0067 |
| 304 | (5S)-3-((1E)-3,3-dimethyl-1-buten-1-yl)-8-fluoro-7-(5-pyrimidinyl)spiro[chromeno[2,3-c]pyridine-5,4'-[1,3]oxazol]-2'-amine | 432 | AA1 | 0.0021 | 0.0239 |
| 305 | (5S)-3-(3,3-dimethyl-1-butyn-1-yl)-8-fluoro-7-(5-pyrimidinyl)spiro[chromeno[2,3-c]pyridine-5,4'-[1,3]oxazol]-2'-amine | 430.1 | AA5 | 0.0099 | 0.0958 |
| 111 | (2S)-2'-(2,2-dimethylpropoxy)-4,4-difluoro-7'-(5-pyrimidinyl)-3,4-dihydrospiro[pyrrole-2,9'-xanthen]-5-amine | 451.2 | BB27 | 0.022 | 1.3235 |
| 112 | (5S)-4',4'-difluoro-3,7-di-3-pyridinyl-3',4'-dihydrospiro[chromeno[2,3-b]pyridine-5,2'-pyrrol]-5'-amine | 442 | BB28 | 0.0632 | 2.1568 |
| 306 | (5S)-7-(3,6-dihydro-2H-pyran-4-yl)-9-fluoro-3-(2-fluoro-3-pyridinyl)spiro[chromeno[2,3-c]pyridine-5,4'-[1,3]oxazol]-2'-amine | 449.3 | AA1 | 0.0015 | 0.0567 |
| 307 | (5S)-7-(3,6-dihydro-2H-pyran-4-yl)-9-fluoro-3-(3-pyridinyl)spiro[chromeno[2,3-c]pyridine-5,4'-[1,3]oxazol]-2'-amine | 431.1 | BB25 | 0.0039 | 0.0581 |
| 308 | 3-((5S)-2'-amino-7-(3,6-dihydro-2H-pyran-4-yl)-9-fluorospiro[chromeno[2,3-c]pyridine-5,4'-[1,3]oxazol]-3-yl)benzonitrile | 455.2 | AA1 | 0.0093 | 0.1166 |
| 309 | (5S)-7-(3,6-dihydro-2H-pyran-4-yl)-9-fluoro-3-phenylspiro[chromeno[2,3-c]pyridine-5,4'-[1,3]oxazol]-2'-amine | 430.1 | AA1 | 0.0172 | |
| 87 | 7-(5-chloro-2-fluorophenyl)-3-((2-methyl-1,3-dioxolan-2-yl)methoxy)spiro[chromeno[2,3-b]pyridine-5,4'-[1,3]oxazol]-2'-amine | 498 | BB1 | 0.0084 | 0.1061 |
| 310 | (4S)-7'-(3-chlorophenyl)-3'-fluoro-2'-((3-methyl-3-oxetanyl)methoxy)spiro[1,3-oxazole-4,9'-xanthen]-2-amine | 481 | AA13 | 0.0032 | 0.1131 |
| 311 | (4S)-3'-fluoro-7'-(2-fluoro-3-pyridinyl)-2'-(1-methyl-1H-pyrazol-4-yl)spiro[1,3-oxazole-4,9'-xanthen]-2-amine | 446 | AA8 | 0.0039 | 0.0195 |
| 312 | (4S)-3'-fluoro-7'-(2-fluoro-3-pyridinyl)-2'-((3-methyl-3-oxetanyl)ethynyl)spiro[1,3-oxazole-4,9'-xanthen]-2-amine | 460 | AA21 | 0.0025 | 0.0303 |
| 313 | (4S)-7'-(3-chlorophenyl)-3'-fluoro-2'-(1-methyl-1H-pyrazol-4-yl)spiro[1,3-oxazole-4,9'-xanthen]-2-amine | 461 | AA8 | 0.0018 | 0.0789 |
| 314 | (5R)-7-(2,3-difluorophenyl)-3-(2-methoxy-2-methylpropoxy)spiro[chromeno[2,3-b]pyridine-5,4'-[1,3]oxazol]-2'-amine | 468 | AA51 | 1.9175 | 3.6567 |
| 315 | (5S)-7-(2,3-difluorophenyl)-3-(2-methoxy-2-methylpropoxy)spiro[chromeno[2,3-b]pyridine-5,4'-[1,3]oxazol]-2'-amine | 468 | AA51 | 0.0052 | 0.0317 |
| 316 | (5R)-3-(2-methoxy-2-methylpropoxy)-7-(3-(trifluoromethyl)phenyl)spiro[chromeno[2,3-b]pyridine-5,4'-[1,3]oxazol]-2'-amine | 500 | AA51 | 0.3928 | 2.0979 |
| 317 | (5S)-3-(2-methoxy-2-methylpropoxy)-7-(3-(trifluoromethyl)phenyl)spiro[chromeno[2,3-b]pyridine-5,4'-[1,3]oxazol]-2'-amine | 500 | AA51 | 0.0025 | 0.0239 |
| 318 | (5R)-7-(5-chloro-2-fluorophenyl)-3-(2-methoxy-2-methylpropoxy)spiro[chromeno[2,3-b]pyridine-5,4'-[1,3]oxazol]-2'-amine | 484 | AA51 | 0.3672 | 1.8147 |
| 319 | (5S)-7-(5-chloro-2-fluorophenyl)-3-(2-methoxy-2-methylpropoxy)spiro[chromeno[2,3-b]pyridine-5,4'-[1,3]oxazol]-2'-amine | 484 | AA51 | 0.0007 | 0.0053 |
| 320 | (4S)-2'-(3,6-dihydro-2H-pyran-4-yl)-3'-fluoro-7'-(2-fluoro-3-pyridinyl)spiro[1,3-oxazole-4,9'-xanthen]-2-amine | 448 | AA8 | 0.0066 | 0.06 |
| 321 | (4S)-3'-fluoro-7'-(2-fluoro-3-pyridinyl)-2'-(4-pyridinyl)spiro[1,3-oxazole-4,9'-xanthen]-2-amine | 443 | AA8 | 0.0203 | 0.0615 |

TABLE I-continued

| Ex. No. | Compound Name | Observed Mass | Method | BACE 1 FRET assay (uM) | HEK cell assay (uM) |
|---|---|---|---|---|---|
| 322 | (5S)-3-(3,6-dihydro-2H-pyran-4-yl)-7-(3-methoxyphenyl)spiro[chromeno[2,3-b]pyridine-5,4'-[1,3]oxazol]-2'-amine | 442 | AA8 | 0.0036 | 0.0261 |
| 323 | (5S)-3-(3,6-dihydro-2H-pyran-4-yl)-7-(2-fluoro-5-methoxyphenyl)spiro[chromeno[2,3-b]pyridine-5,4'-[1,3]oxazol]-2'-amine | 460 | AA8 | 0.0014 | 0.0155 |
| 324 | (5S)-3-(3,6-dihydro-2H-pyran-4-yl)-7-(5-methyl-2-furanyl)spiro[chromeno[2,3-b]pyridine-5,4'-[1,3]oxazol]-2'-amine | 416 | AA8 | 0.042 | 0.1576 |
| 325 | (4S)-7'-(2-chloro-4-pyridinyl)-3'-fluoro-2'-((3-methyl-3-oxetanyl)methoxy)spiro[1,3-oxazole-4,9'-xanthen]-2-amine | 482 | AA13 | 0.0502 | 0.2548 |
| 326 | (4S)-3'-fluoro-7'-(6-fluoro-3-pyridinyl)-2'-((3-methyl-3-oxetanyl)methoxy)spiro[1,3-oxazole-4,9'-xanthen]-2-amine | 466 | AA13 | 0.0197 | 0.0616 |
| 327 | (4S)-3'-fluoro-7'-(5-fluoro-3-pyridinyl)-2'-((3-methyl-3-oxetanyl)methoxy)spiro[1,3-oxazole-4,9'-xanthen]-2-amine | 466 | AA13 | 0.0041 | 0.0215 |
| 328 | (4S)-3'-fluoro-2'-((3-methyl-3-oxetanyl)methoxy)-7'-(5-methyl-3-pyridinyl)spiro[1,3-oxazole-4,9'-xanthen]-2-amine | 462 | AA13 | 0.0236 | 0.0456 |
| 329 | (4S)-3'-fluoro-7'-(5-methoxy-3-pyridinyl)-2'-((3-methyl-3-oxetanyl)methoxy)spiro[1,3-oxazole-4,9'-xanthen]-2-amine | 478 | AA13 | 0.0089 | 0.0525 |
| 330 | 5-((4S)-2-amino-6'-fluoro-7'-((3-methyl-3-oxetanyl)methoxy)spiro[1,3-oxazole-4,9'-xanthen]-2'-yl)-3-pyridinecarbonitrile | 473 | AA13 | 0.0088 | 0.0336 |
| 331 | 3-((4S)-2-amino-6'-fluoro-7'-((3-methyl-3-oxetanyl)methoxy)spiro[1,3-oxazole-4,9'-xanthen]-2'-yl)benzonitrile | 472 | AA13 | 0.0139 | 0.0855 |
| 332 | (4S)-3'-fluoro-2'-((3-methyl-3-oxetanyl)methoxy)-7'-(1-methyl-1H-pyrazol-4-yl)spiro[1,3-oxazole-4,9'-xanthen]-2-amine | 451 | AA13 | 0.5452 | 0.4901 |
| 333 | (4S)-7'-(5-chloro-3-pyridinyl)-3'-fluoro-2'-((3-methyl-3-oxetanyl)methoxy)spiro[1,3-oxazole-4,9'-xanthen]-2-amine | 482 | AA13 | 0.0024 | 0.0218 |
| 334 | (4S)-3'-fluoro-7'-(2-fluoro-3-pyridinyl)-2'-(tetrahydro-2H-pyran-4-yl)spiro[1,3-oxazole-4,9'-xanthen]-2-amine | 450 | AA18 | 0.0189 | 0.0676 |
| 335 | (4S)-3'-fluoro-7'-(4-morpholinyl)-2'-(5-pyrimidinyl)spiro[1,3-oxazole-4,9'-xanthen]-2-amine | 434 | AA16 | 0.0164 | 0.0433 |
| 336 | 4-((4R)-2-amino-6'-fluoro-7'-(5-pyrimidinyl)spiro[1,3-oxazole-4,9'-xanthen]-2'-yl)-2-methyl-3-butyn-2-ol | 431 | AA23 | 0.0064 | 0.0193 |
| 96 | 4-((4R)-2-amino-6'-fluoro-7'-(5-pyrimidinyl)spiro[1,3-oxazole-4,9'-xanthen]-2'-yl)-2-methyl-2-butanol | 435 | BB10 | 0.0107 | 0.0228 |
| 337 | (5S)-3-(3,3-dimethyl-1-butyn-1-yl)-6-fluoro-7-(5-pyrimidinyl)spiro[chromeno[2,3-b]pyridine-5,4'-[1,3]oxazol]-2'-amine | 430 | AA33 | 0.8359 | 0.5353 |
| 338 | (5R)-3-(3,3-dimethyl-1-butyn-1-yl)-8-fluoro-7-(5-pyrimidinyl)spiro[chromeno[2,3-b]pyridine-5,4'-[1,3]oxazol]-2'-amine | 430.2 | AA33 | 0.2127 | 1.2363 |
| 339 | (5R)-3-(3,3-dimethyl-1-butyn-1-yl)-6-fluoro-7-(5-pyrimidinyl)spiro[chromeno[2,3-b]pyridine-5,4'-[1,3]oxazol]-2'-amine | 430 | AA33 | 0.0013 | 0.0144 |
| 340 | (5S)-3-(3,3-dimethyl-1-butyn-1-yl)-8-fluoro-7-(5-pyrimidinyl)spiro[chromeno[2,3-b]pyridine-5,4'-[1,3]oxazol]-2'-amine | 430 | AA33 | 0.0081 | 0.0843 |
| 108 | (5R)-6-fluoro-7-(2-fluoro-3-pyridinyl)-3-((3-methyl-3-oxetanyl)ethynyl)spiro[chromeno[2,3-b]pyridine-5,4'-[1,3]oxazol]-2'-amine | 461 | BB24 | 0.002 | 0.0036 |
| 341 | (5S)-6-fluoro-7-(2-fluoro-3-pyridinyl)-3-((3-methyl-3-oxetanyl)ethynyl)spiro[chromeno[2,3-b]pyridine-5,4'-[1,3]oxazol]-2'-amine | 461 | AA33 | 0.1538 | 0.5656 |
| 342 | (5R)-6-fluoro-7-(6-fluoro-3-pyridinyl)-3-((3-methyl-3-oxetanyl)ethynyl)spiro[chromeno[2,3-b]pyridine-5,4'-[1,3]oxazol]-2'-amine | 461 | AA33 | 0.0024 | 0.016 |
| 343 | (5S)-6-fluoro-7-(6-fluoro-3-pyridinyl)-3-((3-methyl-3-oxetanyl)ethynyl)spiro[chromeno[2,3-b]pyridine-5,4'-[1,3]oxazol]-2'-amine | 461 | AA33 | 0.3914 | 1.842 |
| 344 | (5R)-6-fluoro-3-((3-methyl-3-oxetanyl)ethynyl)-7-(5-pyrimidinyl)spiro[chromeno[2,3-b]pyridine-5,4'-[1,3]oxazol]-2'-amine | 444 | AA33 | 0.001 | 0.0065 |

TABLE I-continued

| Ex. No. | Compound Name | Observed Mass | Method | BACE 1 FRET assay (uM) | HEK cell assay (uM) |
|---|---|---|---|---|---|
| 345 | (5S)-6-fluoro-3-((3-methyl-3-oxetanyl)ethynyl)-7-(5-pyrimidinyl)spiro[chromeno[2,3-b]pyridine-5,4'-[1,3]oxazol]-2'-amine | 444 | AA33 | 0.094 | 0.6496 |
| 346 | (5R)-3-(3,6-dihydro-2H-pyran-4-yl)-6-fluoro-7-(2-fluoro-3-pyridinyl)spiro[chromeno[2,3-b]pyridine-5,4'-[1,3]oxazol]-2'-amine | 449 | AA1 | 0.0008 | 0.0067 |
| 347 | (5S)-3-(3,6-dihydro-2H-pyran-4-yl)-6-fluoro-7-(2-fluoro-3-pyridinyl)spiro[chromeno[2,3-b]pyridine-5,4'-[1,3]oxazol]-2'-amine | 449 | AA1 | 0.3558 | 0.4573 |
| 348 | (5R)-3-(6,6-dimethyl-3,6-dihydro-2H-pyran-4-yl)-6-fluoro-7-(2-fluoro-3-pyridinyl)spiro[chromeno[2,3-b]pyridine-5,4'-[1,3]oxazol]-2'-amine | 477 | AA1 | 0.0008 | 0.0088 |
| 349 | (5R)-3-(2,2-dimethyl-3,6-dihydro-2H-pyran-4-yl)-6-fluoro-7-(2-fluoro-3-pyridinyl)spiro[chromeno[2,3-b]pyridine-5,4'-[1,3]oxazol]-2'-amine | 477 | AA1 | 0.0007 | 0.008 |
| 350 | (5S)-3-(6,6-dimethyl-3,6-dihydro-2H-pyran-4-yl)-6-fluoro-7-(2-fluoro-3-pyridinyl)spiro[chromeno[2,3-b]pyridine-5,4'-[1,3]oxazol]-2'-amine | 477 | AA1 | 0.5301 | 0.685 |
| 351 | (5S)-3-(2,2-dimethyl-3,6-dihydro-2H-pyran-4-yl)-6-fluoro-7-(2-fluoro-3-pyridinyl)spiro[chromeno[2,3-b]pyridine-5,4'-[1,3]oxazol]-2'-amine | 477 | AA1 | 0.3894 | 0.8544 |
| 352 | (5R)-3-(6,6-dimethyl-3,6-dihydro-2H-pyran-4-yl)-6-fluoro-7-(5-pyrimidinyl)spiro[chromeno[2,3-b]pyridine-5,4'-[1,3]oxazol]-2'-amine | 460.2 | AA1 | 0.0028 | 0.0194 |
| 353 | (5R)-3-(2,2-dimethyl-3,6-dihydro-2H-pyran-4-yl)-6-fluoro-7-(5-pyrimidinyl)spiro[chromeno[2,3-b]pyridine-5,4'-[1,3]oxazol]-2'-amine | 460.2 | AA1 | 0.0012 | 0.0158 |
| 354 | (5S)-3-(6,6-dimethyl-3,6-dihydro-2H-pyran-4-yl)-6-fluoro-7-(5-pyrimidinyl)spiro[chromeno[2,3-b]pyridine-5,4'-[1,3]oxazol]-2'-amine | 460.2 | AA1 | 0.0918 | 0.3417 |
| 355 | (5S)-3-(2,2-dimethyl-3,6-dihydro-2H-pyran-4-yl)-6-fluoro-7-(5-pyrimidinyl)spiro[chromeno[2,3-b]pyridine-5,4'-[1,3]oxazol]-2'-amine | 460.2 | AA1 | 0.4069 | 1.2808 |
| 356 | (5R)-6-fluoro-7-(2-fluoro-3-pyridinyl)-3-(1-methyl-1H-pyrazol-4-yl)spiro[chromeno[2,3-b]pyridine-5,4'-[1,3]oxazol]-2'-amine | 447 | AA1 | 0.0009 | 0.0139 |
| 357 | (5S)-6-fluoro-7-(2-fluoro-3-pyridinyl)-3-(1-methyl-1H-pyrazol-4-yl)spiro[chromeno[2,3-b]pyridine-5,4'-[1,3]oxazol]-2'-amine | 447 | AA1 | 1.0455 | 2.1299 |
| 115a | (5R)-6-fluoro-7-(2-fluoro-3-pyridinyl)-3-(3-methoxy-3-methyl-1-butyn-1-yl)spiro[chromeno[2,3-b]pyridine-5,4'-[1,3]oxazol]-2'-amine | 463 | BB31 | 0.0005 | 0.0039 |
| 115b | (5S)-6-fluoro-7-(2-fluoro-3-pyridinyl)-3-(3-methoxy-3-methyl-1-butyn-1-yl)spiro[chromeno[2,3-b]pyridine-5,4'-[1,3]oxazol]-2'-amine | 463 | BB31 | 0.3314 | 0.2787 |
| 358 | (5S)-3-(3,6-dihydro-2H-pyran-4-yl)-7-(4-fluoro-3-pyridinyl)spiro[chromeno[2,3-b]pyridine-5,4'-[1,3]oxazol]-2'-amine | 431.1 | AA36 | 0.0026 | 0.0246 |
| 104 | (5S)-7-(4-fluoro-3-pyridinyl)-3-((3-methyl-3-oxetanyl)ethynyl)spiro[chromeno[2,3-b]pyridine-5,4'-[1,3]oxazol]-2'-amine | 443 | BB19 | 0.0011 | 0.012 |
| 359 | (5R)-7-(2-fluoro-3-pyridinyl)-3-((3-methyl-3-oxetanyl)ethynyl)spiro[chromeno[2,3-b]pyridine-5,4'-[1,3]oxazol]-2'-amine | 443 | AA5 | 0.2249 | |
| 360 | (4S)-3'-fluoro-7'-(2-fluoro-3-pyridinyl)-2'-((3-methyl-3-oxetanyl)methoxy)spiro[1,3-oxazole-4,9'-xanthen]-2-amine | 466 | AA13 | 0.0029 | 0.0224 |
| 361 | (5S)-7-(5-chloro-2-fluoro-3-pyridinyl)-3-(3,6-dihydro-2H-pyran-4-yl)spiro[chromeno[2,3-c]pyridine-5,4'-[1,3]oxazol]-2'-amine | 465 | AA1 | 0.0005 | 0.0061 |
| 362 | (5S)-3-(3,6-dihydro-2H-pyran-4-yl)-7-(5-(3,6-dihydro-2H-pyran-4-yl)-2-fluoro-3-pyridinyl)spiro[chromeno[2,3-c]pyridine-5,4'-[1,3]oxazol]-2'-amine | 513 | AA1 | 0.0063 | 0.1137 |
| 363 | (5S)-7-(6-fluoro-3-pyridinyl)-3-(tetrahydro-2H-pyran-4-yl)spiro[chromeno[2,3-c]pyridine-5,4'-[1,3]oxazol]-2'-amine | 433 | AA11 | 0.0337 | 0.2696 |

TABLE I-continued

| Ex. No. | Compound Name | Observed Mass | Method | BACE 1 FRET assay (uM) | HEK cell assay (uM) |
|---|---|---|---|---|---|
| 364 | (5S)-7-(2-fluoro-3-pyridinyl)-3-(3-methyl-5-isoxazolyl)spiro[chromeno[2,3-c]pyridine-5,4'-[1,3]oxazol]-2'-amine | 430 | AA1 | 0.0069 | 0.0625 |
| 365 | (5S)-7-(6-fluoro-3-pyridinyl)-3-(1-methyl-1H-pyrazol-4-yl)spiro[chromeno[2,3-c]pyridine-5,4'-[1,3]oxazol]-2'-amine | 429 | AA1 | 0.0108 | 0.0424 |
| 366 | (5S)-3-(3-methyl-5-isoxazolyl)-7-phenylspiro[chromeno[2,3-c]pyridine-5,4'-[1,3]oxazol]-2'-amine | 411 | AA1 | 0.0801 | 0.3613 |
| 367 | (5S)-3-(1-methyl-1H-pyrazol-4-yl)-7-phenylspiro[chromeno[2,3-c]pyridine-5,4'-[1,3]oxazol]-2'-amine | 410 | AA1 | 0.0133 | 0.074 |
| 368 | (5S)-3-((4R)-2,2-dimethyltetrahydro-2H-pyran-4-yl)-7-(3-pyridinyl)spiro[chromeno[2,3-c]pyridine-5,4'-[1,3]oxazol]-2'-amine | 443 | AA11 | 0.0104 | 0.0379 |
| 369 | (5S)-3-(6,6-dimethyl-3,6-dihydro-2H-pyran-4-yl)-7-(6-fluoro-3-pyridinyl)spiro[chromeno[2,3-c]pyridine-5,4'-[1,3]oxazol]-2'-amine | 459 | AA1 | 0.0028 | 0.0162 |
| 370 | (5S)-3-(2,2-dimethyl-3,6-dihydro-2H-pyran-4-yl)-7-(6-fluoro-3-pyridinyl)spiro[chromeno[2,3-c]pyridine-5,4'-[1,3]oxazol]-2'-amine | 459 | AA1 | 0.0036 | 0.0237 |
| 135 | (5S)-3-(6,6-dimethyl-3,6-dihydro-2H-pyran-4-yl)-7-(5-fluoro-3-pyridinyl)spiro[chromeno[2,3-c]pyridine-5,4'-[1,3]oxazol]-2'-amine | 459 | AA1 | 0.0013 | 0.01 |
| 371 | (5S)-3-(2,2-dimethyl-3,6-dihydro-2H-pyran-4-yl)-7-(5-fluoro-3-pyridinyl)spiro[chromeno[2,3-c]pyridine-5,4'-[1,3]oxazol]-2'-amine | 459 | AA1 | 0.002 | 0.0107 |
| 372 | (5S)-3-((1E)-3,3-dimethyl-1-buten-1-yl)-7-(5-fluoro-3-pyridinyl)spiro[chromeno[2,3-c]pyridine-5,4'-[1,3]oxazol]-2'-amine | 431 | AA1 | 0.0008 | 0.0149 |
| 373 | (5S)-3,7-bis(5-fluoro-3-pyridinyl)spiro[chromeno[2,3-c]pyridine-5,4'-[1,3]oxazol]-2'-amine | 444 | AA1 | 0.0022 | 0.0228 |
| 374 | (5S)-7-(2-fluoro-3-pyridinyl)-3-((2S)-tetrahydro-2H-pyran-2-yl)spiro[chromeno[2,3-c]pyridine-5,4'-[1,3]oxazol]-2'-amine | 433 | AA11 | 0.0185 | 0.112 |
| 375 | (5S)-7-(2-fluoro-3-pyridinyl)-3-((2R)-tetrahydro-2H-pyran-2-yl)spiro[chromeno[2,3-c]pyridine-5,4'-[1,3]oxazol]-2'-amine | 433 | AA11 | 0.0022 | 0.0143 |
| 376 | (5S)-3-(2-fluoro-4-pyridinyl)-7-(5-fluoro-3-pyridinyl)spiro[chromeno[2,3-c]pyridine-5,4'-[1,3]oxazol]-2'-amine | 444 | AA1 | 0.0026 | 0.033 |
| 377 | (5S)-3-((4R)-2,2-dimethyltetrahydro-2H-pyran-4-yl)-7-(2-fluoro-3-pyridinyl)spiro[chromeno[2,3-c]pyridine-5,4'-[1,3]oxazol]-2'-amine | 461 | AA11 | 0.0059 | 0.0294 |
| 378 | (5S)-3-((4S)-2,2-dimethyltetrahydro-2H-pyran-4-yl)-7-(2-fluoro-3-pyridinyl)spiro[chromeno[2,3-c]pyridine-5,4'-[1,3]oxazol]-2'-amine | 461 | AA11 | 0.0043 | 0.0264 |
| 379 | (5S)-3-((4S)-2,2-dimethyltetrahydro-2H-pyran-4-yl)-7-(6-fluoro-3-pyridinyl)spiro[chromeno[2,3-c]pyridine-5,4'-[1,3]oxazol]-2'-amine | 461 | AA11 | 0.0232 | 0.1758 |
| 380 | (5S)-3-((4S)-2,2-dimethyltetrahydro-2H-pyran-4-yl)-7-(5-fluoro-3-pyridinyl)spiro[chromeno[2,3-c]pyridine-5,4'-[1,3]oxazol]-2'-amine | 461 | AA11 | 0.0302 | 0.1005 |
| 381 | (5S)-7-(5-fluoro-3-pyridinyl)-3-((2S)-tetrahydro-2H-pyran-2-yl)spiro[chromeno[2,3-c]pyridine-5,4'-[1,3]oxazol]-2'-amine | 433 | AA11 | 0.0073 | 0.0626 |
| 382 | (5S)-7-(2-fluoro-3-pyridinyl)-3-((3S)-tetrahydro-2H-pyran-3-yl)spiro[chromeno[2,3-c]pyridine-5,4'-[1,3]oxazol]-2'-amine | 433 | AA11 | 0.0113 | 0.1232 |
| 383 | (5R)-3-chloro-7-((1E)-3,3-dimethyl-1-buten-1-yl)spiro[chromeno[2,3-c]pyridine-5,4'-[1,3]oxazol]-2'-amine | 370 | AA24 | 0.6225 | 2.5613 |
| 384 | (5R)-7-((1E)-3,3-dimethyl-1-buten-1-yl)-3-(5-pyrimidinyl)spiro[chromeno[2,3-c]pyridine-5,4'-[1,3]oxazol]-2'-amine | 414 | AA1 | 0.004 | 0.084 |
| 385 | (5S)-3-(5,6-dihydro-2H-pyran-3-yl)-7-(2-fluoro-3-pyridinyl)spiro[chromeno[2,3-c]pyridine-5,4'-[1,3]oxazol]-2'-amine | 431 | AA1 | 0.0006 | 0.0053 |
| 386 | (5S)-3-(1-cyclohexen-1-yl)-7-(2-fluoro-3-pyridinyl)spiro[chromeno[2,3-c]pyridine-5,4'-[1,3]oxazol]-2'-amine | 429 | AA1 | 0.0004 | 0.0111 |
| 387 | 3-((5S)-2'-amino-3-chlorospiro[chromeno[2,3-c]pyridine-5,4'-[1,3]oxazol]-7-yl)-2-pyridinecarbonitrile | 390 | AA24 | 0.6717 | 10 |

TABLE I-continued

| Ex. No. | Compound Name | Observed Mass | Method | BACE 1 FRET assay (uM) | HEK cell assay (uM) |
|---|---|---|---|---|---|
| 388 | (5S)-3-cyclohexyl-7-(2-fluoro-3-pyridinyl)spiro[chromeno[2,3-c]pyridine-5,4'-[1,3]oxazol]-2'-amine | 431 | AA11 | 0.0029 | 0.1066 |
| 389 | 3-((5S)-2'-amino-3-(3,6-dihydro-2H-pyran-4-yl)spiro[chromeno[2,3-c]pyridine-5,4'-[1,3]oxazol]-7-yl)-2-pyridinecarbonitrile | 438 | AA1 | 0.0111 | 0.0684 |
| 390 | (5S)-3-chloro-7-(4-fluoro-3-pyridinyl)spiro[chromeno[2,3-c]pyridine-5,4'-[1,3]oxazol]-2'-amine | 383 | AA24 | 0.1024 | 0.6397 |
| 391 | (5S)-3-(3,6-dihydro-2H-pyran-4-yl)-7-(4-fluoro-3-pyridinyl)spiro[chromeno[2,3-c]pyridine-5,4'-[1,3]oxazol]-2'-amine | 431 | AA1 | 0.0007 | 0.0058 |
| 392 | (5R)-3-chloro-7-(2-fluoro-4-pyridinyl)spiro[chromeno[2,3-c]pyridine-5,4'-[1,3]oxazol]-2'-amine | 383 | AA24 | 5.5426 | 10 |
| 393 | (5R)-7-(2-fluoro-4-pyridinyl)-3-(5-pyrimidinyl)spiro[chromeno[2,3-c]pyridine-5,4'-[1,3]oxazol]-2'-amine | 427 | AA1 | 0.0633 | 0.2236 |
| 394 | (5S)-3-(3,6-dihydro-2H-pyran-4-yl)-7-(4-fluorophenyl)spiro[chromeno[2,3-c]pyridine-5,4'-[1,3]oxazol]-2'-amine | 430 | AA1 | 0.0094 | 0.1383 |
| 395 | (5S)-7-(4-fluorophenyl)-3-(2-fluoro-4-pyridinyl)spiro[chromeno[2,3-c]pyridine-5,4'-[1,3]oxazol]-2'-amine | 443 | AA1 | 0.0237 | 0.3347 |
| 396 | (5S)-7-(4-fluorophenyl)-3-(5-pyrimidinyl)spiro[chromeno[2,3-c]pyridine-5,4'-[1,3]oxazol]-2'-amine | 426 | AA1 | 0.1356 | 1.0782 |
| 397 | (5S)-7-(2,4-difluoro-3-pyridinyl)-3-(2-fluoro-4-pyridinyl)spiro[chromeno[2,3-c]pyridine-5,4'-[1,3]oxazol]-2'-amine | 462 | AA1 | 0.002 | |
| 398 | (5S)-7-(2,4-difluoro-3-pyridinyl)-3-(4-pyridinyl)spiro[chromeno[2,3-c]pyridine-5,4'-[1,3]oxazol]-2'-amine | 444 | AA1 | 0.002 | |
| 399 | (5S)-3-chloro-7-(2,4-difluoro-3-pyridinyl)spiro[chromeno[2,3-c]pyridine-5,4'-[1,3]oxazol]-2'-amine | 401 | AA24 | 0.0599 | |
| 400 | (5S)-7-(4-fluorophenyl)-3-(tetrahydro-2H-pyran-4-yl)spiro[chromeno[2,3-c]pyridine-5,4'-[1,3]oxazol]-2'-amine | 432 | AA11 | 0.0709 | |
| 401 | (5S)-3-((E)-2-cyclopropylethenyl)-7-(2-fluoro-3-pyridinyl)spiro[chromeno[2,3-c]pyridine-5,4'-[1,3]oxazol]-2'-amine | 415 | AA1 | 0.0044 | 0.0449 |
| 138 | (5S)-3-(3,3-difluoro-1-pyrrolidinyl)-7-(3-pyridinyl)spiro[chromeno[2,3-c]pyridine-5,4'-[1,3]oxazol]-2'-amine | 436 | AA9 | 0.0011 | 0.0052 |
| 402 | (5S)-3-(4,4-difluoro-1-piperidinyl)-7-(3-pyridinyl)spiro[chromeno[2,3-c]pyridine-5,4'-[1,3]oxazol]-2'-amine | 450 | AA9 | 0.0024 | 0.0131 |
| 403 | (5S)-N~3~,N~3~-dimethyl-7-(3-pyridinyl)spiro[chromeno[2,3-c]pyridine-5,4'-[1,3]oxazole]-2',3-diamine | 374 | AA9 | 0.043 | 0.1114 |
| 404 | (5S)-7-(3-pyridinyl)-N~3~-(2,2,2-trifluoroethyl)spiro[chromeno[2,3-c]pyridine-5,4'-[1,3]oxazole]-2',3-diamine | 428 | AA9 | 0.0313 | 0.1626 |
| 405 | (5S)-7-(2-fluoro-3-pyridinyl)-3-((3-methyl-3-oxetanyl)ethynyl)spiro[chromeno[2,3-c]pyridine-5,4'-[1,3]oxazol]-2'-amine | 443 | AA5 | 0.0014 | 0.0111 |
| 406 | (5S)-3-((1E)-3,3-dimethyl-1-buten-1-yl)-7-(2-methoxy-5-pyrimidinyl)spiro[chromeno[2,3-c]pyridine-5,4'-[1,3]oxazol]-2'-amine | 444 | AA1 | 0.1828 | 0.7119 |
| 407 | (5S)-3-((1E)-3,3-dimethyl-1-buten-1-yl)-7-(5-fluoro-2-methoxy-3-pyridinyl)spiro[chromeno[2,3-c]pyridine-5,4'-[1,3]oxazol]-2'-amine | 461 | AA1 | 0.0053 | 0.1577 |
| 408 | (5S)-3-((1E)-3,3-dimethyl-1-buten-1-yl)-7-(2-methoxy-3-pyridinyl)spiro[chromeno[2,3-c]pyridine-5,4'-[1,3]oxazol]-2'-amine | 443 | AA1 | 0.0201 | 0.3107 |
| 409 | (5S)-N~3~-(2-methoxy-2-methylpropyl)-7-(3-pyridinyl)spiro[chromeno[2,3-c]pyridine-5,4'-[1,3]oxazole]-2',3-diamine | 432 | AA9 | 0.0066 | 0.0178 |
| 410 | 1-((5S)-2'-amino-7-(3-pyridinyl)spiro[chromeno[2,3-c]pyridine-5,4'-[1,3]oxazol]-3-yl)-3-azetidinecarbonitrile | 411 | AA9 | 0.0287 | 0.1277 |
| 140 | (5S)-3-(3,3-difluoro-1-pyrrolidinyl)-7-(2-fluoro-3-pyridinyl)spiro[chromeno[2,3-c]pyridine-5,4'-[1,3]oxazol]-2'-amine | 454 | AA9 | 0.0006 | 0.0041 |

TABLE I-continued

| Ex. No. | Compound Name | Observed Mass | Method | BACE 1 FRET assay (uM) | HEK cell assay (uM) |
|---|---|---|---|---|---|
| 411 | (5S)-3-((3R)-3-fluoro-1-pyrrolidinyl)-7-(3-pyridinyl)spiro[chromeno[2,3-c]pyridine-5,4'-[1,3]oxazol]-2'-amine | 417.8 | AA9 | 0.0023 | 0.0045 |
| 412 | (5S)-3-((3S)-3-fluoro-1-pyrrolidinyl)-7-(3-pyridinyl)spiro[chromeno[2,3-c]pyridine-5,4'-[1,3]oxazol]-2'-amine | 417.8 | AA9 | 0.0076 | 0.0208 |
| 137 | (5S)-3-(4,4-difluoro-1-piperidinyl)-7-(2-fluoro-3-pyridinyl)spiro[chromeno[2,3-c]pyridine-5,4'-[1,3]oxazol]-2'-amine | 467.8 | AA9 | 0.0007 | 0.0087 |
| 413 | (5S)-3-(3,3-difluoro-1-pyrrolidinyl)-7-(5-fluoro-3-pyridinyl)spiro[chromeno[2,3-c]pyridine-5,4'-[1,3]oxazol]-2'-amine | 454 | AA9 | 0.0008 | 0.0056 |
| 414 | (5S)-3-(4,4-difluoro-1-piperidinyl)-7-(5-fluoro-3-pyridinyl)spiro[chromeno[2,3-c]pyridine-5,4'-[1,3]oxazol]-2'-amine | 468 | AA9 | 0.0015 | 0.0136 |
| 415 | (5S)-3-(3,3-difluoro-1-pyrrolidinyl)-7-(2-methoxy-5-pyrimidinyl)spiro[chromeno[2,3-c]pyridine-5,4'-[1,3]oxazol]-2'-amine | 467 | AA9 | 0.0817 | 0.3673 |
| 416 | (5S)-7-(2-fluoro-3-pyridinyl)-3-((3R)-3-fluoro-1-pyrrolidinyl)spiro[chromeno[2,3-c]pyridine-5,4'-[1,3]oxazol]-2'-amine | 436 | AA9 | 0.0005 | 0.0049 |
| 133 | (5S)-7-(2-fluoro-3-pyridinyl)-3-((3S)-3-fluoro-1-pyrrolidinyl)spiro[chromeno[2,3-c]pyridine-5,4'-[1,3]oxazol]-2'-amine | 436 | AA9 | 0.0027 | 0.0096 |
| 417 | (5S)-3-((3R)-3-fluoro-1-pyrrolidinyl)-7-(2-methoxy-5-pyrimidinyl)spiro[chromeno[2,3-c]pyridine-5,4'-[1,3]oxazol]-2'-amine | 448.8 | AA9 | 0.0845 | 0.3356 |
| 418 | (5S)-7-(2-fluoro-3-pyridinyl)-N~3~-(2-methoxy-2-methylpropyl)spiro[chromeno[2,3-c]pyridine-5,4'-[1,3]oxazole]-2',3-diamine | 449.8 | AA9 | 0.003 | 0.0141 |
| 419 | (5S)-3-(4,4-difluoro-1-piperidinyl)-7-(2-methoxy-5-pyrimidinyl)spiro[chromeno[2,3-c]pyridine-5,4'-[1,3]oxazol]-2'-amine | 480.8 | AA9 | 0.172 | 0.6018 |
| 420 | (5S)-3-(4,4-difluoro-1-piperidinyl)-7-(2-fluoro-5-methyl-3-pyridinyl)spiro[chromeno[2,3-c]pyridine-5,4'-[1,3]oxazol]-2'-amine | 482 | AA9 | 0.0012 | 0.0151 |
| 421 | (5S)-3-(3,3-difluoro-1-pyrrolidinyl)-7-(2-fluoro-5-methyl-3-pyridinyl)spiro[chromeno[2,3-c]pyridine-5,4'-[1,3]oxazol]-2'-amine | 467.8 | AA9 | 0.0005 | 0.0053 |
| 422 | (5S)-7-(2-fluoro-5-methyl-3-pyridinyl)-3-(2-fluoro-4-pyridinyl)spiro[chromeno[2,3-c]pyridine-5,4'-[1,3]oxazol]-2'-amine | 457.8 | AA1 | 0.0021 | 0.0232 |
| 423 | (5S)-3-(3,3-difluoro-1-pyrrolidinyl)-7-(6-(3,3-difluoro-1-pyrrolidinyl)-3-pyridinyl)spiro[chromeno[2,3-c]pyridine-5,4'-[1,3]oxazol]-2'-amine | 540.8 | AA9 | 0.4575 | 0.4017 |
| 424 | 3-((5S)-2'-amino-3-(4,4-difluoro-1-piperidinyl)spiro[chromeno[2,3-c]pyridine-5,4'-[1,3]oxazol]-7-yl)benzonitrile | 474 | AA9 | 0.0015 | 0.018 |
| 425 | 3-((5S)-2'-amino-3-((3R)-3-fluoro-1-pyrrolidinyl)spiro[chromeno[2,3-c]pyridine-5,4'-[1,3]oxazol]-7-yl)benzonitrile | 442 | AA9 | 0.0008 | 0.0048 |
| 426 | 3-((5S)-2'-amino-3-((3S)-3-fluoro-1-pyrrolidinyl)spiro[chromeno[2,3-c]pyridine-5,4'-[1,3]oxazol]-7-yl)benzonitrile | 442 | AA9 | 0.0035 | 0.0168 |
| 427 | (5S)-3-chloro-7-(5-(3,3-difluoro-1-pyrrolidinyl)-3-pyridinyl)spiro[chromeno[2,3-c]pyridine-5,4'-[1,3]oxazol]-2'-amine | 469.9 | AA9 | 0.6399 | 0.6098 |
| 428 | (5S)-3-chloro-7-(5-((3S)-3-fluoro-1-pyrrolidinyl)-3-pyridinyl)spiro[chromeno[2,3-c]pyridine-5,4'-[1,3]oxazol]-2'-amine | 452 | AA9 | 0.6038 | 2.2049 |
| 429 | (5S)-3-chloro-7-(5-((3R)-3-fluoro-1-pyrrolidinyl)-3-pyridinyl)spiro[chromeno[2,3-c]pyridine-5,4'-[1,3]oxazol]-2'-amine | 452 | AA9 | 3.227 | 2.2128 |
| 430 | (5S)-3-(3,3-difluoro-1-piperidinyl)-7-(2-fluoro-3-pyridinyl)spiro[chromeno[2,3-c]pyridine-5,4'-[1,3]oxazol]-2'-amine | 467.8 | AA9 | 0.0006 | 0.0069 |
| 431 | 3-(3,3-difluoro-1-pyrrolidinyl)-7-methoxyspiro[chromeno[2,3-c]pyridine-5,4'-[1,3]oxazol]-2'-amine | 389 | AA40 | 1.7332 | 10 |
| 432 | (5S)-7-(3-chlorophenyl)-3-(3,3-difluoro-1-pyrrolidinyl)spiro[chromeno[2,3-c]pyridine-5,4'-[1,3]oxazol]-2'-amine | 468.8 | AA16 | 0.002 | |

TABLE I-continued

| Ex. No. | Compound Name | Observed Mass | Method | BACE 1 FRET assay (uM) | HEK cell assay (uM) |
|---|---|---|---|---|---|
| 433 | (5R)-7-(3-chlorophenyl)-3-(3,3-difluoro-1-pyrrolidinyl)spiro[chromeno[2,3-c]pyridine-5,4'-[1,3]oxazol]-2'-amine | 468.8 | AA16 | 0.025 | |
| 434 | (5S)-3-((1E)-3,3-dimethyl-1-buten-1-yl)-7-(6-fluoro-3-pyridinyl)spiro[chromeno[2,3-c]pyridine-5,4'-[1,3]oxazol]-2'-amine | 431 | AA1 | 0.003 | 0.0317 |
| 435 | (5S)-N~3~-methyl-N~3~-(1-methylethyl)-7-(3-pyridinyl)spiro[chromeno[2,3-c]pyridine-5,4'-[1,3]oxazole]-2',3-diamine | 402 | AA9 | 0.0056 | 0.0296 |
| 134 | 3-((5S)-2'-amino-3-(3,3-difluoro-1-pyrrolidinyl)spiro[chromeno[2,3-c]pyridine-5,4'-[1,3]oxazol]-7-yl)benzonitrile | 460 | AA9 | 0.001 | 0.012 |
| 436 | (5S)-3-(4-fluoro-1-piperidinyl)-7-(2-fluoro-3-pyridinyl)spiro[chromeno[2,3-c]pyridine-5,4'-[1,3]oxazol]-2'-amine | 449.8 | AA9 | 0.0006 | 0.008 |
| 437 | (4S)-2'-bromo-4'-fluoro-7'-((3-methyl-3-oxetanyl)methoxy)spiro[1,3-oxazole-4,9'-xanthen]-2-amine | 448.9, 450.8 | A | 0.2022 | 1.916 |
| 438 | (4S)-2'-(3,6-dihydro-2H-pyran-4-yl)-4'-fluoro-7'-((3-methyl-3-oxetanyl)methoxy)spiro[1,3-oxazole-4,9'-xanthen]-2-amine | 453 | AA13 | 0.009 | 0.0346 |
| 439 | (4S)-4'-fluoro-7'-((3-methyl-3-oxetanyl)methoxy)-2'-(2-methyl-4-pyridinyl)spiro[1,3-oxazole-4,9'-xanthen]-2-amine | 462 | AA13 | 0.1858 | 0.1556 |
| 440 | (4S)-4'-fluoro-7'-((3-methyl-3-oxetanyl)methoxy)-2'-(6-methyl-3-pyridinyl)spiro[1,3-oxazole-4,9'-xanthen]-2-amine | 462 | AA13 | 0.0117 | 0.0169 |
| 441 | 3-(((4S)-2-amino-7'-(3,6-dihydro-2H-pyran-4-yl)-5'-fluorospiro[1,3-oxazole-4,9'-xanthen]-2'-yl)oxy)-2,2-dimethylpropanenitrile | 450 | AA13 | 0.004 | 0.0144 |
| 442 | 3-(((4S)-2-amino-7'-bromo-5'-fluorospiro[1,3-oxazole-4,9'-xanthen]-2'-yl)oxy)-2,2-dimethylpropanenitrile | 445.9, 447.8 | A | 0.1522 | 1.8114 |
| 443 | 3-(((4S)-2-amino-5'-fluoro-7'-(6-methyl-3-pyridinyl)spiro[1,3-oxazole-4,9'-xanthen]-2'-yl)oxy)-2,2-dimethylpropanenitrile | 459 | AA13 | 0.005 | 0.0116 |
| 444 | (4S)-4'-fluoro-7'-((3-methyl-3-oxetanyl)methoxy)-2'-(1-methyl-1H-pyrazol-4-yl)spiro[1,3-oxazole-4,9'-xanthen]-2-amine | 451 | AA13 | 0.02 | 0.0386 |
| 445 | (4S)-4'-fluoro-2'-(6-fluoro-5-methyl-3-pyridinyl)-7'-((3-methyl-3-oxetanyl)methoxy)spiro[1,3-oxazole-4,9'-xanthen]-2-amine | 480 | AA13 | 0.0416 | 0.1878 |
| 446 | (4S)-2'-(3,6-dihydro-2H-pyran-4-yl)-4'-fluoro-7'-(5-methyl-3-pyridinyl)spiro[1,3-oxazole-4,9'-xanthen]-2-amine | 444 | AA1 | 0.0019 | 0.0054 |
| 447 | (4S)-2'-(3,6-dihydro-2H-pyran-4-yl)-4'-fluoro-7'-(5-fluoro-3-pyridinyl)spiro[1,3-oxazole-4,9'-xanthen]-2-amine | 448 | AA1 | 0.0011 | 0.0051 |
| 448 | (4S)-4'-fluoro-7'-(5-fluoro-3-pyridinyl)-2'-(tetrahydro-2H-pyran-4-yl)spiro[1,3-oxazole-4,9'-xanthen]-2-amine | 450 | AA18 | 0.0024 | 0.0077 |
| 449 | (4S)-2'-((4S)-2,2-dimethyltetrahydro-2H-pyran-4-yl)-4'-fluoro-7'-(2-pyrazinyl)spiro[1,3-oxazole-4,9'-xanthen]-2-amine | 461 | BB15 | 0.0037 | 0.02 |
| 450 | (4S)-2'-((4R)-2,2-dimethyltetrahydro-2H-pyran-4-yl)-4'-fluoro-7'-(2-pyrazinyl)spiro[1,3-oxazole-4,9'-xanthen]-2-amine | 461 | BB15 | 0.0024 | 0.0177 |
| 451 | (4S)-4'-fluoro-7'-(2-fluoro-3-pyridinyl)-2'-(2-fluoro-4-pyridinyl)spiro[1,3-oxazole-4,9'-xanthen]-2-amine | 461 | AA8 | 0.0005 | 0.0103 |
| 452 | (4S)-2'-(3,6-dihydro-2H-pyran-4-yl)-4'-fluoro-7'-(2-pyrazinyl)spiro[1,3-oxazole-4,9'-xanthen]-2-amine | 431 | AA22 | 0.002 | 0.0115 |
| 453 | (5S)-3-((4R)-2,2-dimethyltetrahydro-2H-pyran-4-yl)-7-(2-fluoro-3-pyridinyl)spiro[chromeno[2,3-b]pyridine-5,4'-[1,3]oxazol]-2'-amine | 461.1 | AA11 | 0.0024 | 0.0122 |
| 454 | (5S)-7-(5-chloro-2-fluoro-3-pyridinyl)-3-(3,6-dihydro-2H-pyran-4-yl)spiro[chromeno[2,3-b]pyridine-5,4'-[1,3]oxazol]-2'-amine | 465 | AA1 | 0.0009 | 0.0032 |
| 455 | 3-((5S)-2'-amino-3-((4R)-2,2-dimethyltetrahydro-2H-pyran-4-yl)spiro[chromeno[2,3-b]pyridine-5,4'-[1,3]oxazol]-7-yl)benzonitrile | 467.1 | AA19 | 0.0028 | 0.0065 |
| 456 | (5S)-7-(5-chloro-2-fluoro-3-pyridinyl)-3-((3-methyl-3-oxetanyl)ethynyl)spiro[chromeno[2,3-b]pyridine-5,4'-[1,3]oxazol]-2'-amine | 477 | AA5 | 0.0006 | 0.0022 |

TABLE I-continued

| Ex. No. | Compound Name | Observed Mass | Method | BACE 1 FRET assay (uM) | HEK cell assay (uM) |
|---|---|---|---|---|---|
| 457 | (5S)-3-(3,6-dihydro-2H-pyran-4-yl)-7-(5-fluoro-3-pyridinyl)spiro[chromeno[2,3-b]pyridine-5,4'-[1,3]oxazol]-2'-amine | 431.1 | AA1 | 0.0015 | 0.0066 |
| 458 | (5S)-7-(5-fluoro-3-pyridinyl)-3-((3-methyl-3-oxetanyl)ethynyl)spiro[chromeno[2,3-b]pyridine-5,4'-[1,3]oxazol]-2'-amine | 443.1 | AA5 | 0.0012 | 0.0051 |
| 459 | (5S)-3-(3,6-dihydro-2H-pyran-4-yl)-7-(5-methoxy-3-pyridinyl)spiro[chromeno[2,3-b]pyridine-5,4'-[1,3]oxazol]-2'-amine | 443.1 | AA1 | 0.0022 | 0.0062 |
| 460 | (5S)-3-(3,6-dihydro-2H-pyran-4-yl)-7-(2-fluoro-3-pyridinyl)spiro[chromeno[2,3-b]pyridine-5,4'-[1,3]oxazol]-2'-amine | 431.1 | AA1 | 0.0015 | 0.0065 |
| 461 | (5S)-7-(5-methoxy-3-pyridinyl)-3-((3-methyl-3-oxetanyl)ethynyl)spiro[chromeno[2,3-b]pyridine-5,4'-[1,3]oxazol]-2'-amine | 455.1 | AA5 | 0.0018 | 0.0063 |
| 462 | (5S)-3-(3,6-dihydro-2H-pyran-4-yl)-7-((3-methyl-3-oxetanyl)ethynyl)spiro[chromeno[2,3-b]pyridine-5,4'-[1,3]oxazol]-2'-amine | 430.2 | AA21 | 0.0059 | 0.0189 |
| 463 | (5S)-7-(3-chloro-2-fluorophenyl)-3-((3-methyl-3-oxetanyl)ethynyl)spiro[chromeno[2,3-b]pyridine-5,4'-[1,3]oxazol]-2'-amine | 476.1 | AA5 | 0.0008 | 0.0143 |
| 464 | (5S)-7-(3,3-dimethyl-1-butyn-1-yl)-3-(4-morpholinyl)spiro[chromeno[2,3-b]pyridine-5,4'-[1,3]oxazol]-2'-amine | 419.4 | AA27 | 0.0128 | 0.069 |
| 465 | (5S)-7-(3-chlorophenyl)-3-((4S)-2,2-dimethyltetrahydro-2H-pyran-4-yl)spiro[chromeno[2,3-b]pyridine-5,4'-[1,3]oxazol]-2'-amine | 476.1 | AA19 | 0.0017 | 0.0111 |
| 466 | (5S)-7-(5-chloro-3-pyridinyl)-3-((4S)-2,2-dimethyltetrahydro-2H-pyran-4-yl)spiro[chromeno[2,3-b]pyridine-5,4'-[1,3]oxazol]-2'-amine | 477.3 | AA19 | 0.0021 | 0.0056 |
| 467 | (5S)-3-(3,6-dihydro-2H-pyran-4-yl)-7-(6-fluoro-5-methyl-3-pyridinyl)spiro[chromeno[2,3-b]pyridine-5,4'-[1,3]oxazol]-2'-amine | 445.2 | AA1 | 0.0208 | 0.0508 |
| 468 | (5S)-7-(6-fluoro-5-methyl-3-pyridinyl)-3-((3-methyl-3-oxetanyl)ethynyl)spiro[chromeno[2,3-b]pyridine-5,4'-[1,3]oxazol]-2'-amine | 457.2 | AA5 | 0.0074 | 0.0287 |
| 469 | (5S)-3-((4R)-2,2-dimethyltetrahydro-2H-pyran-4-yl)-7-(2-fluoro-3-pyridinyl)spiro[chromeno[2,3-b]pyridine-5,4'-[1,3]oxazol]-2'-amine | 461.1 | AA19 | 0.0028 | 0.0139 |
| 470 | (5S)-3-((4S)-2,2-dimethyltetrahydro-2H-pyran-4-yl)-7-(2-fluoro-3-pyridinyl)spiro[chromeno[2,3-b]pyridine-5,4'-[1,3]oxazol]-2'-amine | 461.1 | AA19 | 0.0033 | 0.0149 |
| 471 | 3-((5S)-2'-amino-3-((4R)-2,2-dimethyltetrahydro-2H-pyran-4-yl)spiro[chromeno[2,3-b]pyridine-5,4'-[1,3]oxazol]-7-yl)benzonitrile | 467.1 | AA19 | 0.0051 | 0.014 |
| 472 | 3-((5S)-2'-amino-3-((4S)-2,2-dimethyltetrahydro-2H-pyran-4-yl)spiro[chromeno[2,3-b]pyridine-5,4'-[1,3]oxazol]-7-yl)benzonitrile | 467.1 | AA19 | 0.0023 | 0.0044 |
| 473 | (5S)-7-(3-chlorophenyl)-3-((4R)-2,2-dimethyltetrahydro-2H-pyran-4-yl)spiro[chromeno[2,3-b]pyridine-5,4'-[1,3]oxazol]-2'-amine | 476.1 | AA19 | 0.0021 | 0.0155 |
| 474 | (5S)-7-(3-chlorophenyl)-3-((4S)-2,2-dimethyltetrahydro-2H-pyran-4-yl)spiro[chromeno[2,3-b]pyridine-5,4'-[1,3]oxazol]-2'-amine | 476.1 | AA19 | 0.0009 | 0.0094 |
| 475 | (5S)-7-(5-chloro-3-pyridinyl)-3-((4R)-2,2-dimethyltetrahydro-2H-pyran-4-yl)spiro[chromeno[2,3-b]pyridine-5,4'-[1,3]oxazol]-2'-amine | 477.3 | AA19 | 0.0022 | 0.0073 |
| 476 | (5S)-7-(5-chloro-3-pyridinyl)-3-((4S)-2,2-dimethyltetrahydro-2H-pyran-4-yl)spiro[chromeno[2,3-b]pyridine-5,4'-[1,3]oxazol]-2'-amine | 477.3 | AA19 | 0.0013 | 0.0049 |
| 102 | (5R)-3-(2,2-dimethylpropoxy)-7-(2-fluoro-3-pyridinyl)spiro[chromeno[2,3-c]pyridine-5,4'-[1,3]oxazol]-2'-amine | 435.2 | BB17 | 0.0011 | 0.0262 |
| 477 | (5S)-3-(4,4-difluoro-1-piperidinyl)-7-(2-(4,4-difluoro-1-piperidinyl)-3-pyridinyl)spiro[chromeno[2,3-b]pyridine-5,4'-[1,3]oxazol]-2'-amine | 569.1 | AA9 | 0.3305 | 1.203 |

TABLE I-continued

| Ex. No. | Compound Name | Observed Mass | Method | BACE 1 FRET assay (uM) | HEK cell assay (uM) |
|---|---|---|---|---|---|
| 478 | (5S)-3-(4,4-difluoro-1-piperidinyl)-7-(2-fluoro-3-pyridinyl)spiro[chromeno[2,3-b]pyridine-5,4'-[1,3]oxazol]-2'-amine | 468 | AA9 | 0.0021 | 0.0143 |
| 479 | (5S)-3-(3,3-difluoro-1-pyrrolidinyl)-7-(2-fluoro-3-pyridinyl)spiro[chromeno[2,3-b]pyridine-5,4'-[1,3]oxazol]-2'-amine | 454 | AA9 | 0.0011 | 0.0044 |
| 480 | (5S)-3-(4,4-dimethyl-1-piperidinyl)-7-(2-fluoro-3-pyridinyl)spiro[chromeno[2,3-b]pyridine-5,4'-[1,3]oxazol]-2'-amine | 460 | AA9 | 0.0025 | 0.0094 |
| 481 | (5S)-3-(2,2-dimethyl-4-morpholinyl)-7-(2-fluoro-5-methoxyphenyl)spiro[chromeno[2,3-b]pyridine-5,4'-[1,3]oxazol]-2'-amine | 491 | AA16 | 0.0027 | 0.0192 |
| 482 | (5S)-3-(2,2-dimethyl-4-morpholinyl)-7-(2-fluoro-4-methyl-3-pyridinyl)spiro[chromeno[2,3-b]pyridine-5,4'-[1,3]oxazol]-2'-amine | 476.2 | AA9 | 0.0034 | 0.0144 |
| 483 | (5S)-3-(3,3-dimethyl-1-piperidinyl)-7-(2-fluoro-3-pyridinyl)spiro[chromeno[2,3-b]pyridine-5,4'-[1,3]oxazol]-2'-amine | 460.2 | AA9 | 0.0034 | 0.0223 |
| 484 | (5R)-7-bromo-2-fluorospiro[chromeno[2,3-b]pyridine-5,4'-[1,3]oxazol]-2'-amine | 349.9 | BB5 | 24.592 | 10 |
| 485 | (5R)-2-fluoro-7-(2-fluoro-3-pyridinyl)spiro[chromeno[2,3-b]pyridine-5,4'-[1,3]oxazol]-2'-amine | 367 | BB5 | 0.1754 | 0.8518 |
| 486 | (5R)-1-fluoro-3,7-di-3-pyridinylspiro[chromeno[2,3-c]pyridine-5,4'-[1,3]oxazol]-2'-amine | 426 | AA2 | 0.3006 | 0.3261 |
| 487 | (5S)-7-bromo-3-chloro-1-fluorospiro[chromeno[2,3-c]pyridine-5,4'-[1,3]oxazol]-2'-amine | 383.9 | AA65 | 3.6828 | 0.7398 |
| 488 | (5S)-3-chloro-1-fluoro-7-(2-fluoro-3-pyridinyl)spiro[chromeno[2,3-c]pyridine-5,4'-[1,3]oxazol]-2'-amine | 401 | AA1 | 0.0066 | 0.3581 |
| 130 | (5S)-3-(3,6-dihydro-2H-pyran-4-yl)-1-fluoro-7-(2-fluoro-3-pyridinyl)spiro[chromeno[2,3-c]pyridine-5,4'-[1,3]oxazol]-2'-amine | 449 | AA1 | 0.0004 | 0.0021 |
| 131 | (5S)-1-fluoro-7-(2-fluoro-3-pyridinyl)-3-(tetrahydro-2H-pyran-4-yl)spiro[chromeno[2,3-c]pyridine-5,4'-[1,3]oxazol]-2'-amine | 451 | AA11 | 0.0008 | 0.0065 |
| 489 | (10R)-8-bromo-2-chloro-4-fluorospiro[chromeno[3,2-b]pyridine-10,4'-[1,3]oxazol]-2'-amine | 383.7 | BB20 | 8.1233 | 10 |
| 105 | (10R)-2-(3,6-dihydro-2H-pyran-4-yl)-4-fluoro-8-(2-fluoro-3-pyridinyl)spiro[chromeno[3,2-b]pyridine-10,4'-[1,3]oxazol]-2'-amine | 449 | BB20 | 0.0035 | 0.0144 |
| 490 | (5S)-1-methoxy-3,7-di-3-pyridinylspiro[chromeno[2,3-c]pyridine-5,4'-[1,3]oxazol]-2'-amine | 438 | BB22 | 0.007 | 0.0226 |
| 107 | (5S)-2'-amino-3,7-di-3-pyridinylspiro[chromeno[2,3-c]pyridine-5,4'-[1,3]oxazol]-1(2H)-one | 424 | BB22 | 0.0077 | 0.1799 |
| 491 | (5S)-1-fluoro-3-(2-fluoro-4-pyridinyl)-7-(3-pyridinyl)spiro[chromeno[2,3-c]pyridine-5,4'-[1,3]oxazol]-2'-amine | 443.9 | AA1 | 0.002 | |
| 492 | (5S)-1-fluoro-7-(2-fluoro-3-pyridinyl)-3-(3-pyridinyl)spiro[chromeno[2,3-c]pyridine-5,4'-[1,3]oxazol]-2'-amine | 443.9 | AA1 | 0.002 | |
| 493 | (5S)-1-fluoro-7-(2-fluoro-3-pyridinyl)-3-(4-pyridinyl)spiro[chromeno[2,3-c]pyridine-5,4'-[1,3]oxazol]-2'-amine | 443.9 | AA1 | 0.002 | |
| 494 | (5S)-1-fluoro-3,7-di-3-pyridinylspiro[chromeno[2,3-c]pyridine-5,4'-[1,3]oxazol]-2'-amine | 426 | AA2 | 0.0005 | 0.0053 |
| 495 | (5S)-1-fluoro-3,7-bis(2-fluoro-3-pyridinyl)spiro[chromeno[2,3-c]pyridine-5,4'-[1,3]oxazol]-2'-amine | 462 | AA2 | 0.0013 | 0.0264 |
| 496 | (4R)-7'-((1E)-3,3-dimethyl-1-buten-1-yl)-3'-fluoro-2'-(5-pyrimidinyl)spiro[1,3-oxazole-4,9'-xanthen]-2-amine | 431.2 | AA1 | 0.0014 | 0.0311 |
| 497 | (4R)-7'-(3,3-dimethyl-1-butyn-1-yl)-3'-fluoro-2'-(5-pyrimidinyl)spiro[1,3-oxazole-4,9'-xanthen]-2-amine | 429 | AA66 | 0.0025 | 0.0372 |
| 498 | (4R)-3'-fluoro-7'-((3-methyl-3-oxetanyl)ethynyl)-2'-(5-pyrimidinyl)spiro[1,3-oxazole-4,9'-xanthen]-2-amine | 443 | AA23 | 0.0038 | 0.0191 |

TABLE I-continued

| Ex. No. | Compound Name | Observed Mass | Method | BACE 1 FRET assay (uM) | HEK cell assay (uM) |
|---|---|---|---|---|---|
| 499 | (5S)-7-(2-chloro-5-methoxyphenyl)-3-(3,6-dihydro-2H-pyran-4-yl)spiro[chromeno[2,3-b]pyridine-5,4'-[1,3]oxazol]-2'-amine | 476.1 | AA1 | 0.0022 | 0.0227 |
| 500 | 3-((5S)-2'-amino-3-(3,6-dihydro-2H-pyran-4-yl)spiro[chromeno[2,3-b]pyridine-5,4'-[1,3]oxazol]-7-yl)-4-fluoro-N-methylbenzamide | 487.1 | AA1 | 0.0117 | 0.0368 |
| 501 | (5S)-7-(2,5-dichlorophenyl)-3-(3,6-dihydro-2H-pyran-4-yl)spiro[chromeno[2,3-b]pyridine-5,4'-[1,3]oxazol]-2'-amine | 480.2 | AA1 | 0.0022 | 0.027 |
| 502 | (5S)-3-(3,6-dihydro-2H-pyran-4-yl)-7-(2,5-dimethoxyphenyl)spiro[chromeno[2,3-b]pyridine-5,4'-[1,3]oxazol]-2'-amine | 472.1 | AA1 | 0.0025 | 0.0127 |
| 503 | (5S)-3-(3,6-dihydro-2H-pyran-4-yl)-7-(2,2-dimethylpropoxy)spiro[chromeno[2,3-b]pyridine-5,4'-[1,3]oxazol]-2'-amine | 422.2 | AA13 | 0.0047 | 0.0196 |
| 504 | (5S)-3-(2,2-dimethyl-3,6-dihydro-2H-pyran-4-yl)-7-(2,2-dimethylpropoxy)spiro[chromeno[2,3-b]pyridine-5,4'-[1,3]oxazol]-2'-amine | 450.2 | AA13 | 0.0076 | 0.0297 |
| 505 | (4R)-7'-(2,2-dimethyl-3,6-dihydro-2H-pyran-4-yl)-3'-fluoro-2'-(5-pyrimidinyl)spiro[1,3-oxazole-4,9'-xanthen]-2-amine | 459 | AA8 | 0.0026 | 0.0125 |
| 506 | (5S)-3-(6,6-dimethyl-3,6-dihydro-2H-pyran-4-yl)-7-(2,2-dimethylpropoxy)spiro[chromeno[2,3-b]pyridine-5,4'-[1,3]oxazol]-2'-amine | 450.2 | AA13 | 0.0057 | 0.0361 |
| 507 | (5S)-3-(2,2-dimethyl-3,6-dihydro-2H-pyran-4-yl)-7-(2,2-dimethylpropoxy)spiro[chromeno[2,3-b]pyridine-5,4'-[1,3]oxazol]-2'-amine | 450.2 | AA13 | 0.0056 | 0.031 |
| 508 | (4R)-7'-(6,6-dimethyl-3,6-dihydro-2H-pyran-4-yl)-3'-fluoro-2'-(5-pyrimidinyl)spiro[1,3-oxazole-4,9'-xanthen]-2-amine | 459.2 | AA8 | 0.0037 | 0.0144 |
| 509 | (4R)-7'-(2,2-dimethyl-3,6-dihydro-2H-pyran-4-yl)-3'-fluoro-2'-(5-pyrimidinyl)spiro[1,3-oxazole-4,9'-xanthen]-2-amine | 459.2 | AA8 | 0.0025 | 0.0106 |
| 510 | (4S)-7'-(2,2-dimethylpropoxy)-1'-fluoro-2'-(5-pyrimidinyl)spiro[1,3-oxazole-4,9'-xanthen]-2-amine | 435 | AA13 | 0.0025 | 0.0779 |
| 511 | (4R)-7'-(2,2-dimethylpropoxy)-3'-fluoro-2'-(5-pyrimidinyl)spiro[1,3-oxazole-4,9'-xanthen]-2-amine | 435 | AA13 | 0.0993 | 0.492 |
| 512 | (4S)-7'-(2,2-dimethylpropoxy)-3'-fluoro-2'-(5-pyrimidinyl)spiro[1,3-oxazole-4,9'-xanthen]-2-amine | 435 | AA13 | 0.1031 | 0.3777 |
| 513 | (4R)-7'-(2,2-dimethylpropoxy)-3'-fluoro-2'-(5-pyrimidinyl)spiro[1,3-oxazole-4,9'-xanthen]-2-amine | 435 | AA13 | 0.1929 | 0.6914 |
| 514 | (4R)-7'-(5,6-dihydro-2H-pyran-3-yl)-3'-fluoro-2'-(5-pyrimidinyl)spiro[1,3-oxazole-4,9'-xanthen]-2-amine | 431 | AA8 | 0.0026 | 0.0114 |
| 515 | (4R)-7'-(2,2-dimethylpropoxy)-1'-fluoro-2'-(5-pyrimidinyl)spiro[1,3-oxazole-4,9'-xanthen]-2-amine | 435 | AA13 | 0.0013 | 0.0285 |
| 516 | (4S)-7'-(2,2-dimethylpropoxy)-1'-fluoro-2'-(5-pyrimidinyl)spiro[1,3-oxazole-4,9'-xanthen]-2-amine | 435 | AA13 | 0.0938 | 0.4497 |
| 517 | (4S)-1'-bromo-2'-((3-methyl-3-oxetanyl)methoxy)-7'-(3-pyridinyl)spiro[1,3-oxazole-4,9'-xanthen]-2-amine | 508 | AA14 | 0.0084 | 0.0205 |
| 518 | 4-((4S)-2-amino-2'-((3-methyl-3-oxetanyl)methoxy)-7'-(3-pyridinyl)spiro[1,3-oxazole-4,9'-xanthen]-1'-yl)-2-methyl-3-butyn-2-ol | 512.2 | BB21 | 0.0755 | 0.0649 |
| 519 | 3-(((5S)-2'-amino-7-(2-fluoro-3-pyridinyl)spiro[chromeno[2,3-b]pyridine-5,4'-[1,3]oxazol]-3-yl)ethynyl)-3-oxetanol | 444.9 | AA5 | 0.0032 | 0.0297 |
| 520 | (5S)-3-((3-fluoro-3-oxetanyl)ethynyl)-7-(2-fluoro-3-pyridinyl)spiro[chromeno[2,3-b]pyridine-5,4'-[1,3]oxazol]-2'-amine | 447 | AA5 | 0.0014 | 0.0139 |
| 521 | 2'-bromo-3',5'-difluoro-7'-methoxyspiro[1,3-oxazole-4,9'-xanthen]-2-amine | 397 | Example 2 | 7.2413 | 10 |
| 522 | 3-bromo-7-iodospiro[chromeno[2,3-b]pyridine-5,4'-[1,3]thiazol]-2'-amine | 474 | BB26 | 4.496 | 10 |
| 523 | (4S)-2'-bromo-3',5'-difluoro-7'-methoxyspiro[1,3-oxazole-4,9'-xanthen]-2-amine | 397 | Example 2 | 0.884 | 1.7829 |
| 524 | (4R)-2'-bromo-3',5'-difluoro-7'-methoxyspiro[1,3-oxazole-4,9'-xanthen]-2-amine | 397 | Example 2 | 1.1403 | 1.3117 |

TABLE I-continued

| Ex. No. | Compound Name | Observed Mass | Method | BACE 1 FRET assay (uM) | HEK cell assay (uM) |
|---|---|---|---|---|---|
| 525 | (4R)-7'-(2,2-dimethylpropoxy)-3',5'-difluoro-2'-(5-pyrimidinyl)spiro[1,3-oxazole-4,9'-xanthen]-2-amine | 453.2 | AA14 | 0.1593 | 2.3894 |
| 526 | (4S)-7'-(2,2-dimethylpropoxy)-3',5'-difluoro-2'-(5-pyrimidinyl)spiroy[1,3-oxazole-4,9'-xanthen]-2-amine | 453.2 | AA14 | 0.002 | 0.0091 |
| 527 | (5S)-3,7-bis(3-chlorophenyl)spiro[chromeno[2,3-c]pyridine-5,4'-[1,3]oxazol]-2'-amine | 473.9 | AA1 | 0.0015 | 0.6122 |
| 528 | (5S)-3-chloro-7-(3-chlorophenyl)spiro[chromeno[2,3-c]pyridine-5,4'-[1,3]oxazol]-2'-amine | 398 | AA2 | 0.0553 | 2.3061 |
| 529 | (5S)-7-(2-fluoro-3-pyridinyl)-3-(3,3,4-trimethyl-1-piperazinyl)spiro[chromeno[2,3-c]pyridine-5,4'-[1,3]oxazol]-2'-amine | 475.1 | AA9 | 0.0089 | 0.0044 |
| 530 | (5S)-3-((3S)-3,4-dimethyl-1-piperazinyl)-7-(2-((3S)-3,4-dimethyl-1-piperazinyl)-3-pyridinyl)spiro[chromeno[2,3-c]pyridine-5,4'-[1,3]oxazol]-2'-amine | 555 | AA9 | 3.369 | 0.1947 |
| 531 | (5S)-3-chloro-7-(3-(3,3,4-trimethyl-1-piperazinyl)phenyl)spiro[chromeno[2,3-c]pyridine-5,4'-[1,3]oxazol]-2'-amine | 490.1 | AA40 | 13.738 | 0.3341 |
| 532 | (4S)-4'-fluoro-7'-methoxy-2'-(3,3,4-trimethyl-1-piperazinyl)spiro[1,3-oxazole-4,9'-xanthen]-2-amine | 427.1 | AA40 | 2.3685 | 0.169 |
| 533 | (5S)-3-(3-fluoro-4-methoxyphenyl)-7-(2-fluoro-3-pyridinyl)spiro[chromeno[2,3-c]pyridine-5,4'-[1,3]oxazol]-2'-amine | 473 | AA1 | 0.0014 | 0.0235 |
| 534 | (5S)-3-(3,4-difluorophenyl)-7-(2-fluoro-3-pyridinyl)spiro[chromeno[2,3-c]pyridine-5,4'-[1,3]oxazol]-2'-amine | 461 | AA1 | 0.0005 | 0.0266 |
| 535 | (5S)-7-(3-chlorophenyl)-3-(3-fluoro-4-methoxyphenyl)spiro[chromeno[2,3-c]pyridine-5,4'-[1,3]oxazol]-2'-amine | 488 | AA1 | 0.0007 | 0.1058 |
| 536 | (5S)-3-(2-fluoro-4-pyridinyl)-7-(3-pyridinyl)spiro[chromeno[2,3-c]pyridine-5,4'-[1,3]oxazol]-2'-amine | 425.8 | AA1 | 0.0023 | 0.0271 |
| 537 | (5S)-3-(4-fluoro-3-methoxyphenyl)-7-(2-fluoro-3-pyridinyl)spiro[chromeno[2,3-c]pyridine-5,4'-[1,3]oxazol]-2'-amine | 473 | AA1 | 0.0076 | 0.3026 |
| 538 | (5S)-7-(3-chlorophenyl)-3-(4-fluoro-3-methoxyphenyl)spiro[chromeno[2,3-c]pyridine-5,4'-[1,3]oxazol]-2'-amine | 488 | AA1 | 0.0052 | 0.5834 |
| 539 | (5S)-3-(2-fluoro-4-pyridinyl)-7-(5-pyrimidinyl)spiro[chromeno[2,3-c]pyridine-5,4'-[1,3]oxazol]-2'-amine | 427 | AA1 | 0.0017 | 0.0382 |
| 540 | (5S)-3-(3,3-difluoro-1-pyrrolidinyl)-7-(5-pyrimidinyl)spiro[chromeno[2,3-c]pyridine-5,4'-[1,3]oxazol]-2'-amine | 437 | AA9 | 0.0008 | 0.0072 |
| 541 | (5S)-3-(2,6-difluoro-4-pyridinyl)-7-(2-fluoro-3-pyridinyl)spiro[chromeno[2,3-c]pyridine-5,4'-[1,3]oxazol]-2'-amine | 462 | AA1 | 0.0004 | 0.0123 |
| 542 | (5S)-3-(2,6-difluoro-4-pyridinyl)-7-(5-pyrimidinyl)spiro[chromeno[2,3-c]pyridine-5,4'-[1,3]oxazol]-2'-amine | 445 | AA1 | 0.0011 | 0.0188 |
| 543 | (5S)-3-(6,6-dimethyl-3,6-dihydro-2H-pyran-4-yl)-7-(5-pyrimidinyl)spiro[chromeno[2,3-c]pyridine-5,4'-[1,3]oxazol]-2'-amine | 442.1 | AA1 | 0.0016 | 0.0246 |
| 544 | (5S)-3-((4R)-2,2-dimethyltetrahydro-2H-pyran-4-yl)-7-(5-pyrimidinyl)spiro[chromeno[2,3-c]pyridine-5,4'-[1,3]oxazol]-2'-amine | 444 | AA11 | 0.0084 | 0.1215 |
| 545 | (5S)-7-(2-fluoro-3-pyridinyl)-3-(2-(trifluoromethyl)-4-pyridinyl)spiro[chromeno[2,3-c]pyridine-5,4'-[1,3]oxazol]-2'-amine | 494 | AA1 | 0.0056 | 0.4063 |
| 546 | (5S)-7-(2-fluoro-3-pyridinyl)-3-(2-methyl-5-pyrimidinyl)spiro[chromeno[2,3-c]pyridine-5,4'-[1,3]oxazol]-2'-amine | 441 | AA1 | 0.0103 | |
| 547 | (5S)-3-(3,6-dihydro-2H-pyran-4-yl)-7-(2-fluoro-4-pyridinyl)spiro[chromeno[2,3-c]pyridine-5,4'-[1,3]oxazol]-2'-amine | 431 | AA1 | 0.0261 | |
| 548 | (5S)-3,7-bis(2-fluoro-4-pyridinyl)spiro[chromeno[2,3-c]pyridine-5,4'-[1,3]oxazol]-2'-amine | 444 | AA1 | 0.055 | |
| 549 | (5S)-7-(2,5-difluoro-3-pyridinyl)-3-(2-fluoro-4-pyridinyl)spiro[chromeno[2,3-c]pyridine-5,4'-[1,3]oxazol]-2'-amine | 462 | AA1 | 0.029 | |

TABLE I-continued

| Ex. No. | Compound Name | Observed Mass | Method | BACE 1 FRET assay (uM) | HEK cell assay (uM) |
|---|---|---|---|---|---|
| 550 | (5S)-7-(3-chlorophenyl)-3-(3,4-difluorophenyl)spiro[chromeno[2,3-c]pyridine-5,4'-[1,3]oxazol]-2'-amine | 476 | AA1 | 0.0005 | 0.1271 |
| 551 | (5S)-3-(3,6-dihydro-2H-pyran-4-yl)-7-(4-fluoro-3-methylphenyl)spiro[chromeno[2,3-c]pyridine-5,4'-[1,3]oxazol]-2'-amine | 444.2 | AA1 | 0.0034 | 0.0807 |
| 552 | 5-((4S)-2-amino-5'-fluoro-7'-((3-methyl-3-oxetanyl)methoxy)spiro[1,3-oxazole-4,9'-xanthen]-2'-yl)-3-pyridinecarbonitrile | 473 | AA14 | 0.0009 | 0.0031 |
| 553 | 5-((4S)-2-amino-5'-fluoro-7'-(tetrahydro-2H-pyran-4-ylmethoxy)spiro[1,3-oxazole-4,9'-xanthen]-2'-yl)-3-pyridinecarbonitrile | 487 | AA14 | 0.0024 | 0.0132 |
| 554 | 5-((4S)-2-amino-5'-fluoro-7'-(1-methyl-1H-pyrazol-4-yl)spiro[1,3-oxazole-4,9'-xanthen]-2'-yl)-3-pyridinecarbonitrile | 453 | AA8 | 0.0016 | 0.0063 |
| 555 | (4R)-3',5'-difluoro-7'-methoxy-2'-(5-pyrimidinyl)spiro[1,3-oxazole-4,9'-xanthen]-2-amine | 397.2 | AA2 | 0.2903 | 1.7001 |
| 556 | (4S)-3',5'-difluoro-7'-methoxy-2'-(5-pyrimidinyl)spiro[1,3-oxazole-4,9'-xanthen]-2-amine | 397.2 | AA2 | 0.0089 | 0.1455 |
| 557 | 5-((4S)-2-amino-7'-(3,6-dihydro-2H-pyran-4-yl)-5'-fluorospiro[1,3-oxazole-4,9'-xanthen]-2'-yl)-3-pyridinecarbonitrile | 455 | AA8 | 0.0007 | 0.0037 |
| 558 | 5-((4S)-2-amino-5'-fluoro-7'-(4-morpholinyl)spiro[1,3-oxazole-4,9'-xanthen]-2'-yl)-3-pyridinecarbonitrile | 458 | AA20 | 0.0017 | 0.0057 |
| 559 | (4S)-4'-fluoro-7'-phenyl-2'-(3-pyridazinyl)spiro[1,3-oxazole-4,9'-xanthen]-2-amine | 425 | BB30 | 0.0122 | 0.1511 |
| 560 | 5-((4S)-2-amino-7'-((2R,6S)-2,6-dimethyl-4-morpholinyl)-5'-fluorospiro[1,3-oxazole-4,9'-xanthen]-2'-yl)-3-pyridinecarbonitrile | 486.2 | AA20 | 0.0028 | 0.0142 |
| 561 | (4S)-4'-fluoro-7'-(2-fluoro-3-pyridinyl)-2'-((E)-2-(3-methyl-3-oxetanyl)ethenyl)spiro[1,3-oxazole-4,9'-xanthen]-2-amine | 462.3 | AA22 | 0.002 | 0.0037 |
| 562 | 3-((4S)-2-amino-5'-fluoro-7'-((3-methyl-3-oxetanyl)methoxy)spiro[1,3-oxazole-4,9'-xanthen]-2'-yl)benzonitrile | 472.2 | AA14 | 0.002 | 0.0058 |
| 563 | 3-((4S)-2-amino-5'-fluoro-7'-(1-methyl-1H-pyrazol-4-yl)spiro[1,3-oxazole-4,9'-xanthen]-2'-yl)benzonitrile | 452.1 | AA8 | 0.0013 | 0.0124 |
| 564 | 3-((4S)-2-amino-5'-fluoro-7'-(4-morpholinyl)spiro[1,3-oxazole-4,9'-xanthen]-2'-yl)benzonitrile | 457 | AA20 | 0.0016 | 0.0092 |
| 101 | (4S)-4'-fluoro-7'-(2-fluoro-3-pyridinyl)-2'-(2-(3-methyl-3-oxetanyl)ethyl)spiro[1,3-oxazole-4,9'-xanthen]-2-amine | 464.2 | BB16 | 0.0005 | 0.0045 |
| 565 | (4S)-7'-(2,4-difluoro-3-pyridinyl)-2'-(3,6-dihydro-2H-pyran-4-yl)-4'-fluoro spiro[1,3-oxazole-4,9'-xanthen]-2-amine | 466.2 | AA1 | 0.002 | |
| 566 | 3-(((4S)-2-amino-7'-(2,4-difluoro-3-pyridinyl)-4'-fluorospiro[1,3-oxazole-4,9'-xanthen]-2'-yl)oxy)-2,2-dimethylpropanenitrile | 481.2 | AA14 | 0.002 | |
| 567 | (5S)-3-(4-(dimethylamino)phenyl)-7-(2-fluoro-3-pyridinyl)spiro[chromeno[2,3-c]pyridine-5,4'-[1,3]oxazol]-2'-amine | 468 | AA1 | 0.0046 | 0.0746 |
| 568 | (5S)-7-(2-fluoro-3-pyridinyl)-3-(4-methoxyphenyl)spiro[chromeno[2,3-c]pyridine-5,4'-[1,3]oxazol]-2'-amine | 455 | AA1 | 0.0023 | 0.0295 |
| 569 | (5S)-7-(2-fluoro-3-pyridinyl)-3-(5-fluoro-3-pyridinyl)spiro[chromeno[2,3-c]pyridine-5,4'-[1,3]oxazol]-2'-amine | 444 | AA1 | 0.0012 | 0.0182 |
| 570 | (5S)-3-(5-fluoro-6-methoxy-3-pyridinyl)-7-(2-fluoro-3-pyridinyl)spiro[chromeno[2,3-c]pyridine-5,4'-[1,3]oxazol]-2'-amine | 474 | AA1 | 0.002 | 0.031 |
| 571 | (5S)-7-(2-fluoro-3-pyridinyl)-3-(5-pyrimidinyl)spiro[chromeno[2,3-c]pyridine-5,4'-[1,3]oxazol]-2'-amine | 427 | AA1 | 0.0066 | 0.1095 |
| 572 | (5S)-7-(2-fluoro-3-pyridinyl)-3-(3-fluoro-4-pyridinyl)spiro[chromeno[2,3-c]pyridine-5,4'-[1,3]oxazol]-2'-amine | 444 | AA1 | 0.0118 | 0.1478 |
| 573 | (5S)-3-(2-fluoro-4-pyridinyl)-7-(3-fluoro-4-pyridinyl)spiro[chromeno[2,3-c]pyridine-5,4'-[1,3]oxazol]-2'-amine | 444 | AA1 | 0.0708 | 0.8008 |

TABLE I-continued

| Ex. No. | Compound Name | Observed Mass | Method | BACE 1 FRET assay (uM) | HEK cell assay (uM) |
|---|---|---|---|---|---|
| 574 | (5S)-3-(2-fluoro-3-pyridinyl)-7-(3-fluoro-4-pyridinyl)spiro[chromeno[2,3-c]pyridine-5,4'-[1,3]oxazol]-2'-amine | 444 | AA1 | 0.8558 | 2.2277 |
| 575 | (5S)-7-(3-fluoro-4-pyridinyl)-3-(5-fluoro-3-pyridinyl)spiro[chromeno[2,3-c]pyridine-5,4'-[1,3]oxazol]-2'-amine | 444 | AA1 | 0.083 | 0.9708 |
| 576 | (5S)-7-(2-fluoro-3-pyridinyl)-3-(1,3-thiazol-5-yl)spiro[chromeno[2,3-c]pyridine-5,4'-[1,3]oxazol]-2'-amine | 432 | AA57 | 0.0046 | |
| 577 | (5R)-3-(3,6-dihydro-2H-pyran-4-yl)-7-(2-fluoro-3-pyridinyl)spiro[chromeno[2,3-b]pyridine-5,4'-[1,3]thiazol]-2'-amine | 447.3 | BB12 | 0.0017 | 0.0164 |
| 578 | (5R)-7-(2-fluoro-3-pyridinyl)-3-(6-methyl-3-pyridinyl)spiro[chromeno[2,3-b]pyridine-5,4'-[1,3]thiazol]-2'-amine | 456.3 | BB12 | 0.0019 | 0.0097 |
| 98 | (5R)-7-(2-fluoro-3-pyridinyl)-3-((3-methyl-3-oxetanyl)ethynyl)spiro[chromeno[2,3-b]pyridine-5,4'-[1,3]thiazol]-2'-amine | 459.3 | BB13 | 0.002 | 0.0046 |
| 579 | (5R)-3-bromo-7-iodospiro[chromeno[2,3-b]pyridine-5,4'-[1,3]thiazol]-2'-amine | 476.1 | BB26 | 1.9258 | 3.1813 |
| 580 | (5S)-3-bromo-7-iodospiro[chromeno[2,3-b]pyridine-5,4'-[1,3]thiazol]-2'-amine | 476.1 | BB26 | 2.5115 | 0.6285 |
| 581 | (5R)-3-(3,6-dihydro-2H-pyran-4-yl)-7-(2-fluoro-3-pyridinyl)spiro[chromeno[2,3-b]pyridine-5,4'-[1,3]thiazol]-2'-amine | 447.3 | BB12 | 0.286 | 0.6201 |
| 582 | (5S)-7-(2-fluoro-3-pyridinyl)-3-(6-methyl-3-pyridinyl)spiro[chromeno[2,3-b]pyridine-5,4'-[1,3]thiazol]-2'-amine | 456.3 | BB12 | 0.002 | 0.005 |
| 583 | (5R)-7-(2-fluoro-3-pyridinyl)-3-(6-methyl-3-pyridinyl)spiro[chromeno[2,3-b]pyridine-5,4'-[1,3]thiazol]-2'-amine | 456.3 | BB12 | 0.1671 | 1.4801 |
| 584 | (5S)-7-(2-fluoro-3-pyridinyl)-3-(1-methyl-1H-pyrazol-4-yl)spiro[chromeno[2,3-b]pyridine-5,4'-[1,3]thiazol]-2'-amine | 445.2 | BB12 | 0.002 | 0.0159 |
| 585 | (5R)-3-(3,6-dihydro-2H-pyran-4-yl)-7-(3-pyridinyl)spiro[chromeno[2,3-b]pyridine-5,4'-[1,3]thiazol]-2'-amine | 429.2 | BB12 | 0.0025 | 0.0181 |
| 586 | (5S)-7-(2-fluoro-3-pyridinyl)-3-((3-methyl-3-oxetanyl)ethynyl)spiro[chromeno[2,3-b]pyridine-5,4'-[1,3]thiazol]-2'-amine | 459.3 | BB13 | 0.002 | |
| 587 | (5S)-3,7-bis (2-fluoro-3-pyridinyl)spiro[chromeno[2,3-b]pyridine-5,4'-[1,3]thiazol]-2'-amine | 460.2 | BB12 | 0.002 | |
| 97 | (5S)-3-(3,6-dihydro-2H-pyran-4-yl)-7-(2-fluoro-3-pyridinyl)spiro[chromeno[2,3-b]pyridine-5,4'-[1,3]thiazol]-2'-amine | 447.3 | BB12 | 0.0005 | 0.0076 |
| 588 | (5S)-7-bromo-3-chlorospiro[chromeno[2,3-c]pyridine-5,4'-[1,3]thiazol]-2'-amine | 383.7 | BB26 | 12.677 | 10 |
| 589 | (5S)-7-(2-fluoro-3-pyridinyl)-3-(2-fluoro-4-pyridinyl)spiro[chromeno[2,3-c]pyridine-5,4'-[1,3]thiazol]-2'-amine | 459.8 | BB12 | 0.0011 | 0.039 |
| 590 | (5S)-3-(3,6-dihydro-2H-pyran-4-yl)-7-(2-fluoro-3-pyridinyl)spiro[chromeno[2,3-c]pyridine-5,4'-[1,3]thiazol]-2'-amine | 446.8 | BB12 | 0.0007 | 0.0093 |
| 591 | (5S)-7-(3-chlorophenyl)-3-(3,6-dihydro-2H-pyran-4-yl)spiro[chromeno[2,3-c]pyridine-5,4'-[1,3]thiazol]-2'-amine | 461.8 | BB12 | 0.0007 | 0.0733 |
| 592 | (5S)-3-(3,6-dihydro-2H-pyran-4-yl)-7-(5-fluoro-3-pyridinyl)spiro[chromeno[2,3-c]pyridine-5,4'-[1,3]thiazol]-2'-amine | 446.8 | BB12 | 0.0009 | 0.0213 |
| 593 | (5S)-3-chloro-7-(3-chlorophenyl)spiro[chromeno[2,3-c]pyridine-5,4'-[1,3]thiazol]-2'-amine | 413.8 | BB12 | 0.0316 | |
| 594 | (5S)-3-chloro-7-(2-fluoro-3-pyridinyl)spiro[chromeno[2,3-c]pyridine-5,4'-[1,3]thiazol]-2'-amine | 398.8 | BB12 | 0.0531 | |
| 595 | (5S)-3-chloro-7-(5-fluoro-3-pyridinyl)spiro[chromeno[2,3-c]pyridine-5,4'-[1,3]thiazol]-2'-amine | 398.8 | BB12 | 0.1419 | |
| 596 | (5R)-3-(3,6-dihydro-2H-pyran-4-yl)-7-(3-(3,6-dihydro-2H-pyran-4-yl)phenyl)spiro[chromeno[2,3-c]pyridine-5,4'-[1,3]thiazol]-2'-amine | 509.8 | BB12 | 0.0478 | |

TABLE I-continued

| Ex. No. | Compound Name | Observed Mass | Method | BACE 1 FRET assay (uM) | HEK cell assay (uM) |
|---|---|---|---|---|---|
| 597 | (5S)-7-bromo-3-chloro-1-fluorospiro[chromeno[2,3-c]pyridine-5,4'-[1,3]thiazol]-2'-amine | 401.6 | BB26 | 4.5036 | |
| 598 | (4S)-4'-fluoro-7'-(6-fluoro-3-pyridinyl)-2'-((3-methyl-3-oxetanyl)ethynyl)spiro[1,3-oxazole-4,9'-xanthen]-2-amine | 460 | AA21 | 0.0041 | 0.032 |
| 599 | (4S)-4'-fluoro-7'-(5-fluoro-3-pyridinyl)-2'-((3-methyl-3-oxetanyl)ethynyl)spiro[1,3-oxazole-4,9'-xanthen]-2-amine | 460 | AA21 | 0.0011 | 0.011 |
| 600 | (5S)-7-(2,5-difluoro-3-pyridinyl)-3-(3,6-dihydro-2H-pyran-4-yl)spiro[chromeno[2,3-c]pyridine-5,4'-[1,3]oxazol]-2'-amine | 449 | AA1 | 0.0177 | 0.165 |
| 601 | (5R)-3-(4-morpholinyl)-7-(3-pyridinyl)spiro[chromeno[2,3-b]pyridine-5,4'-[1,3]thiazol]-2'-amine | 432.3 | BB100 | 2.2854 | 0.724 |
| 602 | (5S)-3-(4-morpholinyl)-7-(3-pyridinyl)spiro[chromeno[2,3-b]pyridine-5,4'-[1,3]thiazol]-2'-amine | 432.3 | BB100 | 0.0028 | 0.017 |
| 603 | (5S)-3-bromo-7-(2-fluoro-3-pyridinyl)spiro[chromeno[2,3-b]pyridine-5,4'-[1,3]thiazol]-2'-amine | 443.2 | BB12 | 0.0087 | 0.188 |
| 604 | (4S)-4'-fluoro-7'-(4-fluoro-3-pyridinyl)-2'-((3-methyl-3-oxetanyl)methoxy)spiro[1,3-oxazole-4,9'-xanthen]-2-amine | 466 | AA14 | 0.0006 | 0.005 |
| 605 | 3-(((4S)-2-amino-4'-fluoro-7'-(4-fluoro-3-pyridinyl)spiro[1,3-oxazole-4,9'-xanthen]-2'-yl)oxy)-2,2-dimethylpropanenitrile | 463.1 | AA14 | 0.0008 | 0.01 |
| 606 | (4S)-7'-bromo-4'-fluoro-2'-methoxyspiro[1,3-thiazole-4,9'-xanthen]-2-amine | 395 | BB26 | 0.8129 | 0.279 |
| 607 | (4S)-4'-fluoro-7'-(2-fluoro-3-pyridinyl)-2'-(2-methoxy-4-pyrimidinyl)spiro[1,3-oxazole-4,9'-xanthen]-2-amine | 474 | AA1 | 0.0051 | 0.07 |
| 608 | (4S)-4'-fluoro-7'-(2-fluoro-3-pyridinyl)-2'-methoxyspiro[1,3-thiazole-4,9'-xanthen]-2-amine | 412 | BB12 | 0.0036 | 0.162 |
| 609 | (5S)-3-(2,2-dimethylpropoxy)-7-(2-fluoro-3-pyridinyl)spiro[chromeno[2,3-c]pyridine-5,4'-[1,3]oxazol]-2'-amine | 435 | BB17 | 0.0004 | 0.015 |
| 610 | (5R)-3-(2,2-dimethylpropoxy)-7-(2-fluoro-3-pyridinyl)spiro[chromeno[2,3-c]pyridine-5,4'-[1,3]oxazol]-2'-amine | 435 | BB17 | 0.1164 | 1.13 |
| 611 | 3-chloro-1-fluoro-7-(2-fluoro-3-pyridinyl)spiro[chromeno[2,3-c]pyridine-5,4'-[1,3]thiazol]-2'-amine | 416.8 | BB12 | 0.0061 | 2.954 |
| 612 | (5S)-3-(3,6-dihydro-2H-pyran-4-yl)-7-(2-fluoro-4-methoxy-3-pyridinyl)spiro[chromeno[2,3-c]pyridine-5,4'-[1,3]oxazol]-2'-amine | 461 | AA1 | 0.0006 | 0.003 |
| 613 | (5R)-3-(3,6-dihydro-2H-pyran-4-yl)-7-(2-fluoro-3-pyridinyl)spiro[chromeno[2,3-c]pyridine-5,4'-[1,3]thiazol]-2'-amine | 447 | BB12 | 0.227 | 2.565 |
| 614 | (5S)-3-(3,6-dihydro-2H-pyran-4-yl)-7-(2-fluoro-3-pyridinyl)spiro[chromeno[2,3-c]pyridine-5,4'-[1,3]thiazol]-2'-amine | 447 | BB12 | 0.0003 | 0.005 |
| 615 | (5S)-3-(3,6-dihydro-2H-pyran-4-yl)-1-fluoro-7-(5-fluoro-3-pyridinyl)spiro[chromeno[2,3-c]pyridine-5,4'-[1,3]oxazol]-2'-amine | 449 | AA1 | 0.0003 | 0.002 |
| 616 | (5S)-7-(2,4-difluoro-3-pyridinyl)-3-(tetrahydro-2H-pyran-4-yl)spiro[chromeno[2,3-c]pyridine-5,4'-[1,3]oxazol]-2'-amine | 451 | AA11 | 0.017 | 0.176 |
| 617 | (5S)-7-(2,4-difluoro-3-pyridinyl)-3-((2R)-tetrahydro-2H-pyran-2-yl)spiro[chromeno[2,3-c]pyridine-5,4'-[1,3]oxazol]-2'-amine | 451.1 | AA11 | 0.0052 | 0.042 |
| 618 | (5R)-3-(3,6-dihydro-2H-pyran-4-yl)-7-(5-fluoro-3-pyridinyl)spiro[chromeno[2,3-c]pyridine-5,4'-[1,3]thiazol]-2'-amine | 447 | BB12 | 0.3692 | 6.669 |
| 619 | (5S)-3-(3,6-dihydro-2H-pyran-4-yl)-7-(5-fluoro-3-pyridinyl)spiro[chromeno[2,3-c]pyridine-5,4'-[1,3]thiazol]-2'-amine | 447 | BB12 | 0.0004 | 0.008 |
| 620 | (4S)-4'-fluoro-7'-(2-fluoro-3-pyridinyl)-2'-(3-methyl-1H-pyrazol-1-yl)spiro[1,3-oxazole-4,9'-xanthen]-2-amine | 446.1 | AA9 | 0.0028 | 0.068 |
| 621 | (5S)-8-fluoro-7-(4-fluoro-3-pyridinyl)-3-((3-methyl-3-oxetanyl)ethynyl)spiro[chromeno[2,3-b]pyridine-5,4'-[1,3]oxazol]-2'-amine | 461 | BB19 | 0.0006 | 0.005 |

TABLE I-continued

| Ex. No. | Compound Name | Observed Mass | Method | BACE 1 FRET assay (uM) | HEK cell assay (uM) |
|---|---|---|---|---|---|
| 622 | (5R)-8-fluoro-7-(4-fluoro-3-pyridinyl)-3-((3-methyl-3-oxetanyl)ethynyl)spiro[chromeno[2,3-b]pyridine-5,4'-[1,3]oxazol]-2'-amine | 461 | BB19 | 0.1047 | 0.452 |
| 623 | (5S)-8-fluoro-7-(5-fluoro-3-pyridinyl)-3-((3-methyl-3-oxetanyl)ethynyl)spiro[chromeno[2,3-b]pyridine-5,4-[1,3]oxazol]-2'-amine | 461 | BB19 | 0.0009 | 0.009 |
| 624 | (5R)-8-fluoro-7-(5-fluoro-3-pyridinyl)-3-((3-methyl-3-oxetanyl)ethynyl)spiro[chromeno[2,3-b]pyridine-5,4'-[1,3]oxazol]-2'-amine | 461 | BB19 | 0.9861 | 0.762 |
| 625 | (5R)-7-(5-chloro-3-pyridinyl)-8-fluoro-3-((3-methyl-3-oxetanyl)ethynyl)spiro[chromeno[2,3-b]pyridine-5,4'-[1,3]oxazol]-2'-amine | 477 | BB19 | 0.9011 | 2.211 |
| 626 | (5S)-7-(5-chloro-3-pyridinyl)-8-fluoro-3-((3-methyl-3-oxetanyl)ethynyl)spiro[chromeno[2,3-b]pyridine-5,4'-[1,3]oxazol]-2'-amine | 477 | BB19 | 0.0008 | 0.006 |
| 627 | 2'-amino-7-(2-fluoro-3-pyridinyl)spiro[chromeno[2,3-b]pyridine-5,4'-[1,3]thiazole]-3-carbonitrile | 390 | AA24 | 0.6255 | 1.59 |
| 628 | (4S)-7'-(3,6-dihydro-2H-pyran-4-yl)-3',5'-difluoro-2'-(3-pyridinyl)spiro[1,3-oxazole-4,9'-xanthen]-2-amine | 448 | AA8 | 0.0005 | 0.006 |
| 629 | (5S)-3-(3,3-dimethyl-1-butyn-1-yl)-7-(5-pyrimidinyl)spiro[chromeno[2,3-b]pyridine-5,4'-[1,3]thiazol]-2'-amine | 428.4 | BB13 | 0.0006 | 0.007 |
| 630 | (5S)-1-fluoro-7-(5-fluoro-3-pyridinyl)-3-(3-pyridinyl)spiro[chromeno[2,3-c]pyridine-5,4'-[1,3]oxazol]-2'-amine | 443.9 | AA1 | 0.0003 | 0.011 |
| 631 | (4S)-2-amino-5'-fluoro-7'-(5-methyl-1H-pyrazol-1-yl)spiro[1,3-oxazole-4,9'-xanthen]-2'-ol | 367.1 | AA40 | 0.0214 | 0.184 |
| 632 | (5S)-3-(2-fluoro-4-pyridinyl)-7-(6-fluoro-2-pyridinyl)spiro[chromeno[2,3-c]pyridine-5,4'-[1,3]oxazol]-2'-amine | 444 | AA1 | 0.0301 | 0.332 |
| 633 | (4S)-4'-fluoro-2'-(3-methyl-1H-pyrazol-1-yl)-7'-(3-pyridinyl)spiro[1,3-oxazole-4,9'-xanthen]-2-amine | 428 | AA9 | 0.0039 | 0.034 |
| 634 | (4S)-4'-fluoro-2'-(5-methyl-1H-pyrazol-1-yl)-7'-(3-pyridinyl)spiro[1,3-oxazole-4,9'-xanthen]-2-amine | 428 | AA9 | 0.0303 | 0.154 |
| 635 | (4S)-4'-fluoro-2'-(3-methyl-1H-pyrazol-1-yl)-7'-(5-pyrimidinyl)spiro[1,3-oxazole-4,9'-xanthen]-2-amine | 429 | AA9 | 0.0024 | 0.023 |
| 636 | (4S)-4'-fluoro-2'-(5-methyl-1H-pyrazol-1-yl)-7'-(5-pyrimidinyl)spiro[1,3-oxazole-4,9'-xanthen]-2-amine | 429 | AA9 | 0.0288 | 0.273 |
| 637 | 3-(3,3-dimethyl-1-butyn-1-yl)-7-(2-fluoro-3-pyridinyl)spiro[chromeno[2,3-c]pyridine-5,4'-[1,3]thiazol]-2'-amine | 445.1 | BB13 | 0.0021 | 0.062 |
| 638 | 3-(3,6-dihydro-2H-pyran-4-yl)-1-fluoro-7-(2-fluoro-3-pyridinyl)spiro[chromeno[2,3-c]pyridine-5,4'-[1,3]thiazol]-2'-amine | 464.8 | BB12 | 0.0006 | 0.004 |
| 639 | (5S)-3-(3,6-dihydro-2H-pyran-4-yl)-1-fluoro-7-(3-pyridinyl)spiro[chromeno[2,3-c]pyridine-5,4'-[1,3]oxazol]-2'-amine | 431 | AA1 | 0.0004 | 0.003 |
| 640 | (4S)-4'-fluoro-7'-(2-fluoro-3-pyridinyl)-2'-(6-fluoro-3-pyridinyl)spiro[1,3-oxazole-4,9'-xanthen]-2-amine | 461 | AA1 | 0.0012 | 0.023 |
| 641 | (5S)-8-fluoro-7-(5-fluoro-3-pyridinyl)-3-(3-methoxy-3-methyl-1-butyn-1-yl)spiro[chromeno[2,3-b]pyridine-5,4'-[1,3]oxazol]-2'-amine | 463 | BB19 | 0.0009 | 0.013 |
| 642 | (5R)-8-fluoro-7-(5-fluoro-3-pyridinyl)-3-(3-methoxy-3-methyl-1-butyn-1-yl)spiro[chromeno[2,3-b]pyridine-5,4'-[1,3]oxazol]-2'-amine | 463 | BB19 | 0.1093 | 0.435 |
| 643 | (5S)-8-fluoro-3-(3-methoxy-3-methyl-1-butyn-1-yl)-7-(5-pyrimidinyl)spiro[chromeno[2,3-b]pyridine-5,4'-[1,3]oxazol]-2'-amine | 446 | BB19 | 0.0011 | 0.015 |
| 644 | (5R)-8-fluoro-3-(3-methoxy-3-methyl-1-butyn-1-yl)-7-(5-pyrimidinyl)spiro[chromeno[2,3-b]pyridine-5,4'-[1,3]oxazol]-2'-amine | 446 | BB19 | 0.0682 | 0.228 |
| 645 | (5R)-3-(3,6-dihydro-2H-pyran-4-yl)-8-fluoro-7-(4-fluoro-3-pyridinyl)spiro[chromeno[2,3-b]pyridine-5,4'-[1,3]oxazol]-2'-amine | 449 | AA36 | 0.0531 | 0.291 |
| 646 | (5S)-3-(3,6-dihydro-2H-pyran-4-yl)-8-fluoro-7-(4-fluoro-3-pyridinyl)spiro[chromeno[2,3-b]pyridine-5,4'-[1,3]oxazol]-2'-amine | 449 | AA36 | 0.0022 | 0.016 |

TABLE I-continued

| Ex. No. | Compound Name | Observed Mass | Method | BACE 1 FRET assay (uM) | HEK cell assay (uM) |
|---|---|---|---|---|---|
| 647 | (5S)-3-(3,6-dihydro-2H-pyran-4-yl)-8-fluoro-7-(5-fluoro-3-pyridinyl)spiro[chromeno[2,3-b]pyridine-5,4'-[1,3]oxazol]-2'-amine | 449 | AA36 | 0.0021 | 0.016 |
| 648 | (5R)-3-(3,6-dihydro-2H-pyran-4-yl)-8-fluoro-7-(5-fluoro-3-pyridinyl)spiro[chromeno[2,3-b]pyridine-5,4'-[1,3]oxazol]-2'-amine | 449 | AA36 | 0.3301 | 2.785 |
| 649 | (4S)-4'-fluoro-7'-(6-fluoro-3-pyridinyl)-2'-(2-methyl-5-pyrimidinyl)spiro[1,3-oxazole-4,9'-xanthen]-2-amine | 458 | AA8 | 0.0198 | 0.118 |
| 650 | (4S)-4'-fluoro-2'-methoxy-7'-(3-pyridinyl)spiro[1,3-thiazole-4,9'-xanthen]-2-amine | 394 | BB12 | 0.009 | 0.251 |
| 651 | (4S)-4'-fluoro-7'-(2-fluoro-3-pyridinyl)-2'-(1-propyn-1-yl)spiro[1,3-oxazole-4,9'-xanthen]-2-amine | 404 | AA21 | 0.0019 | 0.037 |
| 652 | (5S)-3-chloro-7-(4-methoxy-3-pyridinyl)spiro[chromeno[2,3-c]pyridine-5,4'-[1,3]oxazol]-2'-amine | 395 | AA24 | 1.2248 | 2.169 |
| 653 | (5S)-3-(3,6-dihydro-2H-pyran-4-yl)-7-(4-methoxy-3-pyridinyl)spiro[chromeno[2,3-c]pyridine-5,4'-[1,3]oxazol]-2'-amine | 443 | AA1 | 0.0104 | 0.009 |
| 654 | (5S)-3-(3,6-dihydro-2H-pyran-4-yl)-7-(4-methyl-3-pyridinyl)spiro[chromeno[2,3-c]pyridine-5,4'-[1,3]oxazol]-2'-amine | 427.1 | AA1 | 0.0061 | 0.013 |
| 655 | 3-((5S)-2'-amino-3-chlorospiro[chromeno[2,3-c]pyridine-5,4'-[1,3]oxazol]-7-yl)-4-pyridinecarbonitrile | 390 | AA24 | 0.6004 | 10 |
| 656 | 3-((5S)-2'-amino-3-(3,6-dihydro-2H-pyran-4-yl)spiro[chromeno[2,3-c]pyridine-5,4'-[1,3]oxazol]-7-yl)-4-pyridinecarbonitrile | 438 | AA1 | 0.0104 | 0.066 |
| 657 | (5S)-3-(3,4-dihydro-2H-pyran-6-yl)-1-fluoro-7-(2-fluoro-3-pyridinyl)spiro[chromeno[2,3-c]pyridine-5,4'-[1,3]oxazol]-2'-amine | 449 | AA1 | 0.0004 | 0.005 |
| 658 | (5S)-1-fluoro-7-(2-fluoro-3-pyridinyl)spiro[chromeno[2,3-c]pyridine-5,4'-[1,3]oxazol]-2'-amine | 367 | AA24 | 0.0272 | 0.846 |
| 659 | (5S)-1-fluoro-7-(2-fluoro-3-pyridinyl)-3-((2S)-tetrahydro-2H-pyran-2-yl)spiro[chromeno[2,3-c]pyridine-5,4'-[1,3]oxazol]-2'-amine | 451 | AA11 | 0.0014 | 0.019 |
| 660 | (5S)-1-fluoro-7-(2-fluoro-3-pyridinyl)-3-((2R)-tetrahydro-2H-pyran-2-yl)spiro[chromeno[2,3-c]pyridine-5,4'-[1,3]oxazol]-2'-amine | 451 | AA11 | 0.0005 | 0.008 |
| 661 | 9-fluoro-3-(5-fluoro-3-pyridinyl)-7-((3-methyl-3-oxetanyl)ethynyl)spiro[chromeno[2,3-c]pyridine-5,4'-[1,3]oxazol]-2'-amine | 461.2 | AA33 | 0.018 | 0.852 |
| 662 | 9-fluoro-3-(2-fluoro-3-pyridinyl)-7-((3-methyl-3-oxetanyl)ethynyl)spiro[chromeno[2,3-c]pyridine-5,4'-[1,3]oxazol]-2'-amine | 461.2 | AA33 | 0.0033 | 0.129 |
| 663 | (4S)-4'-fluoro-7'-methoxy-2'-(5-methyl-1H-pyrazol-1-yl)spiro[1,3-oxazole-4,9'-xanthen]-2-amine | 381 | AA40 | 0.4302 | 8.524 |
| 664 | (4S)-4'-fluoro-7'-methoxy-2'-(3-methyl-1H-pyrazol-1-yl)spiro[1,3-oxazole-4,9'-xanthen]-2-amine | 381 | AA40 | 1.0021 | 6.668 |
| 665 | (4S)-2-amino-5'-fluoro-7'-(1H-pyrazol-1-yl)spiro[1,3-oxazole-4,9'-xanthen]-2'-ol | 353 | AA40 | 1.1025 | 4.583 |
| 666 | (5S)-3-((3-methyl-3-oxetanyl)ethynyl)-7-(2-pyrazinyl)spiro[chromeno[2,3-b]pyridine-5,4'-[1,3]thiazol]-2'-amine | 442.2 | BB13 | 0.0008 | 0.013 |
| 667 | 3-(((4S)-2-amino-4',6'-difluoro-7'-(5-pyrimidinyl)spiro[1,3-oxazole-4,9'-xanthen]-2'-yl)oxy)-2,2-dimethylpropanenitrile | 464 | AA14 | 0.0006 | 0.016 |
| 668 | (4S)-3',5'-difluoro-7'-(2-fluoro-2-methylpropoxy)-2'-(5-pyrimidinyl)spiro[1,3-oxazole-4,9'-xanthen]-2-amine | 457 | AA14 | 0.0008 | 0.011 |
| 669 | (5S)-3-(2,2-dimethyl-3,6-dihydro-2H-pyran-4-yl)-7-(5-pyrimidinyl)spiro[chromeno[2,3-b]pyridine-5,4'-[1,3]thiazol]-2'-amine | 458.4 | BB12 | 0.0008 | 0.01 |
| 670 | (5S)-3-(6,6-dimethyl-3,6-dihydro-2H-pyran-4-yl)-7-(5-pyrimidinyl)spiro[chromeno[2,3-b]pyridine-5,4'-[1,3]thiazol]-2'-amine | 458.4 | BB12 | 0.0009 | 0.009 |
| 671 | (5S)-7-(3-methoxy-3-methyl-1-butyn-1-yl)-3-(3-pyridinyl)spiro[chromeno[2,3-b]pyridine-5,4'-[1,3]thiazol]-2'-amine | 443.4 | BB13 | 0.019 | 0.14 |

TABLE I-continued

| Ex. No. | Compound Name | Observed Mass | Method | BACE 1 FRET assay (uM) | HEK cell assay (uM) |
|---|---|---|---|---|---|
| 672 | (5S)-3-(5,6-dihydro-2H-pyran-3-yl)-7-(2-fluoro-3-pyridinyl)spiro[chromeno[2,3-b]pyridine-5,4'-[1,3]thiazol]-2'-amine | 447.3 | BB12 | 0.0007 | 0.01 |
| 673 | (5S)-1-fluoro-7-(2-fluoro-3-pyridinyl)-3-((3R)-3-fluoro-1-pyrrolidinyl)spiro[chromeno[2,3-c]pyridine-5,4'-[1,3]oxazol]-2'-amine | 454 | AA9 | 0.0003 | 0.003 |
| 674 | (5R)-3-(3,3-dimethyl-1-butyn-1-yl)-2-fluoro-7-(2-fluoro-3-pyridinyl)spiro[chromeno[2,3-b]pyridine-5,4'-[1,3]oxazol]-2'-amine | 447.2 | AA33 | 0.239 | 2.81 |
| 675 | (5S)-3-chloro-7-(2-fluoro-4-pyridinyl)spiro[chromeno[2,3-c]pyridine-5,4'-[1,3]oxazol]-2'-amine | 383 | AA24 | 2.6266 | 0.415 |
| 676 | (5S)-7-(2,4-difluoro-3-pyridinyl)-3-(5,6-dihydro-2H-pyran-3-yl)spiro[chromeno[2,3-c]pyridine-5,4'-[1,3]oxazol]-2'-amine | 449.1 | AA1 | 0.0006 | 0.006 |
| 677 | (5S)-7-(2,4-difluoro-3-pyridinyl)spiro[chromeno[2,3-c]pyridine-5,4'-[1,3]oxazol]-2'-amine | 367.1 | AA24 | 0.0516 | 0.58 |
| 678 | (5S)-3-(6,6-dimethyl-3,6-dihydro-2H-pyran-4-yl)-7-(5-pyrimidinyl)spiro[chromeno[2,3-c]pyridine-5,4'-[1,3]oxazol]-2'-amine | 442 | AA1 | 0.0009 | 0.008 |
| 679 | (5S)-3-(2,2-dimethyl-3,6-dihydro-2H-pyran-4-yl)-7-(5-pyrimidinyl)spiro[chromeno[2,3-c]pyridine-5,4'-[1,3]oxazol]-2'-amine | 442 | AA1 | 0.0016 | 0.014 |
| 680 | (5S)-3-chloro-7-(2-fluoro-4-methoxy-3-pyridinyl)spiro[chromeno[2,3-c]pyridine-5,4'-[1,3]oxazol]-2'-amine | 413 | AA24 | 0.0153 | 0.806 |
| 681 | (5S)-7-(2-fluoro-4-methoxy-3-pyridinyl)-3-(2-fluoro-4-pyridinyl)spiro[chromeno[2,3-c]pyridine-5,4'-[1,3]oxazol]-2'-amine | 474 | AA1 | 0.0005 | 0.012 |
| 682 | 1-fluoro-3,7-bis(2-fluoro-3-pyridinyl)spiro[chromeno[2,3-c]pyridine-5,4'-[1,3]thiazol]-2'-amine | 477.8 | BB12 | 0.0009 | 0.074 |
| 683 | 7-(2-fluoro-3-pyridinyl)-3-((3-methyl-3-oxetanyl)ethynyl)spiro[chromeno[2,3-c]pyridine-5,4'-[1,3]thiazol]-2'-amine | 459 | BB13 | 0.0012 | 0.019 |
| 684 | (4S)-4'-fluoro-2'-(1H-pyrazol-1-yl)-7'-(3-pyridyl)spiro[1,3-oxazole-4,9'-xanthen]-2-amine | 414 | AA9 | 0.0038 | 0.034 |
| 685 | (5S)-3-(3,3-dimethyl-1-butyn-1-yl)-2-fluoro-7-(2-fluoro-3-pyridinyl)spiro[chromeno[2,3-b]pyridine-5,4'-[1,3]oxazol]-2'-amine | 447 | AA33 | 0.0004 | 0.011 |
| 686 | (4S)-4'-fluoro-7'-(2-fluoro-3-pyridinyl)-2'-(4-pyridazinyl)spiro[1,3-oxazole-4,9'-xanthen]-2-amine | 444 | AA1 | 0.0008 | 0.012 |
| 687 | (5S)-7-(5-methoxy-3-pyridinyl)-3-(2-pyrimidinyl)spiro[chromeno[2,3-c]pyridine-5,4'-[1,3]oxazol]-2'-amine | 439.1 | AA1 | 0.0804 | 0.853 |
| 688 | (5S)-3-(5,6-dihydro-2H-pyran-3-yl)-1-fluoro-7-(2-fluoro-3-pyridinyl)spiro[chromeno[2,3-c]pyridine-5,4'-[1,3]oxazol]-2'-amine | 449.1 | AA1 | 0.0003 | 0.005 |
| 689 | (5S)-2'-amino-3-bromospiro[chromeno[2,3-b]pyridine-5,4'-[1,3]oxazol]-7-ol | 349 | Example 3 | 4.0726 | 10 |
| 690 | (5S)-2'-amino-3-((3-methyl-3-oxetanyl)ethynyl)spiro[chromeno[2,3-b]pyridine-5,4'-[1,3]oxazol]-7-ol | 364 | BB36 | 0.3456 | 2.149 |
| 691 | (4S)-4'-fluoro-7'-(2-fluoro-3-pyridinyl)-2'-(1H-pyrazol-1-yl)spiro[1,3-oxazole-4,9'-xanthen]-2-amine | 432 | AA20 | 0.002 | 0.063 |
| 692 | (4S)-4'-fluoro-2'-(1H-pyrazol-1-yl)-7'-(5-pyrimidinyl)spiro[1,3-oxazole-4,9'-xanthen]-2-amine | 415 | AA20 | 0.0037 | 0.074 |
| 693 | 7-(2-fluoro-3-pyridinyl)-N~3~,N~3~-dimethylspiro[chromeno[2,3-c]pyridine-5,4'-[1,3]thiazole]-2',3-diamine | 408 | BB12 | 0.0105 | 0.237 |
| 694 | 2'-amino-9-fluoro-7-((3-methyl-3-oxetanyl)ethynyl)spiro[chromeno[2,3-c]pyridine-5,4'-[1,3]oxazol]-3-yl)benzonitrile | 467 | AA33 | 0.0175 | 1.092 |

Example 695 (Method CC1)

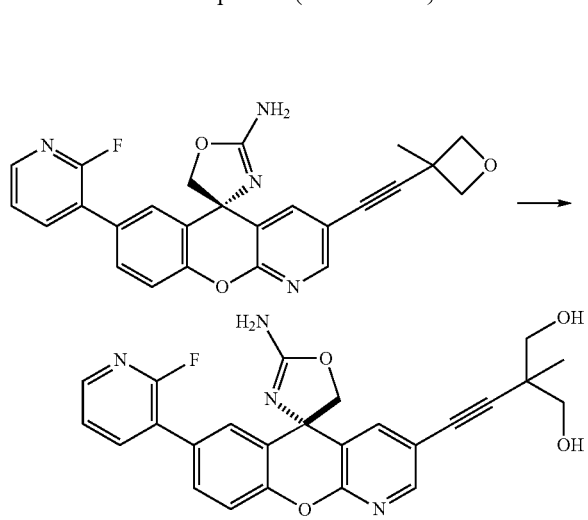

Synthesis of (S)-2-((2'-amino-7-(2-fluoropyridin-3-yl)-5'H-spiro[chromeno[2,3-b]pyridine-5,4'-oxazol]-3-yl)ethynyl)-2-methylpropane-1,3-diol To a vial containing (S)-7-(2-fluoropyridin-3-yl)-((3-methyloxetan-3-yl)ethynyl)-5'H-spiro[chromeno[2,3-b]pyridine-5,4'-oxazol]-2'-amine (250 mg, 0.57 mmol, example 78) was added TFA (4.19 mL, 36.7 mmol) and water (1.02 mL, 56.5 mmol). The reaction vessel was sealed and heated at 80° C. for 2.5 h. The reaction was cooled to rt and concentrated in vacuo. This mixture was quenched with saturated NaHCO₃ (50 mL) poured into a separatory funnel containing CH₂Cl₂ (50 mL). The layers were separated and the aqueous layer was extracted with CH₂Cl₂ (3×25 mL). The combined organic layers were washed with brine, dried over sodium sulfate, filtered and concentrated in vacuo to provide a colorless oil that was purified by silica gel chromatography (Redi-Sep pre-packed silica gel column (40 g), 0-100% DCM to 10:1 methanol in methylenechloride with 0.1% ammonium hydroxide) to provide (S)-2-((2'-amino-7-(2-fluoropyridin-3-yl)-5'H-spiro[chromeno[2,3-b]pyridine-5,4'-oxazole]-3-yl)ethynyl)-2-methylpropane-1,3-diol (63 mg, 0.137 mmol, 24.21% yield) as a white solid.

MS m/z=461.0 [M+H]⁺. Calculated for $C_{25}H_{22}FN_4O_4$: 461.16.

Example 696 (Method CC2)

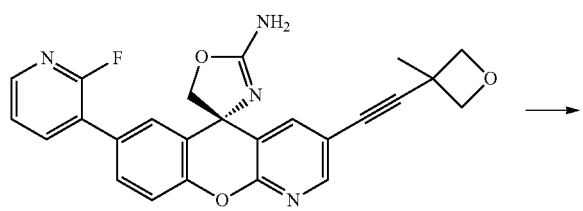

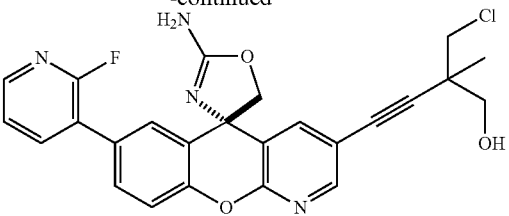

Synthesis of 4-((S)-2'-amino-7-(2-fluoropyridin-3-yl)-5'H-spiro[chromeno[2,3-b]pyridine-5,4'-oxazol]-3-yl)-2-(chloromethyl)-2-methylbut-3-yn-1-ol To a slurry of (S)-7-(2-fluoropyridin-3-yl)-3-((3-methyloxetan-3-yl)ethynyl)-5'H-spiro[chromeno[2,3-b]pyridine-5,4'-oxazol]-2'-amine (500 mg, 1.13 mmol, Example 78) in 10 mL of MeCN was added 10 mL of water followed by 1 mL of 6 N HCl. The resulting solution was heated at 50° C. overnight. The reaction was cooled to rt, diluted with saturated sodium bicarbonate (100 mL) and poured into a separatory funnel containing ethyl acetate (100 mL). The layers were separated and the aqueous layer was extracted with EtOAc (1×50 mL). The combined organic layers were washed with water and then brine, dried over sodium sulfate, filtered and concentrated in vacuo to provide a white solid that was purified by silica gel chromatography (Redi-Sep pre-packed silica gel column (40 g), 0-100% DCM to 10:1 methanol in DCM with 0.1% ammonium hydroxide) to provide 4-((S)-2'-amino-7-(2-fluoropyridin-3-yl)-5'H-spiro[chromeno[2,3-b]pyridine-5,4'-oxazole]-3-yl)-2-(chloromethyl)-2-methylbut-3-yn-1-ol (290 mg, 0.606 mmol, 53.6% yield) as a white solid.

MS m/z=479.0 [M+H]⁺. Calculated for $C_{25}H_{21}ClFN_4O_3$: 479.13.

Example 697 (Method CC3)

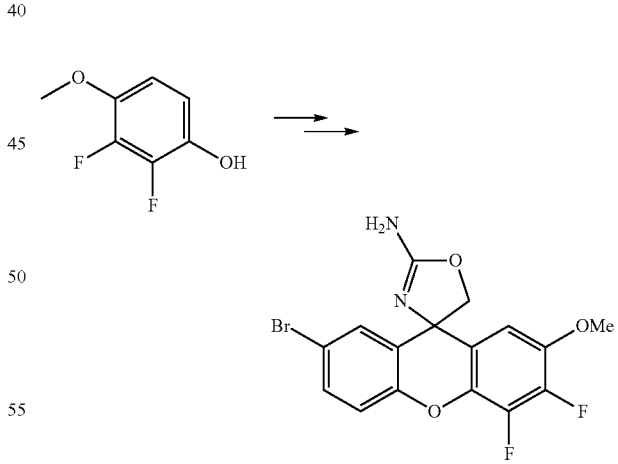

Synthesis of 7'-bromo-3',4'-difluoro-2'-methoxy-5H-spiro[oxazole-4,9'-xanthen]-2-amine Step 1: To a 500 mL flask charged with 2,5-dibromobenzoic acid (14 g, 50.0 mmol) and copper (I) trifluoromethanesulfonate toluene complex (1.29 g, 2.50 mmol) were added toluene (100 mL, 50.0 mmol) followed by EtOAc (0.25 mL, 2.50 mmol) and 2,3-difluoro-4-methoxyphenol (8.41 g, 52.5 mmol). To the resulting green mixture was added cesium carbonate (34.2 g, 105 mmol) in two portions. The mixture was stirred at rt for 5 minutes before being placed in a 110° C. oil bath where it was maintained for 12 h. The reaction was cooled to rt and poured into a separatory funnel containing 1 L of water. The layers were separated and the aqeuous layer was washed with ethyl acetate (2×200 mL). The aqeuous layer was acidified with 6 N HCl and extracted with ethyl acetate (3×500 mL). The combined organic layers were washed with brine, dried over sodium sulfate, filtered and concentrated to provide a brown oil. The derived oil was triturated with ethyl acetate (100 mL) and hexanes (1000 mL). The slurry was cooled to −10° C. for 4 hours then filtered to provide 5-bromo-2-(2,3-difluoro-4-methoxyphenoxy) benzoic acid (11.55 g, 32.2 mmol, 64.3% yield) as a light tan solid.

Step 2: To a 250 mL flask charged with 5-bromo-2-(2,3-difluoro-4-iodophenoxy)benzoic acid (9.1 g, 20.0 mmol) was added sulfuric acid (21.32 mL, 400 mmol). The resulting slurry was heated at 100° C. for 2.5 h. The mixture was cooled to rt and poured into 1 L of ice water. The resulting tan slurry was stirred vigorously for 3 hours. The mixture was filtered through a Buchner funnel and the derived solid was dried under a stream of air for 6 hours to provide 7-bromo-3,4-difluoro-2-iodo-9H-xanthen-9-one (8.10 g, 18.54 mmol, 93% yield) as a tan solid.

Step 3: A solution of 7-bromo-3,4-difluoro-2-methoxy-9H-xanthen-9-one (8.25 g, 24.19 mmol) in THF (242 mL, 24.19 mmol) was cooled to −40° C. To the resulting slurry was added methylmagnesium chloride, 3.0 M solution in tetrahydrofuran (24.19 mL, 72.6 mmol), leading to the formation of a slightly darker mixture. After slowly warming to −10° C. over the course of 30 min TLC showed the clean conversion to a slightly more polar product (1:1 EA in hexanes). The reaction was removed from the cold bath and quenched with saturated ammonium chloride (500 mL). This mixture was poured into a separatory funnel containing ethyl acetate (500 mL). The layers were separated and the aqueous layer was extracted with ethyl acetate (3×100 mL). The combined organic layers were washed with 200 mL of 10% citric acid then brine, dried over sodium sulfate, filtered and concentrated in vacuo to provide 7-bromo-3,4-difluoro-2-methoxy-9-methylene-9H-xanthene as a bright yellow solid that was used immediately. To a solution of iodine (8.98 g, 35.4 mmol) in 150 mL of THF at −25° C. was added silver cyanate (15.91 g, 106 mmol). The reaction was maintained at this temperature for 15 min at which time a solution of 7-bromo-3,4-difluoro-2-methoxy-9-methylene-9H-xanthene (12.0 g, 35.4 mmol) in 3 mL of THF was added. The reaction temperature rose to −15° C. during this addition. The reaction was maintained at −25° C. for 45 min at which time ammonia, 2.0 M solution in 2-propanol (106 mL, 212 mmol) was added. The reaction was allowed to warm to rt and was maintained at that temperature overnight. The reaction was filtered through a pad of celite, washing well with ethyl acetate. This solution was diluted with 10% sodium thiosulfate (1000 mL) and poured into a separatory funnel containing ethyl acetate (500 mL). The layers were separated and the aqueous layer was extracted with ethyl acetate (2×500 mL). The combined organic layers were washed with brine, dried over sodium sulfate, filtered and concentrated in vacuo to provide a light yellow foam. This solid was suspended in 100 mL of CH$_2$Cl$_2$ and 100 mL of ether was added. The slurry was filtered to provide 6.0 g of a light yellow solid. The filtrate was concentrated and purified by silica gel chromatography (Redi-Sep pre-packed silica gel column (330 g), 0-100% CH$_2$Cl$_2$ to 10:1 methanol in CH$_2$Cl$_2$ with 0.1% ammonium hydroxide) to provide 7'-bromo-3',4'-difluoro-2'-methoxy-5H-spiro[oxazole-4,9'-xanthen]-2-amine as an orange solid (7.85 g).

MS m/z=396.8 [M+H]$^+$. Calculated for C$_{16}$H$_{11}$BrF$_2$N$_2$O$_3$: 395.99.

Example 698 (Method CC4)

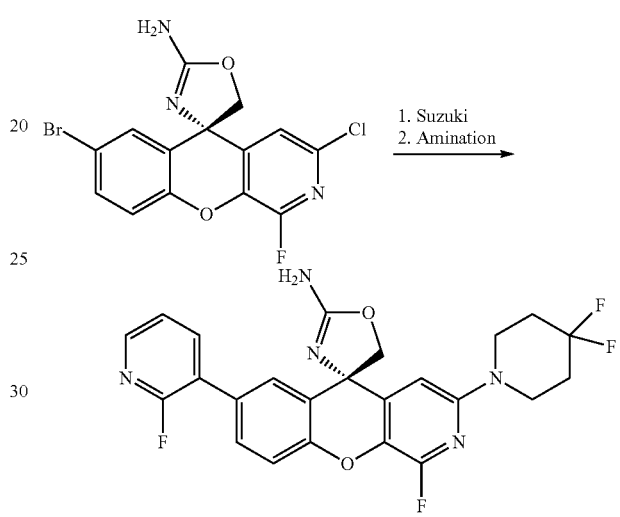

Synthesis of (5S)-3-(4,4-difluoro-1-piperidinyl)-1-fluoro-7-(2-fluoro-3-pyridinyl)spiro[chromeno[2,3-c]pyridine-5,4'-[1,3]oxazol]-2'-amine Step 1: The suzuki coupling was carried out as described on method AA1 using (S)-7-bromo-3-chloro-1-fluoro-5'H-spiro[chromeno[2,3-c]pyridine-5,4'-oxazol]-2'-amine (prepared by steps analogous to those described in Method BB33) and 3-fluoropyridin-2-ylboronic acid.

Step 2: In a sealed tube a mixture of (S)-3-chloro-1-fluoro-7-(pyridin-3-yl)-5'H-spiro[chromeno[2,3-c]pyridine-5,4'-oxazol]-2'-amine, corresponding amine (1.3 eq), and Chloro(2-dicyclohexylphosphino-2',4',6'-tri-1-propyl-1,1'-biphenyl)[2-(2-aminoethyl)phenyl]Pd(II) Me-t-butylether (0.10 eq), was purged with N$_2$ followed by the addition of dioxane (2 mL) and lithium bis(trimethylsilyl)amide (3.6 eq) and the resulting mixture was stirred at room temperature for 1 h. More chloro(2-dicyclohexylphosphino-2',4',6'-tri-1-propyl-1,1'-biphenyl)[2-(2-aminoethyl)phenyl]Pd(II) Me-t-butylether (0.10 eq), amine (1.2 eq) and LHMDS (2.4 eq) were added. After 30 min the reaction went to completion. The reaction mixture was quenched with sat NH$_4$Cl and extracted with EtOAc. The combined organics were dried over Na$_2$SO$_4$, filtered, concentrated, and chromatographed on silica gel using 0-100% EtOAc/hexanes to afford a yellow oil. The products were repurified by HPLC to afford the desired product.

Example 699 (Method CC5)

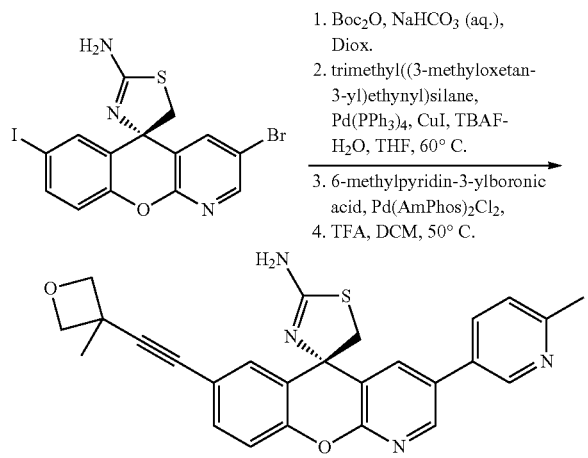

Synthesis of (S)-7-((3-methyloxetan-3-yl)ethynyl)-3-(6-methylpyridin-3-yl)-5'H-spiro[chromeno[2,3-b]pyridine-5,4'-thiazol]-2'-amine Step 1: (S)-3-Bromo-7-iodo-5'H-spiro[chromeno[2,3-b]pyridine-5,4'-thiazol]-2'-amine (2.31 g, 4.87 mmol, prepared as described in Method BB26) was dissolved in dioxane (24.36 mL). 25 mL of saturated sodium bicarbonate solution was added, followed by boc-anhydride (11.31 mL, 48.7 mmol). The reaction was stirred overnight at RT. The reaction was diluted with EtOAc and washed with water. The aqueous layer was extracted with EtOAc, and the combined organic layers were dried with sodium sulfate, filtered, and concentrated. The material was purified via column chromatography on silica gel (0-25% EtOAc:Hex) to afford (S)-tert-butyl 3-bromo-7-iodo-5'H-spiro[chromeno[2,3-b]pyridine-5,4'-thiazole]-2'-ylcarbamate (2.614 g, 4.55 mmol) as a yellow solid. MS m/z=597.9 [M+H]$^+$. Calculated for $C_{19}H_{17}BrIN_3O_3S$: 574.23.

Step 2: A vial was charged with (S)-tert-butyl 3-bromo-7-iodo-5'H-spiro[chromeno[2,3-b]pyridine-5,4'-thiazole]-2'-ylcarbamate (0.194 g, 0.338 mmol), tetrakis(triphenylphosphine)palladium (0.039 g, 0.034 mmol), tetrabutylammonium fluoride hydrate (0.41 g, 1.689 mmol), and copper(I) iodide (6.43 mg, 0.034 mmol). Added THF (1.7 mL) followed by trimethyl((3-methyloxetan-3-yl)ethynyl)silane (0.10 mL, 0.51 mmol). The reaction was stirred at 60° C. for 30 min, then diluted with EtOAc and washed with water. The aqueous layer was extracted with EtOAc, and the combined organic layers were dried with sodium sulfate, filtered, and concentrated. The material was purified via column chromatography on silica gel (0-50% EtOAc:Hex) to afford (S)-tert-butyl 3-bromo-7-((3-methyloxetan-3-yl)ethynyl)-5'H-spiro[chromeno[2,3-b]pyridine-5,4'-thiazole]-2'-ylcarbamate (0.163 g, 0.30 mmol, 89% yield) as a yellow solid.

MS m/z=542.2 [M+H]$^+$. Calculated for $C_{25}H_{24}BrN_3O_4S$: 541.07.

Step 3: A vial was charged with (S)-tert-butyl 3-bromo-7-((3-methyloxetan-3-yl)ethynyl)-5'H-spiro[chromeno[2,3-b]pyridine-5,4'-thiazole]-2'-ylcarbamate (0.054 g, 0.10 mmol), 6-methylpyridin-3-ylboronic acid (0.041 g, 0.30 mmol), potassium carbonate (0.069 g, 0.50 mmol), and Pd(AmPhos)$_2$Cl$_2$ (7.05 mg, 9.95 μmol). The vial was flushed with Ar (g), then dioxane (0.66 mL) and water (0.33 mL) were added in sequence. The vial was sealed and heated at 80° C. for 16 h. The reaction was diluted with EtOAc and washed with water. The aqueous layer was extracted with EtOAc, and the combined organic layers were dried with sodium sulfate, filtered, and concentrated. The material was purified via column chromatography on silica gel (0-75% EtOAc:Hex) to afford (S)-tert-butyl 7-((3-methyloxetan-3-yl)ethynyl)-3-(6-methylpyridin-3-yl)-5'H-spiro[chromeno[2,3-b]pyridine-5,4'-thiazole]-2'-ylcarbamate (0.027 g, 0.049 mmol, 48.9% yield) as a white solid. MS m/z=555.3 [M+H]$^+$. Calculated for $C_{31}H_{30}N_4O_4S$: 554.20.

Step 4: (S)-Tert-butyl 7-((3-methyloxetan-3-yl)ethynyl)-3-(6-methylpyridin-3-yl)-5'H-spiro[chromeno[2,3-b]pyridine-5,4'-thiazole]-2'-ylcarbamate (0.027 g, 0.049 mmol) was taken up in 1.5 mL of DCM and TFA (0.057 mL, 0.735 mmol) was added. The reaction was heated to 50° C. and stirred for 2 h. The reaction was diluted with DCM and washed with saturated sodium bicarbonate solution. The aqueous layer was extracted with DCM, and the combined organic layers were dried with sodium sulfate, filtered, and concentrated to afford (S)-7-((3-methyloxetan-3-yl)ethynyl)-3-(6-methylpyridin-3-yl)-5'H-spiro[chromeno[2,3-b]pyridine-5,4'-thiazol]-2'-amine (0.017 g, 0.037 mmol, 37.6% yield) as a light yellow solid.

MS m/z=455.4 [M+H]$^+$. Calculated for $C_{26}H_{22}N_4O_2S$: 454.15.

Example 700 (Method CC6)

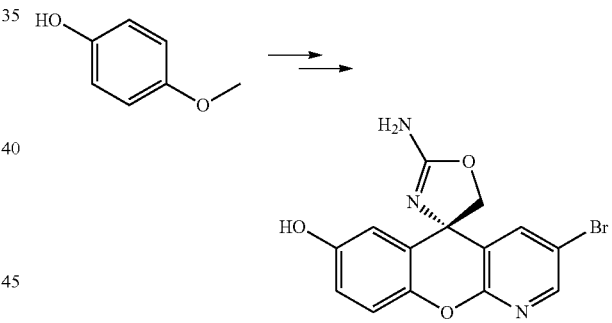

Synthesis of 3-bromo-7-hydroxy-spiro[chromeno[2,3-b]pyridine]-5,4'-[1,3]oxazole]-2'-amine Step 1: To a 500 mL flask charged with NaH (60% dispersion in mineral oil) (5.33 g, 133 mmol) was added DMF (127 mL, 63.4 mmol). To this slurry at 0° C. was added 4-methoxyphenol (7.88 g, 63.4 mmol) portion wise over 1 minute resulting in the evolution of large amounts of hydrogen gas. The mixture was removed from the ice batch and allowed to stir for 5 min, before 5-bromo-2-chloronicotinic acid (15.0 g, 63.4 mmol) was introduced portion wise over 2 min. The resulting green slurry was stirred at rt for 10 min at which point the reaction become homogeneous. The solution was then heated at 140° C. for 1 h. The reaction was cooled to rt and diluted with 800 mL of water. The water was washed twice with ether (300 mL). The aqueous layer was acidified with acetic acid (18.2 ml, 317 mmol) and allowed to stir at rt for 12 h to provide a fine off white solid. Filtered to provide 5-bromo-2-(4-methoxyphenoxy)nicotinic acid as an off white solid. MS m/z=324.0 [M+H]$^+$. Calc'd for $C_{13}H_{11}BrNO_4$: 324.0.

Step 2: A slurry of 5-bromo-2-(4-methoxyphenoxy)nicotinic acid (12.2 g, 37.6 mmol) and polyphosphoric acid (200 g) was heated at 135° C. for 1.5 h. The reaction was cooled to rt and poured onto 300 g of ice before being basified to pH 12 with 50% aq. KOH (1.5 L). The resulting yellow slurry was filtered and washed with 100 mL of ether. The wet solid was then partitioned between water and DCM (1:1, 2000 mL). The layers were separated and the aqueous layer was extracted with DCM 5×500 mL. The combined organics were washed with brine, dried over sodium sulfate, filtered and concentrated to provide 3-bromo-7-methoxy-5H-chromeno[2,3-b]pyridin-5-one as a yellow solid.

MS m/z=306.2 [M+H]$^+$. Calc'd for $C_{13}H_9BrNO_3$: 306.0.

Step 3: To a solution of 3-bromo-7-methoxy-5H-chromeno[2,3-b]pyridin-5-one (4.50 g, 14.7 mmol) in THF (294 mL, 14.7 mmol) at 5° C. was added methylmagnesium bromide (1 M in butyl ether) (36.8 ml, 36.8 mmol). The reaction was removed from the ice bath and stirred for an additional 1 h. TLC showed complete conversion to a lower Rf material. The reaction mixture was quenched with saturated ammonium chloride (250 mL) and to it DCM (100 mL) was added. The mixture was stirred vigorously for 30 min before being poured into a separatory funnel containing 300 mL of DCM. The layers were separated and the aqueous layer was extracted with DCM 2×100 mL. The combined organic layers were washed with brine, dried over $Na_2SO_4$ and filtered. TLC revealed tertiary alcohol and no olefin. The organics were concentrated under reduced pressure at 60° C. Flask was maintained at 60° C. on the rotovap for 1 h at which point TLC and NMR show clean conversion to 3-bromo-7-methoxy-5-methylene-5H-chromeno[2,3-b]pyridine. MS m/z=304.2 [M+H]$^+$. Calc'd for $C_{14}H_{11}BrNO_2$: 304.0.

Step 4: A 500 mL flask containing iodine (3.067 g, 12.08 mmol) and 60 mL of THF was cooled to −15° C. Silver cyanate (5.175 mg, 34.52 mmol) was added in one portion, and the mixture was stirred at −15 to −20° C. for 20 min, after which a solution of 3-bromo-7-methoxy-5-methylene-5H-chromeno[2,3-b]pyridine (3.50 g, 11.51 mmol) in 10 mL of THF was added to the mixture followed by a 2 mL THF wash. The resulting yellow slurry was maintained at −20° C. to −10° C. for 1 h at which point LCMS indicated the complete consumption of the starting material. The mixture was diluted with 20 mL of ether and filtered through a pad of celite. The filter cake was washed with ether and concentrated with minimal heating to provide an orange residue. This residue was taken up in 70 mL of THF and cooled to 0° C. and treated with ammonia (2 M in propanol) (17.26 mL, 34.52 mmol). The mixture was stirred at 0° C. for 5 min then removed from ice bath, warmed to rt and stirred overnight. The reaction was quenched with 10% $Na_2S_2O_3$ 250 mL and poured into EtOAc 250 mL. The layers were separated and the aqueous layer was extracted with EtOAc 2×250 mL. The combined organic layers were washed with brine, dried over $Na_2SO_4$ and filtered. The resulting crude material was purified by flash chromatography eluting with 0-100% EA in hexanes to provide 3-bromo-7-methoxy-spiro[chromeno[2,3-b]pyridine]-5,4'-[1,3]oxazole]-2'-amine as a tan foam. MS m/z=362.1 [M+H]$^+$. Calc'd for $C_{15}H_{13}BrN_3O_3$: 362.0.

Step 5: To a solution of 3-bromo-7-methoxy-spiro[chromeno[2,3-b]pyridine]-5,4'-[1,3]oxazole]-2'-amine (2300 mg, 6.35 mmol) in DCM (127 mL, 6.35 mmol) at 0° C. was added tribromoborane (1.80 mL, 19.05 mmol). Immediately a thick precipitate formed. The resulting red slurry was stirred at 0° C. for 10 min at which point the ice bath was removed and the mixture was allowed to warm to rt and stirred at rt for 1 h. Added another 1 mL of tribromoborane at rt and the mixture was stirred for another hour. The reaction was cooled to 0° C. and carefully quenched with saturated sodium bicarbonate 250 mL and poured into DCM 250 mL. The layers were separated and the aqueous layer was extracted with DCM 3×300 mL. The organic layers were washed with brine, dried over $Na_2SO_4$ and filtered. The extraction process was repeated with DCM. All organic layers were combined and concentrated under reduced pressure to provide 3-bromo-7-hydroxy-spiro[chromeno[2,3-b]pyridine]-5,4'-[1,3]oxazole]-2'-amine as a brown solid. MS m/z=348.0 [M+H]$^+$. Calc'd for $C_{14}H_{11}BrN_3O_3$: 348.0.

Example 701 (Method CC7)

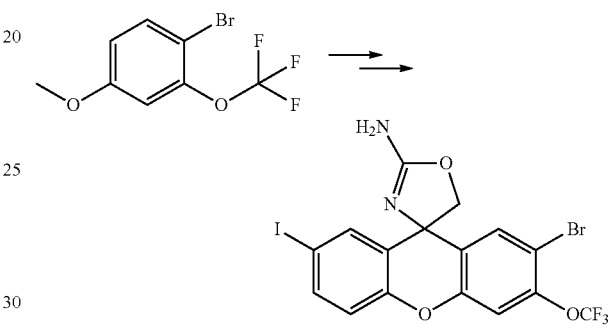

Step 1: In a 500 mL flask, 2-fluoro-5-iodobenzoyl chloride (6.06 g, 21.3 mmol) and 1-bromo-4-methoxy-2-(trifluoromethoxy)benzene (5.77 g, 21.3 mmol) were dissolved in 1,2-dichloroethane (50.7 mL, 21.3 mmol) and the solution was cooled to 0 to 5° C. Aluminum chloride (2.84 g, 21.3 mmol) was added portionwise to the solution. The red solution was warmed to rt. After 2 h, LCMS showed mainly (5-bromo-2-methoxy-4-(trifluoromethoxy)phenyl)(2-fluoro-5-iodophenyl)methanone. The whole was refluxed for 1 h. LCMS showed complete consumption of (5-bromo-2-methoxy-4-(trifluoromethoxy)phenyl)(2-fluoro-5-iodophenyl)methanone. The reaction was cooled to rt. Ice (5-10 chips) and concentrated HCl (2 mL) was added until pH ~1. The whole was stirred at rt for 30 min. The resulting slurry was extracted with ether (3×80 mL). The organic layer was washed with water, dried over $MgSO_4$, filtered, and concentrated to afford a semi-black solid that was carried on to the next step. The crude was added to a mixture of ethanol (85 mL, 21.3 mmol), methanol (30.4 mL, 21.3 mmol), and sodium methoxide (2.30 g, 42.6 mmol) at rt. After refluxing for 1 h, LCMS showed mainly the cyclized xanthenone product. The whole was cooled to rt and concentrated. Water (80 mL) and EtOAc (120 mL) was added. The product was extracted with EtOAc (2×80 mL). The organic layer was separated, combined, dried over $MgSO_4$, filtered, and concentrated. Trituration with hexanes gave 2-bromo-7-iodo-3-(trifluoromethoxy)-9H-xanthen-9-one (2.94 g, 6.06 mmol, 29% yield) as a gray solid. LCMS (ESI) calcd for $C_{14}H_5BrF_3IO_3$: [M]$^+$=484. Found [M+H]$^+$=485.

Step 2: A RBF was charged with 2-bromo-7-iodo-3-(trifluoromethoxy)-9H-xanthen-9-one (2.94 g, 6.06 mmol) and THF (33.7 mL). The black suspension was cooled to −78° C. using an i-PrOH/dry ice bath. Methylmagnesium chloride (3.0 M in THF, 4.45 mL, 13.34 mmol) was added dropwise. After 2 h, LCMS showed olefin product. The whole was quenched with satd' aq NH₄Cl (20 mL) at 0° C., water (50 mL) and diluted with EtOAc (100 mL). The product was extracted with EtOAc (3×50 mL). The organic layer was separated, dried over MgSO₄, filtered, and concentrated to afford yellow oil. 1H NMR confirmed the tertiary alcohol, 2-bromo-7-iodo-9-methyl-3-(trifluoromethoxy)-9H-xanthen-9-ol (3.04 g, 6.07 mmol, 100% yield). LCMS (ESI) calcd for $C_{15}H_9BrF_3IO_3$: [M]⁺=500. Found [M−H₂O+H]⁺=483. Dehydration took place on LCMS to give the olefin, 2-bromo-7-iodo-9-methylene-3-(trifluoromethoxy)-9H-xanthene). This material was carried on to the next step.

Step 3: Under a nitrogen atmosphere, 2-bromo-7-iodo-9-methyl-3-(trifluoromethoxy)-9H-xanthen-9-ol (2.94 g, 5.87 mmol) was taken up in DCM (29.3 mL, 5.87 mmol). PPTS (0.30 g, 1.17 mmol) was added into the reaction. The reaction was heated to 55° C. and stirred for 1.5 h. LCMS showed complete conversion to olefin (Note: TIC of the olefin was very different from the alcohol. The main peak with m/z=381 was no longer in the chromatogram). TLC confirmed the disappearance of alcohol and formation of nonpolar spots that indicated olefin formation. The reaction was concentrated completely, dissolved in minimal THF (10 mL), and added to the slurry below via an additional funnel. To a solution of iodine (1.49 g, 5.87 mmol) in THF (32.6 mL, 5.87 mmol) at −25° C. was added silver cyanate (2.64 g, 17.6 mmol). After holding the internal temperature at −20 to −25° C. for 15 min, the above olefin solution was added while maintaining the same temperature range. After 45 min, LCMS showed conversion of olefin to mainly the vinyl iodide. Then ammonia, 2.0 M solution in 2-propanol (17.6 mL, 35.2 mmol) was added at −20° C. After warming to rt, anhydrous NH₃ gas was bubbling into the suspension for 3 min to give a black mixture. After 2.5 h, LCMS showed 5:1 product:vinyl iodide. Anhydrous NH₃ gas was bubbling into the suspension for another min. After 22 h at rt, LCMS showed complete consumption of vinyl iodide to product. The whole was decantated through a filter. The solid left behind was washed with EtOAc (3×70 mL). The organic layers were combined and concentrated to yield a brown residue. The product was purified by performing a column chromatography using gradient 0 to 50% 90:10:1 DCM:MeOH:NH₄OH in DCM. Fractions containing the product were combined and concentrated to afford 2'-bromo-7'-iodo-3'-(trifluoromethoxy)-5H-spiro[oxazole-4,9'-xanthen]-2-amine (1.54 g, 2.85 mmol, 49% yield) as a brown solid. LCMS (ESI) calcd for $C_{16}H_9BrF_3{}_1N_2O_3$: [M]⁺=540. Found [M+H]⁺=541.

Example 702 (Method CC8)

Synthesis of 3-bromo-1-fluoro-7-(2-fluoropyridin-3-yl)-5'H-spiro[chromeno[2,3-c]pyridine-5,4'-oxazol]-2'-amine Step 1: 5-Bromo-2-fluorobenzaldehyde (5.0 g, 24.63 mmol) was dissolved in a mixture of methanol (20 mL) and DCM (70 mL) and treated with sodium borohydride (1.00 g, 26.4 mmol). The reaction was stirred for 45 min after which the mixture was partitioned between ethyl acetate (300 mL), water (200 mL) and saturated sodium bicarbonate (100 mL). The organic was washed with 1 N HCl (100 mL) then dried with magnesium sulfate and evaporated to dryness under reduced pressure. The crude was used without purification. MS m/z=186.9, 188.9 [M+H−H₂O]⁺. Calculated for $C_7H_6BrFO$: 203.96.

Step 2: The crude oil was dissolved in dioxane (100 mL) and treated with 2-fluoropyridin-3-ylboronic acid (3.47 g, 24.63 mmol), potassium phosphate (5.23 g, 24.63 mmol), and 1,1-bis[(di-t-butyl-p-methylaminophenyl]palladium(II) chloride (0.25 g, 0.35 mmol). Water (10 mL) was added and the reaction heated to 90° C. for 10 min. Water (300 mL) and ethyl acetate (200 mL) were added and the phases mixed and separated. The organic was dried with magnesium sulfate and evaporated to dryness under reduced pressure. Purification of the crude material using silica chromatography (hexane to ethyl acetate gradient) gave (2-fluoro-5-(2-fluoropyridin-3-yl)phenyl)methanol (2.54 g, 47%). MS m/z=222.1 [M+H]⁺. Calculated for $C_{12}H_9F_2NO$: 221.05.

Step 3: (2-Fluoro-5-(2-fluoropyridin-3-yl)phenyl)methanol (2.54 g) was dissolved in dichloromethane (200 mL). Silica gel (30 mL) was added followed by pyridinium chlorochromate (5.31 g, 24.63 mmol). It was stirred at RT and monitored by TLC. Once the oxidation was complete the mixture was filtered through a pad of silica gel (10 mL) and washed with ethyl acetate. Evaporation under reduced pressure gave the desired 2-fluoro-5-(2-fluoropyridin-3-yl)benzaldehyde (4.71 g, 21.49 mmol, 87% yield) as an off white solid. MS m/z=220.1 [M+H]⁺. Calculated for $C_{12}H_7F_2NO$: 219.05.

Step 4: DIPA (90 mL, 637 mmol), lithium chloride (2.50 g, 59.0 mmol) and dry THF (100 mL) were cooled in a dry ice bath under nitrogen. Butyllithium solution (2.5 M in hexanes, 250 mL, 625 mmol) was added by addition funnel and the solution stirred for 15 min A solution of 2-fluoropyridine (50 mL, 581 mmol) in dry THF (400 mL) was added by addition funnel over 25 minutes. After 80 minutes a solution of triisopropyl borate (150 mL, 654 mmol) in dry THF (100 mL) was added via addition funnel over 10 min. After the addition was complete a sample it was stirred for another 20 min then allowed to warm to 0° C. in an ice bath. After another 20 min 10 N NaOH (122 mL, 1221 mmol) and hydrogen peroxide (50 wt. % solution in water, 40 mL, 653 mmol) were added. After 10 min the reaction was taken out of the ice bath and allowed to stir at RT for 30 min. It was concentrated under reduced pressure to remove the bulk of the THF then allowed to stir for another 20 min. Diethyl ether (500 mL) and additional water (500 mL) were added and the phases mixed and separated. The aqueous was returned to an erlenmeyer and the organic (containing unreacted 2-fluoropyridine) discarded. The aqueous was acidified with conc HCl (150 mL) and buffered to pH 7 with saturated potassium phosphate. Extraction with EtOAc (2×300 mL), drying with magnesium sulfate and evaporation to dryness under reduced pressure gave the crude 2-fluoropyridin-3-ol (55 g, 486 mmol, 84% yield) which was used without further purification.

MS m/z=114.1 [M+H]⁺. Calculated for $C_5H_4BFNO$: 113.03.

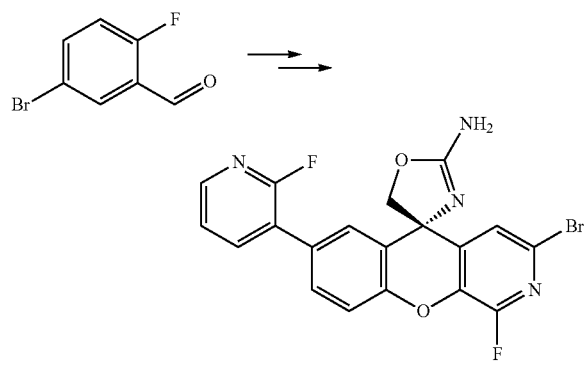

Step 5: 2-Fluoropyridin-3-ol (55 g, 486 mmol) and cesium carbonate (158 g, 486 mmol) were suspended in ACN (400 mL). A solution of chloromethyl methyl ether (40 mL, 527 mmol) in dry tetrahydrofuran (50 mL) was added dropwise via an addition funnel. After 1 hour additional MOM-Cl (5 mL) was added and the reaction stirred for another 2 h. The reaction was evaporated to dryness under reduced pressure and the residue partitioned between diethyl ether (400 mL) and water (500 mL). The organic was washed with saturated sodium bicarbonate (100 mL) then dried with magnesium sulfate and evaporated to dryness under reduced pressure. The crude was purified using silica chromatography (hexane to 1:1 hexane:DCM gradient) to give the desired 2-fluoro-3-(methoxymethoxy)pyridine (53.5 g, 340 mmol, 70.0% yield). MS m/z=158.1 [M+H]$^+$. Calculated for $C_7H_8FNO_2$: 157.05.

Step 6: DIPA (3.5 mL, 24.97 mmol) was dissolved in dry THF (10 mL) under nitrogen and cooled in a dry ice bath. Butyllithium solution (2.5 m in hexanes, 10.0 mL, 25.00 mmol) was added and after stirring for a few minutes 2-fluoro-3-(methoxymethoxy)pyridine (3.71 g, 23.64 mmol) in dry THF (25 mL) was added dropwise. The reaction was stirred for 1 h. A solution of 2-fluoro-5-(2-fluoropyridin-3-yl)benzaldehyde (4.71 g, 21.49 mmol) in dry THF (40 mL) was added dropwise over 10 min. The reaction was removed from the cold bath and stirred for an additional 15 min. Saturated sodium bicarbonate (20 mL) was added followed by EtOAc (300 mL) and water (400 mL). The phases were mixed and separated and the organic dried with magnesium sulfate before evaporating to dryness under reduced pressure. Purification using silica chromatography (hexane to EtOAc gradient) gave the desired (2-fluoro-3-(methoxymethoxy)pyridin-4-yl)(2-fluoro-5-(2-fluoropyridin-3-yl)phenyl)methanol (5.52 g, 14.67 mmol). MS m/z=377.1 [M+H]$^+$. Calculated for $C_{19}H_{15}F_3N_2O_3$: 376.10.

Step 7: (2-Fluoro-3-(methoxymethoxy)pyridin-4-yl)(2-fluoro-5-(2-fluoropyridin-3-yl)phenyl)methanol (5.52 g, 14.67 mmol) was suspended in DCM (150 mL) under nitrogen and cooled in an ice bath. Boron tribromide (neat, 1.5 mL, 15.87 mmol) was added and the reaction stirred for 20 min. The mixture was poured into and erlenmeyer with ice (200 mL) and saturated bicarbonate (80 mL). After a few minutes DCM (300 mL) and water (300 mL) were added and the phases mixed and separated. The organic was dried with brine and evaporated to dryness under reduced pressure. The crude was used without purification for step 5. MS m/z=333.0 [M+H]$^+$. Calculated for $C_{17}H_{11}F_3N_2O_2$: 332.08.

Step 8: The crude from step 4 was suspended in acetic acid (200 mL) and cooled in an ice bath. Potassium acetate (2.0 g, 20.38 mmol) was added followed by dropwise addition of bromine (0.8 mL, 15.53 mmol). After 5 min the reaction was deemed complete. Sodium sulfite (4 g) was added and the mixture allowed to warm to RT. Water (300 mL) and EtOAc (300 mL) were added. The phases were mixed and separated. The organic was washed with water (400 mL), dried with magnesium sulfate and evaporated to dryness under reduced pressure. The crude 6-bromo-2-fluoro-4-((2-fluoro-5-(2-fluoropyridin-3-yl)phenyl)(hydroxy)methyl)pyridin-3-ol was used without purification for step 6. MS m/z=411.0, 413.0 [M+H]$^+$. Calculated for $C_{17}H_{10}BrF_3N_2O_2$: 409.99

Step 9: 6-Bromo-2-fluoro-4-((2-fluoro-5-(2-fluoropyridin-3-yl)phenyl)(hydroxy)methyl)pyridin-3-ol (crude from step 5, 5.75 g, 13.98 mmol) was suspended in DCM and treated with 4-methylmorpholine 4-oxide (1.64 g, 13.98 mmol) and tetrapropylammonium perruthenate (0.18 g, 0.52 mmol). The mixture was stirred at RT for 70 min then heated to reflux. After an additional 90 min the oxidation was complete and the intermediate ketone had cyclized to the desired product. Evaporation under reduced pressure gave the crude product which was triturated with water (300 mL) and filtered through a sintered glass frit. The solids were washed with cold DCM (100 mL) to give the desired 3-bromo-1-fluoro-7-(2-fluoropyridin-3-yl)-5H-chromeno[2,3-c]pyridin-5-one (3.75 g, 9.64 mmol, 68.9% yield) as a grey solid. MS m/z=389.0, 391.0 [M+H]$^+$. Calculated for $C_{17}H_7BrF_2N_2O_2$: 387.97.

Step 10: 3-Bromo-1-fluoro-7-(2-fluoropyridin-3-yl)-5H-chromeno[2,3-c]pyridin-5-one (3.75 g, 9.64 mmol) was suspended in dry THF (100 mL) and cooled in an ice bath under nitrogen. Methylmagnesium bromide (3.0 M in diethyl ether, 10 mL, 30.0 mmol) was added dropwise and the mixture stirred for an additional 10 min before removing from the ice bath. Additional THF (300 mL) and methylmagnesium bromide (15 mL, 4.5 eq) was added slowly. Once the solids had completely dissolved the reaction was stirred for 5 min. It was quenched by careful addition of 5 N HCl. Water (600 mL) and EtOAc (500 mL) were added and the phases mixed and separated. The organic was dried with magnesium sulfate and evaporated to dryness under reduced pressure. The crude alcohol was dissolved in dry THF (200 mL) and treated with hydrogen chloride (4.0 M solution in 1,4-dioxane, 7 mL, 28.0 mmol). The solution was heated to 40° C. for 1 h. The solution was evaporated to dryness under reduced pressure and further dried under high vacuo. The crude 3-bromo-1-fluoro-7-(2-fluoropyridin-3-yl)-5-methylene-5H-chromeno[2,3-c]pyridine (2.20 g, 5.68 mmol, 59.0% yield) was used without purification. It was dissolved in dry THF (80 mL) and cooled in an ice bath under nitrogen. Silver cyanate (2.5 g, 16.68 mmol) was added and the mixture stirred. A solution of iodine (1.45 g, 5.71 mmol) in dry THF (20 mL) was added dropwise. After 30 min the colour of iodine had been consumed and the supernatant was clear. Diethyl ether (200 mL) was added and the mixture filtered through a pad of celite. The filtrate was treated with ammonia (2.0 M solution in methanol, 80 mL, 160 mmol) and the flask sealed. It was stirred overnight. The solution was evaporated to dryness under reduced pressure. The crude solids were triturated with diethyl ether and filtered through a sintered glass frit. The solids were dried under high vacuo to give the desired 3-bromo-1-fluoro-7-(2-fluoropyridin-3-yl)-5'H-spiro[chromeno[2,3-c]pyridine-5,4'-oxazol]-2'-amine (2.25 g, 5.05 mmol, 89% yield). MS m/z=445.0, 446.9 [M+H]$^+$. Calculated for $C_{19}H_{11}BrF_2N_4O_2$: 444.0. Separation of the stereoisomers using SCF gave optically pure (5R)-3-bromo-1-fluoro-7-(2-fluoropyridin-3-yl)-5'H-spiro[chromeno[2,3-c]pyridine-5,4'-oxazol]-2'-amine (MS m/z=445.0, 447.0 [M+H]) and (5S)-3-bromo-1-fluoro-7-(2-fluoropyridin-3-yl)-5'H-spiro[chromeno[2,3-c]pyridine-5,4'-oxazol]-2'-amine MS m/z=445.0, 447.0 [M+H]$^+$. Calculated for $C_{19}H_{11}BrF_2N_4O_2$: 444.0.

Example 703 (Method CC9)

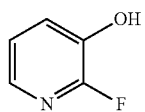

1. Br$_2$, NaOH, HOAc
2. 2-(3,6-dihydro-2H-pyran-4-yl)-4,4,5,5-tetramethyl-1,3,2-dioxaborolane, K$_3$PO$_4$, AmPhos, dioxane, water, 110° C.; Pd/C, MeOH, DCM, 60 psi H$_2$
3. Br$_2$, NaOH, HOAc; MOM-Cl, Cs$_2$CO$_3$, ACN
4. BuLi then 5-Br-2-F-benzaldehyde
5. TPAP, NMMO, DCM; BBr$_3$, DCM; Cs$_2$CO$_3$, ACN
6. MeMgBr, THF; HCl, THF, 50° C.; AgOCN, I$_2$; NH3, MeOH

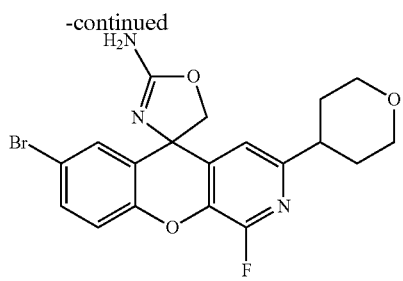

Synthesis of 7-bromo-1-fluoro-3-(tetrahydro-2H-pyran-4-yl)-5'H-spiro[chromeno[2,3-c]pyridine-5,4'-oxazol]-2'-amine Step 1: 2-Fluoropyridin-3-ol (5.96 g, 52.7 mmol) was suspended in acetic acid and cooled in an ice bath. NaOH (10.0 N, 6.0 mL, 60.0 mmol) was added and the mixture stirred for 10 min. Bromine (2.8 mL, 54.4 mmol) was added dropwise and the mixture stirred for 20 min. Sodium sulfite (1.4 g) was added and the mixture stirred for 10 min. Water (400 mL) and EtOAc (400 mL) were added and the phases mixed and separated. The organic was dried with magnesium sulfate and evaporated to dryness under reduced pressure. Purification using silica chromatography (hexane to ethyl acetate gradient) gave the desired 6-bromo-2-fluoropyridin-3-ol (3.67 g, 19.12 mmol, 36.3% yield) MS m/z=192.0, 194.0 [M+H]$^+$. Calculated for $C_5H_3BrFNO$: 190.94.

Step 2: 6-Bromo-2-fluoropyridin-3-ol (3.67 g, 19.12 mmol), 2-(3,6-dihydro-2H-pyran-4-yl)-4,4,5,5-tetramethyl-1,3,2-dioxaborolane (4.02 g, 19.12 mmol), potassium phosphate (6.25 g, 29.4 mmol), and 1,1-bis[(di-t-butyl-p-methylaminophenyl]palladium(ii) chloride (0.23 g, 0.33 mmol) were suspended in a mixture of dioxane (5 mL) and water (0.5 mL) and heated in the microwave to 110° C. for 20 min. The phases were allowed to settle and the organic evaporated to dryness under reduced pressure. Purification using silica chromatography (hexane to EtOAc gradient) gave the desired coupled material. It was dissolved in MeOH (60 mL) and DCM (30 mL) and treated with palladium (10% wt on carbon, 0.26 g, 0.24 mmol) and hydrogenated at 60 psi overnight. The mixture was filtered through a pad of celite and the filtrate evaporated under reduced pressure to give the desired 2-fluoro-6-(tetrahydro-2H-pyran-4-yl)pyridin-3-ol (1.92 g, 9.74 mmol, 50.9% yield). It was used without purification.

MS m/z=198.1 [M+H]$^+$. Calculated for $C_{10}H_{12}FNO_2$: 197.09.

Step 3: 2-Fluoro-6-(tetrahydro-2H-pyran-4-yl)pyridin-3-ol (1.90 g, 9.63 mmol) was dissolved in mixture of HOAc (100 mL) and NaOH (1.0 N, 20 mL, 20.00 mmol). The mixture was cooled in an ice bath and bromine (0.6 mL, 11.65 mmol) was added. It was stirred for 15 min. Sodium sulfite (1.1 g) was added and the mixture stirred for 5 min. Water (300 mL) and EtOAc (400 mL) were added and the phases mixed and separated. The organic was dried with brine (200 mL) then magnesium sulfate before evaporating to dryness under reduced pressure and further dried under high vacuo. The crude was dissolved in ACN (100 mL) and treated with cesium carbonate (0.98 mL, 12.28 mmol). It was cooled in an ice bath and chloromethyl methyl ether (0.90 mL, 11.85 mmol) was added slowly over 2 min. The reaction was stirred for 90 minutes. The mixture was evaporated to dryness under reduced pressure and the crude partitioned between water (300 mL) and ethyl acetate (300 mL). The organic was dried with magnesium sulfate and evaporated to dryness under reduced pressure. Purification using silica chromatography (hexane to ethyl acetate gradient) gave the desired 4-bromo-2-fluoro-3-(methoxymethoxy)-6-(tetrahydro-2H-pyran-4-yl)pyridine (1.80 g, 5.62 mmol, 58.4% yield) as a pale yellow oil. MS m/z=320.0, 322.0 [M+H]$^+$. Calculated for $C_{12}H_{15}BrFNO_3$: 319.02.

Step 4: 4-Bromo-2-fluoro-3-(methoxymethoxy)-6-(tetrahydro-2H-pyran-4-yl)pyridine (1.62 g, 5.06 mmol) was dissolved in dry tetrahydrofuran (50 mL) under nitrogen and cooled in a dry ice bath. Butyllithium solution (2.5 M in hexanes, 2.2 mL, 5.50 mmol) was added and the reaction stirred for 5 min. A solution of 5-bromo-2-fluorobenzaldehyde (1.03 g, 5.06 mmol) in dry THF (10 mL) was added and the reaction stirred for 35 min then quenched by addition of saturated ammonium chloride (20 mL). Water (100 mL) and EtOAc (100 mL) were added and the phases mixed and separated. The organic was dried with magnesium sulfate and evaporated to dryness under reduced pressure. Purification using silica chromatography (hexane to EtOAc gradient) gave recovered starting material (0.30 g, 18%), debrominated 2-fluoro-3-(methoxymethoxy)-6-(tetrahydro-2H-pyran-4-yl)pyridine (0.15 g, 0.61 mmol, 12.0% yield) and the desired (5-bromo-2-fluorophenyl)(2-fluoro-3-(methoxymethoxy)-6-(tetrahydro-2H-pyran-4-yl)pyridin-4-yl)methanol (0.85 g, 1.90 mmol)

MS m/z=444.0, 446.0 [M+H]$^+$. Calculated for $C_{19}H_{20}F_2NO_4$: 443.05.

Step 5: (5-Bromo-2-fluorophenyl)(2-fluoro-3-(methoxymethoxy)-6-(tetrahydro-2H-pyran-4-yl)pyridin-4-yl)methanol (0.84 g, 1.90 mmol) was dissolved in DCM (30 mL) and treated with 4-methylmorpholine 4-oxide (0.56 g, 4.74 mmol). Once the reagent had dissolved tetrapropylammonium perruthenate (0.033 g, 0.095 mmol) was added and the pale yellow solution stirred at RT. After 10 min the mixture had turned dark. Additional DCM (50 mL) was added followed by water (50 mL) and saturated ammonium chloride (50 mL). The phases were mixed and separated and the organic dried with magnesium sulfate before evaporating to dryness under reduced pressure. The crude was redissolved in dichloromethane (25 mL) and cooled in an ice bath under nitrogen. Boron tribromide (neat, 0.25 mL, 2.64 mmol) was added and the mixture turned orange yellow. After 10 min saturated sodium bicarbonate (70 mL) and DCM (100 mL) were added. The phases were mixed and separated and the organic dried with magnesium sulfate before evaporating to dryness under reduced pressure. The crude was treated with excess cesium carbonate (1.2 g) and ACN (50 mL) and stirred at room temperature for 10 min. The mixture was evaporated to dryness under reduced pressure. The crude product was partitioned between DCM (100 mL) and water (100 mL). The organic was dried with magnesium sulfate and evaporated to dryness under reduced pressure to give 7-bromo-1-fluoro-3-(tetrahydro-2H-pyran-4-yl)-5H-chromeno[2,3-c]pyridin-5-one (0.645 g, 1.705 mmol, 90% yield) as a white solid. It was used without purification.

MS m/z=378.0, 380.0 [M+H]$^+$. Calculated for $C_{17}H_{13}BrFNO_3$: 377.01.

Step 6: 7-Bromo-1-fluoro-3-(tetrahydro-2H-pyran-4-yl)-5H-chromeno[2,3-c]pyridin-5-one (0.65 g, 1.71 mmol) was suspended in dry THF (100 mL) under nitrogen and cooled in an ice bath. Methylmagnesium bromide (3.0 M in diethyl ether, 1.70 mL, 5.12 mmol) was added and the solids dissolved. It was stirred for another 15 min then quenched by addition of saturated ammonium chloride (15 mL). Ethyl acetate (100 mL) and water (100 mL) were added and the phases mixed and separated. The organic was dried with magnesium sulfate and evaporated to dryness under reduced pressure. The crude was dissolved in dry tetrahydrofuran (80 mL) and treated with HCl (4.0 M solution in 1,4-dioxane, 1.0 mL, 4.00 mmol). It was stirred at 50° C. for 1 h. The reaction was evaporated to dryness under reduced pressure and the crude partitioned between DCM (100 mL) and saturated sodium bicarbonate (70 mL). The organic was dried with magnesium sulfate and evaporated to dryness under reduced pressure. The crude alkene was dissolved in dry THF (50 mL) and cooled in an ice bath. Silver cyanate (0.77 g, 5.12 mmol) was added followed by dropwise addition of a solution of iodine (0.43 g, 1.71 mmol) in dry THF (10 mL). The mixture was stirred for 15 min then removed from the cold bath. ACN (50 mL) was added and the colour of iodine disappeared within 5 min. The mixture was filtered through a pad of celite and the filtrate treated with ammonia in methanol (2 M, 60 mL, 120 mmol). It was stirred at room temperature overnight then evaporated to dryness under reduced pressure and dry loaded onto silica. Purification (0-10% methanol in DCM gradient) gave the desired 7-bromo-1-fluoro-3-(tetrahydro-2H-pyran-4-yl)-5'H-spiro[chromeno[2,3-c]pyridine-5,4'-oxazol]-2'-amine (0.38 g, 0.86 mmol, 50.6% yield) MS m/z=434.0, 436.0 [M+H]$^+$. Calculated for $C_{19}H_{17}BrFN_3O_3$: 433.04.

Example 704 (Method CC10)

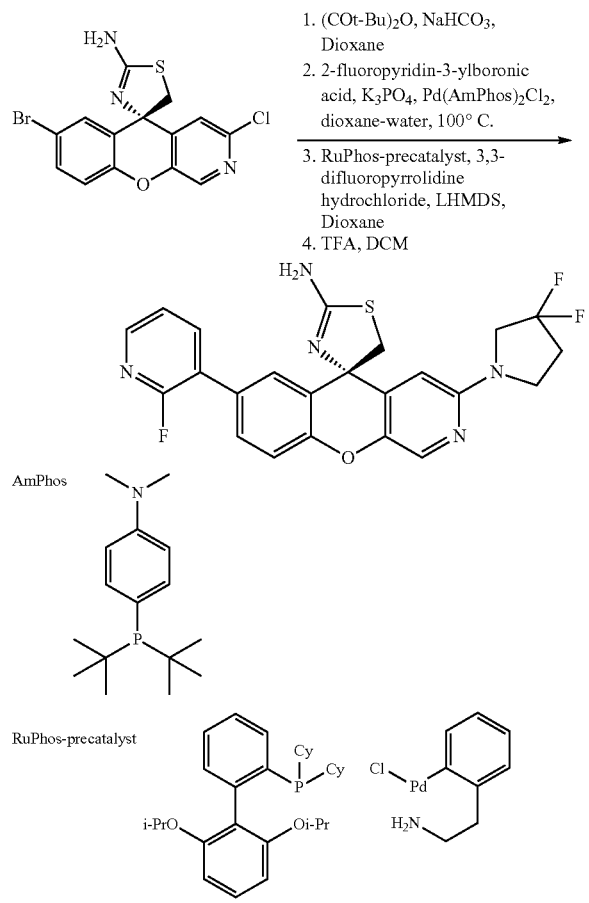

Synthesis of (S)-3-(3,3-difluoropyrrolidin-1-yl)-7-(2-fluoropyridin-3-yl)-5'H-spiro[chromeno[2,3-c]pyridine-5,4'-thiazol]-2'-amine Step 1: To a solution of (S)-7-bromo-3-chloro-5'H-spiro[chromeno[2,3-c]pyridine-5,4'-thiazol]-2'-amine (1.7 g, 4.44 mmol) in 1,4-dioxane (17.77 mL) was added di-tert-butyl dicarbonate (9.70 g, 44.4 mmol) followed by saturated aqueous sodium bicarbonate solution (17.77 mL) at RT. The reaction was stirred at RT for 16 h. The reaction was diluted with water (250 mL) and extracted with EtOAc (3×250 mL). The combined organic layers were washed with brine and dried over sodium sulfate. The solvent was removed under reduced pressure and the crude material was purified by silica gel chromatography to afford (S)-tert-butyl (7-bromo-3-chloro-5'H-spiro[chromeno[2,3-c]pyridine-5,4'-thiazol]-2'-yl)carbamate (1.9933 g, 4.13 mmol, 93% yield)

Step 2: A vial was charged with tert-butyl 7-bromo-3-chloro-5'H-spiro[chromeno[2,3-c]pyridine-5,4'-thiazol]-2'-ylcarbamate (0.250 g, 0.518 mmol), 2-fluoropyridin-3-ylboronic acid (0.15 g, 1.04 mmol), potassium phosphate (0.33 g, 1.55 mmol) and bis-(di-tert-butyl(4-dimethylaminophenyl) phosphine)dichloropalladium(II) (0.018 g, 0.026 mmol). The vial was sealed before evacuating and backfilling with nitrogen. The solids were suspended in 1,4-dioxane (2.22 mL) and water (0.37 mL). The vial was placed in a pre-heated 100° C. oil bath. The reaction was stirred for 1 h before cooling to RT. The reaction was diluted with water (30 mL) and extracted with ether (2×50 mL). The combined organic layers were washed sequentially with water and brine before drying over sodium sulfate. The solvent was removed under reduced pressure and the crude material was purified by silica gel chromatography to afford tert-butyl 3-chloro-7-(2-fluoropyridin-3-yl)-5'H-spiro[chromeno[2,3-c]pyridine-5,4'-thiazole]-2'-ylcarbamate (0.21 g, 0.43 mmol, 83% yield).

Step 3: A vial was charged with (S)-tert-butyl (3-chloro-7-(2-fluoropyridin-3-yl)-5'H-spiro[chromeno[2,3-c]pyridine-5,4'-thiazol]-2'-yl)carbamate (290 mg, 0.58 mmol), RuPhos-precatalyst (42.4 mg, 0.058 mmol) and 3,3-difluoropyrrolidine hydrochloride (167 mg, 1.16 mmol). The vial was sealed before evacuating and backfilling with nitrogen. The solids were suspended in 1,4-dioxane (2 mL) before adding lithium bis(trimethylsilyl)amide solution (1.0M in THF; 2.33 mL, 2.33 mmol) at ambient temperature. The reaction was stirred at ambient temperature for 20 h. Additional amounts of 3,3-difluoropyrrolidine HCl (167 mg, 1.16 mmol), lithium bis(trimethylsilyl)amide solution (1.0M in THF; 1.16 mL, 1.162 mmol), and RuPhos-precatalyst (42.4 mg, 0.058 mmol) were added. After 23 h total reaction time, additional amounts of 3,3-difluoropyrrolidine hydrochloride (167 mg, 1.16 mmol), lithium bis(trimethylsilyl)amide solution (1.0M in THF; 1.16 mL, 1.16 mmol), and RuPhos-precatalyst (42.4 mg, 0.058 mmol) were added. After 29 h total reaction time, additional amounts of 3,3-difluoropyrrolidine hydrochloride (167 mg, 1.16 mmol), lithium bis(trimethylsilyl)amide solution (1.0M in THF; 1.16 mL, 1.16 mmol), and RuPhos-precatalyst (42.4 mg, 0.058 mmol) were added. After 45 h total reaction time, the reaction was diluted with water and EtOAc. The organic layer was separated, washed with brine, and dried over sodium sulfate. The solvent was removed under reduced pressure and the crude was purified by silica gel chromatography to afford (S)-tert-butyl (3-(3,3-difluoropyrolidin-1-yl)-7-(2-fluoropyridin-3-yl)-5'H-spiro[chromeno[2,3-c]pyridine-5,4'-thiazol]-2'-yl)carbamate (76.1 mg, 0.13 mmol, 23.0% yield).

Step 4: To a solution of (S)-tert-butyl 3-(3,3-difluoropyrrolidin-1-yl)-7-(2-fluoropyridin-3-yl)-5'H-spiro[chromeno[2,3-c]pyridine-5,4'-thiazole]-2'-ylcarbamate (76.1 mg, 0.13 mmol) in DCM (1.34 mL) was added TFA (280 µL, 3.63 mmol) at ambient temperature. The reaction was stirred at ambient temperature for 68 hours. The reaction was concentrated under reduced pressure and the resulting material was purified by "catch-and release" technique using a Varian Bond ELUT SCX column. The eluate was concentrated under reduced pressure to afford (S)-3-(3,3-difluoropyrolidin-1-yl)-7-(2-fluoropyridin-3-yl)-5'H-spiro[chromeno[2,3-c]pyridine-5,4'-thiazol]-2'-amine (52.14 mg, 0.11 mmol, 83% yield).

Example 705 (Method CC11)

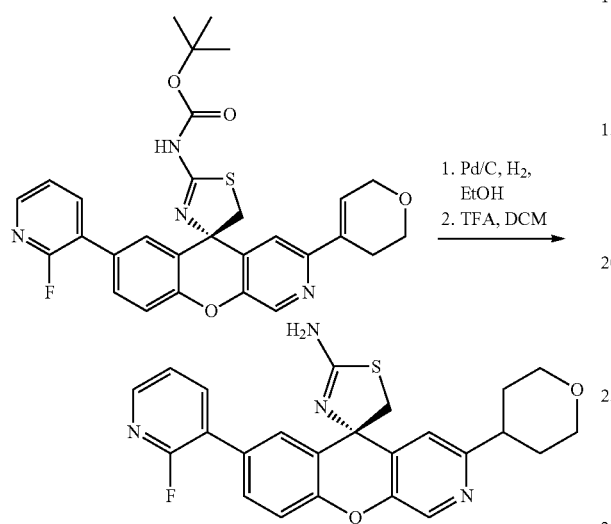

Synthesis of (S)-7-(2-fluoropyridin-3-yl)-3-(tetrahydro-2H-pyran-4-yl)-5'H-spiro[chromeno[2,3-c]pyridine-5,4'-thiazol]-2'-amine Step 1: A flask was charged with (S)-tert-butyl 3-(3,6-dihydro-2H-pyran-4-yl)-7-(2-fluoropyridin-3-yl)-5'H-spiro[chromeno[2,3-c]pyridine-5,4'-thiazole]-2'-ylcarbamate (168.2 mg, 0.31 mmol). The flask was evacuated and backfilled with nitrogen. EtOH (6 mL) was added, followed by palladium on activated carbon (68 mg, 10% wt.). The reaction was placed under a positive atmosphere of hydrogen and stirred at ambient temperature for 64 h. The reaction mixture was filtered through celite and the filtrate was concentrated under reduced pressure. The crude residue was dissolved in EtOH (6 mL). Palladium on activated carbon (68 mg, 10% wt.) was added and the flask was evacuated and backfilled with nitrogen. The reaction was placed under a positive atmosphere of hydrogen and stirred at ambient temperature for 88 hours total reaction time. The reaction was filtered through celite and the filtrate was concentrated under reduced pressure. The crude residue was purified by silica gel chromatography to afford (S)-tert-butyl 7-(2-fluoropyridin-3-yl)-3-(tetrahydro-2H-pyran-4-yl)-5'H-spiro[chromeno[2,3-c]pyridine-5,4'-thiazole]-2'-ylcarbamate (72.4 mg, 0.132 mmol, 42.9% yield).

Step 2: To a solution of (S)-tert-butyl 7-(2-fluoropyridin-3-yl)-3-(tetrahydro-2H-pyran-4-yl)-5'H-spiro[chromeno[2,3-c]pyridine-5,4'-thiazole]-2'-ylcarbamate (72.4 mg, 0.132 mmol) in DCM (1.2 mL) was added TFA (300 µL, 3.89 mmol) at ambient temperature. The reaction was stirred at ambient temperature for 16 h. The reaction was concentrated under reduced pressure and the crude residue was purified by reverse phase chromatography to afford the desired compound as the TFA salt. The purified material was freebased by "catch-and-release" technique using a Varian Bond ELUT SCX column. The eluate was concentrated under reduced pressure to afford (S)-7-(2-fluoropyridin-3-yl)-3-(tetrahydro-2H-pyran-4-yl)-5'H-spiro[chromeno[2,3-c]pyridine-5,4'-thiazol]-2'-amine (20.5 mg, 0.046 mmol, 34.6% yield)

Example 706 (Method CC12)

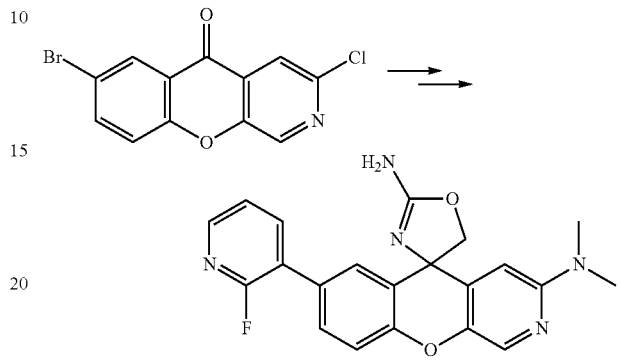

Synthesis of 7-(3-fluoropyridin-2-yl)-N3,N3-dimethyl-5'H-spiro[chromeno[2,3-c]pyridine-5,4'-oxazole]-2',3-diamine Step 1: Dimethylamine, as a solution in water (30 mL, 226 mmol), was added to a solution of 7-bromo-3-chloro-5H-chromeno[2,3-c]pyridin-5-one (2 g, 6.44 mmol) in NMP (90 mL) in a 350 mL pressure tube. The tube was capped with a QianCap™ to vent any excessive pressure and the solution was heated at 100° C. for 14 h. After cooling, the solution was poured into water and the resulting precipitate was collected to afford 7-bromo-3-(dimethylamino)-5H-chromeno[2,3-c]pyridin-5-oneas an orange/yellow solid that contained a small amount of unreacted starting material. The solid was dried in a vacuum oven at 55° C. for over 12 h and then used without further purification. MS m/z=319.0 [M+H].

Step 2: A glass microwave reaction vessel was charged with 7-bromo-3-(dimethylamino)-5H-chromeno[2,3-c]pyridin-5-one (0.50 g, 1.57 mmol), 2-fluoropyridin-3-ylboronic acid (0.44 g, 3.13 mmol), and 2 M aqueous sodium carbonate (4 mL, 8.0 mmol) and dioxane (12 mL). The vessel was capped with a septum and the solution was degassed by bubbling nitrogen gas through the solution for 10 min. Next, Pd(PPh$_3$)$_4$ (0.091 g, 0.078 mmol) was added and the vessel was sealed. The reaction mixture was stirred and heated in a Initiator microwave reactor (Personal Chemistry, Biotage AB, Inc., Upssala, Sweden) at 120° C. for 15 min. The reaction was poured into water and the mixture was extracted with EtOAc and DCM. The combined organic extracts were washed with a 9:1 mixture of aqueous saturated ammonium chloride/ammonium hydroxide, saturated sodium chloride, and dried over sodium sulfate. The solution was filtered and concentrated in vacuo to give the crude material which was used directly for the next reaction. MS m/z=336.1 [M+H].

Step 3: Methylmagnesium chloride, 22 wt % in THF (1.6 mL, 4.76 mmol), was added via syringe to a suspension of 3-(dimethylamino)-7-(2-fluoropyridin-3-yl)-5H-chromeno[2,3-c]pyridin-5-one (0.53 g, 1.57 mmol) in THF (16 mL) at 0° C. The resulting solution was stirred at 0° C. for 1 h. The reaction was quenched with saturated aqueous ammonium chloride at 0° C. and diluted with water and extracted with DCM. The combined organic extracts were washed with a 9:1 mixture of aqueous saturated ammonium chloride/ammonium hydroxide, water, saturated aqueous sodium chloride, and dried over sodium sulfate. The solution was filtered and concentrated in vacuo to give the crude material. The crude material was purified by silica gel chromatography by eluting with 1:2 EtOAc in hexane, to provide 3-(dimethylamino)-7-(2-fluoropyridin-3-yl)-5-methyl-5H-chromeno[2,3-c]pyridin-5-ol as a yellow solid.

Step 4: PPTS (0.082 g, 0.327 mmol) was added in one portion to a suspension of 3-(dimethylamino)-7-(2-fluoropyridin-3-yl)-5-methyl-5H-chromeno[2,3-c]pyridin-5-ol (0.23 g, 0.66 mmol) in DCE (8 mL) and the reaction was heated to 60° C. The resulting solution was stirred until judged complete by LC/MS. The solution was allowed to cool and then poured into saturated aqueous sodium bicarbonate. The layers were seperated and the aqueous layer was extracted with DCM and the combined organic extracts were washed with saturated aqueous sodium chloride and dried over sodium sulfate. The solution was filtered and concentrated in vacuo to afford 7-(2-fluoropyridin-3-yl)-N,N-dimethyl-5-methylene-5H-chromeno[2,3-c]pyridin-3-amine which was used directly for the next reaction without further purification. MS m/z=334.2 [M+H].

Step 5: Silver cyanate (0.15 g, 0.98 mmol) was added in one portion to a solution of iodine (0.091 g, 0.36 mmol) in THF (2 mL) at −15° C. and the mixture was stirred 1 hour before 7-(2-fluoropyridin-3-yl)-N3,N3-dimethyl-5'H-spiro[chromeno[2,3-c]pyridine-5,4'-oxazole]-2',3-diamine as a stock solution in THF (2 mL) was added dropwise and the solution was stirred minutes at 0° C. for 2 h. The reaction was filtered through a pad of celite with THF and then 2 M ammonia in iPrOH (1 mL, 2.0 mmol) was added and the solution was stirred at RT for 12 h and then concentrated. The crude material was taken up in DCM and washed with aqueous sodium thiosulfate, saturated aqueous sodium bicarbonate, saturated aqueous NaCl, and dried over sodium sulfate. The solution was filtered and concentrated in vacuo to give the crude material. The crude material was purified by silica gel chromatography by eluting with 1:25 MeOH in DCM and then repurified by reverse-phase preparative HPLC using a Phenomenex Gemini column, 10 micron, C18, 100 Å, 150× 30 mm, 0.1% TFA in CH$_3$CN/H$_2$O, gradient 5% to 100% over 15 min. The purified compound was partitioned between CHCl$_3$ and 1N NaOH. The layers were separated and the aqueous layer was extracted with CHCl$_3$. The combined organic extracts were washed with aqueous saturated sodium chloride and dried oversodium sulfate. The solution was filtered and concentrated in vacuo to give the above titled compound as the free base. MS m/z=392.2 [M+H].

Example 707 (Method CC13)

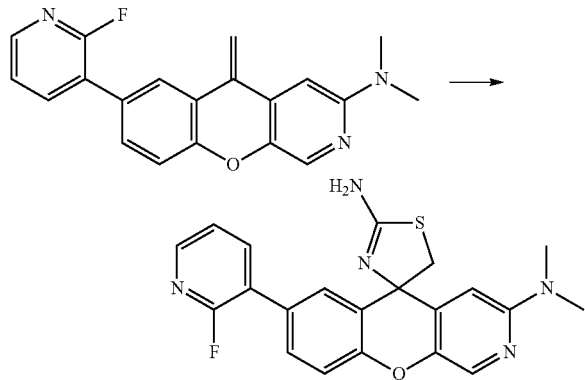

Synthesis of 7-(3-fluoropyridin-2-yl)-N3,N3-dimethyl-5'H-spiro[chromeno[2,3-c]pyridine-5,4'-thiazole]-2',3-diamine Silver thiocyanate (0.16 g, 0.98 mmol) was added in one portion to a solution of iodine (0.091 g, 0.36 mmol) in THF (2 mL) at RT. After 30 minutes, 7-(2-fluoropyridin-3-yl)-N,N-dimethyl-5-methylene-5H-chromeno[2,3-c]pyridin-3-amine (0.11 g, 0.33 mmol, prepared as described in Method CC12) as a stock solution in THF (2 mL) was added dropwise and the solution was stirred 30 min. The reaction was filtered through a pad of celite with THF and then 2 M ammonia in iPrOH (1 mL, 2.0 mmol) was added and the solution was stirred at RT. The reaction was stirred for 2 h and then was concentrated. The crude product was taken up in DCM and filtered. The filtrate was concentrated and the crude material was purified by silica gel chromatography by eluting with 1:25 MeOH in CH$_2$Cl$_2$, to provide the titled compound as an off-white solid. MS m/z=408.2 [M+H].

Example 708 (Method CC14)

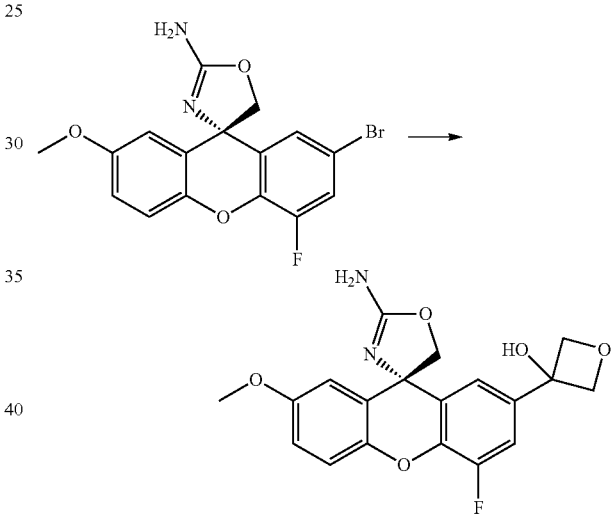

Synthesis of (S)-3-(2-amino-5'-fluoro-2'-methoxy-5H-spiro[oxazole-4,9'-xanthene]-7'-yl)oxetan-3-ol To a RBF was added (S)-2'-bromo-4'-fluoro-7'-methoxy-5H-spiro[oxazole-4,9'-xanthen]-2-amine (2.17 g, 5.72 mmol, prepared as described in Method BB40 but using 4-bromo-2-fluorophenol and 2-bromo-5-methoxybenzoic acid) and THF (30 mL). The resulting mixture was then cooled to −78° C. and butyllithium solution, 2.5M in hexanes (8.01 mL, 20.03 mmol, Aldrich) was added drop wise under N$_2$. The resulting mixture was then stirred at −78° C. for 15 min. Then, oxetan-3-one (1.031 g, 14.31 mmol, Molbridge LLC) in THF (3 mL) was added slowly. After addition, the mixture was stirred at −78° C. for 1.5 h under N$_2$. Then, the mixture was quenched with saturated sodium bicarbonate solution (5 mL) at 0° C. and the mixture was extracted with EtOAc (2×30 mL). The combined organic extracts were dried over MgSO$_4$ and concentrated. The residue was then dissolved in MeOH (30 mL) and silica gel was added. The solvent was removed and the solid mixture was purified by silica gel flash column chromatography using ISCO instrument (solid loading, 50%-

100% EtOAc/hexane, then 10% MeOH in DCM) to give the title compound as a white solid. MS (ESI, positive ion) m/z: 373 (M+H).

Example 709 (Method CC15)

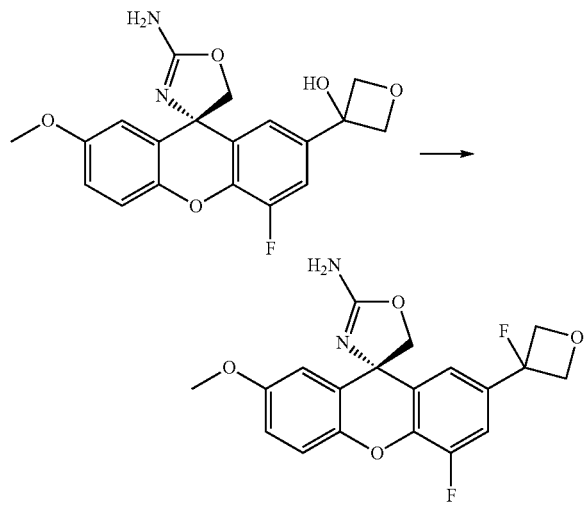

Synthesis of (S)-4'-fluoro-2'-(3-fluorooxetan-3-yl)-7'-methoxy-5H-spiro[oxazole-4,9'-xanthen]-2-amine To a RBF was added (S)-3-(2-amino-5'-fluoro-2'-methoxy-5H-spiro[oxazole-4,9'-xanthene]-7'-yl)oxetan-3-ol (0.28 g, 0.75 mmol, prepared as described in Method CC14) and DCM (5 mL). The resulting mixture was then cooled to 0° C. and (diethylamino)sulfur trifluoride (0.20 mL, 1.50 mmol, Alfa Aesar) was added drop wise. The mixture was then stirred at 0° C. for 15 min and at room temperature for 15 min. Then, the mixture was quenched with saturated sodium bicarbonate (5 mL). The mixture was stirred at 0° C. for 5 min and at RT for 5 min. Then, the organic layer was collected and the aqueous layer was extracted with DCM (1×10 mL). The combined organic extracts were dried over MgSO₄ and silica gel was added. The solvent was removed and the solid mixture was purified by silica gel flash column chromatography using ISCO instrument (solid loading, 20-100% EtOAc/hexane) to give the title compound as a white solid. MS (ESI, positive ion) m/z: 375 (M+H).

Example 710 (Method CC16)

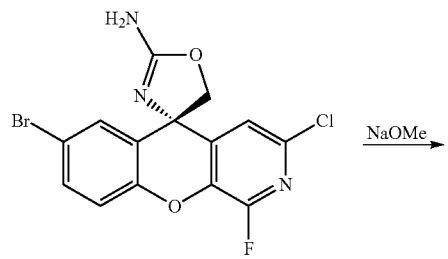

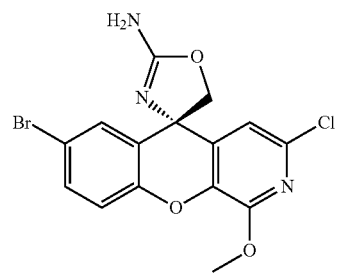

Synthesis of (S)-7-bromo-3-chloro-1-methoxy-5'H-spiro[chromeno[2,3-c]pyridine-5,4'-oxazol]-2'-amine A 100 mL RBF containing a solution of (S)-7-bromo-3-chloro-1-fluoro-5'H-spiro[chromeno[2,3-c]pyridine-5,4'-oxazol]-2'-amine (0.50 g, 1.30 mmol, prepared as described in Method BB33) in methanol (13 mL) was treated with sodium methoxide (0.36 mL, 6.50 mmol) and the resulting suspension was heated to 65° C. for 3 h on a hot-plate. The reaction was cooled to RT and concentrated to dryness under high vacuum. The resulting yellowish residue was taken up in dichloromethane (75 mL), water (25 mL), and the organic layer was separated. The organic layer was dried over sodium sulfate and concentrated to yield the crude product. The crude product was purified by silica gel flash column chromatography and eluted using DCM/MeOH gradient to provide (S)-7-bromo-3-chloro-1-methoxy-5'H-spiro[chromeno[2,3-c]pyridine-5,4'-oxazol]-2'-amine as an amorphous off-white solid. [MS: m/z=395.9 (M+H)].

Example 711 (Method CC17)

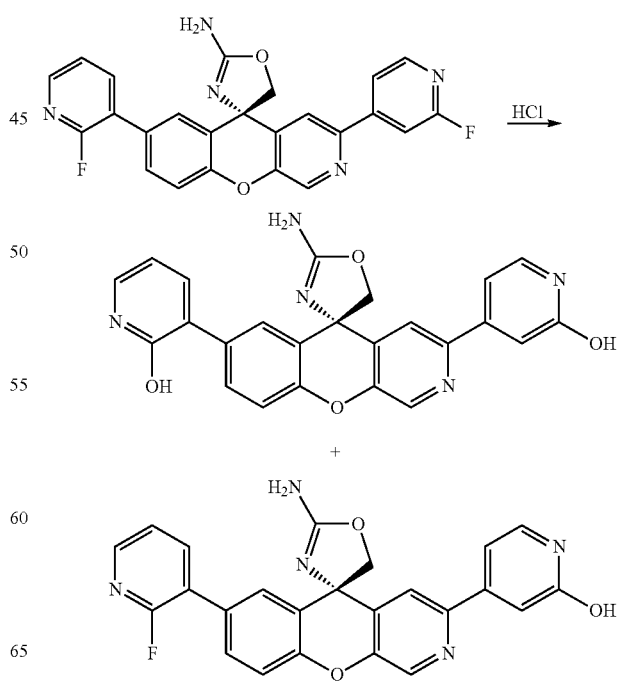

Synthesis of (S)-3-(2'-amino-3-(2-hydroxypyridin-4-yl)-5'H-spiro[chromeno[2,3-c]pyridine-5,4'-oxazole]-7-yl)pyridin-2-ol and (S)-4-(2'-amino-7-(2-fluoropyridin-3-yl)-5'H-spiro[chromeno[2,3-c]pyridine-5,4'-oxazole]-3-yl)pyridin-2-ol A suspension of (S)-7-(2-fluoropyridin-3-yl)-3-(2-fluoropyridin-4-yl)-5'H-spiro[chromeno[2,3-c]pyridine-5,4'-oxazol]-2'-amine (0.55 g, 1.25 mmol, prepared as described in BB41 and AA1 using 2-fluoropyridin-3-ylboronic acid and 2-fluoropyridin-4-ylboronic acid) in 5N HCl (5.5 mL, 27.5 mmol) was heated to 60° C. for 12 h. The reaction was cooled to RT and neutralized with NaOH (5N) till it reached pH ~7.0. Formation of a precipitate was observed. The solid was collected by filtration. The solid was dissolved in MeOH/DMSO (1/3) (5 mL) and loaded on the AGILENT MASS-TRIGERRED HPLC system for purification using a MeCN/Water/0.1% TFA gradient and PHENOMENEX Gemini Axia-5 C-18 column (150×30 mm). The solvent was removed from the pure fractions and the resulting product was dissolved in methanol (3 mL) and neutralized by passing the solution through a Polymer Lab-HCO₃ Macroporous resin cartridge (0.36 mmol loading; 500 mgs), and the filtrate was concentrated and dried under high vacuum. The final products (S)-3,4'-(2'-amino-5'H-spiro[chromeno[2,3-c]pyridine-5,4'-oxazole]-3,7-diyl)dipyridin-2-ol [MS: m/z=440.1 (M+H)] and (S)-4-(2'-amino-7-(2-fluoropyridin-3-yl)-5'H-spiro[chromeno[2,3-c]pyridine-5,4'-oxazole]-3-yl)pyridin-2-ol [MS: m/z=442.1 (M+H)] were collected as amorphous white solids.

Example 712 (Method CC18)

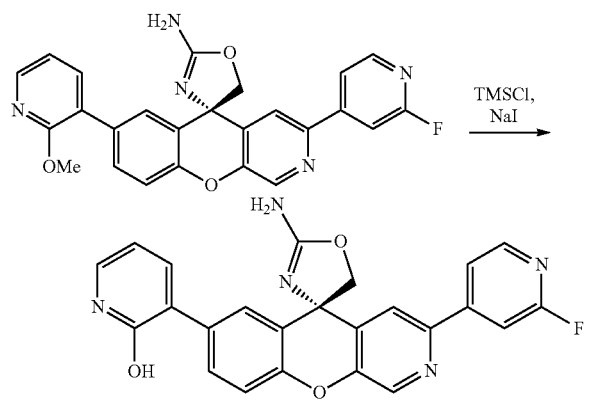

Synthesis of (S)-3-(2'-amino-3-(2-fluoropyridin-4-yl)-5'H-spiro[chromeno[2,3-c]pyridine-5,4'-oxazole]-7-yl)pyridin-2-ol A suspension of (S)-3-(2-fluoropyridin-4-yl)-7-(2-methoxypyridin-3-yl)-5'H-spiro[chromeno[2,3-c]pyridine-5,4'-oxazol]-2'-amine (0.075 g, 0.17 mmol, prepared as described in BB41 and AA1 using 2-methoxypyridin-3-ylboronic acid and 2-fluoropyridin-4-ylboronic acid) and sodium iodide, anhydrous (0.077 g, 0.51 mmol) in acetonitrile (6.0 mL) was treated chlorotrimethylsilane (0.070 mL, 0.55 mmol) and the resulting mixture was stirred at room temperature for 16 h. The reaction was concentrated to dryness on the rotary evaporator, the resulting residue was taken up in dichloromethane (25 mL), water (15 mL), and formation of insoluble solids was observed. The solids were collected by filtration. The solid was dissolved in DMSO (1.5 mL) and loaded on the AGILENT MASS-TRIGGERRED HPLC system for purification using a MeCN/Water/0.1% TFA gradient and PHENOMENEX Gemini Axia-5 C-18 column (150×30 mm). The solvent was removed from the pure fractions in the GENEVAC and the resulting product was dissolved in methanol (1.5 mL) and neutralized by passing the solution through a Polymer Lab-HCO₃ Macroporous resin cartridge (0.36 mmol loading; 500 mgs), and the filtrate was concentrated under high vacuum to yield the product (S)-3-(2'-amino-3-(2-fluoropyridin-4-yl)-5'H-spiro[chromeno[2,3-c]pyridine-5,4'-oxazole]-7-yl)pyridin-2-ol as an amorphous off-white solid [MS: m/z=442.1 (M+H)].

Example 713 (Method CC19)

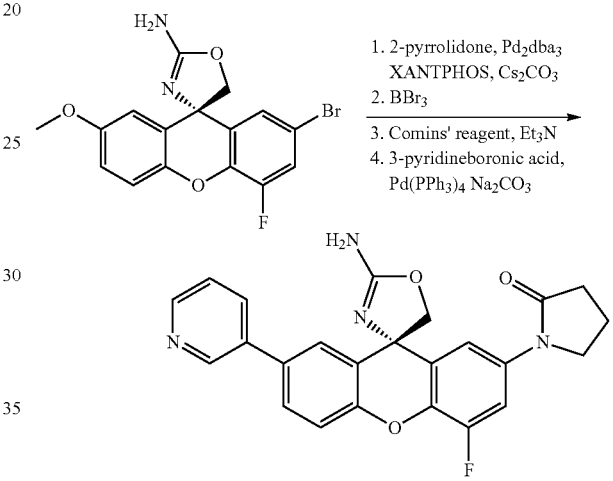

Synthesis of (S)-1-(2-amino-5'-fluoro-2'-(pyridin-3-yl)-5H-spiro[oxazole-4,9'-xanthene]-7'-yl)pyrrolidin-2-one Step 1: Resealable tube was charged with solids: (S)-2'-bromo-4'-fluoro-7'-methoxy-5H-spiro[oxazole-4,9'-xanthen]-2-amine (500 mg, 1.32 mmol, prepared as described in Method BB40 but using 4-bromo-2-fluorophenol and 2-bromo-5-methoxybenzoic acid)), Pd₂ dba₃ (121 mg, 0.13 mmol), (9,9-dimethyl-9H-xanthene-4,5-diyl)bis(diphenylphosphine) (229 mg, 0.40 mmol), cesium carbonate (859 mg, 2.64 mmol). pyrrolidin-2-one (152 μL, 1.98 mmol) and dioxane (5 ml) were added and the mixture was stirred at 100° C. for 60 h. The mixture was diluted with EtOAc, filtered through celite, concentrated and purified on 12 g RediSep Gold column using 10-80% of DCM/MeOH/NH₄OH 90:10:1 in DCM to afford (S)-1-(2-amino-5'-fluoro-2'-methoxy-5H-spiro[oxazole-4,9'-xanthene]-7'-yl)pyrrolidin-2-one.

Step 2: To a solution of (S)-1-(2-amino-5'-fluoro-2'-methoxy-5H-spiro[oxazole-4,9'-xanthene]-7'-yl)pyrrolidin-2-one (377 mg, 0.98 mmol) in DCM (6 mL) boron tribromide (0.2 mL, 2.46 mmol) was added at 0° C. The bath was removed and the mixture was allowed to warm up to RT and stirred for 30 min. The reaction was quenched with sat NaHCO₃ and diluted with DCM. The insoluble material was dissolved by adding MeOH. Organic layer was filtered through celite and concentrated to afford (S)-1-(2-amino-5'-fluoro-2'-hydroxy-5H-spiro[oxazole-4,9'-xanthene]-7'-yl)pyrrolidin-2-one.

Step 3: To a suspension of (S)-1-(2-amino-5'-fluoro-2'-hydroxy-5H-spiro[oxazole-4,9'-xanthene]-7'-yl)pyrrolidin-2-one (300 mg, 0.81 mmol) in DCM (5 mL) N-(5-chloropyridin-2-yl)-1,1,1-trifluoro-N-(trifluoromethylsulfonyl)methanesulfonamide (383 mg, 0.98 mmol) was added at 0° C. The mixture became clear in ~5 min and stirring was continued for another 20 min. The mixture was washed with 1N NaOH, filtered athrough celite, concentrated and purified by FC on 12 g RediSep Gold column using 10-80% DCM/MeOH/NH₄OH 90:10:1 in DCM to afford (S)-2-amino-4'-fluoro-2'-(2-oxopyrolidin-1-yl)-5H-spiro[oxazole-4,9'-xanthene]-7'-yl trifluoromethanesulfonate.

Step 4: Resealable tube was charged with (S)-2-amino-4'-fluoro-2'-(2-oxopyrolidin-1-yl)-5H-spiro[oxazole-4,9'-xanthene]-7'-yl trifluoromethanesulfonate (130 mg, 0.26 mmol), tetrakis(triphenylphosphine)palladium(0) (30.0 mg, 0.026 mmol), pyridin-3-ylboronic acid (51.0 mg, 0.42 mmol). DMF (1.3 mL) and sodium carbonate (2M, 0.4 mL, 0.8 mmol) were added and the mixture was sealed and heated at 90° C. for 2 h. The mixture was partitioned between water (1 mL) and ethyl acetate (5 mL), organic layer was washed with water, concentrated and purified by FC on 12 g RediSep Gold column using 10-80% DCM/MeOH/NH₄OH 90:10:1 in DCM. The fractions containing pure product by TLC were combined and concentrated to afford (S)-1-(2-amino-5'-fluoro-2'-(pyridin-3-yl)-5H-spiro[oxazole-4,9'-xanthene]-7'-yl)pyrolidin-2-one.

Example 714 (Method CC20)

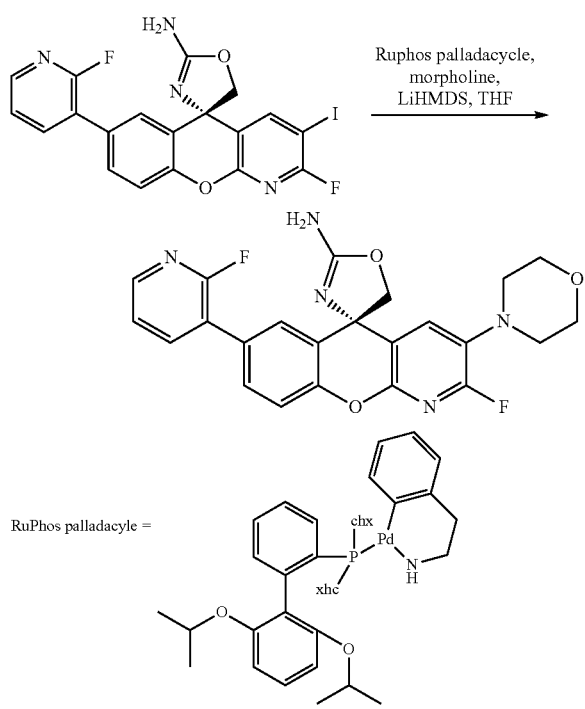

Synthesis of (S)-2-fluoro-7-(2-fluoropyridin-3-yl)-3-morpholino-5'H-spiro[chromeno[2,3-b]pyridine-5,4'-oxazol]-2'-amine A vial charged with (S)-2-fluoro-7-(2-fluoropyridin-3-yl)-3-iodo-5'H-spiro[chromeno[2,3-b]pyridine-5,4'-oxazol]-2'-amine (0.20 g, 0.41 mmol, prepared as described in Method BB34) and Ruphos palladacycle (0.032 g, 0.041 mmol) was treated with morpholine (0.18 mL, 2.03 mmol) and 4 mL THF. LiHMDS (2.03 mL, 2.03 mmol) was added, the vial was capped under argon, and the reaction mixture was allowed to stir overnight. The reaction mixture was purified directly by column chromatography [0-80% (9:1 DCM/MeOH)/heptane] yielding (S)-2-fluoro-7-(2-fluoropyridin-3-yl)-3-morpholino-5'H-spiro[chromeno[2,3-b]pyridine-5,4'-oxazol]-2'-amine (0.044 g, 0.097 mmol). [M+H]+=452.0

Example 715 (Method CC21)

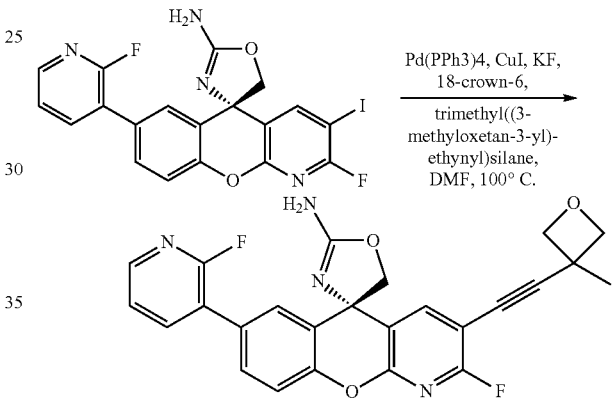

Synthesis of (S)-2-fluoro-7-(2-fluoropyridin-3-yl)-3-((3-methyloxetan-3-yl)ethynyl)-5'H-spiro[chromeno[2,3-b]pyridine-5,4'-oxazol]-2'-amine A vial charged with Pd(Ph₃P)₄ (0.035 g, 0.030 mmol), copper(I) iodide (5.80 mg, 0.030 mmol), 18-crown-6 (0.12 g, 0.46 mmol), potassium fluoride (0.035 g, 0.61 mmol), (S)-2-fluoro-7-(2-fluoropyridin-3-yl)-3-iodo-5'H-spiro[chromeno[2,3-b]pyridine-5,4'-oxazol]-2'-amine (0.15 g, 0.31 mmol, prepared as described in Method BB34), and trimethyl((3-methyloxetan-3-yl)ethynyl)silane (0.077 g, 0.46 mmol) was treated with 1.5 mL DMF, capped under argon, and was heated to 100° C. for 2 h. The reaction mixture was purified directly by column chromatography [0-100% (95:5 EtOAc/MeOH)/hexanes] yielding (S)-2-fluoro-7-(2-fluoropyridin-3-yl)-3-((3-methyloxetan-3-yl)ethynyl)-5'H-spiro[chromeno[2,3-b]pyridine-5,4'-oxazol]-2'-amine (0.095 g, 0.206 mmol, 67.7% yield). MS m/z=461.0 [M+H]+. Calculated for $C_{25}H_{18}F_2N_4O_3$: 460.43.

¹H NMR (400 MHz, MeCN) δ ppm 1.68 (s, 3H) 4.33 (s, 2H) 4.47 (d, J=8 Hz, 2H) 4.81 (d, J=8 Hz, 2H) 7.30 (d, J=8 Hz, 1H) 7.37-7.40 (m, 1H) 7.58-7.62 (m, 2H) 7.92-8.03 (m, 2H) 8.19-8.21 (m, 1H)

Example 716 (Method CC22)

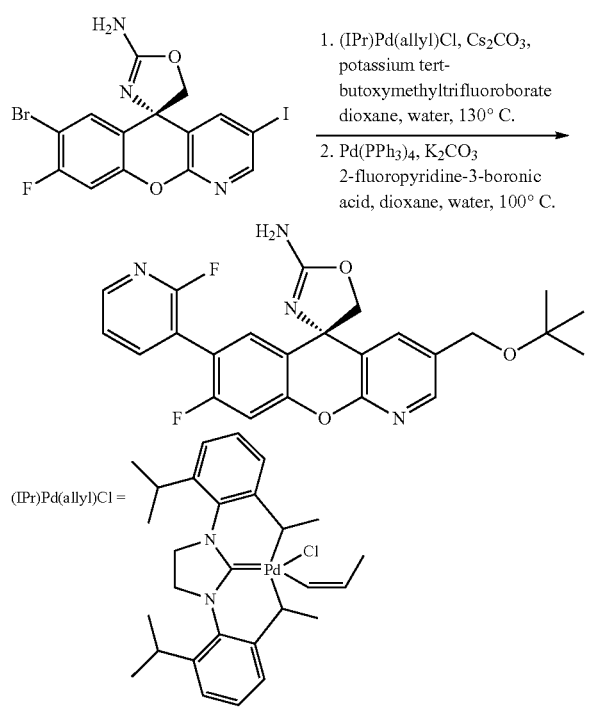

Synthesis of (S)-3-(tert-butoxymethyl)-8-fluoro-7-(2-fluoropyridin-3-yl)-5'H-spiro[chromeno[2,3-b]pyridine-5,4'-oxazol]-2'-amine Step 1: A vial charged with allylchloro[1,3-bis(2,6-di-1-propylphenyl)-4,5-dihydroimidazol-2-ylidene]palladium(ii) (0.072 g, 0.126 mmol), cesium carbonate (1.10 g, 3.36 mmol), potassium tert-butoxymethyltrifluoroborate (0.49 g, 2.52 mmol), and (S)-7-bromo-8-fluoro-3-iodo-5'H-spiro[chromeno[2,3-b]pyridine-5,4'-oxazol]-2'-amine (0.40 g, 0.84 mmol, prepared as described in Method BB24) was treated with 3 mL dioxane and 0.3 mL water, was capped under argon, and was heated to 130° C. overnight. The reaction mixture was diluted with EtOAc, dried over MgSO$_4$ and concentrated. Purification of the crude residue by column chromatography gave (S)-7-bromo-3-(tert-butoxymethyl)-8-fluoro-5'H-spiro[chromeno[2,3-b]pyridine-5,4'-oxazol]-2'-amine (0.073 g, 0.167 mmol, 19.91% yield) with impurities.

Step 2: A solution of pd(Ph$_3$P)$_4$ (0.019 g, 0.017 mmol), 2-fluoropyridin-3-ylboronic acid (0.047 g, 0.34 mmol), (S)-7-bromo-3-(tert-butoxymethyl)-8-fluoro-5'H-spiro[chromeno[2,3-b]pyridine-5,4'-oxazol]-2'-amine (0.073 g, 0.17 mmol), and potassium carbonate (0.12 g, 0.84 mmol) in 1 mL dioxane, was treated with 0.4 mL water and was heated to 100° C. overnight. The reaction mixture was diluted with EtOAc, dried over MgSO$_4$, and concentrated. Purification of the crude residue by column chromatography [0-100% (9:1 DCM:MeOH)/DCM] gave (4'S)-3-(tert-butoxymethyl)-8-fluoro-7-(2-fluoropyridin-3-yl)-5'H-spiro[chromeno[2,3-b]pyridine-5,4'-oxazol]-2'-amine (0.032 g, 0.071 mmol, 42.3% yield). [M+H]+=453.0

Example 717 (Method CC23)

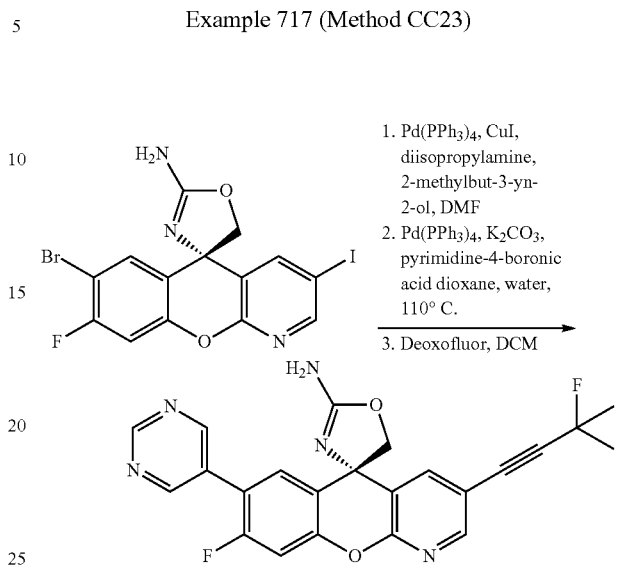

Step 1: A vial charged with Pd(Ph$_3$P)$_4$ (0.073 g, 0.063 mmol), copper(I) iodide (0.012 g, 0.063 mmol), (S)-7-bromo-8-fluoro-3-iodo-5'H-spiro[chromeno[2,3-b]pyridine-5,4'-oxazol]-2'-amine (0.30 g, 0.63 mmol), 2-methylbut-3-yn-2-ol (0.092 mL, 0.95 mmol) and 3 mL DMF was degassed, then treated with DIPA (0.45 mL, 3.15 mmol) and was allowed to stir at RT over the weekend. The reaction mixture was diluted with EtOAc and washed with water. The organics were dried over MgSO$_4$ and concentrated. The crude residue was used in the next step without isolation.

Step 2: The crude residue from step 1 was dissolved in 3 mL dioxane, was treated with pyrimidin-5-ylboronic acid (0.078 g, 0.63 mmol), potassium carbonate (0.44 g, 3.15 mmol), an additional portion of Pd(Ph$_3$P)$_4$ (0.073 g, 0.063 mmol) and 1 mL water. The reaction mixture was placed under argon, and was heated to 110° C. for 2 h. The reaction mixture was then diluted with EtOAc, dried over MgSO$_4$, and concentrated. Purification of the crude residue by column chromatography [0-100% (95:5 EtOAc/MeOH)/heptanes] gave (S)-4-(2'-amino-8-fluoro-7-(pyrimidin-5-yl)-5'H-spiro[chromeno[2,3-b]pyridine-5,4'-oxazole]-3-yl)-2-methylbut-3-yn-2-ol (0.058 g, 0.134 mmol) as a yellow solid.

Step 3: A solution of (S)-4-(2'-amino-8-fluoro-7-(pyrimidin-5-yl)-5'H-spiro[chromeno[2,3-b]pyridine-5,4'-oxazole]-3-yl)-2-methylbut-3-yn-2-ol (0.058 g, 0.13 mmol) in 1.5 mL DCM was cooled to 0° C. and was treated with deoxofluor (0.050 mL, 0.27 mmol). After stirring for one hour, the reaction mixture was quenched with saturated NaHCO$_3$ solution. The reaction mixture was then diluted with EtOAc and washed with water. The organics were dried over MgSO$_4$ and concentrated. Purification of the crude residue by column chromatography [0-80% (9:1 DCM/MeOH)/hexanes] gave (S)-8-fluoro-3-(3-fluoro-3-methylbut-1-ynyl)-7-(pyrimidin-5-yl)-5'H-spiro[chromeno[2,3-b]pyridine-5,4'-oxazol]-2'-amine (0.018 g, 0.042 mmol, 30.9% yield). [M+H]+=434.0

Example 718 (Method CC24)

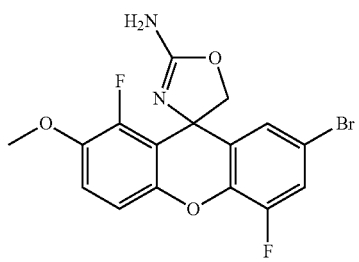 [SMILES: COc1ccc2c(c1F)C1(COC(N)=N1)c1cc(Br)cc(F)c1O2]

Synthesis of 7'-bromo-1',5'-difluoro-2'-methoxy-5H-spiro[oxazole-4,9'-xanthen]-2-amine Step 1: To the suspension of 2-fluoro-3-methoxybenzoic acid (20 g, 118 mmol) in Acetic Acid (100 mL) and water (100 mL) at RT, bromine (12.05 mL, 235 mmol) was added dropwise. The reaction mixture was heated for 1 h at 60° C. The reaction was then cooled to RT and white precipitate was filtered. The solid was washed with excess water and dried to give 6-bromo-2-fluoro-3-methoxybenzoic acid (24.68 g, 99 mmol) as a white solid.

Step 2: To a 1 L RB was added 4-bromo-2-fluorophenol (18.85 mL, 169 mmol), 6-bromo-2-fluoro-3-methoxybenzoic acid (40 g, 161 mmol), copper (I) trifluoromethanesulfonate toluene complex (4.16 g, 8.03 mmol), ethyl acetate (1.6 mL, 16.06 mmol) and cesium carbonate (105 g, 321 mmol) in dry toluene (300 mL). The reaction mixture was stirred at rt for 15 min and heated at 110° C. for overnight. The toluene was decanted and the resulting green sticky precipitate was washed with excess hexanes and then acidified by addition of 6N aqueous HCl. The resulting solution was added water and extracted with EtOAc 3×. The light brown organic phase was then washed by brine and dried by $MgSO_4$. The solution was filtered and concentrated in vacuo to give the crude material 6-(4-bromo-2-fluorophenoxy)-2-fluoro-3-methoxybenzoic acid (45.4 g, 126 mmol, 79% yield) as a brown solid. It was used for next step without further purification.

Step 3: To a 500 mL flask was added 3-bromo-2-fluoro-6-(2-fluoro-4-methoxyphenoxy)benzoic acid (43.45 g, 121 mmol) in conc. sulfuric acid (127 mL, 1815 mmol). The sticky mixture was heated at 60° C. for 2.5 h. The reaction was then poured into ice water very slowly with stirring. The yellow precipitate was filtered through Buchner funnel and washed excess water. Then the filter cake was put in a beaker and carefully neutralized with mixture of 2N aqoueous NaOH solution and saturated aqueous $NaHCO_3$. The mixture was stirred for half an hour and filtered by Buchner funnel again. The light yellow solid was washed by excess water and finally little amount of acetone to yield 2-bromo-1,5-difluoro-7-methoxy-9H-xanthen-9-one (23.34 g, 68.4 mmol, 56.6% yield) as light yellow solid. It was used for next step without further purification.

Step 4: To a slurry of 7-bromo-1,5-difluoro-2-methoxy-9H-xanthen-9-one (22.29 g, 65.3 mmol) in dry tetrahydrofuran (180 mL) was added methylmagnesium bromide (3.0M in diethyl ether) (44.7 mL, 134 mmol) dropwise in ice bath keeping internal temperature at 0° C. After addition of methylmagnesium bromide, the reaction solution was warmed to rt. for 0.5 h. Then the reaction solution was cooled to 0° C. and 100 mL of sat. $NH_4Cl$ was added slowly. The solution was diluted with water and extracted with EtOAc for three times. The organic extract was washed with brine and dried over $MgSO_4$. The solution was filtered and concentrated in vacuo to give the crude material as a yellow foam. It was used for next step without further purification.

Step 5: a) To 7-bromo-1,5-difluoro-2-methoxy-9-methyl-9H-xanthen-9-ol (7.18 g, 20.10 mmol) in dry THF (80 mL) was added HCl (4M in dioxane) (0.30 mL, 1.206 mmol). The reaction mixture was stirred at 50° C. for 1.5 h.

b) To a slurry of silver cyanate (2.3 mL, 60.3 mmol) in 70 mL of THF cooled into 0° C. in ice bath was added iodine (5.36 g, 21.11 mmol) in several portions while keeping the internal temperature at 0° C. The resulting red-brown slurry was stirred for 3 h at 0° C. Then olefin in THF solution from step a) was added slowly through an addition funnel. The reaction mixture was stirred at 0° C. for 45 min. The solution color changed from dark red to grey yellow.

c) Ammonia (2.0M solution in 2-propanol) (50.3 mL, 101 mmol) was added to above solution. The reaction mixture was warmed up to rt and stirred overnight. The reaction mixture was filtered through a pad of celite (if the filtrate is in dark color with $I_2$, then washed by 10% $NaS_2O_3$). The filtrate was concentrated and diluted by EtOAc and water. Then it was transferred into separatory funnel. The organic layer was washed with brine, dired over $MgSO_4$, filtered and concentrated under reduced pressure. The residue was triturate with DCM (~15 mL). The yellow precipitate was collected by Buchner funnel to yield 7'-bromo-1',5'-difluoro-2'-methoxy-5H-spiro[oxazole-4,9'-xanthen]-2-amine (4.5 g, 11.33 mmol, 56.4% yield) as light yellow solid. MS m/z=396.9 [M+H]$^+$.

Example 719 (Method CC25)

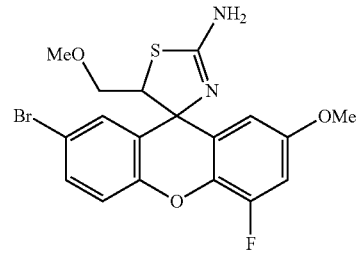 [SMILES: COCC1SC(N)=NC12c1cc(Br)ccc1Oc1c(F)cc(OC)cc12]

Synthesis of 7'-bromo-4'-fluoro-2'-methoxy-5-(methoxymethyl)-5H-spiro[thiazole-4,9'-xanthen]-2-amine Step 1: To a solution of vinylmagnesium chloride (55.9 ml, 89.4 mmol) at −78° C. was added dropwise of a solution of 7-bromo-4-fluoro-2-methoxy-9H-xanthen-9-one (8.0 g, 24.76 mmol) in THF (99 mL). After 30 min, the reaction was allowed to slowly warm to rt, then quenched with 240 mL of saturated aqueous $NH_4Cl$. The mixture was extracted with EtOAc. The organic layer was dried over magnesium sulfate, filtered and concentrated to yield 7-bromo-4-fluoro-2-methoxy-9-vinyl-9H-xanthen-9-ol (8.69 g, 24.76 mmol, 100% yield) as yellow solid.

Step 2: To a 250 mL of RBF were added 7-bromo-4-fluoro-2-methoxy-9-vinyl-9H-xanthen-9-ol (8.69 g, 24.75 mmol), methanol (100 mL, 2475 mmol) and sulfuric acid (0.2M in water) (12.4 mL, 2.48 mmol). The mixture was heated to 55° C. for 25 min. The solvent was removed and the residue was diluted with EtOAc. The organic layer was washed by saturated aqueous $NaHCO_3$. The aqueous layer was further extracted with EtOAc. The organic layers were combined and washed with brine, dried over magnesium sulfate, filtered and concentrated in vacuo to give the crude material as an oil. The crude product was purified by 35% to 50% to 75% to 100% DCM in Heptane to yield 7-bromo-4-fluoro-2-methoxy-9-(2-methoxyethylidene)-9H-xanthene (3.87 g, 10.60 mmol).

Step 3: a) To a solution of iodine (0.19 mL, 3.74 mmol) in THF (14. mL) was added thiocyanatosilver (1.77 g, 10.68 mmol) in one portion. After several minutes, the iodine color disappeared and the mixture became bright yellow. After 35 min, 7-bromo-4-fluoro-2-methoxy-9-(2-methoxyethylidene)-9H-xanthene (1.3 g, 3.56 mmol) was added in one portion and stirring was continued for another 30 min at rt. The resulting yellow suspension was filtered through glass filter funnel and washed with small amount of THF. b) Ammonia (2M solution in 2-propanol) (7.12 ml, 14.24 mmol) was added to the filtrate and the yellow cloudy solution was stirred for 0.5 h at RT. The reaction mixture was concentrated and the residue was diluted with water and extracted with EtOAc. The organic extract was washed with satd NaCl and dried over $MgSO_4$. The solution was filtered and concentrated in vacuo to give the 7'-bromo-4'-fluoro-2'-methoxy-5-(methoxymethyl)-5H-spiro[thiazole-4,9'-xanthen]-2-amine (1.30 g, 2.96 mmol, 83% yield) as a light-yellow foam.

Example 720 (Method CC26)

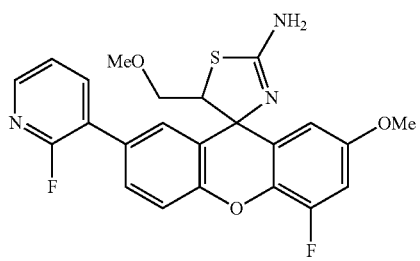 [SMILES: COCC1SC(N)=NC12c1cc(-c3cccnc3F)ccc1Oc1c(F)cc(OC)cc12]

Synthesis of 4'-fluoro-7'-(2-fluoropyridin-3-yl)-2'-methoxy-5-(methoxymethyl)-5H-spiro[thiazole-4,9'-xanthen]-2-amine To a sealed vessel was charge with (2-fluoropyridin-3-yl)boronic acid (1.543 g, 10.95 mmol), 7'-bromo-4'-fluoro-2'-methoxy-5-(methoxymethyl)-5H-spiro[thiazole-4,9'-xanthen]-2-amine (1.34 g, 3.04 mmol, prepared as in Method CC25), potassium carbonate (1.5M in water) (6.08 mL, 9.12 mmol) in dioxane (15 mL). It was purged with $N_2$ and finally AmPHOS (0.13 g, 0.18 mmol) was added. The mixture was heated in oil bath at 100° C. for 20 min. The reaction mixture was allowed to cool to rt. The reaction mixture was diluted with water and extracted with EtOAc. The organic layer was washed with brine, dried over $MgSO_4$, filtered and concentrated in vacuo to give the crude material as an orange oil. The crude material was absorbed onto a plug of silica gel and purified by chromatography through a gold Redi-Sep prepacked silica gel column (40 g), eluting with a gradient of 30% to 50% to 75% DCM/MeOH/NH4OH in 40% EtOAc in heptane, to provide (4S,5S)-4'-fluoro-7'-(2-fluoropyridin-3-yl)-2'-methoxy-5-(methoxymethyl)-5H-spiro[thiazole-4,9'-xanthen]-2-amine (817 mg, 1.80 mmol, 59% yield) as light brown foam.

Example 721 (Method CC27)

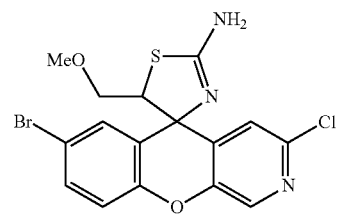 [SMILES: COCC1SC(N)=NC12c1cc(Br)ccc1Oc1cnc(Cl)cc12]

Synthesis of 7-bromo-3-chloro-5'-(methoxymethyl)-5'H-spiro[chromeno[2,3-c]pyridine-5,4'-thiazol]-2'-amine Step 1: To a solution of 7-bromo-3-chloro-5H-chromeno[2,3-c]pyridin-5-one (3.0 g, 9.66 mmol) at –78° C. in THF (48 mL) was added dropwise of vinylmagnesium chloride (17.51 mL, 28.0 mmol). After 30 min, the reaction was allowed to slowly warm to rt, then the reaction was quenched with 60 mL of saturated aqueious $NH_4Cl$. The mixture was extracted with EtOAc. The organic layer was dried over $MgSO_4$, filtered and concentrated in vacuo to yield 3.2 g of crude product as orange foam. This material was added ~4 mL of $Et_2O$ and precipitate was formed and filtered through Bucher funnel to yield 7-bromo-3-chloro-5-vinyl-5H-chromeno[2,3-c]pyridin-5-ol (2.70 g, 7.97 mmol) as a yellow solid.

Step 2: To a sealed vessel was added 7-bromo-3-chloro-5-vinyl-5H-chromeno[2,3-c]pyridin-5-ol (2.50 g, 7.38 mmol), methanol (59.8 mL, 1477 mmol) and sulfuric acid (0.2M in water) (3.70 mL, 0.74 mmol). The clear solution was heated to 50° C. over the weekend. The reaction mixture became light yellow heterogenous. The solvent was removed by rotovap and the residue was diluted with 125 mL of EtOAc. The organic solution was washed with saturated aqueous $NaHCO_3$ and brine, dried over $MgSO_4$, filtered and concentrated in vacuo to give the crude material 7-bromo-3-chloro-5-(2-methoxyethylidene)-5H-chromeno[2,3-c]pyridine (2.40 g, 6.81 mmol, 92% yield) as a yellow solid.

Step 3: a) To a solution of iodine (0.50 ml, 9.78 mmol) in THF (21 mL) was added thiocyanatosilver (3.25 g, 19.57 mmol) in one portion. After 20 minutes, the iodine color disappeared and the mixture became orange. 7-Bromo-3-chloro-5-(2-methoxyethylidene)-5H-chromeno[2,3-c]pyridine (1.5 g, 4.25 mmol) was added and stirring was continued for 40 min at 55° C. and 10 min at 65° C. Then the reaction mixture was cooled to rt and filtered. The filtrate was collected into a 100 mL flask.

b) Ammonia (2M solution in 2-propanol) (8.5 mL, 17.02 mmol) was added to the filtrate and the orange solution was stirred for 1.5 h at rt. The solvent was reduced and the organic mixture was washed by sat. $NaHCO_3$. The aqueous layer was extracted with EtOAc. The organic layers were combined and washed with brine, dried over $MgSO_4$, filtered and concentrated to give the crude material as a orange oil. The crude material was passed through 25 g of SCX column and eluent with 2M $NH_3$ in MeOH with some acetone to give 7-bromo-3-chloro-5'-(methoxymethyl)-5'H-spiro[chromeno[2,3-c]pyridine-5,4'-thiazol]-2'-amine (1.53 g, 3.59 mmol, 84% yield) as light brown foam.

Example 722 (Method CC28)

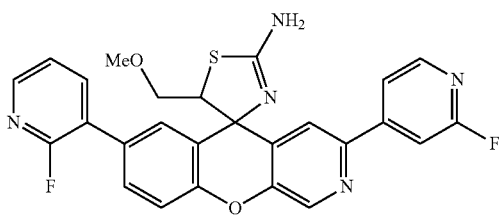 [SMILES: COCC1SC(N)=NC12c1cc(-c3cccnc3F)ccc1Oc1cnc(-c3ccnc(F)c3)cc12]

Synthesis of 7-(2-fluoropyridin-3-yl)-3-(2-fluoropyridin-4-yl)-5'-(methoxymethyl)-5'H-spiro[chromeno[2,3-c]pyridine-5,4'-thiazol]-2'-amine Step 1: To a microwave vessel was added 7-bromo-3-chloro-5'-(methoxymethyl)-5'H-spiro[chromeno[2,3-c]pyridine-5,4'-thiazol]-2'-amine (1.50 g, 3.52 mmol, prepared as described in Method CC27), potassium phosphate (2.24 g, 10.55 mmol), (2-fluoropyridin-3-yl)boronic acid (1.14 g, 8.09 mmol), 1,1-bis[(di-t-butyl-p-dimethylaminophenyl]palladium(ii) chloride (0.25 g, 0.35 mmol), dioxane (13.2 mL), and water (4.4 mL). The resulting mixture was then heated at 100° C. in a microwave for 10 min. The reaction mixture was diluted with water and extracted with EtOAc. The organic extract was washed with brine, dried over MgSO₄, filtered and concentrated in vacuo to give the crude material as an orange solid. The crude material was absorbed onto a plug of silica gel and purified by chromatography through a gold Redi-Sep pre-packed silica gel column (80 g), eluting with a gradient of 30% to 45% to 60% DCM/MeOH/NH4OH (90/10/1) in 40% EtOAc in Heptane, to provide 3-chloro-7-(2-fluoropyridin-3-yl)-5'-(methoxymethyl)-5'H-spiro[chromeno[2,3-c]pyridine-5,4'-thiazol]-2'-amine (1.04 g, 2.35 mmol, 66.8% yield) as off-white solid.

Step 2: To a vial was added 3-chloro-7-(2-fluoropyridin-3-yl)-5'-(methoxymethyl)-5'H-spiro[chromeno[2,3-c]pyridine-5,4'-thiazol]-2'-amine (715 mg, 1.61 mmol), potassium phosphate (1.20 g, 5.65 mmol), (2-fluoropyridin-4-yl)boronic acid (910 mg, 6.46 mmol), and then dioxane (8.1 mL) and water (2.7 mL) were added. The mixture was purged with N₂ and finally 1,1-bis[(di-t-butyl-p-dimethylaminophenyl]palladium(II) chloride (114 mg, 0.16 mmol) was added. The resulting mixture was then heated 135° C. in a microwave for 15 min. The reaction mixture were diluted with EtOAc and water. The organic extract was washed with brine, dried over MgSO₄, filtered and concentrated in vacuo to give the crude material as a orange solid. Small amount of DCM was added and light brown precipitate formed. After filtration through Buchner funnel gave (4'S,5'S)-7-(2-fluoropyridin-3-yl)-3-(2-fluoropyridin-4-yl)-5'-(methoxymethyl)-5'H-spiro[chromeno[2,3-c]pyridine-5,4'-thiazol]-2'-amine (523 mg, 1.04 mmol, 64% yield) as light brown solid.

Example 723 (Method CC29)

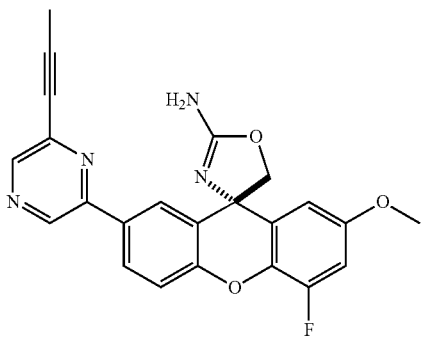

Synthesis of (S)-4'-fluoro-2'-methoxy-7'-(6-(prop-1-ynyl)pyrazin-2-yl)-5H-spiro[oxazole-4,9'-xanthen]-2-amine Combined tetrakis(triphenylphosphine)palladium (54.2 mg, 0.047 mmol), (S)-4'-fluoro-2'-methoxy-7'-(4,4,5,5-tetramethyl-1,3,2-dioxaborolan-2-yl)-5H-spiro[oxazole-4,9'-xanthen]-2-amine (200 mg, 0.47 mmol, prepared as described in Method BB40) and 2-chloro-6-(prop-1-ynyl)pyrazine (93 mg, 0.61 mmol) in a sealable tube and potassium carbonate (1.5 M) (1.6 mL, 2.35 mmol) was added. The tube was sealed and heated at 110° C. in a microwave for 8 min. The reaction solution was diluted with water and extractd by EtOAc. The layers were separated and the aqueous layer was extracted with EtOAc again. The combined organic layers were washed with brine, dried over magnesium sulfate, filtered and concentrated in vacuo to provide a brown oil that was purified by chromatography through a gold Redi-Sep pre-packed silica gel column using a gradient of 25% to 50% to 80% DCM: MeOH: NH₄OH (90:10:1) in 40% EtOAc in hexane to provide (S)-4'-fluoro-2'-methoxy-7'-(6-(prop-1-ynyl)pyrazin-2-yl)-5H-spiro[oxazole-4,9'-xanthen]-2-amine (60 mg, 0.144 mmol, 30.7% yield) as white solid.

Example 724 (Method CC30)

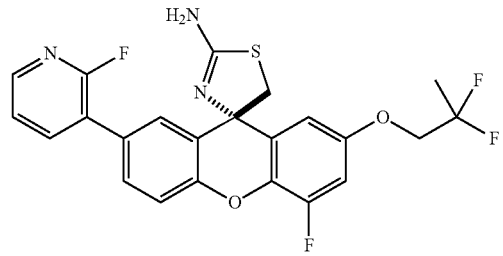

Synthesis of (S)-2'-(2,2-difluoropropoxy)-4'-fluoro-7'-(2-fluoropyridin-3-yl)-5H-spiro[thiazole-4,9'-xanthen]-2-amine A glass microwave reaction vessel was charged with (S)-2-amino-4'-fluoro-7'-(2-fluoropyridin-3-yl)-5H-spiro[thiazole-4,9'-xanthen]-2'-ol (230 mg, 0.58 mmol, prepared as described in Method BB26 and Example 2 but using 7-bromo-4-fluoro-2-methoxy-9H-xanthen-9-one), cesium carbonate (302 mg, 0.93 mmol) and 2,2-difluoropropyl 4-methylbenzenesulfonate (159 mg, 0.64 mmol) in DMF (2.5 mL). The reaction mixture was purged with N₂ and finally potassium iodide (192 mg, 1.16 mmol) was added. The reaction mixture was stirred and heated in a Initiator microwave reactor at 160° C. for 1.5 h. Then it was diluted with water and extractd by EtOAc. The layers were separated and the aqueous layer was extracted with EtOAc again. The combined organic layers were washed with brine, dried over magnesium sulfate, filtered and concentrated in vacuo to provide crude product that was purified by chromatography through a Redi-Sep pre-packed silica gel column (24 g), eluting with a gradient of 15% to 30% to 60% DCM/MeOH/NH4OH (90/10/1) in 40% EtOAc in Heptane to provide (S)-2'-(2,2-difluoropropoxy)-4'-fluoro-7'-(2-fluoropyridin-3-yl)-5H-spiro[thiazole-4,9'-xanthen]-2-amine (18 mg, 0.017 mmol, 4.78% yield) as off-white solid. MS m/z=486.0 [M+H]⁺. ¹H NMR (400 MHz, DMSO-d₆) ppm 1.75 (t, J=19.32 Hz, 3 H) 3.34-3.49 (m, 2 H) 4.19-4.43 (m, 2 H) 6.81 (dd, J=2.89, 1.61 Hz, 1 H) 7.05 (s, 2

H) 7.16 (dd, J=12.28, 2.98 Hz, 1 H) 7.36-7.44 (m, 1 H) 7.50 (ddd, J=7.26, 5.01, 1.91 Hz, 1 H) 7.58-7.66 (m, 2 H) 8.09 (ddd, J=10.34, 7.51, 1.91 Hz, 1 H) 8.25 (dt, J=4.82, 1.55 Hz, 1 H)

Example 725 (Method CC31)

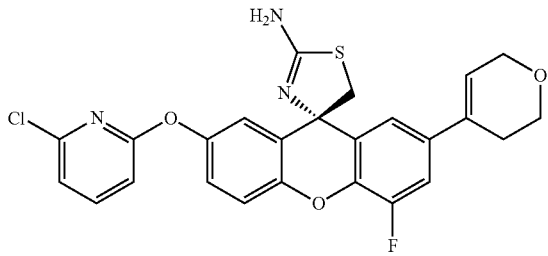 [SMILES: NC1=N[C@@]2(CS1)c1cc(Oc3cccc(Cl)n3)ccc1Oc1c(F)cc(C3=CCOCC3)cc12]

Synthesis of (S)-7'-((6-chloropyridin-2-yl)oxy)-2'-(3, 6-dihydro-2H-pyran-4-yl)-4'-fluoro-5H-spiro[oxazole-4,9'-xanthen]-2-amine A glass microwave reaction vessel was charged with 2-chloro-6-fluoropyridine (88 mg, 0.67 mmol), cesium carbonate (0.027 mL, 0.33 mmol) and (S)-2-amino-2'-(3,6-dihydro-2H-pyran-4-yl)-4'-fluoro-5H-spiro[oxazole-4,9'-xanthen]-7'-ol (82 mg, 0.22 mmol, prepared as described in Method BB40 and Example 2 but using 4-bromo-2-fluorophenol and 2-bromo-5-methoxybenzoic acid) in DMF (0.8 mL). The reaction mixture was stirred and heated in a Initiator microwave reactor at 100° C. for 35 min. Then it was heated at 120° C. for 5 min. The crude material was purified by reverse-phase preparative HPLC using 0.1% TFA in $CH_3CN/H_2O$, gradient 35% to 65% to provide (S)-7'-(6-chloropyridin-2-yloxy)-2'-(3,6-dihydro-2H-pyran-4-yl)-4'-fluoro-5H-spiro[oxazole-4,9'-xanthen]-2-amine (36 mg, 0.075 mmol, 33.7% yield) as a off-white solid.

Example 726 (Method CC32)

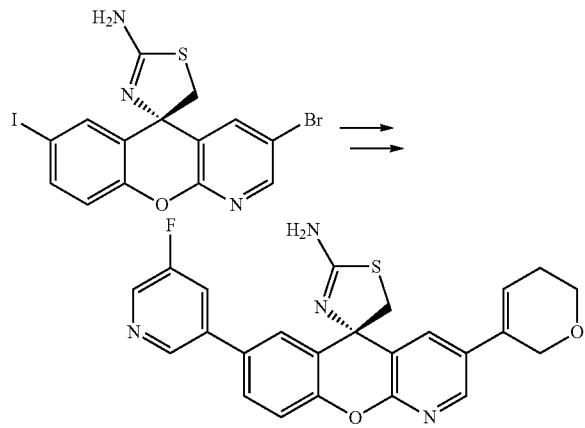

Step 1: A vial was charged with (S)-3-bromo-7-iodo-5'H-spiro[chromeno[2,3-b]pyridine-5,4'-thiazol]-2'-amine (300 mg, 0.63 mmol, prepared as described in Method BB26), potassium carbonate (437 mg, 3.16 mmol), 5-fluoropyridin-3-ylboronic acid (178 mg, 1.27 mmol), tetrakis(triphenylphosphine)palladium(0) (73.1 mg, 0.063 mmol), dioxane (4.22 mL) and water (2.12 mL). The reaction was stirred and heated at 100° C. for 1 h. After cooling for rt, the organic layer was separated with a separatory funnel, dried over sodium sulfate, filtered, and concentrated to afford a yellow oil which was purified by silica gel chromatography (Redi-Sep pre-packed silica gel column (24 g), 0-50% EtOAc in hexanes to provide a white solid, (S)-3-bromo-7-(5-fluoropyridin-3-yl)-5'H-spiro[chromeno[2,3-b]pyridine-5,4'-thiazol]-2'-amine (130 mg, 0.29 mmol, 46%). MS m/z=443.0 [M+H]⁺. Calc'd for $C_{19}H_{12}BrFN_4OS$: 441.99.

Step 2: A microwave vial was charged with (S)-3-bromo-7-(5-fluoropyridin-3-yl)-5'H-spiro[chromeno[2,3-b]pyridine-5,4'-thiazol]-2'-amine (90 mg, 0.20 mmol), potassium carbonate (140 mg, 1.02 mmol), 2-(5,6-dihydro-2H-pyran-3-yl)-4,4,5,5-tetramethyl-1,3,2-dioxaborolane (85 mg, 0.41 mmol), tetrakis(triphenylphosphine)palladium(0) (23.46 mg, 0.020 mmol), dioxane (1.35 mL) and water (0.68 mL). The reaction was heated in the microwave at 100° C. for 40 min. After cooling for rt, the organic layer was separated with a separatory funnel, dried over sodium sulfate, filtered, and concentrated to afford a yellow oil which was purified by silica gel chromatography (Redi-Sep pre-packed silica gel column (12 g), 0-100% EtOAc in 90:10 $CH_2Cl_2$:$CH_3OH$ to provide a white solid, (S)-3-(5,6-dihydro-2H-pyran-3-yl)-7-(5-fluoropyridin-3-yl)-5'H-spiro[chromeno[2,3-b]pyridine-5,4'-thiazol]-2'-amine (45 mg, 0.10 mmol, 50% yield). MS m/z=447.2 [M+H]⁺. Calc'd for $C_{24}H_{19}FN_4O_2S$: 446.5.

Example 727 (Method CC33)

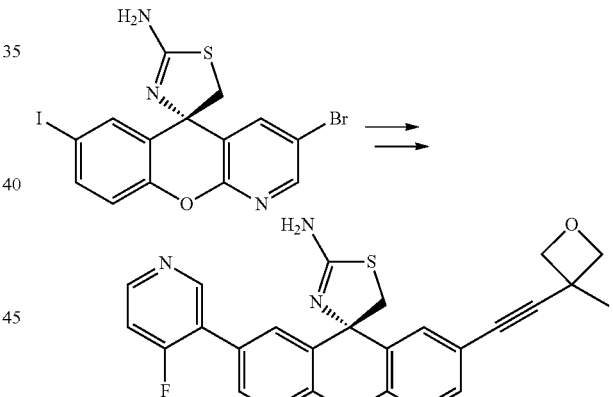

Step 1: A pressure reaction vessel was charged with (S)-3-bromo-7-iodo-5'H-spiro[chromeno[2,3-b]pyridine-5,4'-thiazol]-2'-amine (1.2 g, 2.53 mmol, prepared as described in Method BB26), potassium carbonate (1.75 g, 12.66 mmol), 4-fluoropyridin-3-ylboronic acid (0.71 g, 5.06 mmol), tetrakis(triphenylphosphine)palladium(0) (0.29 g, 0.25 mmol), dioxane (16.87 mL) and water (8.44 mL). The reaction was stirred and heated at 100° C. for 45 min. After cooling for rt, LCMS showed about 50% conversion. More Pd(PPh₃)₄ (30 mg) and 4-fluoropyridin-3-ylboronic acid (300 mg) were added and reaction was heated at 100° C. for another 30 min. After cooling for rt, the organic layer was separated with a separatory funnel, dried over sodium sulfate, filtered, and concentrated to afford yellow oil which was purified with reverse phase HPLC. Fractions containing product were concentrated and saturated aq. NaHCO₃ (25 mL) was added. A white solid precipitated out of solution which was filtered off and dried to afford a white solid, (S)-3-bromo-7-(4-fluoropyridin-3-yl)-5'H-spiro[chromeno[2,3-b]pyridine-5,4'-thiazol]-2'-amine (0.51 g, 1.15 mmol, 46% yield). MS m/z=443.0 [M+H]$^+$. Calc'd for $C_{19}H_{12}BrFN_4OS$: 441.99.

Step 2: A vial was charged with (S)-3-bromo-7-(4-fluoropyridin-3-yl)-5'H-spiro[chromeno[2,3-b]pyridine-5,4'-thiazol]-2'-amine (120 mg, 0.27 mmol), copper(I) iodide (20.62 mg, 0.11 mmol), and tetrakis(triphenylphosphine)palladium (31.3 mg, 0.027 mmol). The vial was flushed with Ar (g), then DMF (1 mL), and trimethyl((3-methyloxetan-3-yl)ethynyl)silane (137 mg, 0.81 mmol), DIPA (574 µL, 4.06 mmol) were added in sequence. The vial was flushed with Ar (g), sealed, and placed in a 90° C. oil bath. The mixture was stirred overnight. After cooling to rt, the crude was purified by silica gel chromatography (Redi-Sep pre-packed silica gel column (40 g), 0-80% EtOAc in 90:10 $CH_2Cl_2$:$CH_3OH$ to provide a white solid, (S)-7-(4-fluoropyridin-3-yl)-3-((3-methyloxetan-3-yl)ethynyl)-5'H-spiro[chromeno[2,3-b]pyridine-5,4'-thiazol]-2'-amine (35 mg, 0.076 mmol, 28% yield).

MS m/z=459.2 [M+H]$^+$. Calc'd for $C_{25}H_{19}FN_4O_2S$: 458.51.

Example 728 (Method CC34)

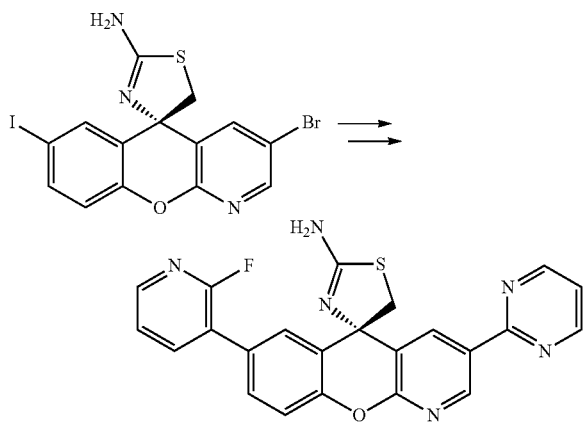

Step 1: A pressure reaction vessel was charged with (S)-3-bromo-7-iodo-5'H-spiro[chromeno[2,3-b]pyridine-5,4'-thiazol]-2'-amine (1.512 g, 3.19 mmol, prepared as described in Method BB26), potassium carbonate (2.20 g, 15.95 mmol), 2-fluoropyridin-3-ylboronic acid (0.72 g, 5.10 mmol), tetrakis(triphenylphosphine)palladium(0) (0.37 g, 0.32 mmol), dioxane (21.26 mL) and water (10.63 mL). The reaction was stirred and heated at 100° C. for 1 h. After cooling for rt, the reaction was diluted with water (25 mL) and poured into a separatory funnel containing ethyl acetate (50 mL). The layers were separated and the aqueous layer was extracted with EtOAc (1×100 mL). The combined organic layers were washed with water, dried over sodium sulfate, filtered, and concentrated in vacuo to provide a brown foam that was purified by silica gel chromatography (Redi-Sep pre-packed silica gel column (40 g), 0-100% EtOAc in 90/10 $CH_2Cl_2$:$CH_3OH$ to provide a white solid, (S)-3-bromo-7-(2-fluoropyridin-3-yl)-5'H-spiro[chromeno[2,3-b]pyridine-5,4'-thiazol]-2'-amine (0.65 g, 1.47 mmol, 46.0% yield). MS m/z=443.0 [M+H]$^+$. Calc'd for $C_{19}H_{12}BrFN_4OS$: 441.99.

Step 2: A vial was charged with (S)-3-bromo-7-(2-fluoropyridin-3-yl)-5'H-spiro[chromeno[2,3-b]pyridine-5,4'-thiazol]-2'-amine (100 mg, 0.23 mmol), AmPhos (15.97 mg, 0.023 mmol), 2-(tributylstannyl)pyrimidine (333 mg, 0.90 mmol) and dioxane (1.50 mL). The vial was purged with Ar (g), sealed, and heated to 100° C. overnight. After cooling to rt, crude was diluted with MeOH (3 mL) and purified with reverse phase HPLC. Fractions containing product were washed with saturated aq. $NaHCO_3$ (15 mL) and extracted with ethyl acetate (1×100 mL). The combined organic layers were dried over sodium sulfate, filtered, and concentrated in vacuo to provide a white solid, (S)-7-(2-fluoropyridin-3-yl)-3-(pyrimidin-2-yl)-5'H-spiro[chromeno[2,3-b]pyridine-5,4'-thiazol]-2'-amine (12 mg, 0.027 mmol, 12% yield). MS m/z=443.0 [M+H]$^+$. Calc'd for $C_{23}H_{15}FN_6OS$: 442.47.

Example 729 (Method CC35)

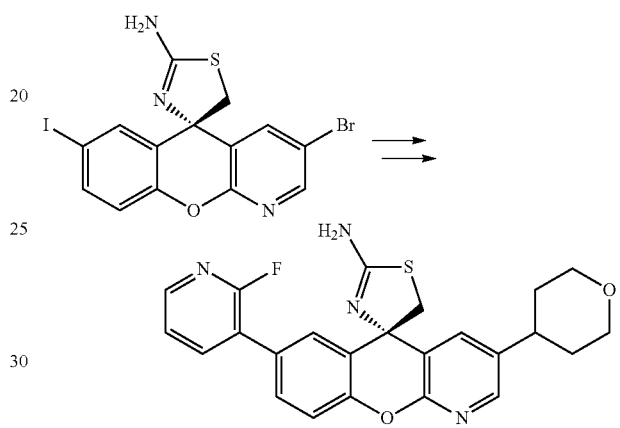

Step 1: A pressure reaction vessel was charged with (S)-3-bromo-7-iodo-5'H-spiro[chromeno[2,3-b]pyridine-5,4'-thiazol]-2'-amine (1.51 g, 3.19 mmol), potassium carbonate (2.20 g, 15.95 mmol), 2-fluoropyridin-3-ylboronic acid (0.72 g, 5.10 mmol), tetrakis(triphenylphosphine)palladium(0) (0.37 g, 0.32 mmol), dioxane (21.3 mL) and water (10.6 mL). The reaction was stirred and heated at 100° C. for 1 h. After cooling to rt, the reaction was diluted with water (25 mL) and poured into a separatory funnel containing EtOAc (50 mL). The layers were separated and the aqueous layer was extracted with EtOAc (1×100 mL). The combined organic layers were washed with water, dried over sodium sulfate, filtered, and concentrated in vacuo to provide a brown foam that was purified by silica gel chromatography (Redi-Sep pre-packed silica gel column (40 g), 0-100% EtOAc in 90:10 $CH_2Cl_2$:$CH_3OH$ to provide a white solid, (S)-3-bromo-7-(2-fluoropyridin-3-yl)-5'H-spiro[chromeno[2,3-b]pyridine-5,4'-thiazol]-2'-amine (0.65 g, 1.47 mmol). MS m/z=443.0 [M+H]$^+$. Calc'd for $C19H_{12}BrFN4OS$: 441.99.

Step 2: A microwave vessel was charged with (S)-3-bromo-7-(2-fluoropyridin-3-yl)-5'H-spiro[chromeno[2,3-b]pyridine-5,4'-thiazol]-2'-amine (0.12 g, 0.27 mmol), potassium carbonate (0.19 g, 1.35 mmol), 2-(3,6-dihydro-2H-pyran-4-yl)-4,4,5,5-tetramethyl-1,3,2-dioxaborolane (0.11 g, 0.54 mmol), tetrakis(triphenylphosphine)palladium(0) (0.031 g, 0.027 mmol), dioxane (1.81 mL) and water (0.90 mL). The reaction was heated in a microwave at 100° C. for 45 min. After cooling to rt, the organic layer was separated with a separatory funnel, dried over sodium sulfate, filtered, and concentrated to afford a yellow oil which was purified by silica gel chromatography (Redi-Sep pre-packed silica gel column (40 g), 0-100% EtOAc in 90/10 $CH_2Cl_2$:$CH_3OH$ to provide a white solid, (S)-3-(3,6-dihydro-2H-pyran-4-yl)-7-(2-fluoropyridin-3-yl)-5'H-spiro[chromeno[2,3-b]pyridine-5,4'-thiazol]-2'-amine (0.1 g, 0.22 mmol, 83% yield). MS m/z=447.2 [M+H]$^+$. Calc'd for $C_{24}H_{19}FN_4O_2S$: 446.5.

Step 3: To a 15-mL round-bottomed flask was added (S)-3-(3,6-dihydro-2H-pyran-4-yl)-7-(2-fluoropyridin-3-yl)-5'H-spiro[chromeno[2,3-b]pyridine-5,4'-thiazol]-2'-amine (100 mg, 0.22 mmol) and palladium on carbon (10% wet, 95 mg, 0.90 mmol) in methanol (2.24 mL). The mixture was stirred under an a hydrogen ballon atmosphere. After 3 h, LC/MS showed no reaction took place. More palladium on carbon (95 mg, 0.90 mmol) was added and the mixture was stirred under a hydrogen ballon atmosphere overnight. Next day LCMS showed a small amount of desired product and rest was the SM. More palladium on carbon (220 mg) was added and stirred under a hydrogen ballon atmosphere overnight. The crude was submitted to DAS group for purification to afford a white solid, ((S)-7-(2-fluoropyridin-3-yl)-3-(tetrahydro-2H-pyran-4-yl)-5'H-spiro[chromeno[2,3-b]pyridine-5,4'-thiazol]-2'-amine (6 mg, 0.013 mmol).

MS m/z=449 [M+H]$^+$. Calc'd for $C_{24}H_{12}FN_4O_2S$: 448.51

Example 730 (Method CC36)

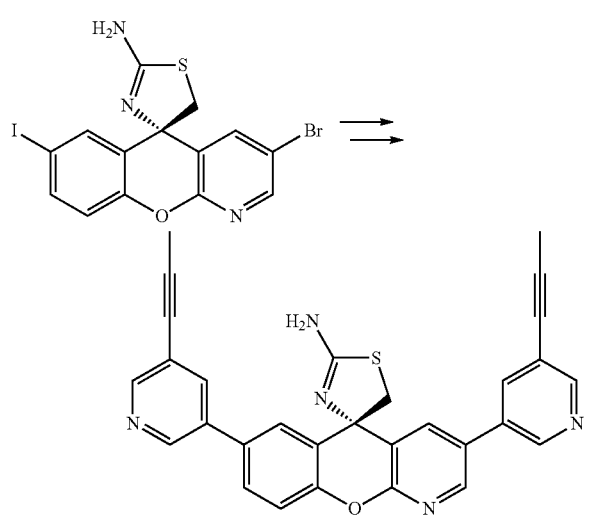

A microwave vial was charged with (S)-3-bromo-7-iodo-5'H-spiro[chromeno[2,3-b]pyridine-5,4'-thiazol]-2'-amine (200 mg, 0.422 mmol, prepared as described in Method BB26), potassium carbonate (292 mg, 2.109 mmol), 5-(prop-1-ynyl)pyridin-3-ylboronic acid (136 mg, 0.844 mmol), tetrakis(triphenylphosphine)palladium(0) (48.7 mg, 0.042 mmol), dioxane (2.8 mL) and water (1.4 mL). The reaction was heated in a microwave at 100° C. for 45 min. After cooling to rt, the organic layer was separated with a separatory funnel, dried over sodium sulfate, filtered, and concentrated to afford a yellow oil which was purified by silica gel chromatography (Redi-Sep pre-packed silica gel column (24 g), 0-100% EtOAc in 90:10 $CH_2Cl_2$:$CH_3OH$ to afford a white solid, (S)-3,7-bis(5-(prop-1-ynyl)pyridin-3-yl)-5'H-spiro [chromeno[2,3-b]pyridine-5,4'-thiazol]-2'-amine (13 mg, 0.026 mmol). MS m/z=500.2 [M+H]$^+$. Calc'd for $C_{30}H_{21}N_5OS$: 449.59

Example 731 (Method CC37)

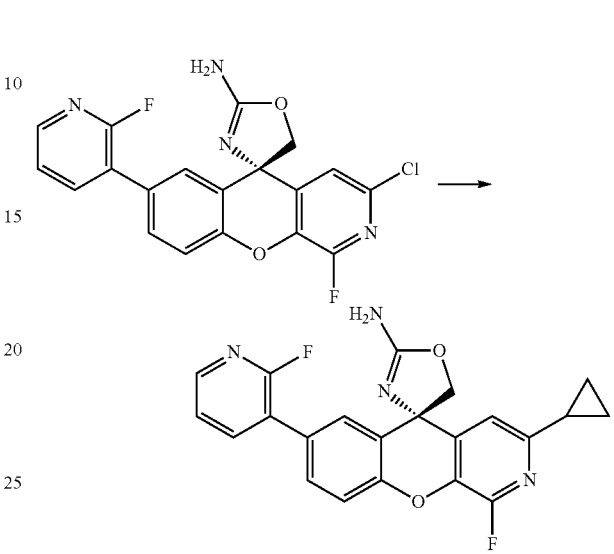

Synthesis of (S)-3-cyclopropyl-1,8-difluoro-7-(2-fluoropyridin-3-yl)-5'H-spiro[chromeno[2,3-c]pyridine-5,4'-oxazol]-2'-amine (S)-3-chloro-1-fluoro-7-(5-fluoropyridin-3-yl)-5'H-spiro [chromeno[2,3-c]pyridine-5,4'-oxazol]-2'-amine (330 mg, 0.82 mmol, prepared as described in Method BB33 and AA1) was combined with cyclopropyl trifluoroborate potassium salt (122 mg, 0.82 mmol), DiAdamtyl-n-butylphoshpine (8.86 mg, 0.025 mmol), palladium(ii) acetate (3.7 mg, 0.016 mmol) and cesium carbonate (805 mmol, 8.47 mmol) in a microwave tube and heated in microwave at 120° C. for 30 min. Then the reaction mixture was heated overnight in 105° C. oil bath. The reaction was cooled to room temperature and added water (25 mL) and sodium bicarbonate (1M, 10 mL). The mixture was extracted with DCM three times. The combined organics were washed with brine, dried with sodium sulfate, filtered and concentrated. The crude material was purified by reverse phase HPLC. The fraction was combined and concentrated, then sodium bicarbonate solution was added followed by ethyl acetate extraction three times. The organid layers were washed with brine, dried on sodium sulfate, filtered and concentrated to give 10 mg of white solid. MS m/z=407.0 [M+H]$^+$.

The following compounds in Table II are additional representative examples of compounds of Formulas I, I-A, I-B, I-C, I-D, II, III, IV and V, and sub-formulas thereof, provided by the present invention. The methods which were used to prepare each exemplary compound are also included in the Table, along with the mass found and biological data (average nM IC$_{50}$'s for the enzyme and cell assays) where available. Compounds named as R/S herein are stereospecific enantiomers. However, the specific stereochemistry has not been identified.

TABLE II

| Ex. No. | Compound Name | Observed Mass | Method | BACE 1 FRET assay (uM) | HEK cell assay (uM) |
|---|---|---|---|---|---|
| 732 | (5S)-3,7-bis(2-fluoro-3-pyridinyl)spiro[chromeno[2,3-b]pyridine-5,4'-[1,3]oxazol]-2'-amine | 444 | AA1 | 0.002 | 0.003 |
| 733 | 1-fluoro-7-(2-fluoro-3-pyridinyl)-3-((3-methyl-3-oxetanyl)ethynyl)spiro[chromeno[2,3-c]pyridine-5,4'-[1,3]oxazol]-2'-amine | 461 | CC8, AA5 | 0.0011 | 0.018 |
| 734 | (5S)-3-bromo-1-fluoro-7-(2-fluoro-3-pyridinyl)spiro[chromeno[2,3-c]pyridine-5,4'-[1,3]oxazol]-2'-amine | 445 | CC8 | 0.0078 | 2.257 |
| 735 | 1-fluoro-7-(2-fluoro-3-pyridinyl)-3-(3-pyridinylethynyl)spiro[chromeno[2,3-c]pyridine-5,4'-[1,3]oxazol]-2'-amine | 468 | CC8, AA5 | 0.0009 | 0.131 |
| 736 | (5R)-3-bromo-1-fluoro-7-(2-fluoro-3-pyridinyl)spiro[chromeno[2,3-c]pyridine-5,4'-[1,3]oxazol]-2'-amine | 445 | CC8 | 2.0937 | 10 |
| 737 | (5R)-1-fluoro-7-(2-fluoro-3-pyridinyl)-3-((3-methyl-3-oxetanyl)ethynyl)spiro[chromeno[2,3-c]pyridine-5,4'-[1,3]oxazol]-2'-amine | 461 | CC8, AA5 | 0.1159 | 4.33 |
| 738 | (5S)-1-fluoro-7-(2-fluoro-3-pyridinyl)-3-((3-methyl-3-oxetanyl)ethynyl)spiro[chromeno[2,3-c]pyridine-5,4'-[1,3]oxazol]-2'-amine | 461 | CC8, AA5 | 0.0006 | 0.01 |
| 739 | (5S)-1-fluoro-7-(5-(1-propyn-1-yl)-3-pyridinyl)-3-(4-pyridinyl)spiro[chromeno[2,3-c]pyridine-5,4'-[1,3]oxazol]-2'-amine | 464 | AA1 | 0.0005 | 0.005 |
| 740 | (5S)-1-fluoro-3-(2-methyl-4-pyridinyl)-7-(5-(1-propyn-1-yl)-3-pyridinyl)spiro[chromeno[2,3-c]pyridine-5,4'-[1,3]oxazol]-2'-amine | 478 | AA1 | 0.0008 | 0.008 |
| 741 | (5S)-1-fluoro-3-(6-methyl-3-pyridinyl)-7-(5-(1-propyn-1-yl)-3-pyridinyl)spiro[chromeno[2,3-c]pyridine-5,4'-[1,3]oxazol]-2'-amine | 477.1 | AA1 | 0.0004 | 0.004 |
| 742 | 3-((5S)-2'-amino-3-(5,6-dihydro-2H-pyran-3-yl)-1-fluorospiro[chromeno[2,3-c]pyridine-5,4'-[1,3]oxazol]-7-yl)benzonitrile | 455 | AA1 | 0.0004 | 0.008 |
| 743 | 3-((5S)-2'-amino-3-(3,6-dihydro-2H-pyran-4-yl)-1-fluorospiro[chromeno[2,3-c]pyridine-5,4'-[1,3]oxazol]-7-yl)benzonitrile | 455 | AA1 | 0.0004 | 0.006 |
| 744 | (5S)-1-fluoro-7-(2-fluoro-3-pyridinyl)-3-(2-methyl-4-pyridinyl)spiro[chromeno[2,3-c]pyridine-5,4'-[1,3]oxazol]-2'-amine | 458.1 | AA1 | 0.0008 | 0.012 |
| 745 | (5S)-3-(5,6-dihydro-2H-pyran-3-yl)-1-fluoro-7-(3-pyridinyl)spiro[chromeno[2,3-c]pyridine-5,4'-[1,3]oxazol]-2'-amine | 431.1 | AA1 | 0.0004 | 0.004 |
| 746 | (5S)-1-fluoro-7-(2-fluoro-3-pyridinyl)-3-(6-methyl-3-pyridinyl)spiro[chromeno[2,3-c]pyridine-5,4'-[1,3]oxazol]-2'-amine | 458.1 | AA1 | 0.0004 | 0.006 |
| 747 | (5R)-1-fluoro-7-(2-fluoro-3-pyridinyl)-3-(3-pyridinylethynyl)spiro[chromeno[2,3-c]pyridine-5,4'-[1,3]oxazol]-2'-amine | 468 | AA5 | 1.1194 | 10 |
| 748 | (5S)-1-fluoro-7-(2-fluoro-3-pyridinyl)-3-(3-pyridinylethynyl)spiro[chromeno[2,3-c]pyridine-5,4'-[1,3]oxazol]-2'-amine | 468 | AA5 | 0.0004 | 0.074 |
| 749 | (5S)-1-fluoro-7-(2-fluoro-3-pyridinyl)-3-(6-fluoro-3-pyridinyl)spiro[chromeno[2,3-c]pyridine-5,4'-[1,3]oxazol]-2'-amine | 462 | AA1 | 0.0003 | 0.019 |
| 750 | 1-fluoro-7-(5-(1-propyn-1-yl)-3-pyridinyl)-3-(tetrahydro-2H-pyran-4-yl)spiro[chromeno[2,3-c]pyridine-5,4'-[1,3]oxazol]-2'-amine | 471.2 | CC9, AA1 | 0.0007 | 0.004 |
| 751 | 3-(2'-amino-1-fluoro-3-(tetrahydro-2H-pyran-4-yl)spiro[chromeno[2,3-c]pyridine-5,4'-[1,3]oxazol]-7-yl)benzonitrile | 457.1 | CC9, AA1 | 0.0032 | 0.042 |
| 752 | 1-fluoro-7-(3-pyridinyl)-3-(tetrahydro-2H-pyran-4-yl)spiro[chromeno[2,3-c]pyridine-5,4'-[1,3]oxazol]-2'-amine | 433.1 | CC9, AA1 | 0.0056 | 0.077 |
| 753 | (5S)-1-fluoro-7-(5-(1-propyn-1-yl)-3-pyridinyl)-3-(tetrahydro-2H-pyran-4-yl)spiro[chromeno[2,3-c]pyridine-5,4'-[1,3]oxazol]-2'-amine | 471.2 | CC9, AA1 | 0.0007 | 0.004 |
| 754 | (5R)-1-fluoro-7-(5-(1-propyn-1-yl)-3-pyridinyl)-3-(tetrahydro-2H-pyran-4-yl)spiro[chromeno[2,3-c]pyridine-5,4'-[1,3]oxazol]-2'-amine | 471.2 | CC9, AA1 | 0.1556 | 0.691 |
| 755 | (5S)-1-fluoro-7-(2-fluoro-3-pyridinyl)-3-(tetrahydro-2H-pyran-3-yl)spiro[chromeno[2,3-c]pyridine-5,4'-[1,3]oxazol]-2'-amine | 451.1 | AA11 | 0.0011 | 0.105 |
| 756 | (5S)-1-fluoro-7-(2-fluoro-3-pyridinyl)-3-((3R)-tetrahydro-2H-pyran-3-yl)spiro[chromeno[2,3-c]pyridine-5,4'-[1,3]oxazol]-2'-amine | 451.1 | AA11 | 0.0011 | 0.034 |

TABLE II-continued

| Ex. No. | Compound Name | Observed Mass | Method | BACE 1 FRET assay (uM) | HEK cell assay (uM) |
|---|---|---|---|---|---|
| 757 | (5S)-1-fluoro-7-(2-fluoro-3-pyridinyl)-3-((3S)-tetrahydro-2H-pyran-3-yl)spiro[chromeno[2,3-c]pyridine-5,4'-[1,3]oxazol]-2'-amine | 451.1 | AA11 | 0.0011 | 0.083 |
| 758 | (5S)-3-(5,6-dihydro-2H-pyran-3-yl)-1-fluoro-7-(5-(1-propyn-1-yl)-3-pyridinyl)spiro[chromeno[2,3-c]pyridine-5,4'-[1,3]oxazol]-2'-amine | 469.1 | AA1 | 0.0004 | 0.002 |
| 759 | (5S)-1-fluoro-7-(5-(1-propyn-1-yl)-3-pyridinyl)-3-(3-pyridinyl)spiro[chromeno[2,3-c]pyridine-5,4'-[1,3]oxazol]-2'-amine | 464.1 | AA1 | 0.0004 | 0.003 |
| 760 | (5S)-3-(3,6-dihydro-2H-pyran-4-yl)-1-fluoro-7-(5-(1-propyn-1-yl)-3-pyridinyl)spiro[chromeno[2,3-c]pyridine-5,4'-[1,3]oxazol]-2'-amine | 469.1 | AA1 | 0.0003 | 0.002 |
| 761 | (5S)-3-chloro-1-fluoro-7-(5-(1-propyn-1-yl)-3-pyridinyl)spiro[chromeno[2,3-c]pyridine-5,4'-[1,3]oxazol]-2'-amine | 421.1 | AA24 | 0.0009 | 0.185 |
| 762 | (5R)-3-bromo-7-iodospiro[chromeno[2,3-b]pyridine-5,4'-[1,3]oxazol]-2'-amine, (5S)-3-bromo-7-iodospiro[chromeno[2,3-b]pyridine-5,4'-[1,3]oxazol]-2'-amine | 457.8 | BB28 | 0.004 | 0.085 |
| 763 | 3-((5S)-2'-amino-3-(3,6-dihydro-2H-pyran-4-yl)spiro[chromeno[2,3-b]pyridine-5,4'-[1,3]thiazol]-7-yl)-2-fluorobenzonitrile | 471 | CC32 | 0.0021 | 0.017 |
| 764 | 5-((5S)-2'-amino-3-(3,6-dihydro-2H-pyran-4-yl)spiro[chromeno[2,3-b]pyridine-5,4'-[1,3]thiazol]-7-yl)-2-fluorobenzonitrile | 471 | CC32 | 0.0006 | 0.006 |
| 765 | (5S)-7-(2-fluoro-3-pyridinyl)-3-(3-pyridinyl)spiro[chromeno[2,3-b]pyridine-5,4'-[1,3]thiazol]-2'-amine | 442.2 | CC32 | 0.001 | 0.008 |
| 766 | (5S)-7-(4-fluoro-3-pyridinyl)-3-(6-methyl-3-pyridinyl)spiro[chromeno[2,3-b]pyridine-5,4'-[1,3]thiazol]-2'-amine | 456.2 | CC32 | 0.0012 | 0.01 |
| 767 | (5S)-7-(2-fluoro-3-pyridinyl)-3-(2-fluoro-4-pyridinyl)spiro[chromeno[2,3-b]pyridine-5,4'-[1,3]thiazol]-2'-amine | 460 | CC32 | 0.001 | 0.023 |
| 768 | (5S)-3-(3,6-dihydro-2H-pyran-4-yl)-7-(4-fluoro-3-pyridinyl)spiro[chromeno[2,3-b]pyridine-5,4'-[1,3]thiazol]-2'-amine | 447.2 | CC32 | 0.0012 | 0.016 |
| 769 | (5S)-7-(4-fluoro-3-pyridinyl)-3-(3-pyridinyl)spiro[chromeno[2,3-b]pyridine-5,4'-[1,3]thiazol]-2'-amine | 442 | CC32 | 0.0023 | 0.044 |
| 726 | (5S)-3-(3,6-dihydro-2H-pyran-4-yl)-7-(5-fluoro-3-pyridinyl)spiro[chromeno[2,3-b]pyridine-5,4'-[1,3]thiazol]-2'-amine | 447.2 | CC32 | 0.0012 | 0.014 |
| 728 | (5S)-7-(2-fluoro-3-pyridinyl)-3-(2-pyrimidinyl)spiro[chromeno[2,3-b]pyridine-5,4'-[1,3]thiazol]-2'-amine | 443 | CC34 | 0.0035 | 0.08 |
| 730 | (5S)-3,7-bis(5-(1-propyn-1-yl)-3-pyridinyl)spiro[chromeno[2,3-b]pyridine-5,4'-[1,3]thiazol]-2'-amine | 500.2 | CC36 | 0.0018 | 0.171 |
| 770 | (5S)-3-(5,6-dihydro-2H-pyran-3-yl)-7-(5-fluoro-3-pyridinyl)spiro[chromeno[2,3-b]pyridine-5,4'-[1,3]thiazol]-2'-amine | 447.2 | CC32 | 0.0006 | 0.01 |
| 771 | (5S)-7-(5-fluoro-3-pyridinyl)-3-(2-pyrimidinyl)spiro[chromeno[2,3-b]pyridine-5,4'-[1,3]thiazol]-2'-amine | 443 | CC34 | 0.0046 | 0.096 |
| 772 | (5S)-3-(3,6-dihydro-2H-pyran-4-yl)-7-(5-(1-propyn-1-yl)-3-pyridinyl)spiro[chromeno[2,3-b]pyridine-5,4'-[1,3]thiazol]-2'-amine | 467.2 | CC32 | 0.0005 | 0.002 |
| 773 | (5S)-3-(5,6-dihydro-2H-pyran-3-yl)-7-(4-fluoro-3-pyridinyl)spiro[chromeno[2,3-b]pyridine-5,4'-[1,3]thiazol]-2'-amine | 447.2 | CC32 | 0.0008 | 0.014 |
| 774 | (5S)-3-(2,2-dimethyl-3,6-dihydro-2H-pyran-4-yl)-7-(2-fluoro-3-pyridinyl)spiro[chromeno[2,3-b]pyridine-5,4'-[1,3]thiazol]-2'-amine | 475.2 | CC32 | 0.0006 | 0.017 |
| 775 | (5S)-7-methoxy-3-(5-(1-propyn-1-yl)-3-pyridinyl)spiro[chromeno[2,3-b]pyridine-5,4'-[1,3]oxazol]-2'-amine | 399.2 | AA24 | 4.8261 | 10 |
| 776 | (4S)-4'-fluoro-7'-methoxy-2'-(5-(1-propyn-1-yl)-3-pyridinyl)spiro[1,3-oxazole-4,9'-xanthen]-2-amine | 416.2 | AA24 | 2.3815 | 10 |
| 777 | (5S)-7-(2-fluoro-3-pyridinyl)-3-(5-(1-propyn-1-yl)-3-pyridinyl)spiro[chromeno[2,3-b]pyridine-5,4'-[1,3]oxazol]-2'-amine | 464.2 | AA1 | 0.1056 | 3.506 |
| 778 | 3-((5S)-2'-amino-3-(5,6-dihydro-2H-pyran-3-yl)spiro[chromeno[2,3-b]pyridine-5,4'-[1,3]thiazol]-7-yl)-2-fluorobenzonitrile | 471 | CC32 | 0.0028 | 0.054 |

TABLE II-continued

| Ex. No. | Compound Name | Observed Mass | Method | BACE 1 FRET assay (uM) | HEK cell assay (uM) |
|---|---|---|---|---|---|
| 779 | 3-((5S)-2'-amino-3-(6,6-dimethyl-3,6-dihydro-2H-pyran-4-yl)spiro[chromeno[2,3-b]pyridine-5,4'-[1,3]thiazol]-7-yl)-2-fluorobenzonitrile | 499 | CC32 | 0.0048 | 0.319 |
| 780 | 3-((5S)-2'-amino-3-((3-methyl-3-oxetanyl)ethynyl)spiro[chromeno[2,3-b]pyridine-5,4'-[1,3]thiazol]-7-yl)-2-fluorobenzonitrile | 483.2 | CC33 | 0.002 | 0.338 |
| 727 | (5S)-7-(4-fluoro-3-pyridinyl)-3-((3-methyl-3-oxetanyl)ethynyl)spiro[chromeno[2,3-b]pyridine-5,4'-[1,3]thiazol]-2'-amine | 459.2 | CC33 | 0.0041 | 0.128 |
| 781 | (5S)-3-(2-fluoro-4-pyridinyl)-7-(5-(1-propyn-1-yl)-3-pyridinyl)spiro[chromeno[2,3-b]pyridine-5,4'-[1,3]thiazol]-2'-amine | 480.2 | CC32 | 0.0003 | 0.003 |
| 782 | (5S)-3-((3-methyl-3-oxetanyl)ethynyl)-7-(5-(1-propyn-1-yl)-3-pyridinyl)spiro[chromeno[2,3-b]pyridine-5,4'-[1,3]thiazol]-2'-amine | 479.2 | CC33 | 0.0009 | 0.004 |
| 783 | 5-((5S)-2'-amino-3-(5,6-dihydro-2H-pyran-3-yl)spiro[chromeno[2,3-b]pyridine-5,4'-[1,3]thiazol]-7-yl)-2-fluorobenzonitrile | 471 | CC32 | 0.0006 | 0.01 |
| 784 | 5-((5S)-2'-amino-3-(6,6-dimethyl-3,6-dihydro-2H-pyran-4-yl)spiro[chromeno[2,3-b]pyridine-5,4'-[1,3]thiazol]-7-yl)-2-fluorobenzonitrile | 499 | CC32 | 0.0014 | 0.015 |
| 785 | 5-((5S)-2'-amino-3-((3-methyl-3-oxetanyl)ethynyl)spiro[chromeno[2,3-b]pyridine-5,4'-[1,3]thiazol]-7-yl)-2-fluorobenzonitrile | 483.2 | CC33 | 0.0016 | 0.013 |
| 786 | 5-((5S)-2'-amino-3-(2-fluoro-4-pyridinyl)spiro[chromeno[2,3-b]pyridine-5,4'-[1,3]oxazol]-7-yl)-2-fluorobenzonitrile | 468.2 | AA1 | 0.0105 | 0.041 |
| 787 | 5-((5S)-2'-amino-3-((3-methyl-3-oxetanyl)ethynyl)spiro[chromeno[2,3-b]pyridine-5,4'-[1,3]oxazol]-7-yl)-2-fluorobenzonitrile | 467.2 | AA5 | 0.0056 | 0.044 |
| 788 | (5S)-3-(2-fluoro-3-pyridinyl)-7-(4-fluoro-3-pyridinyl)spiro[chromeno[2,3-b]pyridine-5,4'-[1,3]thiazol]-2'-amine | 460.2 | CC32 | 0.005 | 0.059 |
| 789 | (5S)-7-(5-(1-propyn-1-yl)-3-pyridinyl)-3-(2-pyrimidinyl)spiro[chromeno[2,3-b]pyridine-5,4'-[1,3]thiazol]-2'-amine | 463 | CC34 | 0.0022 | 0.009 |
| 729 | (5S)-7-(2-fluoro-3-pyridinyl)-3-(tetrahydro-2H-pyran-4-yl)spiro[chromeno[2,3-b]pyridine-5,4'-[1,3]thiazol]-2'-amine | 449 | CC35 | 0.0068 | 0.043 |
| 790 | 3-((5S)-2'-amino-3-(tetrahydro-2H-pyran-4-yl)spiro[chromeno[2,3-b]pyridine-5,4'-[1,3]thiazol]-7-yl)-2-fluorobenzonitrile | 473.2 | CC35 | 0.0145 | 0.097 |
| 791 | (4S)-2'-(3,6-dihydro-2H-pyran-4-yl)-4'-fluoro-7'-(2-fluoro-3-pyridinyl)spiro[1,3-thiazole-4,9'-xanthen]-2-amine | 464 | AA8 | 0.0001 | 0.01 |
| 713 | 1-((4S)-2-amino-4'-fluoro-7'-(2-fluoro-3-pyridinyl)spiro[1,3-oxazole-4,9'-xanthen]-2'-yl)-2-pyrrolidinone | 449 | CC19 | 0.002 | 0.023 |
| 792 | 1-((4S)-2-amino-4'-fluoro-7'-(3-pyridinyl)spiro[1,3-oxazole-4,9'-xanthen]-2'-yl)-2-pyrrolidinone | 431 | CC19 | 0.0051 | 0.03 |
| 793 | (4R)-4'-fluoro-7'-(2-fluoro-3-pyridinyl)-2'-((3-methyl-3-oxetanyl)methoxy)spiro[1,3-thiazole-4,9'-xanthen]-2-amine | 482 | AA14 | 0.1797 | 4.807 |
| 794 | (4S)-4'-fluoro-7'-(2-fluoro-3-pyridinyl)-2'-((3-methyl-3-oxetanyl)methoxy)spiro[1,3-thiazole-4,9'-xanthen]-2-amine | 482 | AA14 | 0.0002 | 0.006 |
| 795 | (4S)-2'-(5,6-dihydro-2H-pyran-3-yl)-4'-fluoro-7'-(3-pyridinyl)spiro[1,3-thiazole-4,9'-xanthen]-2-amine | 446 | AA8 | 0.0005 | 0.01 |
| 796 | (4S)-2'-(3,6-dihydro-2H-pyran-4-yl)-4'-fluoro-7'-(3-pyridinyl)spiro[1,3-thiazole-4,9'-xanthen]-2-amine | 446 | AA8 | 0.0005 | 0.008 |
| 797 | 1-((4S)-2-amino-4'-fluoro-7'-(2-fluoro-3-pyridinyl)spiro[1,3-oxazole-4,9'-xanthen]-2'-yl)-4,4-dimethyl-2-pyrrolidinone | 477 | CC19 | 0.0006 | 0.007 |
| 798 | 1-((4S)-2-amino-4'-fluoro-7'-(3-pyridinyl)spiro[1,3-oxazole-4,9'-xanthen]-2'-yl)-4,4-dimethyl-2-pyrrolidinone | 459 | CC19 | 0.0014 | 0.008 |
| 799 | (4S)-4'-fluoro-2'-(4-morpholinyl)-7'-(3-pyridinyl)spiro[1,3-thiazole-4,9'-xanthen]-2-amine | 449 | AA20 | 0.0015 | 0.018 |
| 800 | 3-(((4S)-2-amino-4'-fluoro-7'-(2-fluoro-3-pyridinyl)spiro[1,3-thiazole-4,9'-xanthen]-2'-yl)oxy)-2,2-dimethylpropanenitrile | 479 | AA14 | 0.0004 | 0.02 |

TABLE II-continued

| Ex. No. | Compound Name | Observed Mass | Method | BACE 1 FRET assay (uM) | HEK cell assay (uM) |
|---|---|---|---|---|---|
| 801 | 4-((4S)-2-amino-4'-fluoro-7'-(2-fluoro-3-pyridinyl)spiro[1,3-oxazole-4,9'-xanthen]-2'-yl)-2(5H)-furanone | 448 | AA22 | 0.0022 | 0.17 |
| 802 | (4S)-2'-(5,6-dihydro-2H-pyran-3-yl)-4'-fluoro-7'-(2-fluoro-3-pyridinyl)spiro[1,3-thiazole-4,9'-xanthen]-2-amine | 464 | AA8 | 0.0002 | 0.012 |
| 803 | (6R)-4-((4S)-2-amino-4'-fluoro-7'-(2-fluoro-3-pyridinyl)spiro[1,3-oxazole-4,9'-xanthen]-2'-yl)-6-methyl-5,6-dihydro-2H-pyran-2-one, (6S)-4-((4S)-2-amino-4'-fluoro-7'-(2-fluoro-3-pyridinyl)spiro[1,3-oxazole-4,9'-xanthen]-2'-yl)-6-methyl-5,6-dihydro-2H-pyran-2-one | 476 | BB30 | 0.0008 | 0.015 |
| 804 | 4-((4S)-2-amino-4'-fluoro-7'-(2-fluoro-3-pyridinyl)spiro[1,3-oxazole-4,9'-xanthen]-2'-yl)-6,6-dimethyl-5,6-dihydro-2H-pyran-2-one | 490 | BB30 | 0.0008 | 0.033 |
| 805 | (4S)-2'-(5-chloro-3,6-dihydro-2H-pyran-4-yl)-4'-fluoro-7'-(2-fluoro-3-pyridinyl)spiro[1,3-oxazole-4,9'-xanthen]-2-amine | 481.8 | AA8 | 0.0002 | 0.003 |
| 806 | (5S)-1-fluoro-7-(2-fluoro-3-pyridinyl)-3-phenylspiro[chromeno[2,3-c]pyridine-5,4'-[1,3]oxazol]-2'-amine | 442.8 | AA1 | 0.0015 | 0.005 |
| 807 | (5S)-3-(3,4-dihydro-2H-pyran-5-yl)-1-fluoro-7-(2-fluoro-3-pyridinyl)spiro[chromeno[2,3-c]pyridine-5,4'-[1,3]oxazol]-2'-amine | 448.8 | AA1 | 0.115 | 3.059 |
| 808 | (5S)-3-(3,6-dihydro-2H-pyran-4-yl)-7-(4-methyl-5-pyrimidinyl)spiro[chromeno[2,3-c]pyridine-5,4'-[1,3]oxazol]-2'-amine | 428.1 | BB3 | 0.003 | 0.093 |
| 809 | (5S)-3-(2-fluoro-4-pyridinyl)-7-(4-methyl-5-pyrimidinyl)spiro[chromeno[2,3-c]pyridine-5,4'-[1,3]oxazol]-2'-amine | 441 | BB3 | 0.0083 | 0.518 |
| 810 | (5S)-3-chloro-7-(5-((3-methyl-3-oxetanyl)ethynyl)-3-pyridinyl)spiro[chromeno[2,3-c]pyridine-5,4'-[1,3]oxazol]-2'-amine | 459 | BB3 | 0.6036 | 10 |
| 811 | (5S)-3-(3,6-dihydro-2H-pyran-4-yl)-7-(5-((3-methyl-3-oxetanyl)ethynyl)-3-pyridinyl)spiro[chromeno[2,3-c]pyridine-5,4'-[1,3]oxazol]-2'-amine | 507.2 | BB3 | 0.0025 | 0.103 |
| 812 | (5S)-3-(2-fluoro-4-pyridinyl)-7-(5-((3-methyl-3-oxetanyl)ethynyl)-3-pyridinyl)spiro[chromeno[2,3-c]pyridine-5,4'-[1,3]oxazol]-2'-amine | 520.1 | BB3 | 0.0055 | 0.46 |
| 813 | (5S)-3-(5,6-dihydro-2H-pyran-3-yl)-7-(5-((3-methyl-3-oxetanyl)ethynyl)-3-pyridinyl)spiro[chromeno[2,3-c]pyridine-5,4'-[1,3]oxazol]-2'-amine | 507.2 | BB3 | 0.0025 | 0.053 |
| 814 | (5S)-3-(5,6-dihydro-2H-pyran-3-yl)-7-(5-(1-propyn-1-yl)-3-pyridinyl)spiro[chromeno[2,3-c]pyridine-5,4'-[1,3]oxazol]-2'-amine | 451.1 | BB3 | 0.0005 | 0.002 |
| 815 | (5S)-7-(5-(cyclopropylethynyl)-3-pyridinyl)-3-(2-fluoro-4-pyridinyl)spiro[chromeno[2,3-c]pyridine-5,4'-[1,3]oxazol]-2'-amine | 490.1 | BB3 | 0.0019 | 0.699 |
| 816 | (5S)-7-(5-(cyclopropylethynyl)-3-pyridinyl)-3-(3,6-dihydro-2H-pyran-4-yl)spiro[chromeno[2,3-c]pyridine-5,4'-[1,3]oxazol]-2'-amine | 477.2 | BB3 | 0.0015 | 0.087 |
| 817 | 4-(5-((5S)-2'-amino-3-(2-fluoro-4-pyridinyl)spiro[chromeno[2,3-c]pyridine-5,4'-[1,3]oxazol]-7-yl)-3-pyridinyl)-2-methyl-3-butyn-2-ol | 508.1 | BB3 | 0.0135 | 1.484 |
| 818 | 4-(5-((5S)-2'-amino-3-(3,6-dihydro-2H-pyran-4-yl)spiro[chromeno[2,3-c]pyridine-5,4'-[1,3]oxazol]-7-yl)-3-pyridinyl)-2-methyl-3-butyn-2-ol | 495.2 | BB3 | 0.0049 | 0.152 |
| 819 | 4-(5-((5S)-2'-amino-3-(5,6-dihydro-2H-pyran-3-yl)spiro[chromeno[2,3-c]pyridine-5,4'-[1,3]oxazol]-7-yl)-3-pyridinyl)-2-methyl-3-butyn-2-ol | 495.2 | BB3 | 0.0052 | 0.238 |
| 820 | 3-(5-((4S)-2-amino-5'-fluoro-7'-methoxyspiro[1,3-oxazole-4,9'-xanthen]-2'-yl)-3-pyridinyl)-2-propyn-1-ol | 432 | BB3 | 0.0011 | 0.021 |
| 821 | (4S)-4'-fluoro-2'-methoxy-7'-(5-((3-methyl-3-oxetanyl)ethynyl)-3-pyridinyl)spiro[1,3-oxazole-4,9'-xanthen]-2-amine | 472.1 | BB3 | 0.0514 | 2.9 |
| 822 | 4-(5-((4S)-2-amino-5'-fluoro-7'-methoxyspiro[1,3-oxazole-4,9'-xanthen]-2'-yl)-3-pyridinyl)-2-methyl-3-butyn-2-ol | 460.1 | BB3 | 0.0933 | 2.996 |

TABLE II-continued

| Ex. No. | Compound Name | Observed Mass | Method | BACE 1 FRET assay (uM) | HEK cell assay (uM) |
|---|---|---|---|---|---|
| 823 | (4S)-4'-fluoro-2'-methoxy-7'-(5-(3-methoxy-3-methyl-1-butyn-1-yl)-3-pyridinyl)spiro[1,3-oxazole-4,9'-xanthen]-2-amine | 474.2 | BB3 | 0.1009 | 4.302 |
| 824 | (4S)-4'-fluoro-2'-methoxy-7'-(5-(1-propyn-1-yl)-3-pyridinyl)spiro[1,3-oxazole-4,9'-xanthen]-2-amine | 416.1 | BB3 | 0.0002 | 0.02 |
| 825 | 3-(5-((5S)-2'-amino-3-(2-fluoro-4-pyridinyl)spiro[chromeno[2,3-c]pyridine-5,4'-[1,3]oxazol]-7-yl)-3-pyridinyl)-2-propyn-1-ol | 480.2 | BB3 | 0.0003 | 0.006 |
| 826 | 3-(5-((5S)-2'-amino-3-(3,6-dihydro-2H-pyran-4-yl)spiro[chromeno[2,3-c]pyridine-5,4'-[1,3]oxazol]-7-yl)-3-pyridinyl)-2-propyn-1-ol | 467.1 | BB3 | 0.0004 | 0.002 |
| 827 | 3-(5-((5S)-2'-amino-3-(5,6-dihydro-2H-pyran-3-yl)spiro[chromeno[2,3-c]pyridine-5,4'-[1,3]oxazol]-7-yl)-3-pyridinyl)-2-propyn-1-ol | 467.1 | BB3 | 0.0005 | 0.002 |
| 710 | (5S)-7-bromo-3-chloro-1-methoxyspiro[chromeno[2,3-c]pyridine-5,4'-[1,3]oxazol]-2'-amine | 395.9 | CC16 | 6.8929 | 10 |
| 828 | (5S)-3-chloro-7-(2-fluoro-3-pyridinyl)-1-methoxyspiro[chromeno[2,3-c]pyridine-5,4'-[1,3]oxazol]-2'-amine | 413 | AA1 | 0.1341 | 10 |
| 829 | (5S)-3-chloro-1-methoxy-7-(5-(1-propyn-1-yl)-3-pyridinyl)spiro[chromeno[2,3-c]pyridine-5,4'-[1,3]oxazol]-2'-amine | 433.1 | AA1 | 0.0302 | 4.105 |
| 830 | (5S)-3-chloro-1-methoxy-7-(3-pyridinyl)spiro[chromeno[2,3-c]pyridine-5,4'-[1,3]oxazol]-2'-amine | 395.1 | AA1 | 0.4686 | 10 |
| 831 | (5S)-7-(2-fluoro-3-pyridinyl)-3-(2-fluoro-4-pyridinyl)-1-methoxyspiro[chromeno[2,3-c]pyridine-5,4'-[1,3]oxazol]-2'-amine | 474 | AA1 | 0.0011 | 0.07 |
| 832 | (5S)-3-(3,6-dihydro-2H-pyran-4-yl)-7-(2-fluoro-3-pyridinyl)-1-methoxyspiro[chromeno[2,3-c]pyridine-5,4'-[1,3]oxazol]-2'-amine | 461.1 | AA1 | 0.0007 | 0.032 |
| 833 | (5S)-3-(5,6-dihydro-2H-pyran-3-yl)-7-(2-fluoro-3-pyridinyl)-1-methoxyspiro[chromeno[2,3-c]pyridine-5,4'-[1,3]oxazol]-2'-amine | 461.1 | AA1 | 0.0007 | 0.021 |
| 834 | (5S)-7-(2-fluoro-3-pyridinyl)-1-methoxy-3-(4-pyridinyl)spiro[chromeno[2,3-c]pyridine-5,4'-[1,3]oxazol]-2'-amine | 456 | AA1 | 0.0035 | 0.07 |
| 835 | (5S)-3-(3,6-dihydro-2H-pyran-4-yl)-1-methoxy-7-(5-(1-propyn-1-yl)-3-pyridinyl)spiro[chromeno[2,3-c]pyridine-5,4'-[1,3]oxazol]-2'-amine | 481.2 | AA1 | 0.0006 | 0.007 |
| 836 | (5S)-3-(5,6-dihydro-2H-pyran-3-yl)-1-methoxy-7-(5-(1-propyn-1-yl)-3-pyridinyl)spiro[chromeno[2,3-c]pyridine-5,4'-[1,3]oxazol]-2'-amine | 481.1 | AA1 | 0.0005 | 0.004 |
| 837 | (5S)-1-methoxy-7-(5-(1-propyn-1-yl)-3-pyridinyl)-3-(4-pyridinyl)spiro[chromeno[2,3-c]pyridine-5,4'-[1,3]oxazol]-2'-amine | 476.1 | AA1 | 0.0007 | 0.009 |
| 838 | (5S)-1-methoxy-7-(3-pyridinyl)-3-(4-pyridinyl)spiro[chromeno[2,3-c]pyridine-5,4'-[1,3]oxazol]-2'-amine | 438.2 | AA1 | 0.0073 | 0.02 |
| 839 | (5S)-3-(2-fluoro-4-pyridinyl)-1-methoxy-7-(3-pyridinyl)spiro[chromeno[2,3-c]pyridine-5,4'-[1,3]oxazol]-2'-amine | 456.2 | AA1 | 0.0021 | 0.011 |
| 840 | (5S)-3-(3,6-dihydro-2H-pyran-4-yl)-1-methoxy-7-(3-pyridinyl)spiro[chromeno[2,3-c]pyridine-5,4'-[1,3]oxazol]-2'-amine | 443.1 | AA1 | 0.0043 | 0.015 |
| 841 | (5S)-3-(5,6-dihydro-2H-pyran-3-yl)-1-methoxy-7-(3-pyridinyl)spiro[chromeno[2,3-c]pyridine-5,4'-[1,3]oxazol]-2'-amine | 443.1 | AA1 | 0.0012 | 0.006 |
| 711 | 3-((5S)-2'-amino-3-(2-hydroxy-4-pyridinyl)spiro[chromeno[2,3-c]pyridine-5,4'-[1,3]oxazol]-7-yl)-2-pyridinol | 440.1 | CC17 | 0.6203 | 10 |
| 842 | 4-((5S)-2'-amino-7-(2-fluoro-3-pyridinyl)spiro[chromeno[2,3-c]pyridine-5,4'-[1,3]oxazol]-3-yl)-2-pyridinol | 442.1 | CC17 | 0.0259 | 2.558 |
| 712 | 3-(2'-amino-3-(2-fluoro-4-pyridinyl)spiro[chromeno[2,3-c]pyridine-5,4'-[1,3]oxazol]-7-yl)-2-pyridinol | 442.1 | CC18 | 0.0697 | 1.089 |
| 843 | 4'-fluoro-2'-methoxy-7'-(5-(3-methoxy-1-propyn-1-yl)-3-pyridinyl)spiro[1,3-oxazole-4,9'-xanthen]-2-amine | 446.1 | BB3 | 0.0088 | 0.057 |

TABLE II-continued

| Ex. No. | Compound Name | Observed Mass | Method | BACE 1 FRET assay (uM) | HEK cell assay (uM) |
|---|---|---|---|---|---|
| 844 | (5S)-7-(2-fluoro-3-pyridinyl)-1-methoxy-3-(tetrahydro-2H-pyran-3-yl)spiro[chromeno[2,3-c]pyridine-5,4'-[1,3]oxazol]-2'-amine | 463.1 | AA11 | 0.0067 | 0.066 |
| 845 | (5S)-1-methoxy-7-(3-pyridinyl)-3-(tetrahydro-2H-pyran-3-yl)spiro[chromeno[2,3-c]pyridine-5,4'-[1,3]oxazol]-2'-amine | 445.1 | AA11 | 0.0155 | 0.07 |
| 846 | (5R)-7-bromo-3-fluoro-1-methoxyspiro[chromeno[2,3-c]pyridine-5,4'-[1,3]oxazol]-2'-amine, (5S)-7-bromo-3-fluoro-1-methoxyspiro[chromeno[2,3-c]pyridine-5,4'-[1,3]oxazol]-2'-amine | 380 | CC16 | 0.0014 | 0.014 |
| 847 | (5R)-3-fluoro-1-methoxy-7-(3-pyridinyl)spiro[chromeno[2,3-c]pyridine-5,4'-[1,3]oxazol]-2'-amine, (5S)-3-fluoro-1-methoxy-7-(3-pyridinyl)spiro[chromeno[2,3-c]pyridine-5,4'-[1,3]oxazol]-2'-amine | 379.1 | CC16 | 0.0004 | 0.01 |
| 848 | 3-ethenyl-1-fluoro-7-(5-fluoro-3-pyridinyl)spiro[chromeno[2,3-c]pyridine-5,4'-[1,3]oxazol]-2'-amine | 393 | AA57 | 0.0004 | 0.002 |
| 731 | (5S)-3-cyclopropyl-1-fluoro-7-(5-fluoro-3-pyridinyl)spiro[chromeno[2,3-c]pyridine-5,4'-[1,3]oxazol]-2'-amine | 407 | CC37 | 0.3162 | 1.152 |
| 849 | (5S)-3-(4,4-difluoro-1-piperidinyl)-7-(2-fluoro-3-pyridinyl)-1-methoxyspiro[chromeno[2,3-c]pyridine-5,4'-[1,3]oxazol]-2'-amine | 498 | CC16 | 0.0042 | 0.078 |
| 850 | (5S)-3-ethyl-1-fluoro-7-(5-fluoro-3-pyridinyl)spiro[chromeno[2,3-c]pyridine-5,4'-[1,3]oxazol]-2'-amine | 395 | AA57, AA11 | 0.0045 | 0.052 |
| 851 | (5S)-1-fluoro-7-(2-fluoro-3-pyridinyl)-3-(3-methyl-5-isoxazolyl)spiro[chromeno[2,3-c]pyridine-5,4'-[1,3]oxazol]-2'-amine | 448 | AA57 | 0.0008 | 0.008 |
| 852 | (5S)-3-(4,4-difluoro-1-piperidinyl)-1-methoxy-7-(2-methoxy-3-pyridinyl)spiro[chromeno[2,3-c]pyridine-5,4'-[1,3]oxazol]-2'-amine | 510 | CC16 | 0.0926 | 0.609 |
| 853 | (4S)-4'-fluoro-7'-(2-fluoro-3-pyridinyl)-N~2~'-methyl-N~2~'-2-propen-1-ylspiro[1,3-oxazole-4,9'-xanthene]-2,2'-diamine | 435 | CC4 | 0.004 | 0.085 |
| 854 | (4S)-4'-fluoro-7'-(2-fluoro-3-pyridinyl)-N~2~'-methyl-N~2~'-3-oxetanylspiro[1,3-oxazole-4,9'-xanthene]-2,2'-diamine | 451.1 | CC4 | 0.0044 | 0.017 |
| 855 | (4S)-4'-fluoro-7'-(2-fluoro-3-pyridinyl)-2'-(5-oxa-2-azaspiro[3.4]oct-2-yl)spiro[1,3-oxazole-4,9'-xanthen]-2-amine | 477 | CC4 | 0.0007 | 0.002 |
| 856 | (4S)-4'-fluoro-7'-(2-fluoro-3-pyridinyl)-2'-(6-oxa-2-azaspiro[3.5]non-2-yl)spiro[1,3-oxazole-4,9'-xanthen]-2-amine | 491.1 | CC4 | 0.0006 | 0.004 |
| 857 | (4S)-4'-fluoro-7'-(2-fluoro-3-pyridinyl)-2'-(2-oxa-6-azaspiro[3.4]oct-6-yl)spiro[1,3-oxazole-4,9'-xanthen]-2-amine | 475.1 | CC4 | <0.0020 | 0.001 |
| 858 | (4S)-7'-(2,4-difluoro-3-pyridinyl)-4'-fluoro-2'-(2-pyrimidinyl)spiro[1,3-oxazole-4,9'-xanthen]-2-amine | 462.2 | AA22 | 0.0005 | 0.018 |
| 859 | (4S)-7'-(2,4-difluoro-3-pyridinyl)-4'-fluoro-2'-(1-methyl-1H-pyrazol-4-yl)spiro[1,3-oxazole-4,9'-xanthen]-2-amine | 464 | AA8 | 0.0005 | 0.011 |
| 860 | 3-(((4S)-2-amino-4',6'-difluoro-7'-(3-pyridinyl)spiro[1,3-oxazole-4,9'-xanthen]-2'-yl)oxy)-2,2-dimethylpropanenitrile | 463.2 | AA14 | 0.0007 | 0.01 |
| 861 | (4S)-3',5'-difluoro-7'-(4-morpholinyl)-2'-(3-pyridinyl)spiro[1,3-oxazole-4,9'-xanthen]-2-amine | 451 | AA20 | 0.001 | 0.015 |
| 862 | 3-(((4S)-2-amino-4',6'-difluoro-7'-(2-fluoro-3-pyridinyl)spiro[1,3-oxazole-4,9'-xanthen]-2'-yl)oxy)-2,2-dimethylpropanenitrile | 481.2 | AA14 | 0.0003 | 0.011 |
| 863 | 3-(((4R)-2-amino-4',6'-difluoro-7'-(2-fluoro-3-pyridinyl)spiro[1,3-oxazole-4,9'-xanthen]-2'-yl)oxy)-2,2-dimethylpropanenitrile | 481.2 | AA14 | 0.0801 | 2.357 |
| 864 | (4S)-3',5'-difluoro-2'-(3-pyridinyl)-7'-(tetrahydro-2H-pyran-4-yl)spiro[1,3-oxazole-4,9'-xanthen]-2-amine | 450 | AA18 | 0.0011 | 0.03 |
| 865 | (4S)-7'-(5,6-dihydro-2H-pyran-3-yl)-3',5'-difluoro-2'-(2-fluoro-3-pyridinyl)spiro[1,3-oxazole-4,9'-xanthen]-2-amine | 466.2 | AA8 | 0.0003 | 0.005 |
| 866 | (4R)-7'-(5,6-dihydro-2H-pyran-3-yl)-3',5'-difluoro-2'-(2-fluoro-3-pyridinyl)spiro[1,3-oxazole-4,9'-xanthen]-2-amine | 466.2 | AA8 | 0.0623 | 1.721 |

TABLE II-continued

| Ex. No. | Compound Name | Observed Mass | Method | BACE 1 FRET assay (uM) | HEK cell assay (uM) |
|---|---|---|---|---|---|
| 867 | (4S)-7'-(3,6-dihydro-2H-pyran-4-yl)-3',5'-difluoro-2'-(2-fluoro-3-pyridinyl)spiro[1,3-oxazole-4,9'-xanthen]-2-amine | 466.2 | AA8 | 0.0003 | 0.005 |
| 868 | (4R)-7'-(3,6-dihydro-2H-pyran-4-yl)-3',5'-difluoro-2'-(2-fluoro-3-pyridinyl)spiro[1,3-oxazole-4,9'-xanthen]-2-amine | 466.2 | AA8 | 0.0521 | 1.132 |
| 869 | (4S)-3',5'-difluoro-2'-(2-fluoro-3-pyridinyl)-7'-(4-morpholinyl)spiro[1,3-oxazole-4,9'-xanthen]-2-amine | 469 | AA20 | 0.0005 | 0.01 |
| 870 | (4R)-3',5'-difluoro-2'-(2-fluoro-3-pyridinyl)-7'-(4-morpholinyl)spiro[1,3-oxazole-4,9'-xanthen]-2-amine | 469 | AA20 | 0.1575 | 6.567 |
| 871 | (4R)-3',5'-difluoro-2'-(2-fluoro-3-pyridinyl)-7'-(tetrahydro-2H-pyran-4-yl)spiro[1,3-oxazole-4,9'-xanthen]-2-amine | 468.2 | AA18 | 0.179 | 6.47 |
| 872 | (4S)-3',5'-difluoro-2'-(2-fluoro-3-pyridinyl)-7'-(tetrahydro-2H-pyran-4-yl)spiro[1,3-oxazole-4,9'-xanthen]-2-amine | 468.2 | AA18 | 0.0006 | 0.015 |
| 873 | (4S)-7'-(5,6-dihydro-2H-pyran-3-yl)-3',5'-difluoro-2'-(5-pyrimidinyl)spiro[1,3-thiazole-4,9'-xanthen]-2-amine | 465.2 | AA8 | 0.0003 | 0.007 |
| 874 | (4R)-7'-(5,6-dihydro-2H-pyran-3-yl)-3',5'-difluoro-2'-(5-pyrimidinyl)spiro[1,3-thiazole-4,9'-xanthen]-2-amine | 465.2 | AA8 | 0.0325 | 0.506 |
| 875 | (4S)-3',5'-difluoro-7'-((3-methyl-3-oxetanyl)methoxy)-2'-(5-pyrimidinyl)spiro[1,3-thiazole-4,9'-xanthen]-2-amine | 483 | AA14 | 0.0005 | 0.008 |
| 876 | (4R)-3',5'-difluoro-7'-((3-methyl-3-oxetanyl)methoxy)-2'-(5-pyrimidinyl)spiro[1,3-thiazole-4,9'-xanthen]-2-amine | 483 | AA14 | 0.0449 | 0.634 |
| 877 | (4R)-3',5'-difluoro-7'-((3-methyl-3-oxetanyl)methoxy)-2'-(3-pyridinyl)spiro[1,3-thiazole-4,9'-xanthen]-2-amine | 482 | AA14 | 0.1834 | 3.002 |
| 878 | (4S)-3',5'-difluoro-7'-((3-methyl-3-oxetanyl)methoxy)-2'-(3-pyridinyl)spiro[1,3-thiazole-4,9'-xanthen]-2-amine | 482 | AA14 | 0.0004 | 0.008 |
| 879 | (4S)-3',5'-difluoro-2'-(2-fluoro-3-pyridinyl)-7'-(4-morpholinyl)spiro[1,3-thiazole-4,9'-xanthen]-2-amine | 485 | AA20 | 0.0003 | 0.011 |
| 880 | (4R)-3',5'-difluoro-2'-(2-fluoro-3-pyridinyl)-7'-(4-morpholinyl)spiro[1,3-thiazole-4,9'-xanthen]-2-amine | 485 | AA20 | 1.2257 | 10 |
| 881 | (4S)-7'-(3,6-dihydro-2H-pyran-4-yl)-3',5'-difluoro-2'-(3-pyridinyl)spiro[1,3-thiazole-4,9'-xanthen]-2-amine | 464 | AA8 | 0.0005 | 0.023 |
| 882 | (4R)-7'-(3,6-dihydro-2H-pyran-4-yl)-3',5'-difluoro-2'-(3-pyridinyl)spiro[1,3-thiazole-4,9'-xanthen]-2-amine | 464 | AA8 | 0.6169 | 10 |
| 883 | (4S)-7'-(5,6-dihydro-2H-pyran-3-yl)-3',5'-difluoro-2'-(3-pyridinyl)spiro[1,3-thiazole-4,9'-xanthen]-2-amine | 464.2 | AA8 | 0.0003 | 0.05 |
| 884 | (4R)-7'-(5,6-dihydro-2H-pyran-3-yl)-3',5'-difluoro-2'-(3-pyridinyl)spiro[1,3-thiazole-4,9'-xanthen]-2-amine | 464.2 | AA8 | 0.1622 | 10 |
| 885 | (4S)-3',5'-difluoro-2'-(2-fluoro-3-pyridinyl)-7'-((3-methyl-3-oxetanyl)methoxy)spiro[1,3-thiazole-4,9'-xanthen]-2-amine | 500.2 | AA14 | 0.0004 | 0.005 |
| 886 | (4R)-3',5'-difluoro-2'-(2-fluoro-3-pyridinyl)-7'-((3-methyl-3-oxetanyl)methoxy)spiro[1,3-thiazole-4,9'-xanthen]-2-amine | 500.2 | AA14 | 0.4752 | 10 |
| 887 | (4R)-3',5'-difluoro-7'-(4-morpholinyl)-2'-(5-pyrimidinyl)spiro[1,3-thiazole-4,9'-xanthen]-2-amine | 468 | AA20 | 4.7418 | 10 |
| 888 | (4S)-3',5'-difluoro-7'-(4-morpholinyl)-2'-(5-pyrimidinyl)spiro[1,3-thiazole-4,9'-xanthen]-2-amine | 468 | AA20 | 0.0021 | 0.01 |
| 706 | (5R)-7-(2-fluoro-3-pyridinyl)-N~3~,N~3~-dimethylspiro[chromeno[2,3-c]pyridine-5,4'-[1,3]oxazole]-2',3-diamine, (5S)-7-(2-fluoro-3-pyridinyl)-N~3~,N~3~-dimethylspiro[chromeno[2,3-c]pyridine-5,4'-[1,3]oxazol]-2',3-diamine | 392.2 | CC12 | 0.0224 | 0.205 |

TABLE II-continued

| Ex. No. | Compound Name | Observed Mass | Method | BACE 1 FRET assay (uM) | HEK cell assay (uM) |
|---|---|---|---|---|---|
| 889 | (5R)-N~3~,N~3~-dimethyl-7-(3-pyridinyl)spiro[chromeno[2,3-c]pyridine-5,4'-[1,3]thiazole]-2',3-diamine, (5S)-N~3~,N~3~-dimethyl-7-(3-pyridinyl)spiro[chromeno[2,3-c]pyridine-5,4'-[1,3]thiazole]-2',3-diamine | 390.1 | CC13 | 0.0199 | 0.54 |
| 890 | (5S)-7-(2-fluoro-3-pyridinyl)-3-(4-morpholinyl)spiro[chromeno[2,3-c]pyridine-5,4'-[1,3]oxazol]-2'-amine | 434.1 | CC4 | 0.0013 | 0.021 |
| 891 | (5S)-7-(2-fluoro-3-pyridinyl)-3-((1S,4S)-2-oxa-5-azabicyclo[2.2.1]hept-5-yl)spiro[chromeno[2,3-c]pyridine-5,4'-[1,3]oxazol]-2'-amine | 446.2 | CC4 | 0.0019 | 0.061 |
| 892 | (5S)-1-fluoro-7-(2-fluoro-3-pyridinyl)-3-(4-morpholinyl)spiro[chromeno[2,3-c]pyridine-5,4'-[1,3]oxazol]-2'-amine | 452.2 | CC4 | 0.0003 | 0.005 |
| 893 | (5S)-1-fluoro-7-(5-fluoro-3-pyridinyl)-3-(4-morpholinyl)spiro[chromeno[2,3-c]pyridine-5,4'-[1,3]oxazol]-2'-amine | 452.1 | CC4 | 0.0003 | 0.007 |
| 894 | 3-((5S)-2'-amino-1-fluoro-3-(4-morpholinyl)spiro[chromeno[2,3-c]pyridine-5,4'-[1,3]oxazol]-7-yl)benzonitrile | 458.2 | CC4 | 0.0003 | 0.01 |
| 895 | 3-((5S)-2'-amino-3-(4-morpholinyl)spiro[chromeno[2,3-c]pyridine-5,4'-[1,3]oxazol]-7-yl)benzonitrile | 440.3 | CC4 | 0.0024 | 0.008 |
| 896 | (5S)-8-fluoro-7-(2-fluoro-3-pyridinyl)-3-(6-fluoro-3-pyridinyl)spiro[chromeno[2,3-b]pyridine-5,4'-[1,3]oxazol]-2'-amine | 462 | AA1 | 0.0024 | 0.074 |
| 897 | (5R)-8-fluoro-7-(2-fluoro-3-pyridinyl)-3-(6-fluoro-3-pyridinyl)spiro[chromeno[2,3-b]pyridine-5,4'-[1,3]oxazol]-2'-amine | 462 | AA1 | 0.1748 | 6.362 |
| 898 | (5S)-2-fluoro-7-(2-fluoro-3-pyridinyl)-3-iodospiro[chromeno[2,3-b]pyridine-5,4'-[1,3]oxazol]-2'-amine | 492.8 | BB34 | 10.552 | 10 |
| 899 | (5R)-2-fluoro-7-(2-fluoro-3-pyridinyl)-3-iodospiro[chromeno[2,3-b]pyridine-5,4'-[1,3]oxazol]-2'-amine | 492.8 | BB34 | 40 | 10 |
| 716 | (5S)-3-(tert-butoxymethyl)-8-fluoro-7-(2-fluoro-3-pyridinyl)spiro[chromeno[2,3-b]pyridine-5,4'-[1,3]oxazol]-2'-amine | 453 | CC22 | 0.0065 | 0.132 |
| 900 | (5R)-2-fluoro-7-(2-fluoro-3-pyridinyl)-3-((3-methyl-3-oxetanyl)ethynyl)spiro[chromeno[2,3-b]pyridine-5,4'-[1,3]oxazol]-2'-amine | 461 | CC21 | 0.0481 | 1.155 |
| 901 | (5S)-2-fluoro-7-(2-fluoro-3-pyridinyl)-3-((3-methyl-3-oxetanyl)ethynyl)spiro[chromeno[2,3-b]pyridine-5,4'-[1,3]oxazol]-2'-amine | 461 | CC21 | 0.0005 | 0.011 |
| 902 | (5R)-3-(5,6-dihydro-2H-pyran-3-yl)-2-fluoro-7-(2-fluoro-3-pyridinyl)spiro[chromeno[2,3-b]pyridine-5,4'-[1,3]oxazol]-2'-amine | 449 | BB35 | 0.1372 | 3.215 |
| 903 | (5S)-3-(5,6-dihydro-2H-pyran-3-yl)-2-fluoro-7-(2-fluoro-3-pyridinyl)spiro[chromeno[2,3-b]pyridine-5,4'-[1,3]oxazol]-2'-amine | 449 | BB35 | 0.0014 | 0.049 |
| 904 | (5R)-2-fluoro-7-(2-fluoro-3-pyridinyl)-3-(4-morpholinyl)spiro[chromeno[2,3-b]pyridine-5,4'-[1,3]oxazol]-2'-amine | 452 | CC20 | 0.269 | 10 |
| 714 | (5S)-2-fluoro-7-(2-fluoro-3-pyridinyl)-3-(4-morpholinyl)spiro[chromeno[2,3-b]pyridine-5,4'-[1,3]oxazol]-2'-amine | 452 | CC20 | 0.0036 | 0.055 |
| 905 | (5R)-2-fluoro-7-(6-fluoro-3-pyridinyl)-3-((3-methyl-3-oxetanyl)ethynyl)spiro[chromeno[2,3-b]pyridine-5,4'-[1,3]oxazol]-2'-amine | 461 | CC21 | 0.1264 | 3.107 |
| 715 | (5S)-2-fluoro-7-(6-fluoro-3-pyridinyl)-3-((3-methyl-3-oxetanyl)ethynyl)spiro[chromeno[2,3-b]pyridine-5,4'-[1,3]oxazol]-2'-amine | 461 | CC21 | 0.0014 | 0.041 |
| 906 | (5R)-2-fluoro-7-(5-fluoro-3-pyridinyl)-3-((3-methyl-3-oxetanyl)ethynyl)spiro[chromeno[2,3-b]pyridine-5,4'-[1,3]oxazol]-2'-amine | 461 | BB44 | 0.0542 | 1.492 |
| 907 | (5S)-2-fluoro-7-(5-fluoro-3-pyridinyl)-3-((3-methyl-3-oxetanyl)ethynyl)spiro[chromeno[2,3-b]pyridine-5,4'-[1,3]oxazol]-2'-amine | 461 | CC21 | 0.0011 | 0.023 |
| 717 | (5S)-8-fluoro-3-(3-fluoro-3-methyl-1-butyn-1-yl)-7-(5-pyrimidinyl)spiro[chromeno[2,3-b]pyridine-5,4'-[1,3]oxazol]-2'-amine | 434 | CC23 | 0.0038 | 0.212 |
| 908 | (5R)-3-(5,6-dihydro-2H-pyran-3-yl)-1-fluoro-7-(2-fluoro-3-pyridinyl)spiro[chromeno[2,3-c]pyridine-5,4'-[1,3]oxazol]-2'-amine | 449.1 | AA1 | 0.0926 | 0.609 |

TABLE II-continued

| Ex. No. | Compound Name | Observed Mass | Method | BACE 1 FRET assay (uM) | HEK cell assay (uM) |
|---|---|---|---|---|---|
| 909 | (5S)-7-(2,4-difluoro-3-pyridinyl)-3-((3R)-tetrahydro-2H-pyran-3-yl)spiro[chromeno[2,3-c]pyridine-5,4'-[1,3]oxazol]-2'-amine, (5S)-7-(2,4-difluoro-3-pyridinyl)-3-((3S)-tetrahydro-2H-pyran-3-yl)spiro[chromeno[2,3-c]pyridine-5,4'-[1,3]oxazol]-2'-amine | 451.1 | AA11 | 0.0198 | 0.266 |
| 910 | (4S)-2'-(5,6-dihydro-2H-pyran-3-yl)-7'-(2,2-dimethylpropoxy)spiro[1,3-oxazole-4,9'-xanthen]-2-amine | 421.3 | N | 0.0223 | 1.768 |
| 911 | (4S)-2'-(2,2-dimethylpropoxy)-7'-((3R)-tetrahydro-2H-pyran-3-yl)spiro[1,3-oxazole-4,9'-xanthen]-2-amine, (4S)-2'-(2,2-dimethylpropoxy)-7'-((3S)-tetrahydro-2H-pyran-3-yl)spiro[1,3-oxazole-4,9'-xanthen]-2-amine | 423.2 | N, AA11 | 0.0192 | 1.286 |
| 912 | (5S)-7-(2,4-difluoro-3-pyridinyl)-3-((3S)-tetrahydro-2H-pyran-3-yl)spiro[chromeno[2,3-c]pyridine-5,4'-[1,3]oxazol]-2'-amine | 451.1 | AA11 | 0.0251 | 0.338 |
| 913 | (5S)-7-(2,4-difluoro-3-pyridinyl)-3-((3R)-tetrahydro-2H-pyran-3-yl)spiro[chromeno[2,3-c]pyridine-5,4'-[1,3]oxazol]-2'-amine | 451.1 | AA11 | 0.0161 | 0.211 |
| 914 | (5S)-7-(2,4-difluoro-3-pyridinyl)-3-((2R)-tetrahydro-2H-pyran-2-yl)spiro[chromeno[2,3-c]pyridine-5,4'-[1,3]oxazol]-2'-amine | 451.1 | AA11 | 0.0135 | 0.102 |
| 915 | (5S)-7-(2,4-difluoro-3-pyridinyl)-3-((2S)-tetrahydro-2H-pyran-2-yl)spiro[chromeno[2,3-c]pyridine-5,4'-[1,3]oxazol]-2'-amine | 451.1 | AA11 | 0.0025 | 0.023 |
| 916 | (5S)-3-(3,3-difluoro-1-pyrrolidinyl)-1-fluoro-7-(3-pyridinyl)spiro[chromeno[2,3-c]pyridine-5,4'-[1,3]oxazol]-2'-amine | 454 | CC4 | 0.0004 | 0.005 |
| 698 | (5S)-3-(4,4-difluoro-1-piperidinyl)-1-fluoro-7-(2-fluoro-3-pyridinyl)spiro[chromeno[2,3-c]pyridine-5,4'-[1,3]oxazol]-2'-amine | 486.1 | CC4 | 0.0003 | 0.006 |
| 917 | (5S)-1-fluoro-7-(2-fluoro-3-pyridinyl)-3-((3S)-3-fluoro-1-pyrrolidinyl)spiro[chromeno[2,3-c]pyridine-5,4'-[1,3]oxazol]-2'-amine | 454.1 | AA9 | 0.0003 | 0.005 |
| 918 | (5S)-3-(3,3-difluoro-1-pyrrolidinyl)-1-fluoro-7-(2-fluoro-3-pyridinyl)spiro[chromeno[2,3-c]pyridine-5,4'-[1,3]oxazol]-2'-amine | 472.1 | CC4 | 0.0002 | 0.004 |
| 919 | 3-((5S)-2'-amino-1-fluoro-3-((3R)-3-fluoro-1-pyrrolidinyl)spiro[chromeno[2,3-c]pyridine-5,4'-[1,3]oxazol]-7-yl)benzonitrile | 460.1 | CC4 | 0.0004 | 0.006 |
| 920 | 3-((5S)-2'-amino-3-(3,3-difluoro-1-pyrrolidinyl)-1-fluorospiro[chromeno[2,3-c]pyridine-5,4'-[1,3]oxazol]-7-yl)benzonitrile | 478.1 | CC4 | 0.0002 | 0.012 |
| 921 | (5S)-1-fluoro-7-(5-fluoro-3-pyridinyl)-3-((3R)-3-fluoro-1-pyrrolidinyl)spiro[chromeno[2,3-c]pyridine-5,4'-[1,3]oxazol]-2'-amine | 454.1 | CC4 | 0.0005 | 0.006 |
| 922 | (5S)-3-(3,3-difluoro-1-pyrrolidinyl)-1-fluoro-7-(5-fluoro-3-pyridinyl)spiro[chromeno[2,3-c]pyridine-5,4'-[1,3]oxazol]-2'-amine | 472.1 | CC4 | 0.0004 | 0.009 |
| 923 | 3-((5S)-2'-amino-3-(4,4-difluoro-1-piperidinyl)-1-fluorospiro[chromeno[2,3-c]pyridine-5,4'-[1,3]oxazol]-7-yl)benzonitrile | 491.9 | CC4 | 0.0003 | 0.032 |
| 924 | 3-((5S)-2'-amino-1-fluoro-3-((3S)-3-fluoro-1-pyrrolidinyl)spiro[chromeno[2,3-c]pyridine-5,4'-[1,3]oxazol]-7-yl)benzonitrile | 460 | CC4 | 0.0005 | 0.018 |
| 925 | (5S)-3-chloro-1-(3,3-difluoro-1-pyrrolidinyl)-7-(5-(1-propyn-1-yl)-3-pyridinyl)spiro[chromeno[2,3-c]pyridine-5,4'-[1,3]oxazol]-2'-amine | 507.9 | CC4 | 0.0246 | 0.547 |
| 926 | (5S)-1-fluoro-7-(5-fluoro-3-pyridinyl)-3-((3S)-3-fluoro-1-pyrrolidinyl)spiro[chromeno[2,3-c]pyridine-5,4'-[1,3]oxazol]-2'-amine | 453.9 | CC4 | 0.0003 | 0.008 |
| 927 | (5S)-3-(4,4-difluoro-1-piperidinyl)-1-fluoro-7-(5-fluoro-3-pyridinyl)spiro[chromeno[2,3-c]pyridine-5,4'-[1,3]oxazol]-2'-amine | 485.9 | CC4 | 0.0003 | 0.01 |
| 928 | (5S)-3-(5,6-dihydro-2H-pyran-3-yl)-7-(2-fluoro-3-pyridinyl)spiro[chromeno[2,3-c]pyridine-5,4'-[1,3]thiazol]-2'-amine | 447 | BB12 | 0.0004 | 0.008 |
| 929 | (5S)-7-(2-fluoro-3-pyridinyl)-3-((3R)-3-fluoro-1-pyrrolidinyl)spiro[chromeno[2,3-c]pyridine-5,4'-[1,3]thiazol]-2'-amine | 451.7 | CC10 | 0.0003 | 0.003 |
| 930 | (5S)-7-(2-fluoro-3-pyridinyl)-3-(tetrahydro-2H-pyran-4-yl)spiro[chromeno[2,3-c]pyridine-5,4'-[1,3]thiazol]-2'-amine | 449.1 | CC11 | 0.004 | 0.057 |

TABLE II-continued

| Ex. No. | Compound Name | Observed Mass | Method | BACE 1 FRET assay (uM) | HEK cell assay (uM) |
|---|---|---|---|---|---|
| 704 | (5S)-3-(3,3-difluoro-1-pyrrolidinyl)-7-(2-fluoro-3-pyridinyl)spiro[chromeno[2,3-c]pyridine-5,4'-[1,3]thiazol]-2'-amine | 470 | CC10 | 0.0003 | 0.012 |
| 931 | (5S)-7-(2-fluoro-3-pyridinyl)-3-((3S)-tetrahydro-2H-pyran-3-yl)spiro[chromeno[2,3-c]pyridine-5,4'-[1,3]thiazol]-2'-amine | 449 | CC11 | 0.0216 | 0.347 |
| 932 | (5S)-7-(2-fluoro-3-pyridinyl)-3-((3R)-tetrahydro-2H-pyran-3-yl)spiro[chromeno[2,3-c]pyridine-5,4'-[1,3]thiazol]-2'-amine | 449 | CC11 | 0.0162 | 0.208 |
| 933 | (5S)-3-(4,4-difluoro-1-piperidinyl)-7-(2-fluoro-3-pyridinyl)spiro[chromeno[2,3-c]pyridine-5,4'-[1,3]thiazol]-2'-amine | 484.1 | CC10 | 0.0005 | 0.033 |
| 934 | (5S)-7-(2-fluoro-3-pyridinyl)-3-(2-methyl-4-pyridinyl)spiro[chromeno[2,3-c]pyridine-5,4'-[1,3]thiazol]-2'-amine | 456 | BB12 | 0.001 | 0.005 |
| 935 | (4S)-4'-fluoro-7'-(2-pyrazinyl)-2'-(tetrahydro-2H-pyran-4-yl)spiro[1,3-oxazole-4,9'-xanthen]-2-amine | 433 | BB15 | 0.0066 | 0.082 |
| 936 | (5S)-7-(5-(1-propyn-1-yl)-3-pyridinyl)-3-(2-pyrimidinyl)spiro[chromeno[2,3-c]pyridine-5,4'-[1,3]oxazol]-2'-amine | 447 | AA1 | 0.003 | 0.028 |
| 937 | (4S)-4'-fluoro-7'-(5-methoxy-3-pyridinyl)-2'-(tetrahydro-2H-pyran-4-yl)spiro[1,3-oxazole-4,9'-xanthen]-2-amine | 462 | AA19 | 0.0017 | 0.028 |
| 708 | 3-((4S)-2-amino-4'-fluoro-7'-methoxyspiro[1,3-oxazole-4,9'-xanthen]-2'-yl)-3-oxetanol | 373 | CC14 | 13.253 | 10 |
| 709 | (4S)-4'-fluoro-2'-(3-fluoro-3-oxetanyl)-7'-methoxyspiro[1,3-oxazole-4,9'-xanthen]-2-amine | 375 | CC15 | 4.5575 | 10 |
| 938 | 4-((4S)-2-amino-4'-fluoro-7'-methoxyspiro[1,3-oxazole-4,9'-xanthen]-2'-yl)tetrahydro-2H-pyran-4-ol | 401 | CC14 | 4.4256 | 3.854 |
| 939 | (4S)-4'-fluoro-2'-(4-fluorotetrahydro-2H-pyran-4-yl)-7'-methoxyspiro[1,3-oxazole-4,9'-xanthen]-2-amine | 403 | CC15 | 1.7057 | 3.56 |
| 940 | (5S)-7-((3-methyl-3-oxetanyl)ethynyl)-3-(6-methyl-3-pyridinyl)spiro[chromeno[2,3-b]pyridine-5,4'-[1,3]thiazol]-2'-amine | 455.4 | CC5 | 0.0054 | 0.06 |
| 941 | (5S)-3-(6-methoxy-3-pyridinyl)-7-((3-methyl-3-oxetanyl)ethynyl)spiro[chromeno[2,3-b]pyridine-5,4'-[1,3]thiazol]-2'-amine | 471.3 | CC5 | 0.0038 | 0.097 |
| 942 | (5S)-3-(3,6-dihydro-2H-pyran-4-yl)-7-(5-(1-propyn-1-yl)-3-pyridinyl)spiro[chromeno[2,3-b]pyridine-5,4'-[1,3]oxazol]-2'-amine | 451.2 | AA1 | 0.0004 | 0.001 |
| 943 | (5S)-3-((3-methyl-3-oxetanyl)ethynyl)-7-(5-(1-propyn-1-yl)-3-pyridinyl)spiro[chromeno[2,3-b]pyridine-5,4'-[1,3]oxazol]-2'-amine | 463.2 | AA5 | 0.0007 | 0.001 |
| 944 | (5S)-3-(1-methyl-1H-pyrazol-4-yl)-7-(5-(1-propyn-1-yl)-3-pyridinyl)spiro[chromeno[2,3-b]pyridine-5,4'-[1,3]oxazol]-2'-amine | 449.4 | AA1 | 0.0005 | 0.001 |
| 945 | 4-((5S)-2'-amino-7-(5-(1-propyn-1-yl)-3-pyridinyl)spiro[chromeno[2,3-b]pyridine-5,4'-[1,3]oxazol]-3-yl)-2-methyl-3-butyn-2-ol | 451.2 | AA5 | 0.0008 | 0.002 |
| 946 | (4S)-2'-(3,6-dihydro-2H-pyran-4-yl)-4'-fluoro-7'-(5-(1-propyn-1-yl)-3-pyridinyl)spiro[1,3-oxazole-4,9'-xanthen]-2-amine | 468.3 | AA8 | 0.0003 | 0.004 |
| 947 | (4S)-4'-fluoro-2'-(1-methyl-1H-pyrazol-4-yl)-7'-(5-(1-propyn-1-yl)-3-pyridinyl)spiro[1,3-oxazole-4,9'-xanthen]-2-amine | 466.2 | AA8 | 0.0004 | 0.004 |
| 948 | 3-(((4S)-2-amino-4'-fluoro-7'-(5-(1-propyn-1-yl)-3-pyridinyl)spiro[1,3-oxazole-4,9'-xanthen]-2'-yl)oxy)-2,2-dimethylpropanenitrile | 483.3 | AA14 | 0.0004 | 0.004 |
| 949 | (4S)-4'-fluoro-2'-((3-methyl-3-oxetanyl)methoxy)-7'-(5-(1-propyn-1-yl)-3-pyridinyl)spiro[1,3-oxazole-4,9'-xanthen]-2-amine | 486.3 | AA14 | 0.0004 | 0.003 |
| 950 | (5S)-3-(5,6-dihydro-2H-pyran-3-yl)-7-(5-(1-propyn-1-yl)-3-pyridinyl)spiro[chromeno[2,3-b]pyridine-5,4'-[1,3]oxazol]-2'-amine | 451.2 | AA1 | 0.0003 | 0.002 |
| 951 | 4-((4S)-2-amino-4'-fluoro-7'-(5-(1-propyn-1-yl)-3-pyridinyl)spiro[1,3-oxazole-4,9'-xanthen]-2'-yl)-2-methyl-3-butyn-2-ol | 468.3 | AA21 | 0.0006 | 0.004 |
| 952 | (4S)-4'-fluoro-2'-(4-morpholinyl)-7'-(5-(1-propyn-1-yl)-3-pyridinyl)spiro[1,3-oxazole-4,9'-xanthen]-2-amine | 471.3 | AA16 | 0.0006 | 0.004 |

TABLE II-continued

| Ex. No. | Compound Name | Observed Mass | Method | BACE 1 FRET assay (uM) | HEK cell assay (uM) |
|---|---|---|---|---|---|
| 953 | (5S)-3-(3,6-dihydro-2H-pyran-4-yl)-7-(2-fluoro-5-(1-propyn-1-yl)-3-pyridinyl)spiro[chromeno[2,3-b]pyridine-5,4'-[1,3]oxazol]-2'-amine | 469.2 | AA1 | 0.0003 | 0.004 |
| 954 | (5S)-7-(2-fluoro-5-(1-propyn-1-yl)-3-pyridinyl)-3-(1-methyl-1H-pyrazol-4-yl)spiro[chromeno[2,3-b]pyridine-5,4'-[1,3]oxazol]-2'-amine | 467.4 | AA1 | 0.0003 | 0.003 |
| 955 | (5S)-7-(2-fluoro-5-(1-propyn-1-yl)-3-pyridinyl)-3-((3-methyl-3-oxetanyl)ethynyl)spiro[chromeno[2,3-b]pyridine-5,4'-[1,3]oxazol]-2'-amine | 481.2 | AA5 | 0.0005 | 0.002 |
| 956 | (5S)-7-(2-fluoro-5-(1-propyn-1-yl)-3-pyridinyl)-3-(2-fluoro-4-pyridinyl)spiro[chromeno[2,3-b]pyridine-5,4'-[1,3]oxazol]-2'-amine | 482.4 | AA1 | 0.0004 | 0.006 |
| 957 | (5S)-7-(2,4-difluoro-3-pyridinyl)-3-((3-methyl-3-oxetanyl)ethynyl)spiro[chromeno[2,3-c]pyridine-5,4'-[1,3]oxazol]-2'-amine | 461.1 | AA5 | 0.0012 | 0.033 |
| 958 | (5S)-3-(6-methyl-3-pyridinyl)-7-(3-pyridinyl)spiro[chromeno[2,3-b]pyridine-5,4'-[1,3]thiazol]-2'-amine | 438 | AA1 | 0.0015 | 0.019 |
| 959 | (5S)-3-(5,6-dihydro-2H-pyran-3-yl)-7-(3-pyridinyl)spiro[chromeno[2,3-b]pyridine-5,4'-[1,3]thiazol]-2'-amine | 429 | AA1 | 0.001 | 0.013 |
| 960 | (5S)-3-(1-methyl-1H-pyrazol-4-yl)-7-(3-pyridinyl)spiro[chromeno[2,3-b]pyridine-5,4'-[1,3]thiazol]-2'-amine | 427 | AA1 | 0.0037 | 0.036 |
| 961 | (5S)-7-(6-fluoro-3-pyridinyl)-3-((3-methyl-3-oxetanyl)ethynyl)spiro[chromeno[2,3-b]pyridine-5,4'-[1,3]thiazol]-2'-amine | 459 | AA5 | 0.001 | 0.018 |
| 962 | (5S)-7-(6-fluoro-3-pyridinyl)-3-(1-methyl-1H-pyrazol-4-yl)spiro[chromeno[2,3-b]pyridine-5,4'-[1,3]thiazol]-2'-amine | 445 | Aa1 | 0.0054 | 0.065 |
| 963 | (5S)-3-bromo-7-(6-fluoro-3-pyridinyl)spiro[chromeno[2,3-b]pyridine-5,4'-[1,3]thiazol]-2'-amine | 443 | AA1 | 0.0433 | 0.833 |
| 964 | (5S)-7-(5-fluoro-3-pyridinyl)-3-((3-methyl-3-oxetanyl)ethynyl)spiro[chromeno[2,3-b]pyridine-5,4'-[1,3]thiazol]-2'-amine | 459 | AA5 | 0.0009 | 0.015 |
| 965 | (5S)-3-bromo-7-(5-fluoro-3-pyridinyl)spiro[chromeno[2,3-b]pyridine-5,4'-[1,3]thiazol]-2'-amine | 443 | AA1 | 0.0233 | 0.785 |
| 966 | (5S)-3-(3,6-dihydro-2H-pyran-4-yl)-7-(6-fluoro-3-pyridinyl)spiro[chromeno[2,3-b]pyridine-5,4'-[1,3]thiazol]-2'-amine | 447 | AA1 | 0.0022 | 0.032 |
| 967 | (5S)-7-(benzyloxy)-3-(3,6-dihydro-2H-pyran-4-yl)spiro[chromeno[2,3-b]pyridine-5,4'-[1,3]oxazol]-2'-amine | 442 | AA14 | 0.0444 | 0.463 |
| 968 | (5S)-N-benzyl-7-(benzyloxy)-3-(3,6-dihydro-2H-pyran-4-yl)spiro[chromeno[2,3-b]pyridine-5,4'-[1,3]oxazol]-2'-amine | 532 | AA14 | 1.2596 | 10 |
| 969 | (5S)-2'-amino-3-(3,6-dihydro-2H-pyran-4-yl)spiro[chromeno[2,3-b]pyridine-5,4'-[1,3]oxazol]-7-ol | 352 | AA24 | 0.8348 | 10 |
| 970 | (5S)-3-(3,6-dihydro-2H-pyran-4-yl)-7-(4-pyridinylmethoxy)spiro[chromeno[2,3-b]pyridine-5,4'-[1,3]oxazol]-2'-amine | 443 | AA14 | 0.1121 | 0.455 |
| 971 | (5S)-3-(3,6-dihydro-2H-pyran-4-yl)-7-(3-pyridinylmethoxy)spiro[chromeno[2,3-b]pyridine-5,4'-[1,3]oxazol]-2'-amine | 443 | AA14 | 0.0336 | 0.154 |
| 972 | (5S)-3-(3,6-dihydro-2H-pyran-4-yl)-7-(2-pyridinylmethoxy)spiro[chromeno[2,3-b]pyridine-5,4'-[1,3]oxazol]-2'-amine | 443 | AA14 | 0.0896 | 0.629 |
| 973 | (5S)-7-(benzyloxy)-3-((3-methyl-3-oxetanyl)ethynyl)spiro[chromeno[2,3-b]pyridine-5,4'-[1,3]oxazol]-2'-amine | 454 | A | 0.187 | 1.368 |
| 974 | (5S)-3-(2-fluoro-4-pyridinyl)-7-(3-pyridinylmethoxy)spiro[chromeno[2,3-b]pyridine-5,4'-[1,3]oxazol]-2'-amine | 456 | AA13 | 0.11 | 2.724 |
| 975 | (5S)-3-(3-pyridinyl)-7-(3-pyridinylmethoxy)spiro[chromeno[2,3-b]pyridine-5,4'-[1,3]oxazol]-2'-amine | 438 | AA13 | 0.1155 | 1.083 |
| 976 | (5S)-3-bromo-7-(3-pyridinylmethoxy)spiro[chromeno[2,3-b]pyridine-5,4'-[1,3]oxazol]-2'-amine | 439 | A | 3.808 | 10 |

TABLE II-continued

| Ex. No. | Compound Name | Observed Mass | Method | BACE 1 FRET assay (uM) | HEK cell assay (uM) |
|---|---|---|---|---|---|
| 977 | (5S)-3-(6-methyl-3-pyridinyl)-7-(3-pyridinylmethoxy)spiro[chromeno[2,3-b]pyridine-5,4'-[1,3]oxazol]-2'-amine | 452 | AA13 | 0.0519 | 0.43 |
| 978 | (5S)-7-((2-bromobenzyl)oxy)-3-(3-pyridinyl)spiro[chromeno[2,3-b]pyridine-5,4'-[1,3]oxazol]-2'-amine | 515 | AA14 | 0.0507 | 0.334 |
| 979 | (5S)-7-((3-bromobenzyl)oxy)-3-(3-pyridinyl)spiro[chromeno[2,3-b]pyridine-5,4'-[1,3]oxazol]-2'-amine | 515 | AA14 | 0.0006 | 0.023 |
| 980 | (5S)-7-((4-bromobenzyl)oxy)-3-(3-pyridinyl)spiro[chromeno[2,3-b]pyridine-5,4'-[1,3]oxazol]-2'-amine | 515 | AA14 | 0.0456 | 0.336 |
| 981 | (5S)-7-(3-phenylpropoxy)-3-(3-pyridinyl)spiro[chromeno[2,3-b]pyridine-5,4'-[1,3]oxazol]-2'-amine | 465 | AA14 | 0.0222 | 0.262 |
| 982 | (5S)-7-((3-fluorobenzyl)oxy)-3-(3-pyridinyl)spiro[chromeno[2,3-b]pyridine-5,4'-[1,3]oxazol]-2'-amine | 455 | AA14 | 0.0668 | 0.644 |
| 983 | (5S)-7-((3-methoxybenzyl)oxy)-3-(3-pyridinyl)spiro[chromeno[2,3-b]pyridine-5,4'-[1,3]oxazol]-2'-amine | 467 | AA14 | 0.0246 | 0.314 |
| 984 | 3-((((5S)-2'-amino-3-(3-pyridinyl)spiro[chromeno[2,3-b]pyridine-5,4'-[1,3]oxazol]-7-yl)oxy)methyl)benzonitrile | 462 | AA14 | 0.0308 | 0.125 |
| 985 | (5S)-3-(3-pyridinyl)-7-((3-(trifluoromethyl)benzyl)oxy)spiro[chromeno[2,3-b]pyridine-5,4'-[1,3]oxazol]-2'-amine | 505 | AA14 | 0.0683 | 0.288 |
| 986 | (4S)-7'-(2-fluoro-3-pyridinyl)-2'-((3-methyl-3-oxetanyl)ethynyl)-3'-(trifluoromethoxy)spiro[1,3-oxazole-4,9'-xanthen]-2-amine | 526 | CC7, AA5 | 0.1929 | 2.82 |
| 987 | (4R)-7'-(2-fluoro-3-pyridinyl)-2'-((3-methyl-3-oxetanyl)ethynyl)-3'-(trifluoromethoxy)spiro[1,3-oxazole-4,9'-xanthen]-2-amine | 526 | CC7, AA5 | 4.628 | 10 |
| 988 | (4R)-2'-bromo-7'-(2-fluoro-3-pyridinyl)-3'-(trifluoromethoxy)spiro[1,3-oxazole-4,9'-xanthen]-2-amine | 510 | CC7, AA24 | 40 | 10 |
| 989 | (4S)-2'-bromo-7'-(2-fluoro-3-pyridinyl)-3'-(trifluoromethoxy)spiro[1,3-oxazole-4,9'-xanthen]-2-amine | 510 | CC7, AA24 | 2.3797 | 10 |
| 990 | (4R)-7'-(2-fluoro-3-pyridinyl)-2'-(2-fluoro-4-pyridinyl)-3'-(trifluoromethoxy)spiro[1,3-oxazole-4,9'-xanthen]-2-amine | 527 | CC7, AA1 | 8.2171 | 7.216 |
| 991 | (4S)-7'-(2-fluoro-3-pyridinyl)-2'-(2-fluoro-4-pyridinyl)-3'-(trifluoromethoxy)spiro[1,3-oxazole-4,9'-xanthen]-2-amine | 527 | CC7, AA1 | 0.1934 | 1.091 |
| 992 | (5R)-7-(2-fluoro-3-pyridinyl)-3-(2-fluoro-4-pyridinyl)spiro[chromeno[2,3-c]pyridine-5,4'-[1,3]thiazol]-2'-amine | 460.1 | BB12 | 0.0425 | 1.829 |
| 993 | (5R)-7-bromo-3-chlorospiro[chromeno[2,3-c]pyridine-5,4'-[1,3]thiazol]-2'-amine | 382 | BB26 | 11.597 | 10 |
| 994 | (5S)-7-bromo-3-chlorospiro[chromeno[2,3-c]pyridine-5,4'-[1,3]thiazol]-2'-amine | 382 | BB26 | 3.1948 | 10 |
| 995 | (5S)-7-(2-fluoro-3-pyridinyl)-3-((3-methyl-3-oxetanyl)ethynyl)spiro[chromeno[2,3-c]pyridine-5,4'-[1,3]thiazol]-2'-amine | 459.1 | BB13 | 0.0008 | 0.015 |
| 996 | (5S)-1-fluoro-7-(2-fluoro-3-pyridinyl)-3-(2-fluoro-4-pyridinyl)spiro[chromeno[2,3-c]pyridine-5,4'-[1,3]thiazol]-2'-amine | 478.1 | BB12 | 0.0002 | 0.013 |
| 997 | (5R)-1-fluoro-7-(2-fluoro-3-pyridinyl)-3-(2-fluoro-4-pyridinyl)spiro[chromeno[2,3-c]pyridine-5,4'-[1,3]thiazol]-2'-amine | 478.1 | BB12 | 0.0175 | 1.175 |
| 998 | (5R)-3-(3,6-dihydro-2H-pyran-4-yl)-1-fluoro-7-(2-fluoro-3-pyridinyl)spiro[chromeno[2,3-c]pyridine-5,4'-[1,3]thiazol]-2'-amine | 465 | BB12 | 0.0135 | 0.218 |
| 999 | (5S)-7-(2-fluoro-3-pyridinyl)-3-(4-morpholinyl)spiro[chromeno[2,3-c]pyridine-5,4'-[1,3]thiazol]-2'-amine | 450.1 | CC10 | 0.0005 | 0.014 |
| 1000 | (5S)-7-(2-fluoro-3-pyridinyl)-3-(2-fluoro-4-pyridinyl)spiro[chromeno[2,3-c]pyridine-5,4'-[1,3]thiazol]-2'-amine | 460.1 | BB12 | 0.0003 | 0.023 |
| 1001 | (5S)-3-(3,6-dihydro-2H-pyran-4-yl)-1-fluoro-7-(2-fluoro-3-pyridinyl)spiro[chromeno[2,3-c]pyridine-5,4'-[1,3]thiazol]-2'-amine | 465 | BB12 | 0.0003 | 0.004 |

TABLE II-continued

| Ex. No. | Compound Name | Observed Mass | Method | BACE 1 FRET assay (uM) | HEK cell assay (uM) |
|---|---|---|---|---|---|
| 695 | 2-(((5S)-2'-amino-7-(2-fluoro-3-pyridinyl)spiro[chromeno[2,3-b]pyridine-5,4'-[1,3]oxazol]-3-yl)ethynyl)-2-methyl-1,3-propanediol | 461 | CC1 | 0.0048 | 0.121 |
| 1002 | (4R)-7'-bromo-3',4'-difluoro-2'-methoxyspiro[1,3-oxazole-4,9'-xanthen]-2-amine | 396.8 | CC3 | 18.144 | 10 |
| 1003 | (4S)-7'-bromo-3',4'-difluoro-2'-methoxyspiro[1,3-oxazole-4,9'-xanthen]-2-amine | 396.8 | CC3 | 1.0894 | 10 |
| 1004 | (4R)-3',4'-difluoro-7'-(2-fluoro-3-pyridinyl)-2'-methoxyspiro[1,3-oxazole-4,9'-xanthen]-2-amine | 414 | AA24 | 5.5609 | 10 |
| 1005 | (4S)-3',4'-difluoro-7'-(2-fluoro-3-pyridinyl)-2'-methoxyspiro[1,3-oxazole-4,9'-xanthen]-2-amine | 414 | AA24 | 0.0058 | 1 |
| 1006 | (4R)-2'-(3,6-dihydro-2H-pyran-4-yl)-3',4'-difluoro-7'-(3-pyridinyl)spiro[1,3-oxazole-4,9'-xanthen]-2-amine | 448 | AA8 | 0.0152 | 0.627 |
| 1007 | (4S)-2'-(3,6-dihydro-2H-pyran-4-yl)-3',4'-difluoro-7'-(3-pyridinyl)spiro[1,3-oxazole-4,9'-xanthen]-2-amine | 448 | AA8 | 0.0019 | 0.024 |
| 1008 | 3-(((4R)-2-amino-3',4'-difluoro-7'-(3-pyridinyl)spiro[1,3-oxazole-4,9'-xanthen]-2'-yl)oxy)-2,2-dimethylpropanenitrile | 463 | AA14 | 0.0179 | 0.775 |
| 1009 | 3-(((4S)-2-amino-3',4'-difluoro-7'-(3-pyridinyl)spiro[1,3-oxazole-4,9'-xanthen]-2'-yl)oxy)-2,2-dimethylpropanenitrile | 463 | AA14 | 0.0017 | 0.032 |
| 1010 | (4R)-2'-(3,6-dihydro-2H-pyran-4-yl)-3',4'-difluoro-7'-(2-fluoro-3-pyridinyl)spiro[1,3-oxazole-4,9'-xanthen]-2-amine | 466 | AA8 | 0.0094 | 0.647 |
| 1011 | (4S)-2'-(3,6-dihydro-2H-pyran-4-yl)-3',4'-difluoro-7'-(2-fluoro-3-pyridinyl)spiro[1,3-oxazole-4,9'-xanthen]-2-amine | 466 | AA8 | 0.0005 | 0.017 |
| 1012 | (4R)-3',4'-difluoro-2'-(2-fluoro-4-pyridinyl)-7'-(3-pyridinyl)spiro[1,3-oxazole-4,9'-xanthen]-2-amine | 461 | AA8 | 0.0597 | 1.854 |
| 1013 | (4S)-3',4'-difluoro-2'-(2-fluoro-4-pyridinyl)-7'-(3-pyridinyl)spiro[1,3-oxazole-4,9'-xanthen]-2-amine | 461 | AA8 | 0.0024 | 0.1 |
| 1014 | (2R)-4-((5S)-2'-amino-7-(2-fluoro-3-pyridinyl)spiro[chromeno[2,3-b]pyridine-5,4'-[1,3]oxazol]-3-yl)-2-(chloromethyl)-2-methyl-3-butyn-1-ol, (2S)-4-((5S)-2'-amino-7-(2-fluoro-3-pyridinyl)spiro[chromeno[2,3-b]pyridine-5,4'-[1,3]oxazol]-3-yl)-2-(chloromethyl)-2-methyl-3-butyn-1-ol | 479 | CC2 | 0.0022 | 0.021 |
| 1015 | (2R)-4-((5S)-2'-amino-7-(2-fluoro-3-pyridinyl)spiro[chromeno[2,3-b]pyridine-5,4'-[1,3]oxazol]-3-yl)-2-(chloromethyl)-2-methyl-3-butyn-1-ol | 479 | CC2 | 0.001 | 0.009 |
| 696 | (2S)-4-((5S)-2'-amino-7-(2-fluoro-3-pyridinyl)spiro[chromeno[2,3-b]pyridine-5,4'-[1,3]oxazol]-3-yl)-2-(chloromethyl)-2-methyl-3-butyn-1-ol | 479 | CC2 | 0.0006 | 0.006 |
| 1016 | (5S)-3-bromo-7-iodospiro[chromeno[2,3-b]pyridine-5,4'-[1,3]oxazol]-2'-amine | 458.1 | N | 0.0007 | 0.012 |
| 1017 | (5R)-3-bromo-7-iodospiro[chromeno[2,3-b]pyridine-5,4'-[1,3]oxazol]-2'-amine | 458.1 | N | 27.644 | 0.886 |
| 1018 | (5S)-3-bromo-7-(2-fluoro-3-pyridinyl)spiro[chromeno[2,3-b]pyridine-5,4'-[1,3]oxazol]-2'-amine | 426.9 | AA24 | 0.5774 | 0.563 |
| 1019 | (5R)-7-(2,4-difluoro-3-pyridinyl)-3-(2-fluoro-4-pyridinyl)spiro[chromeno[2,3-c]pyridine-5,4'-[1,3]thiazol]-2'-amine, (5S)-7-(2,4-difluoro-3-pyridinyl)-3-(2-fluoro-4-pyridinyl)spiro[chromeno[2,3-c]pyridine-5,4'-[1,3]thiazol]-2'-amine | 478 | BB12 | 0.0007 | 0.033 |
| 1020 | (5S)-7-(2-fluoro-3-pyridinyl)-3-(5-methyl-1H-pyrazol-1-yl)spiro[chromeno[2,3-b]pyridine-5,4'-[1,3]oxazol]-2'-amine | 429 | AA16 | 0.0165 | 0.851 |
| 1021 | (5S)-7-(2-fluoro-3-pyridinyl)-3-(3-methyl-1H-pyrazol-1-yl)spiro[chromeno[2,3-b]pyridine-5,4'-[1,3]oxazol]-2'-amine | 429 | AA16 | 0.0035 | 0.119 |
| 1022 | (5S)-3-(3-methyl-1H-pyrazol-1-yl)-7-(3-pyridinyl)spiro[chromeno[2,3-b]pyridine-5,4'-[1,3]oxazol]-2'-amine | 411.2 | AA16 | 0.0072 | 0.106 |
| 1023 | (5S)-7-(2,4-difluoro-3-pyridinyl)-3-(2-fluoro-4-pyridinyl)spiro[chromeno[2,3-c]pyridine-5,4'-[1,3]thiazol]-2'-amine | 478 | BB12 | 0.0004 | 0.018 |

TABLE II-continued

| Ex. No. | Compound Name | Observed Mass | Method | BACE 1 FRET assay (uM) | HEK cell assay (uM) |
|---|---|---|---|---|---|
| 1024 | (5S)-3-chloro-1-fluoro-7-(2-fluoro-3-pyridinyl)spiro[chromeno[2,3-c]pyridine-5,4'-[1,3]thiazol]-2'-amine | 416.9 | AA2 | 0.0066 | 1.435 |
| 1025 | (5S)-1-fluoro-3,7-bis(2-fluoro-3-pyridinyl)spiro[chromeno[2,3-c]pyridine-5,4'-[1,3]thiazol]-2'-amine | 478 | AA2 | 0.001 | 0.141 |
| 1026 | (5S)-3-(3,4-dihydro-2H-pyran-6-yl)-1-fluoro-7-(2-fluoro-3-pyridinyl)spiro[chromeno[2,3-c]pyridine-5,4'-[1,3]thiazol]-2'-amine | 464.9 | AA1 | 0.0002 | 0.011 |
| 1027 | (5S)-1-fluoro-7-(2-fluoro-3-pyridinyl)-3-(4-pyridinyl)spiro[chromeno[2,3-c]pyridine-5,4'-[1,3]thiazol]-2'-amine | 460 | AA1 | 0.0004 | 0.014 |
| 1028 | (5S)-3-(5,6-dihydro-2H-pyran-3-yl)-1-fluoro-7-(2-fluoro-3-pyridinyl)spiro[chromeno[2,3-c]pyridine-5,4'-[1,3]thiazol]-2'-amine | 464.9 | AA1 | 0.0002 | 0.003 |
| 1029 | (5S)-1-fluoro-7-(2-fluoro-3-pyridinyl)-3-(tetrahydro-2H-pyran-4-yl)spiro[chromeno[2,3-c]pyridine-5,4'-[1,3]thiazol]-2'-amine | 467 | AA11 | 0.0004 | 0.007 |
| 1030 | (5S)-1-fluoro-3-(2-fluoro-4-pyridinyl)-7-(3-pyridinyl)spiro[chromeno[2,3-c]pyridine-5,4'-[1,3]thiazol]-2'-amine | 460 | AA1 | 0.0002 | 0.005 |
| 1031 | (5S)-1-fluoro-3,7-di-3-pyridinylspiro[chromeno[2,3-c]pyridine-5,4'-[1,3]thiazol]-2'-amine | 442 | AA2 | 0.0003 | 0.003 |
| 1032 | (5R)-1-fluoro-7-(2-fluoro-3-pyridinyl)-3-(2-methyl-4-pyridinyl)spiro[chromeno[2,3-c]pyridine-5,4'-[1,3]thiazol]-2'-amine, (5S)-1-fluoro-7-(2-fluoro-3-pyridinyl)-3-(2-methyl-4-pyridinyl)spiro[chromeno[2,3-c]pyridine-5,4'-[1,3]thiazol]-2'-amine | 473.9 | AA1 | 0.0004 | 0.003 |
| 1033 | (5S)-3-(6,6-dimethyl-3,6-dihydro-2H-pyran-4-yl)-1-fluoro-7-(2-fluoro-3-pyridinyl)spiro[chromeno[2,3-c]pyridine-5,4'-[1,3]thiazol]-2'-amine | 493 | BB12 | 0.1083 | 0.563 |
| 1034 | (5S)-3-(2,2-dimethyl-3,6-dihydro-2H-pyran-4-yl)-1-fluoro-7-(2-fluoro-3-pyridinyl)spiro[chromeno[2,3-c]pyridine-5,4'-[1,3]thiazol]-2'-amine | 493 | AA1 | 0.0007 | 0.005 |
| 1035 | (5R)-3-(6,6-dimethyl-3,6-dihydro-2H-pyran-4-yl)-1-fluoro-7-(2-fluoro-3-pyridinyl)spiro[chromeno[2,3-c]pyridine-5,4'-[1,3]thiazol]-2'-amine | 493 | AA1 | 0.0013 | 0.014 |
| 1036 | (5R)-3-(2,2-dimethyl-3,6-dihydro-2H-pyran-4-yl)-1-fluoro-7-(2-fluoro-3-pyridinyl)spiro[chromeno[2,3-c]pyridine-5,4'-[1,3]thiazol]-2'-amine | 493 | AA1 | 0.002 | 0.12 |
| 1037 | (5S)-1-fluoro-7-(2-fluoro-3-pyridinyl)-3-(2-methyl-4-pyridinyl)spiro[chromeno[2,3-c]pyridine-5,4'-[1,3]thiazol]-2'-amine | 473.9 | BB12 | 0.0021 | 0.049 |
| 1038 | (4S)-7'-(3,6-dihydro-2H-pyran-4-yl)-3',5'-difluoro-2'-(5-pyrimidinyl)spiro[1,3-oxazole-4,9'-xanthen]-2-amine | 449 | AA8 | 0.0004 | 0.01 |
| 1039 | (4S)-7'-(5,6-dihydro-2H-pyran-3-yl)-3',5'-difluoro-2'-(5-pyrimidinyl)spiro[1,3-oxazole-4,9'-xanthen]-2-amine | 449 | AA8 | 0.0004 | 0.008 |
| 1040 | (4S)-3',5'-difluoro-2'-(5-pyrimidinyl)-7'-(tetrahydro-2H-pyran-4-yl)spiro[1,3-oxazole-4,9'-xanthen]-2-amine | 451 | AA1 | 0.0015 | 0.03 |
| 1041 | (4S)-7'-(3,6-dihydro-2H-pyran-4-yl)-1',5'-difluoro-2'-(5-pyrimidinyl)spiro[1,3-oxazole-4,9'-xanthen]-2-amine | 449 | AA8 | 3.5924 | 10 |
| 1042 | (4R)-7'-(3,6-dihydro-2H-pyran-4-yl)-1',5'-difluoro-2'-(5-pyrimidinyl)spiro[1,3-oxazole-4,9'-xanthen]-2-amine | 449 | AA8 | 0.0135 | 0.117 |
| 1043 | (4S)-4'-fluoro-2'-(2-fluoroethoxy)-7'-(2-fluoro-3-pyridinyl)spiro[1,3-oxazole-4,9'-xanthen]-2-amine | 428.1 | AA14 | 0.001 | 0.057 |
| 1044 | (4S)-2'-(3,6-dihydro-2H-pyran-4-yl)-4'-fluoro-7'-(4-fluoro-3-pyridinyl)spiro[1,3-oxazole-4,9'-xanthen]-2-amine | 448 | AA8 | 0.0005 | 0.018 |
| 1045 | (4S)-2'-(5,6-dihydro-2H-pyran-3-yl)-4'-fluoro-7'-(4-fluoro-3-pyridinyl)spiro[1,3-oxazole-4,9'-xanthen]-2-amine | 448 | AA8 | 0.0006 | 0.012 |
| 1046 | (4R)-7'-(3,6-dihydro-2H-pyran-4-yl)-1',5'-difluoro-2'-(3-pyridinyl)spiro[1,3-oxazole-4,9'-xanthen]-2-amine | 448 | AA8 | 0.0212 | 0.209 |

TABLE II-continued

| Ex. No. | Compound Name | Observed Mass | Method | BACE 1 FRET assay (uM) | HEK cell assay (uM) |
|---|---|---|---|---|---|
| 1047 | (4R)-7'-(3,6-dihydro-2H-pyran-4-yl)-1',5'-difluoro-2'-(2-fluoro-3-pyridinyl)spiro[1,3-oxazole-4,9'-xanthen]-2-amine | 466 | AA8 | 0.0046 | 0.095 |
| 1048 | (4R)-7'-(5,6-dihydro-2H-pyran-3-yl)-1',5'-difluoro-2'-(2-fluoro-3-pyridinyl)spiro[1,3-oxazole-4,9'-xanthen]-2-amine | 466 | AA8 | 0.0039 | 0.036 |
| 1049 | (4R)-7'-(5,6-dihydro-2H-pyran-3-yl)-1',5'-difluoro-2'-(5-pyrimidinyl)spiro[1,3-oxazole-4,9'-xanthen]-2-amine | 449 | AA8 | 0.0156 | 0.085 |
| 1051 | (4R)-1',5'-difluoro-7'-(4-morpholinyl)-2'-(5-pyrimidinyl)spiro[1,3-oxazole-4,9'-xanthen]-2-amine | 452 | AA16 | 0.0468 | 0.182 |
| 1051 | (4R)-1',5'-difluoro-2'-(2-fluoro-3-pyridinyl)-7'-(4-morpholinyl)spiro[1,3-oxazole-4,9'-xanthen]-2-amine | 469 | AA16 | 0.0118 | 0.057 |
| 1052 | (4R)-1',5'-difluoro-7'-((3R)-3-fluoro-1-pyrrolidinyl)-2'-(5-pyrimidinyl)spiro[1,3-oxazole-4,9'-xanthen]-2-amine | 454 | AA16 | 0.0383 | 0.067 |
| 1053 | (4R)-1',5'-difluoro-2'-(2-fluoro-3-pyridinyl)-7'-((3R)-3-fluoro-1-pyrrolidinyl)spiro[1,3-oxazole-4,9'-xanthen]-2-amine | 471 | AA16 | 0.0103 | 0.079 |
| 1054 | (4S)-2'-(3-azabicyclo[3.1.0]hex-3-yl)-4'-fluoro-7'-(2-fluoro-3-pyridinyl)spiro[1,3-oxazole-4,9'-xanthen]-2-amine | 447 | AA20 | 0.0006 | 0.062 |
| 1055 | (4S)-4'-fluoro-7'-(2-fluoro-3-pyridinyl)-2'-((3R)-3-methyl-1-pyrrolidinyl)spiro[1,3-oxazole-4,9'-xanthen]-2-amine, (4S)-4'-fluoro-7'-(2-fluoro-3-pyridinyl)-2'-((3S)-3-methyl-1-pyrrolidinyl)spiro[1,3-oxazole-4,9'-xanthen]-2-amine | 449 | AA20 | 0.0004 | 0.033 |
| 1056 | (4S)-4'-fluoro-7'-(4-fluoro-3-pyridinyl)-2'-(tetrahydro-2H-pyran-4-yl)spiro[1,3-oxazole-4,9'-xanthen]-2-amine | 450 | AA18 | 0.003 | 0.017 |
| 1057 | (4S)-4'-fluoro-7'-((6-methyl-2-pyridinyl)oxy)-2'-(4-morpholinyl)spiro[1,3-oxazole-4,9'-xanthen]-2-amine | 463 | CC31 | 0.0732 | 0.687 |
| 1058 | (4S)-4'-fluoro-7'-((5-methyl-2-pyridinyl)oxy)-2'-(4-morpholinyl)spiro[1,3-oxazole-4,9'-xanthen]-2-amine | 463 | CC31 | 0.0507 | 0.604 |
| 1059 | (4S)-4'-fluoro-7'-((4-methyl-2-pyridinyl)oxy)-2'-(4-morpholinyl)spiro[1,3-oxazole-4,9'-xanthen]-2-amine | 463 | CC31 | 0.0339 | 0.609 |
| 1060 | (4S)-7'-((6-chloro-2-pyridinyl)oxy)-4'-fluoro-2'-(4-morpholinyl)spiro[1,3-oxazole-4,9'-xanthen]-2-amine | 483 | CC31 | 0.0335 | 0.318 |
| 1061 | (4S)-7'-((5-chloro-2-pyridinyl)oxy)-4'-fluoro-2'-(4-morpholinyl)spiro[1,3-oxazole-4,9'-xanthen]-2-amine | 483 | CC31 | 0.0574 | 0.538 |
| 1062 | (4S)-7'-((4-chloro-2-pyridinyl)oxy)-4'-fluoro-2'-(4-morpholinyl)spiro[1,3-oxazole-4,9'-xanthen]-2-amine | 483 | CC31 | 0.0223 | 0.374 |
| 1063 | (4S)-2'-(3,6-dihydro-2H-pyran-4-yl)-4'-fluoro-7'-((6-methyl-2-pyridinyl)oxy)spiro[1,3-oxazole-4,9'-xanthen]-2-amine | 460 | CC31 | 0.0337 | 0.751 |
| 1064 | (4S)-2'-(3,6-dihydro-2H-pyran-4-yl)-4'-fluoro-7'-((5-methyl-2-pyridinyl)oxy)spiro[1,3-oxazole-4,9'-xanthen]-2-amine | 460 | CC31 | 0.0211 | 0.442 |
| 1065 | (4S)-2'-(3,6-dihydro-2H-pyran-4-yl)-4'-fluoro-7'-((4-methyl-2-pyridinyl)oxy)spiro[1,3-oxazole-4,9'-xanthen]-2-amine | 460 | CC31 | 0.0377 | 1.479 |
| 725 | (4S)-7'-((6-chloro-2-pyridinyl)oxy)-2'-(3,6-dihydro-2H-pyran-4-yl)-4'-fluorospiro[1,3-oxazole-4,9'-xanthen]-2-amine | 480 | CC31 | 0.0227 | 1.924 |
| 1066 | (4S)-7'-((5-chloro-2-pyridinyl)oxy)-2'-(3,6-dihydro-2H-pyran-4-yl)-4'-fluorospiro[1,3-oxazole-4,9'-xanthen]-2-amine | 480 | CC31 | 0.0526 | 1.974 |
| 1067 | (4S)-4'-fluoro-2'-(2-fluoro-2-methylpropoxy)-7'-(2-fluoro-3-pyridinyl)spiro[1,3-thiazole-4,9'-xanthen]-2-amine | 472 | AA14 | 0.0003 | 0.015 |
| 1068 | (4S)-4'-fluoro-7'-(2-fluoro-3-pyridinyl)-2'-(4-pyridinyl)spiro[1,3-thiazole-4,9'-xanthen]-2-amine | 459 | AA8 | 0.0023 | 0.062 |
| 1069 | (4S)-4'-fluoro-7'-(2-fluoro-3-pyridinyl)-2'-(4-morpholinyl)spiro[1,3-thiazole-4,9'-xanthen]-2-amine | 467 | AA20 | 0.0006 | 0.01 |

TABLE II-continued

| Ex. No. | Compound Name | Observed Mass | Method | BACE 1 FRET assay (uM) | HEK cell assay (uM) |
|---|---|---|---|---|---|
| 1070 | (4S)-7'-(5-(1,1-difluoroethyl)-3-pyridinyl)-4'-fluoro-2'-methoxyspiro[1,3-oxazole-4,9'-xanthen]-2-amine | 442 | CC29 | 0.3446 | 0.367 |
| 723 | (4S)-4'-fluoro-2'-methoxy-7'-(6-(1-propyn-1-yl)-2-pyrazinyl)spiro[1,3-oxazole-4,9'-xanthen]-2-amine | 417 | CC29 | 0.0926 | 0.958 |
| 1071 | (4S)-4'-fluoro-7'-(2-fluoro-3-pyridinyl)-2'-(2-fluoro-4-pyridinyl)spiro[1,3-thiazole-4,9'-xanthen]-2-amine | 477 | AA8 | 0.0003 | 0.044 |
| 1072 | (4S)-4'-fluoro-7'-(2-fluoro-3-pyridinyl)-2'-(2-methyl-4-pyridinyl)spiro[1,3-thiazole-4,9'-xanthen]-2-amine | 473 | AA8 | 0.0033 | 0.029 |
| 1073 | (4S)-4'-fluoro-2'-methoxy-7'-(5-(trifluoromethyl)-3-pyridinyl)spiro[1,3-oxazole-4,9'-xanthen]-2-amine | 446 | CC29 | 0.0614 | 0.194 |
| 1074 | (5-((4S)-2-amino-5'-fluoro-7'-methoxyspiro[1,3-oxazole-4,9'-xanthen]-2'-yl)-3-pyridinyl)acetonitrile | 417 | CC29 | 0.1307 | 0.324 |
| 1075 | (4S)-4'-fluoro-7'-(2-fluoro-3-pyridinyl)-2'-((3R)-3-fluoro-1-pyrrolidinyl)spiro[1,3-thiazole-4,9'-xanthen]-2-amine | 469.2 | AA20 | 0.0015 | 0.015 |
| 1076 | (4S)-2'-(4,4-difluoro-1-piperidinyl)-4'-fluoro-7'-(2-fluoro-3-pyridinyl)spiro[1,3-thiazole-4,9'-xanthen]-2-amine | 501 | AA20 | 0.0004 | 0.014 |
| 1077 | (4S)-2'-(3,3-difluoro-1-pyrrolidinyl)-4'-fluoro-7'-(2-fluoro-3-pyridinyl)spiro[1,3-thiazole-4,9'-xanthen]-2-amine | 487 | AA20 | 0.0003 | 0.009 |
| 1078 | (4S)-4'-fluoro-7'-(2-fluoro-3-pyridinyl)-2'-(2-oxa-5-azabicyclo[2.2.1]hept-5-yl)spiro[1,3-thiazole-4,9'-xanthen]-2-amine | 479.1 | AA20 | 0.0004 | 0.005 |
| 1079 | (4S)-4'-fluoro-7'-(2-fluoro-3-pyridinyl)-2'-(2-pyrimidinyl)spiro[1,3-thiazole-4,9'-xanthen]-2-amine | 460 | AA22 | 0.0004 | 0.012 |
| 1080 | (4S)-2'-(((1R)-2,2-difluorocyclopropyl)methoxy)-4'-fluoro-7'-(2-fluoro-3-pyridinyl)spiro[1,3-thiazole-4,9'-xanthen]-2-amine, (4S)-2'-(((1S)-2,2-difluorocyclopropyl)methoxy)-4'-fluoro-7'-(2-fluoro-3-pyridinyl)spiro[1,3-thiazole-4,9'-xanthen]-2-amine | 488 | AA14 | 0.0005 | 0.047 |
| 724 | (4S)-2'-(2,2-difluoropropoxy)-4'-fluoro-7'-(2-fluoro-3-pyridinyl)spiro[1,3-thiazole-4,9'-xanthen]-2-amine | 476.1 | CC30 | 0.001 | 0.022 |
| 1081 | (4S)-4'-fluoro-2'-(3-fluoro-2,2-dimethylpropoxy)-7'-(2-fluoro-3-pyridinyl)spiro[1,3-thiazole-4,9'-xanthen]-2-amine | 486 | CC30 | 0.2139 | 0.899 |
| 1082 | (4S)-4'-fluoro-7'-(2-fluoro-3-pyridinyl)-2'-((3S)-3-methyl-4-morpholinyl)spiro[1,3-thiazole-4,9'-xanthen]-2-amine | 481 | AA20 | 0.0003 | 0.004 |
| 1083 | (4S)-4'-fluoro-7'-(2-fluoro-3-pyridinyl)-2'-(3-pyridinyl)spiro[1,3-thiazole-4,9'-xanthen]-2-amine | 459 | AA8 | 0.0012 | 0.018 |
| 1084 | (4S)-4'-fluoro-7'-(2-fluoro-3-pyridinyl)-2'-((1S,4S)-2-oxa-5-azabicyclo[2.2.1]hept-5-yl)spiro[1,3-thiazole-4,9'-xanthen]-2-amine | 479 | AA20 | 0.0075 | 0.102 |
| 1085 | (4S)-4'-fluoro-7'-(2-fluoro-3-pyridinyl)-2'-((1R,4R)-2-oxa-5-azabicyclo[2.2.1]hept-5-yl)spiro[1,3-thiazole-4,9'-xanthen]-2-amine | 479 | AA20 | 0.0003 | 0.023 |
| 1086 | (4S)-4'-fluoro-7'-(2-fluoro-3-pyridinyl)-2'-(6-methyl-3-pyridinyl)spiro[1,3-thiazole-4,9'-xanthen]-2-amine | 473.1 | AA8 | 0.067 | 1.371 |
| 1087 | (4S)-4'-fluoro-7'-(2-fluoro-3-pyridinyl)-2'-(2-oxa-6-azaspiro[3.3]hept-6-yl)spiro[1,3-oxazole-4,9'-xanthen]-2-amine | 463 | AA20 | 0.002 | 0.002 |
| 1088 | (5R)-3-chloro-7-(2-fluoro-3-pyridinyl)-5'-(methoxymethyl)spiro[chromeno[2,3-c]pyridine-5,4'-[1,3]thiazol]-2'-amine, (5S)-3-chloro-7-(2-fluoro-3-pyridinyl)-5'-(methoxymethyl)spiro[chromeno[2,3-c]pyridine-5,4'-[1,3]thiazol]-2'-amine | 443.1 | CC28 | 0.115 | 3.06 |
| 720 | (4R)-4'-fluoro-7'-(2-fluoro-3-pyridinyl)-2'-methoxy-5-(methoxymethyl)spiro[1,3-thiazole-4,9'-xanthen]-2-amine, (4S)-4'-fluoro-7'-(2-fluoro-3-pyridinyl)-2'-methoxy-5-(methoxymethyl)spiro[1,3-thiazole-4,9'-xanthen]-2-amine | 456 | CC26 | 0.067 | 1.37 |

TABLE II-continued

| Ex. No. | Compound Name | Observed Mass | Method | BACE 1 FRET assay (uM) | HEK cell assay (uM) |
|---|---|---|---|---|---|
| 1089 | (4S/R,5S)-4'-fluoro-7'-(2-fluoropyridin-3-yl)-2'-methoxy-5-(methoxymethyl)-5H-spiro[thiazole-4,9'-xanthen]-2-amine | 456 | CC26 | 0.0033 | 0.923 |
| 1090 | (4R)-4'-fluoro-7'-(2-fluoro-3-pyridinyl)-2'-methoxy-5-(methoxymethyl)spiro[1,3-thiazole-4,9'-xanthen]-2-amine | 456 | CC26 | 2.4 | >10 |
| 1091 | (4S)-4'-fluoro-7'-(2-fluoro-3-pyridinyl)-2'-methoxy-5-(methoxymethyl)spiro[1,3-thiazole-4,9'-xanthen]-2-amine | 456 | CC26 | 5.07 | >10 |
| 1085 | (4S)-4'-fluoro-7'-(2-fluoro-3-pyridinyl)-2'-((1R,4R)-2-oxa-5-azabicyclo[2.2.1]hept-5-yl)spiro[1,3-thiazole-4,9'-xanthen]-2-amine | 479 | AA20 | 0.0003 | 0.023 |
| 1092 | (4S/R,5S)-4'-fluoro-7'-(2-fluoropyridin-3-yl)-2'-methoxy-5-(methoxymethyl)-5H-spiro[thiazole-4,9'-xanthen]-2-amine | 456 | CC26 | 0.0057 | 0.498 |
| 1093 | (4'S/R,5'S)-7-(2-fluoropyridin-3-yl)-3-(2-fluoropyridin-4-yl)-5'-(methoxymethyl)-5'H-spiro[chromeno[2,3-c]pyridine-5,4'-thiazol]-2'-amine | 504.2 | CC28 | 0.0057 | 0.495 |
| 1094 | (5R)-7-(2-fluoro-3-pyridinyl)-3-(2-fluoro-4-pyridinyl)-5'-(methoxymethyl)spiro[chromeno[2,3-c]pyridine-5,4'-[1,3]thiazol]-2'-amine | 504.2 | CC28 | 0.0043 | 0.128 |
| 722 | (5S)-7-(2-fluoro-3-pyridinyl)-3-(2-fluoro-4-pyridinyl)-5'-(methoxymethyl)spiro[chromeno[2,3-c]pyridine-5,4'-[1,3]thiazol]-2'-amine | 504.2 | CC28 | 0.335 | 5.93 |
| 1095 | (4'S/R,5'S)-7-(2-fluoropyridin-3-yl)-3-(2-fluoropyridin-4-yl)-5'-(methoxymethyl)-5'H-spiro[chromeno[2,3-c]pyridine-5,4'-thiazol]-2'-amine | 504.2 | CC28 | 0.573 | 5.99 |

Various of the compounds in Tables I and II herein were prepared and characterized as follows:

Example 225

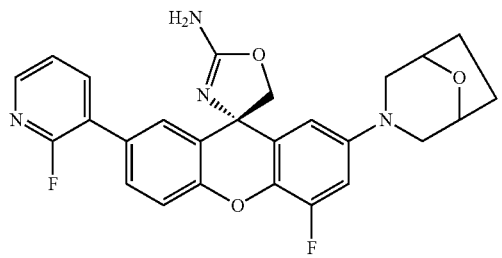 [SMILES: NC1=N[C@@]2(CO1)c1cc(-c3cccnc3F)ccc1Oc1c(F)cc(N3CC4CCC(C3)O4)cc12]

Synthesis of (4S)-2'-(8-oxa-3-azabicyclo[3.2.1]octan-3-yl)-4'-fluoro-7'-(2-fluoropyridin-3-yl)-5H-spiro[oxazole-4,9'-xanthen]-2-amine The titled compound was synthesized by steps analogous to those described in method AA20 above, but using (S)-2-amino-7'-bromo-4'-fluoro-5H-spiro[oxazole-4,9'-xanthen]-2'-ol (prepared as described in Method BB40 and Example 2).

MS m/z=477.0 [M+H]$^+$. Calculated for $C_{26}H_{22}F_2N_4O_3$: 476.17.

$^1$H NMR (400 MHz, DMSO-d$_6$) ppm 1.83 (br. s., 4 H), 2.74-2.84 (m, 2 H), 3.29-3.38 (m, 2 H), 4.19 (s, 2 H), 4.44 (br. s., 2 H), 6.36-6.59 (m, 3 H), 6.88 (dd, J=14.2, 2.8 Hz, 1H), 7.31 (dd, J=8.4, 0.3 Hz, 1 H), 7.48 (ddd, J=7.4, 4.9, 2.0 Hz, 1 H), 7.53-7.61 (m, 2 H), 8.09 (ddd, J=10.4, 7.5, 2.0 Hz, 1 H), 8.22-8.25 (m, 1 H).

Example 226

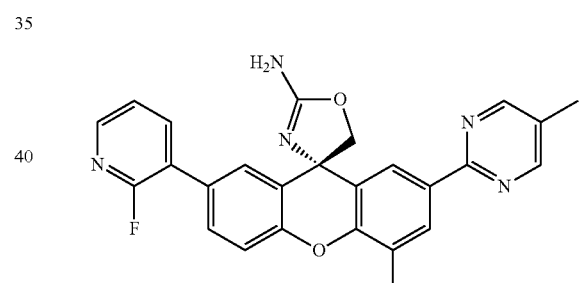

Synthesis of (S)-4'-fluoro-7'-(2-fluoropyridin-3-yl)-2'-(5-methylpyrimidin-2-yl)-5H-spiro[oxazole-4,9'-xanthen]-2-amine The titled compound was synthesized by steps analogous to those described in method AA8 above, but using (S)-2-amino-7'-bromo-4'-fluoro-5H-spiro[oxazole-4,9'-xanthen]-2'-ol (prepared as described in Method BB40 and Example 2).

MS m/z=458.0 [M+H]$^+$. Calculated for $C_{25}H_{17}F_2N_5O_2$: 457.14.

$^1$H NMR (400 MHz, DMSO-d$_6$) δ ppm 2.68 (s, 3 H), 4.32 (d, J=8.6 Hz, 1 H), 4.38 (d, J=8.6 Hz, 1 H), 6.45-6.57 (m, 2 H), 7.41 (d, J=8.4 Hz, 1 H), 7.46-7.53 (m, 2 H), 7.58-7.67 (m, 2 H), 7.83 (dd, J=11.7, 2.2 Hz, 1 H), 8.12 (ddd, J=10.3, 7.5, 1.9 Hz, 1 H), 8.23-8.28 (m, 1 H), 9.00 (s, 2 H)

Example 236

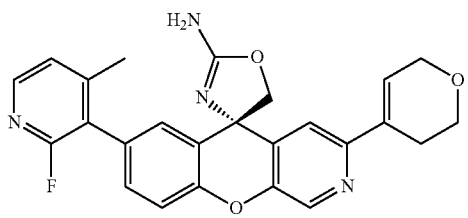 [SMILES: Cc1ccnc(F)c1-c1ccc2c(c1)[C@@]1(COC(N)=N1)c1cc(C3=CCOCC3)ncc1O2]

Synthesis of (S)-3-(3,6-dihydro-2H-pyran-4-yl)-7-(2-fluoro-4-methylpyridin-3-yl)-5'H-spiro[chromeno[2,3-c]pyridine-5,4'-oxazol]-2'-amine The titled compound was synthesized by steps analogous to those described in method AA1 above, but using (S)-7-bromo-3-chloro-5'H-spiro[chromeno[2,3-c]pyridine-5,4'-oxazol]-2'-amine (prepared as described in Method BB41), 2-fluoro-4-methylpyridin-3-ylboronic acid and 2-(3,6-dihydro-2H-pyran-4-yl)-4,4,5,5-tetramethyl-1,3,2-dioxaborolane.

MS m/z=445.2 [M+H]$^+$. Calculated for $C_{25}H_{21}FN_4O_3$: 444.16

$^1$H NMR (400 MHz, DMSO-d6) δ ppm 2.21 (s, 3 H) 2.54 (br.s., 2 H) 3.84 (t, J=5.6 Hz, 2H) 4.28 (d, J=2.5 Hz, 4 H) 6.44-6.72 (m, 3 H) 7.28 (s, 1 H) 7.32-7.36 (m, 2 H) 7.36-7.40 (m, 1 H) 7.42 (s, 1 H) 8.12 (d, J=5.1 Hz, 1 H) 8.51 (s, 1 H)

Example 262

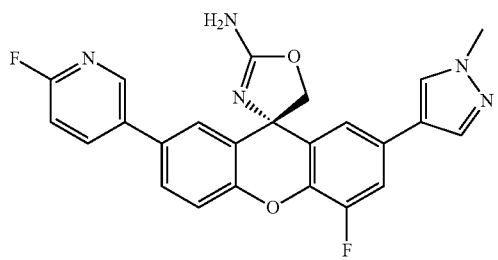 [SMILES: Cn1cc(-c2cc(F)c3c(c2)[C@]2(COC(N)=N2)c2cc(-c4ccc(F)nc4)ccc2O3)cn1]

Synthesis of (S)-4'-fluoro-7'-(6-fluoropyridin-3-yl)-2'-(1-methyl-1H-pyrazol-4-yl)-5H-spiro[oxazole-4,9'-xanthen]-2-amine The titled compound was synthesized by steps analogous to those described in method AA1 above, but using (S)-2-amino-7'-bromo-4'-fluoro-5H-spiro[oxazole-4,9'-xanthen]-2'-ol (prepared by steps analogous to those described in Method BB40 and Example 2).

MS m/z=446 [M+H]$^+$. Chemical Formula: $C_{24}H_{17}F_2N_5O_2$. Exact Mass: 445.14.

$^1$H NMR (400 MHz, DMSO-d$_6$) δ ppm 3.88 (s, 3 H) 4.20-4.44 (m, 2 H) 6.49 (s, 1 H) 7.26-7.33 (m, 2 H) 7.36 (d, J=8.4 Hz, 1 H) 7.55 (dd, J=11.9, 1.6 Hz, 1 H) 7.60 (d, J=2.2 Hz, 1 H) 7.71 (dd, J=8.6, 2.2 Hz, 1 H) 7.83 (s, 1 H) 8.13 (s, 1 H) 8.24 (ddd, J=8.1, 2.5 Hz, 1 H) 8.43-8.59 (m, 1 H)

Example 280

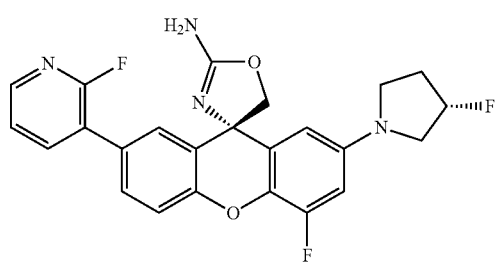 [SMILES: NC1=N[C@@]2(CO1)c1cc(-c3cccnc3F)ccc1Oc1c(F)cc(N3CC[C@H](F)C3)cc12]

Synthesis of (S)-4'-fluoro-7'-(2-fluoropyridin-3-yl)-2'-((S)-3-fluoropyrrolidin-1-yl)-5H-spiro[oxazole-4,9'-xanthen]-2-amine The titled compound was synthesized by steps analogous to those described in method AA20 above, but using (S)-2-amino-7'-bromo-4'-fluoro-5H-spiro[oxazole-4,9'-xanthen]-2'-ol (prepared by steps analogous to those described in Method BB40 and Example 2).

MS m/z=453.2 [M+H]$^+$. Chemical Formula: $C_{24}H_{19}F_3N_4O_2$. Exact Mass: 452.15

$^1$H NMR (400 MHz, DMSO-d$_6$) δ ppm 2.00-2.43 (m, 2 H) 3.24-3.63 (m, 5 H) 3.89-4.52 (m, 2 H) 6.21-6.36 (m, 1 H) 6.37-6.75 (m, 3 H) 7.26-7.38 (m, 1 H) 7.50 (ddd, J=7.3, 5.0, 1.9 Hz, 1 H) 7.53-7.68 (m, 2 H) 8.04-8.17 (m, 1 H) 8.25 (ddd, J=4.8, 1.4 Hz, 1 H)

Example 339

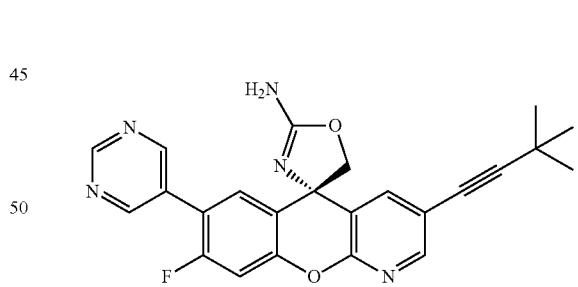

Synthesis of (S)-3-(3,3-dimethylbut-1-yn-1-yl)-8-fluoro-7-(pyrimidin-5-yl)-5'H-spiro[chromeno[2,3-b]pyridine-5,4'-oxazol]-2'-amine The titled compound was synthesized as described in Method AA33 but using 7-bromo-8-fluoro-3-iodo-5'H-spiro[chromeno[2,3-b]pyridine-5,4'-oxazol]-2'-amine (prepared as described in Method BB24).

MS m/z=430.0 [M+H]$^+$. Calculated for $C_{24}H_{20}FN_5O_2$: 429.45.

¹H NMR (400 MHz, MeCN) δ ppm 1.33 (s, 9H) 4.32 (s, 2H) 7.15 (d, J=12 Hz, 1H) 7.57 (d, J=8.0 Hz, 1H) 7.73 (d, J=2 Hz, 1H) 8.24 (d, J=2 Hz, 1H) 8.93 (s, 2H) 9.15 (s, 1H)

Example 369

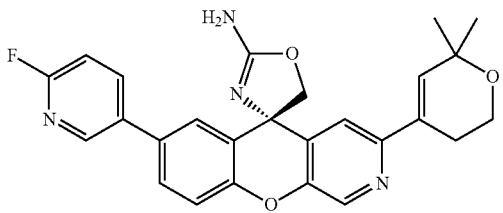 [SMILES: CC1(C)C=C(c2cc3c(cn2)Oc2ccc(-c4ccc(F)nc4)cc2[C@@]32COC(N)=N2)CCO1]

Synthesis of (S)-3-(6,6-dimethyl-3,6-dihydro-2H-pyran-4-yl)-7-(6-fluoropyridin-3-yl)-5'H-spiro[chromeno[2,3-c]pyridine-5,4'-oxazol]-2'-amine The titled compound was synthesized by steps analogous to those described in method AA1 above, but using (S)-7-bromo-3-chloro-5'H-spiro[chromeno[2,3-c]pyridine-5,4'-oxazol]-2'-amine (prepared as described in Method BB41), 6-fluoropyridin-3-ylboronic acid and 2-(6,6-dimethyl-3,6-dihydro-2H-pyran-4-yl)-4,4,5,5-tetramethyl-1,3,2-dioxaborolane. MS m/z=459.0 [M+H]⁺. Calculated for C26H23FN4O3: 458.18 ¹H NMR (400 MHz, CHLOROFORM-d) δ ppm 1.38 (d, J=2.93 Hz, 6 H) 2.53-2.60 (m, 2 H) 3.96 (t, J=5.38 Hz, 2 H) 4.36 (d, J=6.46 Hz, 2 H) 4.55-4.66 (m, 2 H) 6.56 (s, 1 H) 6.98-7.04 (m, 1 H) 7.28 (d, J=8.61 Hz, 1 H) 7.38 (s, 1 H) 7.45-7.53 (m, 1 H) 7.55 (d, J=2.35 Hz, 1 H) 7.87-8.04 (m, 1 H) 8.41 (d, J=2.35 Hz, 1 H) 8.50 (s, 1 H)

Example 385

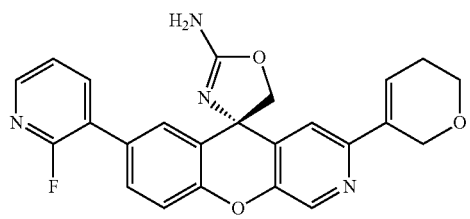 [SMILES: NC1=N[C@@]2(CO1)c1cc(-c3cccnc3F)ccc1Oc1cnc(C3=CCCOC3)cc12]

Synthesis of (S)-3-(5,6-dihydro-2H-pyran-3-yl)-1-fluoro-7-(3-fluoropyridin-2-yl)-5'H-spiro[chromeno[2,3-c]pyridine-5,4'-oxazol]-2'-amine The titled compound was synthesized by steps analogous to those described in method AA1 above, but using (S)-7-bromo-3-chloro-5'H-spiro[chromeno[2,3-c]pyridine-5,4'-oxazol]-2'-amine (prepared as described in Method BB41), 2-fluoropyridin-3-ylboronic acid and 2-(5,6-dihydro-2H-pyran-3-yl)-4,4,5,5-tetramethyl-1,3,2-dioxaborolane.

MS m/z=431.0 [M+H]⁺. Calculated for C24H19FN4O3: 430.14

¹H NMR (400 MHz, CHLOROFORM-d) δ ppm 2.33-2.41 (m, 2 H) 3.86 (s, 2 H) 4.39 (d, J=7.82 Hz, 2 H) 4.66 (br. s., 2 H) 6.60-6.70 (m, 1 H) 7.28 (s, 2 H) 7.39 (s, 1 H) 7.49-7.59 (m, 1 H) 7.59-7.67 (m, 1 H) 7.81-7.99 (m, 1 H) 8.15-8.27 (m, 1 H) 8.45 (s, 1 H)

Example 443

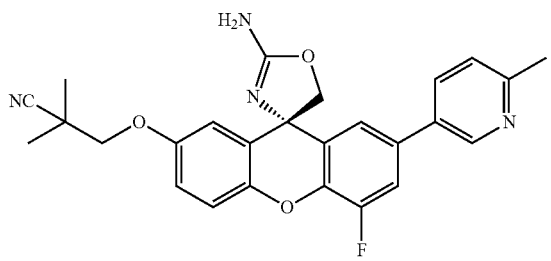 [SMILES: Cc1ccc(-c2cc(F)c3c(c2)[C@]2(COC(N)=N2)c2cc(OCC(C)(C)C#N)ccc2O3)cn1]

Synthesis of (S)-3-(2-amino-4'-fluoro-2'-(6-methylpyridin-3-yl)-5H-spiro[oxazole-4,9'-xanthene]-7'-yloxy)-2,2-dimethylpropanenitrile The titled compound was synthesized by steps analogous to those described in method AA13 above, but using (S)-2-amino-2'-bromo-4'-fluoro-5H-spiro[oxazole-4,9'-xanthen]-7'-ol (prepared as described in Method BB40 but using 4-bromo-2-fluorophenol and 2-bromo-5-methoxybenzoic acid), 2-cyano-2-methylpropyl 4-methylbenzenesulfonate, and (6-methylpyridin-3-yl)boronic acid.

MS m/z=459.0 [M+H]⁺. Calculated for C26H23FN4O3: 458.18.

¹H NMR (400 MHz, MeOH) δ ppm 1.49 (s, 6 H) 2.58 (s, 3 H) 3.95-4.05 (m, 2 H) 4.35-4.44 (m, 2 H) 7.01-7.07 (m, 2 H) 7.18-7.23 (m, 1 H) 7.39 (d, J=8.02 Hz, 1 H) 7.45 (d, J=1.37 Hz, 1 H) 7.52 (dd, J=11.54, 2.15 Hz, 1 H) 7.97 (dd, J=8.12, 2.45 Hz, 1 H) 8.65 (d, J=2.15 Hz, 1 H)

Example 452

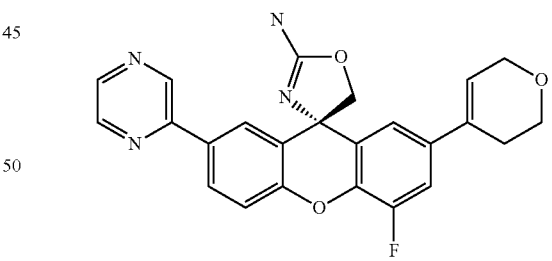

Synthesis of (S)-2'-(3,6-dihydro-2H-pyran-4-yl)-4'-fluoro-7'-(pyrazin-2-yl)-5H-spiro[oxazole-4,9'-xanthen]-2-amine The titled compound was synthesized by steps analogous to those described in method AA22 above, but using (S)-2-amino-2'-bromo-4'-fluoro-5H-spiro[oxazole-4,9'-xanthen]-7'-ol (prepared as described in Method BB40 but using 4-bromo-2-fluorophenol and 2-bromo-5-methoxybenzoic acid), 2-(3,6-dihydro-2H-pyran-4-yl)-4,4,5,5-tetramethyl-1, 3,2-dioxaborolane, and 2-(tributylstannyl)pyrazine MS m/z=431 [M++H]+. Calculated for C$_{24}$H$_{19}$FN$_4$O$_3$: 430.13

$^1$H NMR (400 MHz, MeOH) δ ppm 2.50 (br. s., 2 H) 3.93 (t, J=5.38 Hz, 2 H) 4.30 (d, J=2.54 Hz, 2 H) 4.41 (s, 2 H) 6.21 (br. s., 1 H) 7.28-7.39 (m, 3 H) 8.07-8.12 (m, 1 H) 8.24 (d, J=1.56 Hz, 1 H) 8.52 (d, J=2.15 Hz, 1 H) 8.67 (s, 1 H) 9.11 (s, 1 H)

Example 463

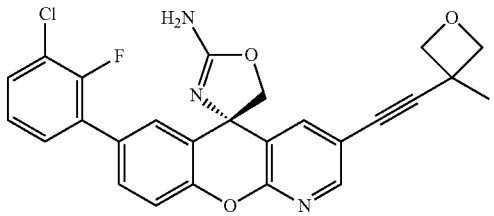 [SMILES: CC1(C#Cc2cnc3c(c2)[C@]2(COC(N)=N2)c2cc(-c4cccc(Cl)c4F)ccc2O3)COC1]

Synthesis of (S)-7-(3-chloro-2-fluorophenyl)-3-((3-methyloxetan-3-yl)ethynyl)-5'H-spiro[chromeno[2,3-b]pyridine-5,4'-oxazol]-2'-amine The titled compound was synthesized by steps analogous to those described in method AA5 above, but using (S)-3-bromo-7-iodo-5'H-spiro[chromeno[2,3-b]pyridine-5,4'-oxazol]-2'-amine (prepared using the same procedures as described in Method CC6 but using 4-iodophenol) 3-chloro-2-fluorophenylboronic acid and trimethyl((3-methyloxetan-3-yl)ethynyl)silane. MS m/z=476.1 [M+H]+. Calculated for C$_{26}$H$_{19}$ClFN$_3$O$_3$: 475.11. $^1$H NMR (400 MHz, DMSO-d$_6$) δ=8.45 (br. s., 1 H), 7.67 (br. s., 2 H), 7.65-7.60 (m, 2H), 7.58-7.50 (m, 1 H), 7.47-7.39 (m, 1 H), 7.38-7.31 (m, 1 H), 4.78 (d, J=5.5 Hz, 4 H), 4.46 (d, J=5.6 Hz, 2 H), 1.66 (s, 3 H)

Example 492

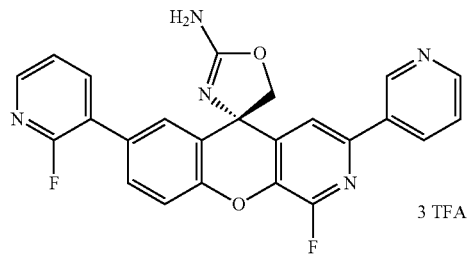 [SMILES: NC1=N[C@@]2(CO1)c1cc(-c3cccnc3F)ccc1Oc1c2cc(-c2cccnc2)nc1F]

(S)-1-fluoro-7-(2-fluoropyridin-3-yl)-3-(pyridin-3-yl)-5'H-spiro[chromeno[2,3-c]pyridine-5,4'-oxazol]-2'-amine The titled compound was synthesized by steps analogous to those described in method AA1 above, but using (S)-3-chloro-1-fluoro-7-(2-fluoropyridin-3-yl)-5'H-spiro [chromeno[2,3-c]pyridine-5,4'-oxazol]-2'-amine (prepared as described as in Method BB33), 2-fluoropyridin-3-ylboronic acid and 3-pyridylboronic acid 19F NMR shows 9:1 integration for TFA peak: core F peak indicating the compound is a 3 TFA salt. MS m/z=444.0 [M+H]+. Calculated for C$_{24}$H$_{15}$F$_2$N$_5$O$_2$: 443.41.

$^1$H NMR (400 MHz, MeOH) δ=9.49 (d, J=1.2 Hz, 1 H), 9.10 (d, J=8.2 Hz, 1 H), 8.84 (d, J=5.1 Hz, 1 H), 8.43 (s, 1 H), 8.26 (d, J=4.7 Hz, 1 H), 8.17 (ddd, J=1.8, 7.7, 9.7 Hz, 1 H), 8.04 (dd, J=5.5, 8.0 Hz, 1 H), 7.89 (s, 1 H), 7.85 (d, J=8.8 Hz, 1 H), 7.56 (d, J=8.6 Hz, 1 H), 7.51-7.44 (m, 1 H), 5.25 (s, 2 H)

Example 508

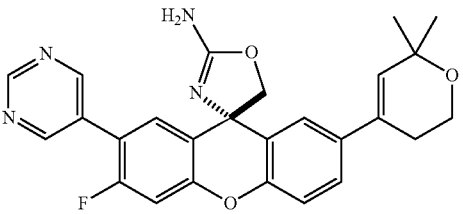

Synthesis of (R)-7'-(6,6-dimethyl-3,6-dihydro-2H-pyran-4-yl)-3'-fluoro-2'-(pyrimidin-5-yl)-5H-spiro [oxazole-4,9'-xanthen]-2-amine The titled compound was synthesized by steps analogous to those described in method AA8 above, but using (S)-2-amino-7'-bromo-3'-fluoro-5H-spiro[oxazole-4,9'-xanthen]-2'-ol (prepared by steps analogous to those described in Method BB42 and Example 2). MS m/z=459.2 [M+H]+. Calculated for C$_{26}$H$_{24}$FN$_4$O$_3$: 459.18.

$^1$H NMR (400 MHz, CHLOROFORM-d) δ ppm 1.35 (s, 3 H) 1.36 (s, 3 H) 2.42-2.50 (m, 2 H) 4.94-3.97 (m, 2 H) 4.28-4.41 (m, 2 H) 5.99 (t, J=1.56 Hz, 1 H) 7.02 (d, J=10.86 Hz, 1 H) 7.12 (d, J=8.61 Hz, 1 H) 7.37 (dd, J=8.51, 2.35 Hz, 1 H) 7.42 (d, J=2.05 Hz, 1 H) 7.48 (d, J=8.22 Hz, 1 H) 8.94 (d, J=1.47 Hz, 2 H)

Example 688

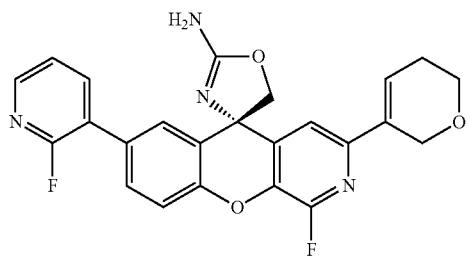 [SMILES: NC1=N[C@@]2(CO1)c1cc(-c3cccnc3F)ccc1Oc1c2cc(C2=CCCOC2)nc1F]

Synthesis of (S)-3-(5,6-dihydro-2H-pyran-3-yl)-1-fluoro-7-(3-fluoropyridin-2-yl)-5'H-spiro[chromeno [2,3-c]pyridine-5,4'-oxazol]-2'-amine The titled compound was synthesized by steps analogous to those described in method AA1 above, but using (S)-7-bromo-3-chloro-1-fluoro-5'H-spiro[chromeno[2,3-c]pyridine-5,4'-oxazol]-2'-amine (prepared as described in Method BB33), 2-fluoropyridin-3-ylboronic acid and 2-(5,6-dihydro-2H-pyran-3-yl)-4,4,5,5-tetramethyl-1,3,2-dioxaborolane. MS m/z=449.10 [M+H]+. Calculated for C$_{24}$H$_{18}$F$_2$N$_4$O$_3$: 448.13

$^1$H NMR (300 MHz, CHLOROFORM-d) δ ppm 2.30-2.44 (m, 2 H) 3.84 (s, 2 H) 4.38 (d, J=5.12 Hz, 2 H) 4.56-4.61 (m, 2 H) 4.61-4.66 (m, 1 H) 6.67-6.77 (m, 1 H) 7.19 (s, 1 H) 7.27-7.30 (m, 1 H) 7.31 (s, 1 H) 7.51-7.59 (m, 1 H) 7.59-7.64 (m, 1 H) 7.81-7.95 (m, 1 H) 8.16-8.26 (m, 1 H)

Example 916

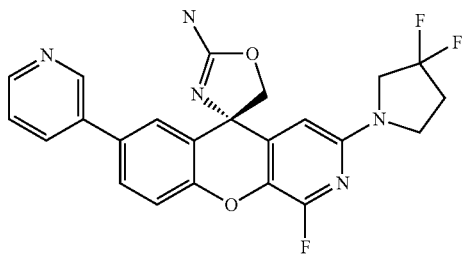 [SMILES: NC1=N[C@@]2(CO1)c1cc(-c3cccnc3)ccc1Oc1c2cc(N2CCC(F)(F)C2)nc1F]

Synthesis of (S)-3-(3,3-difluoropyrrolidin-1-yl)-1-fluoro-7-(pyridin-3-yl)-5'-H-spiro[chromeno[2,3-c]pyridine-5,4'-oxazol]-2'-amine The title compound was synthesized by steps analogous to those described in method CC4 above, but using (S)-7-bromo-3-chloro-1-fluoro-5'H-spiro[chromeno[2,3-c]pyridine-5,4'-oxazol]-2'-amine (prepared by steps analogous to those described in Method BB33) and 3-pyridyl-boronic acid and 3,3-difluoropyrrolidine hydrochloride.

MS m/z=454 [M+H]$^+$. Calculated for $C_{23}H_{18}F_3N_5O_2$: 453.14

$^1$H NMR (300 MHz, CHLOROFORM-d) δ ppm 2.39-2.59 (m, 2 H) 3.68 (s, 2 H) 3.75-3.89 (m, 2 H) 4.33 (d, J=2.48 Hz, 2 H) 6.17 (s, 0 H) 7.21-7.32 (m, 2 H) 7.33-7.40 (m, 1H) 7.49-7.56 (m, 1 H) 7.57-7.60 (m, 1 H) 7.82-7.90 (m, 1 H) 8.55-8.62 (m, 1 H) 8.82-8.87 (m, 1 H).

Example 698

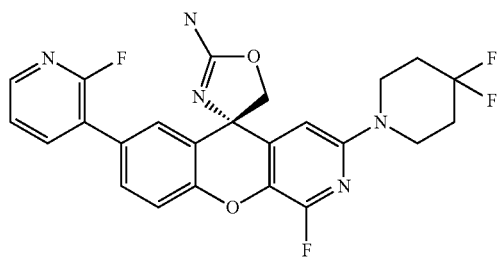 [SMILES: NC1=N[C@@]2(CO1)c1cc(-c3cccnc3F)ccc1Oc1c2cc(N2CCC(F)(F)CC2)nc1F]

Synthesis of (S)-3-(4,4-difluoropyrrolidin-1-yl)-1-fluoro-7-(2-fluoropyridin-3-yl)-5'-H-spiro[chromeno[2,3-c]pyridine-5,4'-oxazol]-2'-amine The title compound was synthesized by steps analogous to those described in method CC4 above, but using (S)-7-bromo-3-chloro-1-fluoro-5'H-spiro[chromeno[2,3-c]pyridine-5,4'-oxazol]-2'-amine (prepared by steps analogous to those described in Method BB33), 2-fluoropyridin-3-ylboronic acid and 4,4-difluoropiperidine hydrochloride.

MS m/z=486.1 [M+H]$^+$. Calculated for $C_{24}H_{19}F_4N_5O_2$: 485.15

$^1$H NMR (300 MHz, CHLOROFORM-d) δ ppm 1.93-2.12 (m, 4 H) 3.58-3.70 (m, 4H) 4.32 (s, 2 H) 6.50 (s, 1 H) 7.20-7.32 (m, 2 H) 7.51 (dt, J=8.48, 1.83 Hz, 1 H) 7.62 (t, J=1.83 Hz, 1 H) 7.85 (ddd, J=9.79, 7.60, 1.90 Hz, 1 H) 8.15 (dt, J=4.71, 1.52 Hz, 1 H)

Example 918

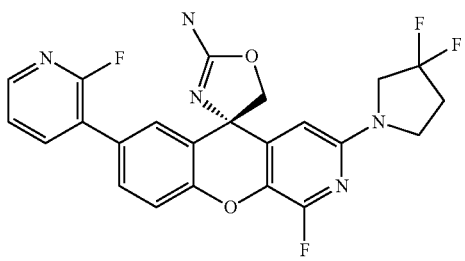 [SMILES: NC1=N[C@@]2(CO1)c1cc(-c3cccnc3F)ccc1Oc1c2cc(N2CCC(F)(F)C2)nc1F]

Synthesis of (S)-3-(3,3-difluoropyrrolidin-1-yl)-1-fluoro-7-(2-fluoropyridin-3-yl)-5'-H-spiro[chromeno[2,3-c]pyridine-5,4'-oxazol]-2'-amine The title compound was synthesized by steps analogous to those described in method CC4 above, but using (S)-7-bromo-3-chloro-1-fluoro-5'H-spiro[chromeno[2,3-c]pyridine-5,4'-oxazol]-2'-amine (prepared by steps analogous to those described in Method BB33), 2-fluoropyridin-3-ylboronic acid and 3,3-difluoropyrrolidine hydrochloride.

MS m/z=472.1 [M+H]$^+$. Calculated for $C_{23}H_{17}F_4N_5O_2$: 471.13

$^1$H NMR (300 MHz, CHLOROFORM-d) δ ppm 2.48 (tt, J=13.78, 6.98 Hz, 2 H) 3.66 (t, J=7.23 Hz, 2 H) 3.81 (t, J=13.08 Hz, 2 H) 4.27-4.38 (m, 2 H) 6.16 (s, 1 H) 7.21-7.33 (m, 2 H) 7.51 (d, J=8.48 Hz, 1 H) 7.61 (s, 1 H) 7.86 (ddd, J=9.72, 7.60, 1.83 Hz, 1 H) 8.17 (d, J=4.68 Hz, 1 H).

Example 922

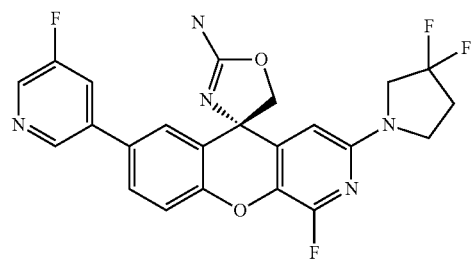 [SMILES: NC1=N[C@@]2(CO1)c1cc(-c3cncc(F)c3)ccc1Oc1c2cc(N2CCC(F)(F)C2)nc1F]

Synthesis of (S)-3-(3,3-difluoropyrrolidin-1-yl)-1-fluoro-7-(5-fluoropyridin-3-yl)-5'-H-spiro[chromeno[2,3-c]pyridine-5,4'-oxazol]-2'-amine The title compound was synthesized by steps analogous to those described in method CC4 above, but using (S)-7-bromo-3-chloro-1-fluoro-5'H-spiro[chromeno[2,3-c]pyridine-5,4'-oxazol]-2'-amine (prepared by steps analogous to those described in BB33), 5-fluoropyridin-3-ylboronic acid and 3,3-difluoropyrrolidine hydrochloride.

MS m/z=472.1 [M+H]$^+$. Calculated for $C_{23}H_{17}F_4N_5O_2$: 471.13

¹H NMR (300 MHz, CHLOROFORM-d) δ ppm 2.38-2.57 (m, 2 H) 3.63 (t, J=7.23 Hz, 2H) 3.77 (td, J=13.01, 3.22 Hz, 2 H) 4.21-4.35 (m, 2 H) 6.12 (s, 1 H) 7.28 (d, J=9.65 Hz, 1 H) 7.42-7.61 (m, 3 H) 8.40 (d, J=2.63 Hz, 1 H) 8.61 (s, 1 H).

Example 927

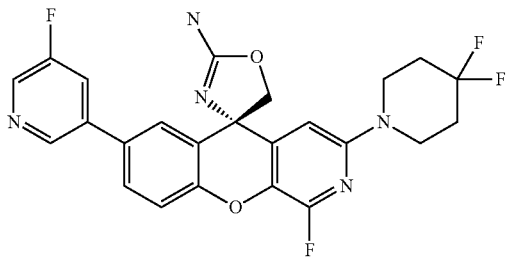 [SMILES: NC1=N[C@@]2(CO1)c1cc(-c3cncc(F)c3)ccc1Oc1c2cc(N2CCC(F)(F)CC2)nc1F]

Synthesis of (S)-3-(4,4-difluoropiperidin-1-yl)-1-fluoro-7-(5-fluoropyridin-3-yl)-5'-H-spiro[chromeno[2,3-c]pyridine-5,4'-oxazol]-2'-amine The title compound was synthesized by steps analogous to those described in method CC4 above, but using (S)-7-bromo-3-chloro-1-fluoro-5'H-spiro[chromeno[2,3-c]pyridine-5,4'-oxazol]-2'-amine (prepared as described in Method BB33), 5-fluoropyridin-3-ylboronic acid and 4,4-difluoropiperidine hydrochloride.

MS m/z=485.9 [M+H]⁺. Calculated for $C_{24}H_{19}F_4N_5O_2$: 485.15

¹H NMR (300 MHz, CHLOROFORM-d) δ ppm 1.93-2.12 (m, 4 H) 3.59-3.72 (m, 4 H) 4.32 (d, J=1.90 Hz, 2 H) 6.50 (s, 1 H) 7.31 (d, J=8.48 Hz, 1 H) 7.49-7.61 (m, 3 H) 8.45 (d, J=2.78 Hz, 1 H) 8.64-8.68 (m, 1 H).

Example 942

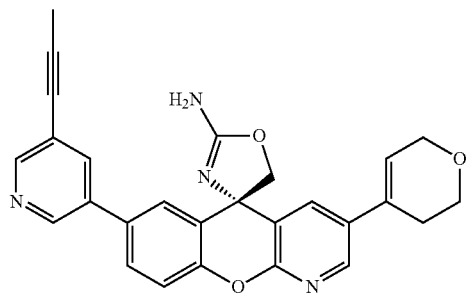 [SMILES: CC#Cc1cncc(-c2ccc3c(c2)[C@@]2(COC(N)=N2)c2cc(C4=CCOCC4)cnc2O3)c1]

Synthesis of (S)-3-(3,6-dihydro-2H-pyran-4-yl)-7-(5-(prop-1-ynyl)pyridin-3-yl)-5'H-spiro[chromeno[2,3-b]pyridine-5,4'-oxazol]-2'-amine The titled compound was synthesized by steps analogous to those described in method AA1 above, but using (S)-3-bromo-7-iodo-5'H-spiro[chromeno[2,3-b]pyridine-5,4'-oxazol]-2'-amine (prepared using the same procedures as described in Method CC6 but using 4-iodophenol), 5-(prop-1-ynyl)pyridin-3-ylboronic acid, and 2-(3,6-dihydro-2H-pyran-4-yl)-4,4,5,5-tetramethyl-1,3,2-dioxaborolane.

MS m/z=451.2 [M+H]⁺. Calculated for $C_{27}H_{22}N_4O_3$: 450.49.

¹H NMR (400 MHz, DMSO-d₆) δ=8.79 (1H, d, J=2.2 Hz, M01), 8.58 (1H, d, J=2.0 Hz, M02), 8.39 (1H, d, J=2.4 Hz, M03), 8.05 (1H, t, J=2.1 Hz, M04), 7.78 (1H, d, J=2.4 Hz, M05), 7.75 (1H, dd, J=8.5 Hz, J=2.3 Hz, M06), 7.62 (1H, d, J=2.3 Hz, M07), 7.34 (1H, d, J=8.5 Hz, M08), 6.50 (2H, s, M09), 6.24-6.36 (1H, m, M10), 4.27-4.41 (2H, m, M11), 4.25 (2H, q, J=2.6 Hz, M12), 3.85 (2H, t, J=5.5 Hz, M13), 2.47 (2H, br. s., M14)

Example 947

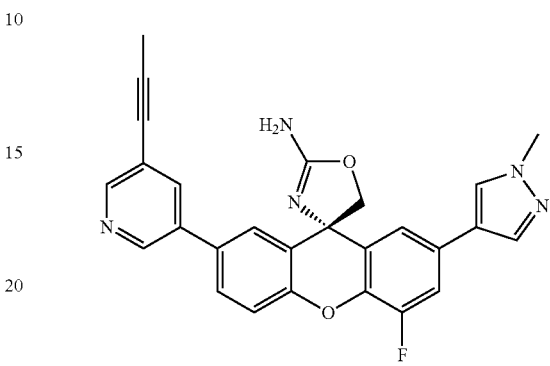

Synthesis of (S)-4'-fluoro-2'-(1-methyl-1H-pyrazol-4-yl)-7'-(5-(prop-1-ynyl)pyridin-3-yl)-5H-spiro[oxazole-4,9'-xanthen]-2-amine The titled compound was synthesized by steps analogous to those described in method AA8 above, but using (S)-2-amino-7'-bromo-4'-fluoro-5H-spiro[oxazole-4,9'-xanthen]-2'-ol (prepared by steps analogous to those described in Method BB40 and Example 2), 5-(prop-1-ynyl)pyridin-3-ylboronic acid, and 1-methyl-4-(4,4,5,5-tetramethyl-1,3,2-dioxaborolan-2-yl)-1H-pyrazole.

MS m/z=466.2 [M+H]⁺. Calculated for $C_{27}H_{20}FN_5O_2$: 465.16.

¹H NMR (400 MHz, DMSO-d₆) δ=8.79 (d, J=2.2 Hz, 1 H), 8.58 (d, J=2.0 Hz, 1 H), 8.12 (d, J=0.4 Hz, 1 H), 8.04 (t, J=2.1 Hz, 1 H), 7.82 (d, J=0.8 Hz, 1 H), 7.74 (dd, J=2.3, 8.5 Hz, 1 H), 7.62 (d, J=2.2 Hz, 1 H), 7.54 (dd, J=2.1, 12.0 Hz, 1 H), 7.34 (d, J=8.5 Hz, 1 H), 7.30-7.27 (m, 1 H), 6.50 (s, 2 H), 4.39-4.26 (m, 2 H), 3.87 (s, 3 H), 2.12 (s, 3 H)

Example 951

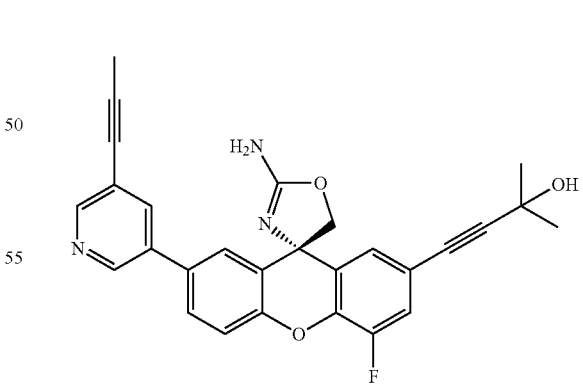

Synthesis of (S)-4-(2-amino-5'-fluoro-2'-(5-(prop-1-ynyl)pyridin-3-yl)-5H-spiro[oxazole-4,9'-xanthene]-7'-yl)-2-methylbut-3-yn-2-ol The titled compound was synthesized by steps analogous to those described in method AA21 above, but using (S)-2- amino-7'-bromo-4'-fluoro-5H-spiro[oxazole-4,9'-xanthen]-2'-ol (prepared by steps analogous to those described in Method BB40 and Example 2), 5-(prop-1-ynyl)pyridin-3-ylboronic acid, and 2-methylbut-3-yn-2-ol.

MS m/z=468.3 [M+H]⁺. Calculated for $C_{28}H_{22}FN_3O_3$: 467.16.

¹H NMR (400 MHz, DMSO-$d_6$) δ=8.92-8.72 (m, 1 H), 8.67-8.49 (m, 1 H), 8.15-7.99 (m, 1 H), 7.76 (d, J=8.5 Hz, 1 H), 7.70-7.62 (m, 1 H), 7.40-7.29 (m, J=8.4 Hz, 2 H), 7.11 (br. s., 1 H), 6.62 (br. s., 2 H), 5.51 (s, 1 H), 4.39-4.17 (m, 2 H), 2.12 (s, 3 H), 1.47 (s, 7 H), 1.37 (s, 2 H)

Example 759

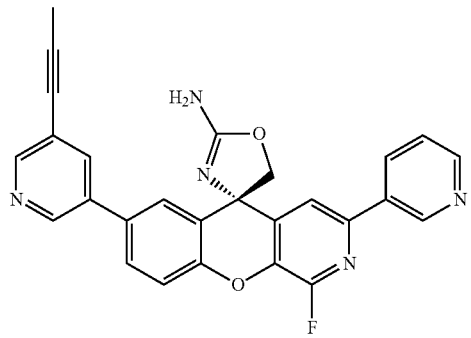 [SMILES: CC#Cc1cncc(-c2ccc3c(c2)[C@@]2(COC(N)=N2)c2cc(-c4cccnc4)nc(F)c2O3)c1]

Synthesis of (S)-1-fluoro-7-(5-(prop-1-ynyl)pyridin-3-yl)-3-(pyridin-3-yl)-5'H-spiro[chromeno[2,3-c]pyridine-5,4'-oxazol]-2'-amine The titled compound was synthesized by steps analogous to those described in method A1 above, but using (S)-7-bromo-3-chloro-1-fluoro-5'H-spiro[chromeno[2,3-c]pyridine-5,4'-oxazol]-2'-amine (prepared as described in Method BB33), pyridin-3-ylboronic acid and 5-(prop-1-ynyl)pyridin-3-ylboronic acid MS m/z=464.1 [M+H]⁺. Calculated for $C_{27}H_{18}FN_5O_2$: 463.14

¹H NMR (300 MHz, CHLOROFORM-d) δ ppm 2.11 (s, 3 H) 4.42 (s, 2 H) 7.33-7.44 (m, 2 H) 7.56 (dd, J=8.48, 2.19 Hz, 1 H) 7.62 (d, J=2.19 Hz, 1 H) 7.68 (s, 1 H) 7.85 (t, J=2.05 Hz, 1 H) 8.23-8.38 (m, 1 H) 8.60 (d, J=1.75 Hz, 1 H) 8.64 (dd, J=4.82, 1.61 Hz, 1 H) 8.71 (d, J=2.19 Hz, 1 H) 9.18 (d, J=1.90 Hz, 1 H)

Example 860

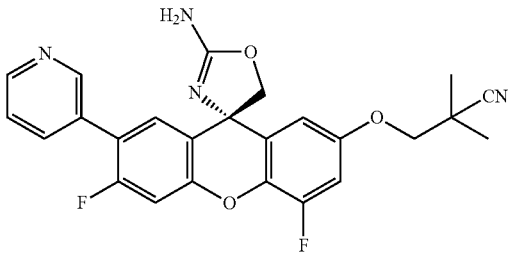 [SMILES: CC(C)(C#N)COc1cc(F)c2c(c1)[C@]1(COC(N)=N1)c1cc(-c3cccnc3)c(F)cc1O2]

Synthesis of (S)-3-(2-amino-3',5'-difluoro-2'-(pyridin-3-yl)-5H-spiro[oxazole-4,9'-xanthene]-7'-yloxy)-2,2-dimethylpropanenitrile The titled compound was synthesized by steps analogous to those described in method AA14 above, but using (S)-2-amino-2'-bromo-3',5'-difluoro-5H-spiro[oxazole-4,9'-xanthen]-7'-ol (prepared using the procedures as described in Method BB38 and Example 2). MS m/z=463.2 [M+H]⁺. Chemical Formula: $C_{25}H_{20}F_2N_4O_3$. Exact Mass: 462.15.

¹H NMR (400 MHz, DMSO-$d_6$) δ ppm 1.30 (s, 3 H) 1.31 (s, 3 H) 3.91 (m, J=15.2 Hz, 2H) 4.08-4.20 (m, 2 H) 6.42 (s, 2 H) 6.57-6.64 (m, 1 H) 7.01 (dd, J=12.3, 2.9 Hz, 1 H) 7.22 (d, J=11.2 Hz, 1 H) 7.33 (d, J=8.6 Hz, 1 H) 7.42 (ddd, J=7.9, 4.8, 1 Hz, 1 H) 7.80-7.87 (m, 1 H) 8.50 (dd, J=4.8, 1.7 Hz, 1 H) 8.57-8.63 (m, 1 H)

Example 867

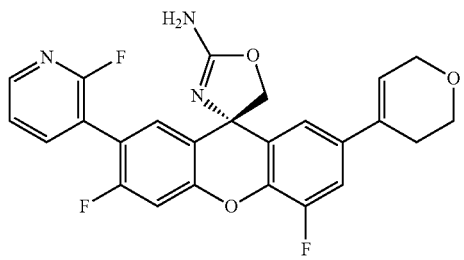

Synthesis of (4S)-7'-(3,6-dihydro-2H-pyran-4-yl)-3',5'-difluoro-2'-(2-fluoropyridin-3-yl)-5H-spiro[oxazole-4,9'-xanthen]-2-amine The titled compound was synthesized by steps analogous to those described in method AA8 above, but using 2-amino-2'-bromo-3',5'-difluoro-5H-spiro[oxazole-4,9'-xanthen]-7'-ol (prepared using the procedures as described in Method BB38 and Example 2). 7'-(3,6-dihydro-2H-pyran-4-yl)-3',5'-difluoro-2'-(2-fluoropyridin-3-yl)-5H-spiro[oxazole-4,9'-xanthen]-2-amine was chromatographed using chiral SFC to afford (4S)-7'-(3,6-dihydro-2H-pyran-4-yl)-3',5'-difluoro-2'-(2-fluoropyridin-3-yl)-5H-spiro[oxazole-4,9'-xanthen]-2-amine (>99% ee).

MS m/z=466.2 [M+H]⁺. Chemical Formula: $C_{25}H_{18}F_3N_3O_3$ Exact Mass: 465.13.

¹H NMR (400 MHz, DMSO-$d_6$) δ ppm 2.37-2.48 (m, 2 H) 3.84 (t, J=5.5 Hz, 2 H) 4.19-4.32 (m, 4 H) 6.23-6.31 (m, 1 H) 6.51 (s, 2 H) 7.16-7.22 (m, 1 H) 7.38 (d, J=10.7 Hz, 1H) 7.41-7.49 (m, 2 H) 7.53 (ddd, J=7.5, 5.0, 1.9 Hz, 1 H) 8.09 (ddd, J=9.6, 7.5, 1.8 Hz, 1H) 8.29-8.37 (m, 1 H)

Example 869

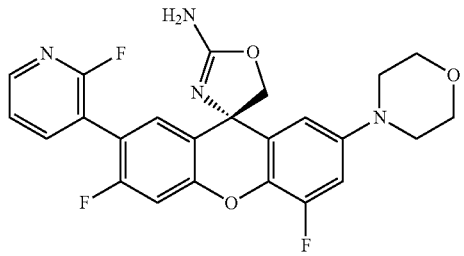 [SMILES: NC1=N[C@@]2(CO1)c1cc(-c3cccnc3F)c(F)cc1Oc1c(F)cc(N3CCOCC3)cc12]

Synthesis of (4S)-3',5'-difluoro-2'-(2-fluoropyridin-3-yl)-7'-morpholino-5H-spiro[oxazole-4,9'-xanthen]-2-amine The titled compound was synthesized by steps analogous to those described in method AA20 above, but using 2-amino-2'-bromo-3',5'-difluoro-5H-spiro[oxazole-4,9'-xanthen]-7'-ol (prepared using the procedures as described in Method BB38 and Example 2). 3',5'-difluoro-2'-(2-fluoropyridin-3-yl)-7'-morpholino-5H-spiro[oxazole-4,9'-xanthen]-2-amine (35 mg, 0.075 mmol, 7.94% yield) was chromatographed using chiral SFC to afford (4S)-3',5'-difluoro-2'-(2-fluoropyridin-3-yl)-7'-morpholino-5H-spiro[oxazole-4,9'-xanthen]-2-amine (99% ee).

MS m/z=469.0 [M+H]$^+$. Chemical Formula: $C_{24}H_{19}F_3N_4O_3$ Exact Mass: 468.14.

$^1$H NMR (400 MHz, DMSO-d$_6$) δ ppm 3.09 (m, J=8.7 Hz, 4 H) 3.75 (t, J=4.8 Hz, 4 H) 4.13-4.32 (m, 2 H) 6.47 (s, 2 H) 6.53-6.71 (m, 1 H) 7.03 (d, J=14.3 Hz, 1 H) 7.33 (d, J=11.0 Hz, 1 H) 7.34-7.48 (m, 1 H) 7.52 (ddd, J=7.2, 5.0, 1.9 Hz, 1 H) 8.02-8.12 (m, 1H) 8.28-8.37 (m, 1 H)

Example 928

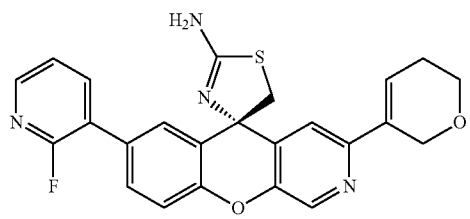

Synthesis of (S)-3-(5,6-dihydro-2H-pyran-3-yl)-7-(2-fluoropyridin-3-yl)-5'H-spiro[chromeno[2,3-c]pyridine-5,4'-thiazol]-2'-amine The titled compound was synthesized by steps analogous to those described in method BB12 above, but using (S)-7-bromo-3-chloro-5'H-spiro[chromeno[2,3-c]pyridine-5,4'-thiazol]-2'-amine (prepared as described in Method BB26 but using 7-bromo-3-chloro-5H-chromeno[2,3-c]pyridin-5-one), 2-fluoropyridin-3-ylboronic acid and 2-(5,6-dihydro-2H-pyran-3-yl)-4,4,5,5-tetramethyl-1,3,2-dioxaborolane.

MS m/z=447.0 [M+H]$^+$. Calculated for $C_{24}H_{19}FN_4O_2S$: 446.50.

$^1$H NMR (300 MHz, CHLOROFORM-d) δ ppm 2.39 (m, J=4.20, 2.70 Hz, 2 H) 3.52-3.66 (m, 2 H) 3.84-3.91 (m, 2 H) 4.60-4.76 (m, 2 H) 6.63-6.70 (m, 1 H) 7.28-7.35 (m, 2 H) 7.47 (s, 1 H) 7.54-7.60 (m, 1 H) 7.66-7.70 (m, 1 H) 7.88 (ddd, J=9.76, 7.56, 1.97 Hz, 1 H) 8.18-8.23 (m, 1 H) 8.50 (s, 1 H)

Example 745

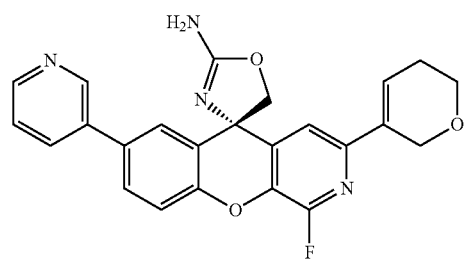 [SMILES: NC1=N[C@@]2(CO1)c1cc(-c3cccnc3)ccc1Oc1c2cc(C2=CCCOC2)nc1F]

Synthesis of (5S)-3-(5,6-dihydro-2-H-pyran-3-yl)-1-fluoro-7-(3-pyridinyl)spiro[chromeno[2,3-c]pyridine-5-4'-[1,3]oxazol]-2'-amine The titled compound was synthesized by steps analogous to those described in method AA1 above, but using (S)-7-bromo-3-chloro-1-fluoro-5'H-spiro[chromeno[2,3-c]pyridine-5,4' oxazol]-2'-amine (prepared as described in Method BB33), 3-pyridinylboronic acid and 2-(5,6-dihydro-2H-pyran-3-yl)-4,4,5,5-tetramethyl-1,3,2-dioxaborolane. MS m/z=431.1 [M+H]$^+$. Calculated for $C_{24}H_{19}FN_4O_3$: 430.14.

1H NMR (400 MHz, CHLOROFORM-d) δ ppm 2.32-2.40 (m, 2 H) 3.83 (t, J=5.5 Hz, 2H) 4.35 (q, J=8.5 Hz, 2 H) 4.54-4.59 (m, 2 H) 6.68-6.73 (m, 1 H) 7.19 (s, 1 H) 7.30-7.37 (m, 2 H) 7.54 (dd, J=8.4, 2.2 Hz, 1 H) 7.60 (d, J=2.0 Hz, 1 H) 8.59 (dd, J=4.8, 1.5 Hz, 1H) 8.83 (d, J=2 Hz, 1 H).

Example 746

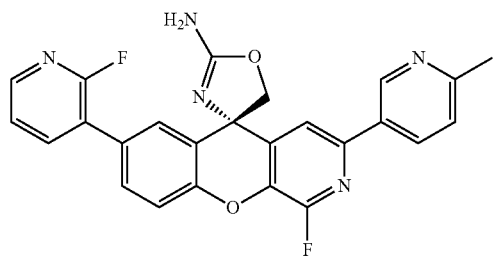 [SMILES: Cc1ccc(-c2cc3c(c(F)n2)Oc2ccc(-c4cccnc4F)cc2[C@@]32COC(N)=N2)cn1]

Synthesis of (5S)-1-fluoro-7-(2-fluoropyridin-3-yl)-3-(6-methylpyridin-3-yl)spiro[chromeno[2,3-c]pyridine-5-4'-[1,3]oxazol]-2'-amine The titled compound was synthesized by steps analogous to those described in method AA1 above, but using (S)-7-bromo-3-chloro-1-fluoro-5'H-spiro[chromeno[2,3-c]pyridine-5,4' oxazol]-2'-amine (prepared as described in Method BB33), 2-fluoro-pyridin-3-ylboronic acid and 2-methyl-pyridin-5-ylboronic acid.

MS m/z=458.1 [M+H]$^+$. Calculated for $C_{25}H_{17}F_2N_5O_2$: 457.14.

1H NMR (400 MHz, CHLOROFORM-d) δ ppm 2.60 (s, 3 H) 4.40 (s, 2 H) 7.19-7.26 (m, 2 H) 7.34 (d, J=8.4 Hz, 1 H) 7.52-7.57 (m, 1 H) 7.62-7.67 (m, 2 H) 7.83-7.89 (m, 1 H) 8.10-8.18 (m, 2 H) 9.02 (d, J=1.8 Hz, 1 H).

Example 893

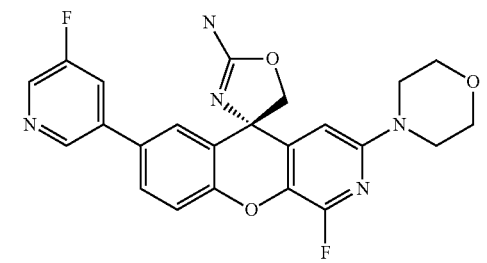 [SMILES: NC1=N[C@@]2(CO1)c1cc(-c3cncc(F)c3)ccc1Oc1c2cc(N2CCOCC2)nc1F]

Synthesis of (5S)-1-fluoro-7-(5-fluoro-3-pyridinyl)-3-(4-morpholinyl)spiro[chromeno[2,3-c]pyridine-5,4'-[1,3]oxazol]-2'-amine The titled compound was synthesized by steps analogous to those described in Method CC4 above using (S)-7-bromo- 3-chloro-1-fluoro-5'H-spiro[chromeno[2,3-c]pyridine-5,4'oxazol]-2'-amine (prepared as described in Method BB33), 5-fluoropyridin-3-ylboronic acid, and morpholine. MS m/z=452.1 [M+H]+. Calculated for $C_{23}H_{19}F_2N_5O_3$: 451.1.

$^1$H NMR (400 MHz, MeOH) δ ppm 3.43 (m, 4 H), 3.81 (m, 4 H), 4.39 (d, J=8.0 Hz, 1 H), 4.43 (d, J=8.0 Hz, 1 H), 6.58 (s, 1 H), 7.32 (br. s., 1 H), 7.33 (d, J=9.0 Hz, 1 H), 7.68-7.75 (m, 1 H), 7.88-7.95 (m, 1 H), 8.43-8.49 (m, 1 H), 8.69 (br. s., 1 H).

Example 892

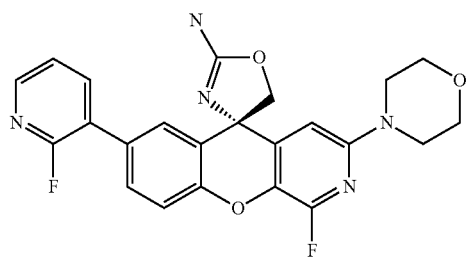 [SMILES: NC1=N[C@@]2(CO1)c1cc(-c3cccnc3F)ccc1Oc1c2cc(N2CCOCC2)nc1F]

Synthesis of (5S)-1-fluoro-7-(2-fluoro-3-pyridinyl)-3-(4-morpholinyl)spiro[chromeno[2,3-c]pyridine-5,4'-[1,3]oxazol]-2'-amine The titled compound was synthesized by steps analogous to those described in Method CC4 above using (S)-7-bromo-3-chloro-1-fluoro-5'H-spiro[chromeno[2,3-c]pyridine-5,4'oxazol]-2'-amine (prepared as described in Method BB33), 2-fluoropyridin-3-ylboronic acid, and morpholine.

MS m/z=452.1 [M+H]+. Calculated for $C_{23}H_{19}F_2N_5O_3$: 451.2.

$^1$H NMR (400 MHz, CHLOROFORM-d) δ ppm. 3.44 (m, 4 H), 3.82 (m, 4 H), 4.34 (s, 2H), 6.44 (s, 1 H), 7.24-7.32 (m, 1 H), 7.49-7.55 (m, 1 H), 7.61 (br. s., 1 H), 7.83-7.91 (m, 1 H), 8.17 (br. s., 1 H), 8.17-8.21 (m, 1 H).

Example 894

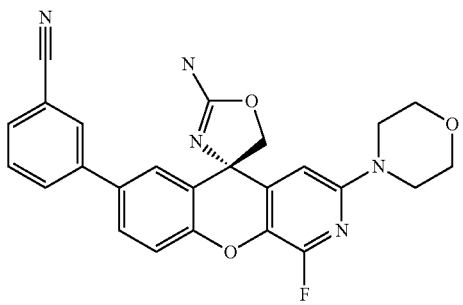 [SMILES: N#Cc1cccc(-c2ccc3c(c2)[C@@]2(COC(N)=N2)c2cc(N4CCOCC4)nc(F)c2O3)c1]

Synthesis of 3-((5S)-2'-amino-1-fluoro-3-(4-morpholinyl)spiro[chromeno[2,3-c]pyridine-5,4'-[1,3]oxazol]-7-yl)benzonitrile The titled compound was synthesized by steps analogous to those described in Method CC4 above using (S)-7-bromo-3-chloro-1-fluoro-5'H-spiro[chromeno[2,3-c]pyridine-5,4'oxazol]-2'-amine (prepared as described in Method BB33), 3-cyanophenylboronic acid and morpholine.

MS m/z=458.2 [M+H]+. Calculated for $C_{25}H_{20}FN_5O_3$: 457.2.

$^1$H NMR (400 MHz, CHLOROFORM-d) δ ppm. 3.46 (m, 4 H), 3.83 (m, 4 H), 4.36 (d, J=8.0 Hz, 1 H), 4.40 (d, J=8.0 Hz, 1 H), 6.44 (s, 1 H), 7.31 (d, J=8.4 Hz, 1 H), 7.51-7.58 (m, 3 H), 7.62-7.65 (m, 1 H), 7.80 (dt, J=7.9, 1.7 Hz, 1 H), 7.85-7.87 (m, 1 H).

Example 1000

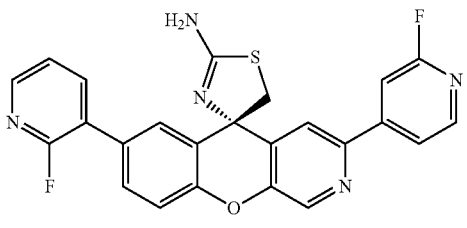 [SMILES: NC1=N[C@@]2(CS1)c1cc(-c3cccnc3F)ccc1Oc1cnc(-c3ccnc(F)c3)cc12]

Synthesis of (S)-7-(2-fluoropyridin-3-yl)-3-(2-fluoropyridin-4-yl)-5'H-spiro[chromeno[2,3-c]pyridine-5,4'-thiazol]-2'-amine The titled compound was synthesized by steps analogous to those described in method BB12 above, but using (S)-7-bromo-3-chloro-5'H-spiro[chromeno[2,3-c]pyridine-5,4'-thiazol]-2'-amine (prepared as described in Method BB26 but using 7-bromo-3-chloro-5H-chromeno[2,3-c]pyridin-5-one), 2-fluoropyridin-3-ylboronic acid and 2-fluoropyridin-4-ylboronic acid.

MS m/z=460.1 [M+H]+. Calculated for $C_{24}H_{15}F_2N_5OS$: 459.10.

$^1$H NMR (300 MHz, DMSO-$d_6$) δ ppm 3.42-3.69 (m, 2 H) 7.15 (s, 2 H) 7.36-7.57 (m, 2H) 7.61-7.78 (m, 3 H) 7.92 (d, J=5.12 Hz, 1 H) 8.02-8.16 (m, 2 H) 8.26 (d, J=4.68 Hz, 1 H) 8.38 (d, J=5.26 Hz, 1 H) 8.76 (s, 1 H)

Example 996

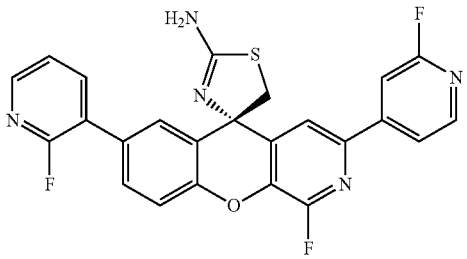 [SMILES: NC1=N[C@@]2(CS1)c1cc(-c3cccnc3F)ccc1Oc1c2cc(-c2ccnc(F)c2)nc1F]

Synthesis of (S)-1-fluoro-7-(2-fluoropyridin-3-yl)-3-(2-fluoropyridin-4-yl)-5'H-spiro[chromeno[2,3-c]pyridine-5,4'-thiazol]-2'-amine The titled compound was synthesized by steps analogous to those described in method BB12 above, but using (S)-7-bromo-3-chloro-1-fluoro-5'H-spiro[chromeno[2,3-c]pyridine-5,4'-thiazol]-2'-amine (prepared as described in Method BB26 but using 7-bromo-3-chloro-1-fluoro-5H-chromeno[2,3-c]pyridin-5-one), 2-fluoropyridin-3-ylboronic acid and 2-fluoropyridin-4-ylboronic acid.

MS m/z=478.1 [M+H]⁺. Calculated for $C_{24}H_{14}F_3N_5OS$: 477.09.

¹H NMR (400 MHz, DMSO-d₆) δ ppm 3.55 (d, J=11.35 Hz, 1 H) 3.68 (d, J=11.54 Hz, 1H) 7.18 (br. s., 2 H) 7.50 (ddd, J=4.99, 2.35, 2.05 Hz, 1 H) 7.52 (s, 1 H) 7.65-7.74 (m, 3H) 7.89 (d, J=5.28 Hz, 1 H) 8.02 (s, 1 H) 8.11 (ddd, J=10.00, 7.60, 1.85 Hz, 1 H) 8.27 (d, 1 H) 8.39 (d, J=5.28 Hz, 1 H).

Example 1001

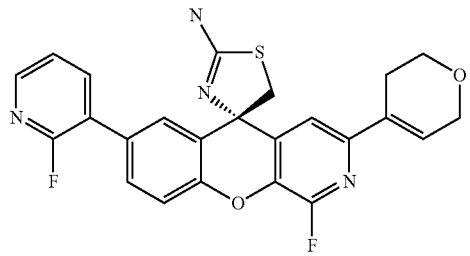 [SMILES: NC1=N[C@@]2(CS1)c1cc(-c3cccnc3F)ccc1Oc1c2cc(C2=CCOCC2)nc1F]

Synthesis of (S)-3-(3,6-dihydro-2H-pyran-4-yl)-1-fluoro-7-(2-fluoropyridin-3-yl)-5'H-spiro[chromeno[2,3-c]pyridine-5,4'-thiazol]-2'-amine The titled compound was synthesized by steps analogous to those described in method BB12 above, but using (S)-7-bromo-3-chloro-1-fluoro-5'H-spiro[chromeno[2,3-c]pyridine-5,4'-thiazol]-2'-amine (prepared as described in Method BB26 but using bromo-3-chloro-1-fluoro-5H-chromeno[2,3-c]pyridin-5-one), 2-fluoropyridin-3-ylboronic acid and 2-(3,6-dihydro-2H-pyran-4-yl)-4,4,5,5-tetramethyl-1,3,2-dioxaborolane.

MS m/z=465.0 [M+H]⁺. Calculated for $C_{24}H_{18}F_2N_4O_2S$: 464.11.

¹H NMR (400 MHz, DMSO-d₆) δ ppm 3.49-3.76 (m, 2 H) 7.05-7.26 (m, 2 H) 7.52 (d, J=8.02 Hz, 2 H) 7.70 (d, J=6.46 Hz, 3 H) 7.85-7.93 (m, 1 H) 8.02 (s, 1 H) 8.06-8.19 (m, 1 H) 8.23-8.30 (m, 1 H) 8.39 (d, J=5.28 Hz, 1 H)

Example 999

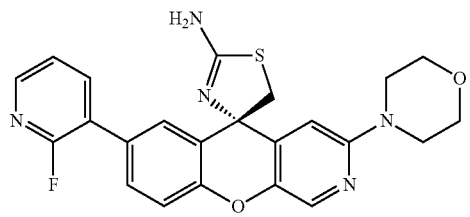 [SMILES: NC1=N[C@@]2(CS1)c1cc(-c3cccnc3F)ccc1Oc1cnc(N3CCOCC3)cc12]

Synthesis of (S)-7-(2-fluoropyridin-3-yl)-3-morpholino-5'H-spiro[chromeno[2,3-c]pyridine-5,4'-thiazol]-2'-amine The titled compound was synthesized by steps analogous to those described in Method CC10 above, but using (S)-7-bromo-3-chloro-1-fluoro-5'H-spiro[chromeno[2,3-c]pyridine-5,4'-thiazol]-2'-amine (prepared as described in Method BB26 but using 7-bromo-3-chloro-5H-chromeno[2,3-c]pyridin-5-one), 2-fluoropyridin-3-ylboronic acid and morpholine. MS m/z=450.1 [M+H]⁺. Calculated for $C_{23}H_{20}FN_5O_2S$: 449.13.

¹H NMR (300 MHz, DMSO-d₆) δ ppm 3.33-3.45 (m, 6 H) 3.73 (t, J=4.82 Hz, 4 H) 6.75 (s, 1 H) 7.08 (br. s., 2 H) 7.35 (d, J=8.33 Hz, 1 H) 7.44-7.52 (m, 1 H) 7.53-7.66 (m, 2 H) 8.07 (t, J=8.55 Hz, 1 H) 8.17-8.29 (m, 2 H).

Example 839

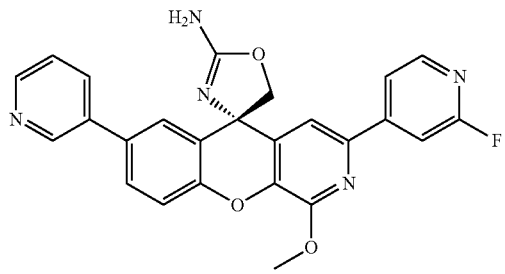 [SMILES: COc1nc(-c2ccnc(F)c2)cc2c1Oc1ccc(-c3cccnc3)cc1[C@@]21COC(N)=N1]

Synthesis of (S)-3-(2-fluoropyridin-4-yl)-1-methoxy-7-(pyridin-3-yl)-5'H-spiro[chromeno[2,3-c]pyridine-5,4'-oxazol]-2'-amine The titled compound was synthesized by steps analogous to those described in method AA1 above, but using (S)-7-bromo-3-chloro-1-methoxy-5'H-spiro[chromeno[2,3-c]pyridine-5,4'-oxazol]-2'-amine (prepared as described in Method CC16), pyridin-3-ylboronic acid and 2-fluoropyridin-4-ylboronic acid.

MS m/z=456.2 [M+H]⁺. Calculated for $C_{25}H_{18}FN_5O_3$: 455.14

¹H NMR (400 MHz, DMSO-d6) δ ppm 4.13 (s, 3 H) 4.43 (s, 2 H) 6.53 (s, 2 H) 7.39 (d, J=8.6 Hz, 1 H) 7.51 (dd, J=7.8, 4.7 Hz, 1 H) 7.60 (d, J=2.2 Hz, 1 H) 7.67 (s, 1 H) 7.73 (dd, J=8.6, 2.3 Hz, 1 H) 7.76 (s, 1 H) 7.95 (d, J=5.3 Hz, 1 H) 8.03 (dt, J=7.9, 1.9 Hz, 1 H) 8.35 (d, J=5.3 Hz, 1 H) 8.58 (dd, J=4.7, 1.4 Hz, 1 H) 8.86 (d, J=2.2 Hz, 1 H)

Example 802

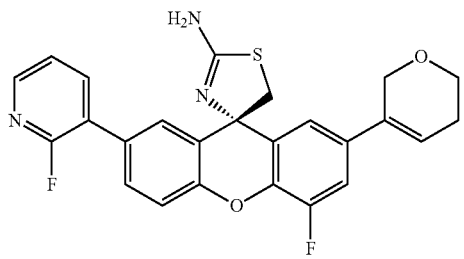 [SMILES: NC1=N[C@@]2(CS1)c1cc(-c3cccnc3F)ccc1Oc1c(F)cc(C3=CCCOC3)cc12]

Synthesis of (S)-2'-(5,6-dihydro-2H-pyran-3-yl)-4'-fluoro-7'-(2-fluoropyridin-3-yl)-5H-spiro[thiazole-4,9'-xanthen]-2-amine The titled compound was synthesized by steps analogous to those described in method AA8 above, but using (S)-7'-bromo-4'-fluoro-2'-methoxy-5H-spiro[thiazole-4,9'-xanthen]-2-amine (prepared as described in Method BB26 but using 7-bromo-4-fluoro-2-methoxy-9H-xanthen-9-one)

MS m/z=464.0 [M+H]$^+$. Calculated for $C_{25}H_{19}F_2N_3O_2S$: 463.12.

$^1$H NMR (400 MHz, DMSO-d$_6$) δ ppm 2.22-2.31 (m, 2 H), 3.42 (s, 2 H), 3.71-3.76 (m, 2 H), 4.28-4.47 (m, 2 H), 6.24-6.32 (m, 1 H), 7.06 (s, 2 H), 7.16-7.19 (m, 1 H), 7.35-7.44 (m, 2H), 7.49 (ddd, J=7.3, 5.1, 1.9 Hz, 1 H), 7.59-7.65 (m, 2 H), 8.09 (ddd, J=10.3, 7.5, 2.0 Hz, 1 H), 8.22-8.27 (m, 1 H).

Example 806

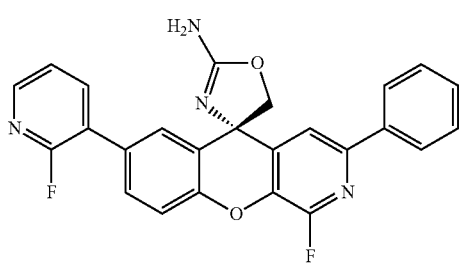 [SMILES: NC1=N[C@@]2(CO1)c1cc(-c3cccnc3F)ccc1Oc1c2cc(-c2ccccc2)nc1F]

Synthesis of (S)-1-fluoro-7-(2-fluoropyridin-3-yl)-3-phenyl-5'H-spiro[chromeno[2,3-c]pyridine-5,4'-oxazol]-2'-amine The titled compound was synthesized by steps analogous to those described in method AA1 above, but using (S)-7-bromo-3-chloro-1-fluoro-5'H-spiro[chromeno[2,3-c]pyridine-5,4'-oxazol]-2'-amine (prepared as described in Method BB33).

MS m/z=442.8 [M+H]$^+$. Calculated for $C_{25}H_{16}F_2N_4O_2S$: 442.12.

$^1$H NMR (400 MHz, DMSO-d$_6$) δ ppm 4.34 (d, J=8.8 Hz, 1 H), 4.46 (d, J=8.8 Hz, 1 H), 6.62 (s, 2 H), 7.41-7.56 (m, 5 H), 7.62 (d, J=1.7 Hz, 1 H), 7.64-7.69 (m, 1 H), 7.73 (s, 1 H), 7.94-7.99 (m, 2 H), 8.14 (ddd, J=10.3, 7.5, 1.9 Hz, 1 H), 8.24-8.28 (m, 1 H).

Example 1067

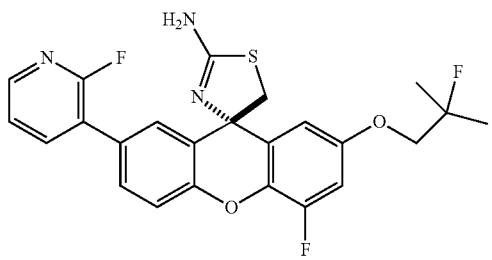

Synthesis of (S)-4'-fluoro-2'-(2-fluoro-2-methylpropoxy)-7'-(2-fluoropyridin-3-yl)-5H-spiro[thiazole-4,9'-xanthen]-2-amine The titled compound was synthesized by steps analogous to those described in method AA14 above, but using (S)-2-amino-7'-bromo-4'-fluoro-5H-spiro[thiazole-4,9'-xanthen]-2'-ol (prepared as described in Method BB26 and Example 2 but using 7-bromo-4-fluoro-2-methoxy-9H-xanthen-9-one), 2-fluoropyridin-3-ylboronic acid and 2-fluoro-2-methylpropyl trifluoromethanesulfonate. MS m/z=472.0 [M+H]$^+$.

$^1$H NMR (400 MHz, DMSO-d$_6$) ppm 1.42 (d, J=20 Hz, 6 H), 3.40 (d, J=3.23 Hz, 2 H) 4.01 (m, 2 H) 6.77 (dd, J=2.84, 1.57 Hz, 1 H) 7.03-7.14 (m, 3 H) 7.36-7.43 (m, 1 H) 7.46-7.52 (m, 1 H) 7.57-7.64 (m, 2 H) 8.03-8.13 (m, 1 H) 8.20-8.30 (m, 1 H)

Example 1076

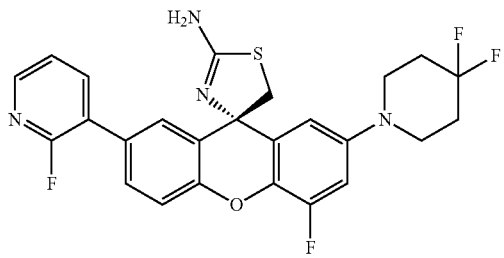 [SMILES: NC1=N[C@@]2(CS1)c1cc(-c3cccnc3F)ccc1Oc1c(F)cc(N3CCC(F)(F)CC3)cc12]

Synthesis of (S)-2'-(4,4-difluoropiperidin-1-yl)-4'-fluoro-7'-(2-fluoropyridin-3-yl)-5H-spiro[thiazole-4,9'-xanthen]-2-amine The titled compound was synthesized by stpes analogous to those described in method AA20 above, but using (S)-2-amino-7'-bromo-4'-fluoro-5H-spiro[thiazole-4,9'-xanthen]-2'-ol (prepared as described in Method BB26 and Example 2 but using 7-bromo-4-fluoro-2-methoxy-9H-xanthen-9-one), 2-fluoropyridin-3-ylboronic acid and 4,4-difluoropiperidine hydrochloride. MS m/z=501.0.0 [M+H]$^+$.

$^1$H NMR (400 MHz, DMSO-d$_6$) δ ppm 1.99-2.17 (m, 4 H) 3.24-3.30 (m, 4 H) 3.34-3.46 (m, 2 H) 6.77 (dd, J=2.84, 1.27 Hz, 1 H) 6.98-7.14 (m, 3 H) 7.33-7.42 (m, 1 H) 7.49 (ddd, J=7.26, 5.01, 1.91 Hz, 1 H) 7.55-7.65 (m, 2 H) 8.07 (ddd, J=10.34, 7.51, 1.91 Hz, 1 H) 8.24 (dt, J=4.79, 1.52 Hz, 1 H)

Example 1077

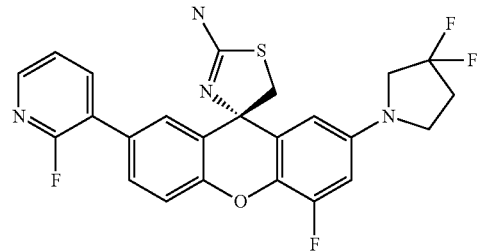 [SMILES: NC1=N[C@@]2(CS1)c1cc(-c3cccnc3F)ccc1Oc1c(F)cc(N3CCC(F)(F)C3)cc12]

Synthesis of (S)-2'-(3,3-difluoropyrrolidin-1-yl)-4'-fluoro-7'-(2-fluoropyridin-3-yl)-5H-spiro[thiazole-4,9'-xanthen]-2-amine The titled compound was synthesized by stpes analogous to those described in method AA20 above, but using (S)-2-amino-7'-bromo-4'-fluoro-5H-spiro[thiazole-4,9'-xanthen]-2'-ol (prepared as described in Method BB26 and Example 2 but using 7-bromo-4-fluoro-2-methoxy-9H-xanthen-9-one), 2-fluoropyridin-3-ylboronic acid and 3,3-difluoropyrrolidine hydrochloride. MS m/z=487.0 [M+H]⁺.

$^1$H NMR (500 MHz, DMSO-$d_6$) δ ppm 2.51-2.61 (m, 2 H) 3.36-3.51 (m, 4 H) 3.58-3.77 (m, 2 H) 6.41 (d, J=1.71 Hz, 1 H) 6.66 (dd, J=13.30, 2.62 Hz, 1 H) 7.00 (br. s., 2 H) 7.33-7.39 (m, 1 H) 7.48 (ddd, J=7.13, 5.10, 1.76 Hz, 1 H) 7.56-7.64 (m, 2 H) 8.02-8.10 (m, 1 H) 8.23 (d, J=4.70 Hz, 1 H)

Example 1079

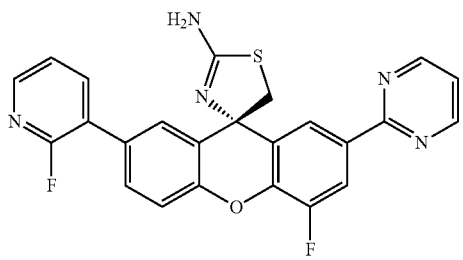 [SMILES: NC1=N[C@@]2(CS1)c1cc(-c3cccnc3F)ccc1Oc1c(F)cc(-c3ncccn3)cc12]

Synthesis of (S)-4'-fluoro-7'-(2-fluoropyridin-3-yl)-2'-(pyrimidin-2-yl)-5H-spiro[thiazole-4,9'-xanthen]-2-amine The titled compound was synthesized by stpes analogous to those described in method AA22 above, but using (S)-2-amino-7'-bromo-4'-fluoro-5H-spiro[thiazole-4,9'-xanthen]-2'-ol (prepared as described in Method BB26 and Example 2 but using 7-bromo-4-fluoro-2-methoxy-9H-xanthen-9-one), 2-fluoropyridin-3-ylboronic acid and 2-(tributylstannyl)pyrimidine. MS m/z=460.0 [M+H]⁺.

$^1$H NMR (500 MHz, DMSO-$d_6$) δ ppm 3.49 (d, J=1.50 Hz, 2 H) 7.08 (s, 2 H) 7.42-7.53 (m, 3 H) 7.62-7.70 (m, 2 H) 8.02-8.15 (m, 1 H) 8.15-8.31 (m, 2 H) 8.41 (s, 1 H) 8.93 (d, J=4.81 Hz, 2 H)

Example 1083

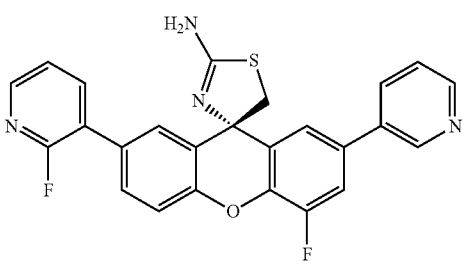 [SMILES: NC1=N[C@@]2(CS1)c1cc(-c3cccnc3F)ccc1Oc1c(F)cc(-c3cccnc3)cc12]

Synthesis of (S)-4'-fluoro-7'-(2-fluoropyridin-3-yl)-2'-(pyridin-3-yl)-5H-spiro[thiazole-4,9'-xanthen]-2-amine The titled compound was synthesized by stpes analogous to those described in method AA8 above, but using (S)-2-amino-7'-bromo-4'-fluoro-5H-spiro[thiazole-4,9'-xanthen]-2'-ol (prepared as described in Method BB26 and Example 2 but using 7-bromo-4-fluoro-2-methoxy-9H-xanthen-9-one), 2-fluoropyridin-3-ylboronic acid and 3-pyridineboronic acid pinacol ester. MS m/z=459.0 [M+H]⁺.

$^1$H NMR (400 MHz, DMSO-$d_6$) δ ppm 3.41-3.58 (m, 2 H) 7.09 (s, 2 H) 7.43-7.55 (m, 4H) 7.61-7.72 (m, 2 H) 7.80 (dd, J=11.79, 2.20 Hz, 1 H) 8.00-8.16 (m, 2 H) 8.22-8.29 (m, 1 H) 8.59 (dd, J=4.70, 1.56 Hz, 1 H) 8.86 (dd, J=2.45, 0.88 Hz, 1 H)

Example 1084

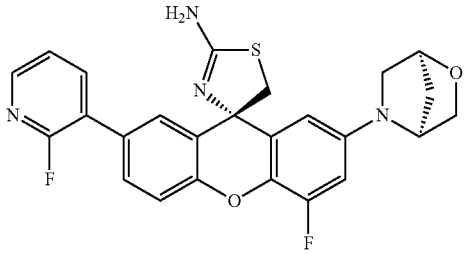 [SMILES: NC1=N[C@@]2(CS1)c1cc(-c3cccnc3F)ccc1Oc1c(F)cc(N3C[C@@H]4C[C@H]3CO4)cc12]

Synthesis of (S)-2'-((1S,4S)-2-oxa-5-azabicyclo[2.2.1]heptan-5-yl)-4'-fluoro-7'-(2-fluoropyridin-3-yl)-5H-spiro[thiazole-4,9'-xanthen]-2-amine The titled compound was synthesized by stpes analogous to those described in method AA20 above, but using (S)-2-amino-7'-bromo-4'-fluoro-5H-spiro[thiazole-4,9'-xanthen]-2'-ol (prepared as described in Method BB26 and Example 2 but using 7-bromo-4-fluoro-2-methoxy-9H-xanthen-9-one), 2-fluoropyridin-3-ylboronic acid and 2-oxa-5-azabicyclo[2.2.1]heptane hydrochloride. MS m/z=479.0 [M+H]⁺.

$^1$H NMR (500 MHz, DMSO-$d_6$) δ ppm 1.85 (d, J=9.30 Hz, 1 H) 1.93 (d, J=8.76 Hz, 1 H) 2.96 (d, J=9.30 Hz, 1 H) 3.34-3.51 (m, 3 H) 3.66 (d, J=7.48 Hz, 1 H) 3.75 (d, J=6.62 Hz, 1 H) 4.49 (s, 1 H) 4.61 (s, 1 H) 6.38 (d, J=1.60 Hz, 1 H) 6.67 (dd, J=13.46, 2.78 Hz, 1 H) 6.99 (s, 2 H) 7.31-7.40 (m, 1 H) 7.44-7.53 (m, 1 H) 7.54-7.65 (m, 2 H) 8.01-8.12 (m, 1 H) 8.23 (d, J=4.60 Hz, 1 H)

Example 1028

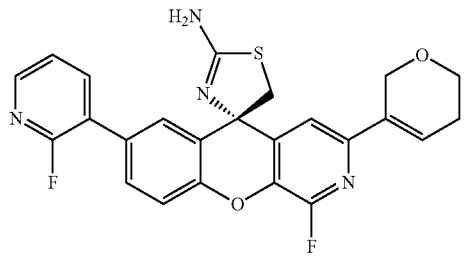 [SMILES: NC1=N[C@@]2(CS1)c1cc(-c3cccnc3F)ccc1Oc1c2cc(C2=CCCOC2)nc1F]

Synthesis of (S)-3-(5,6-dihydro-2H-pyran-3-yl)-1-fluoro-7-(2-fluoropyridin-3-yl)-5'H-spiro[chromeno[2,3-c]pyridine-5,4'-thiazol]-2'-amine The titled compound was synthesized by steps analogous to those described in method AA1 above, but using (S)-7-bromo-3-chloro-1-fluoro-5'H-spiro[chromeno[2,3-c]pyridine-5,4'-thiazol]-2'-amine (prepared as described in Method BB26 but using 7-bromo-3-chloro-1-fluoro-5H-chromeno[2,3-c]pyridin-5-one), 2-fluoropyridin-3-ylboronic acid and 2-(5,6-dihydro-2H-pyran-3-yl)-4,4,5,5-tetramethyl-1,3,2-dioxaborolane MS m/z=464.9 [M+H]⁺. Calculated for C24H18F2N4O2S: 464.49.

¹H NMR (300 MHz, CHLOROFORM-d) δ ppm 2.32-2.44 (m, 2 H) 3.60 (2d, J=12.0 Hz, 2 H) 3.84 (t, J=5.48 Hz, 2 H) 4.54-4.64 (m, 2 H) 6.67-6.77 (m, 1 H) 7.22-7.33 (m, 2 H) 7.37 (d, J=8.48 Hz, 1 H) 7.53-7.61 (m, 1 H) 7.63-7.70 (m, 1 H) 7.82-7.93 (m, 1 H) 8.16-8.24 (m, 1 H)

Example 1029

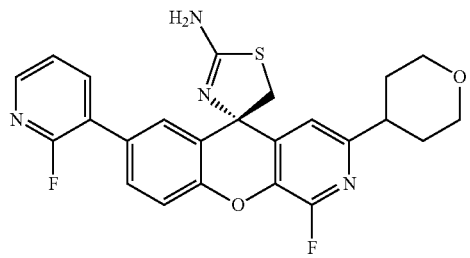 [SMILES: NC1=N[C@@]2(CS1)c1cc(-c3cccnc3F)ccc1Oc1c2cc(C2CCOCC2)nc1F]

Synthesis of (S)-1-fluoro-7-(2-fluoropyridin-3-yl)-3-(tetrahydro-2H-pyran-4-yl)-5'H-spiro[chromeno[2,3-c]pyridine-5,4'-thiazol]-2'-amine The titled compound was synthesized by steps analogous to those described in method AA11 above, but using (S)-7-bromo-3-chloro-1-fluoro-5'H-spiro[chromeno[2,3-c]pyridine-5,4'-thiazol]-2'-amine (prepared as described in Method BB26 but using 7-bromo-3-chloro-1-fluoro-5H-chromeno[2,3-c]pyridin-5-one), 2-fluoropyridin-3-ylboronic acid and 3,6-dihydro-2H-pyran-4-ylboronic acid MS m/z=467.0 [M+H]⁺. Calculated for C24H20F2N4O2S: 466.50.

¹H NMR (300 MHz, MeOH) δ ppm 1.81-2.01 (m, 4 H) 2.97-3.13 (m, 1 H) 3.54-3.67 (m, 2 H) 4.01-4.15 (m, 4 H) 7.45-7.58 (m, 3 H) 7.79-7.86 (m, 1 H) 7.94-7.99 (m, 1H) 8.12-8.21 (m, 1 H) 8.24-8.30 (m, 1 H)

Example 1033

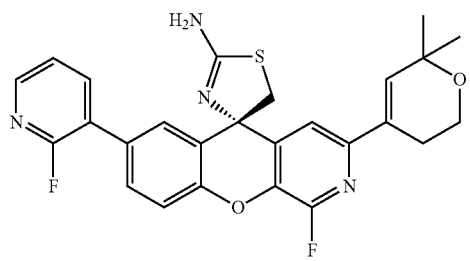 [SMILES: CC1(C)C=C(c2cc3c(c(F)n2)Oc2ccc(-c4cccnc4F)cc2[C@@]32CSC(N)=N2)CCO1]

Synthesis of (S)-3-(6,6-dimethyl-3,6-dihydro-2H-pyran-4-yl)-1-fluoro-7-(2-fluoropyridin-3-yl)-5'H-spiro[chromeno[2,3-c]pyridine-5,4'-thiazol]-2'-amine The titled compound was synthesized by steps analogous to those described in method BB12 above, but using (S)-7-bromo-3-chloro-1-fluoro-5'H-spiro[chromeno[2,3-c]pyridine-5,4'-thiazol]-2'-amine (prepared as described in Method BB26 but using 7-bromo-3-chloro-1-fluoro-5H-chromeno[2,3-c]pyridin-5-one), 2-fluoropyridin-3-ylboronic acid and a mixture of 2-(6,6-dimethyl-3,6-dihydro-2H-pyran-4-yl)-4,4,5,5-tetramethyl-1,3,2-dioxaborolane and 2-(2,2-dimethyl-3,6-dihydro-2H-pyran-4-yl)-4,4,5,5-tetramethyl-1,3,2-dioxaborolane MS m/z=493.0 [M+H]⁺. Calculated for C26H22F2N4O2S: 492.54.

¹H NMR (300 MHz, MeOH) δ ppm 1.36 (s, 6 H) 2.50 (t, J=1.00 Hz, 2 H) 3.62 (2d, J=12.0 Hz, 2 H) 3.95 (t, J=5.48 Hz, 2 H) 6.62 (s, 1 H) 7.37-7.49 (m, 3 H) 7.63-7.71 (m, 1 H) 7.76 (t, J=1.68 Hz, 1 H) 8.03-8.13 (m, 1 H) 8.17-8.25 (m, 1 H)

Example 1037

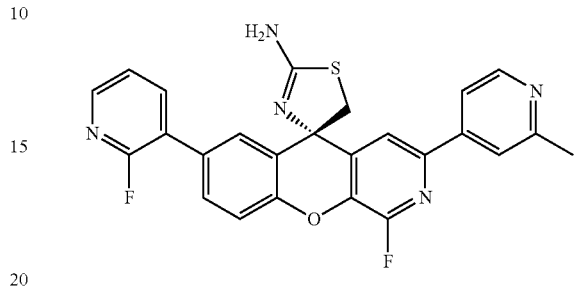

Synthesis of (S)-1-fluoro-7-(2-fluoropyridin-3-yl)-3-(2-methylpyridin-4-yl)-5'H-spiro[chromeno[2,3-c]pyridine-5,4'-thiazol]-2'-amine The titled compound was synthesized by steps analogous to those described in method BB12 above, but using (S)-7-bromo-3-chloro-1-fluoro-5'H-spiro[chromeno[2,3-c]pyridine-5,4'-thiazol]-2'-amine (prepared as described in Method BB26 but using 7-bromo-3-chloro-1-fluoro-5H-chromeno[2,3-c]pyridin-5-one), 2-fluoropyridin-3-ylboronic acid and 2-methyl-4-(4,4,5,5-tetramethyl-1,3,2-dioxaborolan-2-yl)pyridine MS m/z=473.9 [M+H]⁺. Calculated for C25H17F2N5OS: 473.50.

¹H NMR (400 MHz, CHLOROFORM-d) δ ppm 2.68 (s, 3 H) 3.67 (2d, J=12.0 Hz, 2 H) 7.29-7.35 (m, 1 H) 7.40-7.46 (m, 1 H) 7.60-7.70 (m, 2 H) 7.70-7.80 (m, 2 H) 7.83 (s, 1 H) 7.87-7.94 (m, 1 H) 8.19-8.26 (m, 1 H) 8.56-8.65 (m, 1 H)

The present invention also provides methods for making compounds of Formulas I-V, and sub-formulas therein. In one embodiment of the invention, there is provided a method of making a compound of Formula I, the method comprising the step of reacting a compound 20

20

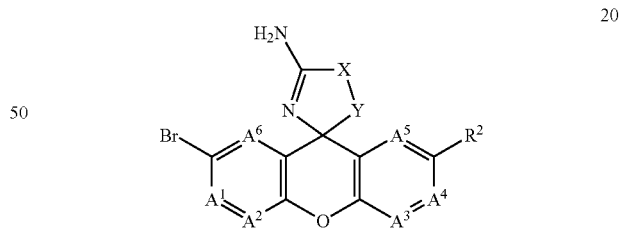

wherein $A^1$, $A^2$, $A^3$, $A^4$, $A^5$, $A^6$, $R^2$, X and Y of Formula I are as defined herein, with a compound having the structure

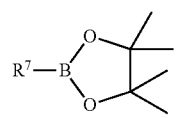

or $R^7$—B(OH)₂, wherein $R^7$ is as defined herein, to make a compound of Formula I.

In another embodiment of the invention, there is provided a method of making a compound of Formula II, the method comprising the step of reacting a compound 20

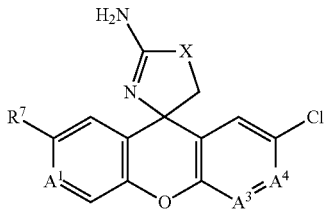

wherein $A^1$, $A^3$, $A^4$, $R^7$ and X of Formula II are as defined herein, with a compound having the structure

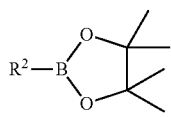

or $R^2$—$B(OH)_2$, wherein $R^2$ is as defined herein, to make a compound of Formula II.

In another embodiment of the invention, there is provided a method of making a compound of Formula V, the method comprising the step of reacting a compound 20

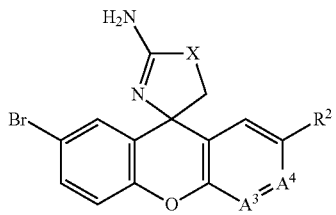

wherein $A^3$, $A^4$, $R^2$ and X of Formula V are as defined herein, with a compound having the structure

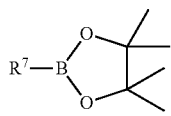

or $R^7$—$B(OH)_2$, wherein $R^7$ is as defined herein, to make a compound of Formula V.

In another embodiment of the invention, there is provided a method of making a compound of Formula I-B, the method comprising the step of reacting a compound 20

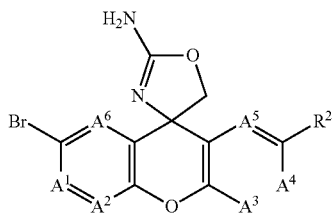

wherein $A^1$, $A^2$, $A^3$, $A^4$, $A^5$, $A^6$ and $R^2$ of Formula I-C are as defined herein, with a compound having the structure

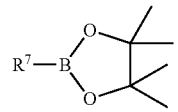

$R^7$—$B(OH)_2$, wherein $R^7$ is as defined herein, to make a compound of Formula I-B.

In another embodiment of the invention, there is provided a method of making a compound of Formula II, the method comprising the step of reacting a compound 20

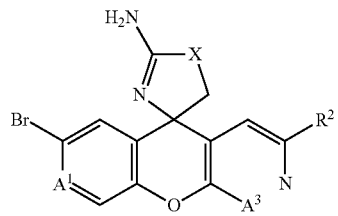

wherein $A^1$, $A^3$, $R^2$ and X of Formula II are as defined herein, with a compound having the structure

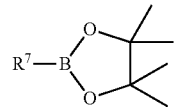

$R^7$—$B(OH)_2$, wherein $R^7$ is as defined herein, to make a compound of Formula II.

As can be appreciated by the skilled artisan, the above synthetic schemes and representative examples are not intended to comprise a comprehensive list of all means by which the compounds described and claimed in this application may be synthesized. Further methods will be evident to those of ordinary skill in the art. Additionally, the various synthetic steps described above may be performed in an alternate sequence or order to give the desired compounds.

For example, in these procedures, the steps may be preceded, or followed, by additional protection/deprotection steps as necessary. Particularly, if one or more functional groups, for example carboxy, hydroxy, amino, or mercapto groups, are or need to be protected in preparing the compounds of the invention, because they are not intended to take part in a specific reaction or chemical transformation, various known conventional protecting groups may be used. For example, protecting groups typically utilized in the synthesis of natural and synthetic compounds, including peptides, nucleic acids, derivatives thereof and sugars, having multiple reactive centers, chiral centers and other sites potentially susceptible to the reaction reagents and/or conditions, may be used.

Synthetic chemistry transformations and protecting group methodologies (protection and deprotection) useful in synthesizing the inhibitor compounds described herein are known in the art and include, for example, those such as described in R. Larock, Comprehensive Organic Transformations, VCH Publishers (1989); T. W. Greene and P. G. M. Wuts, Protective Groups in Organic Synthesis, 3$^{rd}$ edition, John Wiley and Sons (1999); L. Fieser and M. Fieser, Fieser and Fieser's Reagents for Organic Synthesis, John Wiley and Sons (1994); A. Katritzky and A. Pozharski, Handbook of Heterocyclic Chemistry, 2$^{nd}$ edition (2001); M. Bodanszky, A. Bodanszky, The Practice of Peptide Synthesis, Springer-Verlag, Berlin Heidelberg (1984); J. Seyden-Penne, Reductions by the Alumino- and Borohydrides in Organic Synthesis, 2$^{nd}$ edition, Wiley-VCH, (1997); and L. Paquette, editor, Encyclopedia of Reagents for Organic Synthesis, John Wiley and Sons (1995).

Salts, including pharmaceutically acceptable salts, of a compound of the invention having a salt-forming group may be prepared in a conventional manner or manner known to persons skilled in the art. For example, acid addition salts of compounds of the invention may be obtained by treatment with an acid or with a suitable anion exchange reagent. A salt with two acid molecules (for example a dihalogenide) may also be converted into a salt with one acid molecule per compound (for example a monohalogenide); this may be done by heating to a melt, or for example by heating as a solid under a high vacuum at elevated temperature, for example from 50° C. to 170° C., one molecule of the acid being expelled per molecule of the compound. In one embodiment of the invention, there is an acid addition salt of a compound according to any one of originally filed claims 4-11. In another embodiment, the invention provdes a monoacid addition salt of a compound of Formulas I, I-A, I-B, I-C, I-D, II, II-A, III, IV, V or Va. In another embodiment, the invention provdes a di-acid addition salt (same acid) of a compound of Formulas I, I-A, I-B, I-C, I-D, II, II-A, III, IV, V or Va. Examples of suitable acid addition salt(s) in these embodiments are provided herein.

Acid salts can usually be converted to free-base compounds, e.g. by treating the salt with suitable basic agents, for example with alkali metal carbonates, alkali metal hydrogen carbonates, or alkali metal hydroxides, typically potassium carbonate or sodium hydroxide. Exemplary and suitable salts, and their preparation, are described herein in the Definition section of the application.

All synthetic procedures described herein can be carried out under known reaction conditions, advantageously under those described herein, either in the absence or in the presence (usually) of solvents or diluents. As appreciated by those of ordinary skill in the art, the solvents should be inert with respect to, and should be able to dissolve, the starting materials and other reagents used. Solvents should be able to partially or wholly solubilize the reactants in the absence or presence of catalysts, condensing agents or neutralizing agents, for example ion exchangers, typically cation exchangers for example in the H$^+$ form. The ability of the solvent to allow and/or influence the progress or rate of the reaction is generally dependant on the type and properties of the solvent(s), the reaction conditions including temperature, pressure, atmospheric conditions such as in an inert atmosphere under argon or nitrogen, and concentration, and of the reactants themselves.

Suitable solvents for conducting reactions to synthesize compounds of the invention include, without limitation, water; esters, including lower alkyl-lower alkanoates, e.g., EtOAc; ethers including aliphatic ethers, e.g., Et$_2$O and ethylene glycol dimethylether or cyclic ethers, e.g., THF; liquid aromatic hydrocarbons, including benzene, toluene and xylene; alcohols, including MeOH, EtOH, 1-propanol, IPOH, n- and t-butanol; nitriles including CH$_3$CN; halogenated hydrocarbons, including CH$_2$Cl$_2$, CHCl$_3$ and CCl$_4$; acid amides including DMF; sulfoxides, including DMSO; bases, including heterocyclic nitrogen bases, e.g. pyridine; carboxylic acids, including lower alkanecarboxylic acids, e.g., AcOH; inorganic acids including HCl, HBr, HF, H$_2$SO$_4$ and the like; carboxylic acid anhydrides, including lower alkane acid anhydrides, e.g., acetic anhydride; cyclic, linear, or branched hydrocarbons, including cyclohexane, hexane, pentane, isopentane and the like, and mixtures of these solvents, such as purely organic solvent combinations, or water-containing solvent combinations e.g., aqueous solutions. These solvents and solvent mixtures may also be used in "working-up" the reaction as well as in processing the reaction and/or isolating the reaction product(s), such as in chromatography.

Purification methods are known in the art and include, for example, crystallization, chromatography (liquid and gas phase, and the like), extraction, distillation, trituration, reverse phase HPLC and the like. Reactions conditions such as temperature, duration, pressure, and atmosphere (inert gas, ambient) are known in the art and may be adjusted as appropriate for the reaction.

The invention further encompasses "intermediate" compounds, including structures produced from the synthetic procedures described, whether isolated or generated in-situ and not isolated, prior to obtaining the finally desired compound. Structures resulting from carrying out steps from a transient starting material, structures resulting from divergence from the described method(s) at any stage, and structures forming starting materials under the reaction conditions are all "intermediates" included in the invention. Further, structures produced by using starting materials in the form of a reactive derivative or salt, or produced by a compound obtainable by means of the process according to the invention and structures resulting from processing the compounds of the invention in situ are also within the scope of the invention.

The invention also provides new starting materials and/or intermediates, as well as processes for the preparation thereof. In select embodiments, such starting materials are used and reaction conditions so selected as to obtain the desired compound(s). Starting materials of the invention, are either known, commercially available, or can be synthesized in analogy to or according to methods that are known in the art. Many starting materials may be prepared according to known processes and, in particular, can be prepared using processes described in the examples. In synthesizing starting materials, functional groups may be protected with suitable protecting groups when necessary. Protecting groups, their introduction and removal are described above.

Compounds of the present invention can possess, in general, one or more asymmetric carbon atoms and are thus capable of existing in the form of optical isomers as well as in the form of racemic or non-racemic mixtures thereof. While shown without respect to stereochemistry in Formulas I-V, the present invention includes such optical isomers and diastereomers, as well as the racemic and resolved, enantiomerically pure R and S stereoisomers, as well as other mixtures of R and S stereoisomers and pharmaceutically acceptable salts thereof.

The optical isomers can be obtained by resolution of the racemic mixtures according to conventional processes, e.g., by formation of diastereoisomeric salts, by treatment with an optically active acid or base. Examples of appropriate acids are tartaric, diacetyltartaric, dibenzoyltartaric, ditoluoyltartaric, and camphorsulfonic acid and then separation of the mixture of diastereoisomers by crystallization followed by liberation of the optically active bases from these salts. A different process for separation of optical isomers involves the use of a chiral chromatography column optimally chosen to maximize the separation of the enantiomers. Still another available method involves synthesis of covalent diastereoisomeric molecules by reacting compounds of the invention with an optically pure acid in an activated form or an optically pure isocyanate. The synthesized diastereoisomers can be separated by conventional means such as chromatography, distillation, crystallization or sublimation, and then hydrolyzed to deliver the enantiomerically pure compound. The optically active compounds of the invention can likewise be obtained by using optically active starting materials. These isomers may be in the form of a free acid, a free base, an ester or a salt. All such isomeric forms of such compounds are expressly included in the present invention.

The compounds of the invention may also be represented in multiple tautomeric forms. Tautomers often exist in equilibrium with each other, and interconvert under environmental and physiological conditions. The compounds of the invention may also occur in cis- or trans- or E- or Z-double bond isomeric forms. The invention expressly includes all tautomeric forms of the compounds described herein.

All crystal forms of the compounds described herein are expressly included in the present invention.

The present invention also includes isotopically-labeled compounds, which are identical to those recited herein, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorous, fluorine and chlorine, such as $^2$H (deuterium), $^3$H (tritium), $^{13}$C, $^{14}$C, $^{15}$N, $^{16}$O, $^{17}$O, $^{31}$P, $^{32}$P, $^{35}$S, $^{18}$F, and $^{36}$Cl.

Compounds of the present invention that contain the aforementioned isotopes and/or other isotopes of other atoms are within the scope of this invention. Certain isotopically-labeled compounds of the present invention, for example those into which radioactive isotopes such as $^3$H and $^{14}$C are incorporated, are useful in drug and/or substrate tissue distribution assays. Deuterated ($^2$H), Tritiated ($^3$H) and carbon-14, i.e., $^{14}$C, isotopes are particularly preferred for their ease of preparation and detection. Further, substitution with heavier isotopes such as deuterium, i.e., $^2$H, can afford certain therapeutic advantages resulting from greater metabolic stability, for example increased in vivo half-life or reduced dosage requirements and, hence, may be preferred in some circumstances. Isotopically labeled compounds of this invention can generally be prepared by substituting a readily available isotopically labeled reagent for a non-isotopically labeled reagent.

BIOLOGICAL EVALUATION

The compounds of the invention may be modified by appending appropriate functionalities to enhance selective biological properties. The pharmacokinetic and pharmacodynamic properties of a compound relate, directly and indirectly, to its ability to be effective for its intended use.

Although the pharmacological properties of the compounds of the invention (Formulas I-V) vary with structural change, in general, activity possessed by compounds of Formulas I-V may be demonstrated both in vitro as well as in vivo. The following exemplified pharmacological assays have been carried out with the compounds according to the invention, to assess and characterize the compound's ability to modulate BACE activity and to regulate the cleavage of amyloid beta precursor protein, thereby reducing or inhibiting the production of amyloid beta.

In Vitro Enzymatic Bace Fret (Fluorescence Resonance Energy Transfer) Assay (Enzyme Assay Data in the Example Table I)

The assay buffer used in this screen is 0.05 M acetate, pH 4.2, 10% DMSO final, 100 uM genapol (which is a nonionic detergent, below its Critical Micelle Concentration). The Beta Secretase enzyme (0.2 nM) is pre-incubated for one hour with inhibitors, typically in about 1 uL of DMSO according to a serial dilution, are added thereto. This assay is effectively started by the addition of FRET substrate (50 nM) and the combination is incubated for one hour. The FRET assay is terminated with by addition of Tris buffer, which raises the pH to neutrality, and the fluorescence is determined. The FRET substrate is a peptide with commercially available fluorophore and quencher, on opposite sides of the BACE cleavage site. Proteolytic cleavage of the FRET substrate releases quenching of fluorescence (excitation 488 nm and emission 425 nm).

Where available, the in-vitro BACE FRET enzyme data for each of the Examples is provided in Table I. The numeric values of 10 represent the limits of the assay detection. Thus, the actual values may be higher than 10 uM.

In Vitro BACE Cell-Based Assay

The cell-based assay measures inhibition or reduction of $A\beta40$ in conditioned medium of test compound treated cells expressing amyloid precursor protein.

Cells stably expressing Amyloid Precursor Protein (APP) were plated at a density of 40K cells/well in 96 well plates (Costar). The cells were cultivated for 24 hours at 37° C. and 5% $CO_2$ in DMEM supplemented with 10% FBS. The test compounds were then added to cells in 10-point dose response concentrations with the starting concentration being either 100 µM or 10 µM. The compounds were diluted from stock solutions in DMSO and the final DMSO concentration of the test compounds on cells was 0.1%. After 24 h of incubation with the test compounds the supernatant conditioned media was collected and the $A\beta$ 40 levels were determined using a sandwich ELISA. The $IC_{50}$ of the compound was calculated from the percent of control or percent inhibition of $A\beta$ 40 as a function of the concentration of the test compound.

The sandwich ELISA to detect $A\beta$ 40 was performed in 96 well microtiter plates, which were pre-treated with goat anti-rabbit IgG (Pierce). The capture and detecting antibody pair that were used to detect $A\beta$ 40 from cell supernatants were affinity purified pAb40 (Biosource) and biotinylated 6E10 (Signet Labs Inc.), respectively. The optimal concentration for the pAb40 antibody was 3 µg/ml in Superblock/TBS (Pierce) that was supplemented with 0.05% Tween 20 (Sigma). Optimal concentration for the detection antibody 6E10-biotinylated was 0.5 µg/ml in Superblock/TBS (Pierce) that had been supplemented with 2% normal goat serum and 2% normal mouse serum.

Cellular supernatants were incubated with the capture antibody for 3 h at 4° C., followed by 3 wash steps in TBS-tween (0.05%). The detecting antibody incubation was for 2 h at 4° C., again followed by the wash steps as described previously. The final readout of the ELISA is Time-Resolved Fluorescence (counts per minute) using Delfia reagents Streptavidin-Europium and Enhancement solutions (Perkin Elmer) and the Victor 2 multilabel counter (Perkin Elmer).

Where available, the in-vitro BACE cell based data for each of the Examples is provided in Table I. The numeric values of 10 represent the limits of the assay detection. Thus, the actual values may be higher than 10 uM.

In Vivo Inhibition of Beta-Secretase

Several animal models, including mouse, rat, dog, and monkey, may be used to screen for inhibition of beta-secretase activity in vivo following administration of a test compound sample. Animals used in this invention can be wild type, transgenic, or gene knockout animals. For example, the Tg2576 mouse model, prepared and conducted as described in Hsiao et al., 1996, *Science* 274, 99-102, and other non-transgenic or gene knockout animals are useful to analyze in vivo inhibition of Amyloid beta peptide (Abeta) production in the presence of inhibitory test compounds. Generally, 2 to 18 month old Tg2576 mice, gene knockout mice or non-transgenic animals are administered test compounds formulated in vehicles, such as cyclodextran, phosphate buffers, hydroxypropyl methylcellulose or other suitable vehicles. One to twenty-four hours following the administration of compound, animals are sacrificed, and brains as well as cerebrospinal fluid (CSF) and plasma are removed for analysis of A-beta levels and drug or test compound concentrations (Dovey et al., 2001, *Journal of Neurochemistry*, 76, 173-181) Beginning at time 0, animals are administered by oral gavage, or other means of delivery such as intravenous injection, an inhibitory test compound of up to 100 mg/kg in a standard, conventional formulation, such as 2% hydroxypropyl methylcellulose, 1% Tween80. A separate group of animals receive 2% hydroxypropyl methylcellulose, 1% Tween80 alone, containing no test compound, and serve as a vehicle-control group. At the end of the test period, animals are sacrificed and brain tissues, plasma or cerebrospinal fluid are collected. Brains are either homogenized in 10 volumes (w/v) of 0.2% diethylamine (DEA) in 50 mM NaCl (Best et al., 2005, *Journal of Pharmacology and Experimental Therapeutics*, 313, 902-908), or in 10 volumes of 0.5% TritonX-100 in Tris-buffered saline (pH at about 7.6). Homogenates are centrifuged at 355,000 g, 4° C. for 30 minutes. CSF or brain supernatants are then analyzed for the presence of A-beta peptide by specific sandwich ELISA assays based on ECL (Electrochemiluminescence) technology. For example, rat Abeta40 is measured using biotinylated-4G8 (Signet) as a capture antibody and Fab40 (an in-house antibody specific to the C-terminal of Abeta40) as a detection antibody. For example, 4 hours after administration of 30 mg/kg oral dose of the test compound in 2% hydroxypropyl methylcellulose, 1% Tween80 (pH2.2) to 200 g male Sprague Dawley rats, amyloid beta peptide levels are measured for reduction by X % and Y % in cerebrospinal fluid and brain, respectively, when compared to the levels measured in the vehicle-treated or control mice.

Actual vehicles used: Oral: 2% HPMC, 1% Tween80, pH 2.2

IV: 5% EtOH, 45% Propylene glycol in 5% Dextrose

The compounds of the invention may be shown to reduce the formation and/or deposition of amyloid beta peptide in the cerebrospinal fluid (CSF) as well as in the brain of a mouse or rat at either 3 mpk, 10 mpk or 30 mpk (mpk=mg compound per kg weight of the animal) dosing concentrations after 4 hrs. The following examples exhibited the following percent Abeta 40 reductions at 10 mpk (unless otherwise noted) in the CSF and brain of the rat, respectively.

| Example No. | CSF A-beta reduction % at 10 mg/kg | Brain A-beta reduction % at 10 mg/kg |
| --- | --- | --- |
| 89 | 80% | 69% |
| 97 | 46% | 28% |
| 127 | 61% | 45% |
| 128 | 75% | 57% |
| 129 | 74% | 51% |
| 130 | 85% | 80% |
| 131 | 77% | 68% |
| 132 | 54% | 45% |
| 133 | 60% | 55% |
| 134 | 61% | 45% |
| 135 | 61% | 44% |
| 136 | 65% | 49% |
| 137 | 66% | 60% |
| 138 | 67% | 48% |
| 139 | 74% | 64% |
| 140 | 79% | 76% |
| 225 | 64% | 47% |
| 226 | 31% | 19% |
| 236 | 58% | 34% |
| 262 | 36% | 11% |
| 280 | 62% | 45% |
| 339 | 56% | 29% |
| 369 | 46% | 31% |
| 385 | 66% at 3 mpk | 50% at 3 mpk |
| 402 | 52% | 28% |
| 414 | 64% | 44% |
| 443 | 35% | 7% |
| 452 | 56% | 35% |
| 463 | 30% | 9% |
| 492 | 56% at 3 mpk | 44% at 3 mpk |
| 508 | 49% | 25% |
| 668 | 55% at 3 mpk | 46% at 3 mpk |
| 672 | 64% | 47% |
| 673 | 77% at 3 mpk | 82% at 3 mpk |
| 676 | 76% at 3 mpk | 74% at 3 mpk |
| 688 | 74% at 3 mpk | 75% at 3 mpk |
| 745 | 78% | 69% |
| 746 | 38% at 3 mpk | 40% at 3 mpk |
| 759 | 43% at 3 mpk | 43% at 3 mpk |
| 802 | 69% | 57% |
| 839 | 37% | 23% |
| 860 | 0% | 2% |
| 867 | 56% | 39% |
| 869 | 61% | 44% |
| 892 | 84% | 80% |
| 893 | 76% | 70% |
| 894 | 75% | 69% |
| 901 | 56% | 44% |
| 916 | 61% | 44% |
| 698 | 66% at 3 mpk | 56% at 3 mpk |
| 918 | 78% at 3 mpk | 73% at 3 mpk |
| 922 | 69% at 3 mpk | 57% at 3 mpk |
| 927 | 70% | 65% |
| 928 | 82% | 71% |
| 942 | 57% at 3 mpk | 42% at 3 mpk |
| 947 | 22% at 3 mpk | 25% at 3 mpk |
| 951 | 17% at 3 mpk | 13% at 3 mpk |
| 996 | 55% | 43% |
| 999 | 58% at 5 mpk | 40% at 5 mpk |
| 1000 | 63% at 30 mpk | 60% at 30 mpk |
| 1001 | 73% at 3 mpk | 62% at 3 mpk |
| 1029 | 83% | 73% |
| 1033 | 60% at 3 mpk | 52% at 3 mpk |
| 1037 | 67% | 58% |
| 1067 | 69% | 55% |
| 1076 | 63% | 33% |
| 1077 | 69% | 53% |
| 1079 | 67% | 54% |
| 724 | 42% | 27% |
| 1083 | 66% | 53% |
| 1084 | 67% | 50% |

INDICATIONS

The compounds of the invention have been shown to modulate, and specifically inhibit the activity of beta-secretase (Memapsin 2) enzyme, thereby reducing the A-beta peptide fragments believed to be responsible for Alzheimer's Disease (AD). Bapineuzamab, a monoclonal amino-terminus specific anti-amyloid antibody is presently in Phase III clinical trials for the treatment of AD. *Alzheimer's Research & Therapy*, 1:2, 2009. Bapineuzumab targets beta amyloid protein involved in AD. It is the most advanced monoclonal antibody in clinical development to stop the disease progression and degradation of cognitive function. The drug has fast track regulatory status with the USFDA (*Medpedia*, 2011). Hence, it must clearly show a beneficial and lasting effect through validated biomarker of underlying AD disease mechanism. Clinical trials in AD now measure CSF Aβ levels, brain amyloid load, CSF tau, brain volume by MRI and FDG PET scan. Each of the known genetic causes of AD is linked to A-beta.

Other conditions including dementia, Down's Syndrome to APP over-production, are all believed to be linked to the deposition of A-beta on the brain. With methods for identifying brain amyloid deposition, positron emission scanning (PET) and CSF measurements of Ab42, identification of AD suffering individuals needing treatment is becoming more easy. It is firmly believed that by reducing the formation of A-beta, one can begin to pre-treat AD. Vassar et al, *Journal of Neuroscience*, 29 (41):12787-12794, 2009. One published pathway for treatment of AD is inhibition of beta-secretase. Tirrell, Bloomberg News, *The Boston Globe*, Jan. 7, 2010; *Curr. Alzheimer's Res.* 2008, Apr. 5 (2):121-131; *Expert Opin. Drug Discov*. (200( ) 4(4):319-416.

Accordingly, compounds of the invention, and pharmaceutical compositions comprising said compounds, are useful for, but not limited to, the prevention or treatment of beta-secretase related diseases, including Alzheimer's disease, the leading cause of dementia. Particularly, the compounds of the invention are useful to treat various stages of AD, including without limitation mild to moderate AD and prodromal patients pre-disposed to developing AD. The compounds of the invention have the ability to modulate the activity of beta secretase enzyme, thereby regulating the production of amyloid beta (Abeta peptide) and slowing or reducing the formation and deposition of Abeta peptide in both the cerebral spinal fluid as well as in the brain, resulting in a decrease of amyloid plaque on the brain. In one embodiment of the invention, there is provided a method of treating a disorder related to a beta-secretase enzyme in a subject, the method comprising administering to the subject an effective dosage amount of a compound of Formulas I, I-A, I-B, I-C, I-D, II, III, IV or V, or a sub-Formula thereof. In another embodiment, there is provided a method of reducing production of amyloid beta, and of slowing plaque formation on the brain. In another embodiment, there is provided a method for the treatment, prevention or amelioration of a disease or disorder characterized by the elevated beta-amyloid deposits or beta-amyloid levels in a subject, the method comprising administering to the subject a therapeutically effective amount of a compound according to any of Formulas I-V, and sub-Formulas thereof. In yet another embodiment, the invention provides a method of treating Alzheimer's disease, cognitive impairment including mild, moderate and/or severe, Down's Syndrome, cognitive decline, senile dementia, cerebral amyloid angiopathy or a neurodegenerative disorder.

Accordingly, the compounds of the invention would be useful in therapy as CNS agents in treating neurological disorders and related conditions.

In one embodiment, the compounds of the invention are provided for the manufacture of a medicament, or a pharmaceutical composition, for the therapeutic and/or prophylactic treatment of diseases and disorders characterized by elevated levels of β-amyloid and/or β-amyloid oligomers and/or b-amyloid plaques and further deposits, including Alzheimer's Disease. In another embodiment, the invention provides compounds, in effective dosage amounts, for the therapeutic and/or prophylactic treatment of AD. Thus, the compounds of the invention may be used to treat prodromol patients, i.e., subjects exhibiting the biomarkers and/or hallmarks of developing AD.

Besides being useful for human treatment, these compounds are useful for veterinary treatment of companion animals, exotic animals and farm animals, including mammals, rodents, and the like. For example, animals including horses, dogs, and cats may be treated with compounds provided by the invention.

FORMULATIONS AND METHOD OF USE

Treatment of diseases and disorders herein is intended to also include therapeutic administration of a compound of the invention, or a pharmaceutical salt thereof, or a pharmaceutical composition of either to a subject (i.e., an animal, preferably a mammal, most preferably a human) which may be in need of preventative treatment, such as, for example, for pain, inflammation and the like. Treatment also encompasses prophylactic administration of a compound of the invention, or a pharmaceutical salt thereof, or a pharmaceutical composition of either to a subject (i.e., an animal, preferably a mammal, most preferably a human). Generally, the subject is initially diagnosed by a licensed physician and/or authorized medical practitioner, and a regimen for prophylactic and/or therapeutic treatment via administration of the compound(s) or compositions of the invention is suggested, recommended or prescribed.

The amount of compound(s) which is/are administered and the dosage regimen for treating neurological disorders and beta-secretase mediated diseases with the compounds and/or compositions of this invention depends on a variety of factors, including the age, weight, sex and medical condition of the subject, the type of disease, the severity of the disease, the route and frequency of administration, and the particular compound employed. Thus, the dosage regimen may vary widely, but can be determined routinely using standard methods. A daily dose of about 0.01 to 500 mg/kg, advantageously between about 0.01 and about 50 mg/kg, more advantageously about 0.01 and about 30 mg/kg, and even more advantageously between about 0.1 and about 10 mg/kg body weight may be appropriate, and should be useful for all methods of use disclosed herein. The daily dose can be administered in one to four doses per day.

While it may be possible to administer a compound of the invention alone, in the methods described, the compound administered normally will be present as an active ingredient in a pharmaceutical composition. Thus, in another embodiment of the invention, there is provided a pharmaceutical composition comprising a compound of this invention in combination with a pharmaceutically acceptable excipient, which includes diluents, carriers, adjuvants and the like (collectively referred to herein as "excipient" materials) as described herein, and, if desired, other active ingredients. A pharmaceutical composition of the invention may comprise an "effective amount" of a compound of the invention or an "effective dosage amount" of a compound of the invention. An "effective dosage amount" of a compound of the invention includes an amount less than, equal to or greater than an effective amount of the compound. For example, a pharmaceutical composition in which two or more unit dosages, such as in tablets, capsules and the like, are required to administer an effective amount of the compound, or alternatively, a multi-dose pharmaceutical composition, such as powders, liquids and the like, in which an effective amount of the compound is administered by administering a portion of the composition.

The compound(s) of the present invention may be administered by any suitable route, preferably in the form of a pharmaceutical composition adapted to such a route, and in a dose effective for the treatment intended. The compounds and compositions of the present invention may, for example, be administered orally, mucosally, topically, rectally, pulmonarily such as by inhalation spray, or parentally including intravascularly, intravenously, intraperitoneally, subcutaneously, intramuscularly intrasternally and infusion techniques, in dosage unit formulations containing conventional pharmaceutically acceptable carriers, adjuvants, and vehicles.

For oral administration, the pharmaceutical composition may be in the form of, for example, a tablet, capsule, suspension or liquid. The pharmaceutical composition is preferably made in the form of a dosage unit containing a particular amount of the active ingredient. Examples of such dosage units are tablets or capsules. For example, these may contain an amount of active ingredient from about 1 to 2000 mg, advantageously from about 1 to 500 mg, and typically from about 5 to 150 mg. A suitable daily dose for a human or other mammal may vary widely depending on the condition of the patient and other factors, but, once again, can be determined using routine methods and practices.

For therapeutic purposes, the active compounds of this invention are ordinarily combined with one or more adjuvants or other "excipients" appropriate to the indicated route of administration. If orally administered on a per dose basis, the compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, to form the final formulation. For example, the active compound(s) and excipient(s) may be tableted or encapsulated by known and accepted methods for convenient administration. Examples of suitable formulations include, without limitation, pills, tablets, soft and hard-shell gel capsules, troches, orally-dissolvable forms and delayed or controlled-release formulations thereof. Particularly, capsule or tablet formulations may contain one or more controlled-release agents, such as hydroxypropylmethyl cellulose, as a dispersion with the active compound(s).

Formulations for parenteral administration may be in the form of aqueous or non-aqueous isotonic sterile injection solutions or suspensions. These solutions and suspensions may be prepared from sterile powders or granules using one or more of the carriers or diluents mentioned for use in the formulations for oral administration or by using other suitable dispersing or wetting agents and suspending agents. The compounds may be dissolved in water, polyethylene glycol, propylene glycol, ethanol, corn oil, cottonseed oil, peanut oil, sesame oil, benzyl alcohol, sodium chloride, tragacanth gum, and/or various buffers. Other adjuvants and modes of administration are well and widely known in the pharmaceutical art. The active ingredient may also be administered by injection as a composition with suitable carriers including saline, dextrose, or water, or with cyclodextrin (ie. Captisol), cosolvent solubilization (ie. propylene glycol) or micellar solubilization (ie. Tween 80).

The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed, including synthetic mono- or diglycerides. In addition, fatty acids such as oleic acid find use in the preparation of injectables.

The active ingredient may also be administered by injection as a composition with suitable carriers including saline, dextrose, or water. The daily parenteral dosage regimen will be from about 0.1 to about 30 mg/kg of total body weight, and preferably from about 0.1 to about 10 mg/kg.

For pulmonary administration, the pharmaceutical composition may be administered in the form of an aerosol or with an inhaler including dry powder aerosol.

The pharmaceutical compositions may be subjected to conventional pharmaceutical operations such as sterilization and/or may contain conventional adjuvants, such as preservatives, stabilizers, wetting agents, emulsifiers, buffers etc. Tablets and pills can additionally be prepared with enteric coatings. Such compositions may also comprise adjuvants, such as wetting, sweetening, flavoring, and perfuming agents. Accordingly, in yet another embodiment of the present invention, there is provided a method of manufacturing a medicament, the method comprising combining an amount of a compound according to Formulas I-V with a pharmaceutically acceptable carrier to manufacture the medicament.

In yet another embodiment, the invention provides a method of manufacturing a medicament for the treatment of Alzheimer's disease, the method comprising combining an amount of a compound according to Formulas I-V with a pharmaceutically acceptable carrier to manufacture the medicament.

COMBINATIONS

While the compounds of the invention can be dosed or administered as the sole active pharmaceutical agent, they can also be used in combination with one or more compounds of the invention or in conjunction with other agents. When administered as a combination, the therapeutic agents can be formulated as separate compositions that are administered simultaneously or sequentially at different times, or the therapeutic agents can be given as a single composition.

The phrase "co-therapy" (or "combination-therapy"), in defining use of a compound of the present invention and another pharmaceutical agent, is intended to embrace administration of each agent in a sequential manner in a regimen that will provide beneficial effects of the drug combination, and is intended as well to embrace co-administration of these agents in a substantially simultaneous manner, such as in a single capsule having a fixed ratio of these active agents or in multiple, separate capsules for each agent.

Specifically, the compounds of the present invention may be administered in conjunction with additional therapies known to those skilled in the art in the prevention or treatment of beta-secretase, gamma-secretase and/or other reagents known in influence the formation and/or deposition of amyloid beta, otherwise responsible for the formation of plaque on the brain. Thus, the compounds may be co-administered simultaneously or sequentially along with the other therapeutic agent.

If formulated as a fixed dose, such combination products employ the compounds of this invention within the accepted dosage ranges. Compounds of Formulas I-IV, and sub-formulas thereof, may also be administered sequentially with known CNS treating agents when a combination formulation is inappropriate. The invention is not limited in the sequence of administration; compounds of the invention may be administered either prior to, simultaneous with or after administration of the known and used CNS agent.

The foregoing description is merely illustrative of the invention and is not intended to limit the invention to the disclosed compounds, compositions and methods. Variations and changes, which are obvious to one skilled in the art, are intended to be within the scope and nature of the invention, as defined in the appended claims. From the foregoing description, one skilled in the art can easily ascertain the essential characteristics of this invention, and without departing from the spirit and scope thereof, can make various changes and modifications of the invention to adapt it to various usages and conditions. All patents and other publications recited herein are hereby incorporated by reference in their entireties.

What is claimed is:

1. A compound, or a stereoisomer, tautomer or pharmaceutically acceptable salt thereof, selected from 4-((5S)-2'-amino-7-(5-methyl-3-pyridinyl)spiro[chromeno[2,3-c]pyridine-5,4'-[1,3]oxazol]-3-yl)-2-pyridinecarbonitrile;
(5S)-3,7-diphenylspiro[chromeno[2,3-c]pyridine-5,4'-[1,3]oxazol]-2'-amine;
3-((5S)-2'-amino-3-(3,6-dihydro-2H-pyran-4-yl)spiro[chromeno[2,3-c]pyridine-5,4'-[1,3]oxazol]-7-yl) benzonitrile;
(5S)-3-(3,6-dihydro-2H-pyran-4-yl)-7-(5-methoxy-3-pyridinyl)spiro[chromeno[2,3-c]pyridine-5,4'-[1,3]oxazol]-2'-amine;
(5S)-3-(3,6-dihydro-2H-pyran-4-yl)-7-(3-(trifluoromethyl)phenyl)spiro[chromeno[2,3-c]pyridine-5,4'-[1,3]oxazol]-2'-amine;
(5S)-7-(2,4-difluoro-3-pyridinyl)-3-(3,6-dihydro-2H-pyran-4-yl)spiro[chromeno[2,3-c]pyridine-5,4'-[1,3]oxazol]-2'-amine;
(5S)-2-fluoro-7-(2-fluoro-3-pyridinyl)-3-(trimethylsilyl)spiro[chromeno[2,3-b]pyridine-5,4'-[1,3]oxazol]-2'-amine;
2-fluoro-3,7-bis(2-fluoro-3-pyridinyl)spiro[chromeno[2,3-b]pyridine-5,4'-[1,3]oxazol]-2'-amine;
3-(3,3-dimethyl-1-butyn-1-yl)-2-fluoro-7-(2-fluoro-3-pyridinyl)spiro[chromeno[2,3-b]pyridine-5,4'-[1,3]oxazol]-2'-amine;
2-fluoro-7-(2-fluoro-3-pyridinyl)-3-((3-methyl-3-oxetanyl)ethynyl)spiro[chromeno[2,3-b]pyridine-5,4'-[1,3]oxazol]-2'-amine;
3-(3,6-dihydro-2H-pyran-4-yl)-2-fluoro-7-(2-fluoro-3-pyridinyl)spiro[chromeno[2,3-b]pyridine-5,4'-[1,3]oxazol]-2'-amine;
2-fluoro-7-(2-fluoro-3-pyridinyl)-3-(2-fluoro-4-pyridinyl)spiro[chromeno[2,3-b]pyridine-5,4'-[1,3]oxazol]-2'-amine;
(5S)-1-fluoro-7-(2-fluoro-3-pyridinyl)-3-(2-fluoro-4-pyridinyl)spiro[chromeno[2,3-c]pyridine-5,4'-[1,3]oxazol]-2'-amine;
(5S)-7-(5-fluoro-3-pyridinyl)-3-((3-methyl-3-oxetanyl)ethynyl)spiro[chromeno[2,3-c]pyridine-5,4'-[1,3]oxazol]-2'-amine;
(5S)-3-((3-methyl-3-oxetanyl)ethynyl)-7-(3-pyridinyl)spiro[chromeno[2,3-c]pyridine-5,4'-[1,3]oxazol]-2'-amine;
(5S)-3-((3-methyl-3-oxetanyl)ethynyl)-7-phenylspiro[chromeno[2,3-c]pyridine-5,4'-[1,3]oxazol]-2'-amine;
(5S)-7-(6-fluoro-3-pyridinyl)-3-((3-methyl-3-oxetanyl)ethynyl)spiro[chromeno[2,3-c]pyridine-5,4'-[1,3]oxazol]-2'-amine;
(5S)-7-(3-chlorophenyl)-3-((3-methyl-3-oxetanyl)ethynyl)spiro[chromeno[2,3-c]pyridine-5,4'-[1,3]oxazol]-2'-amine;
(5S)-7-(5-chloro-2-fluoro-3-pyridinyl)-3-((3-methyl-3-oxetanyl)ethynyl)spiro[chromeno[2,3-c]pyridine-5,4'-[1,3]oxazol]-2'-amine;
(5S)-7-(cyclopropylethynyl)-3-(3,6-dihydro-2H-pyran-4-yl)spiro[chromeno[2,3-c]pyridine-5,4'-[1,3]oxazol]-2'-amine;
(5S)-3-(3,6-dihydro-2H-pyran-4-yl)-7-((3-methyl-3-oxetanyl)ethynyl)spiro[chromeno[2,3-c]pyridine-5,4'-[1,3]oxazol]-2'-amine;
(5S)-3-(3,6-dihydro-2H-pyran-4-yl)-7-(3,3-dimethyl-1-butyn-1-yl)spiro[chromeno[2,3-c]pyridine-5,4'-[1,3]oxazol]-2'-amine;
(5S)-7-(3,3-dimethyl-1-butyn-1-yl)-3-(2-fluoro-4-pyridinyl)spiro[chromeno[2,3-c]pyridine-5,4'-[1,3]oxazol]-2'-amine;
(5S)-3-(3,3-difluoro-1-pyrrolidinyl)-7-((3-methyl-3-oxetanyl)ethynyl)spiro[chromeno[2,3-c]pyridine-5,4'-[1,3]oxazol]-2'-amine;
3-((5S)-2'-amino-3-((3-methyl-3-oxetanyl)ethynyl)spiro[chromeno[2,3-c]pyridine-5,4'-[1,3]oxazol]-7-yl)benzonitrile;
(5S)-7-(2,4-difluoro-3-pyridinyl)-3-(3,3-dimethyl-1-butyn-1-yl)spiro[chromeno[2,3-c]pyridine-5,4'-[1,3]oxazol]-2'-amine;
(5S)-7-(3-chlorophenyl)-3-(2-pyrazinyl)spiro[chromeno[2,3-b]pyridine-5,4'-[1,3]oxazol]-2'-amine;
(5S)-7-(6-fluoro-3-pyridinyl)-3-((3-methyl-3-oxetanyl)ethynyl)spiro[chromeno[2,3-b]pyridine-5,4'-[1,3]oxazol]-2'-amine;
(5S)-3-((3-methyl-3-oxetanyl)ethynyl)-7-(2-pyrazinyl)spiro[chromeno[2,3-b]pyridine-5,4'-[1,3]oxazol]-2'-amine;
3-((5S)-2'-amino-3-(3,6-dihydro-2H-pyran-4-yl)spiro[chromeno[2,3-b]pyridine-5,4'-[1,3]oxazol]-7-yl)benzonitrile;
3-((5S)-2'-amino-3-((3-methyl-3-oxetanyl)ethynyl)spiro[chromeno[2,3-b]pyridine-5,4'-[1,3]oxazol]-7-yl)benzonitrile;
(5S)-7-(3-chloro-2-fluorophenyl)-3-(3,6-dihydro-2H-pyran-4-yl)spiro[chromeno[2,3-b]pyridine-5,4'-[1,3]oxazol]-2'-amine;
(5S)-3-(5,6-dihydro-2H-pyran-3-yl)-7-(2-fluoro-3-pyridinyl)spiro[chromeno[2,3-b]pyridine-5,4'-[1,3]oxazol]-2'-amine;
(5S)-7-(5-chloro-2-fluorophenyl)-3-(5,6-dihydro-2H-pyran-3-yl)spiro[chromeno[2,3-b]pyridine-5,4'-[1,3]oxazol]-2'-amine;
(5S)-7-(3-chlorophenyl)-3-(5,6-dihydro-2H-pyran-3-yl)spiro[chromeno[2,3-b]pyridine-5,4'-[1,3]oxazol]-2'-amine;
(5S)-7-(2-fluoro-3-pyridinyl)-3-((3S)-tetrahydro-2H-pyran-3-yl)spiro[chromeno[2,3-b]pyridine-5,4'-[1,3]oxazol]-2'-amine;
(5S)-7-(2-fluoro-3-pyridinyl)-3-((E)-2-(3-methyl-3-oxetanyl)ethenyl)spiro[chromeno[2,3-b]pyridine-5,4'-[1,3]oxazol]-2'-amine;
(5S)-7-(6-fluoro-3-pyridinyl)-3-((E)-2-(3-methyl-3-oxetanyl)ethenyl)spiro[chromeno[2,3-b]pyridine-5,4'-[1,3]oxazol]-2'-amine;
(5S)-7-(5-chloro-2-fluorophenyl)-3-((E)-2-(3-methyl-3-oxetanyl)ethenyl)spiro[chromeno[2,3-b]pyridine-5,4'-[1,3]oxazol]-2'-amine;

(5S)-7-(cyclopropylethynyl)-3-(3,3-difluoro-1-pyrolidinyl)spiro[chromeno[2,3-b]pyridine-5,4'-[1,3]oxazol]-2'-amine;
(5S)-7-(cyclopropylethynyl)-3-(2,2-dimethyl-4-morpholinyl)spiro[chromeno[2,3-b]pyridine-5,4'-[1,3]oxazol]-2'-amine;
(5S)-7-(3,3-dimethyl-1-butyn-1-yl)-3-(1-methyl-1H-pyrazol-3-yl)spiro[chromeno[2,3-b]pyridine-5,4'-[1,3]oxazol]-2'-amine;
(5S)-7-(cyclopropylethynyl)-3-(4,4-difluoro-1-piperidinyl)spiro[chromeno[2,3-b]pyridine-5,4'-[1,3]oxazol]-2'-amine;
(5S)-7-(cyclopropylethynyl)-3-(3,3-dimethyl-1-pyrrolidinyl)spiro[chromeno[2,3-b]pyridine-5,4'-[1,3]oxazol]-2'-amine;
(5S)-7-(cyclopropylethynyl)-3-(1-methyl-1H-pyrazol-3-yl)spiro[chromeno[2,3-b]pyridine-5,4'-[1,3]oxazol]-2'-amine;
(5S)-3-((2-methylpropyl)sulfanyl)-7-(3-pyridinyl)spiro[chromeno[2,3-b]pyridine-5,4'-[1,3]oxazol]-2'-amine;
(5S)-7-(5-chloro-3-pyridinyl)-3-((3-methyl-3-oxetanyl)ethynyl)spiro[chromeno[2,3-b]pyridine-5,4'-[1,3]oxazol]-2'-amine;
(5S)-3-((3-methyl-3-oxetanyl)ethynyl)-7-(5-(trifluoromethyl)-3-pyridinyl)spiro[chromeno[2,3-b]pyridine-5,4'-[1,3]oxazol]-2'-amine;
(5S)-3-((2-methylbutyl)sulfanyl)-7-(3-pyridinyl)spiro[chromeno[2,3-b]pyridine-5,4'-[1,3]oxazol]-2'-amine;
(5S)-7-(3,4-difluorophenyl)-3-((3-methyl-3-oxetanyl)ethynyl)spiro[chromeno[2,3-b]pyridine-5,4'-[1,3]oxazol]-2'-amine;
(4S)-4'-fluoro-7'-(2-fluoro-3-pyridinyl)-2'-(2-oxa-7-azaspiro[3.5]non-7-yl)spiro[1,3-oxazole-4,9'-xanthen]-2-amine;
(4R)-2'-(3,6-dihydro-2H-pyran-4-yl)-7'-(2-fluoro-3-pyridinyl)spiro[1,3-oxazole-4,9'-xanthen]-2-amine;
5-((4R)-2-amino-7'-(3,6-dihydro-2H-pyran-4-yl)spiro[1,3-oxazole-4,9'-xanthen]-2'-yl)-3-pyridinecarbonitrile;
(4R)-2'-(3,6-dihydro-2H-pyran-4-yl)-7'-(2-fluoro-5-methyl-3-pyridinyl)spiro[1,3-oxazole-4,9'-xanthen]-2-amine;
(4R)-2'-(3,6-dihydro-2H-pyran-4-yl)-7'-(2-pyrazinyl)spiro[1,3-oxazole-4,9'-xanthen]-2-amine;
(4R)-2'-(3,6-dihydro-2H-pyran-4-yl)-7'-(5-fluoro-3-pyridinyl)spiro[1,3-oxazole-4,9'-xanthen]-2-amine;
(4R)-2'-(3,6-dihydro-2H-pyran-4-yl)-7'-(5-methoxy-3-pyridinyl)spiro[1,3-oxazole-4,9'-xanthen]-2-amine;
3-((4R)-2-amino-7'-(3,6-dihydro-2H-pyran-4-yl)spiro[1,3-oxazole-4,9'-xanthen]-2'-yl)benzonitrile;
(4S)-4'-fluoro-7'-(2-fluoro-3-pyridinyl)-2'-(2-pyridinyl)spiro[1,3-oxazole-4,9'-xanthen]-2-amine;
(4S)-4'-fluoro-7'-(2-fluoro-3-pyridinyl)-2'-(2-pyrimidinyl)spiro[1,3-oxazole-4,9'-xanthen]-2-amine;
(4S)-7'-(3,6-dihydro-2H-pyran-4-yl)-5'-fluoro-N~2~'-(3-methoxyphenyl)spiro[1,3-oxazole-4,9'-xanthene]-2,2'-diamine;
(4S)-5'-fluoro-N~2~'-(3-methoxyphenyl)-7'-(4-morpholinyl)spiro[1,3-oxazole-4,9'-xanthene]-2,2'-diamine;
4-((4S)-2-amino-4'-fluoro-7'-(2-fluoro-3-pyridinyl)spiro[1,3-oxazole-4,9'-xanthen]-2'-yl)-2-methyl-3-butyn-2-ol;
4-((4S)-2-amino-4'-fluoro-7'-(2-fluoro-3-pyridinyl)spiro[1,3-oxazole-4,9'-xanthen]-2'-yl)-2-methyl-2-butanol; and
4-((4S)-2-amino-4'-fluoro-7'-(2-fluoro-3-pyridinyl)spiro[1,3-oxazole-4,9'-xanthen]-2'-yl)-6-methyl-2H-pyran-2-one.

2. A compound, or a stereoisomer, tautomer or pharmaceutically acceptable salt thereof, selected from
(5S)-7-(2,4-difluoro-3-pyridinyl)-3-(3,6-dihydro-2H-pyran-4-yl)spiro[chromeno[2,3-c]pyridine-5,4'-[1,3]oxazol]-2'-amine;
(5S)-3-(3,6-dihydro-2H-pyran-4-yl)-7-(2-fluoro-3-pyridinyl)spiro[chromeno[2,3-b]pyridine-5,4'-[1,3]thiazol]-2'-amine;
3-((5S)-2'-amino-3-((3-methyl-3-oxetanyl)ethynyl)spiro[chromeno[2,3-b]pyridine-5,4'-[1,3]oxazol]-7-yl)benzonitrile;
(4S)-4'-fluoro-7'-(2-fluoro-3-pyridinyl)-2'-(2-pyrimidinyl)spiro[1,3-oxazole-4,9'-xanthen]-2-amine;
(4S)-2'-(5,6-dihydro-2H-pyran-3-yl)-4'-fluoro-7'-(2-fluoro-3-pyridinyl)spiro[1,3-oxazole-4,9'-xanthen]-2-amine;
(5S)-3-(3,6-dihydro-2H-pyran-4-yl)-1-fluoro-7-(2-fluoro-3-pyridinyl)spiro[chromeno[2,3-c]pyridine-5,4'-[1,3]oxazol]-2'-amine;
(5S)-1-fluoro-7-(2-fluoro-3-pyridinyl)-3-(tetrahydro-2H-pyran-4-yl)spiro[chromeno[2,3-c]pyridine-5,4'-[1,3]oxazol]-2'-amine;
(4S)-4'-fluoro-7'-(2-fluoro-5-methyl-3-pyridinyl)-2'-(4-morpholinyl)spiro[1,3-oxazole-4,9'-xanthen]-2-amine;
(5S)-7-(2-fluoro-3-pyridinyl)-3-((3S)-3-fluoro-1-pyrrolidinyl)spiro[chromeno[2,3-c]pyridine-5,4'-[1,3]oxazol]-2'-amine;
3-((5S)-2'-amino-3-(3,3-difluoro-1-pyrrolidinyl)spiro[chromeno[2,3-c]pyridine-5,4'-[1,3]oxazol]-7-yl)benzonitrile;
(5S)-3-(6,6-dimethyl-3,6-dihydro-2H-pyran-4-yl)-7-(5-fluoro-3-pyridinyl)spiro[chromeno[2,3-c]pyridine-5,4'-[1,3]oxazol]-2'-amine;
(4R)-2'-(3,6-dihydro-2H-pyran-4-yl)-7'-(2-fluoro-3-pyridinyl)spiro[1,3-oxazole-4,9'-xanthen]-2-amine;
(5S)-3-(4,4-difluoro-1-piperidinyl)-7-(2-fluoro-3-pyridinyl)spiro[chromeno[2,3-c]pyridine-5,4'-[1,3]oxazol]-2'-amine;
(5S)-3-(3,3-difluoro-1-pyrrolidinyl)-7-(3-pyridinyl)spiro[chromeno[2,3-c]pyridine-5,4'-[1,3]oxazol]-2'-amine;
(4S)-4'-fluoro-7'-(2-fluoro-3-pyridinyl)-2'-(4-morpholinyl)spiro[1,3-oxazole-4,9'-xanthen]-2-amine;
(5S)-3-(3,3-difluoro-1-pyrrolidinyl)-7-(2-fluoro-3-pyridinyl)spiro[chromeno[2,3-c]pyridine-5,4'-[1,3]oxazol]-2'-amine;
(4S)-4'-fluoro-7'-(2-fluoro-3-pyridinyl)-2'-(8-oxa-3-azabicyclo[3.2.1]oct-3-yl)spiro[1,3-oxazole-4,9'-xanthen]-2-amine;
(4S)-4'-fluoro-7'-(2-fluoro-3-pyridinyl)-2'-(2-methyl-5-pyrimidinyl)spiro[1,3-oxazole-4,9'-xanthen]-2-amine;
(5S)-3-(3,6-dihydro-2H-pyran-4-yl)-7-(2-fluoro-4-methyl-3-pyridinyl)spiro[chromeno[2,3-c]pyridine-5,4'-[1,3]oxazol]-2'-amine;
(4S)-4'-fluoro-7'-(6-fluoro-3-pyridinyl)-2'-(1-methyl-1H-pyrazol-4-yl)spiro[1,3-oxazole-4,9'-xanthen]-2-amine;
(4S)-4'-fluoro-7'-(2-fluoro-3-pyridinyl)-2'-((3S)-3-fluoro-1-pyrrolidinyl)spiro[1,3-oxazole-4,9'-xanthen]-2-amine;
(5R)-3-(3,3-dimethyl-1-butyn-1-yl)-8-fluoro-7-(5-pyrimidinyl)spiro[chromeno[2,3-b]pyridine-5,4'-[1,3]oxazol]-2'-amine;
(5S)-3-(6,6-dimethyl-3,6-dihydro-2H-pyran-4-yl)-7-(6-fluoro-3-pyridinyl)spiro[chromeno[2,3-c]pyridine-5,4'-[1,3]oxazol]-2'-amine; and
(5S)-3-(5,6-dihydro-2H-pyran-3-yl)-7-(2-fluoro-3-pyridinyl)spiro[chromeno[2,3-c]pyridine-5,4'-[1,3]oxazol]-2'-amine.

3. A compound, or a stereoisomer, tautomer or pharmaceutically acceptable salt thereof, selected from
- (5S)-3-(4,4-difluoro-1-piperidinyl)-7-(3-pyridinyl)spiro[chromeno[2,3-c]pyridine-5,4'-[1,3]oxazol]-2'-amine;
- (5S)-3-(4,4-difluoro-1-piperidinyl)-7-(5-fluoro-3-pyridinyl)spiro[chromeno[2,3-c]pyridine-5,4'-[1,3]oxazol]-2'-amine;
- 3-(((4S)-2-amino-5'-fluoro-7'-(6-methyl-3-pyridinyl)spiro[1,3-oxazole-4,9'-xanthen]-2'-yl)oxy)-2,2-dimethylpropanenitrile;
- (4S)-2'-(3,6-dihydro-2H-pyran-4-yl)-4'-fluoro-7'-(2-pyrazinyl)spiro[1,3-oxazole-4,9'-xanthen]-2-amine;
- (5S)-7-(3-chloro-2-fluorophenyl)-3-((3-methyl-3-oxetanyl)ethynyl)spiro[chromeno[2,3-b]pyridine-5,4'-[1,3]oxazol]-2'-amine;
- (5S)-1-fluoro-7-(2-fluoro-3-pyridinyl)-3-(3-pyridinyl)spiro[chromeno[2,3-c]pyridine-5,4'-[1,3]oxazol]-2'-amine;
- (4R)-7'-(6,6-dimethyl-3,6-dihydro-2H-pyran-4-yl)-3'-fluoro-2'-(5-pyrimidinyl)spiro[1,3-oxazole-4,9'-xanthen]-2-amine;
- (4S)-3',5'-difluoro-7'-(2-fluoro-2-methylpropoxy)-2'-(5-pyrimidinyl)spiro[1,3-oxazole-4,9'-xanthen]-2-amine;
- (5S)-3-(5,6-dihydro-2H-pyran-3-yl)-7-(2-fluoro-3-pyridinyl)spiro[chromeno[2,3-b]pyridine-5,4'-[1,3]thiazol]-2'-amine;
- (5S)-1-fluoro-7-(2-fluoro-3-pyridinyl)-3-((3R)-3-fluoro-1-pyrrolidinyl)spiro[chromeno[2,3-c]pyridine-5,4'-[1,3]oxazol]-2'-amine;
- (5S)-7-(2,4-difluoro-3-pyridinyl)-3-(5,6-dihydro-2H-pyran-3-yl)spiro[chromeno[2,3-c]pyridine-5,4'-[1,3]oxazol]-2'-amine;
- (5S)-3-(5,6-dihydro-2H-pyran-3-yl)-1-fluoro-7-(2-fluoro-3-pyridinyl)spiro[chromeno[2,3-c]pyridine-5,4'-[1,3]oxazol]-2'-amine;
- (5S)-3-(5,6-dihydro-2H-pyran-3-yl)-1-fluoro-7-(3-pyridinyl)spiro[chromeno[2,3-c]pyridine-5,4'-[1,3]oxazol]-2'-amine;
- (5S)-1-fluoro-7-(2-fluoro-3-pyridinyl)-3-(6-methyl-3-pyridinyl)spiro[chromeno[2,3-c]pyridine-5,4'-[1,3]oxazol]-2'-amine;
- (5S)-1-fluoro-7-(5-(1-propyn-1-yl)-3-pyridinyl)-3-(3-pyridinyl)spiro[chromeno[2,3-c]pyridine-5,4'-[1,3]oxazol]-2'-amine;
- (4S)-2'-(5,6-dihydro-2H-pyran-3-yl)-4'-fluoro-7'-(2-fluoro-3-pyridinyl)spiro[1,3-thiazole-4,9'-xanthen]-2-amine;
- (5S)-3-(2-fluoro-4-pyridinyl)-1-methoxy-7-(3-pyridinyl)spiro[chromeno[2,3-c]pyridine-5,4'-[1,3]oxazol]-2'-amine;
- 3-(((4S)-2-amino-4',6'-difluoro-7'-(3-pyridinyl)spiro[1,3-oxazole-4,9'-xanthen]-2'-yl)oxy)-2,2-dimethylpropanenitrile;
- (4S)-7'-(3,6-dihydro-2H-pyran-4-yl)-3',5'-difluoro-2'-(2-fluoro-3-pyridinyl)spiro[1,3-oxazole-4,9'-xanthen]-2-amine;
- (4S)-3',5'-difluoro-2'-(2-fluoro-3-pyridinyl)-7'-(4-morpholinyl)spiro[1,3-oxazole-4,9'-xanthen]-2-amine;
- (5S)-1-fluoro-7-(2-fluoro-3-pyridinyl)-3-(4-morpholinyl)spiro[chromeno[2,3-c]pyridine-5,4'-[1,3]oxazol]-2'-amine;
- (5S)-1-fluoro-7-(5-fluoro-3-pyridinyl)-3-(4-morpholinyl)spiro[chromeno[2,3-c]pyridine-5,4'-[1,3]oxazol]-2'-amine;
- 3-((5S)-2'-amino-1-fluoro-3-(4-morpholinyl)spiro[chromeno[2,3-c]pyridine-5,4'-[1,3]oxazol]-7-yl)benzonitrile; and
- (5S)-2-fluoro-7-(2-fluoro-3-pyridinyl)-3-((3-methyl-3-oxetanyl)ethynyl)spiro[chromeno[2,3-b]pyridine-5,4'-[1,3]oxazol]-2'-amine.

4. A compound, or a stereoisomer, tautomer or pharmaceutically acceptable salt thereof, selected from
- (5S)-3-(3,3-difluoro-1-pyrrolidinyl)-1-fluoro-7-(3-pyridinyl)spiro[chromeno[2,3-c]pyridine-5,4'-[1,3]oxazol]-2'-amine;
- (5S)-3-(3,3-difluoro-1-pyrrolidinyl)-1-fluoro-7-(2-fluoro-3-pyridinyl)spiro[chromeno[2,3-c]pyridine-5,4'-[1,3]oxazol]-2'-amine;
- (5S)-3-(3,3-difluoro-1-pyrrolidinyl)-1-fluoro-7-(5-fluoro-3-pyridinyl)spiro[chromeno[2,3-c]pyridine-5,4'-[1,3]oxazol]-2'-amine;
- (5S)-3-(4,4-difluoro-1-piperidinyl)-1-fluoro-7-(5-fluoro-3-pyridinyl)spiro[chromeno[2,3-c]pyridine-5,4'-[1,3]oxazol]-2'-amine;
- (5S)-3-(5,6-dihydro-2H-pyran-3-yl)-7-(2-fluoro-3-pyridinyl)spiro[chromeno[2,3-c]pyridine-5,4'-[1,3]thiazol]-2'-amine;
- (5S)-3-(3,6-dihydro-2H-pyran-4-yl)-7-(5-(1-propyn-1-yl)-3-pyridinyl)spiro[chromeno[2,3-b]pyridine-5,4'-[1,3]oxazol]-2'-amine;
- (4S)-4'-fluoro-2'-(1-methyl-1H-pyrazol-4-yl)-7'-(5-(1-propyn-1-yl)-3-pyridinyl)spiro[1,3-oxazole-4,9'-xanthen]-2-amine;
- 4-((4S)-2-amino-4'-fluoro-7'-(5-(1-propyn-1-yl)-3-pyridinyl)spiro[1,3-oxazole-4,9'-xanthen]-2'-yl)-2-methyl-3-butyn-2-ol;
- (5S)-1-fluoro-7-(2-fluoro-3-pyridinyl)-3-(2-fluoro-4-pyridinyl)spiro[chromeno[2,3-c]pyridine-5,4'-[1,3]thiazol]-2'-amine;
- (5S)-7-(2-fluoro-3-pyridinyl)-3-(4-morpholinyl)spiro[chromeno[2,3-c]pyridine-5,4'-[1,3]thiazol]-2'-amine;
- (5S)-7-(2-fluoro-3-pyridinyl)-3-(2-fluoro-4-pyridinyl)spiro[chromeno[2,3-c]pyridine-5,4'-[1,3]thiazol]-2'-amine;
- (5S)-3-(3,6-dihydro-2H-pyran-4-yl)-1-fluoro-7-(2-fluoro-3-pyridinyl)spiro[chromeno[2,3-c]pyridine-5,4'-[1,3]thiazol]-2'-amine;
- (5S)-1-fluoro-7-(2-fluoro-3-pyridinyl)-3-(tetrahydro-2H-pyran-4-yl)spiro[chromeno[2,3-c]pyridine-5,4'-[1,3]thiazol]-2'-amine;
- (5S)-3-(6,6-dimethyl-3,6-dihydro-2H-pyran-4-yl)-1-fluoro-7-(2-fluoro-3-pyridinyl)spiro[chromeno[2,3-c]pyridine-5,4'-[1,3]thiazol]-2'-amine;
- (5S)-1-fluoro-7-(2-fluoro-3-pyridinyl)-3-(2-methyl-4-pyridinyl)spiro[chromeno[2,3-c]pyridine-5,4'-[1,3]thiazol]-2'-amine;
- (4S)-4'-fluoro-2'-(2-fluoro-2-methylpropoxy)-7'-(2-fluoro-3-pyridinyl)spiro[1,3-thiazole-4,9'-xanthen]-2-amine;
- (4S)-2'-(4,4-difluoro-1-piperidinyl)-4'-fluoro-7'-(2-fluoro-3-pyridinyl)spiro[1,3-thiazole-4,9'-xanthen]-2-amine;
- (4S)-2'-(3,3-difluoro-1-pyrrolidinyl)-4'-fluoro-7'-(2-fluoro-3-pyridinyl)spiro[1,3-thiazole-4,9'-xanthen]-2-amine;
- (4S)-4'-fluoro-7'-(2-fluoro-3-pyridinyl)-2'-(2-pyrimidinyl)spiro[1,3-thiazole-4,9'-xanthen]-2-amine;
- (4S)-4'-fluoro-7'-(2-fluoro-3-pyridinyl)-2'-(3-pyridinyl)spiro[1,3-thiazole-4,9'-xanthen]-2-amine; and
- (4S)-4'-fluoro-7'-(2-fluoro-3-pyridinyl)-2'-((1S,4S)-2-oxa-5-azabicyclo[2.2.1]hept-5-yl)spiro[1,3-thiazole-4,9'-xanthen]-2-amine.

5. A compound, or a stereoisomer, tautomer or pharmaceutically acceptable salt thereof, selected from (5S)-7-(2,4-difluoro-3-pyridinyl)-3-(3,6-dihydro-2H-py-ran-4-yl)spiro[chromeno[2,3-c]pyridine-5,4'-[1,3]ox-azol]-2'-amine;

(5S)-3-(5,6-dihydro-2H-pyran-3-yl)-1-fluoro-7-(3-pyridi-nyl)spiro[chromeno[2,3-c]pyridine-5,4'-[1,3]oxazol]-2'-amine;

(5S)-3-(5,6-dihydro-2H-pyran-3-yl)-1-fluoro-7-(2-fluoro-3-pyridinyl)spiro[chromeno[2,3-c]pyridine-5,4'-[1,3]oxazol]-2'-amine;

(4S)-2'-(5,6-dihydro-2H-pyran-3-yl)-4'-fluoro-7'-(2-fluoro-3-pyridinyl)spiro[1,3-thiazole-4,9'-xanthen]-2-amine;

(5S)-3-(3,6-dihydro-2H-pyran-4-yl)-7-(2-fluoro-4-me-thyl-3-pyridinyl)spiro[chromeno[2,3-c]pyridine-5,4'-[1,3]oxazol]-2'-amine;

(4S)-7'-(3,6-dihydro-2H-pyran-4-yl)-3',5'-difluoro-2'-(2-fluoro-3-pyridinyl)spiro[1,3-oxazole-4,9'-xanthen]-2-amine;

(4S)-2'-(5,6-dihydro-2H-pyran-3-yl)-4'-fluoro-7'-(2-fluoro-3-pyridinyl)spiro[1,3-oxazole-4,9'-xanthen]-2-amine;

(5S)-3-(5,6-dihydro-2H-pyran-3-yl)-7-(2-fluoro-3-pyridinyl)spiro[chromeno[2,3-c]pyridine-5,4'-[1,3]oxazol]-2'-amine;

(5S)-3-(6,6-dimethyl-3,6-dihydro-2H-pyran-4-yl)-7-(5-fluoro-3-pyridinyl)spiro[chromeno[2,3-c]pyridine-5,4'-[1,3]oxazol]-2'-amine;

(4S)-2'-(3,6-dihydro-2H-pyran-4-yl)-4'-fluoro-7'-(2-pyrazinyl)spiro[1,3-oxazole-4,9'-xanthen]-2-amine;

(5S)-3-(3,6-dihydro-2H-pyran-4-yl)-7-(5-(1-propyn-1-yl)-3-pyridinyl)spiro[chromeno[2,3-b]pyridine-5,4'-[1,3]oxazol]-2'-amine;

(5S)-3-(3,6-dihydro-2H-pyran-4-yl)-7-(2-fluoro-3-pyridinyl)spiro[chromeno[2,3-b]pyridine-5,4'-[1,3]thiazol]-2'-amine;

(5S)-3-(3,6-dihydro-2H-pyran-4-yl)-1-fluoro-7-(2-fluoro-3-pyridinyl)spiro[chromeno[2,3-c]pyridine-5,4'-[1,3]thiazol]-2'-amine;

(5S)-3-(3,6-dihydro-2H-pyran-4-yl)-1-fluoro-7-(2-fluoro-3-pyridinyl)spiro[chromeno[2,3-c]pyridine-5,4'-[1,3]oxazol]-2'-amine; and (5S)-3-(5,6-dihydro-2H-pyran-3-yl)-1-fluoro-7-(2-fluoro-3-pyridinyl)spiro[chromeno[2,3-c]pyridine-5,4'-[1,3]thiazol]-2'-amine.

6. A compound, or a stereoisomer, tautomer or pharmaceutically acceptable salt thereof, selected from (4S)-4'-fluoro-7'-(2-fluoro-3-pyridinyl)-2'-(4-morpholinyl)spiro[1,3-oxazole-4,9'-xanthen]-2-amine;

(5S)-1-fluoro-7-(2-fluoro-3-pyridinyl)-3-(4-morpholinyl)spiro[chromeno[2,3-c]pyridine-5,4'-[1,3]oxazol]-2'-amine;

(5S)-1-fluoro-7-(5-fluoro-3-pyridinyl)-3-(4-morpholinyl)spiro[chromeno[2,3-c]pyridine-5,4'-[1,3]oxazol]-2'-amine;

3-((5S)-2'-amino-1-fluoro-3-(4-morpholinyl)spiro[chromeno[2,3-c]pyridine-5,4'-[1,3]oxazol]-7-yl)benzonitrile;

(4S)-4'-fluoro-7'-(2-fluoro-3-pyridinyl)-2'-((1S,4S)-2-oxa-5-azabicyclo[2.2.1]hept-5-yl)spiro[1,3-thiazole-4,9'-xanthen]-2-amine.

(5S)-3-(3,3-difluoro-1-pyrrolidinyl)-1-fluoro-7-(3-pyridinyl)spiro[chromeno[2,3-c]pyridine-5,4'-[1,3]oxazol]-2'-amine;

(5S)-3-(4,4-difluoro-1-piperidinyl)-1-fluoro-7-(2-fluoro-3-pyridinyl)spiro[chromeno[2,3-c]pyridine-5,4'[1,3]oxazol]-2'-amine;

(5S)-3-(3,3-difluoro-1-pyrrolidinyl)-1-fluoro-7-(2-fluoro-3-pyridinyl)spiro[chromeno[2,3-c]pyridine-5,4'[1,3]oxazol]-2'-amine;

(5S)-3-(3,3-difluoro-1-pyrrolidinyl)-1-fluoro-7-(5-fluoro-3-pyridinyl)spiro[chromeno[2,3-c]pyridine-5,4'-[1,3]oxazol]-2'-amine;

(5S)-3-(4,4-difluoro-1-piperidinyl)-1-fluoro-7-(5-fluoro-3-pyridinyl)spiro[chromeno[2,3-c]pyridine-5,4'-[1,3]oxazol]-2'-amine;

(5S)-3-(3,3-difluoro-1-pyrrolidinyl)-7-(3-pyridinyl)spiro[chromeno[2,3-c]pyridine-5,4'-[1,3]oxazole]-2'-amine;

(5S)-3-(3,3-difluoro-1-pyrrolidinyl)-7-(2-fluoro-3-pyridinyl)spiro[chromeno[2,3-c]pyridine-5,4'-[1,3]oxazol]-2'-amine;

(5S)-3-(4,4-difluoro-1-piperidinyl)-7-(2-fluoro-3-pyridinyl)spiro[chromeno[2,3-c]pyridine-5,4'-[1,3]oxazol]-2'-amine;

(5S)-7-(2-fluoro-3-pyridinyl)-3-((3S)-3-fluoro-1-pyrrolidinyl)spiro[chromeno[2,3-c]pyridine-5,4'-[1,3]oxazol]-2'-amine;

3-((5S)-2'-amino-3-(3,3-difluoro-1-pyrrolidinyl)spiro[chromeno[2,3-c]pyridine-5,4'-[1,3]oxazol]-7-yl)benzonitrile;

(5S)-1-fluoro-7-(2-fluoro-3-pyridinyl)-3-(tetrahydro-2H-pyran-4-yl)spiro[chromeno[2,3-c]pyridine-5,4'-[1,3]oxazol]-2'-amine; and (4S)-2'-(3,3-difluoro-1-pyrrolidinyl)-4'-fluoro-7'-(2-fluoro-3-pyridinyl)spiro[1,3-thiazole-4,9'-xanthen]-2-amine;

(4S)-4'-fluoro-7'-(2-fluoro-3-pyridinyl)-2'-(2-pyrimidinyl)spiro[1,3-oxazole-4,9'-xanthen]-2-amine;

(5S)-1-fluoro-7-(2-fluoro-3-pyridinyl)-3-(6-methyl-3-pyridinyl)spiro[chromeno[2,3-c]pyridine-5,4'-[1,3]oxazol]-2'-amine;

(5S)-1-fluoro-7-(5-(1-propyn-1-yl)-3-pyridinyl)-3-(3-pyridinyl)spiro[chromeno[2,3-c]pyridine-5,4'-[1,3]oxazol]-2'-amine;

(4S)-4'-fluoro-2'-(1-methyl-1H-pyrazol-4-yl)-7'-(5-(1-propyn-1-yl)-3-pyridinyl)spiro[1,3-oxazole-4,9'-xanthen]-2-amine;

(5S)-1-fluoro-7-(2-fluoro-3-pyridinyl)-3-(2-fluoro-4-pyridinyl)spiro[chromeno[2,3-c]pyridine-5,4'-[1,3]thiazol]-2'-amine;

(5S)-7-(2-fluoro-3-pyridinyl)-3-(2-fluoro-4-pyridinyl)spiro[chromeno[2,3-c]pyridine-5,4'-[1,3]thiazol]-2'-amine;

(5S)-1-fluoro-7-(2-fluoro-3-pyridinyl)-3-(3-pyridinyl)spiro[chromeno[2,3-c]pyridine-5,4'-[1,3]oxazol]-2'-amine;

(4S)-4'-fluoro-7'-(2-fluoro-3-pyridinyl)-2'-(2-pyrimidinyl)spiro[1,3-thiazole-4,9'-xanthen]-2-amine; and (4S)-4'-fluoro-7'-(2-fluoro-3-pyridinyl)-2'-(3-pyridinyl)spiro[1,3-thiazole-4,9'-xanthen]-2-amine.

7. A pharmaceutical composition comprising a compound according to any of claim 1 and a pharmaceutically acceptable excipient.

8. A pharmaceutical composition comprising a compound according to any of claim 2 and a pharmaceutically acceptable excipient.

9. A pharmaceutical composition comprising a compound according to any of claim 3 and a pharmaceutically acceptable excipient.

10. A pharmaceutical composition comprising a compound according to any of claim 4 and a pharmaceutically acceptable excipient.

11. A pharmaceutical composition comprising a compound according to any of claim 5 and a pharmaceutically acceptable excipient.

12. A pharmaceutical composition comprising a compound according to any of claim 6 and a pharmaceutically acceptable excipient.

13. The compound of claim 5, or a stereoisomer, tautomer or pharmaceutically acceptable salt thereof, that is (5S)-3-(5,6-dihydro-2H-pyran-3-yl)-1-fluoro-7-(3-pyridinyl)spiro[chromeno[2,3-c]pyridine-5,4'[1,3]oxazol]-2'-amine.

14. The compound of claim 5, or a stereoisomer, tautomer or pharmaceutically acceptable salt thereof, that is (5S)-3-(5,6-dihydro-2H-pyran-3-yl)-1-fluoro-7-(2-fluoro-3-pyridinyl)spiro[chromeno[2,3-c]pyridine-5,4'-[1,3]oxazol]-2'-amine.

15. The compound of claim 5, or a stereoisomer, tautomer or pharmaceutically acceptable salt thereof, that is (5S)-3-(5,6-dihydro-2H-pyran-3-yl)-7-(2-fluoro-3-pyridinyl)spiro[chromeno[2,3-c]pyridine-5,4'[1,3]oxazol]-2'-amine.

16. The compound of claim 5, or a stereoisomer, tautomer or pharmaceutically acceptable salt thereof, that is (5S)-3-(3,6-dihydro-2H-pyran-4-yl)-1-fluoro-7-(2-fluoro-3-pyridinyl)spiro[chromeno[2,3-c]pyridine-5,4'-[1,3]oxazol]-2'-amine.

17. The compound of claim 5, or a stereoisomer, tautomer or pharmaceutically acceptable salt thereof, that is (5S)-3-(5,6-dihydro-2H-pyran-3-yl)-1-fluoro-7-(2-fluoro-3-pyridinyl)spiro[chromeno[2,3-c]pyridine-5,4'-[1,3]thiazol]-2'-amine.

18. A pharmaceutical compositon comprising the compound, or a pharmaceutically acceptable salt thereof, according to any one of claims 13-17 and a pharmaceutically acceptable excipient.

* * * * *